US007714121B2

(12) United States Patent
Scarlato et al.

(10) Patent No.: US 7,714,121 B2
(45) Date of Patent: May 11, 2010

(54) MENINGOCOCCAL ANTIGENS

(75) Inventors: Vincenzo Scarlato, Siena (IT); Vega Masignani, Siena (IT); Rino Rappuoli, Siena (IT); Mariagrazia Pizza, Siena (IT); Guido Grandi, Siena (IT)

(73) Assignee: Novartis Vaccines and Diagnostics SRL, Siena (IT)

( * ) Notice: Subject to any disclaimer, the term of this patent is extended or adjusted under 35 U.S.C. 154(b) by 0 days.

(21) Appl. No.: 10/695,499

(22) Filed: Oct. 28, 2003

(65) Prior Publication Data

US 2004/0126391 A1 Jul. 1, 2004

Related U.S. Application Data

(60) Division of application No. 09/302,626, filed on Apr. 30, 1999, now Pat. No. 6,709,660, which is a continuation-in-part of application No. PCT/IB99/00103, filed on Jan. 14, 1999.

(30) Foreign Application Priority Data

| Jan. 14, 1998 | (GB) | ................................. 9800760.2 |
| Sep. 1, 1998 | (GB) | ................................. 9819015.0 |
| Oct. 9, 1998 | (GB) | ................................. 9822143.5 |

(51) Int. Cl.
 *C07H 21/04* (2006.01)
(52) U.S. Cl. .................................. 536/23.7; 536/24.32
(58) Field of Classification Search ................ 536/23.7; 424/249.1, 250.1
See application file for complete search history.

(56) References Cited

U.S. PATENT DOCUMENTS

| 5,286,484 | A | 2/1994 | Rodriquez et al. |
| 6,197,312 | B1 | 3/2001 | Peak et al. |
| 6,200,578 | B1 | 3/2001 | St. Geme et al. |
| 6,610,306 | B2 | 8/2003 | Judd et al. |
| 6,709,660 | B1 | 3/2004 | Scarlato et al. |
| 6,780,419 | B1 | 8/2004 | Ruelle |
| 2002/0160016 | A1 | 10/2002 | Peak et al. |
| 2006/0166344 | A1 | 7/2006 | Pizza et al. |

FOREIGN PATENT DOCUMENTS

| EP | 0 467 714 A1 | 1/1992 |
| EP | 0474313 A2 | 3/1992 |
| EP | 0474313 A3 | 3/1992 |
| WO | WO 95/03413 A1 | 2/1995 |
| WO | WO 95/33049 A2 | 12/1995 |
| WO | WO 96/29412 A1 | 9/1996 |
| WO | WO 96/30519 A1 | 10/1996 |
| WO | WO-9726359 | 7/1997 |
| WO | WO-98/02547 A2 | 1/1998 |
| WO | WO-9936544 | 7/1999 |

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Aldeen et al., "The menigococcal transferring-binding proteins 1 and 2 are both surface exposed and generate bactericidal antibodies capable of killing homologous and heterologous strains," *Vaccine* 14(1):49-53, 1996.
Constantino et al., "Development and phase I clinical testing of a conjugate vaccine against meningococcus A and C," *Vaccine* 10:691-698.
Jafari et al., "Control and prevention of meningococcal disease: recommendations of the advisory committee on immunization practices (ACIP)," *MMWR* 46(RR-5):1-10, 1997.
Lieberman et al., "Safety and immunogenicity of a serogrooups A/C *Neisseria meningitides* oligosaccharide-protein conjugate vaccine in young children," *JAMA* 275(19):1499-1503, 1996.
Perkins et al., "Control and prevention of serogroup C meningococcal disease: evaluation and management of suspected outbreaks: recommendations for the advisory committee on immunization practices (ACIP)," *MMWR* 46(RR-5):13-21, 1997.
Poolman, "Development of a mengococcal vaccine," *Infections agents and Disease* 4:13-28, 1995.
Rokbi et al., "Evaluation of recombinant transferring-binding protein B variants from *Neisseria meningitides* for their ability to induce cross-reactive and bactericidal antibodies against agenetically diverse collection of serogroup B strains," *Infection and Immunity* 65(1):55-63, 1997.
Rokbi et al., "Heterogeneity of tbpB, the transferring-binding protein B gene, among serogroup B *Neisseria meningitides* strains of the ET-5 complex," *Clinical and Diagnostic Lab. Immun.* 4(5):522-529, 1997.
Romero et al., "Current status of meningococcal group B vaccine candidates: capsular or noncapsular?" *Clinical Microbio. Reviews* 7(4):559-575, 1994.
Schuchat et al., "Bacterial meningitis in the United States in 1995," *New England J. of Medicine* 337(14):970-976, 1997.
Wedege et al., "Human antibody response to a group B serotype 2a meningococcal vaccine determined by immunoblotting," *Infection and Immunity* 51(2):571-578, 1986.
Zollinger, "New and improved vaccines against meningococcal disease," in *New Generation Vaccines*, $2^{nd}$ Ed., pp. 469-488, 1997.
Paralkar, et al. (1994). "Cloning the Human Gene for Macrophage Migration Inhibitory Factor (MIF)," *Genomics*, 19:48-51.

(Continued)

*Primary Examiner*—Jennifer E Graser
(74) *Attorney, Agent, or Firm*—Amy Hessler; Helen Lee; Robert Gorman

(57) ABSTRACT

The invention provides proteins from *Neisseria meningitidis* (strains A & B), including amino acid sequences, the corresponding nucleotide sequences, expression data, and serological data. The proteins are useful antigens for vaccines, immunogenic compositions, and/or diagnostics.

8 Claims, 15 Drawing Sheets

OTHER PUBLICATIONS

Bernhagen, et al. (1994) "Purification, Bioactivity, and Secondary Structure Analysis of Mouse and Human Macrophage Migration Inhibitory Factor (MIF)," Biochemistry, 33:14144-14155.

Watarai, et al. (2000). "Posttranslational modification of the glycosylation inhibiting factor (GIF) gene product generates bioactive GIF," PNAS Early Edition, p. 1-6.

Carson, S. D. B. et al. (May 1999). "Ferric Enterobactin Binding and Utilization by *Neisseria gonorrhoeae*," Journal of Bacteriology 18:2895-2901.

GenBank Accession No. U56744, located at <http://www.ncbi.nlm.nih.gov/entrez/viewer.fcgi?db=nuccore&id=1621553> visited on Oct. 23, 2007. (1 page).

Tinsley, C. R. et al. (Oct. 1996). "Analysis of the Genetic Differences Between *Neisseria meningitidis* and *Neisseria gonorrhoeae*: Two Closely Related Bacteria Expressing Two Different Pathogenicities," Proceedings of the National Academy of Sciences of USA 93:11109-11114.

Notice to Interference: Declaration-Bd.R. 203(b) filed Jun. 11, 2007. Submitted in *Ruelle* v. *Scarlato*: Interference No. 105,551.

Ruelle Notice of Related Proceedings filed Jun. 21, 2007. Submitted in *Ruelle* v. *Scarlato*: Interference No. 105,551.

Scarlato Notice of Related Proceedings filed Jun. 25, 2007. Submitted in *Ruelle* v. *Scarlato*: Interference No. 105,551.

Ruelle Annotated Copy of Claims filed Jul. 6, 2007. Submitted in *Ruelle* v. *Scarlato*: Interference No. 105,551.

Scarlato Annotated Copy of Claims filed Jul. 9, 2007. Submitted in *Ruelle* v. *Scarlato*: Interference No. 105,551.

Ruelle Substantive Motion No. 1 (for judgment based on prior art). Nov. 16, 2007. Submitted in *Ruelle* v. *Scarlato*: Interference No. 105,551.

Ruelle Substantive Motion No. 2 (for judgment based on prior art). Nov. 16, 2007. Submitted in *Ruelle* v. *Scarlato*: Interference No. 105,551.

Ruelle Substantive Motion No. 3 (for judgment based on prior art). Nov. 16, 2007. Submitted in *Ruelle* v. *Scarlato*: Interference No. 105,551.

Scarlato Substantive Motion 1. Nov. 16, 2007. Submitted in *Ruelle* v. *Scarlato*: Interference No. 105,551.

Ruelle Opposition 1. Feb. 13, 2008. Submitted in *Ruelle* v. *Scarlato*: Interference No. 105,551.

Scarlato Opposition 1. Feb. 13, 2008. Submitted in *Ruelle* v. *Scarlato*: Interference No. 105,551.

Scarlato Opposition 2. Feb. 13, 2008. Submitted in *Ruelle* v. *Scarlato*: Interference No. 105,551.

Ruelle Reply 1. Mar. 10, 2008. Submitted in *Ruelle* v. *Scarlato*: Interference No. 105,551.

Ruelle Reply 2. Mar. 10, 2008. Submitted in *Ruelle* v. *Scarlato*: Interference No. 105,551.

Scarlato Reply 1. Mar. 10, 2008. Submitted in *Ruelle* v. *Scarlato*: Interference No. 105,551.

Order—Decision On Motions. Mar. 11, 2009. Submitted in *Ruelle* v. *Scarlato*: Interference No. 105,551.

Ruelle Request for Rehearing. Mar. 25, 2009. Submitted in *Ruelle* v. *Scarlato*: Interference No. 105,551.

Declaration of Garnett H. Kelsoe, D.Sc. Submitted in *Ruelle* v. *Scarlato*: Interference No. 105,551 as Exhibit No. 1001. 37 pages.

Curriculum Vitae of Garnett Herrel Kelsoe III. Submitted in *Ruelle* v. *Scarlato*: Interference No. 105,551 as Exhibit No. 1002. 21 pages.

SEQUENCE LISTING

<160> NUMBER OF SEQ ID NOS: 195

<210> SEQ ID NO 1
<211> LENGTH: 736
<212> TYPE: DNA
<213> ORGANISM: Neisseria meningitidis

<400> SEQUENCE: 1

```
acactgttgt ttgcaacggt tcaggcaagt gctaaccaat gaagagcaag aagaagattt      60
atatttagac cccgtacaac gcactgttgc cgtgttgata gtcaattccg ataaagaagg     120
cacgggagaa aaagaaaaag tagaagaaaa ttcagattgg gcagtatatt tcaacgagaa     180
aggagtacta acagccagag aaatcaccyt caaagccggc gacaacctga aaatcaaaca     240
aaacggcaca aacttcacct actcgctgaa aaagacctc acagatctga ccagtgttgg     300
aactgaaaaa ttatcgttta gcgcaaacgg caataaagtc aacatcacaa gcgacaccaa     360
aggcttgaat tttgcgaaag aaacggctgg sacgaacggc gacaccacgg ttcatctgaa     420
cggtattggt tcgactttga ccgatacgct gctgaatacc ggagcgacca caaacgtaac     480
caacgacaac gttaccgatg acgagaaaaa acgtgcggca agcgttaaag acgtattaaa     540
cgctggctgg aacattaaag gcgttaaacc cggtacaaca gcttccgata acgttgattt     600
cgtccgcact tacgacacag tcgagttctt gagcgcagat acgaaaacaa cgactgttaa     660
tgtggaaagc aaagacaacg gcaagaaaac cgaagttaaa atcggtgcga agacttctgt     720
tattaaagaa aaagac                                                     736
```

<210> SEQ ID NO 2
<211> LENGTH: 245
<212> TYPE: PRT
<213> ORGANISM: Neisseria meningitidis
<220> FEATURE:
<221> NAME/KEY: SITE
<222> LOCATION: (70)
<223> OTHER INFORMATION: unknown

<400> SEQUENCE: 2

```
Thr Leu Leu Phe Ala Thr Val Gln Ala Ser Ala Asn Gln Glu Glu Gln
  1               5                  10                  15

Glu Glu Asp Leu Tyr Leu Asp Pro Val Gln Arg Thr Val Ala Val Leu
             20                  25                  30

Ile Val Asn Ser Asp Lys Glu Gly Thr Gly Glu Lys Glu Lys Val Glu
         35                  40                  45

Glu Asn Ser Asp Trp Ala Val Tyr Phe Asn Glu Lys Gly Val Leu Thr
     50                  55                  60

Ala Arg Glu Ile Thr Xaa Lys Ala Gly Asp Asn Leu Lys Ile Lys Gln
 65                  70                  75                  80

Asn Gly Thr Asn Phe Thr Tyr Ser Leu Lys Lys Asp Leu Thr Asp Leu
                 85                  90                  95

Thr Ser Val Gly Thr Glu Lys Leu Ser Phe Ser Ala Asn Gly Asn Lys
            100                 105                 110

Val Asn Ile Thr Ser Asp Thr Lys Gly Leu Asn Phe Ala Lys Glu Thr
        115                 120                 125

Ala Gly Thr Asn Gly Asp Thr Val His Leu Asn Gly Ile Gly Ser
    130                 135                 140

Thr Leu Thr Asp Thr Leu Leu Asn Thr Gly Ala Thr Thr Asn Val Thr
145                 150                 155                 160
```

```
Asn Asp Asn Val Thr Asp Asp Glu Lys Lys Arg Ala Ala Ser Val Lys
                165                 170                 175

Asp Val Leu Asn Ala Gly Trp Asn Ile Lys Gly Val Lys Pro Gly Thr
            180                 185                 190

Thr Ala Ser Asp Asn Val Asp Phe Val Arg Thr Tyr Asp Thr Val Glu
        195                 200                 205

Phe Leu Ser Ala Asp Thr Lys Thr Thr Thr Val Asn Val Glu Ser Lys
    210                 215                 220

Asp Asn Gly Lys Lys Thr Glu Val Lys Ile Gly Ala Lys Thr Ser Val
225                 230                 235                 240

Ile Lys Glu Lys Asp
            245

<210> SEQ ID NO 3
<211> LENGTH: 1776
<212> TYPE: DNA
<213> ORGANISM: Neisseria meningitidis

<400> SEQUENCE: 3
atgaacaaaa taccgcat catttggaat agtgccctca atgcctgggt cgtcgtatcc    60
gagctcacac gcaaccacac caaacgcgcc tccgcaaccg tgaagaccgc cgtattggcg   120
acactgttgt ttgcaacggt tcaggcaagt gctaacaatg aagagcaaga agaagattta   180
tatttagacc ccgtacaacg cactgttgcc gtgttgatag tcaattccga taaagaaggc   240
acgggagaaa agaaaaagt agaagaaaat tcagattggg cagtatattt caacgagaaa   300
ggagtactaa cagccagaga aatcaccctc aaagccggcg acaacctgaa aatcaaacaa   360
aacggcacaa acttcaccta ctcgctgaaa aagacctca cagatctgac cagtgttgga   420
actgaaaaat tatcgtttag cgcaaacggc aataaagtca acatcacaag cgacaccaaa   480
ggcttgaatt ttgcgaaaga aacggctggg acgaacggcg acaccacggt tcatctgaac   540
ggtattggtt cgactttgac cgatacgctg ctgaataccg gagcgaccac aaacgtaacc   600
aacgacaacg ttaccgatga cgagaaaaaa cgtgcggcaa gcgttaaaga cgtattaaac   660
gctggctgga acattaaagg cgttaaaccc ggtacaacag cttccgataa cgttgatttc   720
gtccgcactt acgacacagt cgagttcttg agcgcagata cgaaaacaac gactgttaat   780
gtggaaagca agacaacgg caagaaaacc gaagttaaaa tcggtgcgaa gacttctgtt   840
attaaagaaa aagacggtaa gttggttact ggtaaagaca aaggcgagaa tggttcttct   900
acagacgaag gcgaaggctt agtgactgca aaagaagtga ttgatgcagt aaacaaggct   960
ggttggagaa tgaaaacaac aaccgctaat ggtcaaacag gtcaagctga caagtttgaa  1020
accgttacat caggcacaaa tgtaaccttt gctagtggta aaggtacaac tgcgactgta  1080
agtaaagatg atcaaggcaa catcactgtt atgtatgatg taaatgtcgg cgatgcccta  1140
aacgtcaatc agctgcaaaa cagcggttgg aatttggatt ccaaagcggt tgcaggttct  1200
tcgggcaaag tcatcagcgg caatgttccg ccgagcaagg aaagatgga tgaaaccgtc  1260 aacattaatg ccggcaacaa catcgagatt acccgcaacg gtaaaaatat cgacatcgcc  1320
acttcgatga ccccgcagtt ttccagcgtt tcgctcggcg cggggcgga tgcgcccact  1380 ttgagcgtgg atgggacgc attgaatgtc ggcagcaaga aggacaacaa acccgtccgc  1440
attaccaatg tcgcccccgg cgttaaagag gggatgtta caaacgtcgc acaacttaaa  1500
ggcgtggcgc aaaacttgaa caaccgcatc gacaatgtgg acggcaacgc gcgtgcgggc  1560
```

```
atcgcccaag cgattgcaac cgcaggtctg gttcaggcgt atttgcccgg caagagtatg   1620
atggcgatcg gcggcggcac ttatcgcggc gaagccggtt acgccatcgg ctactccagt   1680
atttccgacg gcggaaattg gattatcaaa ggcacggctt ccggcaattc gcgcggccat   1740
ttcggtgctt ccgcatctgt cggttatcag tggtaa                              1776
```

<210> SEQ ID NO 4
<211> LENGTH: 591
<212> TYPE: PRT
<213> ORGANISM: Neisseria meningitidis

<400> SEQUENCE: 4

```
Met Asn Lys Ile Tyr Arg Ile Ile Trp Asn Ser Ala Leu Asn Ala Trp
  1               5                  10                  15

Val Val Val Ser Glu Leu Thr Arg Asn His Thr Lys Arg Ala Ser Ala
                 20                  25                  30

Thr Val Lys Thr Ala Val Leu Ala Thr Leu Leu Phe Ala Thr Val Gln
             35                  40                  45

Ala Ser Ala Asn Asn Glu Glu Gln Glu Glu Asp Leu Tyr Leu Asp Pro
         50                  55                  60

Val Gln Arg Thr Val Ala Val Leu Ile Val Asn Ser Asp Lys Glu Gly
 65                  70                  75                  80

Thr Gly Glu Lys Glu Lys Val Glu Glu Asn Ser Asp Trp Ala Val Tyr
                 85                  90                  95

Phe Asn Glu Lys Gly Val Leu Thr Ala Arg Glu Ile Thr Leu Lys Ala
            100                 105                 110

Gly Asp Asn Leu Lys Ile Lys Gln Asn Gly Thr Asn Phe Thr Tyr Ser
        115                 120                 125

Leu Lys Lys Asp Leu Thr Asp Leu Thr Ser Val Gly Thr Glu Lys Leu
    130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
            180                 185                 190

Thr Gly Ala Thr Thr Asn Val Thr Asn Asp Asn Val Thr Asp Asp Glu
        195                 200                 205

Lys Lys Arg Ala Ala Ser Val Lys Asp Val Leu Asn Ala Gly Trp Asn
    210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Asp Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335
```

```
Asp Lys Phe Glu Thr Val Thr Ser Gly Thr Asn Val Thr Phe Ala Ser
                340                 345                 350

Gly Lys Gly Thr Thr Ala Thr Val Ser Lys Asp Asp Gln Gly Asn Ile
            355                 360                 365

Thr Val Met Tyr Asp Val Asn Val Gly Asp Ala Leu Asn Val Asn Gln
        370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
            420                 425                 430

Asn Gly Lys Asn Ile Asp Ile Ala Thr Ser Met Thr Pro Gln Phe Ser
        435                 440                 445

Ser Val Ser Leu Gly Ala Gly Ala Asp Ala Pro Thr Leu Ser Val Asp
    450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
            500                 505                 510

Val Asp Gly Asn Ala Arg Ala Gly Ile Ala Gln Ala Ile Ala Thr Ala
        515                 520                 525

Gly Leu Val Gln Ala Tyr Leu Pro Gly Lys Ser Met Met Ala Ile Gly
    530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
            580                 585                 590

<210> SEQ ID NO 5
<211> LENGTH: 1779
<212> TYPE: DNA
<213> ORGANISM: Neisseria meningitidis
<220> FEATURE:
<221> NAME/KEY: misc_feature
<222> LOCATION: (48)
<223> OTHER INFORMATION: any nucleotide
<220> FEATURE:
<221> NAME/KEY: misc_feature
<222> LOCATION: (420)
<223> OTHER INFORMATION: any nucleotide
<220> FEATURE:
<221> NAME/KEY: misc_feature
<222> LOCATION: (608)
<223> OTHER INFORMATION: any nucleotide
<220> FEATURE:
<221> NAME/KEY: misc_feature
<222> LOCATION: (682)..(684)
<223> OTHER INFORMATION: any nucleotide
<220> FEATURE:
<221> NAME/KEY: misc_feature
<222> LOCATION: (763)
<223> OTHER INFORMATION: any nucleotide
<220> FEATURE:
<221> NAME/KEY: misc_feature
<222> LOCATION: (774)
<223> OTHER INFORMATION: any nucleotide
<220> FEATURE:
<221> NAME/KEY: misc_feature
```

```
<222> LOCATION: (1473)
<223> OTHER INFORMATION: any nucleotide
<220> FEATURE:
<221> NAME/KEY: misc_feature
<222> LOCATION: (1492)
<223> OTHER INFORMATION: any nucleotide
<220> FEATURE:
<221> NAME/KEY: misc_feature
<222> LOCATION: (1560)
<223> OTHER INFORMATION: any nucleotide

<400> SEQUENCE: 5
atgaacaaaa tataccgcat catttggaat agtgccctca atgcctgngt cgccgtatcc      60
gagctcacac gcaaccacac caaacgcgcc tccgcaaccg tgaagaccgc cgtattggcg     120
acactgttgt ttgcaacggt tcaggcgaat gctaccgatg aagatgaaga agaagagtta     180
gaatccgtac aacgctctgt cgtagggagc attcaagcca gtatggaagg cagcggcgaa     240
ttggaaacga tatcattatc aatgactaac gacagcaagg aatttgtaga cccatacata     300
gtagttaccc tcaaagccgg cgacaacctg aaaatcaaac aaaacaccaa tgaaaacacc     360
aatgccagta gcttcaccta ctcgctgaaa aagacctca caggcctgat caatgttgan     420
actgaaaaat tatcgtttgg cgcaaacggc aagaaagtca acatcataag cgacaccaaa     480
ggcttgaatt tcgcgaaaga aacggctggg acgaacggcg acaccacggt tcatctgaac     540
ggtatcggtt cgactttgac cgatacgctt gcgggttctt ctgcttctca cgttgatgcg     600
ggtaaccnaa gtacacatta cactcgtgca gcaagtatta aggatgtgtt gaatgcgggt     660
tggaatatta agggtgttaa annnggctca acaactggtc aatcagaaaa tgtcgatttc     720
gtccgcactt acgacacagt cgagttcttg agcgcagata cgnaaacaac gacngttaat     780
gtggaaagca agacaacgg caagagaacc gaagttaaaa tcggtgcgaa gacttctgtt     840
attaaagaaa aagacggtaa gttggttact ggtaaaggca aggcgagaa tggttcttct     900
acagacgaag gcgaaggctt agtgactgca aagaagtga ttgatgcagt aaacaaggct     960
ggttggagaa tgaaaacaac aaccgctaat ggtcaaacag gtcaagctga caagtttgaa    1020
accgttacat caggcacaaa tgtaaccttt gctagtggta aggtacaac tgcgactgta    1080
agtaaagatg atcaaggcaa catcactgtt atgtatgatg taaatgtcgg cgatgcccta    1140
aacgtcaatc agctgcaaaa cagcggttgg aatttggatt ccaaagcggt tgcaggttct    1200
tcgggcaaag tcatcagcgg caatgtttcg ccgagcaagg gaaagatgga tgaaaccgtc    1260
aacattaatg ccggcaacaa catcgagatt agccgcaacg gtaaaaatat cgacatcgcc    1320
acttcgatgg cgccgcagtt ttccagcgtt tcgctcggcg cggggggcaga tgcgcccact    1380
ttaagcgtgg atgacgaggg cgcgttgaat gtcggcagca aggatgccaa caaacccgtc    1440
cgcattacca atgtcgcccc gggcgttaaa gangggggatg ttacaaacgt cncacaactt    1500
aaaggcgtgg cgcaaaactt gaacaaccgc atcgacaatg tggacggcaa cgcgcgtgcn    1560
ggcatcgccc aagcgattgc aaccgcaggt ctggttcagg cgtatctgcc cggcaagagt    1620
atgatggcga tcggcggcgg cacttatcgc ggcgaagccg gttacgccat cggctactcc    1680
agtatttccg acggcggaaa ttggattatc aaaggcacgg cttccggcaa ttcgcgcggc    1740
catttcggtg cttccgcatc tgtcggttat cagtggtaa                           1779

<210> SEQ ID NO 6
<211> LENGTH: 592
<212> TYPE: PRT
<213> ORGANISM: Neisseria meningitidis
<220> FEATURE:
```

```
<221> NAME/KEY: SITE
<222> LOCATION: (16)
<223> OTHER INFORMATION: unknown
<220> FEATURE:
<221> NAME/KEY: SITE
<222> LOCATION: (140)
<223> OTHER INFORMATION: unknown
<220> FEATURE:
<221> NAME/KEY: SITE
<222> LOCATION: (203)
<223> OTHER INFORMATION: unknown
<220> FEATURE:
<221> NAME/KEY: SITE
<222> LOCATION: (228)
<223> OTHER INFORMATION: unknown
<220> FEATURE:
<221> NAME/KEY: SITE
<222> LOCATION: (255)
<223> OTHER INFORMATION: unknown
<220> FEATURE:
<221> NAME/KEY: SITE
<222> LOCATION: (491)
<223> OTHER INFORMATION: unknown
<220> FEATURE:
<221> NAME/KEY: SITE
<222> LOCATION: (498)
<223> OTHER INFORMATION: unknown

<400> SEQUENCE: 6
```

Met Asn Lys Ile Tyr Arg Ile Ile Trp Asn Ser Ala Leu Asn Ala Xaa
 1               5                  10                  15

Val Ala Val Ser Glu Leu Thr Arg Asn His Thr Lys Arg Ala Ser Ala
                20                  25                  30

Thr Val Lys Thr Ala Val Leu Ala Thr Leu Phe Ala Thr Val Gln
            35                  40                  45

Ala Asn Ala Thr Asp Glu Asp Glu Glu Leu Glu Ser Val Gln
        50                  55                  60

Arg Ser Val Val Gly Ser Ile Gln Ala Ser Met Glu Gly Ser Gly Glu
 65                  70                  75                  80

Leu Glu Thr Ile Ser Leu Ser Met Thr Asn Asp Ser Lys Glu Phe Val
                85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
        115                 120                 125

Leu Lys Lys Asp Leu Thr Gly Leu Ile Asn Val Xaa Thr Glu Lys Leu
130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Ala Gly
            180                 185                 190

Ser Ser Ala Ser His Val Asp Ala Gly Asn Xaa Ser Thr His Tyr Thr
        195                 200                 205

Arg Ala Ala Ser Ile Lys Asp Val Leu Asn Ala Gly Trp Asn Ile Lys
210                 215                 220

Gly Val Lys Xaa Gly Ser Thr Thr Gly Gln Ser Glu Asn Val Asp Phe
225                 230                 235                 240

Val Arg Thr Tyr Asp Thr Val Glu Phe Leu Ser Ala Asp Thr Xaa Thr
                245                 250                 255

Thr Thr Val Asn Val Glu Ser Lys Asp Asn Gly Lys Arg Thr Glu Val

```
                260                 265                 270
Lys Ile Gly Ala Lys Thr Ser Val Ile Lys Glu Lys Asp Gly Lys Leu
            275                 280                 285
Val Thr Gly Lys Gly Lys Gly Glu Asn Gly Ser Ser Thr Asp Glu Gly
        290                 295                 300
Glu Gly Leu Val Thr Ala Lys Glu Val Ile Asp Ala Val Asn Lys Ala
305                 310                 315                 320
Gly Trp Arg Met Lys Thr Thr Ala Asn Gly Gln Thr Gly Gln Ala
            325                 330                 335
Asp Lys Phe Glu Thr Val Thr Ser Gly Thr Asn Val Thr Phe Ala Ser
        340                 345                 350
Gly Lys Gly Thr Thr Ala Thr Val Ser Lys Asp Asp Gln Gly Asn Ile
            355                 360                 365
Thr Val Met Tyr Asp Val Asn Val Gly Asp Ala Leu Asn Val Asn Gln
        370                 375                 380
Leu Gln Asn Ser Gly Trp Asn Leu Asp Ser Lys Ala Val Ala Gly Ser
385                 390                 395                 400
Ser Gly Lys Val Ile Ser Gly Asn Val Ser Pro Ser Lys Gly Lys Met
            405                 410                 415
Asp Glu Thr Val Asn Ile Asn Ala Gly Asn Asn Ile Glu Ile Ser Arg
        420                 425                 430
Asn Gly Lys Asn Ile Asp Ile Ala Thr Ser Met Ala Pro Gln Phe Ser
435                 440                 445
Ser Val Ser Leu Gly Ala Gly Ala Asp Ala Pro Thr Leu Ser Val Asp
    450                 455                 460
Asp Glu Gly Ala Leu Asn Val Gly Ser Lys Asp Ala Asn Lys Pro Val
465                 470                 475                 480
Arg Ile Thr Asn Val Ala Pro Gly Val Lys Xaa Gly Asp Val Thr Asn
            485                 490                 495
Val Xaa Gln Leu Lys Gly Val Ala Gln Asn Leu Asn Asn Arg Ile Asp
        500                 505                 510
Asn Val Asp Gly Asn Ala Arg Ala Gly Ile Ala Gln Ala Ile Ala Thr
        515                 520                 525
Ala Gly Leu Val Gln Ala Tyr Leu Pro Gly Lys Ser Met Met Ala Ile
    530                 535                 540
Gly Gly Gly Thr Tyr Arg Gly Glu Ala Gly Tyr Ala Ile Gly Tyr Ser
545                 550                 555                 560
Ser Ile Ser Asp Gly Gly Asn Trp Ile Ile Lys Gly Thr Ala Ser Gly
            565                 570                 575
Asn Ser Arg Gly His Phe Gly Ala Ser Ala Ser Val Gly Tyr Gln Trp
        580                 585                 590

<210> SEQ ID NO 7
<211> LENGTH: 492
<212> TYPE: DNA
<213> ORGANISM: Neisseria meningitidis

<400> SEQUENCE: 7
atgttacgtt tgactgcttt agccgtatgc accgccctcg ctttgggcgc gtgttcgccg      60
caaaattccg actctgcccc acaagccaaa gaacaggcgg tttccgccgc acaaaccgaa     120
ggcgcgtccg ttaccgtcaa aaccgcgcgc ggcgacgttc aaataccgca aaaccccgaa     180
cgcatcgccg tttacgattt gggtatgctc gacaccttga gcaaactggg cgtgaaaacc     240
ggtttgtccg tcgataaaaa ccgcctgccg tatttagagg aatatttcaa aacgacaaaa     300
```

```
cctgccggca ctttgttcga gccggattac gaaacgctca acgcttacaa accgcagctc    360
atcatcatcg gcagccgcgc cgccaaggcg tttgacaaat tgaacgaaat cgcgccgacc    420
atcgrmwtga ccgccgatac cgccaacctc aaagaaagtg ccaargaggc atcgacgctg    480
gcgcaaatct tc                                                        492
```

```
<210> SEQ ID NO 8
<211> LENGTH: 164
<212> TYPE: PRT
<213> ORGANISM: Neisseria meningitidis
<220> FEATURE:
<221> NAME/KEY: SITE
<222> LOCATION: (142)..(143)
<223> OTHER INFORMATION: unknown

<400> SEQUENCE: 8
```

```
Met Leu Arg Leu Thr Ala Leu Ala Val Cys Thr Ala Leu Ala Leu Gly
 1               5                  10                  15

Ala Cys Ser Pro Gln Asn Ser Asp Ser Ala Pro Gln Ala Lys Glu Gln
            20                  25                  30

Ala Val Ser Ala Ala Gln Thr Glu Gly Ala Ser Val Thr Val Lys Thr
        35                  40                  45

Ala Arg Gly Asp Val Gln Ile Pro Gln Asn Pro Glu Arg Ile Ala Val
    50                  55                  60

Tyr Asp Leu Gly Met Leu Asp Thr Leu Ser Lys Leu Gly Val Lys Thr
65                  70                  75                  80

Gly Leu Ser Val Asp Lys Asn Arg Leu Pro Tyr Leu Glu Glu Tyr Phe
                85                  90                  95

Lys Thr Thr Lys Pro Ala Gly Thr Leu Phe Glu Pro Asp Tyr Glu Thr
            100                 105                 110

Leu Asn Ala Tyr Lys Pro Gln Leu Ile Ile Ile Gly Ser Arg Ala Ala
        115                 120                 125

Lys Ala Phe Asp Lys Leu Asn Glu Ile Ala Pro Thr Ile Xaa Xaa Thr
    130                 135                 140

Ala Asp Thr Ala Asn Leu Lys Glu Ser Ala Lys Glu Ala Ser Thr Leu
145                 150                 155                 160

Ala Gln Ile Phe
```

```
<210> SEQ ID NO 9
<211> LENGTH: 966
<212> TYPE: DNA
<213> ORGANISM: Neisseria meningitidis

<400> SEQUENCE: 9
atgttacgtt tgactgcttt agccgtatgc accgccctcg ctttgggcgc gtgttcgccg     60
caaaattccg actctgcccc acaagccaaa gaacaggcgg tttccgccgc acaaccgaa    120 ggcgcgtccg ttaccgtcaa aaccgcgcgc ggcgacgttc aaataccgca aaaccccgaa    180
cgcatcgccg tttacgattt gggtatgctc gacaccttga gcaaactggg cgtgaaaacc    240
ggtttgtccg tcgataaaaa ccgcctgccg tatttagagg aatatttcaa aacgacaaaa    300
cctgccggca ctttgttcga gccggattac gaaacgctca acgcttacaa accgcagctc    360
atcatcatcg gcagccgcgc cgccaaggcg tttgacaaat tgaacgaaat cgcgccgacc    420
atcgaaatga ccgccgatac cgccaacctc aaagaaagtg ccaaagagcg catcgacgcg    480
ctggcgcaaa tcttcggcaa acaggcggaa gccgacaagc tgaaggcgga aatcgacgcg    540
```

```
tcttttgaag ccgcgaaaac tgccgcacaa ggtaagggca aaggtttggt gattttggtc    600
aacggcggca agatgtcggc tttcggcccg tcttcacgct gggcggctg gctgcacaaa    660 gacatcggcg ttcccgctgt cgatgaatca attaaagaag gcagccacgg tcagcctatc    720
agctttgaat acctgaaaga gaaaaatccc gactggctgt ttgtccttga ccgaagcgcg    780
gccatcggcg aagagggtca ggcggcgaaa gacgtgttgg ataatccgct ggttgccgaa    840
acaaccgctt ggaaaaaagg acaggtcgtg tacctcgttc ctgaaactta tttggcagcc    900
ggtggcgcgc aagagctgct gaatgcaagc aaacaggttg ccgacgcttt taacgcggca    960
aaataa                                                                966

<210> SEQ ID NO 10
<211> LENGTH: 321
<212> TYPE: PRT
<213> ORGANISM: Neisseria meningitidis

<400> SEQUENCE: 10
```

Met Leu Arg Leu Thr Ala Leu Ala Val Cys Thr Ala Leu Ala Leu Gly
1               5                   10                  15

Ala Cys Ser Pro Gln Asn Ser Asp Ser Ala Pro Gln Ala Lys Glu Gln
            20                  25                  30

Ala Val Ser Ala Ala Gln Thr Glu Gly Ala Ser Val Thr Val Lys Thr
        35                  40                  45

Ala Arg Gly Asp Val Gln Ile Pro Gln Asn Pro Glu Arg Ile Ala Val
    50                  55                  60

Tyr Asp Leu Gly Met Leu Asp Thr Leu Ser Lys Leu Gly Val Lys Thr
65                  70                  75                  80

Gly Leu Ser Val Asp Lys Asn Arg Leu Pro Tyr Leu Glu Glu Tyr Phe
                85                  90                  95

Lys Thr Thr Lys Pro Ala Gly Thr Leu Phe Glu Pro Asp Tyr Glu Thr
            100                 105                 110

Leu Asn Ala Tyr Lys Pro Gln Leu Ile Ile Ile Gly Ser Arg Ala Ala
        115                 120                 125

Lys Ala Phe Asp Lys Leu Asn Glu Ile Ala Pro Thr Ile Glu Met Thr
    130                 135                 140

Ala Asp Thr Ala Asn Leu Lys Glu Ser Ala Lys Glu Arg Ile Asp Ala
145                 150                 155                 160

Leu Ala Gln Ile Phe Gly Lys Gln Ala Glu Ala Asp Lys Leu Lys Ala
                165                 170                 175

Glu Ile Asp Ala Ser Phe Glu Ala Ala Lys Thr Ala Ala Gln Gly Lys
            180                 185                 190

Gly Lys Gly Leu Val Ile Leu Val Asn Gly Gly Lys Met Ser Ala Phe
        195                 200                 205

Gly Pro Ser Ser Arg Leu Gly Gly Trp Leu His Lys Asp Ile Gly Val
    210                 215                 220

Pro Ala Val Asp Glu Ser Ile Lys Glu Gly Ser His Gly Gln Pro Ile
225                 230                 235                 240

Ser Phe Glu Tyr Leu Lys Glu Lys Asn Pro Asp Trp Leu Phe Val Leu
                245                 250                 255

Asp Arg Ser Ala Ala Ile Gly Glu Glu Gly Gln Ala Ala Lys Asp Val
            260                 265                 270

Leu Asp Asn Pro Leu Val Ala Glu Thr Thr Ala Trp Lys Lys Gly Gln
        275                 280                 285

Val Val Tyr Leu Val Pro Glu Thr Tyr Leu Ala Ala Gly Gly Ala Gln

```
                        290                 295                 300
Glu Leu Leu Asn Ala Ser Lys Gln Val Ala Asp Ala Phe Asn Ala Ala
305                 310                 315                 320

Lys

<210> SEQ ID NO 11
<211> LENGTH: 966
<212> TYPE: DNA
<213> ORGANISM: Neisseria meningitidis

<400> SEQUENCE: 11
atgttacgtt tgactgcttt agccgtatgc accgccctcg ctttgggcgc gtgttcgccg      60
caaaattccg actctgcccc acaagccaaa gaacaggcgg tttccgccgc acaatccgaa     120
ggcgtgtccg ttaccgtcaa acggcgcgc ggcgatgttc aaataccgca aaccccgaa      180 cgtatcgccg tttacgattt gggtatgctc gacaccttga gcaaactggg cgtgaaaacc     240
ggtttgtccg tcgataaaaa ccgcctgccg tatttagagg aatatttcaa aacgacaaaa     300
cctgccggaa ctttgttcga gccggattac gaaacgctca acgcttacaa accgcagctc     360
atcatcatcg gcagccgcgc agccaaagcg tttgacaaat gaacgaaat cgcgccgacc     420 atcgaaatga ccgccgatac cgccaacctc aaagaaagtg ccaaagagcg tatcgacgcg     480
ctggcgcaaa tcttcggcaa aaaggcggaa gccgacaagc tgaaggcgga aatcgacgcg     540
tcttttgaag ccgcgaaaac tgccgcgcaa ggcaaaggca agggtttggt gattttggtc     600
aacggcggca agatgtccgc cttcggcccg tcttcacgac tgggcggctg gctgcacaaa     660
gacatcggcg ttcccgctgt tgacgaagcc atcaaagaag gcagccacgg tcagcctatc     720
agctttgaat acctgaaaga gaaaaatccc gactggctgt tgtccttga ccgcagcgcg     780 gccatcggcg aagagggtca ggcggcgaaa gacgtgttga caatccgct ggttgccgaa     840 acaaccgctt ggaaaaaagg acaagtcgtt taccttgttc ctgaaactta tttggcagcc     900
ggtggcgcgc aagagctact gaatgcaagc aaacaggttg ccgacgcttt taacgcggca     960
aaataa                                                                 966

<210> SEQ ID NO 12
<211> LENGTH: 321
<212> TYPE: PRT
<213> ORGANISM: Neisseria meningitidis

<400> SEQUENCE: 12

Met Leu Arg Leu Thr Ala Leu Ala Val Cys Thr Ala Leu Ala Leu Gly
1               5                   10                  15

Ala Cys Ser Pro Gln Asn Ser Asp Ser Ala Pro Gln Ala Lys Glu Gln
                20                  25                  30

Ala Val Ser Ala Ala Gln Ser Glu Gly Val Ser Val Thr Val Lys Thr
            35                  40                  45

Ala Arg Gly Asp Val Gln Ile Pro Gln Asn Pro Glu Arg Ile Ala Val
        50                  55                  60

Tyr Asp Leu Gly Met Leu Asp Thr Leu Ser Lys Leu Gly Val Lys Thr
65                  70                  75                  80

Gly Leu Ser Val Asp Lys Asn Arg Leu Pro Tyr Leu Glu Glu Tyr Phe
                85                  90                  95

Lys Thr Thr Lys Pro Ala Gly Thr Leu Phe Glu Pro Asp Tyr Glu Thr
                100                 105                 110

Leu Asn Ala Tyr Lys Pro Gln Leu Ile Ile Ile Gly Ser Arg Ala Ala
```

-continued

```
                115                 120                 125
Lys Ala Phe Asp Lys Leu Asn Glu Ile Ala Pro Thr Ile Glu Met Thr
    130                 135                 140

Ala Asp Thr Ala Asn Leu Lys Glu Ser Ala Lys Glu Arg Ile Asp Ala
145                 150                 155                 160

Leu Ala Gln Ile Phe Gly Lys Lys Ala Glu Ala Asp Lys Leu Lys Ala
                165                 170                 175

Glu Ile Asp Ala Ser Phe Glu Ala Ala Lys Thr Ala Ala Gln Gly Lys
            180                 185                 190

Gly Lys Gly Leu Val Ile Leu Val Asn Gly Gly Lys Met Ser Ala Phe
        195                 200                 205

Gly Pro Ser Ser Arg Leu Gly Gly Trp Leu His Lys Asp Ile Gly Val
    210                 215                 220

Pro Ala Val Asp Glu Ala Ile Lys Glu Gly Ser His Gly Gln Pro Ile
225                 230                 235                 240

Ser Phe Glu Tyr Leu Lys Glu Lys Asn Pro Asp Trp Leu Phe Val Leu
                245                 250                 255

Asp Arg Ser Ala Ala Ile Gly Glu Glu Gly Gln Ala Ala Lys Asp Val
            260                 265                 270

Leu Asn Asn Pro Leu Val Ala Glu Thr Thr Ala Trp Lys Lys Gly Gln
        275                 280                 285

Val Val Tyr Leu Val Pro Glu Thr Tyr Leu Ala Ala Gly Gly Ala Gln
    290                 295                 300

Glu Leu Leu Asn Ala Ser Lys Gln Val Ala Asp Ala Phe Asn Ala Ala
305                 310                 315                 320

Lys
```

```
<210> SEQ ID NO 13
<211> LENGTH: 375
<212> TYPE: DNA
<213> ORGANISM: Neisseria meningitidis

<400> SEQUENCE: 13
atgaaacttc tgaccaccgc aatcctgtct ccgcaatcg cgctcagcag tatggctgcc        60
gccgctggca cggacaaccc cactgttgca aaaaaaaccg tcagctacgt ctgccagcaa      120
ggtaaaaaag tcaaagtaac ctacggcttc aacaaacagg gtctgaccac atacgcttcc      180
gccgtcatca acggcaaacg cgtgcaaatg cctgtcaatt tggacaaatc cgacaatgtg      240
gaaacattct acggcaaaga aggcggttat gttttgggta ccggcgtgat ggatggcaaa      300
tcctaccgca aacagcccat tatgattacc gcacctgaca accaaatcgt cttcaaagac      360
tgttccccac gttaa                                                        375
```

```
<210> SEQ ID NO 14
<211> LENGTH: 124
<212> TYPE: PRT
<213> ORGANISM: Neisseria meningitidis

<400> SEQUENCE: 14

Met Lys Leu Leu Thr Thr Ala Ile Leu Ser Ala Ile Ala Leu Ser
1               5                   10                  15

Ser Met Ala Ala Ala Gly Thr Asp Asn Pro Thr Val Ala Lys Lys
            20                  25                  30

Thr Val Ser Tyr Val Cys Gln Gln Gly Lys Lys Val Lys Val Thr Tyr
        35                  40                  45
```

```
Gly Phe Asn Lys Gln Gly Leu Thr Thr Tyr Ala Ser Ala Val Ile Asn
    50                  55                  60

Gly Lys Arg Val Gln Met Pro Val Asn Leu Asp Lys Ser Asp Asn Val
65                  70                  75                  80

Glu Thr Phe Tyr Gly Lys Glu Gly Gly Tyr Val Leu Gly Thr Gly Val
                85                  90                  95

Met Asp Gly Lys Ser Tyr Arg Lys Gln Pro Ile Met Ile Thr Ala Pro
            100                 105                 110

Asp Asn Gln Ile Val Phe Lys Asp Cys Ser Pro Arg
            115                 120
```

<210> SEQ ID NO 15
<211> LENGTH: 375
<212> TYPE: DNA
<213> ORGANISM: Neisseria meningitidis

<400> SEQUENCE: 15

```
atgaaacttc tgaccaccgc aatcctgtct tccgcaatcg cgctcagcag tatggctgct    60
gctgccggca cgaacaaccc caccgttgcc aaaaaaaccg tcagctacgt ctgccagcaa   120
ggtaaaaaag tcaaagtaac ctacggcttt aacaaacagg gcctgaccac atacgcttcc   180
gccgtcatca cggcaaacg tgtgcaaatg cctgtcaatt tggacaaatc cgacaatgtg   240
gaaacattct acggcaaaga aggcggttat gttttgggta ccggcgtgat ggatggcaaa   300
tcctatcgca acagcctat tatgattacc gcacctgaca ccaaatcgt cttcaaagac   360
tgttccccac gttaa                                                   375
```

<210> SEQ ID NO 16
<211> LENGTH: 124
<212> TYPE: PRT
<213> ORGANISM: Neisseria meningitidis

<400> SEQUENCE: 16

```
Met Lys Leu Leu Thr Thr Ala Ile Leu Ser Ser Ala Ile Ala Leu Ser
1               5                   10                  15

Ser Met Ala Ala Ala Gly Thr Asn Asn Pro Thr Val Ala Lys Lys
            20                  25                  30

Thr Val Ser Tyr Val Cys Gln Gln Gly Lys Lys Val Lys Val Thr Tyr
        35                  40                  45

Gly Phe Asn Lys Gln Gly Leu Thr Thr Tyr Ala Ser Ala Val Ile Asn
    50                  55                  60

Gly Lys Arg Val Gln Met Pro Val Asn Leu Asp Lys Ser Asp Asn Val
65                  70                  75                  80

Glu Thr Phe Tyr Gly Lys Glu Gly Gly Tyr Val Leu Gly Thr Gly Val
                85                  90                  95

Met Asp Gly Lys Ser Tyr Arg Lys Gln Pro Ile Met Ile Thr Ala Pro
            100                 105                 110

Asp Asn Gln Ile Val Phe Lys Asp Cys Ser Pro Arg
            115                 120
```

<210> SEQ ID NO 17
<211> LENGTH: 519
<212> TYPE: DNA
<213> ORGANISM: Neisseria meningitidis
<220> FEATURE:
<221> NAME/KEY: misc_feature
<222> LOCATION: (425)
<223> OTHER INFORMATION: any nucleotide
<220> FEATURE:

```
<221> NAME/KEY: misc_feature
<222> LOCATION: (485)
<223> OTHER INFORMATION: any nucleotide
<220> FEATURE:
<221> NAME/KEY: misc_feature
<222> LOCATION: (489)
<223> OTHER INFORMATION: any nucleotide

<400> SEQUENCE: 17
ggcaccgaat tcaaaaccac cctttccgga gccgacatac aggcaggggt gggtgaaaaa        60
gcccgagccg atgcgaaaat tatcctaaaa ggcatcgtta accgcatcca aaccgaagaa       120
aagctggaat ccaactcgac cgtatggcaa aagcaggccg aagcggcag cacgttgaa         180 acgctgaagc taccgagctt tgaagggccg gcactgccta agctgaccgc tcccggcggc       240
tatatcgccg acatccccaa aggcaacctc aaaaccgaaa tcgaaaagct ggccaaacag       300
cccgaatatg cctatctgaa acagcttcag acggtcaagg acgtgaactg gaaccaagta       360
cagctcgctt acgacaaatg ggactataaa caggaaggcc taaccggagc cggagccgca       420
attancgcac tggccgttac cgtggtcacc tcaggcgcag gaaccggagc cgtattggga       480
ttaanacgng tggccgccgc cgcaaccgat gcagcattt                              519

<210> SEQ ID NO 18
<211> LENGTH: 173
<212> TYPE: PRT
<213> ORGANISM: Neisseria meningitidis
<220> FEATURE:
<221> NAME/KEY: SITE
<222> LOCATION: (142)
<223> OTHER INFORMATION: unknown
<220> FEATURE:
<221> NAME/KEY: SITE
<222> LOCATION: (162)
<223> OTHER INFORMATION: unknown

<400> SEQUENCE: 18

Gly Thr Glu Phe Lys Thr Thr Leu Ser Gly Ala Asp Ile Gln Ala Gly
  1               5                  10                  15

Val Gly Glu Lys Ala Arg Ala Asp Ala Lys Ile Ile Leu Lys Gly Ile
             20                  25                  30

Val Asn Arg Ile Gln Thr Glu Glu Lys Leu Glu Ser Asn Ser Thr Val
         35                  40                  45

Trp Gln Lys Gln Ala Gly Ser Gly Ser Thr Val Glu Thr Leu Lys Leu
     50                  55                  60

Pro Ser Phe Glu Gly Pro Ala Leu Pro Lys Leu Thr Ala Pro Gly Gly
 65                  70                  75                  80

Tyr Ile Ala Asp Ile Pro Lys Gly Asn Leu Lys Thr Glu Ile Glu Lys
                 85                  90                  95

Leu Ala Lys Gln Pro Glu Tyr Ala Tyr Leu Lys Gln Leu Gln Thr Val
            100                 105                 110

Lys Asp Val Asn Trp Asn Gln Val Gln Leu Ala Tyr Asp Lys Trp Asp
        115                 120                 125

Tyr Lys Gln Glu Gly Leu Thr Gly Ala Gly Ala Ile Xaa Ala Leu
    130                 135                 140

Ala Val Thr Val Val Thr Ser Gly Ala Gly Thr Gly Ala Val Leu Gly
145                 150                 155                 160

Leu Xaa Arg Val Ala Ala Ala Thr Asp Ala Ala Phe
                165                 170

<210> SEQ ID NO 19
```

-continued

<211> LENGTH: 1923
<212> TYPE: DNA
<213> ORGANISM: Neisseria meningitidis

<400> SEQUENCE: 19

```
atgcaactgc tggcagccga aggcattcac caacaccaat tgaatgttca gaaaagtacc     60
cgtttcatcg gcatcaaagt gggtaaaagc aattacagca aaaacgagct gaacgaaacc    120
aaactgcccg tacgcgttat cgcccaaaca gccaaaaccc gttccggctg ggataccgta    180
ctcgaaggca ccgaattcaa aaccaccctt tccggagccg acatacaggc aggggtgggt    240
gaaaaagccc gagccgatgc gaaaattatc ctaaaaggca tcgttaaccg catccaaacc    300
gaagaaaagc tggaatccaa ctcgaccgta tggcaaaagc aggccggaag cggcagcacg    360
gttgaaacgc tgaagctacc gagctttgaa gggccggcac tgcctaagct gaccgctccc    420
ggcggctata tcgccgacat ccccaaaggc aacctcaaaa ccgaaatcga aaagctggcc    480
aaacagcccg aatatgccta tctgaaacag cttcagacgg tcaaggacgt gaactggaac    540
caagtacagc tcgcttacga caaatgggac tataaacagg aaggcctaac cggagccgga    600
gccgcaatta tcgcactggc cgttaccgtg gtcacctcag gcgcaggaac cggagccgta    660
ttgggattaa acggtgcggc cgccgccgca accgatgcag catttgcctc tttggccagc    720
caggcttccg tatcgttcat caacaacaaa ggcaatatcg gtaacaccct gaaagagctg    780
ggcagaagca gcacggtgaa aaatctgatg gttgccgtcg ctaccgcagg cgtagccgac    840
aaaatcggtg cttcggcact gaacaatgtc agcgataagc agtggatcaa caacctgacc    900
gtcaacctgg ccaatgcggg cagtgccgca ctgattaata ccgctgtcaa cggcggcagc    960
ctgaaagaca atctggaagc gaatatcctt gcggctttgg tgaatactgc gcatggagag   1020
gcagcaagta aaatcaaaca gttggatcag cactacattg cccataagat tgcccatgcc   1080
atagcgggct gtgcggcagc ggcggcgaat aagggcaagt gtcaagatgg tgcgatcggt   1140
gcggcggtcg gtgaaatcct tggcgaaacc ctactggacg gcagagaccc tggcagcctg   1200
aatgtgaagg acagggcaaa aatcattgct aaggcgaagc tggcagcagg ggcggttgcg   1260
gcgttgagta agggggatgt gagtacggcg gcgaatgcgg ctgctgtggc ggtagagaat   1320
aattctttaa atgatataca ggatcgtttg ttgagtggaa attatgcttt atgtatgagt   1380
gcaggaggag cagaaagctt ttgtgagtct tatcgaccac tgggcttgcc acactttgta   1440
agtgtttcag gagaaatgaa attacctaat aaattcggga atcgtatggt taatggaaaa   1500
ttaattatta acactagaaa tggcaatgta tatttctctg taggtaaaat atggagtact   1560
gtaaaatcaa caaaatcaaa tataagtggg gtatctgtcg gttgggtttt aaatgtttcc   1620
cctaatgatt atttaaaaga agcatctatg aatgatttca gaaatagtaa tcaaaataaa   1680
gcctatgcag aaatgatttc ccagactttg gtaggtgaga gtgttggtgg tagtctttgt   1740
ctgacaagag cctgcttttc ggtaagttca acaatatcta aatctaaatc tccttttaaa   1800
gattcaaaaa ttattgggga aatcggtttg ggaagtggtg ttgctgcagg agtagaaaaa   1860
acaatataca taggtaacat aaaagatatt gataaattta ttagtgcaaa cataaaaaaa   1920
tag                                                                 1923
```

<210> SEQ ID NO 20
<211> LENGTH: 640
<212> TYPE: PRT
<213> ORGANISM: Neisseria meningitidis

<400> SEQUENCE: 20

-continued

```
Met Gln Leu Leu Ala Ala Glu Gly Ile His Gln His Gln Leu Asn Val
  1               5                  10                  15

Gln Lys Ser Thr Arg Phe Ile Gly Ile Lys Val Gly Lys Ser Asn Tyr
             20                  25                  30

Ser Lys Asn Glu Leu Asn Glu Thr Lys Leu Pro Val Arg Val Ile Ala
         35                  40                  45

Gln Thr Ala Lys Thr Arg Ser Gly Trp Asp Thr Val Leu Glu Gly Thr
     50                  55                  60

Glu Phe Lys Thr Thr Leu Ser Gly Ala Asp Ile Gln Ala Gly Val Gly
 65                  70                  75                  80

Glu Lys Ala Arg Ala Asp Ala Lys Ile Ile Leu Lys Gly Ile Val Asn
                 85                  90                  95

Arg Ile Gln Thr Glu Glu Lys Leu Glu Ser Asn Ser Thr Val Trp Gln
                100                 105                 110

Lys Gln Ala Gly Ser Gly Ser Thr Val Glu Thr Leu Lys Leu Pro Ser
            115                 120                 125

Phe Glu Gly Pro Ala Leu Pro Lys Leu Thr Ala Pro Gly Gly Tyr Ile
        130                 135                 140

Ala Asp Ile Pro Lys Gly Asn Leu Lys Thr Glu Ile Glu Lys Leu Ala
145                 150                 155                 160

Lys Gln Pro Glu Tyr Ala Tyr Leu Lys Gln Leu Gln Thr Val Lys Asp
                165                 170                 175

Val Asn Trp Asn Gln Val Gln Leu Ala Tyr Asp Lys Trp Asp Tyr Lys
            180                 185                 190

Gln Glu Gly Leu Thr Gly Ala Gly Ala Ala Ile Ile Ala Leu Ala Val
        195                 200                 205

Thr Val Val Thr Ser Gly Ala Gly Thr Gly Ala Val Leu Gly Leu Asn
    210                 215                 220

Gly Ala Ala Ala Ala Thr Asp Ala Ala Phe Ala Ser Leu Ala Ser
225                 230                 235                 240

Gln Ala Ser Val Ser Phe Ile Asn Asn Lys Gly Asn Ile Gly Asn Thr
                245                 250                 255

Leu Lys Glu Leu Gly Arg Ser Ser Thr Val Lys Asn Leu Met Val Ala
            260                 265                 270

Val Ala Thr Ala Gly Val Ala Asp Lys Ile Gly Ala Ser Ala Leu Asn
        275                 280                 285

Asn Val Ser Asp Lys Gln Trp Ile Asn Asn Leu Thr Val Asn Leu Ala
    290                 295                 300

Asn Ala Gly Ser Ala Ala Leu Ile Asn Thr Ala Val Asn Gly Gly Ser
305                 310                 315                 320

Leu Lys Asp Asn Leu Glu Ala Asn Ile Leu Ala Ala Leu Val Asn Thr
                325                 330                 335

Ala His Gly Glu Ala Ala Ser Lys Ile Lys Gln Leu Asp Gln His Tyr
            340                 345                 350

Ile Ala His Lys Ile Ala His Ala Ile Ala Gly Cys Ala Ala Ala Ala
        355                 360                 365

Ala Asn Lys Gly Lys Cys Gln Asp Gly Ala Ile Gly Ala Ala Val Gly
    370                 375                 380

Glu Ile Leu Gly Glu Thr Leu Leu Asp Gly Arg Asp Pro Gly Ser Leu
385                 390                 395                 400

Asn Val Lys Asp Arg Ala Lys Ile Ile Ala Lys Ala Lys Leu Ala Ala
                405                 410                 415
```

-continued

```
Gly Ala Val Ala Ala Leu Ser Lys Gly Asp Val Ser Thr Ala Ala Asn
            420                 425                 430

Ala Ala Ala Val Ala Val Glu Asn Asn Ser Leu Asn Asp Ile Gln Asp
        435                 440                 445

Arg Leu Leu Ser Gly Asn Tyr Ala Leu Cys Met Ser Ala Gly Gly Ala
    450                 455                 460

Glu Ser Phe Cys Glu Ser Tyr Arg Pro Leu Gly Leu Pro His Phe Val
465                 470                 475                 480

Ser Val Ser Gly Glu Met Lys Leu Pro Asn Lys Phe Gly Asn Arg Met
                485                 490                 495

Val Asn Gly Lys Leu Ile Ile Asn Thr Arg Asn Gly Asn Val Tyr Phe
            500                 505                 510

Ser Val Gly Lys Ile Trp Ser Thr Val Lys Ser Thr Lys Ser Asn Ile
        515                 520                 525

Ser Gly Val Ser Val Gly Trp Val Leu Asn Val Ser Pro Asn Asp Tyr
    530                 535                 540

Leu Lys Glu Ala Ser Met Asn Asp Phe Arg Asn Ser Asn Gln Asn Lys
545                 550                 555                 560

Ala Tyr Ala Glu Met Ile Ser Gln Thr Leu Val Gly Glu Ser Val Gly
                565                 570                 575

Gly Ser Leu Cys Leu Thr Arg Ala Cys Phe Ser Val Ser Ser Thr Ile
            580                 585                 590

Ser Lys Ser Lys Ser Pro Phe Lys Asp Ser Lys Ile Ile Gly Glu Ile
        595                 600                 605

Gly Leu Gly Ser Gly Val Ala Ala Gly Val Glu Lys Thr Ile Tyr Ile
    610                 615                 620

Gly Asn Ile Lys Asp Ile Asp Lys Phe Ile Ser Ala Asn Ile Lys Lys
625                 630                 635                 640
```

<210> SEQ ID NO 21
<211> LENGTH: 2291
<212> TYPE: DNA
<213> ORGANISM: Neisseria meningitidis
<220> FEATURE:
<221> NAME/KEY: misc_feature
<222> LOCATION: (1)
<223> OTHER INFORMATION: any nucleotide
<220> FEATURE:
<221> NAME/KEY: misc_feature
<222> LOCATION: (85)
<223> OTHER INFORMATION: any nucleotide
<220> FEATURE:
<221> NAME/KEY: misc_feature
<222> LOCATION: (149)
<223> OTHER INFORMATION: any nucleotide
<220> FEATURE:
<221> NAME/KEY: misc_feature
<222> LOCATION: (238)
<223> OTHER INFORMATION: any nucleotide
<220> FEATURE:
<221> NAME/KEY: misc_feature
<222> LOCATION: (426)
<223> OTHER INFORMATION: any nucleotide
<220> FEATURE:
<221> NAME/KEY: misc_feature
<222> LOCATION: (679)
<223> OTHER INFORMATION: any nucleotide
<220> FEATURE:
<221> NAME/KEY: misc_feature
<222> LOCATION: (863)
<223> OTHER INFORMATION: any nucleotide
<220> FEATURE:
<221> NAME/KEY: misc_feature
<222> LOCATION: (971)
<223> OTHER INFORMATION: any nucleotide

```
<220> FEATURE:
<221> NAME/KEY: misc_feature
<222> LOCATION: (1336)
<223> OTHER INFORMATION: any nucleotide
<220> FEATURE:
<221> NAME/KEY: misc_feature
<222> LOCATION: (1388)
<223> OTHER INFORMATION: any nucleotide
<220> FEATURE:
<221> NAME/KEY: misc_feature
<222> LOCATION: (1837)
<223> OTHER INFORMATION: any nucleotide
<220> FEATURE:
<221> NAME/KEY: misc_feature
<222> LOCATION: (1909)
<223> OTHER INFORMATION: any nucleotide
<220> FEATURE:
<221> NAME/KEY: misc_feature
<222> LOCATION: (1939)
<223> OTHER INFORMATION: any nucleotide
<220> FEATURE:
<221> NAME/KEY: misc_feature
<222> LOCATION: (1941)
<223> OTHER INFORMATION: any nucleotide
<220> FEATURE:
<221> NAME/KEY: misc_feature
<222> LOCATION: (1959)
<223> OTHER INFORMATION: any nucleotide
<220> FEATURE:
<221> NAME/KEY: misc_feature
<222> LOCATION: (2079)
<223> OTHER INFORMATION: any nucleotide
<220> FEATURE:
<221> NAME/KEY: misc_feature
<222> LOCATION: (2084)..(2085)
<223> OTHER INFORMATION: any nucleotide
<220> FEATURE:
<221> NAME/KEY: misc_feature
<222> LOCATION: (2113)
<223> OTHER INFORMATION: any nucleotide
<220> FEATURE:
<221> NAME/KEY: misc_feature
<222> LOCATION: (2120)
<223> OTHER INFORMATION: any nucleotide
<220> FEATURE:
<221> NAME/KEY: misc_feature
<222> LOCATION: (2236)..(2238)
<223> OTHER INFORMATION: any nucleotide
<220> FEATURE:
<221> NAME/KEY: misc_feature
<222> LOCATION: (2242)
<223> OTHER INFORMATION: any nucleotide
<220> FEATURE:
<221> NAME/KEY: misc_feature
<222> LOCATION: (2244)
<223> OTHER INFORMATION: any nucleotide

<400> SEQUENCE: 21
ntgcaactgc tggcagaaga aggcatccac aagcacgagt tggatgtcca aaaaagccgc      60
cgctttatcg gcatcaaggt aggtnagagc aattacagta aaaacgaact gaacgaaacc     120
aaattgcctg tccgcgtcgt cgcccaaant gcagccaccc gttcaggctg ggataccgtg     180
ctcgaaggta ccgaattcaa aaccacgctg gccggtgccg acattcaggc aggtgtangc     240
gaaaaagccc gtgtcgatgc gaaaattatc ctcaaaggca ttgtgaaccg tatccagtcg     300
gaagaaaaat tagaaaccaa ctcaaccgta tggcagaaac aggccggacg cggcagcact     360
atcgaaacgc taaaactgcc cagcttcgaa agccctactc cgcccaaatt gtccgcaccc     420
ggcggntata tcgtcgacat tccgaaaggc aatctgaaaa ccgaaatcga aaagctgtcc     480
aaacagcccg agtatgccta tctgaaacag ctccaagtag cgaaaaacat caactggaat     540
caggtgcagc ttgcttacga cagatgggac tacaaacagg agggcttaac cgaagcaggt     600
```

```
gcggcgatta tcgcactggc cgttaccgtg gtcacctcag gcgcaggaac cggagccgta      660
ttgggattaa acggtgcgnc cgccgccgca accgatgcag cattcgcctc tttggccagc      720
caggcttccg tatcgttcat caacaacaaa ggcgatgtcg gcaaaaccct gaaagagctg      780
ggcagaagca gcacggtgaa aaatctggtg gttgccgccg ctaccgcagg cgtagccgac      840
aaaatcggcg cttcggcact gancaatgtc agcgataagc agtggatcaa caacctgacc      900
gtcaacctag ccaatgcggg cagtgccgca ctgattaata ccgctgtcaa cggcggcagc      960
ctgaaagaca ntctggaagc gaatatcctt gcggctttgg tcaataccgc gcatggagaa     1020
gcagccagta aaatcaaaca gttggatcag cactacatag tccacaagat tgcccatgcc     1080
atagcgggct gtgcggcagc ggcggcgaat aagggcaagt gtcaggatgg tgcgataggt     1140
gcggctgtgg gcgagatagt cggggaggct ttgacaaacg gcaaaaatcc tgacactttg     1200
acagctaaag aacgcgaaca gattttggca tacagcaaac tggttgccgg tacggtaagc     1260
ggtgtggtcg gcggcgatgt aaatgcgcg gcgaatgcgg ctgaggtagc ggtgaaaaat     1320
aatcagctta gcgacnaaga gggtagagaa tttgataacg aaatgactgc atgcgccaaa     1380
cagaatantc ctcaactgtg cagaaaaaat actgtaaaaa agtatcaaaa tgttgctgat     1440
aaaagacttg ctgcttcgat tgcaatatgt acggatatat cccgtagtac tgaatgtaga     1500
acaatcagaa acaacatttt gatcgatagt agaagccttc attcatcttg gaagcaggt     1560 ctaattggta aagatgatga atggtataaa ttattcagca aatcttacac ccaagcagat     1620
ttggctttac agtcttatca tttgaatact gctgctaaat cttggcttca atcgggcaat     1680
acaaagcctt tatccgaatg gatgtccgac caaggttata cacttatttc aggagttaat     1740
cctagattca ttccaatacc aagagggttt gtaaaacaaa atacacctat tactaatgtc     1800
aaatacccgg aaggcatcag tttcgataca aacctanaaa gacatctggc aaatgctgat     1860
ggttttagtc aagaacaggg cattaaagga gcccataacc gcaccaatnt tatggcagaa     1920
ctaaattcac gaggaggang ngtaaaatct gaaacccana ctgatattga aggcattacc     1980
cgaattaaat atgagattcc tacactagac aggacaggta aacctgatgg tggatttaag     2040
gaaatttcaa gtataaaaac tgtttataat cctaaaaant tttnngatga taaaatactt     2100
caaatggctc aanatgctgn ttcacaagga tattcaaaag cctctaaaat tgctcaaaat     2160
gaaagaacta atcaatatc ggaaagaaaa aatgtcattc aattctcaga aacctttgac     2220
ggaatcaaat ttagannnta tntngatgta aatacaggaa gaattacaaa cattcaccca     2280
gaataattta a                                                          2291
```

<210> SEQ ID NO 22
<211> LENGTH: 761
<212> TYPE: PRT
<213> ORGANISM: Neisseria meningitidis
<220> FEATURE:
<221> NAME/KEY: SITE
<222> LOCATION: (1)
<223> OTHER INFORMATION: unknown
<220> FEATURE:
<221> NAME/KEY: SITE
<222> LOCATION: (29)
<223> OTHER INFORMATION: unknown
<220> FEATURE:
<221> NAME/KEY: SITE
<222> LOCATION: (50)
<223> OTHER INFORMATION: unknown
<220> FEATURE:
<221> NAME/KEY: SITE
<222> LOCATION: (80)
<223> OTHER INFORMATION: unknown

```
<220> FEATURE:
<221> NAME/KEY: SITE
<222> LOCATION: (227)
<223> OTHER INFORMATION: unknown
<220> FEATURE:
<221> NAME/KEY: SITE
<222> LOCATION: (288)
<223> OTHER INFORMATION: unknown
<220> FEATURE:
<221> NAME/KEY: SITE
<222> LOCATION: (324)
<223> OTHER INFORMATION: unknown
<220> FEATURE:
<221> NAME/KEY: SITE
<222> LOCATION: (446)
<223> OTHER INFORMATION: unknown
<220> FEATURE:
<221> NAME/KEY: SITE
<222> LOCATION: (463)
<223> OTHER INFORMATION: unknown
<220> FEATURE:
<221> NAME/KEY: SITE
<222> LOCATION: (613)
<223> OTHER INFORMATION: unknown
<220> FEATURE:
<221> NAME/KEY: SITE
<222> LOCATION: (637)
<223> OTHER INFORMATION: unknown
<220> FEATURE:
<221> NAME/KEY: SITE
<222> LOCATION: (647)
<223> OTHER INFORMATION: unknown
<220> FEATURE:
<221> NAME/KEY: SITE
<222> LOCATION: (653)
<223> OTHER INFORMATION: unknown
<220> FEATURE:
<221> NAME/KEY: SITE
<222> LOCATION: (693)
<223> OTHER INFORMATION: unknown
<220> FEATURE:
<221> NAME/KEY: SITE
<222> LOCATION: (695)
<223> OTHER INFORMATION: unknown
<220> FEATURE:
<221> NAME/KEY: SITE
<222> LOCATION: (705)
<223> OTHER INFORMATION: unknown
<220> FEATURE:
<221> NAME/KEY: SITE
<222> LOCATION: (707)
<223> OTHER INFORMATION: unknown
<220> FEATURE:
<221> NAME/KEY: SITE
<222> LOCATION: (746)
<223> OTHER INFORMATION: unknown
<220> FEATURE:
<221> NAME/KEY: SITE
<222> LOCATION: (748)
<223> OTHER INFORMATION: unknown

<400> SEQUENCE: 22

Xaa Gln Leu Leu Ala Glu Glu Gly Ile His Lys His Glu Leu Asp Val
  1               5                  10                  15

Gln Lys Ser Arg Arg Phe Ile Gly Ile Lys Val Gly Xaa Ser Asn Tyr
             20                  25                  30

Ser Lys Asn Glu Leu Asn Glu Thr Lys Leu Pro Val Arg Val Val Ala
         35                  40                  45

Gln Xaa Ala Ala Thr Arg Ser Gly Trp Asp Thr Val Leu Glu Gly Thr
     50                  55                  60

Glu Phe Lys Thr Thr Leu Ala Gly Ala Asp Ile Gln Ala Gly Val Xaa
 65                  70                  75                  80

Glu Lys Ala Arg Val Asp Ala Lys Ile Ile Leu Lys Gly Ile Val Asn
```

-continued

```
                85                  90                  95
Arg Ile Gln Ser Glu Glu Lys Leu Glu Thr Asn Ser Thr Val Trp Gln
            100                 105                 110
Lys Gln Ala Gly Arg Gly Ser Thr Ile Glu Thr Leu Lys Leu Pro Ser
            115                 120                 125
Phe Glu Ser Pro Thr Pro Lys Leu Ser Ala Pro Gly Gly Tyr Ile
    130                 135                 140
Val Asp Ile Pro Lys Gly Asn Leu Lys Thr Glu Ile Glu Lys Leu Ser
145                 150                 155                 160
Lys Gln Pro Glu Tyr Ala Tyr Leu Lys Gln Leu Gln Val Ala Lys Asn
                165                 170                 175
Ile Asn Trp Asn Gln Val Gln Leu Ala Tyr Asp Arg Trp Asp Tyr Lys
            180                 185                 190
Gln Glu Gly Leu Thr Glu Ala Gly Ala Ile Ile Ala Leu Ala Val
                195                 200                 205
Thr Val Val Thr Ser Gly Ala Gly Thr Gly Ala Val Leu Gly Leu Asn
    210                 215                 220
Gly Ala Xaa Ala Ala Ala Thr Asp Ala Ala Phe Ala Ser Leu Ala Ser
225                 230                 235                 240
Gln Ala Ser Val Ser Phe Ile Asn Asn Lys Gly Asp Val Gly Lys Thr
                245                 250                 255
Leu Lys Glu Leu Gly Arg Ser Ser Thr Val Lys Asn Leu Val Val Ala
            260                 265                 270
Ala Ala Thr Ala Gly Val Ala Asp Lys Ile Gly Ala Ser Ala Leu Xaa
            275                 280                 285
Asn Val Ser Asp Lys Gln Trp Ile Asn Asn Leu Thr Val Asn Leu Ala
    290                 295                 300
Asn Ala Gly Ser Ala Ala Leu Ile Asn Thr Ala Val Asn Gly Gly Ser
305                 310                 315                 320
Leu Lys Asp Xaa Leu Glu Ala Asn Ile Leu Ala Ala Leu Val Asn Thr
                325                 330                 335
Ala His Gly Glu Ala Ala Ser Lys Ile Lys Gln Leu Asp Gln His Tyr
            340                 345                 350
Ile Val His Lys Ile Ala His Ala Ile Ala Gly Cys Ala Ala Ala Ala
            355                 360                 365
Ala Asn Lys Gly Lys Cys Gln Asp Gly Ala Ile Gly Ala Ala Val Gly
    370                 375                 380
Glu Ile Val Gly Glu Ala Leu Thr Asn Gly Lys Asn Pro Asp Thr Leu
385                 390                 395                 400
Thr Ala Lys Glu Arg Glu Gln Ile Leu Ala Tyr Ser Lys Leu Val Ala
                405                 410                 415
Gly Thr Val Ser Gly Val Val Gly Gly Asp Val Asn Ala Ala Ala Asn
            420                 425                 430
Ala Ala Glu Val Ala Val Lys Asn Asn Gln Leu Ser Asp Xaa Glu Gly
            435                 440                 445
Arg Glu Phe Asp Asn Glu Met Thr Ala Cys Ala Lys Gln Asn Xaa Pro
    450                 455                 460
Gln Leu Cys Arg Lys Asn Thr Val Lys Tyr Gln Asn Val Ala Asp
465                 470                 475                 480
Lys Arg Leu Ala Ala Ser Ile Ala Ile Cys Thr Asp Ile Ser Arg Ser
                485                 490                 495
Thr Glu Cys Arg Thr Ile Arg Lys Gln His Leu Ile Asp Ser Arg Ser
            500                 505                 510
```

Leu His Ser Ser Trp Glu Ala Gly Leu Ile Gly Lys Asp Asp Glu Trp
        515                 520                 525

Tyr Lys Leu Phe Ser Lys Ser Tyr Thr Gln Ala Asp Leu Ala Leu Gln
            530                 535                 540

Ser Tyr His Leu Asn Thr Ala Ala Lys Ser Trp Leu Gln Ser Gly Asn
545                 550                 555                 560

Thr Lys Pro Leu Ser Glu Trp Met Ser Asp Gln Gly Tyr Thr Leu Ile
                565                 570                 575

Ser Gly Val Asn Pro Arg Phe Ile Pro Ile Pro Arg Gly Phe Val Lys
            580                 585                 590

Gln Asn Thr Pro Ile Thr Asn Val Lys Tyr Pro Glu Gly Ile Ser Phe
        595                 600                 605

Asp Thr Asn Leu Xaa Arg His Leu Ala Asn Ala Asp Gly Phe Ser Gln
    610                 615                 620

Glu Gln Gly Ile Lys Gly Ala His Asn Arg Thr Asn Xaa Met Ala Glu
625                 630                 635                 640

Leu Asn Ser Arg Gly Gly Xaa Val Lys Ser Glu Thr Xaa Thr Asp Ile
                645                 650                 655

Glu Gly Ile Thr Arg Ile Lys Tyr Glu Ile Pro Thr Leu Asp Arg Thr
            660                 665                 670

Gly Lys Pro Asp Gly Gly Phe Lys Glu Ile Ser Ser Ile Lys Thr Val
        675                 680                 685

Tyr Asn Pro Lys Xaa Phe Xaa Asp Asp Lys Ile Leu Gln Met Ala Gln
    690                 695                 700

Xaa Ala Xaa Ser Gln Gly Tyr Ser Lys Ala Ser Lys Ile Ala Gln Asn
705                 710                 715                 720

Glu Arg Thr Lys Ser Ile Ser Glu Arg Lys Asn Val Ile Gln Phe Ser
                725                 730                 735

Glu Thr Phe Asp Gly Ile Lys Phe Arg Xaa Tyr Xaa Asp Val Asn Thr
            740                 745                 750

Gly Arg Ile Thr Asn Ile His Pro Glu
        755                 760

<210> SEQ ID NO 23
<211> LENGTH: 336
<212> TYPE: DNA
<213> ORGANISM: Neisseria meningitidis

<400> SEQUENCE: 23
cggatcgttg taggtttgcg gatttcttgc gccgtagtca ccgtagtccc aagtataacc      60
caaggctttg tcttcgcctt tcattccgat aagggatatg acgctttggt cggtatagcc     120
gtcttgggaa cctttgtcca cccaacgcat atctgcctgc ggattctcat gccgcttct     180 tggctgctga ttttctgcc ttcgcgtttt tcaacttcgc gcttgagggc ttcggcatat     240
ttgtcggcca acgccatttc tttcggatgc agctgcctat tgttccaatc tacattcgca     300
cccaccacag caccaccact accaccagtt gcatag                                336

<210> SEQ ID NO 24
<211> LENGTH: 111
<212> TYPE: PRT
<213> ORGANISM: Neisseria meningitidis

<400> SEQUENCE: 24

Arg Ile Val Val Gly Leu Arg Ile Ser Cys Ala Val Val Thr Val Val
1               5                   10                  15

```
Pro Ser Ile Thr Gln Gly Phe Val Phe Ala Phe His Ser Asp Lys Gly
            20                  25                  30

Tyr Asp Ala Leu Val Gly Ile Ala Val Leu Gly Thr Phe Val His Pro
        35                  40                  45

Thr His Ile Cys Leu Arg Ile Leu Ile Ala Ala Ser Trp Leu Leu Ile
    50                  55                  60

Phe Leu Pro Ser Arg Phe Ser Thr Ser Arg Leu Arg Ala Ser Ala Tyr
65                  70                  75                  80

Leu Ser Ala Asn Ala Ile Ser Phe Gly Cys Ser Cys Leu Leu Phe Gln
                85                  90                  95

Ser Thr Phe Ala Pro Thr Thr Ala Pro Pro Leu Pro Pro Val Ala
            100                 105                 110

<210> SEQ ID NO 25
<211> LENGTH: 1716
<212> TYPE: DNA
<213> ORGANISM: Neisseria meningitidis
<220> FEATURE:
<221> NAME/KEY: unsure
<222> LOCATION: (496)..(1542)
<223> OTHER INFORMATION: N = Unknown
<220> FEATURE:
<221> NAME/KEY: unsure
<222> LOCATION: (1673)..(1674)
<223> OTHER INFORMATION: N= Unknown

<400> SEQUENCE: 25
aagtttgact ttacctggtt tattccggcg gtaatcaaat accgccggtt gttttttgaa      60
gtattggtgg tgtcggtggt gttgcagctg tttgcgctga ttacgcctct gttttttccaa   120 gtggtgatgg acaaggtgct ggtacatcgg ggattctcta ctttggatgt ggtgtcggtg    180
gctttgttgg tggtgtcgct gtttgagatt gtgttgggcg gtttgcggac gtatctgttt    240
gcacatacga cttcacgtat tgatgtggaa ttgggcgcgc gtttgttccg gcatctgctt    300
tccctgcctt tatcctattt cgagcacaga cgagtgggtg atacggtggc tcgggtgcgg    360
gaattggagc agattcgcaa tttcttgacc ggtcaggcgc tgacttcggt gttggatttg    420
gcgttttcgt ttatctttct ggcggtgatg tggtattaca gctccactct gacttgggtg    480
gtattggctt cgttgnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnnnnnnnn nnnnnnnnnn nnnnnnnnnn nnnnnnnnnn   1260
nnnnnnnnnn nnnnnnnnnn nnnnnnnnnn nnnnnnnnnn nnnnnnnnnn nnnnnnnnnn   1320
```

```
nnnnnnnnnn nnnnnnnnnn nnnnnnnnnn nnnnnnnnnn nnnnnnnnnn nnnnnnnnnn   1380
nnnnnnnnnn nnnnnnnnnn nnnnnnnnnn nnnnnnnnnn nnnnnnnnnn nnnnnnnnnn   1440
nnnnnnnnnn nnnnnnnnnn nnnnnnnnnn nnnnnnnnnn nnnnnnnnnn nnnnnnnnnn   1500
nnnnnnnnnn nnnnnnnnnn nnnnnnnnnn nnnnnnnnnn nnatttgcgc caaccggacg   1560
gtgctgatta tcgcccaccg tctgtccact gttaaaacgg cacaccggat cattgccatg   1620
gataaaggca ggattgtgga agcgggaaca cagcaggaat tgctggcgaa cgnnaacgga   1680
tattaccgct atctgtatga tttacagaac gggtag                            1716
```

<210> SEQ ID NO 26
<211> LENGTH: 571
<212> TYPE: PRT
<213> ORGANISM: Neisseria meningitidis
<220> FEATURE:
<221> NAME

```
                    260                 265                 270
Xaa Xaa Xaa Xaa Xaa Xaa Xaa Xaa Xaa Xaa Xaa Xaa Xaa Xaa Xaa
            275                 280                 285
Xaa Xaa Xaa Xaa Xaa Xaa Xaa Xaa Xaa Xaa Xaa Xaa Xaa Xaa Xaa
        290                 295                 300
Xaa Xaa Xaa Xaa Xaa Xaa Xaa Xaa Xaa Xaa Xaa Xaa Xaa Xaa Xaa
305                 310                 315                 320
Xaa Xaa Xaa Xaa Xaa Xaa Xaa Xaa Xaa Xaa Xaa Xaa Xaa Xaa Xaa
                325                 330                 335
Xaa Xaa Xaa Xaa Xaa Xaa Xaa Xaa Xaa Xaa Xaa Xaa Xaa Xaa Xaa
            340                 345                 350
Xaa Xaa Xaa Xaa Xaa Xaa Xaa Xaa Xaa Xaa Xaa Xaa Xaa Xaa Xaa
        355                 360                 365
Xaa Xaa Xaa Xaa Xaa Xaa Xaa Xaa Xaa Xaa Xaa Xaa Xaa Xaa Xaa
    370                 375                 380
Xaa Xaa Xaa Xaa Xaa Xaa Xaa Xaa Xaa Xaa Xaa Xaa Xaa Xaa Xaa
385                 390                 395                 400
Xaa Xaa Xaa Xaa Xaa Xaa Xaa Xaa Xaa Xaa Xaa Xaa Xaa Xaa Xaa
                405                 410                 415
Xaa Xaa Xaa Xaa Xaa Xaa Xaa Xaa Xaa Xaa Xaa Xaa Xaa Xaa Xaa
            420                 425                 430
Xaa Xaa Xaa Xaa Xaa Xaa Xaa Xaa Xaa Xaa Xaa Xaa Xaa Xaa Xaa
        435                 440                 445
Xaa Xaa Xaa Xaa Xaa Xaa Xaa Xaa Xaa Xaa Xaa Xaa Xaa Xaa Xaa
    450                 455                 460
Xaa Xaa Xaa Xaa Xaa Xaa Xaa Xaa Xaa Xaa Xaa Xaa Xaa Xaa Xaa
465                 470                 475                 480
Xaa Xaa Xaa Xaa Xaa Xaa Xaa Xaa Xaa Xaa Xaa Xaa Xaa Xaa Xaa
                485                 490                 495
Xaa Xaa Xaa Xaa Xaa Xaa Xaa Xaa Xaa Xaa Xaa Xaa Xaa Xaa Xaa
            500                 505                 510
Xaa Xaa Ile Cys Ala Asn Arg Thr Val Leu Ile Ile Ala His Arg Leu
        515                 520                 525
Ser Thr Val Lys Thr Ala His Arg Ile Ile Ala Met Asp Lys Gly Arg
    530                 535                 540
Ile Val Glu Ala Gly Thr Gln Gln Glu Leu Leu Ala Asn Xaa Asn Gly
545                 550                 555                 560
Tyr Tyr Arg Tyr Leu Tyr Asp Leu Gln Asn Gly
            565                 570

<210> SEQ ID NO 27
<211> LENGTH: 2133
<212> TYPE: DNA
<213> ORGANISM: Neisseria meningitidis

<400> SEQUENCE: 27
atgtctatcg tatccgcacc gctcccgcc ctttccgccc tcatcatcct cgcccattac    60
cacggcattg ccgccaatcc tgccgatata cagcatgaat tttgtacttc cgcacagagc   120
gatttaaatg aaacgcaatg gctgttagcc gccaaatctt tgggattgaa ggcaaaggta   180
gtccgccagc ctattaaacg tttggctatg gcgactttac ccgcattggt atggtgtgat   240
gacggcaacc atttcatttt ggccaaaaca gacggtgagg gtgagcatgc ccaattttttg  300 atacaggatt tggttacgaa taagtctgcg gtattgtctt ttgccgaatt ttctaacaga   360
```

-continued

```
tattcgggca aactgatatt ggttgcttcc cgcgcttcgg tattgggcag tttggcaaag    420
tttgactttta cctggtttat tccggcggta atcaaatacc gccggttgtt ttttgaagta    480
ttggtggtgt cggtggtgtt gcagctgttt gcgctgatta cgcctctgtt tttccaagtg    540
gtgatggaca aggtgctggt acatcgggga ttctctactt tggatgtggt gtcggtggct    600
ttgttggtgg tgtcgctgtt tgagattgtg ttgggcggtt tgcggacgta tctgtttgca    660
catacgactt cacgtattga tgtggaattg ggcgcgcgtt tgttccggca tctgctttcc    720
ctgcctttat cctatttcga gcacagacga gtgggtgata cggtggctcg ggtgcgggaa    780
ttggagcaga ttcgcaattt cttgaccggt caggcgctga cttcggtgtt ggatttggcg    840
ttttcgttta tctttctggc ggtgatgtgg tattacagct ccactctgac ttgggtggta    900
ttggcttcgt tgcctgccta tgcgttttgg tcggcattta tcagtccgat actgcggacg    960
cgtctgaacg ataagttcgc gcgcaatgca gacaaccagt cgttttttagt agaaagcatc   1020
actgcggtgg gtacggtaaa ggcgatggcg gtggagccgc agatgacgca gcgttgggac   1080
aatcagttgg cggcttatgt ggcttcggga tttcgggtaa cgaagttggc ggtggtcggc   1140
cagcaggggg tgcagctgat tcagaagctg gtgacggtgg cgacgttgtg gattggcgca   1200
cggctggtaa ttgagagcaa gctgacggtg gggcagctga ttgcgtttaa tatgctctcg   1260
ggacaggtgg cggcgcctgt tatccgtttg gcgcagttgt ggcaggattt ccagcaggtg   1320
gggatttcgg tggcgcgttt gggggatatt ctgaatgcgc cgaccgagaa tgcgtcttcg   1380
catttggctt tgcccgatat ccggggggag attacgttcg aacatgtcga tttccgctat   1440
aaggcggacg gcaggctgat tttgcaggat ttgaacctgc ggattcgggc ggggaagtg    1500
ctggggattg tgggacgttc ggggtcgggc aaatccacac tcaccaaatt ggtgcagcgt   1560
ctgtatgtac cggagcaggg acgggtgttg gtggacggca acgatttggc tttggccgct   1620
cctgcctggc tgcggcggca ggtcggcgtg gtcttgcagg agaatgtgct gctcaaccgc   1680
agcatacgcg acaatatcgc gctgacggat acgggtatgc cgctggaacg cattatcgaa   1740
gcagccaaac tggcgggcgc acacgagttt attatggagc tgccggaagg ctacggcacc   1800
gtggtgggcg aacaagggc cggcttgtcg ggcggacagc ggcagcgtat tgcgattgcc    1860
cgcgcgttaa tcaccaatcc gcgcattctg attttttgatg aagccaccag cgcgctggat   1920
tatgaaagtg aacgagcgat tatgcagaac atgcaggcca tttgcgccaa ccggacggtg   1980
ctgattatcg cccaccgtct gtccactgtt aaaacggcac accggatcat tgccatggat   2040
aaaggcagga ttgtggaagc gggaacacag caggaattgc tggcgaagcc gaacggatat   2100
taccgctatc tgtatgattt acagaacggg tag                                2133
```

<210> SEQ ID NO 28
<211> LENGTH: 710
<212> TYPE: PRT
<213> ORGANISM: Neisseria meningitidis

<400> SEQUENCE: 28

```
Met Ser Ile Val Ser Ala Pro Leu Pro Ala Leu Ser Ala Leu Ile Ile
  1               5                  10                  15

Leu Ala His Tyr His Gly Ile Ala Ala Asn Pro Ala Asp Ile Gln His
             20                  25                  30

Glu Phe Cys Thr Ser Ala Gln Ser Asp Leu Asn Glu Thr Gln Trp Leu
         35                  40                  45

Leu Ala Ala Lys Ser Leu Gly Leu Lys Ala Lys Val Val Arg Gln Pro
     50                  55                  60
```

```
Ile Lys Arg Leu Ala Met Ala Thr Leu Pro Ala Leu Val Trp Cys Asp
 65                  70                  75                  80

Asp Gly Asn His Phe Ile Leu Ala Lys Thr Asp Gly Glu Gly Glu His
                 85                  90                  95

Ala Gln Phe Leu Ile Gln Asp Leu Val Thr Asn Lys Ser Ala Val Leu
            100                 105                 110

Ser Phe Ala Glu Phe Ser Asn Arg Tyr Ser Gly Lys Leu Ile Leu Val
        115                 120                 125

Ala Ser Arg Ala Ser Val Leu Gly Ser Leu Ala Lys Phe Asp Phe Thr
130                 135                 140

Trp Phe Ile Pro Ala Val Ile Lys Tyr Arg Arg Leu Phe Phe Glu Val
145                 150                 155                 160

Leu Val Val Ser Val Val Leu Gln Leu Phe Ala Leu Ile Thr Pro Leu
                165                 170                 175

Phe Phe Gln Val Val Met Asp Lys Val Leu Val His Arg Gly Phe Ser
            180                 185                 190

Thr Leu Asp Val Val Ser Val Ala Leu Leu Val Val Ser Leu Phe Glu
        195                 200                 205

Ile Val Leu Gly Gly Leu Arg Thr Tyr Leu Phe Ala His Thr Thr Ser
    210                 215                 220

Arg Ile Asp Val Glu Leu Gly Ala Arg Leu Phe Arg His Leu Leu Ser
225                 230                 235                 240

Leu Pro Leu Ser Tyr Phe Glu His Arg Arg Val Gly Asp Thr Val Ala
                245                 250                 255

Arg Val Arg Glu Leu Glu Gln Ile Arg Asn Phe Leu Thr Gly Gln Ala
            260                 265                 270

Leu Thr Ser Val Leu Asp Leu Ala Phe Ser Phe Ile Phe Leu Ala Val
        275                 280                 285

Met Trp Tyr Tyr Ser Ser Thr Leu Thr Trp Val Val Leu Ala Ser Leu
    290                 295                 300

Pro Ala Tyr Ala Phe Trp Ser Ala Phe Ile Ser Pro Ile Leu Arg Thr
305                 310                 315                 320

Arg Leu Asn Asp Lys Phe Ala Arg Asn Ala Asp Asn Gln Ser Phe Leu
                325                 330                 335

Val Glu Ser Ile Thr Ala Val Gly Thr Val Lys Ala Met Ala Val Glu
            340                 345                 350

Pro Gln Met Thr Gln Arg Trp Asp Asn Gln Leu Ala Ala Tyr Val Ala
        355                 360                 365

Ser Gly Phe Arg Val Thr Lys Leu Ala Val Val Gly Gln Gln Gly Val
    370                 375                 380

Gln Leu Ile Gln Lys Leu Val Thr Val Ala Thr Leu Trp Ile Gly Ala
385                 390                 395                 400

Arg Leu Val Ile Glu Ser Lys Leu Thr Val Gly Gln Leu Ile Ala Phe
                405                 410                 415

Asn Met Leu Ser Gly Gln Val Ala Ala Pro Val Ile Arg Leu Ala Gln
            420                 425                 430

Leu Trp Gln Asp Phe Gln Gln Val Gly Ile Ser Val Ala Arg Leu Gly
        435                 440                 445

Asp Ile Leu Asn Ala Pro Thr Glu Asn Ala Ser Ser His Leu Ala Leu
    450                 455                 460

Pro Asp Ile Arg Gly Glu Ile Thr Phe Glu His Val Asp Phe Arg Tyr
465                 470                 475                 480
```

-continued

```
Lys Ala Asp Gly Arg Leu Ile Leu Gln Asp Leu Asn Leu Arg Ile Arg
                485                 490                 495
Ala Gly Glu Val Leu Gly Ile Val Gly Arg Ser Gly Ser Gly Lys Ser
            500                 505                 510
Thr Leu Thr Lys Leu Val Gln Arg Leu Tyr Val Pro Glu Gln Gly Arg
        515                 520                 525
Val Leu Val Asp Gly Asn Asp Leu Ala Leu Ala Pro Ala Trp Leu
    530                 535                 540
Arg Arg Gln Val Gly Val Leu Gln Glu Asn Val Leu Leu Asn Arg
545                 550                 555                 560
Ser Ile Arg Asp Asn Ile Ala Leu Thr Asp Thr Gly Met Pro Leu Glu
                565                 570                 575
Arg Ile Ile Glu Ala Ala Lys Leu Ala Gly Ala His Glu Phe Ile Met
            580                 585                 590
Glu Leu Pro Glu Gly Tyr Gly Thr Val Val Gly Glu Gln Gly Ala Gly
        595                 600                 605
Leu Ser Gly Gly Gln Arg Gln Arg Ile Ala Ile Ala Arg Ala Leu Ile
    610                 615                 620
Thr Asn Pro Arg Ile Leu Ile Phe Asp Glu Ala Thr Ser Ala Leu Asp
625                 630                 635                 640
Tyr Glu Ser Glu Arg Ala Ile Met Gln Asn Met Gln Ala Ile Cys Ala
                645                 650                 655
Asn Arg Thr Val Leu Ile Ile Ala His Arg Leu Ser Thr Val Lys Thr
            660                 665                 670
Ala His Arg Ile Ile Ala Met Asp Lys Gly Arg Ile Val Glu Ala Gly
        675                 680                 685
Thr Gln Gln Glu Leu Leu Ala Lys Pro Asn Gly Tyr Tyr Arg Tyr Leu
    690                 695                 700
Tyr Asp Leu Gln Asn Gly
705                 710

<210> SEQ ID NO 29
<211> LENGTH: 2133
<212> TYPE: DNA
<213> ORGANISM: Neisseria meningitidis

<400> SEQUENCE: 29
atgtctatcg tatccgcacc gctccccgcc ctttccgccc tcatcatcct cgccattac        60 cacggcattg ccgccaatcc tgccgatata cagcatgaat tttgtacttc cgcacagagc       120
gatttaaatg aaacgcaatg gctgttagcc gccaaatctt gggattgaa ggcaaaggta       180 gtccgccagc ctattaaacg tttggctatg gcgactttac ccgcattggt atggtgtgat       240
gacggcaacc atttattttt ggctaaaaca gacggtgggg gtgagcatgc ccaatatcta       300
atacaggatt taactacgaa taagtctgcg gtattgtctt ttgccgaatt ttctaacaga       360
tattcgggca aactgatatt ggttgcttcc cgcgcttcgg tattgggcag tttggcaaag       420
tttgacttta cctggtttat tccggcggta atcaaatacc gccggttgtt ttttgaagta       480
ttggtggtgt cggtggtgtt gcagctgttt gcgctgatta cgcctctgtt tttccaagtg       540
gtgatggaca aggtgctggt acatcgggga ttctctactt ggatgtggt gtcggtggct       600 ttgttggtgg tgtcgctgtt tgagattgtg ttgggcggtt gcggacgta tctgtttgca       660 catacgactt cacgtattga tgtggaattg ggcgcgcgtt tgttccggca tctgcttccc       720
ctgcctttat cctatttcga gcacagacga gtgggtgata cggtggctcg ggtgcgggaa       780
```

```
ttggagcaga ttcgcaattt cttgaccggt caggcgctga cttcggtgtt ggatttggcg    840
ttttcgttta tctttctggc ggtgatgtgg tattacagct ccactctgac ttgggtggta    900
ttggcttcgt tgcctgccta tgcgttttgg tcggcattta tcagtccgat actgcggacg    960
cgtctgaacg ataagttcgc gcgcaatgca gacaaccagt cgttttagt agaaagcatc    1020
actgcggtgg gtacggtaaa ggcgatggcg gtggagccgc agatgacgca gcgttgggac    1080
aatcagttgg cggcttatgt ggcttcggga tttcgggtaa cgaagttggc ggtggtcggc    1140
cagcaggggg tgcagctgat tcagaagctg gtgacggtgg cgacgttgtg gattggcgca    1200
cggctggtaa ttgagagcaa gctgacggtg gggcagctga ttgcgtttaa tatgctctcg    1260
ggacaggtgg cggcgcctgt tatccgtttg gcgcagttgt ggcaggattt ccagcaggtg    1320
gggatttcgg tggcgcgttt gggggatatt ctgaatgcgc cgaccgagaa tgcgtcttcg    1380
catttggctt tgcccgatat ccggggggag attacgttcg aacatgtcga tttccgctat    1440
aaggcggacg gcaggctgat tttgcaggat ttgaacctgc ggattcgggc gggggaagtg    1500
ctggggattg tgggacgttc ggggtcgggc aaatccacac tcaccaaatt ggtgcagcgt    1560
ctgtatgtac cggcgcaggg acgggtgttg gtggacggca acgatttggc tttggccgct    1620
cctgcttggc tgcggcggca ggtcggcgtg gtcttgcagg agaatgtgct gctcaaccgc    1680
agcatacgcg acaatatcgc gctgacggat acgggtatgc cgctgaacg cattatcgaa    1740
gcagccaaac tggcgggcgc acacgagttt attatggagc tgccggaagg ctacggcacc    1800
gtggtgggcg aacaaggggc cggcttgtcg gcggacagc ggcagcgtat tgcgattgcc    1860
cgcgcgttaa tcaccaatcc gcgcattctg attttgatg aagccaccag cgcgctggat    1920
tatgaaagtg aacgagcgat tatgcagaac atgcaggcca tttgcgccaa ccggacggtg    1980
ctgattatcg cccaccgtct gtccactgtt aaaacggcac accggatcat tgccatggat    2040
aaaggcagga ttgtggaagc gggaacacag caggaattgc tggcgaagcc gaacggatat    2100
taccgctatc tgtatgattt acagaacggg tag                                  2133

<210> SEQ ID NO 30
<211> LENGTH: 710
<212> TYPE: PRT
<213> ORGANISM: Neisseria meningitidis

<400> SEQUENCE: 30

Met Ser Ile Val Ser Ala Pro Leu Pro Ala Leu Ser Ala Leu Ile Ile
  1               5                  10                  15

Leu Ala His Tyr His Gly Ile Ala Ala Asn Pro Ala Asp Ile Gln His
                 20                  25                  30

Glu Phe Cys Thr Ser Ala Gln Ser Asp Leu Asn Glu Thr Gln Trp Leu
             35                  40                  45

Leu Ala Ala Lys Ser Leu Gly Leu Lys Ala Lys Val Val Arg Gln Pro
         50                  55                  60

Ile Lys Arg Leu Ala Met Ala Thr Leu Pro Ala Leu Val Trp Cys Asp
 65                  70                  75                  80

Asp Gly Asn His Phe Ile Leu Ala Lys Thr Asp Gly Gly Glu His
                 85                  90                  95

Ala Gln Tyr Leu Ile Gln Asp Leu Thr Thr Asn Lys Ser Ala Val Leu
            100                 105                 110

Ser Phe Ala Glu Phe Ser Asn Arg Tyr Ser Gly Lys Leu Ile Leu Val
            115                 120                 125

Ala Ser Arg Ala Ser Val Leu Gly Ser Leu Ala Lys Phe Asp Phe Thr
```

```
            130                 135                 140
Trp Phe Ile Pro Ala Val Ile Lys Tyr Arg Arg Leu Phe Phe Glu Val
145                 150                 155                 160

Leu Val Val Ser Val Val Leu Gln Leu Phe Ala Leu Ile Thr Pro Leu
                165                 170                 175

Phe Phe Gln Val Val Met Asp Lys Val Leu Val His Arg Gly Phe Ser
                180                 185                 190

Thr Leu Asp Val Val Ser Val Ala Leu Leu Val Val Ser Leu Phe Glu
                195                 200                 205

Ile Val Leu Gly Gly Leu Arg Thr Tyr Leu Phe Ala His Thr Thr Ser
210                 215                 220

Arg Ile Asp Val Glu Leu Gly Ala Arg Leu Phe Arg His Leu Leu Ser
225                 230                 235                 240

Leu Pro Leu Ser Tyr Phe Glu His Arg Arg Val Gly Asp Thr Val Ala
                245                 250                 255

Arg Val Arg Glu Leu Glu Gln Ile Arg Asn Phe Leu Thr Gly Gln Ala
                260                 265                 270

Leu Thr Ser Val Leu Asp Leu Ala Phe Ser Phe Ile Phe Leu Ala Val
                275                 280                 285

Met Trp Tyr Tyr Ser Ser Thr Leu Thr Trp Val Val Leu Ala Ser Leu
                290                 295                 300

Pro Ala Tyr Ala Phe Trp Ser Ala Phe Ile Ser Pro Ile Leu Arg Thr
305                 310                 315                 320

Arg Leu Asn Asp Lys Phe Ala Arg Asn Ala Asp Asn Gln Ser Phe Leu
                325                 330                 335

Val Glu Ser Ile Thr Ala Val Gly Thr Val Lys Ala Met Ala Val Glu
                340                 345                 350

Pro Gln Met Thr Gln Arg Trp Asp Asn Gln Leu Ala Ala Tyr Val Ala
                355                 360                 365

Ser Gly Phe Arg Val Thr Lys Leu Ala Val Val Gly Gln Gln Gly Val
                370                 375                 380

Gln Leu Ile Gln Lys Leu Val Thr Val Ala Thr Leu Trp Ile Gly Ala
385                 390                 395                 400

Arg Leu Val Ile Glu Ser Lys Leu Thr Val Gly Gln Leu Ile Ala Phe
                405                 410                 415

Asn Met Leu Ser Gly Gln Val Ala Ala Pro Val Ile Arg Leu Ala Gln
                420                 425                 430

Leu Trp Gln Asp Phe Gln Gln Val Gly Ile Ser Val Ala Arg Leu Gly
                435                 440                 445

Asp Ile Leu Asn Ala Pro Thr Glu Asn Ala Ser Ser His Leu Ala Leu
450                 455                 460

Pro Asp Ile Arg Gly Glu Ile Thr Phe Glu His Val Asp Phe Arg Tyr
465                 470                 475                 480

Lys Ala Asp Gly Arg Leu Ile Leu Gln Asp Leu Asn Leu Arg Ile Arg
                485                 490                 495

Ala Gly Glu Val Leu Gly Ile Val Gly Arg Ser Gly Ser Gly Lys Ser
                500                 505                 510

Thr Leu Thr Lys Leu Val Gln Arg Leu Tyr Val Pro Ala Gln Gly Arg
                515                 520                 525

Val Leu Val Asp Gly Asn Asp Leu Ala Leu Ala Ala Pro Ala Trp Leu
                530                 535                 540

Arg Arg Gln Val Gly Val Val Leu Gln Glu Asn Val Leu Leu Asn Arg
545                 550                 555                 560
```

```
Ser Ile Arg Asp Asn Ile Ala Leu Thr Asp Thr Gly Met Pro Leu Glu
            565                 570                 575

Arg Ile Ile Glu Ala Ala Lys Leu Ala Gly Ala His Glu Phe Ile Met
        580                 585                 590

Glu Leu Pro Glu Gly Tyr Gly Thr Val Val Gly Glu Gln Gly Ala Gly
    595                 600                 605

Leu Ser Gly Gly Gln Arg Gln Arg Ile Ala Ile Ala Arg Ala Leu Ile
610                 615                 620

Thr Asn Pro Arg Ile Leu Ile Phe Asp Glu Ala Thr Ser Ala Leu Asp
625                 630                 635                 640

Tyr Glu Ser Glu Arg Ala Ile Met Gln Asn Met Gln Ala Ile Cys Ala
            645                 650                 655

Asn Arg Thr Val Leu Ile Ile Ala His Arg Leu Ser Thr Val Lys Thr
                660                 665                 670

Ala His Arg Ile Ile Ala Met Asp Lys Gly Arg Ile Val Glu Ala Gly
            675                 680                 685

Thr Gln Gln Glu Leu Leu Ala Lys Pro Asn Gly Tyr Tyr Arg Tyr Leu
    690                 695                 700

Tyr Asp Leu Gln Asn Gly
705                 710

<210> SEQ ID NO 31
<211> LENGTH: 186
<212> TYPE: DNA
<213> ORGANISM: Neisseria meningitidis

<400> SEQUENCE: 31
atgaaatact tgatccgcac cgccttactc gcagtcgcag ccgccggcat ctacgcctgc      60
caaccgcaat ccgaagccgc agtgcaagtc aaggctgaaa acagcctgac cgctatgcgc     120
ttagccgtcg ccgacaaaca ggcagagatt gacggggtga acgcccaaak sgacgccgaa     180
atcaga                                                                186

<210> SEQ ID NO 32
<211> LENGTH: 62
<212> TYPE: PRT
<213> ORGANISM: Neisseria meningitidis
<220> FEATURE:
<221> NAME/KEY: SITE
<222> LOCATION: (57)
<223> OTHER INFORMATION: unknown

<400> SEQUENCE: 32

Met Lys Tyr Leu Ile Arg Thr Ala Leu Leu Ala Val Ala Ala Ala Gly
1               5                   10                  15

Ile Tyr Ala Cys Gln Pro Gln Ser Glu Ala Ala Val Gln Val Lys Ala
            20                  25                  30

Glu Asn Ser Leu Thr Ala Met Arg Leu Ala Val Ala Asp Lys Gln Ala
        35                  40                  45

Glu Ile Asp Gly Leu Asn Ala Gln Xaa Asp Ala Glu Ile Arg
    50                  55                  60

<210> SEQ ID NO 33
<211> LENGTH: 261
<212> TYPE: DNA
<213> ORGANISM: Neisseria meningitidis

<400> SEQUENCE: 33
```

```
atgaaatact tgatccgcac cgccttactc gcagtcgcag ccgccggcat ctacgcctgc      60
caaccgcaat ccgaagccgc agtgcaagtc aaggctgaaa acagcctgac cgctatgcgc     120
ttagccgtcg ccgacaaaca ggcagagatt gacgggttga acgcccaaat cgacgccgaa     180
atcagacaac gcgaagccga agaattgaaa gactaccgat ggatacacgg cgacgcggaa     240
gtgccggagc tggaaaaatg a                                               261
```

<210> SEQ ID NO 34
<211> LENGTH: 86
<212> TYPE: PRT
<213> ORGANISM: Neisseria meningitidis

<400> SEQUENCE: 34

```
Met Lys Tyr Leu Ile Arg Thr Ala Leu Leu Ala Val Ala Ala Ala Gly
  1               5                  10                  15

Ile Tyr Ala Cys Gln Pro Gln Ser Glu Ala Ala Val Gln Val Lys Ala
             20                  25                  30

Glu Asn Ser Leu Thr Ala Met Arg Leu Ala Val Ala Asp Lys Gln Ala
         35                  40                  45

Glu Ile Asp Gly Leu Asn Ala Gln Ile Asp Ala Glu Ile Arg Gln Arg
     50                  55                  60

Glu Ala Glu Glu Leu Lys Asp Tyr Arg Trp Ile His Gly Asp Ala Glu
 65                  70                  75                  80

Val Pro Glu Leu Glu Lys
                 85
```

<210> SEQ ID NO 35
<211> LENGTH: 279
<212> TYPE: DNA
<213> ORGANISM: Neisseria meningitidis

<400> SEQUENCE: 35

```
atggttatcg gaatattact cgcatcaagc aagcatgctc ttgtcattac tctattgtta      60
aatcccgtct ccatgcatc cagttgcgta tcgcgttsgg caatacggaa taaaatctgc     120
tgttctgctt tggctaaatt tgccaaattg tttattgttt ctttaggagc agcttgctta     180
gccgccttcg ctttcgacaa cgcccccaca ggcgcttccc aagcgttgcc taccgttacc     240
gcacccgtgg cgattcccgc gcccgcttcg gcagcctga                            279
```

<210> SEQ ID NO 36
<211> LENGTH: 92
<212> TYPE: PRT
<213> ORGANISM: Neisseria meningitidis
<220> FEATURE:
<221> NAME/KEY: SITE
<222> LOCATION: (33)
<223> OTHER INFORMATION: unknown

<400> SEQUENCE: 36

```
Met Val Ile Gly Ile Leu Leu Ala Ser Ser Lys His Ala Leu Val Ile
  1               5                  10                  15

Thr Leu Leu Leu Asn Pro Val Phe His Ala Ser Ser Cys Val Ser Arg
             20                  25                  30

Xaa Ala Ile Arg Asn Lys Ile Cys Cys Ser Ala Leu Ala Lys Phe Ala
         35                  40                  45

Lys Leu Phe Ile Val Ser Leu Gly Ala Ala Cys Leu Ala Ala Phe Ala
     50                  55                  60

Phe Asp Asn Ala Pro Thr Gly Ala Ser Gln Ala Leu Pro Thr Val Thr
```

Ala Pro Val Ala Ile Pro Ala Pro Ala Ser Ala Ala
              85                  90

<210> SEQ ID NO 37
<211> LENGTH: 312
<212> TYPE: DNA
<213> ORGANISM: Neisseria meningitidis

<400> SEQUENCE: 37
atggcttgta caggtttgat ggttttccg ttaatggtta tcggaatatt acttgcatca      60
agcaagcctg ctcctttcct tactctattg ttaaatcccg tcttccatgc atccagttgc    120
gtatcgcgtt gggcaatacg gaataaaatc tgctgttctg ctttggctaa atttgccaaa    180
ttgtttattg tttctttagg agcagcttgc ttagccgcct tcgctttcga caacgcccccc   240 acaggcgctt cccaagcgtt gcctaccgtt accgcacccg tggcgattcc cgcgcccgct   300
tcggcagcct ga                                                        312

<210> SEQ ID NO 38
<211> LENGTH: 103
<212> TYPE: PRT
<213> ORGANISM: Neisseria meningitidis

<400> SEQUENCE: 38

Met Ala Cys Thr Gly Leu Met Val Phe Pro Leu Met Val Ile Gly Ile
 1               5                  10                  15

Leu Leu Ala Ser Ser Lys Pro Ala Pro Phe Leu Thr Leu Leu Leu Asn
             20                  25                  30

Pro Val Phe His Ala Ser Ser Cys Val Ser Arg Trp Ala Ile Arg Asn
         35                  40                  45

Lys Ile Cys Cys Ser Ala Leu Ala Lys Phe Ala Lys Leu Phe Ile Val
     50                  55                  60

Ser Leu Gly Ala Ala Cys Leu Ala Ala Phe Ala Phe Asp Asn Ala Pro
 65                  70                  75                  80

Thr Gly Ala Ser Gln Ala Leu Pro Thr Val Thr Ala Pro Val Ala Ile
                 85                  90                  95

Pro Ala Pro Ala Ser Ala Ala
            100

<210> SEQ ID NO 39
<211> LENGTH: 255
<212> TYPE: DNA
<213> ORGANISM: Neisseria meningitidis

<400> SEQUENCE: 39
atgttcagta ttttaaatgt gtttcttcat tgtattctgg cttgtgtagt ctctggtgag     60
acgcctacta tatttggtat ccttgctctt ttttacttat tgtatctttc ttatcttgct   120
gtttttaaga ttttctttttc ttttttctta gacagagttt cactccggtc tcccaggctg  180
gagtgcaaat ggcatgaccc tttggctcac tggctcacgg ccacttctgc tattctgccg   240
cctcagcctc caggg                                                     255

<210> SEQ ID NO 40
<211> LENGTH: 85
<212> TYPE: PRT
<213> ORGANISM: Neisseria meningitidis

<400> SEQUENCE: 40

Met Phe Ser Ile Leu Asn Val Phe Leu His Cys Ile Leu Ala Cys Val
1               5                   10                  15

Val Ser Gly Glu Thr Pro Thr Ile Phe Gly Ile Leu Ala Leu Phe Tyr
                20                  25                  30

Leu Leu Tyr Leu Ser Tyr Leu Ala Val Phe Lys Ile Phe Ser Phe
            35                  40                  45

Phe Leu Asp Arg Val Ser Leu Arg Ser Pro Arg Leu Glu Cys Lys Trp
    50                  55                  60

His Asp Pro Leu Ala His Trp Leu Thr Ala Thr Ser Ala Ile Leu Pro
65                  70                  75                  80

Pro Gln Pro Pro Gly
            85

<210> SEQ ID NO 41
<211> LENGTH: 237
<212> TYPE: DNA
<213> ORGANISM: Neisseria meningitidis

<400> SEQUENCE: 41
gtgcggacgt ggttggtttt ttggttgcag cgtttgaaat accgttgtt gctttggatt    60 gcggatatgt tgctgtaccg gttgttgggc ggcgcggaaa tcgaatgcgg ccgttgccct   120
gtgccgccga tgacggattg cagcattttt tgccggcga tgggaacggt gtcggcttgg   180
gtggcggtga tttgggcata cctgatgatt gaaagtgaaa aaaacggaag atattga      237

<210> SEQ ID NO 42
<211> LENGTH: 78
<212> TYPE: PRT
<213> ORGANISM: Neisseria meningitidis

<400> SEQUENCE: 42

Val Arg Thr Trp Leu Val Phe Trp Leu Gln Arg Leu Lys Tyr Pro Leu
1               5                   10                  15

Leu Leu Trp Ile Ala Asp Met Leu Leu Tyr Arg Leu Leu Gly Gly Ala
                20                  25                  30

Glu Ile Glu Cys Gly Arg Cys Pro Val Pro Pro Met Thr Asp Trp Gln
            35                  40                  45

His Phe Leu Pro Ala Met Gly Thr Val Ser Ala Trp Val Ala Val Ile
    50                  55                  60

Trp Ala Tyr Leu Met Ile Glu Ser Glu Lys Asn Gly Arg Tyr
65                  70                  75

<210> SEQ ID NO 43
<211> LENGTH: 237
<212> TYPE: DNA
<213> ORGANISM: Neisseria meningitidis

<400> SEQUENCE: 43
gtgcggacgt ggttggtttt ttggttgcag cgtttgaaat accgttgtt gctttgtatt    60 gcggatatgc tgctgtaccg gttgttgggc ggcgcggaaa tcgaatgcgg ccgttgccct   120
gtaccgccga tgacggattg cagcattttt tgccgacga tgggaacggt ggcggcttgg   180
gtggcggtga tttgggcata cctgatgatt gaaagtgaaa aaaacggaag atattga      237

<210> SEQ ID NO 44
<211> LENGTH: 78
<212> TYPE: PRT
<213> ORGANISM: Neisseria meningitidis

<400> SEQUENCE: 44

Val Arg Thr Trp Leu Val Phe Trp Leu Gln Arg Leu Lys Tyr Pro Leu
 1               5                  10                  15

Leu Leu Cys Ile Ala Asp Met Leu Leu Tyr Arg Leu Leu Gly Gly Ala
            20                  25                  30

Glu Ile Glu Cys Gly Arg Cys Pro Val Pro Pro Met Thr Asp Trp Gln
        35                  40                  45

His Phe Leu Pro Thr Met Gly Thr Val Ala Ala Trp Val Ala Val Ile
    50                  55                  60

Trp Ala Tyr Leu Met Ile Glu Ser Glu Lys Asn Gly Arg Tyr
65                  70                  75

<210> SEQ ID NO 45
<211> LENGTH: 660
<212> TYPE: DNA
<213> ORGANISM: Neisseria meningitidis

<400> SEQUENCE: 45
atgtttcaaa attttgattt gggcgtgttc ctgcttgccg tcctcccgt gctgccctcc      60 attaccgtct cgcacgtggc gcgcggctat acggcgcgct actggggaga caacactgcc    120
gaacaatacg gcaggctgac actgaacccc ctgccccata tcgatttggt cggcacaatc    180
atcgtaccgc tgcttacttt gatgttcacg cccttcctgt tcggctgggc gcgtccgatt    240
cctatcgatt cgcgcaactt ccgcaacccg cgccttgcct ggcgttgcgt tgccgcgtcc    300
ggcccgctgt cgaatctagc gatggctgtw ctgtggggcg tggttttggt gctgactccg    360
tatgtcggcg gggcgtatca gatgccgttg gctcaaatgg caaactacgg tattctgatc    420
aatgcgattc tgttcgcgct caacatcatc cccatcctgc cttgggacgg cggcattttc    480
atcgacacct tcctgtcggc gaaatattcg caagcgttcc gcaaaatcga accttatggg    540
acgtggatta tcctactgct gatgctgacc sgggttttgg gtgcgtttat wgcaccgatt    600
stgcggmtgc gtgattgcrt ttgtgcagat gtwcgtctga ctggctttca gacggcataa    660

<210> SEQ ID NO 46
<211> LENGTH: 219
<212> TYPE: PRT
<213> ORGANISM: Neisseria meningitidis
<220> FEATURE:
<221> NAME/KEY: SITE
<222> LOCATION: (191)
<223> OTHER INFORMATION: unknown
<220> FEATURE:
<221> NAME/KEY: SITE
<222> LOCATION: (201)
<223> OTHER INFORMATION: unknown
<220> FEATURE:
<221> NAME/KEY: SITE
<222> LOCATION: (203)
<223> OTHER INFORMATION: unknown
<220> FEATURE:
<221> NAME/KEY: SITE
<222> LOCATION: (207)
<223> OTHER INFORMATION: unknown

<400> SEQUENCE: 46

Met Phe Gln Asn Phe Asp Leu Gly Val Phe Leu Leu Ala Val Leu Pro
 1               5                  10                  15

Val Leu Pro Ser Ile Thr Val Ser His Val Ala Arg Gly Tyr Thr Ala
            20                  25                  30

Arg Tyr Trp Gly Asp Asn Thr Ala Glu Gln Tyr Gly Arg Leu Thr Leu

```
                35                  40                  45
Asn Pro Leu Pro His Ile Asp Leu Val Gly Thr Ile Ile Val Pro Leu
         50                  55                  60
Leu Thr Leu Met Phe Thr Pro Phe Leu Phe Gly Trp Ala Arg Pro Ile
 65                  70                  75                  80
Pro Ile Asp Ser Arg Asn Phe Arg Asn Pro Arg Leu Ala Trp Arg Cys
                 85                  90                  95
Val Ala Ala Ser Gly Pro Leu Ser Asn Leu Ala Met Ala Val Leu Trp
            100                 105                 110
Gly Val Val Leu Val Leu Thr Pro Tyr Val Gly Gly Ala Tyr Gln Met
        115                 120                 125
Pro Leu Ala Gln Met Ala Asn Tyr Gly Ile Leu Ile Asn Ala Ile Leu
    130                 135                 140
Phe Ala Leu Asn Ile Ile Pro Ile Leu Pro Trp Asp Gly Gly Ile Phe
145                 150                 155                 160
Ile Asp Thr Phe Leu Ser Ala Lys Tyr Ser Gln Ala Phe Arg Lys Ile
                165                 170                 175
Glu Pro Tyr Gly Thr Trp Ile Ile Leu Leu Leu Met Leu Thr Xaa Val
            180                 185                 190
Leu Gly Ala Phe Ile Ala Pro Ile Xaa Arg Xaa Arg Asp Cys Xaa Cys
        195                 200                 205
Ala Asp Val Arg Leu Thr Gly Phe Gln Thr Ala
    210                 215
```

<210> SEQ ID NO 47
<211> LENGTH: 639
<212> TYPE: DNA
<213> ORGANISM: Neisseria meningitidis

<400> SEQUENCE: 47

```
atgtttcaaa attttgattt gggcgtgttt ctgcttgccg tcctgcccgt gctgctctcc      60
attaccgtca gggaggtggc gcgcggctat acggcgcgct actggggaga caacactgcc    120
gaacaatacg gcaggctgac actgaacccc ctgccccata tcgatttggt cggcacaatc    180
atcgtaccgc tgcttacttt gatgttcacg cccttcctgt tcggctgggc cgtccgatt    240
cctatcgatt cgcgcaactt ccgcaacccg cgccttgcct ggcgttgcgt tgccgcgtcc    300
ggcccgctgt cgaatctagc gatggctgtt ctgtggggcg tggttttggt gctgactccg    360
tatgtcggcg gggcgtatca gatgccgttg gctcaaatgg caaactacgg tattctgatc    420
aatgcgattc tgttcgcgct caacatcatc cccatcctgc cttgggacgg cggcattttc    480
atcgacacct tcctgtcggc gaaatattcg caagcgttcc gcaaaatcga accttatggg    540
acgtggatta tcctactgct gatgctgacc ggggttttgg gtgcgtttat tgcaccgatt    600
gtgcggctgg tgattgcgtt tgtgcagatg ttcgtctga                            639
```

<210> SEQ ID NO 48
<211> LENGTH: 212
<212> TYPE: PRT
<213> ORGANISM: Neisseria meningitidis

<400> SEQUENCE: 48

```
Met Phe Gln Asn Phe Asp Leu Gly Val Phe Leu Leu Ala Val Leu Pro
  1               5                  10                  15
Val Leu Leu Ser Ile Thr Val Arg Glu Val Ala Arg Gly Tyr Thr Ala
             20                  25                  30
```

```
Arg Tyr Trp Gly Asp Asn Thr Ala Glu Gln Tyr Gly Arg Leu Thr Leu
         35                  40                  45

Asn Pro Leu Pro His Ile Asp Leu Val Gly Thr Ile Ile Val Pro Leu
 50                  55                  60

Leu Thr Leu Met Phe Thr Pro Phe Leu Phe Gly Trp Ala Arg Pro Ile
 65                  70                  75                  80

Pro Ile Asp Ser Arg Asn Phe Arg Asn Pro Arg Leu Ala Trp Arg Cys
             85                  90                  95

Val Ala Ala Ser Gly Pro Leu Ser Asn Leu Ala Met Ala Val Leu Trp
            100                 105                 110

Gly Val Leu Val Leu Thr Pro Tyr Val Gly Ala Tyr Gln Met
            115                 120                 125

Pro Leu Ala Gln Met Ala Asn Tyr Gly Ile Leu Ile Asn Ala Ile Leu
130                 135                 140

Phe Ala Leu Asn Ile Ile Pro Ile Leu Pro Trp Asp Gly Gly Ile Phe
145                 150                 155                 160

Ile Asp Thr Phe Leu Ser Ala Lys Tyr Ser Gln Ala Phe Arg Lys Ile
                165                 170                 175

Glu Pro Tyr Gly Thr Trp Ile Ile Leu Leu Leu Met Leu Thr Gly Val
            180                 185                 190

Leu Gly Ala Phe Ile Ala Pro Ile Val Arg Leu Val Ile Ala Phe Val
            195                 200                 205

Gln Met Phe Val
    210

<210> SEQ ID NO 49
<211> LENGTH: 558
<212> TYPE: DNA
<213> ORGANISM: Neisseria meningitidis
<220> FEATURE:
<221> NAME/KEY: misc_feature
<222> LOCATION: (312)
<223> OTHER INFORMATION: any nucleotide
<220> FEATURE:
<221> NAME/KEY: misc_feature
<222> LOCATION: (328)..(330)
<223> OTHER INFORMATION: any nucleotide
<220> FEATURE:
<221> NAME/KEY: misc_feature
<222> LOCATION: (353)
<223> OTHER INFORMATION: any nucleotide
<220> FEATURE:
<221> NAME/KEY: misc_feature
<222> LOCATION: (420)
<223> OTHER INFORMATION: any nucleotide
<220> FEATURE:
<221> NAME/KEY: misc_feature
<222> LOCATION: (426)
<223> OTHER INFORMATION: any nucleotide
<220> FEATURE:
<221> NAME/KEY: misc_feature
<222> LOCATION: (473)
<223> OTHER INFORMATION: any nucleotide
<220> FEATURE:
<221> NAME/KEY: misc_feature
<222> LOCATION: (506)
<223> OTHER INFORMATION: any nucleotide

<400> SEQUENCE: 49
cgcggctata cagcgcgcta ctggggtgac aacactgccg aacaatacgg caggctgaca      60
ctgaaccccc tgcccatat cgatttggtc ggcacaatca tcgtaccgct gcttactttg     120
atgtttacgc ccttcctgtt cggctgggcg cgtccgattc ctatcgattc gcgcaacttc    180
cgcaacccgc gccttgcctg cgttgcgtt gccgcgtccg gcccgctgtc gaatctggcg    240
```

```
atggctgttc tgtggggcgt ggttttggtg ctgactccgt atgtcggtgg ggcgtatcag    300
atgccgttgg cncaaatggc aaactacnnn attctgatca atgcgattct gtncgcgctc    360
aacatcatcc ccatcctgcc ttgggacggc ggcattttca tcgacacctt cctgtcggcn    420
aaatantcgc aagcgttccg caaaatcgaa ccttatggga cgtggattat ccngctgctt    480
atgctgaccg ggttttggg tgcgtntatt gcaccgattg tgcagctggt gattgcgttt    540
gtgcagatgt tcgtctga                                                  558
```

<210> SEQ ID NO 50
<211> LENGTH: 185
<212> TYPE: PRT
<213> ORGANISM: Neisseria meningitidis
<220> FEATURE:
<221> NAME/KEY: SITE
<222> LOCATION: (110)
<223> OTHER INFORMATION: unknown
<220> FEATURE:
<221> NAME/KEY: SITE
<222> LOCATION: (118)
<223> OTHER INFORMATION: unknown
<220> FEATURE:
<221> NAME/KEY: SITE
<222> LOCATION: (142)
<223> OTHER INFORMATION: unknown
<220> FEATURE:
<221> NAME/KEY: SITE
<222> LOCATION: (158)
<223> OTHER INFORMATION: unknown
<220> FEATURE:
<221> NAME/KEY: SITE
<222> LOCATION: (169)
<223> OTHER INFORMATION: unknown

<400> SEQUENCE: 50

Arg Gly Tyr Thr Ala Arg Tyr Trp Gly Asp Asn Thr Ala Glu Gln Tyr
 1               5                  10                  15

Gly Arg Leu Thr Leu Asn Pro Leu Pro His Ile Asp Leu Val Gly Thr
            20                  25                  30

Ile Ile Val Pro Leu Leu Thr Leu Met Phe Thr Pro Phe Leu Phe Gly
        35                  40                  45

Trp Ala Arg Pro Ile Pro Ile Asp Ser Arg Asn Phe Arg Asn Pro Arg
    50                  55                  60

Leu Ala Trp Arg Cys Val Ala Ala Ser Gly Pro Leu Ser Asn Leu Ala
65                  70                  75                  80

Met Ala Val Leu Trp Gly Val Val Leu Val Thr Pro Tyr Val Gly
                85                  90                  95

Gly Ala Tyr Gln Met Pro Leu Ala Gln Met Ala Asn Tyr Xaa Ile Leu
            100                 105                 110

Ile Asn Ala Ile Leu Xaa Ala Leu Asn Ile Ile Pro Ile Leu Pro Trp
        115                 120                 125

Asp Gly Gly Ile Phe Ile Asp Thr Phe Leu Ser Ala Lys Xaa Ser Gln
    130                 135                 140

Ala Phe Arg Lys Ile Glu Pro Tyr Gly Thr Trp Ile Ile Xaa Leu Leu
145                 150                 155                 160

Met Leu Thr Gly Val Leu Gly Ala Xaa Ile Ala Pro Ile Val Gln Leu
                165                 170                 175

Val Ile Ala Phe Val Gln Met Phe Val
            180                 185

<210> SEQ ID NO 51

<211> LENGTH: 498
<212> TYPE: DNA
<213> ORGANISM: Neisseria meningitidis

<400> SEQUENCE: 51

```
atgaacctga tttcacgtta catcatccgt caaatggcgg ttatggcggt ttacgcgctc    60
cttgccttcc tcgctttgta cagcttttt gaaatcctgt acgaaaccgg caacctcggc   120
aaaggcagtt acggcatatg ggaaatgctg ggctacaccg ccctcaaaat gcccgccgc   180
gcctacgaac tgattcccct cgccgtcctt atcggcggac tggtctccct cagccagctt   240
gccgccggca gcgaactgac cgtcatcaaa gccagcggga tgagcaccaa aaagctgctg   300
ttgattctgt cgcagttcgg tttttatttt gctattgcca ccgtcgcgct cggcgaatgg   360
gttgcgccca cactgagcca aaagccgaa aacatcaaag ccgccgccat caacggcaaa   420
atcagcaccg gcaataccgg cctttggctg aaagaaaaaa acagcgtgat caatgtgcgc   480
gaaatgttgc ccgaccat                                                 498
```

<210> SEQ ID NO 52
<211> LENGTH: 166
<212> TYPE: PRT
<213> ORGANISM: Neisseria meningitidis

<400> SEQUENCE: 52

```
Met Asn Leu Ile Ser Arg Tyr Ile Ile Arg Gln Met Ala Val Met Ala
  1               5                  10                  15
Val Tyr Ala Leu Leu Ala Phe Leu Ala Leu Tyr Ser Phe Phe Glu Ile
                 20                  25                  30
Leu Tyr Glu Thr Gly Asn Leu Gly Lys Gly Ser Tyr Gly Ile Trp Glu
             35                  40                  45
Met Leu Gly Tyr Thr Ala Leu Lys Met Pro Ala Arg Ala Tyr Glu Leu
         50                  55                  60
Ile Pro Leu Ala Val Leu Ile Gly Gly Leu Val Ser Leu Ser Gln Leu
 65                  70                  75                  80
Ala Ala Gly Ser Glu Leu Thr Val Ile Lys Ala Ser Gly Met Ser Thr
                 85                  90                  95
Lys Lys Leu Leu Leu Ile Leu Ser Gln Phe Gly Phe Ile Phe Ala Ile
                100                 105                 110
Ala Thr Val Ala Leu Gly Glu Trp Val Ala Pro Thr Leu Ser Gln Lys
            115                 120                 125
Ala Glu Asn Ile Lys Ala Ala Ala Ile Asn Gly Lys Ile Ser Thr Gly
        130                 135                 140
Asn Thr Gly Leu Trp Leu Lys Glu Lys Asn Ser Val Ile Asn Val Arg
145                 150                 155                 160
Glu Met Leu Pro Asp His
                165
```

<210> SEQ ID NO 53
<211> LENGTH: 980
<212> TYPE: DNA
<213> ORGANISM: Neisseria meningitidis

<400> SEQUENCE: 53

```
atgaacctga tttcacgtta catcatccgt caaatggcgg ttatggcggt ttacgcgctc    60
cttgccttcc tcgctttgta cagcttttt gaaatcctgt acgaaaccgg caacctcggc   120
aaaggcagtt acggcatatg ggaaatgctg ggctacaccg ccctcaaaat gcccgccgc   180
```

-continued

```
gcctacgaac tgattcccct cgccgtcctt atcggcggac tggtctccct cagccagctt    240
gccgccggca gcgaactgac cgtcatcaaa gccagcggca tgagcaccaa aaagctgctg    300
ttgattctgt cgcagttcgg ttttattttt gctattgcca ccgtcgcgct cggcgaatgg    360
gttgcgccca cactgagcca aaagccgaaa acatcaaag ccgccgccat caacggcaaa     420
atcagcaccg gcaataccgg cctttggctg aaagaaaaaa acagcrtkat caatgtgcgc    480
gaaatgttgc ccgaccatac gcttttgggc atcaaaattt gggcgcgcaa cgataaaaac    540
gaattggcag aggcagtgga agccgattcc gccgttttga acagcgacgg cagttggcag    600
ttgaaaaaca tccgccgcag cacgcttggc gaagacaaag tcgaggtctc tattgcggct    660
gaagaaaact ggccgatttc cgtcaaacgc aacctgatgg acgtattgct cgtcaaaccc    720
gaccaaatgt ccgtcggcga actgaccacc tacatccgcc acctccaaaa caacagccaa    780
aacacccgaa tctacgccat cgcatggtgg cgcaaattgg tttacccccgc cgcagcctgg   840 gtgatggcgc tcgtcgcctt tgcctttacc ccgcaaacca cccgccacgg caatatgggc    900
ttaaaactct tcggcggcat ctgtstcgga ttgctgttcc accttgccgg acggctcttt    960
gggtttacca gccaactcgg                                                980
```

```
<210> SEQ ID NO 54
<211> LENGTH: 326
<212> TYPE: PRT
<213> ORGANISM: Neisseria meningitidis
<220> FEATURE:
<221> NAME/KEY: SITE
<222> LOCATION: (156)
<223> OTHER INFORMATION: unknown
<220> FEATURE:
<221> NAME/KEY: SITE
<222> LOCATION: (309)
<223> OTHER INFORMATION: unknown

<400> SEQUENCE: 54
```

Met Asn Leu Ile Ser Arg Tyr Ile Ile Arg Gln Met Ala Val Met Ala
1               5                   10                  15

Val Tyr Ala Leu Leu Ala Phe Leu Ala Leu Tyr Ser Phe Phe Glu Ile
            20                  25                  30

Leu Tyr Glu Thr Gly Asn Leu Gly Lys Gly Ser Tyr Gly Ile Trp Glu
        35                  40                  45

Met Leu Gly Tyr Thr Ala Leu Lys Met Pro Ala Arg Ala Tyr Glu Leu
    50                  55                  60

Ile Pro Leu Ala Val Leu Ile Gly Gly Leu Val Ser Leu Ser Gln Leu
65                  70                  75                  80

Ala Ala Gly Ser Glu Leu Thr Val Ile Lys Ala Ser Gly Met Ser Thr
                85                  90                  95

Lys Lys Leu Leu Leu Ile Leu Ser Gln Phe Gly Phe Ile Phe Ala Ile
            100                 105                 110

Ala Thr Val Ala Leu Gly Glu Trp Val Ala Pro Thr Leu Ser Gln Lys
        115                 120                 125

Ala Glu Asn Ile Lys Ala Ala Ala Ile Asn Gly Lys Ile Ser Thr Gly
    130                 135                 140

Asn Thr Gly Leu Trp Leu Lys Glu Lys Asn Ser Xaa Ile Asn Val Arg
145                 150                 155                 160

Glu Met Leu Pro Asp His Thr Leu Leu Gly Ile Lys Ile Trp Ala Arg
                165                 170                 175

Asn Asp Lys Asn Glu Leu Ala Glu Ala Val Glu Ala Asp Ser Ala Val
            180                 185                 190

```
Leu Asn Ser Asp Gly Ser Trp Gln Leu Lys Asn Ile Arg Arg Ser Thr
        195                 200                 205

Leu Gly Glu Asp Lys Val Glu Val Ser Ile Ala Ala Glu Glu Asn Trp
    210                 215                 220

Pro Ile Ser Val Lys Arg Asn Leu Met Asp Val Leu Leu Val Lys Pro
225                 230                 235                 240

Asp Gln Met Ser Val Gly Glu Leu Thr Thr Tyr Ile Arg His Leu Gln
                245                 250                 255

Asn Asn Ser Gln Asn Thr Arg Ile Tyr Ala Ile Ala Trp Trp Arg Lys
            260                 265                 270

Leu Val Tyr Pro Ala Ala Ala Trp Val Met Ala Leu Val Ala Phe Ala
        275                 280                 285

Phe Thr Pro Gln Thr Thr Arg His Gly Asn Met Gly Leu Lys Leu Phe
        290                 295                 300

Gly Gly Ile Cys Xaa Gly Leu Leu Phe His Leu Ala Gly Arg Leu Phe
305                 310                 315                 320

Gly Phe Thr Ser Gln Leu
                325

<210> SEQ ID NO 55
<211> LENGTH: 1071
<212> TYPE: DNA
<213> ORGANISM: Neisseria meningitidis
<220> FEATURE:
<221> NAME/KEY: misc_feature
<222> LOCATION: (148)
<223> OTHER INFORMATION: any nucleotide
<220> FEATURE:
<221> NAME/KEY: misc_feature
<222> LOCATION: (153)
<223> OTHER INFORMATION: any nucleotide
<220> FEATURE:
<221> NAME/KEY: misc_feature
<222> LOCATION: (172)
<223> OTHER INFORMATION: any nucleotide
<220> FEATURE:
<221> NAME/KEY: misc_feature
<222> LOCATION: (229)
<223> OTHER INFORMATION: any nucleotide
<220> FEATURE:
<221> NAME/KEY: misc_feature
<222> LOCATION: (260)
<223> OTHER INFORMATION: any nucleotide
<220> FEATURE:
<221> NAME/KEY: misc_feature
<222> LOCATION: (669)
<223> OTHER INFORMATION: any nucleotide
<220> FEATURE:
<221> NAME/KEY: misc_feature
<222> LOCATION: (770)..(772)
<223> OTHER INFORMATION: any nucleotide
<220> FEATURE:
<221> NAME/KEY: misc_feature
<222> LOCATION: (907)
<223> OTHER INFORMATION: any nucleotide
<220> FEATURE:
<221> NAME/KEY: misc_feature
<222> LOCATION: (951)
<223> OTHER INFORMATION: any nucleotide
<220> FEATURE:
<221> NAME/KEY: misc_feature
<222> LOCATION: (961)
<223> OTHER INFORMATION: any nucleotide
<220> FEATURE:
<221> NAME/KEY: misc_feature
<222> LOCATION: (1001)
<223> OTHER INFORMATION: any nucleotide

<400> SEQUENCE: 55
```

```
atgaacctga tttcacgtta catcatccgt caaatggcgg ttatggcggt ttacgcgctc      60
cttgccttcc tcgctttgta cagctttttt gaaatcctgt acgaaaccgg caacctcggc     120
aaaggcagtt acggcatatg ggaaatgntg ggntacaccg ccctcaaaat gnccgcccgc     180
gcctacgaac tgatgcccct cgccgtcctt atcggcggac tggtctctnt cagccagctt     240
gccgccggca gcgaactgan cgtcatcaaa gccagcggca tgagcaccaa aaagctgctg     300
ttgattctgt cgcagttcgg tttattttt gctattgcca ccgtcgcgct cggcgaatgg      360
gttgcgccca cactgagcca aaagccgaa aacatcaaag ccgcggccat caacggcaaa      420
atcagtaccg gcaataccgg cctttggctg aaagaaaaaa acagcattat caatgtgcgc     480
gaaatgttgc ccgaccatac cctgctgggc attaaaatct gggcccgcaa cgataaaaac     540
gaactggcag aggcagtgga agccgattcc gccgttttga acagcgacgg cagttggcag     600
ttgaaaaaca tccgccgcag cacgcttggc gaagacaaag tcgaggtctc tattgcggct     660
gaagaaaant ggccgatttc cgtcaaacgc aacctgatgg acgtattgct cgtcaaaccc     720
gaccaaatgt ccgtcggcga actgaccacc tacatccgcc acctccaaan nnacagccaa     780
aacacccgaa tctacgccat cgcatggtgg cgcaaattgg tttacccgc cgcagcctgg      840 gtgatggcgc tcgtcgcctt tgcctttacc ccgcaaacca cccgccacgg caatatgggc     900
ttaaaantct tcggcggcat ctgtctcgga ttgctgttcc accttgccgg ncggtcttc      960 nggtttacca gccaactcta cggcatcccg cccttcctcg ncggcgcact acctaccata    1020
gccttcgcct gctcgccgt ttggctgata cgcaaacagg aaaaacgcta a              1071
```

```
<210> SEQ ID NO 56
<211> LENGTH: 356
<212> TYPE: PRT
<213> ORGANISM: Neisseria meningitidis
<220> FEATURE:
<221> NAME/KEY: SITE
<222> LOCATION: (50)
<223> OTHER INFORMATION: unknown
<220> FEATURE:
<221> NAME/KEY: SITE
<222> LOCATION: (58)
<223> OTHER INFORMATION: unknown
<220> FEATURE:
<221> NAME/KEY: SITE
<222> LOCATION: (77)
<223> OTHER INFORMATION: unknown
<220> FEATURE:
<221> NAME/KEY: SITE
<222> LOCATION: (87)
<223> OTHER INFORMATION: unknown
<220> FEATURE:
<221> NAME/KEY: SITE
<222> LOCATION: (223)
<223> OTHER INFORMATION: unknown
<220> FEATURE:
<221> NAME/KEY: SITE
<222> LOCATION: (257)..(258)
<223> OTHER INFORMATION: unknown
<220> FEATURE:
<221> NAME/KEY: SITE
<222> LOCATION: (303)
<223> OTHER INFORMATION: unknown
<220> FEATURE:
<221> NAME/KEY: SITE
<222> LOCATION: (321)
<223> OTHER INFORMATION: unknown
<220> FEATURE:
<221> NAME/KEY: SITE
<222> LOCATION: (334)
<223> OTHER INFORMATION: unknown
```

-continued

```
<400> SEQUENCE: 56

Met Asn Leu Ile Ser Arg Tyr Ile Ile Arg Gln Met Ala Val Met Ala
  1               5                  10                  15

Val Tyr Ala Leu Leu Ala Phe Leu Ala Leu Tyr Ser Phe Phe Glu Ile
             20                  25                  30

Leu Tyr Glu Thr Gly Asn Leu Gly Lys Gly Ser Tyr Gly Ile Trp Glu
         35                  40                  45

Met Xaa Gly Tyr Thr Ala Leu Lys Met Xaa Ala Arg Ala Tyr Glu Leu
     50                  55                  60

Met Pro Leu Ala Val Leu Ile Gly Gly Leu Val Ser Xaa Ser Gln Leu
 65                  70                  75                  80

Ala Ala Gly Ser Glu Leu Xaa Val Ile Lys Ala Ser Gly Met Ser Thr
                 85                  90                  95

Lys Lys Leu Leu Leu Ile Leu Ser Gln Phe Gly Phe Ile Phe Ala Ile
            100                 105                 110

Ala Thr Val Ala Leu Gly Glu Trp Val Ala Pro Thr Leu Ser Gln Lys
        115                 120                 125

Ala Glu Asn Ile Lys Ala Ala Ile Asn Gly Lys Ile Ser Thr Gly
130                 135                 140

Asn Thr Gly Leu Trp Leu Lys Glu Lys Asn Ser Ile Ile Asn Val Arg
145                 150                 155                 160

Glu Met Leu Pro Asp His Thr Leu Leu Gly Ile Lys Ile Trp Ala Arg
                165                 170                 175

Asn Asp Lys Asn Glu Leu Ala Glu Ala Val Glu Ala Asp Ser Ala Val
            180                 185                 190

Leu Asn Ser Asp Gly Ser Trp Gln Leu Lys Asn Ile Arg Arg Ser Thr
        195                 200                 205

Leu Gly Glu Asp Lys Val Glu Val Ser Ile Ala Ala Glu Xaa Trp
    210                 215                 220

Pro Ile Ser Val Lys Arg Asn Leu Met Asp Val Leu Leu Val Lys Pro
225                 230                 235                 240

Asp Gln Met Ser Val Gly Glu Leu Thr Thr Tyr Ile Arg His Leu Gln
                245                 250                 255

Xaa Xaa Ser Gln Asn Thr Arg Ile Tyr Ala Ile Ala Trp Trp Arg Lys
            260                 265                 270

Leu Val Tyr Pro Ala Ala Ala Trp Val Met Ala Leu Val Ala Phe Ala
        275                 280                 285

Phe Thr Pro Gln Thr Thr Arg His Gly Asn Met Gly Leu Lys Xaa Phe
    290                 295                 300

Gly Gly Ile Cys Leu Gly Leu Leu Phe His Leu Ala Gly Arg Leu Phe
305                 310                 315                 320

Xaa Phe Thr Ser Gln Leu Tyr Gly Ile Pro Pro Phe Leu Xaa Gly Ala
                325                 330                 335

Leu Pro Thr Ile Ala Phe Ala Leu Leu Ala Val Trp Leu Ile Arg Lys
            340                 345                 350

Gln Glu Lys Arg
            355

<210> SEQ ID NO 57
<211> LENGTH: 854
<212> TYPE: DNA
<213> ORGANISM: Neisseria meningitidis

<400> SEQUENCE: 57
```

```
gcagtagccg aaactgccaa cagccagggc aaaggtaaac aggcaggcag ttcggtttct      60
gtttcactga aaacttcagg cgacctttgc ggcaaactca aaaccaccct taaaactttg     120
gtctgctctt tggtttccct gagtatggta ttgcctgccc atgcccaaat taccaccgac     180
aaatcagcac ctaaaaacca gcaggtcgtt atccttaaaa ccaacactgg tgcccccttg     240
gtgaatatcc aaactccgaa tggacgcgga ttgagccaca accgctatac gcatttgatg     300
ttgacaacaa aggggcagtg ttaaacaacg accgtaacaa taatccgttt gtggtcaaag     360
gcagtgcgca attgattttg aacgaggtac gcggtacggc tagcaaactc aacggcatcg     420
ttaccgtagg cggtcaaaag gccgacgtga ttattgccaa ccccaacggc attaccgtta     480
atggcggcgg ctttaaaaat gtcggtcggg gcatcttaac taccggtgcg ccccaaatcg     540
gcaaagacgt tgcactgaca ggatttgatg tgcgtcaagg cacattggac cgtagragca     600
gcaggttgga atgataaagg cggagcmrmy tacaccgggg tacttgctcg tgcagttgct     660
ttgcagggga aattwmmggg taaaaactgg cggtttctac cggtcctcag aaagtagatt     720
acgccagcgg cgaaatcagt gcaggtacgg cagcgggtac gaaaccgact attgcccttg     780
atactgccgc actgggcggt atgtacgccg acagcatcac actgattgcc aatgaaaaag     840
gcgtaggcgt ctaa                                                       854

<210> SEQ ID NO 58
<211> LENGTH: 284
<212> TYPE: PRT
<213> ORGANISM: Neisseria meningitidis
<220> FEATURE:
<221> NAME/KEY: SITE
<222> LOCATION: (96)
<223> OTHER INFORMATION: unknown
<220> FEATURE:
<221> NAME/KEY: SITE
<222> LOCATION: (199)
<223> OTHER INFORMATION: unknown
<220> FEATURE:
<221> NAME/KEY: SITE
<222> LOCATION: (210)
<223> OTHER INFORMATION: unknown
<220> FEATURE:
<221> NAME/KEY: SITE
<222> LOCATION: (225)..(226)
<223> OTHER INFORMATION: unknown
<220> FEATURE:
<221> NAME/KEY: SITE
<222> LOCATION: (229)
<223> OTHER INFORMATION: unknown

<400> SEQUENCE: 58

Ala Val Ala Glu Thr Ala Asn Ser Gln Gly Lys Gly Lys Gln Ala Gly
 1               5                  10                  15

Ser Ser Val Ser Val Ser Leu Lys Thr Ser Gly Asp Leu Cys Gly Lys
                20                  25                  30

Leu Lys Thr Thr Leu Lys Thr Leu Val Cys Ser Leu Val Ser Leu Ser
            35                  40                  45

Met Val Leu Pro Ala His Ala Gln Ile Thr Thr Asp Lys Ser Ala Pro
        50                  55                  60

Lys Asn Gln Gln Val Val Ile Leu Lys Thr Asn Thr Gly Ala Pro Leu
    65                  70                  75                  80

Val Asn Ile Gln Thr Pro Asn Gly Arg Gly Leu Ser His Asn Arg Xaa
                85                  90                  95

Tyr Ala Phe Asp Val Asp Asn Lys Gly Ala Val Leu Asn Asn Asp Arg
               100                 105                 110
```

```
Asn Asn Asn Pro Phe Val Val Lys Gly Ser Ala Gln Leu Ile Leu Asn
        115                 120                 125

Glu Val Arg Gly Thr Ala Ser Lys Leu Asn Gly Ile Val Thr Val Gly
130                 135                 140

Gly Gln Lys Ala Asp Val Ile Ile Ala Asn Pro Asn Gly Ile Thr Val
145                 150                 155                 160

Asn Gly Gly Phe Lys Asn Val Gly Arg Gly Ile Leu Thr Thr Gly
                165                 170                 175

Ala Pro Gln Ile Gly Lys Asp Gly Ala Leu Thr Gly Phe Asp Val Val
            180                 185                 190

Lys Ala His Trp Thr Val Xaa Ala Ala Gly Trp Asn Asp Lys Gly Gly
        195                 200                 205

Ala Xaa Tyr Thr Gly Val Leu Ala Arg Ala Val Ala Leu Gln Gly Lys
    210                 215                 220

Xaa Xaa Gly Lys Xaa Leu Ala Val Ser Thr Gly Pro Gln Lys Val Asp
225                 230                 235                 240

Tyr Ala Ser Gly Glu Ile Ser Ala Gly Thr Ala Gly Thr Lys Pro
                245                 250                 255

Thr Ile Ala Leu Asp Thr Ala Ala Leu Gly Gly Met Tyr Ala Asp Ser
            260                 265                 270

Ile Thr Leu Ile Ala Asn Glu Lys Gly Val Gly Val
        275                 280

<210> SEQ ID NO 59
<211> LENGTH: 5937
<212> TYPE: DNA
<213> ORGANISM: Neisseria meningitidis

<400> SEQUENCE: 59
atgaataaag gtttacatcg cattatcttt agtaaaaagc acagcaccat ggttgcagta      60
gccgaaactg ccaacagcca gggcaaaggt aaacaggcag cagttcggt ttctgtttca     120 ctgaaaactt caggcgacct ttgcggcaaa ctcaaaacca cccttaaaac tttggtctgc    180
tctttggttt ccctgagtat ggtattgcct gcccatgccc aaattaccac cgacaaatca    240
gcacctaaaa accagcaggt cgttatcctt aaaaccaaca ctggtgcccc cttggtgaat    300
atccaaactc cgaatggacg cggattgagc acaaccgct atacgcagtt tgatgttgac     360
aacaaagggg cagtgttaaa caacgaccgt aacaataatc cgtttgtggt caaaggcagt    420
gcgcaattga ttttgaacga ggtacgcggt acggctagca aactcaacgg catcgttacc    480
gtaggcggtc aaaaggccga cgtgattatt gccaacccca acggcattac cgttaatggc    540
ggcggcttta aaaatgtcgg tcggggcatc ttaactaccg gtgcgcccca aatcggcaaa    600
gacggtgcac tgacaggatt tgatgtgcgt caaggcacat tgaccgtagg agcagcaggt    660
tggaatgata aggcggagc cgactacacc ggggtacttg ctcgtgcagt tgctttgcag    720
gggaaattac agggtaaaaa cctggcggtt tctaccggtc ctcagaaagt agattacgcc    780
agcggcgaaa tcagtgcagg tacggcagcg ggtacgaaac cgactattgc ccttgatact    840
gccgcactgg gcggtatgta cgccgacagc atcacactga ttgccaatga aaaaggcgta    900
ggcgtcaaaa atgccggcac actcgaagcg gccaagcaat tgattgtgac ttcgtcaggc    960
cgcattgaaa acagcggccg catcgccacc actgccgacg gcaccgaagc ttcaccgact   1020
tatctctcca tcgaaaccac cgaaaaagga gcggcaggca catttatctc caatggtggt   1080
cggatcgaga gcaaaggctt attggttatt gagacgggag aagatatcag cttgcgtaac   1140
```

```
ggagccgtgg tgcagaataa cggcagtcgc ccagctacca cggtattaaa tgctggtcat   1200
aatttggtga ttgagagcaa aactaatgtg aacaatgcca aaggcccggc tactctgtcg   1260
gccgacggcc gtaccgtcat caaggaggcc agtattcaga ctggcactac cgtatacagt   1320
tccagcaaag gcaacgccga attaggcaat aacacacgca ttaccggggc agatgttacc   1380
gtattatcca acggcaccat cagcagttcc gccgtaatag atgccaaaga caccgcacac   1440
atcgaagcag gcaaaccgct ttctttggaa gcttcaacag ttacctccga tatccgctta   1500
aacggaggca gtatcaaggg cggcaagcag cttgctttac tggcagacga taacattact   1560
gccaaaacta ccaatctgaa tactcccggc aatctgtatg ttcatacagg taaagatctg   1620
aatttgaatg ttgataaaga tttgtctgcc gccagcatcc atttgaaatc ggataacgct   1680
gcccatatta ccggcaccag taaaaccctc actgcctcaa aagacatggg tgtggaggca   1740
ggctcgctga atgttaccaa taccaatctg cgtaccaact cgggtaatct gcacattcag   1800
gcagccaaag gcaatattca gcttcgcaat accaagctga acgcagccaa ggctctcgaa   1860
accaccgcat tgcagggcaa tatcgtttca gacggccttc atgctgtttc tgcagacggt   1920
catgtatcct tattggccaa cggtaatgcc gactttaccg gtcacaatac cctgacagcc   1980
aaggccgatg tcaatgcagg atcggttggt aaaggccgtc tgaaagcaga caataccaat   2040
atcacttcat cttcaggaga tattacgttg gttgccggca acggtattca gcttggtgac   2100
ggaaaacaac gcaattcaat caacggaaaa cacatcagca tcaaaaacaa cggtggtaat   2160
gccgacttaa aaaaccttaa cgtccatgcc aaaagcgggg cattgaacat tcattccgac   2220
cgggcattga gcatagaaaa taccaagctg gagtctaccc ataatacgca tcttaatgca   2280
caacacgagc gggtaacgct caaccaagta gatgcctacg cacaccgtca tctaagcatt   2340
accggcagcc agatttggca aaacgacaaa ctgccttctg ccaacaagct ggtggctaac   2400
ggtgtattgg cactcaatgc gcgctattcc caaattgccg acaacaccac gctgagagcg   2460
ggtgcaatca accttactgc cggtaccgcc ctagtcaagc gcggcaacat caattggagt   2520
accgtttcga ccaaaacttt ggaagataat gccgaattaa aaccattggc cggacggctg   2580
aatattgaag caggtagcgg cacattaacc atcgaacctg ccaaccgcat cagtgcgcat   2640
accgacctga gcatcaaaac aggcggaaaa ttgctgttgt ctgcaaaagg aggaaatgca   2700
ggtgcgccta gtgctcaagt ttcctcattg gaagcaaaag gcaatatccg tctggttaca   2760
ggagaaacag atttaagagg ttctaaaatt acagccggta aaaacttggt tgtcgccacc   2820
accaaaggca agttgaatat cgaagccgta aacaactcat tcagcaatta ttttcctaca   2880
caaaaagcgg ctgaactcaa ccaaaaatcc aaagaattgg aacagcagat tgcgcagttg   2940
aaaaaaagct cgcctaaaag caagctgatt ccaaccctgc aagaagaacg cgaccgtctc   3000
gctttctata ttcaagccat caacaaggaa gttaaaggta aaaacccaa aggcaaagaa   3060 tacctgcaag ccaagctttc tgcacaaaat attgacttga tttccgcaca aggcatcgaa   3120
atcagcggtt ccgatattac cgcttccaaa aaactgaacc ttcacgccgc aggcgtattg   3180
ccaaaggcag cagattcaga ggcggctgct attctgattg acggcataac cgaccaatat   3240
gaaattggca agcccaccta caagagtcac tacgacaaag ctgctctgaa caagccttca   3300
cgtttgaccg gacgtacagg ggtaagtatt catgcagctg cggcactcga tgatgcacgt   3360
attattatcg gtgcatccga aatcaaagct ccctcaggca gcatagacat caaagcccat   3420
agtgatattg tactggaggc tggacaaaac gatgcctata ccttcttaaa aaccaaaggt   3480
aaaagcggca aaatcatcag aaaaaccaag tttaccagca cccgcgacca cctgattatg   3540
```

```
ccagccccg tcgagctgac cgccaacggc ataacgcttc aggcaggcgg caacatcgaa    3600
gctaatacca cccgcttcaa tgcccctgca ggtaaagtta ccctggttgc gggtgaagag    3660
ctgcaactgc tggcagaaga aggcatccac aagcacgagt tggatgtcca aaaaagccgc    3720
cgctttatcg gcatcaaggt aggcaagagc aattacagta aaaacgaact gaacgaaacc    3780
aaattgcctg tccgcgtcgt cgcccaaact gcagccaccc gttcaggctg ggataccgtg    3840
ctcgaaggta ccgaattcaa aaccacgctg gccggtgcgg acattcaggc aggtgtaggc    3900
gaaaaagccc gtgccgatgc gaaaattatc ctcaaaggca ttgtgaaccg tatccagtcg    3960
gaagaaaaat tagaaaccaa ctcaaccgta tggcagaaac aggccggacg cggcagcact    4020
atcgaaacgc tgaaactgcc cagcttcgaa agccctactc cgcccaaact gaccgccccc    4080
ggtggctata tcgtcgacat tccgaaaggc aatttgaaaa ccgaaatcga aagctggcc    4140 aaacagcccg agtatgccta tctgaaacag ctccaagtag cgaaaaacgt caactggaac    4200
caggtgcaac tggcttacga taaatgggac tataagcagg aaggcttaac cagagccggt    4260
gcagcgattg ttaccataat cgtaaccgca ctgacttatg gatcggcgc aaccgcagcg    4320 ggcggtgtag ccgcttcagg aagtagtaca gccgcagctg ccggaacagc cgccacaacg    4380
acagcagcag ctactaccgt ttctacagcg actgccatgc aaaccgctgc tttagcctcc    4440
ttgtatagcc aagcagctgt atccatcatc aataataaag gtgatgtcgg caaagcgttg    4500
aaagatctcg gcaccagtga tacggtcaag cagattgtca cttctgccct gacggcgggt    4560
gcattaaatc agatgggcgc agatattgcc caattgaaca gcaaggtaag aaccgaactg    4620
ttcagcagta cgggcaatca aactattgcc aaccttggag gcagactggc taccaatctc    4680
agtaatgcag gtatctcagc tggtatcaat accgccgtca acggcggcag cctgaaagac    4740
aacttaggca atgccgcatt aggagcattg gttaatagct tccaaggaga agccgccagc    4800
aaaatcaaaa caaccttcag cgacgattat gttgccaaac agttcgccca cgctttggct    4860
gggtgtgtta gcggattggt acaaggaaaa tgtaaagacg gggcaattgg cgcagcagtt    4920
ggggaaatcg tagccgactc catgcttggc ggcagaaacc ctgctacact cagcgatgcg    4980
gaaaagcata aggttatcag ttactcgaag attattgccg gcagcgtggc ggcactcaac    5040
ggcggcgatg tgaatactgc ggcgaatgcg gctgaggtgg cggtagtgaa taatgctttg    5100
aattttgaca gtaccctac caatgcgaaa aagcatcaac cgcagaagcc cgacaaaacc    5160
gcactggaaa aaattatcca aggtattatg cctgcacatg cagcaggtgc gatgactaat    5220
ccgcaggata aggatgctgc catttggata agcaatatcc gtaatggcat cacaggcccg    5280
attgtgatta ccagctatgg ggtttatgct gcaggttgga cagctccgct gatcggtaca    5340
gcgggtaaat tagctatcag cacctgcatg gctaatcctt ctggttgtac tgtcatggtc    5400
actcaggctg ccgaagcggg cgcgggaatc gccacgggtg cggtaacggt aggcaacgct    5460
tgggaagcgc ctgtggggc gttgtcgaaa gcgaaggcgg ccaagcaggc tataccaacc    5520
cagacagtta agaacttga tggcttacta caagaatcaa aaaatatagg tgctgtaaat    5580
acacgaatta atatagcgaa tagtactact cgatatacac caatgagaca acgggacaa    5640 ccggtatctg ctggctttga gcatgttctt gagggcact tccataggcc tattgcgaat    5700
aaccgttcag ttttttaccat ctccccaaat gaattgaagg ttatacttca agtaataaa    5760 gtagtttctt ctcccgtatc gatgactcct gatggccaat atatgcggac tgtcgatgta    5820
ggaaaagtta ttggtactac ttctattaaa gaaggtggac aacccacaac tacaattaaa    5880
```
gtatttacag ataagtcagg aaatttgatt actacatacc cagtaaaagg aaactaa    5937

<210> SEQ ID NO 60
<211> LENGTH: 1978
<212> TYPE: PRT
<213> ORGANISM: Neisseria meningitidis

<400> SEQUENCE: 60

Met Asn Lys Gly Leu His Arg Ile Ile Phe Ser Lys Lys His Ser Thr
1               5                   10                  15

Met Val Ala Val Ala Glu Thr Ala Asn Ser Gln Gly Lys Gly Lys Gln
            20                  25                  30

Ala Gly Ser Ser Val Ser Val Ser Leu Lys Thr Ser Gly Asp Leu Cys
        35                  40                  45

Gly Lys Leu Lys Thr Thr Leu Lys Thr Leu Val Cys Ser Leu Val Ser
    50                  55                  60

Leu Ser Met Val Leu Pro Ala His Ala Gln Ile Thr Thr Asp Lys Ser
65                  70                  75                  80

Ala Pro Lys Asn Gln Gln Val Val Ile Leu Lys Thr Asn Thr Gly Ala
                85                  90                  95

Pro Leu Val Asn Ile Gln Thr Pro Asn Gly Arg Gly Leu Ser His Asn
            100                 105                 110

Arg Tyr Thr Gln Phe Asp Val Asp Asn Lys Gly Ala Val Leu Asn Asn
        115                 120                 125

Asp Arg Asn Asn Asn Pro Phe Val Val Lys Gly Ser Ala Gln Leu Ile
    130                 135                 140

Leu Asn Glu Val Arg Gly Thr Ala Ser Lys Leu Asn Gly Ile Val Thr
145                 150                 155                 160

Val Gly Gly Gln Lys Ala Asp Val Ile Ile Ala Asn Pro Asn Gly Ile
                165                 170                 175

Thr Val Asn Gly Gly Phe Lys Asn Val Gly Arg Gly Ile Leu Thr
            180                 185                 190

Thr Gly Ala Pro Gln Ile Gly Lys Asp Gly Ala Leu Thr Gly Phe Asp
        195                 200                 205

Val Arg Gln Gly Thr Leu Thr Val Gly Ala Ala Gly Trp Asn Asp Lys
    210                 215                 220

Gly Gly Ala Asp Tyr Thr Gly Val Leu Ala Arg Ala Val Ala Leu Gln
225                 230                 235                 240

Gly Lys Leu Gln Gly Lys Asn Leu Ala Val Ser Thr Gly Pro Gln Lys
                245                 250                 255

Val Asp Tyr Ala Ser Gly Glu Ile Ser Ala Gly Thr Ala Ala Gly Thr
            260                 265                 270

Lys Pro Thr Ile Ala Leu Asp Thr Ala Ala Leu Gly Gly Met Tyr Ala
        275                 280                 285

Asp Ser Ile Thr Leu Ile Ala Asn Glu Lys Gly Val Gly Val Lys Asn
    290                 295                 300

Ala Gly Thr Leu Glu Ala Ala Lys Gln Leu Ile Val Thr Ser Ser Gly
305                 310                 315                 320

Arg Ile Glu Asn Ser Gly Arg Ile Ala Thr Ala Asp Gly Thr Glu
                325                 330                 335

Ala Ser Pro Thr Tyr Leu Ser Ile Glu Thr Thr Glu Lys Gly Ala Ala
            340                 345                 350

Gly Thr Phe Ile Ser Asn Gly Gly Arg Ile Glu Ser Lys Gly Leu Leu
        355                 360                 365

-continued

```
Val Ile Glu Thr Gly Glu Asp Ile Ser Leu Arg Asn Gly Ala Val Val
    370                 375                 380

Gln Asn Asn Gly Ser Arg Pro Ala Thr Thr Val Leu Asn Ala Gly His
385                 390                 395                 400

Asn Leu Val Ile Glu Ser Lys Thr Asn Val Asn Ala Lys Gly Pro
                405                 410                 415

Ala Thr Leu Ser Ala Asp Gly Arg Thr Val Ile Lys Glu Ala Ser Ile
                420                 425                 430

Gln Thr Gly Thr Thr Val Tyr Ser Ser Lys Gly Asn Ala Glu Leu
                435                 440                 445

Gly Asn Asn Thr Arg Ile Thr Gly Ala Asp Val Thr Val Leu Ser Asn
    450                 455                 460

Gly Thr Ile Ser Ser Ala Val Ile Asp Ala Lys Asp Thr Ala His
465                 470                 475                 480

Ile Glu Ala Gly Lys Pro Leu Ser Leu Glu Ala Ser Thr Val Thr Ser
                485                 490                 495

Asp Ile Arg Leu Asn Gly Gly Ser Ile Lys Gly Gly Lys Gln Leu Ala
                500                 505                 510

Leu Leu Ala Asp Asp Asn Ile Thr Ala Lys Thr Thr Asn Leu Asn Thr
                515                 520                 525

Pro Gly Asn Leu Tyr Val His Thr Gly Lys Asp Leu Asn Leu Asn Val
    530                 535                 540

Asp Lys Asp Leu Ser Ala Ala Ser Ile His Leu Lys Ser Asp Asn Ala
545                 550                 555                 560

Ala His Ile Thr Gly Thr Ser Lys Thr Leu Thr Ala Ser Lys Asp Met
                565                 570                 575

Gly Val Glu Ala Gly Ser Leu Asn Val Thr Asn Thr Asn Leu Arg Thr
                580                 585                 590

Asn Ser Gly Asn Leu His Ile Gln Ala Ala Lys Gly Asn Ile Gln Leu
    595                 600                 605

Arg Asn Thr Lys Leu Asn Ala Ala Lys Ala Leu Glu Thr Thr Ala Leu
610                 615                 620

Gln Gly Asn Ile Val Ser Asp Gly Leu His Ala Val Ser Ala Asp Gly
625                 630                 635                 640

His Val Ser Leu Leu Ala Asn Gly Asn Ala Asp Phe Thr Gly His Asn
                645                 650                 655

Thr Leu Thr Ala Lys Ala Asp Val Asn Ala Gly Ser Val Gly Lys Gly
                660                 665                 670

Arg Leu Lys Ala Asp Asn Thr Asn Ile Thr Ser Ser Gly Asp Ile
    675                 680                 685

Thr Leu Val Ala Gly Asn Gly Ile Gln Leu Gly Asp Gly Lys Gln Arg
    690                 695                 700

Asn Ser Ile Asn Gly Lys His Ile Ser Ile Lys Asn Asn Gly Gly Asn
705                 710                 715                 720

Ala Asp Leu Lys Asn Leu Asn Val His Ala Lys Ser Gly Ala Leu Asn
                725                 730                 735

Ile His Ser Asp Arg Ala Leu Ser Ile Glu Asn Thr Lys Leu Glu Ser
                740                 745                 750

Thr His Asn Thr His Leu Asn Ala Gln His Glu Arg Val Thr Leu Asn
    755                 760                 765

Gln Val Asp Ala Tyr Ala His Arg His Leu Ser Ile Thr Gly Ser Gln
    770                 775                 780

Ile Trp Gln Asn Asp Lys Leu Pro Ser Ala Asn Lys Leu Val Ala Asn
```

```
                785                 790                 795                 800
Gly Val Leu Ala Leu Asn Ala Arg Tyr Ser Gln Ile Ala Asp Asn Thr
                    805                 810                 815
Thr Leu Arg Ala Gly Ala Ile Asn Leu Thr Ala Gly Thr Ala Leu Val
            820                 825                 830
Lys Arg Gly Asn Ile Asn Trp Ser Thr Val Ser Thr Lys Thr Leu Glu
        835                 840                 845
Asp Asn Ala Glu Leu Lys Pro Leu Ala Gly Arg Leu Asn Ile Glu Ala
    850                 855                 860
Gly Ser Gly Thr Leu Thr Ile Glu Pro Ala Asn Arg Ile Ser Ala His
865                 870                 875                 880
Thr Asp Leu Ser Ile Lys Thr Gly Gly Lys Leu Leu Leu Ser Ala Lys
                885                 890                 895
Gly Gly Asn Ala Gly Ala Pro Ser Ala Gln Val Ser Ser Leu Glu Ala
            900                 905                 910
Lys Gly Asn Ile Arg Leu Val Thr Gly Glu Thr Asp Leu Arg Gly Ser
        915                 920                 925
Lys Ile Thr Ala Gly Lys Asn Leu Val Val Ala Thr Thr Lys Gly Lys
    930                 935                 940
Leu Asn Ile Glu Ala Val Asn Asn Ser Phe Ser Asn Tyr Phe Pro Thr
945                 950                 955                 960
Gln Lys Ala Ala Glu Leu Asn Gln Lys Ser Lys Glu Leu Glu Gln Gln
                965                 970                 975
Ile Ala Gln Leu Lys Lys Ser Ser Pro Lys Ser Lys Leu Ile Pro Thr
            980                 985                 990
Leu Gln Glu Glu Arg Asp Arg Leu Ala Phe Tyr Ile Gln Ala Ile Asn
        995                 1000                1005
Lys Glu Val Lys Gly Lys Lys Pro Lys Gly Lys Glu Tyr Leu Gln Ala
    1010                1015                1020
Lys Leu Ser Ala Gln Asn Ile Asp Leu Ile Ser Ala Gln Gly Ile Glu
1025                1030                1035                1040
Ile Ser Gly Ser Asp Ile Thr Ala Ser Lys Lys Leu Asn Leu His Ala
                1045                1050                1055
Ala Gly Val Leu Pro Lys Ala Ala Asp Ser Glu Ala Ala Ile Leu
            1060                1065                1070
Ile Asp Gly Ile Thr Asp Gln Tyr Glu Ile Gly Lys Pro Thr Tyr Lys
        1075                1080                1085
Ser His Tyr Asp Lys Ala Ala Leu Asn Lys Pro Ser Arg Leu Thr Gly
    1090                1095                1100
Arg Thr Gly Val Ser Ile His Ala Ala Ala Leu Asp Asp Ala Arg
1105                1110                1115                1120
Ile Ile Ile Gly Ala Ser Glu Ile Lys Ala Pro Ser Gly Ser Ile Asp
                1125                1130                1135
Ile Lys Ala His Ser Asp Ile Val Leu Glu Ala Gly Gln Asn Asp Ala
            1140                1145                1150
Tyr Thr Phe Leu Lys Thr Lys Gly Lys Ser Gly Lys Ile Ile Arg Lys
        1155                1160                1165
Thr Lys Phe Thr Ser Thr Arg Asp His Leu Ile Met Pro Ala Pro Val
    1170                1175                1180
Glu Leu Thr Ala Asn Gly Ile Thr Leu Gln Ala Gly Gly Asn Ile Glu
1185                1190                1195                1200
Ala Asn Thr Thr Arg Phe Asn Ala Pro Ala Gly Lys Val Thr Leu Val
                1205                1210                1215
```

-continued

Ala Gly Glu Glu Leu Gln Leu Leu Ala Glu Glu Gly Ile His Lys His
        1220                1225                1230

Glu Leu Asp Val Gln Lys Ser Arg Arg Phe Ile Gly Ile Lys Val Gly
        1235                1240                1245

Lys Ser Asn Tyr Ser Lys Asn Glu Leu Asn Glu Thr Lys Leu Pro Val
        1250                1255                1260

Arg Val Val Ala Gln Thr Ala Ala Thr Arg Ser Gly Trp Asp Thr Val
1265                1270                1275                1280

Leu Glu Gly Thr Glu Phe Lys Thr Thr Leu Ala Gly Ala Asp Ile Gln
        1285                1290                1295

Ala Gly Val Gly Glu Lys Ala Arg Ala Asp Ala Lys Ile Ile Leu Lys
        1300                1305                1310

Gly Ile Val Asn Arg Ile Gln Ser Glu Glu Lys Leu Glu Thr Asn Ser
        1315                1320                1325

Thr Val Trp Gln Lys Gln Ala Gly Arg Gly Ser Thr Ile Glu Thr Leu
        1330                1335                1340

Lys Leu Pro Ser Phe Glu Ser Pro Thr Pro Lys Leu Thr Ala Pro
1345                1350                1355                1360

Gly Gly Tyr Ile Val Asp Ile Pro Lys Gly Asn Leu Lys Thr Glu Ile
        1365                1370                1375

Glu Lys Leu Ala Lys Gln Pro Glu Tyr Ala Tyr Leu Lys Gln Leu Gln
        1380                1385                1390

Val Ala Lys Asn Val Asn Trp Asn Gln Val Gln Leu Ala Tyr Asp Lys
        1395                1400                1405

Trp Asp Tyr Lys Gln Glu Gly Leu Thr Arg Ala Gly Ala Ala Ile Val
        1410                1415                1420

Thr Ile Ile Val Thr Ala Leu Thr Tyr Gly Tyr Gly Ala Thr Ala Ala
1425                1430                1435                1440

Gly Gly Val Ala Ala Ser Gly Ser Ser Thr Ala Ala Ala Ala Gly Thr
        1445                1450                1455

Ala Ala Thr Thr Thr Ala Ala Ala Thr Thr Val Ser Thr Ala Thr Ala
        1460                1465                1470

Met Gln Thr Ala Ala Leu Ala Ser Leu Tyr Ser Gln Ala Ala Val Ser
        1475                1480                1485

Ile Ile Asn Asn Lys Gly Asp Val Gly Lys Ala Leu Lys Asp Leu Gly
        1490                1495                1500

Thr Ser Asp Thr Val Lys Gln Ile Val Thr Ser Ala Leu Thr Ala Gly
1505                1510                1515                1520

Ala Leu Asn Gln Met Gly Ala Asp Ile Ala Gln Leu Asn Ser Lys Val
        1525                1530                1535

Arg Thr Glu Leu Phe Ser Ser Thr Gly Asn Gln Thr Ile Ala Asn Leu
        1540                1545                1550

Gly Gly Arg Leu Ala Thr Asn Leu Ser Asn Ala Gly Ile Ser Ala Gly
        1555                1560                1565

Ile Asn Thr Ala Val Asn Gly Gly Ser Leu Lys Asp Asn Leu Gly Asn
        1570                1575                1580

Ala Ala Leu Gly Ala Leu Val Asn Ser Phe Gln Gly Glu Ala Ala Ser
1585                1590                1595                1600

Lys Ile Lys Thr Thr Phe Ser Asp Asp Tyr Val Ala Lys Gln Phe Ala
        1605                1610                1615

His Ala Leu Ala Gly Cys Val Ser Gly Leu Val Gln Gly Lys Cys Lys
        1620                1625                1630

```
Asp Gly Ala Ile Gly Ala Ala Val Gly Glu Ile Val Ala Asp Ser Met
        1635                1640                1645

Leu Gly Gly Arg Asn Pro Ala Thr Leu Ser Asp Ala Glu Lys His Lys
    1650                1655                1660

Val Ile Ser Tyr Ser Lys Ile Ile Ala Gly Ser Val Ala Ala Leu Asn
1665                1670                1675                1680

Gly Gly Asp Val Asn Thr Ala Ala Asn Ala Ala Glu Val Ala Val Val
            1685                1690                1695

Asn Asn Ala Leu Asn Phe Asp Ser Thr Pro Thr Asn Ala Lys Lys His
        1700                1705                1710

Gln Pro Gln Lys Pro Asp Lys Thr Ala Leu Glu Lys Ile Ile Gln Gly
    1715                1720                1725

Ile Met Pro Ala His Ala Ala Gly Ala Met Thr Asn Pro Gln Asp Lys
1730                1735                1740

Asp Ala Ala Ile Trp Ile Ser Asn Ile Arg Asn Gly Ile Thr Gly Pro
1745                1750                1755                1760

Ile Val Ile Thr Ser Tyr Gly Val Tyr Ala Ala Gly Trp Thr Ala Pro
            1765                1770                1775

Leu Ile Gly Thr Ala Gly Lys Leu Ala Ile Ser Thr Cys Met Ala Asn
        1780                1785                1790

Pro Ser Gly Cys Thr Val Met Val Thr Gln Ala Ala Glu Ala Gly Ala
    1795                1800                1805

Gly Ile Ala Thr Gly Ala Val Thr Val Gly Asn Ala Trp Glu Ala Pro
1810                1815                1820

Val Gly Ala Leu Ser Lys Ala Lys Ala Ala Lys Gln Ala Ile Pro Thr
1825                1830                1835                1840

Gln Thr Val Lys Glu Leu Asp Gly Leu Leu Gln Glu Ser Lys Asn Ile
            1845                1850                1855

Gly Ala Val Asn Thr Arg Ile Asn Ile Ala Asn Ser Thr Thr Arg Tyr
        1860                1865                1870

Thr Pro Met Arg Gln Thr Gly Gln Pro Val Ser Ala Gly Phe Glu His
    1875                1880                1885

Val Leu Glu Gly His Phe His Arg Pro Ile Ala Asn Asn Arg Ser Val
1890                1895                1900

Phe Thr Ile Ser Pro Asn Glu Leu Lys Val Ile Leu Gln Ser Asn Lys
1905                1910                1915                1920

Val Val Ser Ser Pro Val Ser Met Thr Pro Asp Gly Gln Tyr Met Arg
            1925                1930                1935

Thr Val Asp Val Gly Lys Val Ile Gly Thr Thr Ser Ile Lys Glu Gly
        1940                1945                1950

Gly Gln Pro Thr Thr Thr Ile Lys Val Phe Thr Asp Lys Ser Gly Asn
    1955                1960                1965

Leu Ile Thr Thr Tyr Pro Val Lys Gly Asn
 1970                1975

<210> SEQ ID NO 61
<211> LENGTH: 4599
<212> TYPE: DNA
<213> ORGANISM: Neisseria meningitidis
<220> FEATURE:
<221> NAME/KEY: misc_feature
<222> LOCATION: (203)
<223> OTHER INFORMATION: any nucleotide
<220> FEATURE:
<221> NAME/KEY: misc_feature
<222> LOCATION: (207)
<223> OTHER INFORMATION: any nucleotide
```

```
<220> FEATURE:
<221> NAME/KEY: misc_feature
<222> LOCATION: (209)..(212)
<223> OTHER INFORMATION: any nucleotide
<220> FEATURE:
<221> NAME/KEY: misc_feature
<222> LOCATION: (214)..(215)
<223> OTHER INFORMATION: any nucleotide
<220> FEATURE:
<221> NAME/KEY: misc_feature
<222> LOCATION: (217)
<223> OTHER INFORMATION: any nucleotide
<220> FEATURE:
<221> NAME/KEY: misc_feature
<222> LOCATION: (255)
<223> OTHER INFORMATION: any nucleotide
<220> FEATURE:
<221> NAME/KEY: misc_feature
<222> LOCATION: (887)
<223> OTHER INFORMATION: any nucleotide
<220> FEATURE:
<221> NAME/KEY: misc_feature
<222> LOCATION: (1026)..(1027)
<223> OTHER INFORMATION: any nucleotide
<220> FEATURE:
<221> NAME/KEY: misc_feature
<222> LOCATION: (1029)
<223> OTHER INFORMATION: any nucleotide
<220> FEATURE:
<221> NAME/KEY: misc_feature
<222> LOCATION: (1053)..(1054)
<223> OTHER INFORMATION: any nucleotide
<220> FEATURE:
<221> NAME/KEY: misc_feature
<222> LOCATION: (1130)
<223> OTHER INFORMATION: any nucleotide
<220> FEATURE:
<221> NAME/KEY: misc_feature
<222> LOCATION: (1249)
<223> OTHER INFORMATION: any nucleotide
<220> FEATURE:
<221> NAME/KEY: misc_feature
<222> LOCATION: (1341)
<223> OTHER INFORMATION: any nucleotide
<220> FEATURE:
<221> NAME/KEY: misc_feature
<222> LOCATION: (1993)
<223> OTHER INFORMATION: any nucleotide
<220> FEATURE:
<221> NAME/KEY: misc_feature
<222> LOCATION: (2078)..(2081)
<223> OTHER INFORMATION: any nucleotide
<220> FEATURE:
<221> NAME/KEY: misc_feature
<222> LOCATION: (2244)
<223> OTHER INFORMATION: any nucleotide
<220> FEATURE:
<221> NAME/KEY: misc_feature
<222> LOCATION: (2342)
<223> OTHER INFORMATION: any nucleotide
<220> FEATURE:
<221> NAME/KEY: misc_feature
<222> LOCATION: (2413)
<223> OTHER INFORMATION: any nucleotide
<220> FEATURE:
<221> NAME/KEY: misc_feature
<222> LOCATION: (2708)
<223> OTHER INFORMATION: any nucleotide
<220> FEATURE:
<221> NAME/KEY: misc_feature
<222> LOCATION: (2765)
<223> OTHER INFORMATION: any nucleotide
<220> FEATURE:
<221> NAME/KEY: misc_feature
<222> LOCATION: (2876)
<223> OTHER INFORMATION: any nucleotide
<220> FEATURE:
<221> NAME/KEY: misc_feature
<222> LOCATION: (2888)
```

```
<223> OTHER INFORMATION: any nucleotide
<220> FEATURE:
<221> NAME/KEY: misc_feature
<222> LOCATION: (2890)..(2892)
<223> OTHER INFORMATION: any nucleotide
<220> FEATURE:
<221> NAME/KEY: misc_feature
<222> LOCATION: (2894)..(2895)
<223> OTHER INFORMATION: any nucleotide
<220> FEATURE:
<221> NAME/KEY: misc_feature
<222> LOCATION: (2954)
<223> OTHER INFORMATION: any nucleotide
<220> FEATURE:
<221> NAME/KEY: misc_feature
<222> LOCATION: (3469)
<223> OTHER INFORMATION: any nucleotide
<220> FEATURE:
<221> NAME/KEY: misc_feature
<222> LOCATION: (3491)
<223> OTHER INFORMATION: any nucleotide
<220> FEATURE:
<221> NAME/KEY: misc_feature
<222> LOCATION: (3495)
<223> OTHER INFORMATION: any nucleotide
<220> FEATURE:
<221> NAME/KEY: misc_feature
<222> LOCATION: (3507)
<223> OTHER INFORMATION: any nucleotide
<220> FEATURE:
<221> NAME/KEY: misc_feature
<222> LOCATION: (3523)
<223> OTHER INFORMATION: any nucleotide
<220> FEATURE:
<221> NAME/KEY: misc_feature
<222> LOCATION: (3528)
<223> OTHER INFORMATION: any nucleotide
<220> FEATURE:
<221> NAME/KEY: misc_feature
<222> LOCATION: (3549)
<223> OTHER INFORMATION: any nucleotide
<220> FEATURE:
<221> NAME/KEY: misc_feature
<222> LOCATION: (3658)
<223> OTHER INFORMATION: any nucleotide
<220> FEATURE:
<221> NAME/KEY: misc_feature
<222> LOCATION: (3661)
<223> OTHER INFORMATION: any nucleotide
<220> FEATURE:
<221> NAME/KEY: misc_feature
<222> LOCATION: (3745)
<223> OTHER INFORMATION: any nucleotide
<220> FEATURE:
<221> NAME/KEY: misc_feature
<222> LOCATION: (3809)
<223> OTHER INFORMATION: any nucleotide
<220> FEATURE:
<221> NAME/KEY: misc_feature
<222> LOCATION: (3898)
<223> OTHER INFORMATION: any nucleotide
<220> FEATURE:
<221> NAME/KEY: misc_feature
<222> LOCATION: (4086)
<223> OTHER INFORMATION: any nucleotide
<220> FEATURE:
<221> NAME/KEY: misc_feature
<222> LOCATION: (4339)
<223> OTHER INFORMATION: any nucleotide
<220> FEATURE:
<221> NAME/KEY: misc_feature
<222> LOCATION: (4523)
<223> OTHER INFORMATION: any nucleotide
<220> FEATURE:
<221> NAME/KEY: misc_feature
<222> LOCATION: (4577)
<223> OTHER INFORMATION: any nucleotide

<400> SEQUENCE: 61
```

-continued

```
atgaataaag gtttacatcg cattatcttt agtaaaaagc acagcaccat ggttgcagta      60
gccgaaactg ccaacagcca gggcaaaggt aaacaggcag gcagttcggt ttctgtttca     120
ctgaaaactt caggcgacct ttgcggcaaa ctcaaaacca cccttaaaac cttggtctgc     180
tctttggttt ccctgagtat ggnattncnn nncnntnccc aaattaccac cgacaaatca     240
gcacctaaaa accancaggt cgttatcctt aaaaccaaca ctggtgcccc cttggtgaat     300
atccaaactc cgaatggacg cggattgagc cacaaccgct atacgcagtt tgatgttgac     360
aacaaagggg cagtgttaaa caacgaccgt aacaataatc cgtttctggt caaaggcagt     420
gcgcaattga ttttgaacga ggtacgcggt acggctagca aactcaacgg catcgttacc     480
gtaggcggtc aaaaggccga cgtgattatt gccaaccccca acggcattac cgttaatggc     540
ggcggcttta aaaatgtcgg tcgggcatc ttaactatcg gtgcgcccca aatcggcaaa     600
gacggtgcac tgacaggatt tgatgtgcgt caaggcacat tgaccgtagg agcagcaggt     660
tggaatgata aggcggagc cgactacacc ggggtacttg ctcgtgcagt tgctttgcag     720
gggaaattac agggtaaaaa cctggcggtt tctaccggtc ctcagaaagt agattacgcc     780
agcggcgaaa tcagtgcagg tacggcagcg ggtacgaaac cgactattgc ccttgatact     840
gccgcactgg gcggtatgta cgccgacagc atcacactga ttgccantga aaaaggcgta     900
ggcgtcaaaa atgccggcac actcgaagcg gccaagcaat tgattgtgac ttcgtcaggc     960
cgcattgaaa acagcggccg catcgccacc actgccgacg gcaccgaagc ttcaccgact    1020
tatctnncna tcgaaaccac cgaaaaagga gcnncaggca catttatctc caatggtggt    1080
cggatcgaga gcaaaggctt attggttatt gagacgggag aagatatcan cttgcgtaac    1140
ggagccgtgg tgcagaataa cggcagtcgc ccagctacca cggtattaaa tgctggtcat    1200
aatttggtga ttgagagtaa aactaatgtg aacaatgcca aaggctcgnc taatctgtcg    1260
gccggcggtc gtactacgat caatgatgct actattcaag cggcagttc cgtgtacagc    1320
tccaccaaag gcgatactga nttgggtgaa atacccgta ttattgctga aaacgtaacc    1380
gtattatcta acggtagtat tggcagtgct gctgtaattg aggctaaaga cactgcacac    1440
attgaatcgg gcaaaccgct ttcttagaa acctcgaccg ttgcctccaa catccgtttg    1500
aacaacggta acattaaagg cggaaagcag cttgctttac tggcagacga taacattact    1560
gccaaaacta ccaatctgaa tactcccggc aatctgtatg ttcatacagg taaagatctg    1620
aatttgaatt tgataaaga tttgtctgcc gccagcatcc atttgaaatc ggataacgct    1680
gcccatatta ccggcaccag taaaaccctc actgcctcaa aagacatggg tgtggaggca    1740
ggcttgctga atgttaccaa taccaatctg cgtaccaact cgggtaatct gcacattcag    1800
gcagccaaag gcaatattca gcttcgcaat accaagctga acgcagccaa ggctctcgaa    1860
accaccgcat tgcagggcaa tatcgttttca gacggccttc atgctgtttc tgcagacggt    1920
catgtatcct tattggccaa cggtaatgcc gactttaccg gtcacaatac cctgacagcc    1980
aaggccgatg tcnatgcagg atcggttggt aaaggccgtc tgaaagcaga caataccaat    2040
atcacttcat cttcaggaga tattacgttg gttgccgnnn ncggtattca gcttggtgac    2100
ggaaaacaac gcaattcaat caacggaaaa cacatcagca tcaaaaacaa cggtggtaat    2160
gccgacttaa aaaaccttaa cgtccatgcc aaaagcgggg cattgaacat tcattccgac    2220
cgggcattga gcatagaaaa tacnaagctg gagtctaccc ataatacgca tcttaatgca    2280
caacacgagc gggtaacgct caaccaagta gatgcctacg cacaccgtca tctaagcatt    2340
```

```
ancggcagcc agatttggca aaacgacaaa ctgccttctg ccaacaagct ggtggctaac    2400
ggtgtattgg cantcaatgc gcgctattcc caaattgccg acaacaccac gctgagagcg    2460
ggtgcaatca accttactgc cggtaccgcc ctagtcaagc gcggcaacat caattggagt    2520
accgtttcga ccaagacttt ggaagataat gccgaattaa aaccattggc cggacggctg    2580
aatattgaag caggtagcgg cacattaacc atcgaacctg ccaaccgcat cagtgcgcat    2640
accgacctga gcatcaaaac aggcggaaaa ttgctgttgt ctgcaaaagg aggaaatgca    2700
ggtgcgcnta gtgctcaagt ttcctcattg gaagcaaaag gcaatatccg tctggttaca    2760
ggagnaacag atttaagagg ttctaaaatt acagccggta aaaacttggt tgtcgccacc    2820
accaaaggca agttgaatat cgaagccgta acaactcat tcagcaatta ttttcntaca    2880
caaaaagngn nngnnctcaa ccaaaaatcc aagaattgg aacagcagat tgcgcagttg    2940
aaaaaaagct cgcntaaaag caagctgatt ccaaccctgc aagaagaacg cgaccgtctc    3000
gctttctata ttcaagccat caacaaggaa gttaaaggta aaaaacccaa aggcaaagaa    3060
tacctgcaag ccaagctttc tgcacaaaat attgacttga tttccgcaca aggcatcgaa    3120
atcagcggtt ccgatattac cgcttccaaa aaactgaacc ttcacgccgc aggcgtattg    3180
ccaaaggcag cagattcaga ggcggctgct attctgattg acggcataac cgaccaatat    3240
gaaattggca agcccaccta caagagtcac tacgacaaag ctgctctgaa caagccttca    3300
cgtttgaccg gacgtacggg ggtaagtatt catgcagctg cggcactcga tgatgcacgt    3360
attattatcg gtgcatccga aatcaaagct ccctcaggca gcatagacat caaagcccat    3420
agtgatattg tactggaggc tggacaaaac gatgcctata ccttcttana accaaaggt    3480 aaaagcggca naatnatcag aaaaacnaag tttaccagca ccngcganca cctgattatg    3540
ccagccccng tcgagctgac cgccaacggt atcacgcttc aggcaggcgg caacatcgaa    3600
gctaatacca cccgcttcaa tgcccctgca ggtaaagtta ccctggttgc gggtgaanag    3660
ntgcaactgc tggcagaaga aggcatccac aagcacgagt tggatgtcca aaaaagccgc    3720
cgctttatcg gcatcaaggt aggtnagagc aattacagta aaaacgaact gaacgaaacc    3780
aaattgcctg tccgcgtcgt cgcccaaant gcagccaccc gttcaggctg ggataccgtg    3840
ctcgaaggta ccgaattcaa aaccacgctg gccggtgccg acattcaggc aggtgtangc    3900
gaaaaagccc gtgtcgatgc gaaaattatc ctcaaaggca ttgtgaaccg tatccagtcg    3960
gaagaaaaat tagaaaccaa ctcaaccgta tggcagaaac aggccggacg cggcagcact    4020
atcgaaacgc taaaactgcc cagcttcgaa agccctactc cgcccaaatt gtccgcaccc    4080
ggcggntata tcgtcgacat tccgaaaggc aatctgaaaa ccgaaatcga aaagctgtcc    4140
aaacagcccg agtatgccta tctgaaacag ctccaagtag cgaaaaacat caactggaat    4200
caggtgcagc ttgcttacga cagatgggac tacaaacagg agggcttaac cgaagcaggt    4260
gcggcgatta tcgcactggc cgttaccgtg gtcacctcag cgcaggaac cggagccgta    4320 ttgggattaa acggtgcgnc cgccgccgca accgatgcag cattcgcctc tttggccagc    4380
caggcttccg tatcgttcat caacaacaaa ggcgatgtcg gcaaaacccct gaaagagctg    4440 ggcagaagca gcacggtgaa aaatctggtg gttgccgccg ctaccgcagg cgtagccgac    4500
aaaatcggcg cttcggcact gancaatgtc agcgataagc agtggatcaa caacctgacc    4560
gtcaacctag ccaatgncgg gcagtgccgc actgattaa                          4599
```

<210> SEQ ID NO 62
<211> LENGTH: 1532

```
<212> TYPE: PRT
<213> ORGANISM: Neisseria meningitidis
<220> FEATURE:
<221> NAME/KEY: SITE
<222> LOCATION: (68)..(73)
<223> OTHER INFORMATION: unknown
<220> FEATURE:
<221> NAME/KEY: SITE
<222> LOCATION: (85)
<223> OTHER INFORMATION: unknown
<220> FEATURE:
<221> NAME/KEY: SITE
<222> LOCATION: (296)
<223> OTHER INFORMATION: unknown
<220> FEATURE:
<221> NAME/KEY: SITE
<222> LOCATION: (343)
<223> OTHER INFORMATION: unknown
<220> FEATURE:
<221> NAME/KEY: SITE
<222> LOCATION: (352)
<223> OTHER INFORMATION: unknown
<220> FEATURE:
<221> NAME/KEY: SITE
<222> LOCATION: (377)
<223> OTHER INFORMATION: unknown
<220> FEATURE:
<221> NAME/KEY: SITE
<222> LOCATION: (417)
<223> OTHER INFORMATION: unknown
<220> FEATURE:
<221> NAME/KEY: SITE
<222> LOCATION: (477)
<223> OTHER INFORMATION: unknown
<220> FEATURE:
<221> NAME/KEY: SITE
<222> LOCATION: (665)
<223> OTHER INFORMATION: unknown
<220> FEATURE:
<221> NAME/KEY: SITE
<222> LOCATION: (693)..(694)
<223> OTHER INFORMATION: unknown
<220> FEATURE:
<221> NAME/KEY: SITE
<222> LOCATION: (781)
<223> OTHER INFORMATION: unknown
<220> FEATURE:
<221> NAME/KEY: SITE
<222> LOCATION: (805)
<223> OTHER INFORMATION: unknown
<220> FEATURE:
<221> NAME/KEY: SITE
<222> LOCATION: (903)
<223> OTHER INFORMATION: unknown
<220> FEATURE:
<221> NAME/KEY: SITE
<222> LOCATION: (922)
<223> OTHER INFORMATION: unknown
<220> FEATURE:
<221> NAME/KEY: SITE
<222> LOCATION: (959)
<223> OTHER INFORMATION: unknown
<220> FEATURE:
<221> NAME/KEY: SITE
<222> LOCATION: (963)..(965)
<223> OTHER INFORMATION: unknown
<220> FEATURE:
<221> NAME/KEY: SITE
<222> LOCATION: (985)
<223> OTHER INFORMATION: unknown
<220> FEATURE:
<221> NAME/KEY: SITE
<222> LOCATION: (1157)
<223> OTHER INFORMATION: unknown
<220> FEATURE:
<221> NAME/KEY: SITE
<222> LOCATION: (1164)..(1165)
<223> OTHER INFORMATION: unknown
<220> FEATURE:
```

```
<221> NAME/KEY: SITE
<222> LOCATION: (1175)..(1176)
<223> OTHER INFORMATION: unknown
<220> FEATURE:
<221> NAME/KEY: SITE
<222> LOCATION: (1220)..(1221)
<223> OTHER INFORMATION: unknown
<220> FEATURE:
<221> NAME/KEY: SITE
<222> LOCATION: (1249)
<223> OTHER INFORMATION: unknown
<220> FEATURE:
<221> NAME/KEY: SITE
<222> LOCATION: (1270)
<223> OTHER INFORMATION: unknown
<220> FEATURE:
<221> NAME/KEY: SITE
<222> LOCATION: (1300)
<223> OTHER INFORMATION: unknown
<220> FEATURE:
<221> NAME/KEY: SITE
<222> LOCATION: (1447)
<223> OTHER INFORMATION: unknown
<220> FEATURE:
<221> NAME/KEY: SITE
<222> LOCATION: (1508)
<223> OTHER INFORMATION: unknown
<220> FEATURE:
<221> NAME/KEY: SITE
<222> LOCATION: (1526)
<223> OTHER INFORMATION: unknown

<400> SEQUENCE: 62

Met Asn Lys Gly Leu His Arg Ile Ile Phe Ser Lys Lys His Ser Thr
  1               5                  10                  15

Met Val Ala Val Ala Glu Thr Ala Asn Ser Gln Gly Lys Gly Lys Gln
             20                  25                  30

Ala Gly Ser Ser Val Ser Val Ser Leu Lys Thr Ser Gly Asp Leu Cys
         35                  40                  45

Gly Lys Leu Lys Thr Thr Leu Lys Thr Leu Val Cys Ser Leu Val Ser
     50                  55                  60

Leu Ser Met Xaa Xaa Xaa Xaa Xaa Gln Ile Thr Thr Asp Lys Ser
 65                  70                  75                  80

Ala Pro Lys Asn Xaa Gln Val Val Ile Leu Lys Thr Asn Thr Gly Ala
                 85                  90                  95

Pro Leu Val Asn Ile Gln Thr Pro Asn Gly Arg Gly Leu Ser His Asn
            100                 105                 110

Arg Tyr Thr Gln Phe Asp Val Asp Asn Lys Gly Ala Val Leu Asn Asn
        115                 120                 125

Asp Arg Asn Asn Asn Pro Phe Leu Val Lys Gly Ser Ala Gln Leu Ile
    130                 135                 140

Leu Asn Glu Val Arg Gly Thr Ala Ser Lys Leu Asn Gly Ile Val Thr
145                 150                 155                 160

Val Gly Gly Gln Lys Ala Asp Val Ile Ala Asn Pro Asn Gly Ile
                165                 170                 175

Thr Val Asn Gly Gly Phe Lys Asn Val Gly Arg Gly Ile Leu Thr
            180                 185                 190

Ile Gly Ala Pro Gln Ile Gly Lys Asp Gly Ala Leu Thr Gly Phe Asp
        195                 200                 205

Val Arg Gln Gly Thr Leu Thr Val Gly Ala Ala Gly Trp Asn Asp Lys
    210                 215                 220

Gly Gly Ala Asp Tyr Thr Gly Val Leu Ala Arg Ala Val Ala Leu Gln
225                 230                 235                 240
```

-continued

```
Gly Lys Leu Gln Gly Lys Asn Leu Ala Val Ser Thr Gly Pro Gln Lys
            245                 250                 255

Val Asp Tyr Ala Ser Gly Glu Ile Ser Ala Gly Thr Ala Ala Gly Thr
        260                 265                 270

Lys Pro Thr Ile Ala Leu Asp Thr Ala Ala Leu Gly Gly Met Tyr Ala
    275                 280                 285

Asp Ser Ile Thr Leu Ile Ala Xaa Glu Lys Gly Val Gly Val Lys Asn
290                 295                 300

Ala Gly Thr Leu Glu Ala Ala Lys Gln Leu Ile Val Thr Ser Ser Gly
305                 310                 315                 320

Arg Ile Glu Asn Ser Gly Arg Ile Ala Thr Thr Ala Asp Gly Thr Glu
            325                 330                 335

Ala Ser Pro Thr Tyr Leu Xaa Ile Glu Thr Thr Glu Lys Gly Ala Xaa
        340                 345                 350

Gly Thr Phe Ile Ser Asn Gly Gly Arg Ile Glu Ser Lys Gly Leu Leu
    355                 360                 365

Val Ile Glu Thr Gly Glu Asp Ile Xaa Leu Arg Asn Gly Ala Val Val
370                 375                 380

Gln Asn Asn Gly Ser Arg Pro Ala Thr Thr Val Leu Asn Ala Gly His
385                 390                 395                 400

Asn Leu Val Ile Glu Ser Lys Thr Asn Val Asn Asn Ala Lys Gly Ser
            405                 410                 415

Xaa Asn Leu Ser Ala Gly Gly Arg Thr Thr Ile Asn Asp Ala Thr Ile
        420                 425                 430

Gln Ala Gly Ser Ser Val Tyr Ser Thr Lys Gly Asp Thr Xaa Leu
    435                 440                 445

Gly Glu Asn Thr Arg Ile Ile Ala Glu Asn Val Thr Val Leu Ser Asn
450                 455                 460

Gly Ser Ile Gly Ser Ala Ala Val Ile Glu Ala Lys Asp Thr Ala His
465                 470                 475                 480

Ile Glu Ser Gly Lys Pro Leu Ser Leu Glu Thr Ser Thr Val Ala Ser
            485                 490                 495

Asn Ile Arg Leu Asn Asn Gly Asn Ile Lys Gly Gly Lys Gln Leu Ala
        500                 505                 510

Leu Leu Ala Asp Asp Asn Ile Thr Ala Lys Thr Thr Asn Leu Asn Thr
    515                 520                 525

Pro Gly Asn Leu Tyr Val His Thr Gly Lys Asp Leu Asn Leu Asn Val
530                 535                 540

Asp Lys Asp Leu Ser Ala Ala Ser Ile His Leu Lys Ser Asp Asn Ala
545                 550                 555                 560

Ala His Ile Thr Gly Thr Ser Lys Thr Leu Thr Ala Ser Lys Asp Met
            565                 570                 575

Gly Val Glu Ala Gly Leu Leu Asn Val Thr Asn Thr Asn Leu Arg Thr
        580                 585                 590

Asn Ser Gly Asn Leu His Ile Gln Ala Ala Lys Gly Asn Ile Gln Leu
    595                 600                 605

Arg Asn Thr Lys Leu Asn Ala Ala Lys Ala Leu Glu Thr Ala Leu
610                 615                 620

Gln Gly Asn Ile Val Ser Asp Gly Leu His Ala Val Ser Ala Asp Gly
625                 630                 635                 640

His Val Ser Leu Leu Ala Asn Gly Asn Ala Asp Phe Thr Gly His Asn
            645                 650                 655

Thr Leu Thr Ala Lys Ala Asp Val Xaa Ala Gly Ser Val Gly Lys Gly
```

-continued

```
                660                 665                 670
Arg Leu Lys Ala Asp Asn Thr Asn Ile Thr Ser Ser Ser Gly Asp Ile
            675                 680                 685

Thr Leu Val Ala Xaa Xaa Gly Ile Gln Leu Gly Asp Gly Lys Gln Arg
            690                 695                 700

Asn Ser Ile Asn Gly Lys His Ile Ser Ile Lys Asn Asn Gly Gly Asn
705                 710                 715                 720

Ala Asp Leu Lys Asn Leu Asn Val His Ala Lys Ser Gly Ala Leu Asn
                725                 730                 735

Ile His Ser Asp Arg Ala Leu Ser Ile Glu Asn Thr Lys Leu Glu Ser
            740                 745                 750

Thr His Asn Thr His Leu Asn Ala Gln His Glu Arg Val Thr Leu Asn
            755                 760                 765

Gln Val Asp Ala Tyr Ala His Arg His Leu Ser Ile Xaa Gly Ser Gln
            770                 775                 780

Ile Trp Gln Asn Asp Lys Leu Pro Ser Ala Asn Lys Leu Val Ala Asn
785                 790                 795                 800

Gly Val Leu Ala Xaa Asn Ala Arg Tyr Ser Gln Ile Ala Asp Asn Thr
                805                 810                 815

Thr Leu Arg Ala Gly Ala Ile Asn Leu Thr Ala Gly Thr Ala Leu Val
            820                 825                 830

Lys Arg Gly Asn Ile Asn Trp Ser Thr Val Ser Thr Lys Thr Leu Glu
            835                 840                 845

Asp Asn Ala Glu Leu Lys Pro Leu Ala Gly Arg Leu Asn Ile Glu Ala
            850                 855                 860

Gly Ser Gly Thr Leu Thr Ile Glu Pro Ala Asn Arg Ile Ser Ala His
865                 870                 875                 880

Thr Asp Leu Ser Ile Lys Thr Gly Gly Lys Leu Leu Leu Ser Ala Lys
                885                 890                 895

Gly Gly Asn Ala Gly Ala Xaa Ser Ala Gln Val Ser Ser Leu Glu Ala
                900                 905                 910

Lys Gly Asn Ile Arg Leu Val Thr Gly Xaa Thr Asp Leu Arg Gly Ser
            915                 920                 925

Lys Ile Thr Ala Gly Lys Asn Leu Val Val Ala Thr Thr Lys Gly Lys
            930                 935                 940

Leu Asn Ile Glu Ala Val Asn Ser Phe Ser Asn Tyr Phe Xaa Thr
945                 950                 955                 960

Gln Lys Xaa Xaa Xaa Leu Asn Gln Lys Ser Lys Glu Leu Glu Gln Gln
                965                 970                 975

Ile Ala Gln Leu Lys Lys Ser Ser Xaa Lys Ser Lys Leu Ile Pro Thr
            980                 985                 990

Leu Gln Glu Glu Arg Asp Arg Leu Ala Phe Tyr Ile Gln Ala Ile Asn
            995                1000                1005

Lys Glu Val Lys Gly Lys Lys Pro Lys Gly Lys Glu Tyr Leu Gln Ala
        1010                1015                1020

Lys Leu Ser Ala Gln Asn Ile Asp Leu Ile Ser Ala Gln Gly Ile Glu
1025                1030                1035                1040

Ile Ser Gly Ser Asp Ile Thr Ala Ser Lys Lys Leu Asn Leu His Ala
                1045                1050                1055

Ala Gly Val Leu Pro Lys Ala Ala Asp Ser Glu Ala Ala Ile Leu
        1060                1065                1070

Ile Asp Gly Ile Thr Asp Gln Tyr Glu Ile Gly Lys Pro Thr Tyr Lys
            1075                1080                1085
```

```
Ser His Tyr Asp Lys Ala Ala Leu Asn Lys Pro Ser Arg Leu Thr Gly
    1090                1095                1100

Arg Thr Gly Val Ser Ile His Ala Ala Ala Leu Asp Asp Ala Arg
1105                1110                1115                1120

Ile Ile Ile Gly Ala Ser Glu Ile Lys Ala Pro Ser Gly Ser Ile Asp
                1125                1130                1135

Ile Lys Ala His Ser Asp Ile Val Leu Glu Ala Gly Gln Asn Asp Ala
            1140                1145                1150

Tyr Thr Phe Leu Xaa Thr Lys Gly Lys Ser Gly Xaa Xaa Ile Arg Lys
        1155                1160                1165

Thr Lys Phe Thr Ser Thr Xaa Xaa His Leu Ile Met Pro Ala Pro Val
    1170                1175                1180

Glu Leu Thr Ala Asn Gly Ile Thr Leu Gln Ala Gly Gly Asn Ile Glu
1185                1190                1195                1200

Ala Asn Thr Thr Arg Phe Asn Ala Pro Ala Gly Lys Val Thr Leu Val
                1205                1210                1215

Ala Gly Glu Xaa Xaa Gln Leu Leu Ala Glu Glu Gly Ile His Lys His
            1220                1225                1230

Glu Leu Asp Val Gln Lys Ser Arg Arg Phe Ile Gly Ile Lys Val Gly
        1235                1240                1245

Xaa Ser Asn Tyr Ser Lys Asn Glu Leu Asn Glu Thr Lys Leu Pro Val
    1250                1255                1260

Arg Val Val Ala Gln Xaa Ala Ala Thr Arg Ser Gly Trp Asp Thr Val
1265                1270                1275                1280

Leu Glu Gly Thr Glu Phe Lys Thr Thr Leu Ala Gly Ala Asp Ile Gln
                1285                1290                1295

Ala Gly Val Xaa Glu Lys Ala Arg Val Asp Ala Lys Ile Ile Leu Lys
            1300                1305                1310

Gly Ile Val Asn Arg Ile Gln Ser Glu Glu Lys Leu Glu Thr Asn Ser
        1315                1320                1325

Thr Val Trp Gln Lys Gln Ala Gly Arg Gly Ser Thr Ile Glu Thr Leu
    1330                1335                1340

Lys Leu Pro Ser Phe Glu Ser Pro Thr Pro Pro Lys Leu Ser Ala Pro
1345                1350                1355                1360

Gly Gly Tyr Ile Val Asp Ile Pro Lys Gly Asn Leu Lys Thr Glu Ile
                1365                1370                1375

Glu Lys Leu Ser Lys Gln Pro Glu Tyr Ala Tyr Leu Lys Gln Leu Gln
            1380                1385                1390

Val Ala Lys Asn Ile Asn Trp Asn Gln Val Gln Leu Ala Tyr Asp Arg
        1395                1400                1405

Trp Asp Tyr Lys Gln Glu Gly Leu Thr Glu Ala Gly Ala Ala Ile Ile
    1410                1415                1420

Ala Leu Ala Val Thr Val Val Thr Ser Gly Ala Gly Thr Gly Ala Val
1425                1430                1435                1440

Leu Gly Leu Asn Gly Ala Xaa Ala Ala Ala Thr Asp Ala Ala Phe Ala
                1445                1450                1455

Ser Leu Ala Ser Gln Ala Ser Val Ser Phe Ile Asn Asn Lys Gly Asp
            1460                1465                1470

Val Gly Lys Thr Leu Lys Glu Leu Gly Arg Ser Ser Thr Val Lys Asn
        1475                1480                1485

Leu Val Val Ala Ala Ala Thr Ala Gly Val Ala Asp Lys Ile Gly Ala
    1490                1495                1500
```

-continued

```
Ser Ala Leu Xaa Asn Val Ser Asp Lys Gln Trp Ile Asn Asn Leu Thr
1505                1510                1515                1520

Val Asn Leu Ala Asn Xaa Gly Gln Cys Arg Thr Asp
            1525                1530

<210> SEQ ID NO 63
<211> LENGTH: 1782
<212> TYPE: DNA
<213> ORGANISM: Neisseria meningitidis
<220> FEATURE:
<221> NAME/KEY: misc_feature
<222> LOCATION: (89)
<223> OTHER INFORMATION: any nucleotide
<220> FEATURE:
<221> NAME/KEY: unsure
<222> LOCATION: (697)
<223> OTHER INFORMATION: N = Unknown
<220> FEATURE:
<221> NAME/KEY: unsure
<222> LOCATION: (862)
<223> OTHER INFORMATION: N = Unknown
<220> FEATURE:
<221> NAME/KEY: misc_feature
<222> LOCATION: (959)..(960)
<223> OTHER INFORMATION: any nucleotide

<400> SEQUENCE: 63
cgcttcattc atgatgaagc agtcggcagc aacatcggcg gcggcaaaat gattgttgca      60
gccgggcagg atatcaatgt acgcggcana agccttattt ctgataaggg cattgtttta     120
aaagcaggac acgacatcga tatttctact gcccataatc gctataccgg caatgaatac     180
cacgagagca waaawtcagg cgtcatgggt actggcggat tgggctttac tatcggtaac     240
cggaaaacta ccgatgacac tgatcgtacc aatattgtsc atacaggcag cattataggc     300
agcctgaatg gagacaccgt tacagttgca ggaaaccgct accgacaaac cggcagtacc     360
gtctccagcc ccgagggggcg caataccgtc acagccaaaw gcatagatgt agagttcgca     420
aacaaccggt atgccactga ctacgcccat acccagggaa caaaaaggcc ttaccgtcgc     480
cctcaatgtc ccggttgtcc aagctgcaca aaacttcata caagcagccc aaaatgtggg     540
caaaagtaaa aataaacgcg ttaatgccat ggctgcagcc aatgctgcat ggcagagtta     600
tcaagcaacc caacaaatgc aacaatttgc tccaagcagc agtgcgggac aaggtcaaaa     660
ctacaatcaa agccccagta tcagtgtgtc cattacntac ggcgaacaga aaagtcgtaa     720
cgagcaaaaa agacattaca ccgaagcggc agcaagtcaa attatcggca aagggcaaac     780
cacacttgcg gcaacaggaa gtggggagca gtccaatatc aatattacag gttccgatgt     840
catcggccat gcaggtactc cnctcattgc cgacaaccat atcagactcc aatctgccaa     900
acaggacggc agcgagcaaa gcaaaaacaa aagcagtggt tggaatgcag gcgtacgtnn     960
caaaataggc aacggcatca ggtttggaat taccgccgga ggaaatatcg gtaaaggtaa    1020
agagcaaggg ggaagtacta cccaccgcca cacccatgtc ggcagcacaa ccggcaaaac    1080
taccatccga agcggcgggg gataccaccc tcaaaggtgt gcagctcatc ggcaaaggca    1140
tacaggcaga tacgcgcaac ctgcatatag aaagtgttca agatactgaa acctatcaga    1200
gcaaacagca aaacggcaat gtccaagttt actgtcggtt acggattcag tgcaagcggc    1260
agttaccgcc aaagcaaagt caaagcagac catgcctccg taaccgggca aagcggtatt    1320
tatgccggag aagacggcta tcaaatyaaa gtyagagaca acacagacct yaagggcggt    1380
atcatcacgt ctagccaaag cgcagaagat aagggcaaaa acctttttca gacggccacc    1440
cttactgcca gcgacattca aaaccacagc cgctacgaag gcagaagctt cggcataggc    1500
```

```
ggcagtttcg acctgaacgg cggctgggac ggcacggtta ccgacaaaca aggcaggcct    1560
accgacagga taagcccggc agccggctac ggcagcgacg gagacagcaa aaacagcacc    1620
acccgcagcg cgtcaacac ccacaacata cacatcaccg acgaagcggg acaacttgcc     1680
cgaacaggca ggactgcaaa agaaaccgaa gcgcgtatct acaccggcat cgacaccgaa    1740
actgcggatc aacactcagg ccatctgaaa aacagcttcg ac                       1782
```

```
<210> SEQ ID NO 64
<211> LENGTH: 593
<212> TYPE: PRT
<213> ORGANISM: Neisseria meningitidis
<220> FEATURE:
<221> NAME/KEY: SITE
<222> LOCATION: (30)
<223> OTHER INFORMATION: unknown
<220> FEATURE:
<221> NAME/KEY: SITE
<222> LOCATION: (64)..(65)
<223> OTHER INFORMATION: unknown
<220> FEATURE:
<221> NAME/KEY: SITE
<222> LOCATION: (134)
<223> OTHER INFORMATION: unknown
<220> FEATURE:
<221> NAME/KEY: SITE
<222> LOCATION: (232)
<223> OTHER INFORMATION: unknown
<220> FEATURE:
<221> NAME/KEY: SITE
<222> LOCATION: (287)
<223> OTHER INFORMATION: unknown
<220> FEATURE:
<221> NAME/KEY: SITE
<222> LOCATION: (320)
<223> OTHER INFORMATION: unknown

<400> SEQUENCE: 64
```

```
Arg Phe Ile His Asp Glu Ala Val Gly Ser Asn Ile Gly Gly Gly Lys
  1               5                  10                  15

Met Ile Val Ala Ala Gly Gln Asp Ile Asn Val Arg Gly Xaa Ser Leu
             20                  25                  30

Ile Ser Asp Lys Gly Ile Val Leu Lys Ala Gly His Asp Ile Asp Ile
         35                  40                  45

Ser Thr Ala His Asn Arg Tyr Thr Gly Asn Glu Tyr His Glu Ser Xaa
     50                  55                  60

Xaa Ser Gly Val Met Gly Thr Gly Gly Leu Gly Phe Thr Ile Gly Asn
 65                  70                  75                  80

Arg Lys Thr Thr Asp Asp Thr Asp Arg Thr Asn Ile Val His Thr Gly
                 85                  90                  95

Ser Ile Ile Gly Ser Leu Asn Gly Asp Thr Val Thr Val Ala Gly Asn
            100                 105                 110

Arg Tyr Arg Gln Thr Gly Ser Thr Val Ser Ser Pro Glu Gly Arg Asn
        115                 120                 125

Thr Val Thr Ala Lys Xaa Ile Asp Val Glu Phe Ala Asn Asn Arg Tyr
    130                 135                 140

Ala Thr Asp Tyr Ala His Thr Gln Glu Gln Lys Gly Leu Thr Val Ala
145                 150                 155                 160

Leu Asn Val Pro Val Gln Ala Ala Gln Asn Phe Ile Gln Ala Ala
                165                 170                 175

Gln Asn Val Gly Lys Ser Lys Asn Lys Arg Val Asn Ala Met Ala Ala
            180                 185                 190
```

```
Ala Asn Ala Ala Trp Gln Ser Tyr Gln Ala Thr Gln Gln Met Gln Gln
        195                 200                 205

Phe Ala Pro Ser Ser Ala Gly Gln Gly Gln Asn Tyr Asn Gln Ser
    210                 215                 220

Pro Ser Ile Ser Val Ser Ile Xaa Tyr Gly Glu Gln Lys Ser Arg Asn
225                 230                 235                 240

Glu Gln Lys Arg His Tyr Thr Glu Ala Ala Ser Gln Ile Ile Gly
            245                 250                 255

Lys Gly Gln Thr Thr Leu Ala Ala Thr Gly Ser Gly Glu Gln Ser Asn
                260                 265                 270

Ile Asn Ile Thr Gly Ser Asp Val Ile Gly His Ala Gly Thr Xaa Leu
        275                 280                 285

Ile Ala Asp Asn His Ile Arg Leu Gln Ser Ala Lys Gln Asp Gly Ser
    290                 295                 300

Glu Gln Ser Lys Asn Lys Ser Ser Gly Trp Asn Ala Gly Val Arg Xaa
305                 310                 315                 320

Lys Ile Gly Asn Gly Ile Arg Phe Gly Ile Thr Ala Gly Asn Ile
            325                 330                 335

Gly Lys Gly Lys Glu Gln Gly Gly Ser Thr Thr His Arg His Thr His
                340                 345                 350

Val Gly Ser Thr Thr Gly Lys Thr Thr Ile Arg Ser Gly Gly Asp Thr
        355                 360                 365

Thr Leu Lys Gly Val Gln Leu Ile Gly Lys Gly Ile Gln Ala Asp Thr
    370                 375                 380

Arg Asn Leu His Ile Glu Ser Val Gln Asp Thr Glu Thr Tyr Gln Ser
385                 390                 395                 400

Lys Gln Gln Asn Gly Asn Val Gln Val Thr Val Gly Tyr Gly Phe Ser
                405                 410                 415

Ala Ser Gly Ser Tyr Arg Gln Ser Lys Val Lys Ala Asp His Ala Ser
            420                 425                 430

Val Thr Gly Gln Ser Gly Ile Tyr Ala Gly Glu Asp Gly Tyr Gln Ile
        435                 440                 445

Lys Val Arg Asp Asn Thr Asp Leu Lys Gly Gly Ile Ile Thr Ser Ser
    450                 455                 460

Gln Ser Ala Glu Asp Lys Gly Lys Asn Leu Phe Gln Thr Ala Thr Leu
465                 470                 475                 480

Thr Ala Ser Asp Ile Gln Asn His Ser Arg Tyr Glu Gly Arg Ser Phe
                485                 490                 495

Gly Ile Gly Gly Ser Phe Asp Leu Asn Gly Gly Trp Asp Gly Thr Val
            500                 505                 510

Thr Asp Lys Gln Gly Arg Pro Thr Asp Arg Ile Ser Pro Ala Ala Gly
        515                 520                 525

Tyr Gly Ser Asp Gly Asp Ser Lys Asn Ser Thr Thr Arg Ser Gly Val
    530                 535                 540

Asn Thr His Asn Ile His Ile Thr Asp Glu Ala Gly Gln Leu Ala Arg
545                 550                 555                 560

Thr Gly Arg Thr Ala Lys Glu Thr Glu Ala Arg Ile Tyr Thr Gly Ile
                565                 570                 575

Asp Thr Glu Thr Ala Asp Gln His Ser Gly His Leu Lys Asn Ser Phe
            580                 585                 590

Asp

<210> SEQ ID NO 65
```

```
<211> LENGTH: 390
<212> TYPE: DNA
<213> ORGANISM: Neisseria meningitidis

<400> SEQUENCE: 65
acgaccggca gcctcggcgg catactggcc ggcggcggca cttcccttgc cgcaccgtat    60
ttggacaaag cggcgaaaaa cctcggtccg gcgggcaaag cggcggtcaa cgcactgggc   120
ggtgcggcca tcggctatgc aactggtggt agtggtggtg ctgtggtggg tgcgaatgta   180
gattggaaca ataggcagct gcatccgaaa gaaatggcgt tggccgacaa atatgccgaa   240
gccctcaagc gcgaagttga aaacgcgaa ggcagaaaaa tcagcagcca agaagcggca   300
atgagaatcc gcaggcagat atgcgttggg tggacaaagg ttcccaagac ggctataccg   360
accaaagcgt catatccctt atcggaatga                                    390

<210> SEQ ID NO 66
<211> LENGTH: 129
<212> TYPE: PRT
<213> ORGANISM: Neisseria meningitidis

<400> SEQUENCE: 66

Thr Thr Gly Ser Leu Gly Gly Ile Leu Ala Gly Gly Thr Ser Leu
 1               5                  10                  15

Ala Ala Pro Tyr Leu Asp Lys Ala Ala Glu Asn Leu Gly Pro Ala Gly
             20                  25                  30

Lys Ala Ala Val Asn Ala Leu Gly Gly Ala Ala Ile Gly Tyr Ala Thr
         35                  40                  45

Gly Gly Ser Gly Gly Ala Val Val Gly Ala Asn Val Asp Trp Asn Asn
     50                  55                  60

Arg Gln Leu His Pro Lys Glu Met Ala Leu Ala Asp Lys Tyr Ala Glu
 65                  70                  75                  80

Ala Leu Lys Arg Glu Val Glu Lys Arg Glu Gly Arg Lys Ile Ser Ser
                 85                  90                  95

Gln Glu Ala Ala Met Arg Ile Arg Arg Gln Ile Cys Val Gly Trp Thr
            100                 105                 110

Lys Val Pro Lys Thr Ala Ile Pro Thr Lys Ala Ser Tyr Pro Leu Ser
        115                 120                 125

Glu

<210> SEQ ID NO 67
<211> LENGTH: 960
<212> TYPE: DNA
<213> ORGANISM: Neisseria meningitidis

<400> SEQUENCE: 67
caatgccgtc tgaaaagctc acaattttac agacggcatt tgttatgcaa gtacatatac    60
agattcccta tatactgccc agrkgcgtgc gtggctgaag cacccccta cgcttgctat   120 ttgraacagc tccaagtcac caaagacgtc aactggaacc aggtacwact ggcgtacgac   180
aaatgggact ataaacagga aggcttaacc ggagccggag cagcgattat tgcgctggct   240
gttaccgtgg ttactgcggg cgcgggagcc ggagccgcac tgggcttaaa cggcgcggcc   300
gcagcggcaa ccgatgccgc attcgcctcg ctggccagcc aggcttccgt atcgctcatc   360
aacaacaaag gcaatatcgg taacaccctg aaagagctgg cagaagcag cacggtgaaa   420 aatctgatgg ttgccgtcgc taccgcaggc gtagccgaca aaatcggtgc ttcggcactg   480
aacaatgtca gcgataagca gtggatcaac aacctgaccg tcaacctggc caatgcgggc   540
```

```
agtgccgcac tgattaatac cgctgtcaac ggcggcagcc tgaaagacaa tctggaagcg    600
aatatccttg cggctttggt gaatactgcg catggagaag cagccagtaa atcaaacag     660 ttggatcagc actacattac ccacaagatt gcccatgcca tagcgggctg tgcggctgcg    720
gcggcgaata agggcaagtg tcaggatggt gcgataggtg cggctgtggg cgagatagtc    780
ggggaggctt tgacaaacgg caaaaatcct gacactttga cagctaaaga acgcgaacag    840
attttggcat acagcaaact ggttgccggt acggtaagcg gtgtggtcgg cggcgatgta    900
aatgcggcgg cgaatgcggc tgaggtagcg gtgaaaaata atcagcttag cgacaaatga    960
```

<210> SEQ ID NO 68
<211> LENGTH: 319
<212> TYPE: PRT
<213> ORGANISM: Neisseria meningitidis
<220> FEATURE:
<221> NAME/KEY: SITE
<222> LOCATION: (28)
<223> OTHER INFORMATION: unknown
<220> FEATURE:
<221> NAME/KEY: SITE
<222> LOCATION: (42)
<223> OTHER INFORMATION: unknown
<220> FEATURE:
<221> NAME/KEY: SITE
<222> LOCATION: (56)
<223> OTHER INFORMATION: unknown

<400> SEQUENCE: 68

Gln Cys Arg Leu Lys Ser Ser Gln Phe Tyr Arg Arg His Leu Leu Cys
 1               5                  10                  15

Lys Tyr Ile Tyr Arg Phe Pro Ile Tyr Cys Pro Xaa Ala Cys Val Ala
             20                  25                  30

Glu Asp Thr Pro Tyr Ala Cys Tyr Leu Xaa Gln Leu Gln Val Thr Lys
         35                  40                  45

Asp Val Asn Trp Asn Gln Val Xaa Leu Ala Tyr Asp Lys Trp Asp Tyr
     50                  55                  60

Lys Gln Glu Gly Leu Thr Gly Ala Gly Ala Ala Ile Ile Ala Leu Ala
 65                  70                  75                  80

Val Thr Val Thr Ala Gly Ala Gly Ala Gly Ala Ala Leu Gly Leu
                 85                  90                  95

Asn Gly Ala Ala Ala Ala Thr Asp Ala Ala Phe Ala Ser Leu Ala
            100                 105                 110

Ser Gln Ala Ser Val Ser Leu Ile Asn Asn Lys Gly Asn Ile Gly Asn
            115                 120                 125

Thr Leu Lys Glu Leu Gly Arg Ser Ser Thr Val Lys Asn Leu Met Val
    130                 135                 140

Ala Val Ala Thr Ala Gly Val Ala Asp Lys Ile Gly Ala Ser Ala Leu
145                 150                 155                 160

Asn Asn Val Ser Asp Lys Gln Trp Ile Asn Asn Leu Thr Val Asn Leu
                165                 170                 175

Ala Asn Ala Gly Ser Ala Ala Leu Ile Asn Thr Ala Val Asn Gly Gly
            180                 185                 190

Ser Leu Lys Asp Asn Leu Glu Ala Asn Ile Leu Ala Ala Leu Val Asn
        195                 200                 205

Thr Ala His Gly Glu Ala Ala Ser Lys Ile Lys Gln Leu Asp Gln His
    210                 215                 220

Tyr Ile Thr His Lys Ile Ala His Ala Ile Ala Gly Cys Ala Ala Ala
225                 230                 235                 240

```
Ala Ala Asn Lys Gly Lys Cys Gln Asp Gly Ala Ile Gly Ala Ala Val
            245                 250                 255

Gly Glu Ile Val Gly Glu Ala Leu Thr Asn Gly Lys Asn Pro Asp Thr
        260                 265                 270

Leu Thr Ala Lys Glu Arg Glu Gln Ile Leu Ala Tyr Ser Lys Leu Val
    275                 280                 285

Ala Gly Thr Val Ser Gly Val Val Gly Gly Asp Val Asn Ala Ala Ala
        290                 295                 300

Asn Ala Ala Glu Val Ala Val Lys Asn Asn Gln Leu Ser Asp Lys
305                 310                 315

<210> SEQ ID NO 69
<211> LENGTH: 1860
<212> TYPE: DNA
<213> ORGANISM: Neisseria meningitidis

<400> SEQUENCE: 69
atgcaagtaa atattcagat tccctatata ctgcccagat gcgtgcgtgc tgaagacacc      60
ccctacgctt gctatttgaa acagctccaa gtcaccaaag acgtcaactg gaaccaggta     120
caactggcgt acgacaaatg ggactataaa caggaaggct taaccggagc cggagcagcg     180
attattgcgc tggctgttac cgtggttact gcgggcgcgg gagccggagc cgcactgggc     240
ttaaacggcg cggccgcagc ggcaaccgat gccgcattcg cctcgctggc cagccaggct     300
tccgtatcgc tcatcaacaa caaaggcaat atcggtaaca ccctgaaaga gctgggcaga     360
agcagcacgg tgaaaaatct gatggttgcc gtcgctaccg caggcgtagc cgacaaaatc     420
ggtgcttcgg cactgaacaa tgtcagcgat aagcagtgga tcaacaacct gaccgtcaac     480
ctggccaatg cgggcagtgc cgcactgatt aataccgctg tcaacggcgg cagcctgaaa     540
gacaatctgg aagcgaatat ccttgcggct ttggtgaata ctgcgcatgg agaagcagcc     600
agtaaaatca acagttgga tcagcactac attacccaca gattgcccca tgccatagcg     660
ggctgtgcgg ctgcggcggc gaataagggc aagtgtcagg atggtgcgat aggtgcggct     720
gtgggcgaga tagtcgggga ggcttttgaca acggcaaaa atcctgacac tttgacagct     780
aaagaacgcg aacagatttt ggcatacagc aaactggttg ccggtacggt aagcggtgtg     840
gtcggcggcg atgtaaatgc ggcggcgaat gcggctgagg tagcggtgaa aaataatcag     900
cttagcgaca agagggtag agaatttgat aacgaaatga ctgcatgcgc caaacagaat     960
aatcctcaac tgtgcagaaa aaatactgta aaaagtatc aaaatgttgc tgataaaaga    1020
cttgctgctt cgattgcaat atgtacggat atatcccgta gtactgaatg tagaacaatc    1080
agaaaacaac atttgatcga tagtagaagc cttcattcat cttgggaagc aggtctaatt    1140
ggtaaagatg atgaatggta taaattattc agcaaatctt acacccaagc agatttggct    1200
ttacagtctt atcatttgaa tactgctgct aaatcttggc ttcaatcggg caatacaaag    1260
cctttatccg aatggatgtc cgaccaaggt tatacactta tttcaggagt taatcctaga    1320
ttcattccaa taccaagagg gtttgtaaaa caaaatacac ctattactaa tgtcaaatac    1380
ccggaaggca tcagttttcga tacaaaccta aaaagacatc tggcaaatgc tgatggtttt    1440
agtcaaaaac agggcattaa aggagcccat aaccgcacca ttttatggc agaactaaat    1500 tcacgaggag gacgcgtaaa atctgaaacc caaactgata ttgaaggcat acccgaatt    1560 aaatatgaga ttcctacact agacaggaca ggtaaacctg atggtggatt taaggaaatt    1620
tcaagtataa aaactgttta taatcctaaa aaattttctg atgataaaat acttcaaatg    1680
```

-continued

```
gctcaaaatg ctgcttcaca aggatattca aaagcctcta aaattgctca aaatgaaaga   1740
actaaatcaa tatcggaaag aaaaaatgtc attcaattct cagaaacctt tgacggaatc   1800
aaatttagat catattttga tgtaaataca ggaagaatta caaacattca cccagaataa   1860
```

```
<210> SEQ ID NO 70
<211> LENGTH: 619
<212> TYPE: PRT
<213> ORGANISM: Neisseria meningitidis

<400> SEQUENCE: 70

Met Gln Val Asn Ile Gln Ile Pro Tyr Ile Leu Pro Arg Cys Val Arg
 1               5                  10                  15

Ala Glu Asp Thr Pro Tyr Ala Cys Tyr Leu Lys Gln Leu Gln Val Thr
                20                  25                  30

Lys Asp Val Asn Trp Asn Gln Val Gln Leu Ala Tyr Asp Lys Trp Asp
            35                  40                  45

Tyr Lys Gln Glu Gly Leu Thr Gly Ala Gly Ala Ala Ile Ile Ala Leu
        50                  55                  60

Ala Val Thr Val Val Thr Ala Gly Ala Gly Ala Gly Ala Ala Leu Gly
    65                  70                  75                  80

Leu Asn Gly Ala Ala Ala Ala Thr Asp Ala Ala Phe Ala Ser Leu
                85                  90                  95

Ala Ser Gln Ala Ser Val Ser Leu Ile Asn Asn Lys Gly Asn Ile Gly
               100                 105                 110

Asn Thr Leu Lys Glu Leu Gly Arg Ser Ser Thr Val Lys Asn Leu Met
           115                 120                 125

Val Ala Val Ala Thr Ala Gly Val Ala Asp Lys Ile Gly Ala Ser Ala
       130                 135                 140

Leu Asn Asn Val Ser Asp Lys Gln Trp Ile Asn Asn Leu Thr Val Asn
145                 150                 155                 160

Leu Ala Asn Ala Gly Ser Ala Ala Leu Ile Asn Thr Ala Val Asn Gly
                165                 170                 175

Gly Ser Leu Lys Asp Asn Leu Glu Ala Asn Ile Leu Ala Ala Leu Val
            180                 185                 190

Asn Thr Ala His Gly Glu Ala Ala Ser Lys Ile Lys Gln Leu Asp Gln
        195                 200                 205

His Tyr Ile Thr His Lys Ile Ala His Ala Ile Ala Gly Cys Ala Ala
    210                 215                 220

Ala Ala Ala Asn Lys Gly Lys Cys Gln Asp Gly Ala Ile Gly Ala Ala
225                 230                 235                 240

Val Gly Glu Ile Val Gly Glu Ala Leu Thr Asn Gly Lys Asn Pro Asp
                245                 250                 255

Thr Leu Thr Ala Lys Glu Arg Glu Gln Ile Leu Ala Tyr Ser Lys Leu
            260                 265                 270

Val Ala Gly Thr Val Ser Gly Val Gly Gly Asp Val Asn Ala Ala
        275                 280                 285

Ala Asn Ala Ala Glu Val Ala Val Lys Asn Asn Gln Leu Ser Asp Lys
    290                 295                 300

Glu Gly Arg Glu Phe Asp Asn Glu Met Thr Ala Cys Ala Lys Gln Asn
305                 310                 315                 320

Asn Pro Gln Leu Cys Arg Lys Asn Thr Val Lys Lys Tyr Gln Asn Val
                325                 330                 335

Ala Asp Lys Arg Leu Ala Ala Ser Ile Ala Ile Cys Thr Asp Ile Ser
```

-continued

```
                     340              345             350
Arg Ser Thr Glu Cys Arg Thr Ile Arg Lys Gln His Leu Ile Asp Ser
            355                 360             365
Arg Ser Leu His Ser Ser Trp Glu Ala Gly Leu Ile Gly Lys Asp Asp
        370                 375             380
Glu Trp Tyr Lys Leu Phe Ser Lys Ser Tyr Thr Gln Ala Asp Leu Ala
385                 390                 395                 400
Leu Gln Ser Tyr His Leu Asn Thr Ala Ala Lys Ser Trp Leu Gln Ser
                405                 410             415
Gly Asn Thr Lys Pro Leu Ser Glu Trp Met Ser Asp Gln Gly Tyr Thr
            420                 425             430
Leu Ile Ser Gly Val Asn Pro Arg Phe Ile Pro Ile Pro Arg Gly Phe
            435                 440             445
Val Lys Gln Asn Thr Pro Ile Thr Asn Val Lys Tyr Pro Glu Gly Ile
        450                 455             460
Ser Phe Asp Thr Asn Leu Lys Arg His Leu Ala Asn Ala Asp Gly Phe
465                 470                 475                 480
Ser Gln Lys Gln Gly Ile Lys Gly Ala His Asn Arg Thr Asn Phe Met
                485                 490             495
Ala Glu Leu Asn Ser Arg Gly Gly Arg Val Lys Ser Glu Thr Gln Thr
            500                 505             510
Asp Ile Glu Gly Ile Thr Arg Ile Lys Tyr Glu Ile Pro Thr Leu Asp
        515                 520             525
Arg Thr Gly Lys Pro Asp Gly Gly Phe Lys Glu Ile Ser Ser Ile Lys
        530                 535             540
Thr Val Tyr Asn Pro Lys Lys Phe Ser Asp Asp Lys Ile Leu Gln Met
545                 550                 555                 560
Ala Gln Asn Ala Ala Ser Gln Gly Tyr Ser Lys Ala Ser Lys Ile Ala
                565                 570             575
Gln Asn Glu Arg Thr Lys Ser Ile Ser Glu Arg Lys Asn Val Ile Gln
            580                 585             590
Phe Ser Glu Thr Phe Asp Gly Ile Lys Phe Arg Ser Tyr Phe Asp Val
        595                 600             605
Asn Thr Gly Arg Ile Thr Asn Ile His Pro Glu
    610                 615
```

<210> SEQ ID NO 71
<211> LENGTH: 1788
<212> TYPE: DNA
<213> ORGANISM: Neisseria meningitidis
<220> FEATURE:
<221> NAME/KEY: misc_feature
<222> LOCATION: (181)
<223> OTHER INFORMATION: any nucleotide
<220> FEATURE:
<221> NAME/KEY: misc_feature
<222> LOCATION: (365)
<223> OTHER INFORMATION: any nucleotide
<220> FEATURE:
<221> NAME/KEY: misc_feature
<222> LOCATION: (473)
<223> OTHER INFORMATION: any nucleotide
<220> FEATURE:
<221> NAME/KEY: misc_feature
<222> LOCATION: (838)
<223> OTHER INFORMATION: any nucleotide
<220> FEATURE:
<221> NAME/KEY: misc_feature
<222> LOCATION: (890)
<223> OTHER INFORMATION: any nucleotide
<220> FEATURE:

<220> FEATURE:
<221> NAME/KEY: misc_feature
<222> LOCATION: (1339)
<223> OTHER INFORMATION: any nucleotide
<220> FEATURE:
<221> NAME/KEY: misc_feature
<222> LOCATION: (1411)
<223> OTHER INFORMATION: any nucleotide
<220> FEATURE:
<221> NAME/KEY: misc_feature
<222> LOCATION: (1441)
<223> OTHER INFORMATION: any nucleotide
<220> FEATURE:
<221> NAME/KEY: misc_feature
<222> LOCATION: (1443)
<223> OTHER INFORMATION: any nucleotide
<220> FEATURE:
<221> NAME/KEY: misc_feature
<222> LOCATION: (1461)
<223> OTHER INFORMATION: any nucleotide
<220> FEATURE:
<221> NAME/KEY: misc_feature
<222> LOCATION: (1581)
<223> OTHER INFORMATION: any nucleotide
<220> FEATURE:
<221> NAME/KEY: misc_feature
<222> LOCATION: (1586)..(1587)
<223> OTHER INFORMATION: any nucleotide
<220> FEATURE:
<221> NAME/KEY: misc_feature
<222> LOCATION: (1615)
<223> OTHER INFORMATION: any nucleotide
<220> FEATURE:
<221> NAME/KEY: misc_feature
<222> LOCATION: (1622)
<223> OTHER INFORMATION: any nucleotide
<220> FEATURE:
<221> NAME/KEY: misc_feature
<222> LOCATION: (1738)..(1740)
<223> OTHER INFORMATION: any nucleotide
<220> FEATURE:
<221> NAME/KEY: misc_feature
<222> LOCATION: (1744)
<223> OTHER INFORMATION: any nucleotide
<220> FEATURE:
<221> NAME/KEY: misc_feature
<222> LOCATION: (1746)
<223> OTHER INFORMATION: any nucleotide

<400> SEQUENCE: 71

| | | | | | |
|---|---|---|---|---|---|
| tatctgaaac | agctccaagt | agcgaaaaac | atcaactgga | atcaggtgca | gcttgcttac | 60 |
| gacagatggg | actacaaaca | ggagggctta | accgaagcag | gtgcggcgat | tatcgcactg | 120 |
| gccgttaccg | tggtcacctc | aggcgcagga | accggagccg | tattgggatt | aaacggtgcg | 180 |
| nccgccgccg | caaccgatgc | agcattcgcc | tctttggcca | gccaggcttc | cgtatcgttc | 240 |
| atcaacaaca | aaggcgatgt | cggcaaaacc | ctgaaagagc | tgggcagaag | cagcacggtg | 300 |
| aaaaatctgg | tggttgccgc | cgctaccgca | ggcgtagccg | acaaaatcgg | cgcttcggca | 360 |
| ctgancaatg | tcagcgataa | gcagtggatc | aacaacctga | ccgtcaacct | agccaatgcg | 420 |
| ggcagtgccg | cactgattaa | taccgctgtc | aacggcggca | gcctgaaaga | cantctggaa | 480 |
| gcgaatatcc | ttgcggcttt | ggtcaatacc | gcgcatggag | aagcagccag | taaaatcaaa | 540 |
| cagttggatc | agcactacat | agtccacaag | attgcccatg | ccatagcggg | ctgtgcggca | 600 |
| gcggcggcga | ataagggcaa | gtgtcaggat | ggtgcgatag | gtgcggctgt | gggcgagata | 660 |
| gtcgggagg | ctttgacaaa | cggcaaaaat | cctgacactt | tgacagctaa | agaacgcgaa | 720 |
| cagattttgg | catacagcaa | actggttgcc | ggtacggtaa | gcggtgtggt | cggcggcgat | 780 |
| gtaaatgcgg | cggcgaatgc | ggctgaggta | gcggtgaaaa | ataatcagct | tagcgacnaa | 840 |
| gagggtagag | aatttgataa | cgaaatgact | gcatgcgcca | aacagaatan | tcctcaactg | 900 |

-continued

```
tgcagaaaaa atactgtaaa aaagtatcaa aatgttgctg ataaaagact tgctgcttcg      960
attgcaatat gtacggatat atcccgtagt actgaatgta gaacaatcag aaaacaacat     1020
ttgatcgata gtagaagcct tcattcatct tgggaagcag gtctaattgg taaagatgat     1080
gaatggtata aattattcag caaatcttac acccaagcag atttggcttt acagtcttat     1140
catttgaata ctgctgctaa atcttggctt caatcgggca atacaaagcc tttatccgaa     1200
tggatgtccg accaaggtta tacacttatt tcaggagtta atcctagatt cattccaata     1260
ccaagagggt ttgtaaaaca aaatacacct attactaatg tcaaataccc ggaaggcatc     1320
agtttcgata caaacctana agacatctg gcaaatgctg atggttttag tcaagaacag     1380
ggcattaaag gagcccataa ccgcaccaat nttatggcag aactaaattc acgaggagga     1440
ngngtaaaat ctgaaaccca nactgatatt gaaggcatta cccgaattaa atatgagatt     1500
cctacactag acaggacagg taaacctgat ggtggattta aggaaatttc aagtataaaa     1560
actgtttata atcctaaaaa nttttnngat gataaaatac ttcaaatggc tcaanatgct     1620
gnttcacaag gatattcaaa agcctctaaa attgctcaaa atgaaagaac taaatcaata     1680
tcggaaagaa aaaatgtcat tcaattctca gaaacctttg acggaatcaa atttagannn     1740
tatntngatg taaatacagg aagaattaca acattcacc cagaataa                   1788
```

<210> SEQ ID NO 72
<211> LENGTH: 595
<212> TYPE: PRT
<213> ORGANISM: Neisseria meningitidis
<220> FEATURE:
<221> NAME/KEY: SITE
<222> LOCATION: (61)
<223> OTHER INFORMATION: unknown
<220> FEATURE:
<221> NAME/KEY: SITE
<222> LOCATION: (122)
<223> OTHER INFORMATION: unknown
<220> FEATURE:
<221> NAME/KEY: SITE
<222> LOCATION: (158)
<223> OTHER INFORMATION: unknown
<220> FEATURE:
<221> NAME/KEY: SITE
<222> LOCATION: (280)
<223> OTHER INFORMATION: unknown
<220> FEATURE:
<221> NAME/KEY: SITE
<222> LOCATION: (297)
<223> OTHER INFORMATION: unknown
<220> FEATURE:
<221> NAME/KEY: SITE
<222> LOCATION: (447)
<223> OTHER INFORMATION: unknown
<220> FEATURE:
<221> NAME/KEY: SITE
<222> LOCATION: (471)
<223> OTHER INFORMATION: unknown
<220> FEATURE:
<221> NAME/KEY: SITE
<222> LOCATION: (481)
<223> OTHER INFORMATION: unknown
<220> FEATURE:
<221> NAME/KEY: SITE
<222> LOCATION: (487)
<223> OTHER INFORMATION: unknown
<220> FEATURE:
<221> NAME/KEY: SITE
<222> LOCATION: (527)
<223> OTHER INFORMATION: unknown
<220> FEATURE:
<221> NAME/KEY: SITE
<222> LOCATION: (529)

```
<223> OTHER INFORMATION: unknown
<220> FEATURE:
<221> NAME/KEY: SITE
<222> LOCATION: (539)
<223> OTHER INFORMATION: unknown
<220> FEATURE:
<221> NAME/KEY: SITE
<222> LOCATION: (541)
<223> OTHER INFORMATION: unknown
<220> FEATURE:
<221> NAME/KEY: SITE
<222> LOCATION: (580)
<223> OTHER INFORMATION: unknown
<220> FEATURE:
<221> NAME/KEY: SITE
<222> LOCATION: (582)
<223> OTHER INFORMATION: unknown

<400> SEQUENCE: 72

Tyr Leu Lys Gln Leu Gln Val Ala Lys Asn Ile Asn Trp Asn Gln Val
 1               5                  10                  15

Gln Leu Ala Tyr Asp Arg Trp Asp Tyr Lys Gln Glu Gly Leu Thr Glu
             20                  25                  30

Ala Gly Ala Ala Ile Ile Ala Leu Ala Val Thr Val Thr Ser Gly
         35                  40                  45

Ala Gly Thr Gly Ala Val Leu Gly Leu Asn Gly Ala Xaa Ala Ala Ala
     50                  55                  60

Thr Asp Ala Ala Phe Ala Ser Leu Ala Ser Gln Ala Ser Val Ser Phe
 65                  70                  75                  80

Ile Asn Asn Lys Gly Asp Val Gly Lys Thr Leu Lys Glu Leu Gly Arg
                 85                  90                  95

Ser Ser Thr Val Lys Asn Leu Val Val Ala Ala Thr Ala Gly Val
            100                 105                 110

Ala Asp Lys Ile Gly Ala Ser Ala Leu Xaa Asn Val Ser Asp Lys Gln
            115                 120                 125

Trp Ile Asn Asn Leu Thr Val Asn Leu Ala Asn Ala Gly Ser Ala Ala
130                 135                 140

Leu Ile Asn Thr Ala Val Asn Gly Gly Ser Leu Lys Asp Xaa Leu Glu
145                 150                 155                 160

Ala Asn Ile Leu Ala Ala Leu Val Asn Thr Ala His Gly Glu Ala Ala
                165                 170                 175

Ser Lys Ile Lys Gln Leu Asp Gln His Tyr Ile Val His Lys Ile Ala
            180                 185                 190

His Ala Ile Ala Gly Cys Ala Ala Ala Ala Asn Lys Gly Lys Cys
            195                 200                 205

Gln Asp Gly Ala Ile Gly Ala Ala Val Gly Glu Ile Val Gly Glu Ala
        210                 215                 220

Leu Thr Asn Gly Lys Asn Pro Asp Thr Leu Thr Ala Lys Glu Arg Glu
225                 230                 235                 240

Gln Ile Leu Ala Tyr Ser Lys Leu Val Ala Gly Thr Val Ser Gly Val
                245                 250                 255

Val Gly Gly Asp Val Asn Ala Ala Ala Asn Ala Ala Glu Val Ala Val
            260                 265                 270

Lys Asn Asn Gln Leu Ser Asp Xaa Glu Gly Arg Glu Phe Asp Asn Glu
        275                 280                 285

Met Thr Ala Cys Ala Lys Gln Asn Xaa Pro Gln Leu Cys Arg Lys Asn
290                 295                 300

Thr Val Lys Lys Tyr Gln Asn Val Ala Asp Lys Arg Leu Ala Ala Ser
305                 310                 315                 320
```

Ile Ala Ile Cys Thr Asp Ile Ser Arg Ser Thr Glu Cys Arg Thr Ile
              325                 330                 335

Arg Lys Gln His Leu Ile Asp Ser Arg Ser Leu His Ser Ser Trp Glu
            340                 345                 350

Ala Gly Leu Ile Gly Lys Asp Asp Glu Trp Tyr Lys Leu Phe Ser Lys
        355                 360                 365

Ser Tyr Thr Gln Ala Asp Leu Ala Leu Gln Ser Tyr His Leu Asn Thr
    370                 375                 380

Ala Ala Lys Ser Trp Leu Gln Ser Gly Asn Thr Lys Pro Leu Ser Glu
385                 390                 395                 400

Trp Met Ser Asp Gln Gly Tyr Thr Leu Ile Ser Gly Val Asn Pro Arg
                405                 410                 415

Phe Ile Pro Ile Pro Arg Gly Phe Val Lys Gln Asn Thr Pro Ile Thr
            420                 425                 430

Asn Val Lys Tyr Pro Glu Gly Ile Ser Phe Asp Thr Asn Leu Xaa Arg
        435                 440                 445

His Leu Ala Asn Ala Asp Gly Phe Ser Gln Glu Gln Gly Ile Lys Gly
    450                 455                 460

Ala His Asn Arg Thr Asn Xaa Met Ala Glu Leu Asn Ser Arg Gly Gly
465                 470                 475                 480

Xaa Val Lys Ser Glu Thr Xaa Thr Asp Ile Gly Ile Thr Arg Ile
                485                 490                 495

Lys Tyr Glu Ile Pro Thr Leu Asp Arg Thr Gly Lys Pro Asp Gly Gly
            500                 505                 510

Phe Lys Glu Ile Ser Ser Ile Lys Thr Val Tyr Asn Pro Lys Xaa Phe
        515                 520                 525

Xaa Asp Asp Lys Ile Leu Gln Met Ala Gln Xaa Ala Xaa Ser Gln Gly
    530                 535                 540

Tyr Ser Lys Ala Ser Lys Ile Ala Gln Asn Glu Arg Thr Lys Ser Ile
545                 550                 555                 560

Ser Glu Arg Lys Asn Val Ile Gln Phe Ser Glu Thr Phe Asp Gly Ile
                565                 570                 575

Lys Phe Arg Xaa Tyr Xaa Asp Val Asn Thr Gly Arg Ile Thr Asn Ile
            580                 585                 590

His Pro Glu
    595

<210> SEQ ID NO 73
<211> LENGTH: 453
<212> TYPE: DNA
<213> ORGANISM: Neisseria meningitidis

<400> SEQUENCE: 73
atggcaatca ttacattgta ttattctgtc aatggtattt taaatgtatg tgcaaaagca      60
aaaaatattc aagtagttgc caataataag aatatggttc tttttgggtt tttggsmrgc     120
atcatcggcg gttcaaccaa tgccatgtct cccatattgt taatattttt gcttagcgaa     180
acagaaaata aaaatcgtat cgtaaaatca agcaatctat gctatctttt ggcgaaaatt     240
gttcaaatat atatgctaag agaccagtat tggttattaa ataagagtga atacgdttta     300
atatttttac tgtccgtatt gtctgttatt ggattgtatg ttggaattcg gttaaggact     360
aagattagcc caatttttt taaaatgtta atttttattg ttttattggt attggctctg     420
aaaatcgggc attcgggttt aatcaaactt taa                                  453

<210> SEQ ID NO 74
<211> LENGTH: 150
<212> TYPE: PRT
<213> ORGANISM: Neisseria meningitidis
<220> FEATURE:
<221> NAME/KEY: SITE
<222> LOCATION: (39)..(40)
<223> OTHER INFORMATION: unknown
<220> FEATURE:
<221> NAME/KEY: SITE
<222> LOCATION: (99)
<223> OTHER INFORMATION: unknown

<400> SEQUENCE: 74

```
Met Ala Ile Ile Thr Leu Tyr Tyr Ser Val Asn Gly Ile Leu Asn Val
  1               5                  10                  15

Cys Ala Lys Ala Lys Asn Ile Gln Val Ala Asn Asn Lys Asn Met
                 20                  25                  30

Val Leu Phe Gly Phe Leu Xaa Xaa Ile Ile Gly Gly Ser Thr Asn Ala
             35                  40                  45

Met Ser Pro Ile Leu Leu Ile Phe Leu Leu Ser Glu Thr Glu Asn Lys
         50                  55                  60

Asn Arg Ile Val Lys Ser Ser Asn Leu Cys Tyr Leu Leu Ala Lys Ile
 65                  70                  75                  80

Val Gln Ile Tyr Met Leu Arg Asp Gln Tyr Trp Leu Leu Asn Lys Ser
                 85                  90                  95

Glu Tyr Xaa Leu Ile Phe Leu Leu Ser Val Leu Ser Val Ile Gly Leu
            100                 105                 110

Tyr Val Gly Ile Arg Leu Arg Thr Lys Ile Ser Pro Asn Phe Phe Lys
        115                 120                 125

Met Leu Ile Phe Ile Val Leu Leu Val Leu Ala Leu Lys Ile Gly His
    130                 135                 140

Ser Gly Leu Ile Lys Leu
145                 150
```

<210> SEQ ID NO 75
<211> LENGTH: 768
<212> TYPE: DNA
<213> ORGANISM: Neisseria meningitidis

<400> SEQUENCE: 75

```
atgcaagaaa taatgcaatc tatcgttttt gttgctgccg caatactgca cggaattaca      60
ggcatgggat ttccgatgct cggtacaacc gcattggctt ttatcatgcc attgtctaag     120
gttgttgcct tggtggcatt accaagcctg ttaatgagct tgttggttct atgcagcaat     180
aacaaaaagg ttttttggca agagattgtt tattatttaa aaacctataa attgcttgct     240
atcggcagcg tcgttggcag cattttgggg gtgaagttgc ttttgatact tccagtgtct     300
tggctgcttt tactgatggc aatcattaca ttgtattatt ctgtcaatgg tattttaaat     360
gtatgtgcaa aagcaaaaaa tattcaagta gttgccaata taagaatat ggttctttt     420
gggttttttgg caggcatcat cggcggttca accaatgcca tgtctcccat attgttaata     480
tttttgctta gcgaaacaga aaataaaaat cgtatcgtaa aatcaagcaa tctatgctat     540
cttttggcga aaattgttca atatatatg ctaagagacc agtattggtt attaaataag     600
agtgaatacg gttaatatt tttactgtcc gtattgtctg ttattggatt gtatgttgga     660
attcggttaa ggactaagat tagcccaaat ttttttaaaa tgttaatttt tattgtttta     720
ttggtattgg ctctgaaaat cgggcattcg ggtttaatca aacttttaa                 768
```

<210> SEQ ID NO 76
<211> LENGTH: 255
<212> TYPE: PRT
<213> ORGANISM: Neisseria meningitidis

<400> SEQUENCE: 76

```
Met Gln Glu Ile Met Gln Ser Ile Val Phe Val Ala Ala Ala Ile Leu
  1               5                  10                  15

His Gly Ile Thr Gly Met Gly Phe Pro Met Leu Gly Thr Thr Ala Leu
             20                  25                  30

Ala Phe Ile Met Pro Leu Ser Lys Val Val Ala Leu Val Ala Leu Pro
         35                  40                  45

Ser Leu Leu Met Ser Leu Leu Val Leu Cys Ser Asn Asn Lys Lys Gly
     50                  55                  60

Phe Trp Gln Glu Ile Val Tyr Tyr Leu Lys Thr Tyr Lys Leu Leu Ala
 65                  70                  75                  80

Ile Gly Ser Val Val Gly Ser Ile Leu Gly Val Lys Leu Leu Leu Ile
                 85                  90                  95

Leu Pro Val Ser Trp Leu Leu Leu Met Ala Ile Ile Thr Leu Tyr
            100                 105                 110

Tyr Ser Val Asn Gly Ile Leu Asn Val Cys Ala Lys Ala Lys Asn Ile
            115                 120                 125

Gln Val Val Ala Asn Asn Lys Asn Met Val Leu Phe Gly Phe Leu Ala
        130                 135                 140

Gly Ile Ile Gly Gly Ser Thr Asn Ala Met Ser Pro Ile Leu Leu Ile
145                 150                 155                 160

Phe Leu Leu Ser Glu Thr Glu Asn Lys Asn Arg Ile Val Lys Ser Ser
                165                 170                 175

Asn Leu Cys Tyr Leu Leu Ala Lys Ile Val Gln Ile Tyr Met Leu Arg
            180                 185                 190

Asp Gln Tyr Trp Leu Leu Asn Lys Ser Glu Tyr Gly Leu Ile Phe Leu
        195                 200                 205

Leu Ser Val Leu Ser Val Ile Gly Leu Tyr Val Gly Ile Arg Leu Arg
    210                 215                 220

Thr Lys Ile Ser Pro Asn Phe Phe Lys Met Leu Ile Phe Ile Val Leu
225                 230                 235                 240

Leu Val Leu Ala Leu Lys Ile Gly His Ser Gly Leu Ile Lys Leu
                245                 250                 255
```

<210> SEQ ID NO 77
<211> LENGTH: 768
<212> TYPE: DNA
<213> ORGANISM: Neisseria meningitidis

<400> SEQUENCE: 77

| | |
|---|---|
| atgcaagaaa taatgcaatc tatcgttttt gttgctgccg caatactgca cggaattaca | 60 |
| ggcatgggat ttccgatgct cggtacaacc gcattggctt ttatcatgcc attgtctaag | 120 |
| gttgttgcct tggtggcatt accaagcctg ttaatgagct tgttggttct atgcagcaat | 180 |
| aacaaaaagg ttttttggca agagattgtt tattatttaa aaacctataa attgcttgct | 240 |
| atcggcagcg tcgttggcag cattttgggg gtgaagttgc ttttgatact tccagtgtct | 300 |
| tggctgcttt tactgatggc aatcattaca ttgtattatt ctgtcaatgg tattttaaat | 360 |
| gtatgtgcaa aagcaaaaaa tattcaagta gttgccaata taagaatat ggttcttttt | 420 |

```
gggttttt gg caggcatcat cggcggttca accaatgcca tgtctcccat attgttaata    480
tttttgctta gcgaaacaga gaataaaaat cgtatcgcaa atcaagcaa tctatgctat     540 cttttggcaa aaattgttca atatatatg ctaagagacc agtattggtt attaaataag     600
agtgaatacg gtttaatatt tttactgtcc gtattgtctg ttattggatt gtatgttgga   660
attcggttaa ggactaagat tagcccaaat tttttaaaa tgttaatttt tattgttta     720 ttggtattgg ctctgaaaat cgggtattca ggtttaatca aacttaa                 768
```

<210> SEQ ID NO 78
<211> LENGTH: 255
<212> TYPE: PRT
<213> ORGANISM: Neisseria meningitidis

<400> SEQUENCE: 78

```
Met Gln Glu Ile Met Gln Ser Ile Val Phe Val Ala Ala Ala Ile Leu
 1               5                  10                  15

His Gly Ile Thr Gly Met Gly Phe Pro Met Leu Gly Thr Thr Ala Leu
            20                  25                  30

Ala Phe Ile Met Pro Leu Ser Lys Val Val Ala Leu Val Ala Leu Pro
        35                  40                  45

Ser Leu Leu Met Ser Leu Leu Val Leu Cys Ser Asn Asn Lys Lys Gly
    50                  55                  60

Phe Trp Gln Glu Ile Val Tyr Tyr Leu Lys Thr Tyr Lys Leu Leu Ala
65                  70                  75                  80

Ile Gly Ser Val Val Gly Ser Ile Leu Gly Val Lys Leu Leu Leu Ile
                85                  90                  95

Leu Pro Val Ser Trp Leu Leu Leu Met Ala Ile Ile Thr Leu Tyr
           100                 105                 110

Tyr Ser Val Asn Gly Ile Leu Asn Val Cys Ala Lys Ala Lys Asn Ile
        115                 120                 125

Gln Val Val Ala Asn Asn Lys Asn Met Val Leu Phe Gly Phe Leu Ala
    130                 135                 140

Gly Ile Ile Gly Gly Ser Thr Asn Ala Met Ser Pro Ile Leu Leu Ile
145                 150                 155                 160

Phe Leu Leu Ser Glu Thr Glu Asn Lys Asn Arg Ile Ala Lys Ser Ser
                165                 170                 175

Asn Leu Cys Tyr Leu Leu Ala Lys Ile Val Gln Ile Tyr Met Leu Arg
            180                 185                 190

Asp Gln Tyr Trp Leu Leu Asn Lys Ser Glu Tyr Gly Leu Ile Phe Leu
        195                 200                 205

Leu Ser Val Leu Ser Val Ile Gly Leu Tyr Val Gly Ile Arg Leu Arg
    210                 215                 220

Thr Lys Ile Ser Pro Asn Phe Phe Lys Met Leu Ile Phe Ile Val Leu
225                 230                 235                 240

Leu Val Leu Ala Leu Lys Ile Gly Tyr Ser Gly Leu Ile Lys Leu
                245                 250                 255
```

<210> SEQ ID NO 79
<211> LENGTH: 516
<212> TYPE: DNA
<213> ORGANISM: Neisseria meningitidis

<400> SEQUENCE: 79

```
atgagacata tgaaaataca aaattattta ctagtattta tagttttaca tatagccttg    60
atagtaatta atatagtgtt tggttatttt gttttctat ttgattttt tgcgttttg     120
```

-continued

```
tttttttgcaa acgtctttct tgctgtaaat ttattatttt tagaaaaaaa cataaaaaac      180
aaattattgt ttttattgcc gatttctatt attatatgga tggtaattca tattagtatg      240
ataaatataa aattttataa atttgagcat caaataaagg aacaaaatat atcctcgatt      300
actggggtga taaaaccaca tgatagttat aattatgttt atgactcaaa tggatatgct      360
aaattaaaag ataatcatag atatggtagg gtaattagag aaacacctta tattgatgta      420
gttgcatctg atgttaaaaa taaatccata agattaagct tggtttgtgg tattcattca      480
tatgctccat gtgccaattt tataaaattt gtcagg                                 516
```

<210> SEQ ID NO 80
<211> LENGTH: 172
<212> TYPE: PRT
<213> ORGANISM: Neisseria meningitidis

<400> SEQUENCE: 80

```
Met Arg His Met Lys Ile Gln Asn Tyr Leu Leu Val Phe Ile Val Leu
 1               5                  10                  15

His Ile Ala Leu Ile Val Ile Asn Ile Val Phe Gly Tyr Phe Val Phe
                20                  25                  30

Leu Phe Asp Phe Phe Ala Phe Leu Phe Phe Ala Asn Val Phe Leu Ala
            35                  40                  45

Val Asn Leu Leu Phe Leu Glu Lys Asn Ile Lys Asn Lys Leu Leu Phe
        50                  55                  60

Leu Leu Pro Ile Ser Ile Ile Trp Met Val Ile His Ile Ser Met
 65              70                  75                  80

Ile Asn Ile Lys Phe Tyr Lys Phe Glu His Gln Ile Lys Glu Gln Asn
                85                  90                  95

Ile Ser Ser Ile Thr Gly Val Ile Lys Pro His Asp Ser Tyr Asn Tyr
            100                 105                 110

Val Tyr Asp Ser Asn Gly Tyr Ala Lys Leu Lys Asp Asn His Arg Tyr
        115                 120                 125

Gly Arg Val Ile Arg Glu Thr Pro Tyr Ile Asp Val Val Ala Ser Asp
    130                 135                 140

Val Lys Asn Lys Ser Ile Arg Leu Ser Leu Val Cys Gly Ile His Ser
145                 150                 155                 160

Tyr Ala Pro Cys Ala Asn Phe Ile Lys Phe Val Arg
                165                 170
```

<210> SEQ ID NO 81
<211> LENGTH: 729
<212> TYPE: DNA
<213> ORGANISM: Neisseria meningitidis

<400> SEQUENCE: 81

```
atgagacata tgaaaataaa aattatttta ctagtatttta tagttttaca tatagccttg       60
atagtaatta atatagtgtt tggttatttt gttttctat ttgatttttt tgcgttttg        120 tttttttgcaa acgtctttct tgctgtaaat ttattatttt tagaaaaaaa cataaaaaac      180
aaattattgt ttttattgcc gatttctatt attatatgga tggtaattca tattagtatg      240
ataaatataa aattttataa atttgagcat caaataaagg aacaaaatat atcctcgatt      300
actggggtga taaaaccaca tgatagttat aattatgttt atgactcaaa tggatatgct      360
aaattaaaag ataatcatag atatggtagg gtaattagag aaacacctta tattgatgta      420
gttgcatctg atgttaaaaa taaatccata agattaagct tggtttgtgg tattcattca      480
```

-continued

| | |
|---|---|
| tatgctccat gtgccaattt tataaaattt gcaaaaaaac ctgttaaaat ttattttat | 540 |
| aatcaacctc aaggagattt tatagataat gtaatatttg aaattaatga tggaaacaaa | 600 |
| agtttgtact tgttagataa gtataaaaca ttttttctta ttgaaaacag tgtttgtatc | 660 |
| gtattaatta ttttatattt aaaatttaat ttgcttttat ataggactta cttcaatgag | 720 |
| ttggaatag | 729 |

<210> SEQ ID NO 82
<211> LENGTH: 242
<212> TYPE: PRT
<213> ORGANISM: Neisseria meningitidis

<400> SEQUENCE: 82

Met Arg His Met Lys Asn Lys Asn Tyr Leu Leu Val Phe Ile Val Leu
1               5                   10                  15

His Ile Ala Leu Ile Val Ile Asn Ile Val Phe Gly Tyr Phe Val Phe
            20                  25                  30

Leu Phe Asp Phe Phe Ala Phe Leu Phe Phe Ala Asn Val Phe Leu Ala
        35                  40                  45

Val Asn Leu Leu Phe Leu Glu Lys Asn Ile Lys Asn Lys Leu Leu Phe
    50                  55                  60

Leu Leu Pro Ile Ser Ile Ile Trp Met Val Ile His Ile Ser Met
65                  70                  75                  80

Ile Asn Ile Lys Phe Tyr Lys Phe Glu His Gln Ile Lys Glu Gln Asn
                85                  90                  95

Ile Ser Ser Ile Thr Gly Val Ile Lys Pro His Asp Ser Tyr Asn Tyr
            100                 105                 110

Val Tyr Asp Ser Asn Gly Tyr Ala Lys Leu Lys Asp Asn His Arg Tyr
        115                 120                 125

Gly Arg Val Ile Arg Glu Thr Pro Tyr Ile Asp Val Val Ala Ser Asp
    130                 135                 140

Val Lys Asn Lys Ser Ile Arg Leu Ser Leu Val Cys Gly Ile His Ser
145                 150                 155                 160

Tyr Ala Pro Cys Ala Asn Phe Ile Lys Phe Ala Lys Lys Pro Val Lys
                165                 170                 175

Ile Tyr Phe Tyr Asn Gln Pro Gln Gly Asp Phe Ile Asp Asn Val Ile
            180                 185                 190

Phe Glu Ile Asn Asp Gly Asn Lys Ser Leu Tyr Leu Leu Asp Lys Tyr
        195                 200                 205

Lys Thr Phe Phe Leu Ile Glu Asn Ser Val Cys Ile Val Leu Ile Ile
    210                 215                 220

Leu Tyr Leu Lys Phe Asn Leu Leu Leu Tyr Arg Thr Tyr Phe Asn Glu
225                 230                 235                 240

Leu Glu

<210> SEQ ID NO 83
<211> LENGTH: 729
<212> TYPE: DNA
<213> ORGANISM: Neisseria meningitidis

<400> SEQUENCE: 83

| | |
|---|---|
| atgagacata tgaaaaataa aaattattta ctagtattta tagttttaca tataaccttg | 60 |
| atagtaatta atatagtgtt tggttatttt gttttctat ttgattttt tgcgttttg | 120 |
| ttttttgcaa acgtctttct tgctgtaaat ttattatttt tagaaaaaaa cataaaaaac | 180 |

```
aaattattgt tttttattgcc gatttctatt attatatgga tggtaattca tattagtatg      240
ataaatataa aatttttataa atttgagcat caaataaagg aacaaaatat atcctcgatt      300
actggggtga taaaaccaca tgatagttat aattatgttt atgactcaaa tggatatgct      360
aaattaaaag ataatcatag atatggtagg gtaattagag aaacaccttta tattgatgta    420 gttgcatctg atgttaaaaa taaatccata agattaagct tggtttgtgg tattcattca     480
tatgctccat gtgccaattt tataaaattt gcaaaaaaac ctgttaaaat ttattttttat    540 aatcaacctc aaggagattt tatagataat gtaatatttg aaattaatga tggaaaaaaa     600
agtttgtact tgttagataa gtataaaaca tttttttctta ttgaaaacag tgtttgtatc    660
gtattaatta ttttatattt aaaatttaat ttgcttttat ataggactta cttcaatgag    720
ttggaatag                                                             729

<210> SEQ ID NO 84
<211> LENGTH: 242
<212> TYPE: PRT
<213> ORGANISM: Neisseria meningitidis

<400> SEQUENCE: 84

Met Arg His Met Lys Asn Lys Asn Tyr Leu Leu Val Phe Ile Val Leu
  1               5                  10                  15

His Ile Thr Leu Ile Val Ile Asn Ile Val Phe Gly Tyr Phe Val Phe
             20                  25                  30

Leu Phe Asp Phe Phe Ala Phe Leu Phe Phe Ala Asn Val Phe Leu Ala
         35                  40                  45

Val Asn Leu Leu Phe Leu Glu Lys Asn Ile Lys Asn Lys Leu Leu Phe
     50                  55                  60

Leu Leu Pro Ile Ser Ile Ile Trp Met Val Ile His Ile Ser Met
 65                  70                  75                  80

Ile Asn Ile Lys Phe Tyr Lys Phe Glu His Gln Ile Lys Glu Gln Asn
                 85                  90                  95

Ile Ser Ser Ile Thr Gly Val Ile Lys Pro His Asp Ser Tyr Asn Tyr
            100                 105                 110

Val Tyr Asp Ser Asn Gly Tyr Ala Lys Leu Lys Asp Asn His Arg Tyr
        115                 120                 125

Gly Arg Val Ile Arg Glu Thr Pro Tyr Ile Asp Val Val Ala Ser Asp
    130                 135                 140

Val Lys Asn Lys Ser Ile Arg Leu Ser Leu Val Cys Gly Ile His Ser
145                 150                 155                 160

Tyr Ala Pro Cys Ala Asn Phe Ile Lys Phe Ala Lys Lys Pro Val Lys
                165                 170                 175

Ile Tyr Phe Tyr Asn Gln Pro Gln Gly Asp Phe Ile Asp Asn Val Ile
            180                 185                 190

Phe Glu Ile Asn Asp Gly Lys Lys Ser Leu Tyr Leu Leu Asp Lys Tyr
        195                 200                 205

Lys Thr Phe Phe Leu Ile Glu Asn Ser Val Cys Ile Val Leu Ile Ile
    210                 215                 220

Leu Tyr Leu Lys Phe Asn Leu Leu Tyr Arg Thr Tyr Phe Asn Glu
225                 230                 235                 240

Leu Glu

<210> SEQ ID NO 85
<211> LENGTH: 552
```

<210> SEQ ID NO 85
<211> LENGTH: 552
<212> TYPE: DNA
<213> ORGANISM: Neisseria meningitidis

<400> SEQUENCE: 85

```
acccccaaca gcgtgaccgt cttgccgtct ttcggcggat tcgggcgtac cggcgcgacc      60
atcaatgcag caggcggggt cggcatgact gccttttcga caaccttaat ttccgtagcc     120
gagggcgcgg ttgtagagct gcaggccgtg agagccaaag ccgtcaatgc aaccgccgct     180
tgcatttttta cggtcttgag taaggacatt ttcgatttcc ttttttatttt ccgttttcag     240
acggctgact tccgcctgta ttttcgccaa agccatgccg acagcgtgcg ccttgacttc     300
atatttaaaa gcttccgcgc gtgccagttc cagttcgcgc gcatagtttt gagccgacaa     360
cagcagggct tgcgccttgt cgcgctccat cttgtcgatg accgcctgca gcttcgcaaa     420
tgccgacttg tagccttgat ggtgcgacac agccaagccc gtgccgacaa gcgcgataat     480
ggcaatcggt tgccagtaat tcgccagcag tttcacgaga ttcattctcg acctcctgac     540
gcttcacgct ga                                                        552
```

<210> SEQ ID NO 86
<211> LENGTH: 183
<212> TYPE: PRT
<213> ORGANISM: Neisseria meningitidis

<400> SEQUENCE: 86

Thr Pro Asn Ser Val Thr Val Leu Pro Ser Phe Gly Gly Phe Gly Arg
 1               5                  10                  15

Thr Gly Ala Thr Ile Asn Ala Ala Gly Gly Val Gly Met Thr Ala Phe
            20                  25                  30

Ser Thr Thr Leu Ile Ser Val Ala Glu Gly Ala Val Val Glu Leu Gln
        35                  40                  45

Ala Val Arg Ala Lys Ala Val Asn Ala Thr Ala Ala Cys Ile Phe Thr
    50                  55                  60

Val Leu Ser Lys Asp Ile Phe Asp Phe Leu Phe Ile Phe Arg Phe Gln
65                  70                  75                  80

Thr Ala Asp Phe Arg Leu Tyr Phe Arg Gln Ser His Ala Asp Ser Val
                85                  90                  95

Arg Leu Asp Phe Ile Phe Lys Ser Phe Arg Ala Cys Gln Phe Gln Phe
            100                 105                 110

Ala Arg Ile Val Leu Ser Arg Gln Gln Gln Gly Leu Arg Leu Val Ala
        115                 120                 125

Leu His Leu Val Asp Asp Arg Leu Gln Leu Arg Lys Cys Arg Leu Val
    130                 135                 140

Ala Leu Met Val Arg His Ser Gln Ala Arg Ala Asp Lys Arg Asp Asn
145                 150                 155                 160

Gly Asn Arg Leu Pro Val Ile Arg Gln Gln Phe His Glu Ile His Ser
                165                 170                 175

Arg Pro Pro Asp Ala Ser Arg
            180

<210> SEQ ID NO 87
<211> LENGTH: 468
<212> TYPE: DNA
<213> ORGANISM: Neisseria meningitidis

<400> SEQUENCE: 87

```
atgactgcct ttcgacaac cttaatttcc gtagccgagg gcgcggttgt agagctgcag       60
```

-continued

```
gccgtgagag ccaaagccgt caatgcaacc gccgcttgca ttttacggt cttgagtaag        120 gacattttcg atttccttt tatttccgt tttcagacgg ctgacttccg cctgtttttt        180
cgccaaagcc atgccgacag cgtgcgcctt gacttcatat tttttagctt ccgcgcgtgc        240
cagttccagt tcgcgcgcat agttttgagc cgacaacagc agggcttgcg ccttgtcgcg        300
ctccatcttg tcgatgaccg cctgctgctt cgcaaatgcc gacttgtagc cttgatggtg        360
cgacacagcc aagcccgtgc cgacaagcgc gataatggca atcggttgcc agttattcgc        420
cagcagtttc acgagattca ttctcgacct cctgacgctt cacgctga                     468
```

<210> SEQ ID NO 88
<211> LENGTH: 155
<212> TYPE: PRT
<213> ORGANISM: Neisseria meningitidis

<400> SEQUENCE: 88

```
Met Thr Ala Phe Ser Thr Thr Leu Ile Ser Val Ala Glu Gly Ala Val
  1               5                  10                  15

Val Glu Leu Gln Ala Val Arg Ala Lys Ala Val Asn Ala Thr Ala Ala
             20                  25                  30

Cys Ile Phe Thr Val Leu Ser Lys Asp Ile Phe Asp Phe Leu Phe Ile
         35                  40                  45

Phe Arg Phe Gln Thr Ala Asp Phe Arg Leu Phe Arg Gln Ser His
     50                  55                  60

Ala Asp Ser Val Arg Leu Asp Phe Ile Phe Ser Phe Arg Ala Cys
 65                  70                  75                  80

Gln Phe Gln Phe Ala Arg Ile Val Leu Ser Arg Gln Gln Gly Leu
             85                  90                  95

Arg Leu Val Ala Leu His Leu Val Asp Asp Arg Leu Leu Arg Lys
            100                 105                 110

Cys Arg Leu Val Ala Leu Met Val Arg His Ser Gln Ala Arg Ala Asp
            115                 120                 125

Lys Arg Asp Asn Gly Asn Arg Leu Pro Val Ile Arg Gln Gln Phe His
        130                 135                 140

Glu Ile His Ser Arg Pro Pro Asp Ala Ser Arg
145                 150                 155
```

<210> SEQ ID NO 89
<211> LENGTH: 462
<212> TYPE: DNA
<213> ORGANISM: Neisseria meningitidis

<400> SEQUENCE: 89

```
atgaccgcct ttcgacaac cttaatttcc gtagccgagg gcgcgcttgt agagctgcaa         60
gccgtgatgg ccaaagccgt caatacaacc gccgcctgca ttttacggt cttgagtaag        120 gacattttcg atttccttt tatttccgt tttcagacgg ctgacttccg cctgtttttt        180
cgccaaagcc atgccgacgg cgtgcgcctt gacttcatat tttttagctt ccgcacgcgc        240
ctgttccagt tcgcgggcgt agttttgagc cgacaacagc agggcttgcg ccttgtcgcg        300
cttcattttc tcaatgaccg cctgctgctt cgcaaaagcc gacttgtagc cttgatggtg        360
cgacaccgcc aaacccgtgc cgacaagcgc gatgatggca atcggttgcc agttattcgc        420
cagcagtttc acgagattca ttctcgacct cctgacgttt ga                           462
```

<210> SEQ ID NO 90
<211> LENGTH: 153

```
<212> TYPE: PRT
<213> ORGANISM: Neisseria meningitidis

<400> SEQUENCE: 90

Met Thr Ala Phe Ser Thr Thr Leu Ile Ser Val Ala Glu Gly Ala Leu
 1               5                  10                  15

Val Glu Leu Gln Ala Val Met Ala Lys Ala Val Asn Thr Thr Ala Ala
             20                  25                  30

Cys Ile Phe Thr Val Leu Ser Lys Asp Ile Phe Asp Phe Leu Phe Ile
         35                  40                  45

Phe Arg Phe Gln Thr Ala Asp Phe Arg Leu Phe Phe Arg Gln Ser His
     50                  55                  60

Ala Asp Gly Val Arg Leu Asp Phe Ile Phe Ser Phe Arg Thr Arg
 65                  70                  75                  80

Leu Phe Gln Phe Ala Gly Val Val Leu Ser Arg Gln Gln Gly Leu
                 85                  90                  95

Arg Leu Val Ala Leu His Phe Leu Asn Asp Arg Leu Leu Arg Lys
            100                 105                 110

Ser Arg Leu Val Ala Leu Met Val Arg His Arg Gln Thr Arg Ala Asp
            115                 120                 125

Lys Arg Asp Asp Gly Asn Arg Leu Pro Val Ile Arg Gln Gln Phe His
130                 135                 140

Glu Ile His Ser Arg Pro Pro Asp Val
145                 150

<210> SEQ ID NO 91
<211> LENGTH: 592
<212> TYPE: PRT
<213> ORGANISM: Neisseria meningitidis

<400> SEQUENCE: 91

Met Asn Lys Ile Tyr Arg Ile Ile Trp Asn Ser Ala Leu Asn Ala Trp
 1               5                  10                  15

Val Ala Val Ser Glu Leu Thr Arg Asn His Thr Lys Arg Ala Ser Ala
             20                  25                  30

Thr Val Lys Thr Ala Val Leu Ala Thr Leu Phe Ala Thr Val Gln
         35                  40                  45

Ala Asn Ala Thr Asp Glu Asp Glu Glu Glu Leu Glu Ser Val Gln
     50                  55                  60

Arg Ser Val Val Gly Ser Ile Gln Ala Ser Met Glu Gly Ser Gly Glu
 65                  70                  75                  80

Leu Glu Thr Ile Ser Leu Ser Met Thr Asn Asp Ser Lys Glu Phe Val
                 85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
            115                 120                 125

Leu Lys Lys Asp Leu Thr Gly Leu Ile Asn Val Glu Thr Glu Lys Leu
130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Ala Gly
                180                 185                 190
```

```
Ser Ser Ala Ser His Val Asp Ala Gly Asn Gln Ser Thr His Tyr Thr
            195                 200                 205

Arg Ala Ala Ser Ile Lys Asp Val Leu Asn Ala Gly Trp Asn Ile Lys
        210                 215                 220

Gly Val Lys Thr Gly Ser Thr Gly Gln Ser Glu Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Arg Thr Glu Val
            260                 265                 270

Lys Ile Gly Ala Lys Thr Ser Val Ile Lys Glu Lys Asp Gly Lys Leu
        275                 280                 285

Val Thr Gly Lys Gly Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
                325                 330                 335

Asp Lys Phe Glu Thr Val Thr Ser Gly Thr Asn Val Thr Phe Ala Ser
                340                 345                 350

Gly Lys Gly Thr Thr Ala Thr Val Ser Lys Asp Asp Gln Gly Asn Ile
            355                 360                 365

Thr Val Met Tyr Asp Val Asn Val Gly Asp Ala Leu Asn Val Asn Gln
    370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Ser Arg
                420                 425                 430

Asn Gly Lys Asn Ile Asp Ile Ala Thr Ser Met Ala Pro Gln Phe Ser
            435                 440                 445

Ser Val Ser Leu Gly Ala Gly Ala Asp Ala Pro Thr Leu Ser Val Asp
    450                 455                 460

Asp Glu Gly Ala Leu Asn Val Gly Ser Lys Asp Ala Asn Lys Pro Val
465                 470                 475                 480

Arg Ile Thr Asn Val Ala Pro Gly Val Lys Glu Gly Asp Val Thr Asn
                485                 490                 495

Val Ala Gln Leu Lys Gly Val Ala Gln Asn Leu Asn Asn Arg Ile Asp
            500                 505                 510

Asn Val Asp Gly Asn Ala Arg Ala Gly Ile Ala Gln Ala Ile Ala Thr
        515                 520                 525

Ala Gly Leu Val Gln Ala Tyr Leu Pro Gly Lys Ser Met Met Ala Ile
    530                 535                 540

Gly Gly Gly Thr Tyr Arg Gly Glu Ala Gly Tyr Ala Ile Gly Tyr Ser
545                 550                 555                 560

Ser Ile Ser Asp Gly Gly Asn Trp Ile Ile Lys Gly Thr Ala Ser Gly
                565                 570                 575

Asn Ser Arg Gly His Phe Gly Ala Ser Ala Ser Val Gly Tyr Gln Trp
            580                 585                 590

<210> SEQ ID NO 92
<211> LENGTH: 594
<212> TYPE: PRT
```

-continued

<213> ORGANISM: Neisseria meningitidis

<400> SEQUENCE: 92

```
Met Asn Lys Ile Tyr Arg Ile Ile Trp Asn Ser Ala Leu Asn Ala Trp
 1               5                  10                  15

Val Val Val Ser Glu Leu Thr Arg Asn His Thr Lys Arg Ala Ser Ala
            20                  25                  30

Thr Val Ala Thr Ala Val Leu Ala Thr Leu Leu Phe Ala Thr Val Gln
        35                  40                  45

Ala Asn Ala Thr Asp Asp Asp Leu Tyr Leu Glu Pro Val Gln Arg
    50                  55                  60

Thr Ala Val Val Leu Ser Phe Arg Ser Asp Lys Glu Gly Thr Gly Glu
65                  70                  75                  80

Lys Glu Gly Thr Glu Asp Ser Asn Trp Ala Val Tyr Phe Asp Glu Lys
                85                  90                  95

Arg Val Leu Lys Ala Gly Ala Ile Thr Leu Lys Ala Gly Asp Asn Leu
            100                 105                 110

Lys Ile Lys Gln Asn Thr Asn Glu Asn Thr Asn Asp Ser Ser Phe Thr
        115                 120                 125

Tyr Ser Leu Lys Lys Asp Leu Thr Asp Leu Thr Ser Val Glu Thr Glu
    130                 135                 140

Lys Leu Ser Phe Gly Ala Asn Gly Asn Lys Val Asn Ile Thr Ser Asp
145                 150                 155                 160

Thr Lys Gly Leu Asn Phe Ala Lys Glu Thr Ala Gly Thr Asn Gly Asp
                165                 170                 175

Pro Thr Val His Leu Asn Gly Ile Gly Ser Thr Leu Thr Asp Thr Leu
            180                 185                 190

Leu Asn Thr Gly Ala Thr Thr Asn Val Thr Asn Asp Asn Val Thr Asp
        195                 200                 205

Asp Glu Lys Lys Arg Ala Ala Ser Val Lys Asp Val Leu Asn Ala Gly
    210                 215                 220

Trp Asn Ile Lys Gly Val Lys Pro Gly Thr Thr Ala Ser Asp Asn Val
225                 230                 235                 240

Asp Phe Val Arg Thr Tyr Asp Thr Val Glu Phe Leu Ser Ala Asp Thr
                245                 250                 255

Lys Thr Thr Thr Val Asn Val Glu Ser Lys Asp Asn Gly Lys Lys Thr
            260                 265                 270

Glu Val Lys Ile Gly Ala Lys Thr Ser Val Ile Lys Glu Lys Asp Gly
        275                 280                 285

Lys Leu Val Thr Gly Lys Gly Lys Asp Glu Asn Gly Ser Ser Thr Asp
    290                 295                 300

Glu Gly Glu Gly Leu Val Thr Ala Lys Glu Val Ile Asp Ala Val Asn
305                 310                 315                 320

Lys Ala Gly Trp Arg Met Lys Thr Thr Ala Asn Gly Gln Thr Gly
                325                 330                 335

Gln Ala Asp Lys Phe Glu Thr Val Thr Ser Gly Thr Asn Val Thr Phe
            340                 345                 350

Ala Ser Gly Lys Gly Thr Thr Ala Thr Val Ser Lys Asp Asp Gln Gly
        355                 360                 365

Asn Ile Thr Val Lys Tyr Asp Val Asn Val Gly Asp Ala Leu Asn Val
    370                 375                 380

Asn Gln Leu Gln Asn Ser Gly Trp Asn Leu Asp Ser Lys Ala Val Ala
385                 390                 395                 400
```

```
Gly Ser Ser Gly Lys Val Ile Ser Gly Asn Val Ser Pro Ser Lys Gly
                405                 410                 415

Lys Met Asp Glu Thr Val Asn Ile Asn Ala Gly Asn Asn Ile Glu Ile
            420                 425                 430

Thr Arg Asn Gly Lys Asn Ile Asp Ile Ala Thr Ser Met Ala Pro Gln
        435                 440                 445

Phe Ser Ser Val Ser Leu Gly Ala Gly Ala Asp Ala Pro Thr Leu Ser
    450                 455                 460

Val Asp Asp Glu Gly Ala Leu Asn Val Gly Ser Lys Asp Thr Asn Lys
465                 470                 475                 480

Pro Val Arg Ile Thr Asn Val Ala Pro Gly Val Lys Glu Gly Asp Val
                485                 490                 495

Thr Asn Val Ala Gln Leu Lys Gly Val Ala Gln Asn Leu Asn Asn Arg
            500                 505                 510

Ile Asp Asn Val Asp Gly Asn Ala Arg Ala Gly Ile Ala Gln Ala Ile
        515                 520                 525

Ala Thr Ala Gly Leu Val Gln Ala Tyr Leu Pro Gly Lys Ser Met Met
    530                 535                 540

Ala Ile Gly Gly Asp Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
                565                 570                 575

Ser Gly Asn Ser Arg Gly His Phe Gly Ala Ser Ala Ser Val Gly Tyr
            580                 585                 590

Gln Trp

<210> SEQ ID NO 93
<211> LENGTH: 594
<212> TYPE: PRT
<213> ORGANISM: Neisseria meningitidis

<400> SEQUENCE: 93

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Ala Thr Ala Val Leu Ala Thr Leu Leu Phe Ala Thr Val Gln
        35                  40                  45

Ala Ser Thr Thr Asp Asp Asp Leu Tyr Leu Glu Pro Val Gln Arg
    50                  55                  60

Thr Ala Pro Val Leu Ser Phe His Ala Asp Ser Glu Gly Thr Gly Glu
65                  70                  75                  80

Lys Glu Val Thr Glu Asp Ser Asn Trp Gly Val Tyr Phe Asp Lys Lys
                85                  90                  95

Gly Val Leu Thr Ala Gly Thr Ile Thr Leu Lys Ala Gly Asp Asn Leu
            100                 105                 110

Lys Ile Lys Gln Asn Thr Asp Glu Asn Thr Asn Ala Ser Ser Phe Thr
        115                 120                 125

Tyr Ser Leu Lys Lys Asp Leu Thr Asp Leu Thr Ser Val Glu Thr Glu
    130                 135                 140

Lys Leu Ser Phe Gly Ala Asn Gly Lys Lys Val Asn Ile Thr Ser Asp
145                 150                 155                 160

Thr Lys Gly Leu Asn Phe Ala Lys Glu Thr Ala Gly Thr Asn Gly Asp
                165                 170                 175
```

-continued

```
Thr Thr Val His Leu Asn Gly Ile Gly Ser Thr Leu Thr Asp Thr Leu
            180                 185                 190
Leu Asn Thr Gly Ala Thr Thr Asn Val Thr Asn Asp Asn Val Thr Asp
        195                 200                 205
Asp Glu Lys Lys Arg Ala Ala Ser Val Lys Asp Val Leu Asn Ala Gly
    210                 215                 220
Trp Asn Ile Lys Gly Val Lys Pro Gly Thr Thr Ala Ser Asp Asn Val
225                 230                 235                 240
Asp Phe Val Arg Thr Tyr Asp Thr Val Glu Phe Leu Ser Ala Asp Thr
                245                 250                 255
Lys Thr Thr Thr Val Asn Val Glu Ser Lys Asp Asn Gly Lys Lys Thr
            260                 265                 270
Glu Val Lys Ile Gly Ala Lys Thr Ser Val Ile Lys Glu Lys Asp Gly
        275                 280                 285
Lys Leu Val Thr Gly Lys Asp Lys Gly Glu Asn Gly Ser Ser Thr Asp
    290                 295                 300
Glu Gly Glu Gly Leu Val Thr Ala Lys Glu Val Ile Asp Ala Val Asn
305                 310                 315                 320
Lys Ala Gly Trp Arg Met Lys Thr Thr Ala Asn Gly Gln Thr Gly
                325                 330                 335
Gln Ala Asp Lys Phe Glu Thr Val Thr Ser Gly Thr Lys Val Thr Phe
            340                 345                 350
Ala Ser Gly Asn Gly Thr Thr Ala Thr Val Ser Lys Asp Asp Gln Gly
        355                 360                 365
Asn Ile Thr Val Lys Tyr Asp Val Asn Val Gly Asp Ala Leu Asn Val
    370                 375                 380
Asn Gln Leu Gln Asn Ser Gly Trp Asn Leu Asp Ser Lys Ala Val Ala
385                 390                 395                 400
Gly Ser Ser Gly Lys Val Ile Ser Gly Asn Val Ser Pro Ser Lys Gly
                405                 410                 415
Lys Met Asp Glu Thr Val Asn Ile Asn Ala Gly Asn Asn Ile Glu Ile
            420                 425                 430
Thr Arg Asn Gly Lys Asn Ile Asp Ile Ala Thr Ser Met Thr Pro Gln
        435                 440                 445
Phe Ser Ser Val Ser Leu Gly Ala Gly Ala Asp Ala Pro Thr Leu Ser
    450                 455                 460
Val Asp Asp Glu Gly Ala Leu Asn Val Gly Ser Lys Asp Ala Asn Lys
465                 470                 475                 480
Pro Val Arg Ile Thr Asn Val Ala Pro Gly Val Lys Glu Gly Asp Val
                485                 490                 495
Thr Asn Val Ala Gln Leu Lys Gly Val Ala Gln Asn Leu Asn Asn His
            500                 505                 510
Ile Asp Asn Val Asp Gly Asn Ala Arg Ala Gly Ile Ala Gln Ala Ile
        515                 520                 525
Ala Thr Ala Gly Leu Val Gln Ala Tyr Leu Pro Gly Lys Ser Met Met
    530                 535                 540
Ala Ile Gly Gly Gly Thr Tyr Arg Gly Glu Ala Gly Tyr Ala Ile Gly
545                 550                 555                 560
Tyr Ser Ser Ile Ser Asp Gly Gly Asn Trp Ile Ile Lys Gly Thr Ala
                565                 570                 575
Ser Gly Asn Ser Arg Gly His Phe Gly Ala Ser Ala Ser Val Gly Tyr
            580                 585                 590
Gln Trp
```

<210> SEQ ID NO 94
<211> LENGTH: 594
<212> TYPE: PRT
<213> ORGANISM: Neisseria meningitidis

<400> SEQUENCE: 94

```
Met Asn Lys Ile Tyr Arg Ile Ile Trp Asn Ser Ala Leu Asn Ala Trp
  1               5                  10                  15

Val Val Val Ser Glu Leu Thr Arg Asn His Thr Lys Arg Ala Ser Ala
             20                  25                  30

Thr Val Ala Thr Ala Val Leu Ala Thr Leu Phe Ala Thr Val Gln
         35                  40                  45

Ala Asn Ala Thr Asp Asp Asp Leu Tyr Leu Glu Pro Val Gln Arg
     50                  55                  60

Thr Ala Val Val Leu Ser Phe Arg Ser Asp Lys Glu Gly Thr Gly Glu
 65                  70                  75                  80

Lys Glu Gly Thr Glu Asp Ser Asn Trp Ala Val Tyr Phe Asp Glu Lys
                 85                  90                  95

Arg Val Leu Lys Ala Gly Ala Ile Thr Leu Lys Ala Gly Asp Asn Leu
            100                 105                 110

Lys Ile Lys Gln Asn Thr Asn Glu Asn Thr Asn Asp Ser Ser Phe Thr
        115                 120                 125

Tyr Ser Leu Lys Lys Asp Leu Thr Asp Leu Thr Ser Val Glu Thr Glu
    130                 135                 140

Lys Leu Ser Phe Gly Ala Asn Gly Asn Lys Val Asn Ile Thr Ser Asp
145                 150                 155                 160

Thr Lys Gly Leu Asn Phe Ala Lys Glu Thr Ala Gly Thr Asn Gly Asp
                165                 170                 175

Pro Thr Val His Leu Asn Gly Ile Gly Ser Thr Leu Thr Asp Thr Leu
            180                 185                 190

Leu Asn Thr Gly Ala Thr Thr Asn Val Thr Asn Asp Asn Val Thr Asp
        195                 200                 205

Asp Glu Lys Lys Arg Ala Ala Ser Val Lys Asp Val Leu Asn Ala Gly
    210                 215                 220

Trp Asn Ile Lys Gly Val Lys Pro Gly Thr Thr Ala Ser Asp Asn Val
225                 230                 235                 240

Asp Phe Val Arg Thr Tyr Asp Thr Val Glu Phe Leu Ser Ala Asp Thr
                245                 250                 255

Lys Thr Thr Thr Val Asn Val Glu Ser Lys Asp Asn Gly Lys Lys Thr
            260                 265                 270

Glu Val Lys Ile Gly Ala Lys Thr Ser Val Ile Lys Glu Lys Asp Gly
        275                 280                 285

Lys Leu Val Thr Gly Lys Gly Lys Asp Glu Asn Gly Ser Ser Thr Asp
    290                 295                 300

Glu Gly Glu Gly Leu Val Thr Ala Lys Glu Val Ile Asp Ala Val Asn
305                 310                 315                 320

Lys Ala Gly Trp Arg Met Lys Thr Thr Thr Ala Asn Gly Gln Thr Gly
                325                 330                 335

Gln Ala Asp Lys Phe Glu Thr Val Thr Ser Gly Thr Asn Val Thr Phe
            340                 345                 350

Ala Ser Gly Lys Gly Thr Thr Ala Thr Val Ser Lys Asp Asp Gln Gly
        355                 360                 365

Asn Ile Thr Val Lys Tyr Asp Val Asn Val Gly Asp Ala Leu Asn Val
```

```
                    370                 375                 380
Asn Gln Leu Gln Asn Ser Gly Trp Asn Leu Asp Ser Lys Ala Val Ala
385                 390                 395                 400

Gly Ser Ser Gly Lys Val Ile Ser Gly Asn Val Ser Pro Ser Lys Gly
                405                 410                 415

Lys Met Asp Glu Thr Val Asn Ile Asn Ala Gly Asn Asn Ile Glu Ile
                420                 425                 430

Thr Arg Asn Gly Lys Asn Ile Asp Ile Ala Thr Ser Met Ala Pro Gln
                435                 440                 445

Phe Ser Ser Val Ser Leu Gly Ala Gly Ala Asp Ala Pro Thr Leu Ser
                450                 455                 460

Val Asp Asp Glu Gly Ala Leu Asn Val Gly Ser Lys Asp Thr Asn Lys
465                 470                 475                 480

Pro Val Arg Ile Thr Asn Val Ala Pro Gly Val Lys Glu Gly Asp Val
                485                 490                 495

Thr Asn Val Ala Gln Leu Lys Gly Val Ala Gln Asn Leu Asn Asn Arg
                500                 505                 510

Ile Asp Asn Val Asp Gly Asn Ala Arg Ala Gly Ile Ala Gln Ala Ile
                515                 520                 525

Ala Thr Ala Gly Leu Val Gln Ala Tyr Leu Pro Gly Lys Ser Met Met
                530                 535                 540

Ala Ile Gly Gly Asp Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
                565                 570                 575

Ser Gly Asn Ser Arg Gly His Phe Gly Ala Ser Ala Ser Val Gly Tyr
                580                 585                 590

Gln Trp

<210> SEQ ID NO 95
<211> LENGTH: 591
<212> TYPE: PRT
<213> ORGANISM: Neisseria meningitidis

<400> SEQUENCE: 95

Met Asn Lys Ile Tyr Arg Ile Ile Trp Asn Ser Ala Leu Asn Ala Trp
  1               5                  10                  15

Val Val Val Ser Glu Leu Thr Arg Asn His Thr Lys Arg Ala Ser Ala
                 20                  25                  30

Thr Val Glu Thr Ala Val Leu Ala Thr Leu Leu Phe Ala Thr Val Gln
                 35                  40                  45

Ala Ser Ala Asn Asn Glu Glu Gln Glu Glu Asp Leu Tyr Leu Asp Pro
             50                  55                  60

Val Gln Arg Thr Val Ala Val Leu Ile Val Asn Ser Asp Lys Glu Gly
 65                  70                  75                  80

Thr Gly Glu Lys Glu Lys Val Glu Glu Asn Ser Asp Trp Ala Val Tyr
                 85                  90                  95

Phe Asn Glu Lys Gly Val Leu Thr Ala Arg Glu Ile Thr Leu Lys Ala
                100                 105                 110

Gly Asp Asn Leu Lys Ile Lys Gln Asn Gly Thr Asn Phe Thr Tyr Ser
            115                 120                 125

Leu Lys Lys Asp Leu Thr Asp Leu Thr Ser Val Gly Thr Glu Lys Leu
    130                 135                 140

Ser Phe Ser Ala Asn Gly Asn Lys Val Asn Ile Thr Ser Asp Thr Lys
```

-continued

```
            145                 150                 155                 160
        Gly Leu Asn Phe Ala Lys Glu Thr Ala Gly Thr Asn Gly Asp Thr Thr
                        165                 170                 175
        Val His Leu Asn Gly Ile Gly Ser Thr Leu Thr Asp Thr Leu Leu Asn
                        180                 185                 190
        Thr Gly Ala Thr Thr Asn Val Thr Asn Asp Asn Val Thr Asp Asp Glu
                        195                 200                 205
        Lys Lys Arg Ala Ala Ser Val Lys Asp Val Leu Asn Ala Gly Trp Asn
                        210                 215                 220
        Ile Lys Gly Val Lys Pro Gly Thr Thr Ala Ser Asp Asn Val Asp Phe
        225                 230                 235                 240
        Val Arg Thr Tyr Asp Thr Val Glu Phe Leu Ser Ala Asp Thr Lys Thr
                        245                 250                 255
        Thr Thr Val Asn Val Glu Ser Lys Asp Asn Gly Lys Lys Thr Glu Val
                        260                 265                 270
        Lys Ile Gly Ala Lys Thr Ser Val Ile Lys Glu Lys Asp Gly Lys Leu
                        275                 280                 285
        Val Thr Gly Lys Asp Lys Gly Glu Asn Gly Ser Ser Thr Asp Glu Gly
                        290                 295                 300
        Glu Gly Leu Val Thr Ala Lys Glu Val Ile Asp Ala Val Asn Lys Ala
        305                 310                 315                 320
        Gly Trp Arg Met Lys Thr Thr Ala Asn Gly Gln Thr Gly Gln Ala
                        325                 330                 335
        Asp Lys Phe Glu Thr Val Thr Ser Gly Thr Asn Val Thr Phe Ala Ser
                        340                 345                 350
        Gly Lys Gly Thr Thr Ala Thr Val Ser Lys Asp Asp Gln Gly Asn Ile
                        355                 360                 365
        Thr Val Met Tyr Asp Val Asn Val Gly Asp Ala Leu Asn Val Asn Gln
                        370                 375                 380
        Leu Gln Asn Ser Gly Trp Asn Leu Asp Ser Lys Ala Val Ala Gly Ser
        385                 390                 395                 400
        Ser Gly Lys Val Ile Ser Gly Asn Val Ser Pro Ser Lys Gly Lys Met
                        405                 410                 415
        Asp Glu Thr Val Asn Ile Asn Ala Gly Asn Asn Ile Glu Ile Thr Arg
                        420                 425                 430
        Asn Gly Lys Asn Ile Asp Ile Ala Thr Ser Met Thr Pro Gln Phe Ser
                        435                 440                 445
        Ser Val Ser Leu Gly Ala Gly Ala Asp Ala Pro Thr Leu Ser Val Asp
                        450                 455                 460
        Gly Asp Ala Leu Asn Val Gly Ser Lys Lys Asp Asn Lys Pro Val Arg
        465                 470                 475                 480
        Ile Thr Asn Val Ala Pro Gly Val Lys Glu Gly Asp Val Thr Asn Val
                        485                 490                 495
        Ala Gln Leu Lys Gly Val Ala Gln Asn Leu Asn Asn Arg Ile Asp Asn
                        500                 505                 510
        Val Asp Gly Asn Ala Arg Ala Gly Ile Ala Gln Ala Ile Ala Thr Ala
                        515                 520                 525
        Gly Leu Val Gln Ala Tyr Leu Pro Gly Lys Ser Met Met Ala Ile Gly
                        530                 535                 540
        Gly Gly Thr Tyr Arg Gly Glu Ala Gly Tyr Ala Ile Gly Tyr Ser Ser
        545                 550                 555                 560
        Ile Ser Asp Gly Gly Asn Trp Ile Ile Lys Gly Thr Ala Ser Gly Asn
                        565                 570                 575
```

Ser Arg Gly His Phe Gly Ala Ser Ala Ser Val Gly Tyr Gln Trp
         580                 585                 590

<210> SEQ ID NO 96
<211> LENGTH: 591
<212> TYPE: PRT
<213> ORGANISM: Neisseria meningitidis

<400> SEQUENCE: 96

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Ser Ala Asn Asn Glu Glu Gln Glu Glu Asp Leu Tyr Leu Asp Pro
    50                  55                  60

Val Gln Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
            100                 105                 110

Gly Asp Asn Leu Lys Ile Lys Gln Asn Gly Thr Asn Phe Thr Tyr Ser
        115                 120                 125

Leu Lys Lys Asp Leu Thr Asp Leu Thr Ser Val Gly Thr Glu Lys Leu
130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
            180                 185                 190

Thr Gly Ala Thr Thr Asn Val Thr Asn Asp Asn Val Thr Asp Asp Glu
        195                 200                 205

Lys Lys Arg Ala Ala Ser Val Lys Asp Val Leu Asn Ala Gly Trp Asn
    210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Asp Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile

-continued

```
                355                 360                 365
Thr Val Met Tyr Asp Val Asn Val Gly Asp Ala Leu Asn Val Asn Gln
    370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
                420                 425                 430

Asn Gly Lys Asn Ile Asp Ile Ala Thr Ser Met Thr Pro Gln Phe Ser
                435                 440                 445

Ser Val Ser Leu Gly Ala Gly Ala Asp Ala Pro Thr Leu Ser Val Asp
    450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
                500                 505                 510

Val Asp Gly Asn Ala Arg Ala Gly Ile Ala Gln Ala Ile Ala Thr Ala
                515                 520                 525

Gly Leu Val Gln Ala Tyr Leu Pro Gly Lys Ser Met Met Ala Ile Gly
    530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
                580                 585                 590

<210> SEQ ID NO 97
<211> LENGTH: 595
<212> TYPE: PRT
<213> ORGANISM: Neisseria meningitidis

<400> SEQUENCE: 97

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Glu Thr Ala Val Leu Ala Thr Leu Leu Phe Ala Thr Val Gln
            35                  40                  45

Ala Asn Ala Thr Asp Thr Asp Glu Asp Asp Glu Leu Glu Pro Val Val
        50                  55                  60

Arg Ser Ala Leu Val Leu Gln Phe Met Ile Asp Lys Glu Gly Asn Gly
65                  70                  75                  80

Glu Ile Glu Ser Thr Gly Asp Ile Gly Trp Ser Ile Tyr Tyr Asp Asp
                85                  90                  95

His Asn Thr Leu His Gly Ala Thr Val Thr Leu Lys Ala Gly Asp Asn
                100                 105                 110

Leu Lys Ile Lys Gln Asn Thr Asp Glu Asn Thr Asn Ala Ser Ser Phe
            115                 120                 125

Thr Tyr Ser Leu Lys Lys Asp Leu Thr Asp Leu Thr Ser Val Gly Thr
        130                 135                 140
```

-continued

```
Glu Glu Leu Ser Phe Gly Ala Asn Gly Asn Lys Val Asn Ile Thr Ser
145                 150                 155                 160

Asp Thr Lys Gly Leu Asn Phe Ala Lys Lys Thr Ala Gly Thr Asn Gly
                165                 170                 175

Asp Thr Thr Val His Leu Asn Gly Ile Gly Ser Thr Leu Thr Asp Thr
            180                 185                 190

Leu Ala Gly Ser Ser Ala Ser His Val Asp Ala Gly Asn Gln Ser Thr
        195                 200                 205

His Tyr Thr Arg Ala Ala Ser Ile Lys Asp Val Leu Asn Ala Gly Trp
    210                 215                 220

Asn Ile Lys Gly Val Lys Thr Gly Ser Thr Thr Gly Gln Ser Glu Asn
225                 230                 235                 240

Val Asp Phe Val Arg Thr Tyr Asp Thr Val Glu Phe Leu Ser Ala Asp
                245                 250                 255

Thr Lys Thr Thr Thr Val Asn Val Glu Ser Lys Asp Asn Gly Lys Arg
            260                 265                 270

Thr Glu Val Lys Ile Gly Ala Lys Thr Ser Val Ile Lys Glu Lys Asp
        275                 280                 285

Gly Lys Leu Val Thr Gly Lys Gly Lys Gly Glu Asn Gly Ser Ser Thr
    290                 295                 300

Asp Glu Gly Glu Gly Leu Val Thr Ala Lys Glu Val Ile Asp Ala Val
305                 310                 315                 320

Asn Lys Ala Gly Trp Arg Met Lys Thr Thr Thr Ala Asn Gly Gln Thr
                325                 330                 335

Gly Gln Ala Asp Lys Phe Glu Thr Val Thr Ser Gly Thr Asn Val Thr
            340                 345                 350

Phe Ala Ser Gly Lys Gly Thr Thr Ala Thr Val Ser Lys Asp Asp Gln
        355                 360                 365

Gly Asn Ile Thr Val Lys Tyr Asp Val Asn Val Gly Asp Ala Leu Asn
    370                 375                 380

Val Asn Gln Leu Gln Asn Ser Gly Trp Asn Leu Asp Ser Lys Ala Val
385                 390                 395                 400

Ala Gly Ser Ser Gly Lys Val Ile Ser Gly Asn Val Ser Pro Ser Lys
                405                 410                 415

Gly Lys Met Asp Glu Thr Val Asn Ile Asn Ala Gly Asn Asn Ile Glu
            420                 425                 430

Ile Thr Arg Asn Gly Lys Asn Ile Asp Ile Ala Thr Ser Met Thr Pro
        435                 440                 445

Gln Phe Ser Ser Val Ser Leu Gly Ala Gly Ala Asp Ala Pro Thr Leu
    450                 455                 460

Ser Val Asp Asp Glu Gly Ala Leu Asn Val Gly Ser Lys Asp Ala Asn
465                 470                 475                 480

Lys Pro Val Arg Ile Thr Asn Val Ala Pro Gly Val Lys Glu Gly Asp
                485                 490                 495

Val Thr Asn Val Ala Gln Leu Lys Gly Val Ala Gln Asn Leu Asn Asn
            500                 505                 510

His Ile Asp Asn Val Asp Gly Asn Ala Arg Ala Gly Ile Ala Gln Ala
        515                 520                 525

Ile Ala Thr Ala Gly Leu Val Gln Ala Tyr Leu Pro Gly Lys Ser Met
    530                 535                 540

Met Ala Ile Gly Gly Gly Thr Tyr Arg Gly Glu Ala Gly Tyr Ala Ile
545                 550                 555                 560

Gly Tyr Ser Ser Ile Ser Asp Gly Gly Asn Trp Ile Ile Lys Gly Thr
```

```
                    565                 570                 575
Ala Ser Gly Asn Ser Arg Gly His Phe Gly Ala Ser Ala Ser Val Gly
            580                 585                 590

Tyr Gln Trp
        595

<210> SEQ ID NO 98
<211> LENGTH: 592
<212> TYPE: PRT
<213> ORGANISM: Neisseria meningitidis

<400> SEQUENCE: 98

Met Asn Lys Ile Tyr Arg Ile Ile Trp Asn Ser Ala Leu Asn Ala Trp
  1               5                  10                  15

Val Ala Val Ser Glu Leu Thr Arg Asn His Thr Lys Arg Ala Ser Ala
             20                  25                  30

Thr Val Lys Thr Ala Val Leu Ala Thr Leu Leu Phe Ala Thr Val Gln
         35                  40                  45

Ala Asn Ala Thr Asp Glu Asp Glu Glu Glu Leu Glu Ser Val Gln
     50                  55                  60

Arg Ser Val Val Gly Ser Ile Gln Ala Ser Met Glu Gly Ser Gly Glu
 65                  70                  75                  80

Leu Glu Thr Ile Ser Leu Ser Met Thr Asn Asp Ser Lys Glu Phe Val
                 85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
        115                 120                 125

Leu Lys Lys Asp Leu Thr Gly Leu Ile Asn Val Glu Thr Glu Lys Leu
    130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Ala Gly
            180                 185                 190

Ser Ser Ala Ser His Val Asp Ala Gly Asn Gln Ser Thr His Tyr Thr
        195                 200                 205

Arg Ala Ala Ser Ile Lys Asp Val Leu Asn Ala Gly Trp Asn Ile Lys
    210                 215                 220

Gly Val Lys Thr Gly Ser Thr Thr Gly Gln Ser Glu Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Arg Thr Glu Val
            260                 265                 270

Lys Ile Gly Ala Lys Thr Ser Val Ile Lys Glu Lys Asp Gly Lys Leu
        275                 280                 285

Val Thr Gly Lys Gly Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335
```

```
Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
            355                 360                 365

Thr Val Met Tyr Asp Val Asn Val Gly Asp Ala Leu Asn Val Asn Gln
    370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
            405                 410                 415

Asp Glu Thr Val Asn Ile Asn Ala Gly Asn Asn Ile Glu Ile Ser Arg
            420                 425                 430

Asn Gly Lys Asn Ile Asp Ile Ala Thr Ser Met Ala Pro Gln Phe Ser
            435                 440                 445

Ser Val Ser Leu Gly Ala Gly Ala Asp Ala Pro Thr Leu Ser Val Asp
    450                 455                 460

Asp Glu Gly Ala Leu Asn Val Gly Ser Lys Asp Ala Asn Lys Pro Val
465                 470                 475                 480

Arg Ile Thr Asn Val Ala Pro Gly Val Lys Glu Gly Asp Val Thr Asn
            485                 490                 495

Val Ala Gln Leu Lys Gly Val Ala Gln Asn Leu Asn Asn Arg Ile Asp
            500                 505                 510

Asn Val Asp Gly Asn Ala Arg Ala Gly Ile Ala Gln Ala Ile Ala Thr
            515                 520                 525

Ala Gly Leu Val Gln Ala Tyr Leu Pro Gly Lys Ser Met Met Ala Ile
            530                 535                 540

Gly Gly Gly Thr Tyr Arg Gly Glu Ala Gly Tyr Ala Ile Gly Tyr Ser
545                 550                 555                 560

Ser Ile Ser Asp Gly Gly Asn Trp Ile Ile Lys Gly Thr Ala Ser Gly
            565                 570                 575

Asn Ser Arg Gly His Phe Gly Ala Ser Ala Ser Val Gly Tyr Gln Trp
            580                 585                 590

<210> SEQ ID NO 99
<211> LENGTH: 594
<212> TYPE: PRT
<213> ORGANISM: Neisseria meningitidis

<400> SEQUENCE: 99

Met Asn Lys Ile Tyr Arg Ile Ile Trp Asn Ser Ala Leu Asn Ala Trp
  1               5                  10                  15

Val Val Val Ser Glu Leu Thr Arg Asn His Thr Lys Arg Ala Ser Ala
             20                  25                  30

Thr Val Ala Thr Ala Val Leu Ala Thr Leu Leu Phe Ala Thr Val Gln
         35                  40                  45

Ala Ser Thr Thr Asp Asp Asp Leu Tyr Leu Glu Pro Val Gln Arg
     50                  55                  60

Thr Ala Pro Val Leu Ser Phe His Ala Asp Ser Glu Gly Thr Gly Glu
 65                  70                  75                  80

Lys Glu Val Thr Glu Asp Ser Asn Trp Gly Val Tyr Phe Asp Lys Lys
                 85                  90                  95

Gly Val Leu Thr Ala Gly Thr Ile Thr Leu Lys Ala Gly Asp Asn Leu
            100                 105                 110

Lys Ile Lys Gln Asn Thr Asp Glu Asn Thr Asn Ala Ser Ser Phe Thr
            115                 120                 125
```

-continued

```
Tyr Ser Leu Lys Lys Asp Leu Thr Asp Leu Thr Ser Val Glu Thr Glu
    130                 135                 140

Lys Leu Ser Phe Gly Ala Asn Gly Lys Lys Val Asn Ile Thr Ser Asp
145                 150                 155                 160

Thr Lys Gly Leu Asn Phe Ala Lys Glu Thr Ala Gly Thr Asn Gly Asp
                165                 170                 175

Thr Thr Val His Leu Asn Gly Ile Gly Ser Thr Leu Thr Asp Thr Leu
            180                 185                 190

Leu Asn Thr Gly Ala Thr Thr Asn Val Thr Asn Asp Asn Val Thr Asp
        195                 200                 205

Asp Glu Lys Lys Arg Ala Ala Ser Val Lys Asp Val Leu Asn Ala Gly
    210                 215                 220

Trp Asn Ile Lys Gly Val Lys Pro Gly Thr Thr Ala Ser Asp Asn Val
225                 230                 235                 240

Asp Phe Val Arg Thr Tyr Asp Thr Val Glu Phe Leu Ser Ala Asp Thr
                245                 250                 255

Lys Thr Thr Thr Val Asn Val Glu Ser Lys Asp Asn Gly Lys Lys Thr
            260                 265                 270

Glu Val Lys Ile Gly Ala Lys Thr Ser Val Ile Lys Glu Lys Asp Gly
        275                 280                 285

Lys Leu Val Thr Gly Lys Asp Lys Gly Glu Asn Gly Ser Ser Thr Asp
    290                 295                 300

Glu Gly Glu Gly Leu Val Thr Ala Lys Glu Val Ile Asp Ala Val Asn
305                 310                 315                 320

Lys Ala Gly Trp Arg Met Lys Thr Thr Thr Ala Asn Gly Gln Thr Gly
                325                 330                 335

Gln Ala Asp Lys Phe Glu Thr Val Thr Ser Gly Thr Lys Val Thr Phe
            340                 345                 350

Ala Ser Gly Asn Gly Thr Thr Ala Thr Val Ser Lys Asp Asp Gln Gly
        355                 360                 365

Asn Ile Thr Val Lys Tyr Asp Val Asn Val Gly Asp Ala Leu Asn Val
    370                 375                 380

Asn Gln Leu Gln Asn Ser Gly Trp Asn Leu Asp Ser Lys Ala Val Ala
385                 390                 395                 400

Gly Ser Ser Gly Lys Val Ile Ser Gly Asn Val Ser Pro Ser Lys Gly
                405                 410                 415

Lys Met Asp Glu Thr Val Asn Ile Asn Ala Gly Asn Asn Ile Glu Ile
            420                 425                 430

Thr Arg Asn Gly Lys Asn Ile Asp Ile Ala Thr Ser Met Thr Pro Gln
        435                 440                 445

Phe Ser Ser Val Ser Leu Gly Ala Gly Ala Asp Ala Pro Thr Leu Ser
    450                 455                 460

Val Asp Asp Glu Gly Ala Leu Asn Val Gly Ser Lys Asp Ala Asn Lys
465                 470                 475                 480

Pro Val Arg Ile Thr Asn Val Ala Pro Gly Val Lys Glu Gly Asp Val
                485                 490                 495

Thr Asn Val Ala Gln Leu Lys Gly Val Ala Gln Asn Leu Asn Asn His
            500                 505                 510

Ile Asp Asn Val Asp Gly Asn Ala Arg Ala Gly Ile Ala Gln Ala Ile
        515                 520                 525

Ala Thr Ala Ser Leu Val Gln Ala Tyr Leu Pro Gly Lys Ser Met Met
    530                 535                 540
```

```
Ala Ile Gly Gly Gly Thr Tyr Arg Gly Glu Ala Gly Tyr Ala Ile Gly
545                 550                 555                 560

Tyr Ser Ser Ile Ser Asp Gly Asn Trp Ile Ile Lys Gly Thr Ala
                565                 570                 575

Ser Gly Asn Ser Arg Gly His Phe Gly Ala Ser Ala Ser Val Gly Tyr
            580                 585                 590

Gln Trp

<210> SEQ ID NO 100
<211> LENGTH: 599
<212> TYPE: PRT
<213> ORGANISM: Neisseria meningitidis

<400> SEQUENCE: 100

Met Asn Lys Ile Tyr Arg Ile Ile Trp Asn Ser Ala Leu Asn Ala Trp
 1               5                  10                  15

Val Ala Val Ser Glu Leu Thr Arg Asn His Thr Lys Arg Ala Ser Ala
             20                  25                  30

Thr Val Lys Thr Ala Val Leu Ala Thr Leu Leu Phe Ala Thr Val Gln
         35                  40                  45

Ala Asn Ala Thr Asp Glu Asp Glu Glu Glu Leu Glu Pro Val Val
     50                  55                  60

Arg Ser Ala Leu Val Leu Gln Phe Met Ile Asp Lys Glu Gly Asn Gly
 65                  70                  75                  80

Glu Asn Glu Ser Thr Gly Asn Ile Gly Trp Ser Ile Tyr Tyr Asp Asn
                 85                  90                  95

His Asn Thr Leu His Gly Ala Thr Val Thr Leu Lys Ala Gly Asp Asn
            100                 105                 110

Leu Lys Ile Lys Gln Asn Thr Asn Lys Asn Thr Asn Glu Asn Thr Asn
        115                 120                 125

Asp Ser Ser Phe Thr Tyr Ser Leu Lys Asp Leu Thr Asp Leu Thr
    130                 135                 140

Ser Val Glu Thr Glu Lys Leu Ser Phe Gly Ala Asn Gly Asn Lys Val
145                 150                 155                 160

Asn Ile Thr Ser Asp Thr Lys Gly Leu Asn Phe Ala Lys Glu Thr Ala
                165                 170                 175

Gly Thr Asn Gly Asp Thr Val His Leu Asn Gly Ile Gly Ser Thr
            180                 185                 190

Leu Thr Asp Thr Leu Leu Asn Thr Gly Ala Thr Thr Asn Val Thr Asn
        195                 200                 205

Asp Asn Val Thr Asp Lys Lys Arg Ala Ala Ser Val Lys Asp
    210                 215                 220

Val Leu Asn Ala Gly Trp Asn Ile Lys Gly Val Lys Pro Gly Thr Thr
225                 230                 235                 240

Ala Ser Asp Asn Val Asp Phe Val His Thr Tyr Asp Thr Val Glu Phe
                245                 250                 255

Leu Ser Ala Asp Thr Lys Thr Thr Val Asn Val Glu Ser Lys Asp
            260                 265                 270

Asn Gly Lys Arg Thr Glu Val Lys Ile Gly Ala Lys Thr Ser Val Ile
        275                 280                 285

Lys Glu Lys Asp Gly Lys Leu Val Thr Gly Lys Gly Lys Gly Glu Asn
    290                 295                 300

Gly Ser Ser Thr Asp Glu Gly Glu Gly Leu Val Thr Ala Lys Glu Val
305                 310                 315                 320
```

```
Ile Asp Ala Val Asn Lys Ala Gly Trp Arg Met Lys Thr Thr Thr Ala
            325                 330                 335

Asn Gly Gln Thr Gly Gln Ala Asp Lys Phe Glu Thr Val Thr Ser Gly
            340                 345                 350

Thr Asn Val Thr Phe Ala Ser Gly Lys Gly Thr Thr Ala Thr Val Ser
            355                 360                 365

Lys Asp Asp Gln Gly Asn Ile Thr Val Lys Tyr Asp Val Asn Val Gly
    370                 375                 380

Asp Ala Leu Asn Val Asn Gln Leu Gln Asn Ser Gly Trp Asn Leu Asp
385                 390                 395                 400

Ser Lys Ala Val Ala Gly Ser Ser Gly Lys Val Ile Ser Gly Asn Val
            405                 410                 415

Ser Pro Ser Lys Gly Lys Met Asp Glu Thr Val Asn Ile Asn Ala Gly
            420                 425                 430

Asn Asn Ile Glu Ile Thr Arg Asn Gly Lys Asn Ile Asp Ile Ala Thr
            435                 440                 445

Ser Met Thr Pro Gln Phe Ser Ser Val Ser Leu Gly Ala Gly Ala Asp
    450                 455                 460

Ala Pro Thr Leu Ser Val Asp Asp Lys Gly Ala Leu Asn Val Gly Ser
465                 470                 475                 480

Lys Asp Ala Asn Lys Pro Val Arg Ile Thr Asn Val Ala Pro Gly Val
            485                 490                 495

Lys Glu Gly Asp Val Thr Asn Val Ala Gln Leu Lys Gly Val Ala Gln
            500                 505                 510

Asn Leu Asn Asn Arg Ile Asp Asn Val Asp Gly Asn Ala Arg Ala Gly
            515                 520                 525

Ile Ala Gln Ala Ile Ala Thr Ala Gly Leu Val Gln Ala Tyr Leu Pro
    530                 535                 540

Gly Lys Ser Met Met Ala Ile Gly Gly Gly Thr Tyr Arg Gly Glu Ala
545                 550                 555                 560

Gly Tyr Ala Ile Gly Tyr Ser Ser Ile Ser Asp Gly Gly Asn Trp Ile
            565                 570                 575

Ile Lys Gly Thr Ala Ser Gly Asn Ser Arg Gly His Phe Gly Ala Ser
            580                 585                 590

Ala Ser Val Gly Tyr Gln Trp
            595

<210> SEQ ID NO 101
<211> LENGTH: 598
<212> TYPE: PRT
<213> ORGANISM: Neisseria meningitidis

<400> SEQUENCE: 101

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Ala Thr Ala Val Leu Ala Thr Leu Leu Phe Ala Thr Val Gln
            35                  40                  45

Ala Asn Ala Thr Asp Asp Asp Leu Tyr Leu Glu Pro Val Gln Arg
    50                  55                  60

Thr Ala Val Val Leu Ser Phe Arg Ser Asp Lys Glu Gly Thr Gly Glu
65                  70                  75                  80

Lys Glu Gly Thr Glu Asp Ser Asn Trp Ala Val Tyr Phe Asp Glu Lys
            85                  90                  95
```

```
Arg Val Leu Lys Ala Gly Ala Ile Thr Leu Lys Ala Gly Asp Asn Leu
                100                 105                 110

Lys Ile Lys Gln Asn Thr Asn Glu Asn Thr Asn Glu Asn Thr Asn Asp
            115                 120                 125

Ser Ser Phe Thr Tyr Ser Leu Lys Lys Asp Leu Thr Asp Leu Thr Ser
        130                 135                 140

Val Glu Thr Glu Lys Leu Ser Phe Gly Ala Asn Gly Asn Lys Val Asn
145                 150                 155                 160

Ile Thr Ser Asp Thr Lys Gly Leu Asn Phe Ala Lys Glu Thr Ala Gly
                165                 170                 175

Thr Asn Gly Asp Pro Thr Val His Leu Asn Gly Ile Gly Ser Thr Leu
            180                 185                 190

Thr Asp Thr Leu Leu Asn Thr Gly Ala Thr Thr Asn Val Thr Asn Asp
        195                 200                 205

Asn Val Thr Asp Asp Glu Lys Lys Arg Ala Ala Ser Val Lys Asp Val
210                 215                 220

Leu Asn Ala Gly Trp Asn Ile Lys Gly Val Lys Pro Gly Thr Thr Ala
225                 230                 235                 240

Ser Asp Asn Val Asp Phe Val Arg Thr Tyr Asp Thr Val Glu Phe Leu
                245                 250                 255

Ser Ala Asp Thr Lys Thr Thr Thr Val Asn Val Glu Ser Lys Asp Asn
            260                 265                 270

Gly Lys Lys Thr Glu Val Lys Ile Gly Ala Lys Thr Ser Val Ile Lys
        275                 280                 285

Glu Lys Asp Gly Lys Leu Val Thr Gly Lys Gly Lys Asp Glu Asn Gly
        290                 295                 300

Ser Ser Thr Asp Glu Gly Glu Gly Leu Val Thr Ala Lys Glu Val Ile
305                 310                 315                 320

Asp Ala Val Asn Lys Ala Gly Trp Arg Met Lys Thr Thr Thr Ala Asn
                325                 330                 335

Gly Gln Thr Gly Gln Ala Asp Lys Phe Glu Thr Val Thr Ser Gly Thr
            340                 345                 350

Lys Val Thr Phe Ala Ser Gly Asn Gly Thr Thr Ala Thr Val Ser Lys
        355                 360                 365

Asp Asp Gln Gly Asn Ile Thr Val Lys Tyr Asp Val Asn Val Gly Asp
        370                 375                 380

Ala Leu Asn Val Asn Gln Leu Gln Asn Ser Gly Trp Asn Leu Asp Ser
385                 390                 395                 400

Lys Ala Val Ala Gly Ser Ser Gly Lys Val Ile Ser Gly Asn Val Ser
                405                 410                 415

Pro Ser Lys Gly Lys Met Asp Glu Thr Val Asn Ile Asn Ala Gly Asn
            420                 425                 430

Asn Ile Glu Ile Thr Arg Asn Gly Lys Asn Ile Asp Ile Ala Thr Ser
        435                 440                 445

Met Thr Pro Gln Phe Ser Ser Val Ser Leu Gly Ala Gly Ala Asp Ala
        450                 455                 460

Pro Thr Leu Ser Val Asp Asp Glu Gly Ala Leu Asn Val Gly Ser Lys
465                 470                 475                 480

Asp Ala Asn Lys Pro Val Arg Ile Thr Asn Val Ala Pro Gly Val Lys
                485                 490                 495

Glu Gly Asp Val Thr Asn Val Ala Gln Leu Lys Gly Val Ala Gln Asn
            500                 505                 510
```

-continued

```
Leu Asn Asn Arg Ile Asp Asn Val Asp Gly Asn Ala Arg Ala Gly Ile
        515                 520                 525

Ala Gln Ala Ile Ala Thr Ala Gly Leu Ala Gln Ala Tyr Leu Pro Gly
    530                 535                 540

Lys Ser Met Met Ala Ile Gly Gly Thr Tyr Arg Gly Glu Ala Gly
545                 550                 555                 560

Tyr Ala Ile Gly Tyr Ser Ser Ile Ser Asp Thr Gly Asn Trp Val Ile
                565                 570                 575

Lys Gly Thr Ala Ser Gly Asn Ser Arg Gly His Phe Gly Ala Ser Ala
            580                 585                 590

Ser Val Gly Tyr Gln Trp
        595

<210> SEQ ID NO 102
<211> LENGTH: 594
<212> TYPE: PRT
<213> ORGANISM: Neisseria meningitidis

<400> SEQUENCE: 102

Met Asn Lys Ile Tyr Arg Ile Ile Trp Asn Ser Ala Leu Asn Ala Trp
 1               5                  10                  15

Val Ala Val Ser Glu Leu Thr Arg Asn His Thr Lys Arg Ala Ser Ala
            20                  25                  30

Thr Val Ala Thr Ala Val Leu Ala Thr Leu Leu Phe Ala Thr Val Gln
        35                  40                  45

Ala Ser Thr Thr Asp Asp Asp Leu Tyr Leu Glu Pro Val Gln Arg
    50                  55                  60

Thr Ala Pro Val Leu Ser Phe His Ala Asp Ser Glu Gly Thr Gly Glu
65                  70                  75                  80

Lys Glu Val Thr Glu Asp Ser Asn Trp Gly Val Tyr Phe Asp Lys Lys
                85                  90                  95

Gly Val Leu Thr Ala Gly Thr Ile Thr Leu Lys Ala Gly Asp Asn Leu
            100                 105                 110

Lys Ile Lys Gln Asn Thr Asp Glu Asn Thr Asn Ala Ser Ser Phe Thr
        115                 120                 125

Tyr Ser Leu Lys Lys Asp Leu Thr Asp Leu Thr Ser Val Glu Thr Glu
    130                 135                 140

Lys Leu Ser Phe Gly Ala Asn Gly Lys Lys Val Asn Ile Thr Ser Asp
145                 150                 155                 160

Thr Lys Gly Leu Asn Phe Ala Lys Glu Thr Ala Gly Thr Asn Gly Asp
                165                 170                 175

Thr Thr Val His Leu Asn Gly Ile Gly Ser Thr Leu Thr Asp Thr Leu
            180                 185                 190

Leu Asn Thr Gly Ala Thr Thr Asn Val Thr Asn Asp Asn Val Thr Asp
        195                 200                 205

Asp Glu Lys Lys Arg Ala Ala Ser Val Lys Asp Val Leu Asn Ala Gly
    210                 215                 220

Trp Asn Ile Lys Gly Val Lys Pro Gly Thr Thr Ala Ser Asp Asn Val
225                 230                 235                 240

Asp Phe Val Arg Thr Tyr Asp Thr Val Glu Phe Leu Ser Ala Asp Thr
                245                 250                 255

Lys Thr Thr Thr Val Asn Val Glu Ser Lys Asp Asn Gly Lys Lys Thr
            260                 265                 270

Glu Val Lys Ile Gly Ala Lys Ser Val Ile Lys Glu Lys Asp Gly
        275                 280                 285
```

-continued

```
Lys Leu Val Thr Gly Lys Asp Lys Gly Glu Asn Gly Ser Ser Thr Asp
        290                 295                 300

Glu Gly Glu Gly Leu Val Thr Ala Lys Glu Val Ile Asp Ala Val Asn
305                 310                 315                 320

Lys Ala Gly Trp Arg Met Lys Thr Thr Thr Ala Asn Gly Gln Thr Gly
                325                 330                 335

Gln Ala Asp Lys Phe Glu Thr Val Thr Ser Gly Thr Lys Val Thr Phe
            340                 345                 350

Ala Ser Gly Asn Gly Thr Thr Ala Thr Val Ser Lys Asp Asp Gln Gly
        355                 360                 365

Asn Ile Thr Val Lys Tyr Asp Val Asn Val Gly Asp Ala Leu Asn Val
    370                 375                 380

Asn Gln Leu Gln Asn Ser Gly Trp Asn Leu Asp Ser Lys Ala Val Ala
385                 390                 395                 400

Gly Ser Ser Gly Lys Val Ile Ser Gly Asn Val Ser Pro Ser Lys Gly
                405                 410                 415

Lys Met Asp Glu Thr Val Asn Ile Asn Ala Gly Asn Asn Ile Glu Ile
            420                 425                 430

Thr Arg Asn Gly Lys Asn Ile Asp Ile Ala Thr Ser Met Thr Pro Gln
        435                 440                 445

Phe Ser Ser Val Ser Leu Gly Ala Gly Ala Asp Ala Pro Thr Leu Ser
    450                 455                 460

Val Asp Asp Glu Gly Ala Leu Asn Val Gly Ser Lys Asp Ala Asn Lys
465                 470                 475                 480

Pro Val Arg Ile Thr Asn Val Ala Pro Gly Val Lys Glu Gly Asp Val
                485                 490                 495

Thr Asn Val Ala Gln Leu Lys Gly Val Ala Gln Asn Leu Asn Asn His
            500                 505                 510

Ile Asp Asn Val Asp Gly Asn Ala Arg Ala Gly Ile Ala Gln Ala Ile
        515                 520                 525

Ala Thr Ala Gly Leu Val Gln Ala Tyr Leu Pro Gly Lys Ser Met Met
    530                 535                 540

Ala Ile Gly Gly Gly Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
                565                 570                 575

Ser Gly Asn Ser Arg Gly His Phe Gly Ala Ser Ala Ser Val Gly Tyr
            580                 585                 590

Gln Trp
```

```
<210> SEQ ID NO 103
<211> LENGTH: 591
<212> TYPE: PRT
<213> ORGANISM: Neisseria meningitidis

<400> SEQUENCE: 103
```

```
Met Asn Lys Ile Tyr Arg Ile Ile Trp Asn Ser Ala Leu Asn Ala Trp
  1               5                  10                  15

Val Val Ser Glu Leu Thr Arg Asn His Thr Lys Arg Ala Ser Ala
                20                  25                  30

Thr Val Lys Thr Ala Val Leu Ala Thr Leu Phe Ala Thr Val Gln
            35                  40                  45

Ala Ser Ala Asn Asn Glu Glu Gln Glu Glu Asp Leu Tyr Leu Asp Pro
    50                  55                  60
```

-continued

```
Val Gln Arg Thr Val Ala Val Leu Ile Val Asn Ser Asp Lys Glu Gly
 65                  70                  75                  80

Thr Gly Glu Lys Glu Lys Val Glu Glu Asn Ser Asp Trp Ala Val Tyr
                 85                  90                  95

Phe Asn Glu Lys Gly Val Leu Thr Ala Arg Glu Ile Thr Leu Lys Ala
            100                 105                 110

Gly Asp Asn Leu Lys Ile Lys Gln Asn Gly Thr Asn Phe Thr Tyr Ser
            115                 120                 125

Leu Lys Lys Asp Leu Thr Asp Leu Thr Ser Val Gly Thr Glu Lys Leu
        130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
            180                 185                 190

Thr Gly Ala Thr Thr Asn Val Thr Asn Asp Asn Val Thr Asp Asp Glu
            195                 200                 205

Lys Lys Arg Ala Ala Ser Val Lys Asp Val Leu Asn Ala Gly Trp Asn
210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
            275                 280                 285

Val Thr Gly Lys Asp Lys Gly Glu Asn Gly Ser Ser Thr Asp Glu Gly
        290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
            355                 360                 365

Thr Val Met Tyr Asp Val Asn Val Gly Asp Ala Leu Asn Val Asn His
        370                 375                 380

Leu Gln Asn Ser Gly Trp Asp Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
            420                 425                 430

Asn Gly Lys Asn Ile Asp Ile Ala Thr Ser Met Thr Pro Gln Phe Ser
            435                 440                 445

Ser Val Ser Leu Gly Ala Gly Ala Asp Ala Pro Thr Leu Ser Val Asp
        450                 455                 460

Gly Asp Ala Leu Asn Val Gly Ser Lys Lys Asp Asn Lys Pro Val Arg
465                 470                 475                 480
```

```
Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
                500                 505                 510

Val Asp Gly Asn Ala Arg Ala Gly Ile Ala Gln Ala Ile Ala Thr Ala
                515                 520                 525

Gly Leu Val Gln Ala Tyr Leu Pro Gly Lys Ser Met Met Ala Ile Gly
                530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
                580                 585                 590

<210> SEQ ID NO 104
<211> LENGTH: 591
<212> TYPE: PRT
<213> ORGANISM: Neisseria meningitidis

<400> SEQUENCE: 104

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Lys Thr Ala Val Leu Ala Thr Leu Leu Phe Ala Thr Val Gln
            35                  40                  45

Ala Ser Ala Asn Asn Glu Glu Gln Glu Glu Asp Leu Tyr Leu Asp Pro
        50                  55                  60

Val Gln Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
                100                 105                 110

Gly Asp Asn Leu Lys Ile Lys Gln Asn Gly Thr Asn Phe Thr Tyr Ser
                115                 120                 125

Leu Lys Lys Asp Leu Thr Asp Leu Thr Ser Val Gly Thr Glu Lys Leu
            130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
                180                 185                 190

Thr Gly Ala Thr Thr Asn Val Thr Asn Asp Asn Val Thr Asp Asp Glu
            195                 200                 205

Lys Lys Arg Ala Ala Ser Val Lys Asp Val Leu Asn Ala Gly Trp Asn
210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
                260                 265                 270
```

```
Lys Ile Gly Ala Lys Thr Ser Val Ile Lys Glu Lys Asp Gly Lys Leu
            275                 280                 285

Val Thr Gly Lys Asp Lys Gly Glu Asn Gly Ser Ser Thr Asp Glu Gly
            290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
            325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
            355                 360                 365

Thr Val Met Tyr Asp Val Asn Val Gly Asp Ala Leu Asn Val Asn Gln
            370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
            405                 410                 415

Asp Glu Thr Val Asn Ile Asn Ala Gly Asn Asn Ile Glu Ile Thr Arg
            420                 425                 430

Asn Gly Lys Asn Ile Asp Ile Ala Thr Ser Met Thr Pro Gln Phe Ser
            435                 440                 445

Ser Val Ser Leu Gly Ala Gly Ala Asp Ala Pro Thr Leu Ser Val Asp
450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
            485                 490                 495

Ala Gln Leu Lys Gly Val Ala Gln Asn Leu Asn Asn Arg Ile Asp Asn
            500                 505                 510

Val Asp Gly Asn Ala Arg Ala Gly Ile Ala Gln Ala Ile Ala Thr Ala
            515                 520                 525

Gly Leu Val Gln Ala Tyr Leu Pro Gly Lys Ser Met Met Ala Ile Gly
            530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
            565                 570                 575

Ser Arg Gly His Phe Gly Ala Ser Ala Ser Val Gly Tyr Gln Trp
            580                 585                 590

<210> SEQ ID NO 105
<211> LENGTH: 591
<212> TYPE: PRT
<213> ORGANISM: Neisseria meningitidis

<400> SEQUENCE: 105

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
            35                  40                  45

Ala Ser Ala Asn Asn Glu Glu Gln Glu Glu Asp Leu Tyr Leu Asp Pro
```

-continued

```
               50                  55                  60
Val Gln Arg Thr Val Ala Val Leu Ile Val Asn Ser Asp Lys Glu Gly
 65                  70                  75                  80

Thr Gly Glu Lys Glu Lys Val Glu Glu Asn Ser Asp Trp Ala Val Tyr
                 85                  90                  95

Phe Asn Glu Lys Gly Val Leu Thr Ala Arg Glu Ile Thr Leu Lys Ala
                100                 105                 110

Gly Asp Asn Leu Lys Ile Lys Gln Asn Gly Thr Asn Phe Thr Tyr Ser
                115                 120                 125

Leu Lys Lys Asp Leu Thr Asp Leu Thr Ser Val Gly Thr Glu Lys Leu
130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
                180                 185                 190

Thr Gly Ala Thr Thr Asn Val Thr Asn Asp Asn Val Thr Asp Asp Glu
                195                 200                 205

Lys Lys Arg Ala Ala Ser Val Lys Asp Val Leu Asn Ala Gly Trp Asn
210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Thr Lys Thr
                245                 250                 255

Thr Thr Val Asn Val Glu Ser Lys Asp Asn Gly Lys Lys Thr Glu Val
                260                 265                 270

Lys Ile Gly Ala Lys Thr Ser Val Ile Lys Glu Lys Asp Gly Lys Leu
                275                 280                 285

Val Thr Gly Lys Asp Lys Gly Glu Asn Gly Ser Ser Thr Asp Glu Gly
                290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
                325                 330                 335

Asp Lys Phe Glu Thr Val Thr Ser Gly Thr Asn Val Thr Phe Ala Ser
                340                 345                 350

Gly Lys Gly Thr Thr Ala Thr Val Ser Lys Asp Gln Gly Asn Ile
                355                 360                 365

Thr Val Met Tyr Asp Val Asn Val Gly Asp Ala Leu Asn Val Asn Gln
                370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
                420                 425                 430

Asn Gly Lys Asn Ile Asp Ile Ala Thr Ser Met Thr Pro Gln Phe Ser
                435                 440                 445

Ser Val Ser Leu Gly Ala Gly Ala Asp Ala Pro Thr Leu Ser Val Asp
                450                 455                 460

Gly Asp Ala Leu Asn Val Gly Ser Lys Lys Asp Asn Lys Pro Val Arg
465                 470                 475                 480
```

```
Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
            500                 505                 510

Val Asp Gly Asn Ala Arg Ala Gly Ile Ala Gln Ala Ile Ala Thr Ala
        515                 520                 525

Gly Leu Val Gln Ala Tyr Leu Pro Gly Lys Ser Met Met Ala Ile Gly
    530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
            580                 585                 590

<210> SEQ ID NO 106
<211> LENGTH: 592
<212> TYPE: PRT
<213> ORGANISM: Neisseria meningitidis

<400> SEQUENCE: 106

Met Asn Lys Ile Tyr Arg Ile Ile Trp Asn Ser Ala Leu Asn Ala Trp
 1               5                  10                  15

Val Ala Val Ser Glu Leu Thr Arg Asn His Thr Lys Arg Ala Ser Ala
                20                  25                  30

Thr Val Lys Thr Ala Val Leu Ala Thr Leu Phe Ala Thr Val Gln
            35                  40                  45

Ala Asn Ala Thr Asp Glu Asp Glu Glu Leu Glu Ser Val Gln
        50                  55                  60

Arg Ser Val Val Gly Ser Ile Gln Ala Ser Met Glu Gly Ser Gly Glu
 65                  70                  75                  80

Leu Glu Thr Ile Ser Leu Ser Met Thr Asn Asp Ser Lys Glu Phe Val
                85                  90                  95

Asp Pro Tyr Ile Val Val Thr Leu Lys Ala Gly Asp Asn Leu Lys Ile
                100                 105                 110

Lys Gln Asn Thr Asn Glu Asn Thr Asn Ala Ser Ser Phe Thr Tyr Ser
            115                 120                 125

Leu Lys Lys Asp Leu Thr Gly Leu Ile Asn Val Glu Thr Glu Lys Leu
        130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Ala Gly
            180                 185                 190

Ser Ser Ala Ser His Val Asp Ala Gly Asn Gln Ser Thr His Tyr Thr
        195                 200                 205

Arg Ala Ala Ser Ile Lys Asp Val Leu Asn Ala Gly Trp Asn Ile Lys
    210                 215                 220

Gly Val Lys Thr Gly Ser Thr Thr Gly Gln Ser Glu Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Arg Thr Glu Val
```

-continued

```
                    260                 265                 270
Lys Ile Gly Ala Lys Thr Ser Val Ile Lys Glu Lys Asp Gly Lys Leu
            275                 280                 285
Val Thr Gly Lys Gly Lys Gly Glu Asn Gly Ser Ser Thr Asp Glu Gly
        290                 295                 300
Glu Gly Leu Val Thr Ala Lys Glu Val Ile Asp Ala Val Asn Lys Ala
305                 310                 315                 320
Gly Trp Arg Met Lys Thr Thr Ala Asn Gly Gln Thr Gly Gln Ala
                325                 330                 335
Asp Lys Phe Glu Thr Val Thr Ser Gly Thr Asn Val Thr Phe Ala Ser
            340                 345                 350
Gly Lys Gly Thr Thr Ala Thr Val Ser Lys Asp Asp Gln Gly Asn Ile
        355                 360                 365
Thr Val Met Tyr Asp Val Asn Val Gly Asp Ala Leu Asn Val Asn Gln
    370                 375                 380
Leu Gln Asn Ser Gly Trp Asn Leu Asp Ser Lys Ala Val Ala Gly Ser
385                 390                 395                 400
Ser Gly Lys Val Ile Ser Gly Asn Val Ser Pro Ser Lys Gly Lys Met
                405                 410                 415
Asp Glu Thr Val Asn Ile Asn Ala Gly Asn Asn Ile Glu Ile Ser Arg
            420                 425                 430
Asn Gly Lys Asn Ile Asp Ile Ala Thr Ser Met Ala Pro Gln Phe Ser
        435                 440                 445
Ser Val Ser Leu Gly Ala Gly Ala Asp Ala Pro Thr Leu Ser Val Asp
    450                 455                 460
Asp Glu Gly Ala Leu Asn Val Gly Ser Lys Asp Ala Asn Lys Pro Val
465                 470                 475                 480
Arg Ile Thr Asn Val Ala Pro Gly Val Lys Glu Gly Asp Val Thr Asn
                485                 490                 495
Val Ala Gln Leu Lys Gly Val Ala Gln Asn Leu Asn Asn Arg Ile Asp
            500                 505                 510
Asn Val Asp Gly Asn Ala Arg Ala Gly Ile Ala Gln Ala Ile Ala Thr
        515                 520                 525
Ala Gly Leu Val Gln Ala Tyr Leu Pro Gly Lys Ser Met Met Ala Ile
    530                 535                 540
Gly Gly Gly Thr Tyr Arg Gly Glu Ala Gly Tyr Ala Ile Gly Tyr Ser
545                 550                 555                 560
Ser Ile Ser Asp Gly Gly Asn Trp Ile Ile Lys Gly Thr Ala Ser Gly
                565                 570                 575
Asn Ser Arg Gly His Phe Gly Ala Ser Ala Ser Val Gly Tyr Gln Trp
            580                 585                 590

<210> SEQ ID NO 107
<211> LENGTH: 592
<212> TYPE: PRT
<213> ORGANISM: Neisseria meningitidis

<400> SEQUENCE: 107

Met Asn Lys Ile Tyr Arg Ile Ile Trp Asn Ser Ala Leu Asn Ala Trp
1               5                   10                  15
Val Ala Val Ser Glu Leu Thr Arg Asn His Thr Lys Arg Ala Ser Ala
            20                  25                  30
Thr Val Lys Thr Ala Val Leu Ala Thr Leu Leu Phe Ala Thr Val Gln
        35                  40                  45
```

-continued

```
Ala Asn Ala Thr Asp Glu Asp Glu Glu Glu Leu Glu Ser Val Gln
    50                  55                  60

Arg Ser Val Val Gly Ser Ile Gln Ala Ser Met Glu Gly Ser Gly Glu
 65                  70                  75                  80

Leu Glu Thr Ile Ser Leu Ser Met Thr Asn Asp Ser Lys Glu Phe Val
                 85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
            115                 120                 125

Leu Lys Lys Asp Leu Thr Gly Leu Ile Asn Val Glu Thr Glu Lys Leu
        130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Ala Gly
            180                 185                 190

Ser Ser Ala Ser His Val Asp Ala Gly Asn Gln Ser Thr His Tyr Thr
        195                 200                 205

Arg Ala Ala Ser Ile Lys Asp Val Leu Asn Ala Gly Trp Asn Ile Lys
210                 215                 220

Gly Val Lys Thr Gly Ser Thr Thr Gly Gln Ser Glu Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Arg Thr Glu Val
            260                 265                 270

Lys Ile Gly Ala Lys Thr Ser Val Ile Lys Glu Lys Asp Gly Lys Leu
        275                 280                 285

Val Thr Gly Lys Gly Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
        355                 360                 365

Thr Val Met Tyr Asp Val Asn Val Gly Asp Ala Leu Asn Val Asn Gln
    370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Ser Arg
            420                 425                 430

Asn Gly Lys Asn Ile Asp Ile Ala Thr Ser Met Ala Pro Gln Phe Ser
        435                 440                 445

Ser Val Ser Leu Gly Ala Gly Ala Asp Ala Pro Thr Leu Ser Val Asp
    450                 455                 460

Asp Glu Gly Ala Leu Asn Val Gly Ser Lys Asp Ala Asn Lys Pro Val
```

```
                   465                 470                 475                 480
Arg Ile Thr Asn Val Ala Pro Gly Val Lys Glu Gly Asp Val Thr Asn
                485                 490                 495

Val Ala Gln Leu Lys Gly Val Ala Gln Asn Leu Asn Asn Arg Ile Asp
                500                 505                 510

Asn Val Asp Gly Asn Ala Arg Ala Gly Ile Ala Gln Ala Ile Ala Thr
                515                 520                 525

Ala Gly Leu Val Gln Ala Tyr Leu Pro Gly Lys Ser Met Met Ala Ile
                530                 535                 540

Gly Gly Gly Thr Tyr Arg Gly Glu Ala Gly Tyr Ala Ile Gly Tyr Ser
545                 550                 555                 560

Ser Ile Ser Asp Gly Gly Asn Trp Ile Ile Lys Gly Thr Ala Ser Gly
                565                 570                 575

Asn Ser Arg Gly His Phe Gly Ala Ser Ala Ser Val Gly Tyr Gln Trp
                580                 585                 590

<210> SEQ ID NO 108
<211> LENGTH: 589
<212> TYPE: PRT
<213> ORGANISM: Neisseria meningitidis

<400> SEQUENCE: 108

Met Asn Lys Ile Tyr Arg Ile Ile Trp Asn Ser Ala Leu Asn Ala Trp
  1               5                  10                  15

Val Val Val Ser Glu Leu Thr Arg Asn His Thr Lys Arg Ala Ser Ala
                 20                  25                  30

Thr Val Ala Thr Ala Val Leu Ala Thr Leu Leu Ser Ala Thr Val Gln
             35                  40                  45

Ala Asn Ala Thr Asp Thr Asp Glu Asp Glu Glu Leu Glu Ser Val Val
         50                  55                  60

Arg Ser Ala Leu Val Leu Gln Phe Met Ile Asp Lys Glu Gly Asn Gly
 65                  70                  75                  80

Glu Ile Glu Ser Thr Gly Asp Ile Gly Trp Ser Ile Tyr Tyr Asp Asp
                 85                  90                  95

His Asn Thr Leu His Gly Ala Thr Val Thr Leu Lys Ala Gly Asp Asn
                100                 105                 110

Leu Lys Ile Lys Gln Ser Gly Lys Asp Phe Thr Tyr Ser Leu Lys Lys
            115                 120                 125

Glu Leu Lys Asp Leu Thr Ser Val Glu Thr Glu Lys Leu Ser Phe Gly
        130                 135                 140

Ala Asn Gly Asn Lys Val Asn Ile Thr Ser Asp Thr Lys Gly Leu Asn
145                 150                 155                 160

Phe Ala Lys Glu Thr Ala Gly Thr Asn Gly Asp Pro Thr Val His Leu
                165                 170                 175

Asn Gly Ile Gly Ser Thr Leu Thr Asp Thr Leu Ala Gly Ser Ser Ala
                180                 185                 190

Ser His Val Asp Ala Gly Asn Gln Ser Thr His Tyr Thr Arg Ala Ala
            195                 200                 205

Ser Ile Lys Asp Val Leu Asn Ala Gly Trp Asn Ile Lys Gly Val Lys
        210                 215                 220

Thr Gly Ser Thr Thr Gly Gln Ser Glu Asn Val Asp Phe Val Arg Thr
225                 230                 235                 240

Tyr Asp Thr Val Glu Phe Leu Ser Ala Asp Thr Lys Thr Thr Thr Val
                245                 250                 255
```

```
Asn Val Glu Ser Lys Asp Asn Gly Lys Arg Thr Glu Val Lys Ile Gly
            260                 265                 270

Ala Lys Thr Ser Val Ile Lys Glu Lys Asp Gly Lys Leu Val Thr Gly
            275                 280                 285

Lys Gly Lys Gly Glu Asn Gly Ser Ser Thr Asp Glu Gly Gly Leu
            290                 295                 300

Val Thr Ala Lys Glu Val Ile Asp Ala Val Asn Lys Ala Gly Trp Arg
305                 310                 315                 320

Met Lys Thr Thr Thr Ala Asn Gly Gln Thr Gly Gln Ala Asp Lys Phe
                325                 330                 335

Glu Thr Val Thr Ser Gly Thr Lys Val Thr Phe Ala Ser Gly Asn Gly
            340                 345                 350

Thr Thr Ala Thr Val Ser Lys Asp Asp Gln Gly Asn Ile Thr Val Lys
            355                 360                 365

Tyr Asp Val Asn Val Gly Asp Ala Leu Asn Val Asn Gln Leu Gln Asn
            370                 375                 380

Ser Gly Trp Asn Leu Asp Ser Lys Ala Val Ala Gly Ser Ser Gly Lys
385                 390                 395                 400

Val Ile Ser Gly Asn Val Ser Pro Ser Lys Gly Lys Met Asp Glu Thr
                405                 410                 415

Val Asn Ile Asn Ala Gly Asn Asn Ile Glu Ile Thr Arg Asn Gly Lys
            420                 425                 430

Asn Ile Asp Ile Ala Thr Ser Met Thr Pro Gln Phe Ser Ser Val Ser
            435                 440                 445

Leu Gly Ala Gly Ala Asp Ala Pro Thr Leu Ser Val Asp Asp Glu Gly
            450                 455                 460

Ala Leu Asn Val Gly Ser Lys Asp Ala Asn Lys Pro Val Arg Ile Thr
465                 470                 475                 480

Asn Val Ala Pro Gly Val Lys Glu Gly Asp Val Thr Asn Val Ala Gln
                485                 490                 495

Leu Lys Gly Val Ala Gln Asn Leu Asn Asn Arg Ile Asp Asn Val Asp
            500                 505                 510

Gly Asn Ala Arg Ala Gly Ile Ala Gln Ala Ile Ala Thr Ala Gly Leu
            515                 520                 525

Ala Gln Ala Tyr Leu Pro Gly Lys Ser Met Met Ala Ile Gly Gly Gly
            530                 535                 540

Thr Tyr Arg Gly Glu Ala Gly Tyr Ala Ile Gly Tyr Ser Ser Ile Ser
545                 550                 555                 560

Asp Thr Gly Asn Trp Val Ile Lys Gly Thr Ala Ser Gly Asn Ser Arg
                565                 570                 575

Gly His Phe Gly Thr Ser Ala Ser Val Gly Tyr Gln Trp
            580                 585
```

<210> SEQ ID NO 109
<211> LENGTH: 589
<212> TYPE: PRT
<213> ORGANISM: Neisseria meningitidis

<400> SEQUENCE: 109

```
Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Ala Thr Ala Val Leu Ala Thr Leu Leu Ser Ala Thr Val Gln
            35                  40                  45
```

-continued

```
Ala Asn Ala Thr Asp Thr Asp Glu Asp Glu Leu Glu Ser Val Val
     50                  55                  60

Arg Ser Ala Leu Val Leu Gln Phe Met Ile Asp Lys Glu Gly Asn Gly
 65                  70                  75                  80

Glu Ile Glu Ser Thr Gly Asp Ile Gly Trp Ser Ile Tyr Tyr Asp Asp
                 85                  90                  95

His Asn Thr Leu His Gly Ala Thr Val Thr Leu Lys Ala Gly Asp Asn
                100                 105                 110

Leu Lys Ile Lys Gln Ser Gly Lys Asp Phe Thr Tyr Ser Leu Lys Lys
            115                 120                 125

Glu Leu Lys Asp Leu Thr Ser Val Glu Thr Glu Lys Leu Ser Phe Gly
130                 135                 140

Ala Asn Gly Asn Lys Val Asn Ile Thr Ser Asp Thr Lys Gly Leu Asn
145                 150                 155                 160

Phe Ala Lys Glu Thr Ala Gly Thr Asn Gly Asp Pro Thr Val His Leu
                165                 170                 175

Asn Gly Ile Gly Ser Thr Leu Thr Asp Thr Leu Ala Gly Ser Ser Ala
            180                 185                 190

Ser His Val Asp Ala Gly Asn Gln Ser Thr His Tyr Thr Arg Ala Ala
    195                 200                 205

Ser Ile Lys Asp Val Leu Asn Ala Gly Trp Asn Ile Lys Gly Val Lys
    210                 215                 220

Thr Gly Ser Thr Thr Gly Gln Ser Glu Asn Val Asp Phe Val Arg Thr
225                 230                 235                 240

Tyr Asp Thr Val Glu Phe Leu Ser Ala Asp Thr Lys Thr Thr Thr Val
                245                 250                 255

Asn Val Glu Ser Lys Asp Asn Gly Lys Arg Thr Glu Val Lys Ile Gly
            260                 265                 270

Ala Lys Thr Ser Val Ile Lys Glu Lys Asp Gly Lys Leu Val Thr Gly
            275                 280                 285

Lys Gly Lys Gly Glu Asn Gly Ser Ser Thr Asp Glu Gly Glu Gly Leu
290                 295                 300

Val Thr Ala Lys Glu Val Ile Asp Ala Val Asn Lys Ala Gly Trp Arg
305                 310                 315                 320

Met Lys Thr Thr Thr Ala Asn Gly Gln Thr Gly Gln Ala Asp Lys Phe
                325                 330                 335

Glu Thr Val Thr Ser Gly Thr Lys Val Thr Phe Ala Ser Gly Asn Gly
            340                 345                 350

Thr Thr Ala Thr Val Ser Lys Asp Asp Gln Gly Asn Ile Thr Val Lys
            355                 360                 365

Tyr Asp Val Asn Val Gly Asp Ala Leu Asn Val Asn Gln Leu Gln Asn
    370                 375                 380

Ser Gly Trp Asn Leu Asp Ser Lys Ala Val Ala Gly Ser Ser Gly Lys
385                 390                 395                 400

Val Ile Ser Gly Asn Val Ser Pro Ser Lys Gly Lys Met Asp Glu Thr
                405                 410                 415

Val Asn Ile Asn Ala Gly Asn Asn Ile Glu Ile Thr Arg Asn Gly Lys
            420                 425                 430

Asn Ile Asp Ile Ala Thr Ser Met Thr Pro Gln Phe Ser Ser Val Ser
            435                 440                 445

Leu Gly Ala Gly Ala Asp Ala Pro Thr Leu Ser Val Asp Asp Glu Gly
450                 455                 460
```

```
Ala Leu Asn Val Gly Ser Lys Asp Ala Asn Lys Pro Val Arg Ile Thr
465                 470                 475                 480

Asn Val Ala Pro Gly Val Lys Glu Gly Asp Val Thr Asn Val Ala Gln
                485                 490                 495

Leu Lys Gly Val Ala Gln Asn Leu Asn Asn Arg Ile Asp Asn Val Asp
            500                 505                 510

Gly Asn Ala Arg Ala Gly Ile Ala Gln Ala Ile Ala Thr Ala Gly Leu
        515                 520                 525

Ala Gln Ala Tyr Leu Pro Gly Lys Ser Met Met Ala Ile Gly Gly Gly
530                 535                 540

Thr Tyr Arg Gly Glu Ala Gly Tyr Ala Ile Gly Tyr Ser Ser Ile Ser
545                 550                 555                 560

Asp Thr Gly Asn Trp Val Ile Lys Gly Thr Ala Ser Gly Asn Ser Arg
                565                 570                 575

Gly His Phe Gly Thr Ser Ala Ser Val Gly Tyr Gln Trp
            580                 585
```

<210> SEQ ID NO 110
<211> LENGTH: 592
<212> TYPE: PRT
<213> ORGANISM: Neisseria meningitidis

<400> SEQUENCE: 110

```
Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
                20                  25                  30

Thr Val Lys Thr Ala Val Leu Ala Thr Leu Phe Ala Thr Val Gln
            35                  40                  45

Ala Asn Ala Thr Asp Glu Asp Glu Glu Glu Leu Glu Ser Val Gln
        50                  55                  60

Arg Ser Val Val Gly Ser Ile Gln Ala Ser Met Gly Gly Ser Gly Glu
65                  70                  75                  80

Leu Glu Thr Ile Ser Leu Ser Met Thr Asn Asp Ser Lys Glu Phe Val
                85                  90                  95

Asp Pro Tyr Ile Val Val Thr Leu Lys Ala Gly Asp Asn Leu Lys Ile
                100                 105                 110

Lys Gln Asn Thr Asn Glu Asn Thr Asn Ala Ser Ser Phe Thr Tyr Ser
            115                 120                 125

Leu Lys Lys Asp Leu Thr Gly Leu Ile Asn Val Glu Thr Glu Lys Leu
        130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Met Leu Leu Asn
                180                 185                 190

Thr Gly Ala Thr Thr Asn Val Thr Asn Asp Asn Val Thr Asp Asp Glu
            195                 200                 205

Lys Lys Arg Ala Ala Ser Val Lys Asp Val Leu Asn Ala Gly Trp Asn
        210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255
```

-continued

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Gly Lys Gly Glu Asn Gly Ser Ser Thr Asp Glu Gly
        290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
            325                 330                 335

Asp Lys Phe Glu Thr Val Thr Ser Gly Thr Asn Val Thr Phe Ala Ser
        340                 345                 350

Gly Lys Gly Thr Thr Ala Thr Val Ser Lys Asp Asp Gln Gly Asn Ile
        355                 360                 365

Thr Val Met Tyr Asp Val Asn Val Gly Asp Ala Leu Asn Val Asn Gln
        370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
            405                 410                 415

Asp Glu Thr Val Asn Ile Asn Ala Gly Asn Asn Ile Glu Ile Thr Arg
        420                 425                 430

Asn Gly Lys Asn Ile Asp Ile Ala Thr Ser Met Thr Pro Gln Phe Ser
        435                 440                 445

Ser Val Ser Leu Gly Ala Gly Ala Asp Ala Pro Thr Leu Ser Val Asp
        450                 455                 460

Asp Lys Gly Ala Leu Asn Val Gly Ser Lys Asp Ala Asn Lys Pro Val
465                 470                 475                 480

Arg Ile Thr Asn Val Ala Pro Gly Val Lys Glu Gly Asp Val Thr Asn
            485                 490                 495

Val Ala Gln Leu Lys Gly Val Ala Gln Asn Leu Asn Asn Arg Ile Asp
        500                 505                 510

Asn Val Asp Gly Asn Ala Arg Ala Gly Ile Ala Gln Ala Ile Ala Thr
        515                 520                 525

Ala Gly Leu Val Gln Ala Tyr Leu Pro Gly Lys Ser Met Met Ala Ile
        530                 535                 540

Gly Gly Gly Thr Tyr Arg Gly Glu Ala Gly Tyr Ala Ile Gly Tyr Ser
545                 550                 555                 560

Ser Ile Ser Asp Gly Gly Asn Trp Ile Ile Lys Gly Thr Ala Ser Gly
            565                 570                 575

Asn Ser Arg Gly His Phe Gly Ala Ser Ala Ser Val Gly Tyr Gln Trp
        580                 585                 590

<210> SEQ ID NO 111
<211> LENGTH: 600
<212> TYPE: PRT
<213> ORGANISM: Neisseria meningitidis

<400> SEQUENCE: 111

Met Asn Lys Ile Tyr Arg Ile Ile Trp Asn Ile Ala Leu Asn Ala Trp
1               5                   10                  15

Val Val Val Ser Glu Leu Thr Arg Asn His Thr Lys Arg Ala Ser Ala
            20                  25                  30

Thr Val Ala Thr Ala Val Leu Ala Thr Leu Leu Ser Ala Thr Val Gln

-continued

```
                35                  40                  45
Ala Asn Ala Thr Asp Glu Glu Asp Asn Glu Asp Leu Glu Pro Val Val
 50                  55                  60
Arg Thr Ala Pro Val Leu Ser Phe His Ser Asp Lys Glu Gly Thr Gly
 65                  70                  75                  80
Glu Lys Glu Glu Val Gly Ala Ser Ser Asn Leu Thr Val Tyr Phe Asp
                 85                  90                  95
Lys Asn Arg Val Leu Lys Ala Gly Thr Ile Thr Leu Lys Ala Gly Asp
                100                 105                 110
Asn Leu Lys Ile Lys Gln Asn Thr Asn Glu Asn Thr Asn Glu Asn Thr
            115                 120                 125
Asn Ala Ser Ser Phe Thr Tyr Ser Leu Lys Lys Asp Leu Thr Gly Leu
130                 135                 140
Ile Asn Val Glu Thr Glu Lys Leu Ser Phe Gly Ala Asn Gly Lys Lys
145                 150                 155                 160
Val Asn Ile Ile Ser Asp Thr Lys Gly Leu Asn Phe Ala Lys Glu Thr
                165                 170                 175
Ala Gly Thr Asn Gly Asp Pro Thr Val His Leu Asn Gly Ile Gly Ser
                180                 185                 190
Thr Leu Thr Asp Thr Leu Ala Gly Ser Ser Ala Ser His Val Asp Ala
            195                 200                 205
Gly Asn Gln Ser Thr His Tyr Thr Arg Ala Ala Ser Ile Lys Asp Val
        210                 215                 220
Leu Asn Ala Gly Trp Asn Ile Lys Gly Val Lys Thr Gly Ser Thr Thr
225                 230                 235                 240
Gly Gln Ser Glu Asn Val Asp Phe Val Arg Thr Tyr Asp Thr Val Glu
                245                 250                 255
Phe Leu Ser Ala Asp Thr Lys Thr Thr Thr Val Asn Val Glu Ser Lys
                260                 265                 270
Asp Asn Gly Lys Arg Thr Glu Val Lys Ile Gly Ala Lys Thr Ser Val
            275                 280                 285
Ile Lys Glu Lys Asp Gly Lys Leu Val Thr Gly Lys Gly Lys Gly Glu
290                 295                 300
Asn Gly Ser Ser Thr Asp Glu Gly Glu Gly Leu Val Thr Ala Lys Glu
305                 310                 315                 320
Val Ile Asp Ala Val Asn Lys Ala Gly Trp Arg Met Lys Thr Thr Thr
                325                 330                 335
Ala Asn Gly Gln Thr Gly Gln Ala Asp Lys Phe Glu Thr Val Thr Ser
            340                 345                 350
Gly Thr Lys Val Thr Phe Ala Ser Gly Asn Gly Thr Thr Ala Thr Val
        355                 360                 365
Ser Lys Asp Asp Gln Gly Asn Ile Thr Val Lys Tyr Asp Val Asn Val
    370                 375                 380
Gly Asp Ala Leu Asn Val Asn Gln Leu Gln Asn Ser Gly Trp Asn Leu
385                 390                 395                 400
Asp Ser Lys Ala Val Ala Gly Ser Ser Gly Lys Val Ile Ser Gly Asn
                405                 410                 415
Val Ser Pro Ser Lys Gly Lys Met Asp Glu Thr Val Asn Ile Asn Ala
                420                 425                 430
Gly Asn Asn Ile Glu Ile Thr Arg Asn Gly Lys Asn Ile Asp Ile Ala
            435                 440                 445
Thr Ser Met Thr Pro Gln Phe Ser Ser Val Ser Leu Gly Ala Gly Ala
        450                 455                 460
```

```
Asp Ala Pro Thr Leu Ser Val Asp Asp Glu Gly Ala Leu Asn Val Gly
465                 470                 475                 480
Ser Lys Asp Ala Asn Lys Pro Val Arg Ile Thr Asn Val Ala Pro Gly
                485                 490                 495
Val Lys Glu Gly Asp Val Thr Asn Val Ala Gln Leu Lys Gly Val Ala
            500                 505                 510
Gln Asn Leu Asn Asn Arg Ile Asp Asn Val Asp Gly Asn Ala Arg Ala
        515                 520                 525
Gly Ile Ala Gln Ala Ile Ala Thr Ala Gly Leu Val Gln Ala Tyr Leu
    530                 535                 540
Pro Gly Lys Ser Met Met Ala Ile Gly Gly Gly Thr Tyr Arg Gly Glu
545                 550                 555                 560
Ala Gly Tyr Ala Ile Gly Tyr Ser Ser Ile Ser Asp Gly Gly Asn Trp
                565                 570                 575
Ile Ile Lys Gly Thr Ala Ser Gly Asn Ser Arg Gly His Phe Gly Ala
            580                 585                 590
Ser Ala Ser Val Gly Tyr Gln Trp
        595                 600

<210> SEQ ID NO 112
<211> LENGTH: 32
<212> TYPE: DNA
<213> ORGANISM: Neisseria meningitidis

<400> SEQUENCE: 112
cgcggatccc atatgtcgcc gcaaaattcc ga                              32

<210> SEQ ID NO 113
<211> LENGTH: 28
<212> TYPE: DNA
<213> ORGANISM: Neisseria meningitidis

<400> SEQUENCE: 113
cccgctcgag ttttgccgcg ttaaaagc                                   28

<210> SEQ ID NO 114
<211> LENGTH: 30
<212> TYPE: DNA
<213> ORGANISM: Neisseria meningitidis

<400> SEQUENCE: 114
cgcggatccc atatgaccgt gaagaccgcc                                 30

<210> SEQ ID NO 115
<211> LENGTH: 28
<212> TYPE: DNA
<213> ORGANISM: Neisseria meningitidis

<400> SEQUENCE: 115
cccgctcgag ccactgataa ccgacaga                                   28

<210> SEQ ID NO 116
<211> LENGTH: 34
<212> TYPE: DNA
<213> ORGANISM: Neisseria meningitidis

<400> SEQUENCE: 116
cgcggatccc atatgtattt gaaacagctc caag                            34
```

```
<210> SEQ ID NO 117
<211> LENGTH: 26
<212> TYPE: DNA
<213> ORGANISM: Neisseria meningitidis

<400> SEQUENCE: 117
cccgctcgag ttctgggtga atgtta                                       26

<210> SEQ ID NO 118
<211> LENGTH: 29
<212> TYPE: DNA
<213> ORGANISM: Neisseria meningitidis

<400> SEQUENCE: 118
gcggatccca tatgggcacg gacaaccccc                                   29

<210> SEQ ID NO 119
<211> LENGTH: 26
<212> TYPE: DNA
<213> ORGANISM: Neisseria meningitidis

<400> SEQUENCE: 119
cccgctcgag acgtggggaa cagtct                                       26

<210> SEQ ID NO 120
<211> LENGTH: 34
<212> TYPE: DNA
<213> ORGANISM: Neisseria meningitidis

<400> SEQUENCE: 120
gcggatccca tatgaaaaat attcaagtag ttgc                              34

<210> SEQ ID NO 121
<211> LENGTH: 27
<212> TYPE: DNA
<213> ORGANISM: Neisseria meningitidis

<400> SEQUENCE: 121
cccgctcgag aagtttgatt aaacccg                                      27

<210> SEQ ID NO 122
<211> LENGTH: 31
<212> TYPE: DNA
<213> ORGANISM: Neisseria meningitidis

<400> SEQUENCE: 122
cgcggatccc atatgtgcca accgcaatcc g                                 31

<210> SEQ ID NO 123
<211> LENGTH: 27
<212> TYPE: DNA
<213> ORGANISM: Neisseria meningitidis

<400> SEQUENCE: 123
cccgctcgag tttttccagc tccggca                                      27

<210> SEQ ID NO 124
<211> LENGTH: 33
<212> TYPE: DNA
<213> ORGANISM: Neisseria meningitidis

<400> SEQUENCE: 124
gcggatccca tatggttatc ggaatattac tcg                               33
```

```
<210> SEQ ID NO 125
<211> LENGTH: 25
<212> TYPE: DNA
<213> ORGANISM: Neisseria meningitidis

<400> SEQUENCE: 125
cccgctcgag ggctgcagaa gctgg                                            25

<210> SEQ ID NO 126
<211> LENGTH: 32
<212> TYPE: DNA
<213> ORGANISM: Neisseria meningitidis

<400> SEQUENCE: 126
cgcggatccc atatgcggac gtggttggtt tt                                    32

<210> SEQ ID NO 127
<211> LENGTH: 30
<212> TYPE: DNA
<213> ORGANISM: Neisseria meningitidis

<400> SEQUENCE: 127
cccgctcgag atatcttccg ttttttttcac                                      30

<210> SEQ ID NO 128
<211> LENGTH: 36
<212> TYPE: DNA
<213> ORGANISM: Neisseria meningitidis

<400> SEQUENCE: 128
cgcggatccg ctagcgtaaa tttattattt ttagaa                                36

<210> SEQ ID NO 129
<211> LENGTH: 28
<212> TYPE: DNA
<213> ORGANISM: Neisseria meningitidis

<400> SEQUENCE: 129
cccgctcgag ttccaactca ttgaagta                                         28

<210> SEQ ID NO 130
<211> LENGTH: 35
<212> TYPE: DNA
<213> ORGANISM: Neisseria meningitidis

<400> SEQUENCE: 130
cgcggatccc atatgaataa aggtttacat cgcat                                 35

<210> SEQ ID NO 131
<211> LENGTH: 26
<212> TYPE: DNA
<213> ORGANISM: Neisseria meningitidis

<400> SEQUENCE: 131
cccgctcgag aatcgctgca ccggct                                           26

<210> SEQ ID NO 132
<211> LENGTH: 30
<212> TYPE: DNA
<213> ORGANISM: Neisseria meningitidis

<400> SEQUENCE: 132
cgcggatccc atatgactgc cttttcgaca                                       30
```

<210> SEQ ID NO 133
<211> LENGTH: 26
<212> TYPE: DNA
<213> ORGANISM: Neisseria meningitidis

<400> SEQUENCE: 133
cccgctcgag gcgtgaagcg tcagga                                          26

<210> SEQ ID NO 134
<211> LENGTH: 15
<212> TYPE: DNA
<213> ORGANISM: Artificial Sequence
<220> FEATURE:
<223> OTHER INFORMATION: Description of Artificial Sequence:  BamHI -
      NdeI

<400> SEQUENCE: 134
cgcggatccc atatg                                                      15

<210> SEQ ID NO 135
<211> LENGTH: 15
<212> TYPE: DNA
<213> ORGANISM: Artificial Sequence
<220> FEATURE:
<223> OTHER INFORMATION: Description of Artificial Sequence:  BamHI -
      NheI

<400> SEQUENCE: 135
cgcggatccg ctagc                                                      15

<210> SEQ ID NO 136
<211> LENGTH: 17
<212> TYPE: DNA
<213> ORGANISM: Artificial Sequence
<220> FEATURE:
<223> OTHER INFORMATION: Description of Artificial Sequence:  EcoRI -
      NheI

<400> SEQUENCE: 136
ccggaattct agctagc                                                    17

<210> SEQ ID NO 137
<211> LENGTH: 10
<212> TYPE: DNA
<213> ORGANISM: Artificial Sequence
<220> FEATURE:
<223> OTHER INFORMATION: Description of Artificial Sequence:  XhoI

<400> SEQUENCE: 137
cccgctcgag                                                            10

<210> SEQ ID NO 138
<211> LENGTH: 291
<212> TYPE: PRT
<213> ORGANISM: Artificial Sequence
<220> FEATURE:
<223> OTHER INFORMATION: Description of Artificial Sequence: ORF40a
<220> FEATURE:
<221> NAME/KEY: SITE
<222> LOCATION: (6)
<223> OTHER INFORMATION: place-holder
<220> FEATURE:
<221> NAME/KEY: SITE
<222> LOCATION: (130)
<223> OTHER INFORMATION: place-holder
<220> FEATURE:
<221> NAME/KEY: SITE
<222> LOCATION: (193)
<223> OTHER INFORMATION: place-holder
<220> FEATURE:
<221> NAME/KEY: SITE
<222> LOCATION: (218)
<223> OTHER INFORMATION: place-holder
<220> FEATURE:
<221> NAME/KEY: SITE
<222> LOCATION: (245)
<223> OTHER INFORMATION: place-holder

<400> SEQUENCE: 138

```
Ser Ala Leu Asn Ala Xaa Val Ala Val Ser Glu Leu Thr Arg Asn His
 1               5                  10                  15

Thr Lys Arg Ala Ser Ala Thr Val Lys Thr Ala Val Leu Ala Thr Leu
            20                  25                  30

Leu Phe Ala Thr Val Gln Ala Asn Ala Thr Asp Glu Asp Glu Glu Glu
        35                  40                  45

Glu Leu Glu Ser Val Gln Arg Ser Val Val Gly Ser Ile Gln Ala Ser
    50                  55                  60

Met Glu Gly Ser Gly Glu Leu Glu Thr Ile Ser Leu Ser Met Thr Asn
 65                 70                  75                  80

Asp Ser Lys Glu Phe Val Asp Pro Tyr Ile Val Thr Leu Lys Ala
                85                  90                  95

Gly Asp Asn Leu Lys Ile Lys Gln Asn Thr Glu Asn Thr Asn Ala
                100                 105                 110

Ser Ser Phe Thr Tyr Ser Leu Lys Lys Asp Leu Thr Gly Leu Ile Asn
            115                 120                 125

Val Xaa Thr Glu Lys Leu Ser Phe Gly Ala Asn Gly Lys Lys Val Asn
        130                 135                 140

Ile Ile Ser Asp Thr Lys Gly Leu Asn Phe Ala Lys Glu Thr Ala Gly
145                 150                 155                 160

Thr Asn Gly Asp Thr Thr Val His Leu Asn Gly Ile Gly Ser Thr Leu
                165                 170                 175

Thr Asp Thr Leu Ala Gly Ser Ser Ala Ser His Val Asp Ala Gly Asn
            180                 185                 190

Xaa Ser Thr His Tyr Thr Arg Ala Ala Ser Ile Lys Asp Val Leu Asn
        195                 200                 205

Ala Gly Trp Asn Ile Lys Gly Val Lys Xaa Gly Ser Thr Thr Gly Gln
    210                 215                 220

Ser Glu Asn Val Asp Phe Val Arg Thr Tyr Asp Thr Val Glu Phe Leu
225                 230                 235                 240

Ser Ala Asp Thr Xaa Thr Thr Val Asn Val Glu Ser Lys Asp Asn
                245                 250                 255

Gly Lys Arg Thr Glu Val Lys Ile Gly Ala Lys Thr Ser Val Ile Lys
            260                 265                 270

Glu Lys Asp Gly Lys Leu Val Thr Gly Lys Gly Lys Gly Glu Asn Gly
        275                 280                 285

Ser Ser Thr
    290
```

<210> SEQ ID NO 139
<211> LENGTH: 240
<212> TYPE: PRT
<213> ORGANISM: Artificial Sequence
<220> FEATURE:
<223> OTHER INFORMATION: Description of Artificial Sequence: Hsf

<400> SEQUENCE: 139

```
Thr Leu Leu Phe Ala Thr Val Gln Ala Asn Ala Thr Asp Glu Asp Glu
  1               5                  10                  15

Glu Leu Asp Pro Val Arg Thr Ala Pro Val Leu Ser Phe His Ser
             20                  25                  30

Asp Lys Glu Gly Thr Gly Lys Glu Val Thr Glu Asn Ser Asn Trp
         35                  40                  45

Gly Ile Tyr Phe Asp Asn Lys Gly Val Leu Lys Ala Gly Ala Ile Thr
     50                  55                  60

Leu Lys Ala Gly Asp Asn Leu Lys Ile Lys Gln Asn Thr Asp Glu Ser
 65                  70                  75                  80

Thr Asn Ala Ser Ser Phe Thr Tyr Ser Leu Lys Lys Asp Leu Thr Asp
                 85                  90                  95

Leu Thr Ser Val Ala Thr Glu Lys Leu Ser Phe Gly Ala Asn Gly Asp
                100                 105                 110

Lys Val Asp Ile Thr Ser Asp Ala Asn Gly Leu Lys Leu Ala Lys Thr
                115                 120                 125

Gly Asn Gly Asn Val His Leu Asn Gly Leu Asp Ser Thr Leu Pro Asp
130                 135                 140

Ala Val Thr Asn Thr Gly Val Leu Ser Ser Ser Ser Phe Thr Pro Asn
145                 150                 155                 160

Asp Val Glu Lys Thr Arg Ala Ala Thr Val Lys Asp Val Leu Asn Ala
                165                 170                 175

Gly Trp Asn Ile Lys Gly Ala Lys Thr Ala Gly Gly Asn Val Glu Ser
                180                 185                 190

Val Asp Leu Val Ser Ala Tyr Asn Asn Val Glu Phe Ile Thr Gly Asp
            195                 200                 205

Lys Asn Thr Leu Asp Val Val Leu Thr Ala Lys Glu Asn Gly Lys Thr
        210                 215                 220

Thr Glu Val Lys Phe Thr Pro Lys Thr Ser Val Ile Lys Glu Lys Asp
225                 230                 235                 240

<210> SEQ ID NO 140
<211> LENGTH: 251
<212> TYPE: PRT
<213> ORGANISM: Artificial Sequence
<220> FEATURE:
<223> OTHER INFORMATION: Description of Artificial Sequence: overlap
      identity
<220> FEATURE:
<221> NAME/KEY: SITE
<222> LOCATION: (10)
<223> OTHER INFORMATION: absent or positive
<220> FEATURE:
<221> NAME/KEY: SITE
<222> LOCATION: (12)..(13)
<223> OTHER INFORMATION: absent or positive
<220> FEATURE:
<221> NAME/KEY: SITE
<222> LOCATION: (15)..(16)
<223> OTHER INFORMATION: absent or positive
<220> FEATURE:
<221> NAME/KEY: SITE
<222> LOCATION: (18)..(21)
<223> OTHER INFORMATION: absent or positive
<220> FEATURE:
<221> NAME/KEY: SITE
<222> LOCATION: (26)
<223> OTHER INFORMATION: absent or positive
<220> FEATURE:
<221> NAME/KEY: SITE
<222> LOCATION: (29)..(30)
<223> OTHER INFORMATION: absent or positive
<220> FEATURE:
```

-continued

```
<221> NAME/KEY: SITE
<222> LOCATION: (33)..(35)
<223> OTHER INFORMATION: absent or positive
<220> FEATURE:
<221> NAME/KEY: SITE
<222> LOCATION: (38)..(49)
<223> OTHER INFORMATION: absent or positive
<220> FEATURE:
<221> NAME/KEY: SITE
<222> LOCATION: (52)
<223> OTHER INFORMATION: absent or positive
<220> FEATURE:
<221> NAME/KEY: SITE
<222> LOCATION: (54)..(55)
<223> OTHER INFORMATION: absent or positive
<220> FEATURE:
<221> NAME/KEY: SITE
<222> LOCATION: (58)..(59)
<223> OTHER INFORMATION: absent or positive
<220> FEATURE:
<221> NAME/KEY: SITE
<222> LOCATION: (64)
<223> OTHER INFORMATION: absent or positive
<220> FEATURE:
<221> NAME/KEY: SITE
<222> LOCATION: (66)..(67)
<223> OTHER INFORMATION: absent or positive
<220> FEATURE:
<221> NAME/KEY: SITE
<222> LOCATION: (70)
<223> OTHER INFORMATION: absent or positive
<220> FEATURE:
<221> NAME/KEY: SITE
<222> LOCATION: (82)..(90)
<223> OTHER INFORMATION: absent or positive
<220> FEATURE:
<221> NAME/KEY: SITE
<222> LOCATION: (106)
<223> OTHER INFORMATION: absent or positive
<220> FEATURE:
<221> NAME/KEY: SITE
<222> LOCATION: (113)
<223> OTHER INFORMATION: absent or positive
<220> FEATURE:
<221> NAME/KEY: SITE
<222> LOCATION: (117)
<223> OTHER INFORMATION: absent or positive
<220> FEATURE:
<221> NAME/KEY: SITE
<222> LOCATION: (120)
<223> OTHER INFORMATION: absent or positive
<220> FEATURE:
<221> NAME/KEY: SITE
<222> LOCATION: (125)..(126)
<223> OTHER INFORMATION: absent or positive
<220> FEATURE:
<221> NAME/KEY: SITE
<222> LOCATION: (129)..(130)
<223> OTHER INFORMATION: absent or positive
<220> FEATURE:
<221> NAME/KEY: SITE
<222> LOCATION: (133)..(138)
<223> OTHER INFORMATION: absent or positive
<220> FEATURE:
<221> NAME/KEY: SITE
<222> LOCATION: (140)..(142)
<223> OTHER INFORMATION: absent or positive
<220> FEATURE:
<221> NAME/KEY: SITE
<222> LOCATION: (148)..(149)
<223> OTHER INFORMATION: absent or positive
<220> FEATURE:
<221> NAME/KEY: SITE
<222> LOCATION: (153)
<223> OTHER INFORMATION: absent or positive
<220> FEATURE:
<221> NAME/KEY: SITE
<222> LOCATION: (155)..(157)
<223> OTHER INFORMATION: absent or positive
```

```
<220> FEATURE:
<221> NAME/KEY: SITE
<222> LOCATION: (161)..(173)
<223> OTHER INFORMATION: absent or positive
<220> FEATURE:
<221> NAME/KEY: SITE
<222> LOCATION: (176)
<223> OTHER INFORMATION: absent or positive
<220> FEATURE:
<221> NAME/KEY: SITE
<222> LOCATION: (180)
<223> OTHER INFORMATION: absent or positive
<220> FEATURE:
<221> NAME/KEY: SITE
<222> LOCATION: (194)
<223> OTHER INFORMATION: absent or positive
<220> FEATURE:
<221> NAME/KEY: SITE
<222> LOCATION: (196)..(203)
<223> OTHER INFORMATION: absent or positive
<220> FEATURE:
<221> NAME/KEY: SITE
<222> LOCATION: (206)
<223> OTHER INFORMATION: absent or positive
<220> FEATURE:
<221> NAME/KEY: SITE
<222> LOCATION: (208)..(209)
<223> OTHER INFORMATION: absent or positive
<220> FEATURE:
<221> NAME/KEY: SITE
<222> LOCATION: (211)..(212)
<223> OTHER INFORMATION: absent or positive
<220> FEATURE:
<221> NAME/KEY: SITE
<222> LOCATION: (216)..(218)
<223> OTHER INFORMATION: absent or positive
<220> FEATURE:
<221> NAME/KEY: SITE
<222> LOCATION: (220)..(221)
<223> OTHER INFORMATION: absent or positive
<220> FEATURE:
<221> NAME/KEY: SITE
<222> LOCATION: (223)..(224)
<223> OTHER INFORMATION: absent or positive
<220> FEATURE:
<221> NAME/KEY: SITE
<222> LOCATION: (226)..(229)
<223> OTHER INFORMATION: absent or positive
<220> FEATURE:
<221> NAME/KEY: SITE
<222> LOCATION: (231)
<223> OTHER INFORMATION: absent or positive
<220> FEATURE:
<221> NAME/KEY: SITE
<222> LOCATION: (235)
<223> OTHER INFORMATION: absent or positive
<220> FEATURE:
<221> NAME/KEY: SITE
<222> LOCATION: (240)..(242)
<223> OTHER INFORMATION: absent or positive

<400> SEQUENCE: 140

Thr Leu Leu Phe Ala Thr Val Gln Ala Xaa Ala Xaa Xaa Glu Xaa Xaa
  1               5                  10                  15

Glu Xaa Xaa Xaa Xaa Leu Asp Pro Val Xaa Arg Thr Xaa Xaa Val Leu
             20                  25                  30

Xaa Xaa Xaa Ser Asp Xaa Xaa Xaa Xaa Xaa Xaa Xaa Xaa Xaa Xaa Xaa
         35                  40                  45

Xaa Asn Ser Xaa Trp Xaa Xaa Tyr Phe Xaa Xaa Lys Gly Val Leu Xaa
     50                  55                  60

Ala Xaa Xaa Ile Thr Xaa Lys Ala Gly Asp Asn Leu Lys Ile Lys Gln
 65                  70                  75                  80

Asn Xaa Xaa Xaa Xaa Xaa Xaa Xaa Xaa Xaa Phe Thr Tyr Ser Leu Lys
```

```
                        85                  90                  95

Lys Asp Leu Thr Asp Leu Thr Ser Val Xaa Thr Glu Lys Leu Ser Phe
                    100                 105                 110

Xaa Ala Asn Gly Xaa Lys Val Xaa Ile Thr Ser Asp Xaa Xaa Gly Leu
                115                 120                 125

Xaa Xaa Ala Lys Xaa Xaa Xaa Xaa Xaa Gly Xaa Xaa Xaa Val His
            130                 135                 140

Leu Asn Gly Xaa Xaa Ser Thr Leu Xaa Asp Xaa Xaa Xaa Asn Thr Gly
145                 150                 155                 160

Xaa Xaa Xaa Xaa Xaa Xaa Xaa Xaa Xaa Xaa Xaa Xaa Glu Lys Xaa
                165                 170                 175

Arg Ala Ala Xaa Val Lys Asp Val Leu Asn Ala Gly Trp Asn Ile Lys
                180                 185                 190

Gly Xaa Lys Xaa Xaa Xaa Xaa Xaa Xaa Xaa Val Asp Xaa Val Xaa
                195                 200                 205

Xaa Tyr Xaa Xaa Val Glu Phe Xaa Xaa Xaa Asp Xaa Xaa Thr Xaa Xaa
                210                 215                 220

Val Xaa Xaa Xaa Xaa Lys Xaa Asn Gly Lys Xaa Thr Glu Val Lys Xaa
225                 230                 235                 240

Xaa Xaa Lys Thr Ser Val Ile Lys Glu Lys Asp
                245                 250

<210> SEQ ID NO 141
<211> LENGTH: 36
<212> TYPE: PRT
<213> ORGANISM: Artificial Sequence
<220> FEATURE:
<223> OTHER INFORMATION: Description of Artificial Sequence: ORF40a

<400> SEQUENCE: 141

Val Ala Val Ser Glu Leu Thr Arg Asn His Thr Lys Arg Ala Ser Ala
  1               5                  10                  15

Thr Val Lys Thr Ala Val Leu Ala Thr Leu Leu Phe Ala Thr Val Gln
            20                  25                  30

Ala Asn Ala Thr
        35

<210> SEQ ID NO 142
<211> LENGTH: 36
<212> TYPE: PRT
<213> ORGANISM: Artificial Sequence
<220> FEATURE:
<223> OTHER INFORMATION: Description of Artificial Sequence: homology
<220> FEATURE:
<221> NAME/KEY: SITE
<222> LOCATION: (2)
<223> OTHER INFORMATION: absent or positive
<220> FEATURE:
<221> NAME/KEY: SITE
<222> LOCATION: (9)
<223> OTHER INFORMATION: absent or positive
<220> FEATURE:
<221> NAME/KEY: SITE
<222> LOCATION: (19)
<223> OTHER INFORMATION: absent or positive

<400> SEQUENCE: 142

Val Xaa Val Ser Glu Leu Thr Arg Xaa His Thr Lys Arg Ala Ser Ala
  1               5                  10                  15

Thr Val Xaa Thr Ala Val Leu Ala Thr Leu Leu Phe Ala Thr Val Gln
            20                  25                  30
```

```
Ala Asn Ala Thr
        35

<210> SEQ ID NO 143
<211> LENGTH: 36
<212> TYPE: PRT
<213> ORGANISM: Artificial Sequence
<220> FEATURE:
<223> OTHER INFORMATION: Description of Artificial Sequence: Hsf

<400> SEQUENCE: 143

Val Val Val Ser Glu Leu Thr Arg Thr His Thr Lys Arg Ala Ser Ala
  1               5                  10                  15

Thr Val Glu Thr Ala Val Leu Ala Thr Leu Leu Phe Ala Thr Val Gln
             20                  25                  30

Ala Asn Ala Thr
        35

<210> SEQ ID NO 144
<211> LENGTH: 38
<212> TYPE: PRT
<213> ORGANISM: Artificial Sequence
<220> FEATURE:
<223> OTHER INFORMATION: Description of Artificial Sequence: Orf40a

<400> SEQUENCE: 144

Val Thr Leu Lys Ala Gly Asp Asn Leu Lys Ile Lys Gln Asn Thr Asn
  1               5                  10                  15

Glu Asn Thr Asn Ala Ser Ser Phe Thr Tyr Ser Leu Lys Lys Asp Leu
             20                  25                  30

Thr Gly Leu Ile Asn Val
        35

<210> SEQ ID NO 145
<211> LENGTH: 38
<212> TYPE: PRT
<213> ORGANISM: Artificial Sequence
<220> FEATURE:
<223> OTHER INFORMATION: Description of Artificial Sequence: homology
<220> FEATURE:
<221> NAME/KEY: SITE
<222> LOCATION: (1)
<223> OTHER INFORMATION: absent or positive
<220> FEATURE:
<221> NAME/KEY: SITE
<222> LOCATION: (16)
<223> OTHER INFORMATION: absent or positive
<220> FEATURE:
<221> NAME/KEY: SITE
<222> LOCATION: (18)
<223> OTHER INFORMATION: absent or positive
<220> FEATURE:
<221> NAME/KEY: SITE
<222> LOCATION: (34)
<223> OTHER INFORMATION: absent or positive
<220> FEATURE:
<221> NAME/KEY: SITE
<222> LOCATION: (36)..(37)
<223> OTHER INFORMATION: absent or positive

<400> SEQUENCE: 145

Xaa Thr Leu Lys Ala Gly Asp Asn Leu Lys Ile Lys Gln Asn Thr Xaa
  1               5                  10                  15

Glu Xaa Thr Asn Ala Ser Ser Phe Thr Tyr Ser Leu Lys Lys Asp Leu
             20                  25                  30

Thr Xaa Leu Xaa Xaa Val
        35
```

```
<210> SEQ ID NO 146
<211> LENGTH: 38
<212> TYPE: PRT
<213> ORGANISM: Artificial Sequence
<220> FEATURE:
<223> OTHER INFORMATION: Description of Artificial Sequence: Hsf

<400> SEQUENCE: 146

Ile Thr Leu Lys Ala Gly Asp Asn Leu Lys Ile Lys Gln Asn Thr Asp
 1               5                  10                  15

Glu Ser Thr Asn Ala Ser Ser Phe Thr Tyr Ser Leu Lys Asp Leu
            20                  25                  30

Thr Asp Leu Thr Ser Val
        35

<210> SEQ ID NO 147
<211> LENGTH: 29
<212> TYPE: PRT
<213> ORGANISM: Artificial Sequence
<220> FEATURE:
<223> OTHER INFORMATION: Description of Artificial Sequence: Orf40a

<400> SEQUENCE: 147

Val Thr Glu Lys Leu Ser Phe Gly Ala Asn Gly Lys Lys Val Asn Ile
 1               5                  10                  15

Ile Ser Asp Thr Lys Gly Leu Asn Phe Ala Lys Glu Thr
            20                  25

<210> SEQ ID NO 148
<211> LENGTH: 29
<212> TYPE: PRT
<213> ORGANISM: Artificial Sequence
<220> FEATURE:
<223> OTHER INFORMATION: Description of Artificial Sequence: homology
<220> FEATURE:
<221> NAME/KEY: SITE
<222> LOCATION: (2)..(3)
<223> OTHER INFORMATION: absent or positive
<220> FEATURE:
<221> NAME/KEY: SITE
<222> LOCATION: (7)
<223> OTHER INFORMATION: absent or positive
<220> FEATURE:
<221> NAME/KEY: SITE
<222> LOCATION: (9)
<223> OTHER INFORMATION: absent or positive
<220> FEATURE:
<221> NAME/KEY: SITE
<222> LOCATION: (12)
<223> OTHER INFORMATION: absent or positive
<220> FEATURE:
<221> NAME/KEY: SITE
<222> LOCATION: (17)
<223> OTHER INFORMATION: absent or positive
<220> FEATURE:
<221> NAME/KEY: SITE
<222> LOCATION: (28)..(29)
<223> OTHER INFORMATION: absent or positive

<400> SEQUENCE: 148

Val Xaa Xaa Lys Leu Ser Xaa Gly Xaa Asn Gly Xaa Lys Val Asn Ile
 1               5                  10                  15

Xaa Ser Asp Thr Lys Gly Leu Asn Phe Ala Lys Xaa Xaa
            20                  25

<210> SEQ ID NO 149
<211> LENGTH: 29
```

```
<212> TYPE: PRT
<213> ORGANISM: Artificial Sequence
<220> FEATURE:
<223> OTHER INFORMATION: Description of Artificial Sequence: Hsf

<400> SEQUENCE: 149

Val Ser Asp Lys Leu Ser Leu Gly Thr Asn Gly Asn Lys Val Asn Ile
1               5                   10                  15

Thr Ser Asp Thr Lys Gly Leu Asn Phe Ala Lys Asp Ser
            20                  25

<210> SEQ ID NO 150
<211> LENGTH: 32
<212> TYPE: PRT
<213> ORGANISM: Artificial Sequence
<220> FEATURE:
<223> OTHER INFORMATION: Description of Artificial Sequence: ORF40a

<400> SEQUENCE: 150

Thr Asn Gly Asp Thr Thr Val His Leu Asn Gly Ile Gly Ser Thr Leu
1               5                   10                  15

Thr Asp Thr Leu Ala Gly Ser Ser Ala Ser His Val Asp Ala Gly Asn
            20                  25                  30

<210> SEQ ID NO 151
<211> LENGTH: 32
<212> TYPE: PRT
<213> ORGANISM: Artificial Sequence
<220> FEATURE:
<223> OTHER INFORMATION: Description of Artificial Sequence: homology
<220> FEATURE:
<221> NAME/KEY: SITE
<222> LOCATION: (2)..(3)
<223> OTHER INFORMATION: absent or positive
<220> FEATURE:
<221> NAME/KEY: SITE
<222> LOCATION: (5)..(7)
<223> OTHER INFORMATION: absent or positive
<220> FEATURE:
<221> NAME/KEY: SITE
<222> LOCATION: (13)
<223> OTHER INFORMATION: absent or positive
<220> FEATURE:
<221> NAME/KEY: SITE
<222> LOCATION: (21)..(22)
<223> OTHER INFORMATION: absent or positive
<220> FEATURE:
<221> NAME/KEY: SITE
<222> LOCATION: (24)
<223> OTHER INFORMATION: absent or positive
<220> FEATURE:
<221> NAME/KEY: SITE
<222> LOCATION: (26)..(30)
<223> OTHER INFORMATION: absent or positive

<400> SEQUENCE: 151

Thr Xaa Xaa Asp Xaa Xaa Xaa His Leu Asn Gly Ile Xaa Ser Thr Leu
1               5                   10                  15

Thr Asp Thr Leu Xaa Xaa Ser Xaa Ala Xaa Xaa Xaa Xaa Xaa Gly Asn
            20                  25                  30

<210> SEQ ID NO 152
<211> LENGTH: 32
<212> TYPE: PRT
<213> ORGANISM: Artificial Sequence
<220> FEATURE:
<223> OTHER INFORMATION: Description of Artificial Sequence: Hsf

<400> SEQUENCE: 152
```

Thr Gly Asp Asp Ala Asn Ile His Leu Asn Gly Ile Ala Ser Thr Leu
 1               5                  10                  15

Thr Asp Thr Leu Leu Asn Ser Gly Ala Thr Thr Asn Leu Gly Gly Asn
                20                  25                  30

<210> SEQ ID NO 153
<211> LENGTH: 19
<212> TYPE: PRT
<213> ORGANISM: Artificial Sequence
<220> FEATURE:
<223> OTHER INFORMATION: Description of Artificial Sequence: ORF40a

<400> SEQUENCE: 153

Arg Ala Ala Ser Ile Lys Asp Val Leu Asn Ala Gly Trp Asn Ile Lys
 1               5                  10                  15

Gly Val Lys

<210> SEQ ID NO 154
<211> LENGTH: 19
<212> TYPE: PRT
<213> ORGANISM: Artificial Sequence
<220> FEATURE:
<223> OTHER INFORMATION: Description of Artificial Sequence: homology
<220> FEATURE:
<221> NAME/KEY: SITE
<222> LOCATION: (5)
<223> OTHER INFORMATION: absent or positive
<220> FEATURE:
<221> NAME/KEY: SITE
<222> LOCATION: (15)..(16)
<223> OTHER INFORMATION: absent or positive

<400> SEQUENCE: 154

Arg Ala Ala Ser Xaa Lys Asp Val Leu Asn Ala Gly Trp Asn Xaa Xaa
 1               5                  10                  15

Gly Val Lys

<210> SEQ ID NO 155
<211> LENGTH: 19
<212> TYPE: PRT
<213> ORGANISM: Artificial Sequence
<220> FEATURE:
<223> OTHER INFORMATION: Description of Artificial Sequence: Hsf

<400> SEQUENCE: 155

Arg Ala Ala Ser Val Lys Asp Val Leu Asn Ala Gly Trp Asn Val Arg
 1               5                  10                  15

Gly Val Lys

<210> SEQ ID NO 156
<211> LENGTH: 28
<212> TYPE: PRT
<213> ORGANISM: Artificial Sequence
<220> FEATURE:
<223> OTHER INFORMATION: Description of Artificial Sequence: ORF40a

<400> SEQUENCE: 156

Ser Thr Thr Gly Gln Ser Glu Asn Val Asp Phe Val Arg Thr Tyr Asp
 1               5                  10                  15

Thr Val Glu Phe Leu Ser Ala Asp Thr Thr Thr Thr
                20                  25

<210> SEQ ID NO 157
<211> LENGTH: 28
<212> TYPE: PRT

```
<213> ORGANISM: Artificial Sequence
<220> FEATURE:
<223> OTHER INFORMATION: Description of Artificial Sequence: homology
<220> FEATURE:
<221> NAME/KEY: SITE
<222> LOCATION: (2)..(4)
<223> OTHER INFORMATION: absent or positive
<220> FEATURE:
<221> NAME/KEY: SITE
<222> LOCATION: (6)
<223> OTHER INFORMATION: absent or positive
<220> FEATURE:
<221> NAME/KEY: SITE
<222> LOCATION: (9)
<223> OTHER INFORMATION: absent or positive
<220> FEATURE:
<221> NAME/KEY: SITE
<222> LOCATION: (13)
<223> OTHER INFORMATION: absent or positive
<220> FEATURE:
<221> NAME/KEY: SITE
<222> LOCATION: (19)
<223> OTHER INFORMATION: absent or positive
<220> FEATURE:
<221> NAME/KEY: SITE
<222> LOCATION: (21)
<223> OTHER INFORMATION: absent or positive
<220> FEATURE:
<221> NAME/KEY: SITE
<222> LOCATION: (23)
<223> OTHER INFORMATION: absent or positive
<220> FEATURE:
<221> NAME/KEY: SITE
<222> LOCATION: (25)..(26)
<223> OTHER INFORMATION: absent or positive

<400> SEQUENCE: 157

Ser Xaa Xaa Xaa Gln Xaa Glu Asn Xaa Asp Phe Val Xaa Thr Tyr Asp
 1               5                  10                  15

Thr Val Xaa Phe Xaa Ser Xaa Asp Xaa Xaa Thr Thr
            20                  25

<210> SEQ ID NO 158
<211> LENGTH: 28
<212> TYPE: PRT
<213> ORGANISM: Artificial Sequence
<220> FEATURE:
<223> OTHER INFORMATION: Description of Artificial Sequence: Hsf

<400> SEQUENCE: 158

Ser Ala Asn Asn Gln Val Glu Asn Ile Asp Phe Val Ala Thr Tyr Asp
 1               5                  10                  15

Thr Val Asp Phe Val Ser Gly Asp Lys Asp Thr Thr
            20                  25

<210> SEQ ID NO 159
<211> LENGTH: 240
<212> TYPE: PRT
<213> ORGANISM: Artificial Sequence
<220> FEATURE:
<223> OTHER INFORMATION: Description of Artificial Sequence: ORF38a

<400> SEQUENCE: 159

Met Leu Arg Leu Thr Ala Leu Ala Val Cys Thr Ala Leu Ala Leu Gly
 1               5                  10                  15

Ala Cys Ser Pro Gln Asn Ser Asp Ser Ala Pro Gln Ala Lys Glu Gln
            20                  25                  30

Ala Val Ser Ala Ala Gln Ser Glu Gly Val Ser Val Thr Val Lys Thr
        35                  40                  45
```

```
Ala Arg Gly Asp Val Gln Ile Pro Gln Asn Pro Glu Arg Ile Ala Val
        50                  55                  60

Tyr Asp Leu Gly Met Leu Asp Thr Leu Ser Lys Leu Gly Val Lys Thr
 65                  70                  75                  80

Gly Leu Ser Val Asp Lys Asn Arg Leu Pro Tyr Leu Glu Glu Tyr Phe
                 85                  90                  95

Lys Thr Thr Lys Pro Ala Gly Thr Leu Phe Glu Pro Asp Tyr Glu Thr
            100                 105                 110

Leu Asn Ala Tyr Lys Pro Gln Leu Ile Ile Ile Gly Ser Arg Ala Ala
            115                 120                 125

Lys Ala Phe Asp Lys Leu Asn Glu Ile Ala Pro Thr Ile Glu Met Thr
130                 135                 140

Ala Asp Thr Ala Asn Leu Lys Glu Ser Ala Lys Glu Arg Ile Asp Ala
145                 150                 155                 160

Leu Ala Gln Ile Phe Gly Lys Lys Ala Glu Ala Asp Lys Leu Lys Ala
                165                 170                 175

Glu Ile Asp Ala Ser Phe Glu Ala Ala Lys Thr Ala Ala Gln Gly Lys
            180                 185                 190

Gly Lys Gly Leu Val Ile Leu Val Asn Gly Gly Lys Met Ser Ala Phe
        195                 200                 205

Gly Pro Ser Ser Arg Leu Gly Gly Trp Leu His Lys Asp Ile Gly Val
210                 215                 220

Pro Ala Val Asp Glu Ala Ile Lys Glu Gly Ser His Gly Gln Pro Ile
225                 230                 235                 240

<210> SEQ ID NO 160
<211> LENGTH: 94
<212> TYPE: PRT
<213> ORGANISM: Artificial Sequence
<220> FEATURE:
<223> OTHER INFORMATION: Description of Artificial Sequence: ORF38

<400> SEQUENCE: 160

Glu Gly Ala Ser Val Thr Val Lys Thr Ala Arg Gly Asp Val Gln Ile
 1               5                  10                  15

Pro Gln Asn Pro Glu Arg Ile Ala Val Tyr Asp Leu Gly Met Leu Asp
            20                  25                  30

Thr Leu Ser Lys Leu Gly Val Lys Thr Gly Leu Ser Val Asp Lys Asn
        35                  40                  45

Arg Leu Pro Tyr Leu Glu Glu Tyr Phe Lys Thr Thr Lys Pro Ala Gly
    50                  55                  60

Thr Leu Phe Glu Pro Asp Tyr Glu Thr Leu Asn Ala Tyr Lys Pro Gln
 65                  70                  75                  80

Leu Ile Ile Ile Gly Ser Arg Ala Ala Lys Ala Phe Asp Lys
                85                  90

<210> SEQ ID NO 161
<211> LENGTH: 96
<212> TYPE: PRT
<213> ORGANISM: Artificial Sequence
<220> FEATURE:
<223> OTHER INFORMATION: Description of Artificial Sequence: overlap
      identity
<220> FEATURE:
<221> NAME/KEY: SITE
<222> LOCATION: (3)
<223> OTHER INFORMATION: absent or positive
<220> FEATURE:
<221> NAME/KEY: SITE
<222> LOCATION: (5)..(6)
```

```
<223> OTHER INFORMATION: absent or positive
<220> FEATURE:
<221> NAME/KEY: SITE
<222> LOCATION: (9)..(11)
<223> OTHER INFORMATION: absent or positive
<220> FEATURE:
<221> NAME/KEY: SITE
<222> LOCATION: (13)..(16)
<223> OTHER INFORMATION: absent or positive
<220> FEATURE:
<221> NAME/KEY: SITE
<222> LOCATION: (18)
<223> OTHER INFORMATION: absent or positive
<220> FEATURE:
<221> NAME/KEY: SITE
<222> LOCATION: (21)..(26)
<223> OTHER INFORMATION: absent or positive
<220> FEATURE:
<221> NAME/KEY: SITE
<222> LOCATION: (30)
<223> OTHER INFORMATION: absent or positive
<220> FEATURE:
<221> NAME/KEY: SITE
<222> LOCATION: (34)..(36)
<223> OTHER INFORMATION: absent or positive
<220> FEATURE:
<221> NAME/KEY: SITE
<222> LOCATION: (38)..(45)
<223> OTHER INFORMATION: absent or positive
<220> FEATURE:
<221> NAME/KEY: SITE
<222> LOCATION: (47)..(50)
<223> OTHER INFORMATION: absent or positive
<220> FEATURE:
<221> NAME/KEY: SITE
<222> LOCATION: (53)..(57)
<223> OTHER INFORMATION: absent or positive
<220> FEATURE:
<221> NAME/KEY: SITE
<222> LOCATION: (60)..(64)
<223> OTHER INFORMATION: absent or positive
<220> FEATURE:
<221> NAME/KEY: SITE
<222> LOCATION: (66)..(70)
<223> OTHER INFORMATION: absent or positive
<220> FEATURE:
<221> NAME/KEY: SITE
<222> LOCATION: (72)
<223> OTHER INFORMATION: absent or positive
<220> FEATURE:
<221> NAME/KEY: SITE
<222> LOCATION: (74)..(75)
<223> OTHER INFORMATION: absent or positive
<220> FEATURE:
<221> NAME/KEY: SITE
<222> LOCATION: (78)
<223> OTHER INFORMATION: absent or positive
<220> FEATURE:
<221> NAME/KEY: SITE
<222> LOCATION: (81)
<223> OTHER INFORMATION: absent or positive
<220> FEATURE:
<221> NAME/KEY: SITE
<222> LOCATION: (86)..(87)
<223> OTHER INFORMATION: absent or positive
<220> FEATURE:
<221> NAME/KEY: SITE
<222> LOCATION: (89)..(90)
<223> OTHER INFORMATION: absent or positive
<220> FEATURE:
<221> NAME/KEY: SITE
<222> LOCATION: (92)..(93)
<223> OTHER INFORMATION: absent or positive

<400> SEQUENCE: 161

Glu Gly Xaa Ser Xaa Xaa Val Lys Xaa Xaa Xaa Gly Xaa Xaa Xaa Xaa
  1               5                  10                  15
```

```
Pro Xaa Asn Pro Xaa Xaa Xaa Xaa Xaa Asp Leu Gly Xaa Leu Asp
            20                  25                  30

Thr Xaa Xaa Leu Xaa Xaa Xaa Xaa Xaa Xaa Xaa Val Xaa Xaa
        35                  40                  45

Xaa Xaa Leu Pro Xaa Xaa Xaa Xaa Phe Lys Xaa Xaa Xaa Xaa
 50                  55                  60

Gly Xaa Xaa Xaa Xaa Asp Xaa Glu Xaa Xaa Asn Ala Xaa Lys Pro
 65                  70                  75                  80

Xaa Leu Ile Ile Ile Xaa Xaa Arg Xaa Xaa Lys Xaa Xaa Asp Lys Leu
                85                  90                  95

<210> SEQ ID NO 162
<211> LENGTH: 96
<212> TYPE: PRT
<213> ORGANISM: Artificial Sequence
<220> FEATURE:
<223> OTHER INFORMATION: Description of Artificial Sequence: Lipo

<400> SEQUENCE: 162

Glu Gly Asp Ser Phe Leu Val Lys Asp Ser Leu Gly Glu Asn Lys Thr
 1               5                  10                  15

Pro Lys Asn Pro Ser Lys Val Val Ile Leu Asp Leu Gly Ile Leu Asp
            20                  25                  30

Thr Phe Asp Ala Leu Lys Leu Asn Asp Lys Val Ala Gly Val Pro Ala
        35                  40                  45

Lys Asn Leu Pro Lys Tyr Leu Gln Gln Phe Lys Asn Lys Pro Ser Val
 50                  55                  60

Gly Gly Val Gln Gln Val Asp Phe Glu Ala Ile Asn Ala Leu Lys Pro
 65                  70                  75                  80

Asp Leu Ile Ile Ile Ser Gly Arg Gln Ser Lys Phe Tyr Asp Lys Leu
                85                  90                  95

<210> SEQ ID NO 163
<211> LENGTH: 91
<212> TYPE: PRT
<213> ORGANISM: Artificial Sequence
<220> FEATURE:
<223> OTHER INFORMATION: Description of Artificial Sequence: ORF44

<400> SEQUENCE: 163

Thr Val Ser Tyr Val Cys Gln Gln Gly Lys Lys Val Lys Val Thr Tyr
 1               5                  10                  15

Gly Phe Asn Lys Gln Gly Leu Thr Thr Tyr Ala Ser Ala Val Ile Asn
            20                  25                  30

Gly Lys Arg Val Gln Met Pro Val Asn Leu Asp Lys Ser Asp Asn Val
        35                  40                  45

Glu Thr Phe Tyr Gly Lys Glu Gly Gly Tyr Val Leu Gly Thr Gly Val
 50                  55                  60

Met Asp Gly Lys Ser Tyr Arg Lys Gln Pro Ile Met Ile Thr Ala Pro
 65                  70                  75                  80

Asp Asn Gln Ile Val Phe Lys Asp Cys Ser Pro
                85                  90

<210> SEQ ID NO 164
<211> LENGTH: 91
<212> TYPE: PRT
<213> ORGANISM: Artificial Sequence
<220> FEATURE:
<223> OTHER INFORMATION: Description of Artificial Sequence: overlap
      identity
```

```
<220> FEATURE:
<221> NAME/KEY: SITE
<222> LOCATION: (1)
<223> OTHER INFORMATION: absent or positive
<220> FEATURE:
<221> NAME/KEY: SITE
<222> LOCATION: (3)
<223> OTHER INFORMATION: absent or positive
<220> FEATURE:
<221> NAME/KEY: SITE
<222> LOCATION: (10)..(13)
<223> OTHER INFORMATION: absent or positive
<220> FEATURE:
<221> NAME/KEY: SITE
<222> LOCATION: (15)
<223> OTHER INFORMATION: absent or positive
<220> FEATURE:
<221> NAME/KEY: SITE
<222> LOCATION: (17)
<223> OTHER INFORMATION: absent or positive
<220> FEATURE:
<221> NAME/KEY: SITE
<222> LOCATION: (20)..(21)
<223> OTHER INFORMATION: absent or positive
<220> FEATURE:
<221> NAME/KEY: SITE
<222> LOCATION: (23)..(24)
<223> OTHER INFORMATION: absent or positive
<220> FEATURE:
<221> NAME/KEY: SITE
<222> LOCATION: (26)
<223> OTHER INFORMATION: absent or positive
<220> FEATURE:
<221> NAME/KEY: SITE
<222> LOCATION: (28)..(31)
<223> OTHER INFORMATION: absent or positive
<220> FEATURE:
<221> NAME/KEY: SITE
<222> LOCATION: (33)..(38)
<223> OTHER INFORMATION: absent or positive
<220> FEATURE:
<221> NAME/KEY: SITE
<222> LOCATION: (40)
<223> OTHER INFORMATION: absent or positive
<220> FEATURE:
<221> NAME/KEY: SITE
<222> LOCATION: (43)..(44)
<223> OTHER INFORMATION: absent or positive
<220> FEATURE:
<221> NAME/KEY: SITE
<222> LOCATION: (49)
<223> OTHER INFORMATION: absent or positive
<220> FEATURE:
<221> NAME/KEY: SITE
<222> LOCATION: (51)..(56)
<223> OTHER INFORMATION: absent or positive
<220> FEATURE:
<221> NAME/KEY: SITE
<222> LOCATION: (59)
<223> OTHER INFORMATION: absent or positive
<220> FEATURE:
<221> NAME/KEY: SITE
<222> LOCATION: (61)
<223> OTHER INFORMATION: absent or positive
<220> FEATURE:
<221> NAME/KEY: SITE
<222> LOCATION: (63)..(64)
<223> OTHER INFORMATION: absent or positive
<220> FEATURE:
<221> NAME/KEY: SITE
<222> LOCATION: (67)..(69)
<223> OTHER INFORMATION: absent or positive
<220> FEATURE:
<221> NAME/KEY: SITE
<222> LOCATION: (72)
<223> OTHER INFORMATION: absent or positive
<220> FEATURE:
<221> NAME/KEY: SITE
<222> LOCATION: (74)
```

<223> OTHER INFORMATION: absent or positive
<220> FEATURE:
<221> NAME/KEY: SITE
<222> LOCATION: (76)..(78)
<223> OTHER INFORMATION: absent or positive
<220> FEATURE:
<221> NAME/KEY: SITE
<222> LOCATION: (81)..(82)
<223> OTHER INFORMATION: absent or positive
<220> FEATURE:
<221> NAME/KEY: SITE
<222> LOCATION: (84)..(86)
<223> OTHER INFORMATION: absent or positive

<400> SEQUENCE: 164

Xaa Val Xaa Tyr Val Cys Gln Gln Gly Xaa Xaa Xaa Xaa Val Xaa Tyr
1               5                   10                  15

Xaa Phe Asn Xaa Xaa Gly Xaa Xaa Thr Xaa Ala Xaa Xaa Xaa Xaa Asn
            20                  25                  30

Xaa Xaa Xaa Xaa Xaa Xaa Pro Xaa Asn Leu Xaa Xaa Ser Asp Asn Val
        35                  40                  45

Xaa Thr Xaa Xaa Xaa Xaa Xaa Xaa Gly Tyr Xaa Leu Xaa Thr Xaa Xaa
    50                  55                  60

Met Asp Xaa Xaa Xaa Tyr Arg Xaa Gln Xaa Ile Xaa Xaa Xaa Ala Pro
65                  70                  75                  80

Xaa Xaa Gln Xaa Xaa Xaa Lys Asp Cys Ser Pro
                85                  90

<210> SEQ ID NO 165
<211> LENGTH: 90
<212> TYPE: PRT
<213> ORGANISM: Artificial Sequence
<220> FEATURE:
<223> OTHER INFORMATION: Description of Artificial Sequence: LecA

<400> SEQUENCE: 165

Ser Val Ala Tyr Val Cys Gln Gln Gly Arg Arg Leu Asn Val Asn Tyr
1               5                   10                  15

Arg Phe Asn Ser Ala Gly Val Pro Thr Ser Ala Glu Leu Arg Val Asn
            20                  25                  30

Asn Arg Asn Leu Arg Leu Pro Tyr Asn Leu Ser Ala Ser Asp Asn Val
        35                  40                  45

Asp Thr Val Phe Ser Ala Asn Gly Tyr Arg Leu Thr Thr Asn Ala Met
    50                  55                  60

Asp Ser Ala Asn Tyr Arg Ser Gln Asp Ile Ile Val Ser Ala Pro Asn
65                  70                  75                  80

Gly Gln Met Leu Tyr Lys Asp Cys Ser Pro
                85                  90

<210> SEQ ID NO 166
<211> LENGTH: 240
<212> TYPE: PRT
<213> ORGANISM: Artificial Sequence
<220> FEATURE:
<223> OTHER INFORMATION: Description of Artificial Sequence: ORF49a
<220> FEATURE:
<221> NAME/KEY: SITE
<222> LOCATION: (18)
<223> OTHER INFORMATION: place-holder
<220> FEATURE:
<221> NAME/KEY: SITE
<222> LOCATION: (48)
<223> OTHER INFORMATION: place-holder
<220> FEATURE:
<221> NAME/KEY: SITE

```
<222> LOCATION: (195)
<223> OTHER INFORMATION: place-holder

<400> SEQUENCE: 166

Ser Lys Asn Glu Leu Asn Glu Thr Lys Leu Pro Val Arg Val Ala
 1               5                  10                  15

Gln Xaa Ala Ala Thr Arg Ser Gly Trp Asp Thr Val Leu Glu Gly Thr
            20                  25                  30

Glu Phe Lys Thr Thr Leu Ala Gly Ala Asp Ile Gln Ala Gly Val Xaa
        35                  40                  45

Glu Lys Ala Arg Val Asp Ala Lys Ile Ile Leu Lys Gly Ile Val Asn
 50                  55                  60

Arg Ile Gln Ser Glu Glu Lys Leu Glu Thr Asn Ser Thr Val Trp Gln
 65                  70                  75                  80

Lys Gln Ala Gly Arg Gly Ser Thr Ile Glu Thr Leu Lys Leu Pro Ser
                85                  90                  95

Phe Glu Ser Pro Thr Pro Pro Lys Leu Ser Ala Pro Gly Gly Tyr Ile
            100                 105                 110

Val Asp Ile Pro Lys Gly Asn Leu Lys Thr Glu Ile Glu Lys Leu Ser
        115                 120                 125

Lys Gln Pro Glu Tyr Ala Tyr Leu Lys Gln Leu Gln Val Ala Lys Asn
130                 135                 140

Ile Asn Trp Asn Gln Val Gln Leu Ala Tyr Asp Arg Trp Asp Tyr Lys
145                 150                 155                 160

Gln Glu Gly Leu Thr Glu Ala Gly Ala Ile Ile Ala Leu Ala Val
                165                 170                 175

Thr Val Val Thr Ser Gly Ala Gly Thr Gly Ala Val Leu Gly Leu Asn
            180                 185                 190

Gly Ala Xaa Ala Ala Ala Thr Asp Ala Ala Phe Ala Ser Leu Ala Ser
            195                 200                 205

Gln Ala Ser Val Ser Phe Ile Asn Asn Lys Gly Asp Val Gly Lys Thr
        210                 215                 220

Leu Lys Glu Leu Gly Arg Ser Ser Thr Val Lys Asn Leu Val Val Ala
225                 230                 235                 240

<210> SEQ ID NO 167
<211> LENGTH: 540
<212> TYPE: PRT
<213> ORGANISM: Artificial Sequence
<220> FEATURE:
<223> OTHER INFORMATION: Description of Artificial Sequence: ORF49a
<220> FEATURE:
<221> NAME/KEY: SITE
<222> LOCATION: (1)
<223> OTHER INFORMATION: place-holder
<220> FEATURE:
<221> NAME/KEY: SITE
<222> LOCATION: (29)
<223> OTHER INFORMATION: place-holder
<220> FEATURE:
<221> NAME/KEY: SITE
<222> LOCATION: (50)
<223> OTHER INFORMATION: place-holder
<220> FEATURE:
<221> NAME/KEY: SITE
<222> LOCATION: (80)
<223> OTHER INFORMATION: place-holder
<220> FEATURE:
<221> NAME/KEY: SITE
<222> LOCATION: (227)
<223> OTHER INFORMATION: place-holder
<220> FEATURE:
<221> NAME/KEY: SITE
```

```
<222> LOCATION: (288)
<223> OTHER INFORMATION: place-holder
<220> FEATURE:
<221> NAME/KEY: SITE
<222> LOCATION: (324)
<223> OTHER INFORMATION: place-holder
<220> FEATURE:
<221> NAME/KEY: SITE
<222> LOCATION: (446)
<223> OTHER INFORMATION: place-holder
<220> FEATURE:
<221> NAME/KEY: SITE
<222> LOCATION: (463)
<223> OTHER INFORMATION: place-holder

<400> SEQUENCE: 167

Xaa Gln Leu Leu Ala Glu Glu Gly Ile His Lys His Glu Leu Asp Val
 1               5                  10                  15

Gln Lys Ser Arg Arg Phe Ile Gly Ile Lys Val Gly Xaa Ser Asn Tyr
             20                  25                  30

Ser Lys Asn Glu Leu Asn Glu Thr Lys Leu Pro Val Arg Val Val Ala
         35                  40                  45

Gln Xaa Ala Ala Thr Arg Ser Gly Trp Asp Thr Val Leu Glu Gly Thr
     50                  55                  60

Glu Phe Lys Thr Thr Leu Ala Gly Ala Asp Ile Gln Ala Gly Val Xaa
 65                  70                  75                  80

Glu Lys Ala Arg Val Asp Ala Lys Ile Ile Leu Lys Gly Ile Val Asn
                 85                  90                  95

Arg Ile Gln Ser Glu Lys Leu Glu Thr Asn Ser Thr Val Trp Gln
            100                 105                 110

Lys Gln Ala Gly Arg Gly Ser Thr Ile Glu Thr Leu Lys Leu Pro Ser
            115                 120                 125

Phe Glu Ser Pro Thr Pro Lys Leu Ser Ala Pro Gly Gly Tyr Ile
130                 135                 140

Val Asp Ile Pro Lys Gly Asn Leu Lys Thr Glu Ile Glu Lys Leu Ser
145                 150                 155                 160

Lys Gln Pro Glu Tyr Ala Tyr Leu Lys Gln Leu Gln Val Ala Lys Asn
                165                 170                 175

Ile Asn Trp Asn Gln Val Gln Leu Ala Tyr Asp Arg Trp Asp Tyr Lys
            180                 185                 190

Gln Glu Gly Leu Thr Glu Ala Gly Ala Ile Ile Ala Leu Ala Val
            195                 200                 205

Thr Val Val Thr Ser Gly Ala Gly Thr Gly Ala Val Leu Gly Leu Asn
210                 215                 220

Gly Ala Xaa Ala Ala Ala Thr Asp Ala Ala Phe Ala Ser Leu Ala Ser
225                 230                 235                 240

Gln Ala Ser Val Ser Phe Ile Asn Asn Lys Gly Asp Val Gly Lys Thr
                245                 250                 255

Leu Lys Glu Leu Gly Arg Ser Ser Thr Val Lys Asn Leu Val Val Ala
            260                 265                 270

Ala Ala Thr Ala Gly Val Ala Asp Lys Ile Gly Ala Ser Ala Leu Xaa
            275                 280                 285

Asn Val Ser Asp Lys Gln Trp Ile Asn Asn Leu Thr Val Asn Leu Ala
290                 295                 300

Asn Ala Gly Ser Ala Ala Leu Ile Asn Thr Ala Val Asn Gly Gly Ser
305                 310                 315                 320

Leu Lys Asp Xaa Leu Glu Ala Asn Ile Leu Ala Ala Leu Val Asn Thr
            325                 330                 335
```

```
Ala His Gly Glu Ala Ala Ser Lys Ile Lys Gln Leu Asp Gln His Tyr
            340                 345                 350

Ile Val His Lys Ile Ala His Ala Ile Ala Gly Cys Ala Ala Ala Ala
            355                 360                 365

Ala Asn Lys Gly Lys Cys Gln Asp Gly Ala Ile Gly Ala Ala Val Gly
            370                 375                 380

Glu Ile Val Gly Glu Ala Leu Thr Asn Gly Lys Asn Pro Asp Thr Leu
385                 390                 395                 400

Thr Ala Lys Glu Arg Glu Gln Ile Leu Ala Tyr Ser Lys Leu Val Ala
            405                 410                 415

Gly Thr Val Ser Gly Val Val Gly Gly Asp Val Asn Ala Ala Ala Asn
            420                 425                 430

Ala Ala Glu Val Ala Val Lys Asn Asn Gln Leu Ser Asp Xaa Glu Gly
            435                 440                 445

Arg Glu Phe Asp Asn Glu Met Thr Ala Cys Ala Lys Gln Asn Xaa Pro
450                 455                 460

Gln Leu Cys Arg Lys Asn Thr Val Lys Lys Tyr Gln Asn Val Ala Asp
465                 470                 475                 480

Lys Arg Leu Ala Ala Ser Ile Ala Ile Cys Thr Asp Ile Ser Arg Ser
            485                 490                 495

Thr Glu Cys Arg Thr Ile Arg Lys Gln His Leu Ile Asp Ser Arg Ser
            500                 505                 510

Leu His Ser Ser Trp Glu Ala Gly Leu Ile Gly Lys Asp Asp Glu Trp
            515                 520                 525

Tyr Lys Leu Phe Ser Lys Ser Tyr Thr Gln Ala Asp
            530                 535                 540

<210> SEQ ID NO 168
<211> LENGTH: 540
<212> TYPE: PRT
<213> ORGANISM: Artificial Sequence
<220> FEATURE:
<223> OTHER INFORMATION: Description of Artificial Sequence: ORF49-1

<400> SEQUENCE: 168

Met Gln Leu Leu Ala Ala Glu Gly Ile His Gln His Gln Leu Asn Val
1               5                   10                  15

Gln Lys Ser Thr Arg Phe Ile Gly Ile Lys Val Gly Lys Ser Asn Tyr
            20                  25                  30

Ser Lys Asn Glu Leu Asn Glu Thr Lys Leu Pro Val Arg Val Ile Ala
        35                  40                  45

Gln Thr Ala Lys Thr Arg Ser Gly Trp Asp Thr Val Leu Glu Gly Thr
    50                  55                  60

Glu Phe Lys Thr Thr Leu Ser Gly Ala Asp Ile Gln Ala Gly Val Gly
65                  70                  75                  80

Glu Lys Ala Arg Ala Asp Ala Lys Ile Ile Leu Lys Gly Ile Val Asn
                85                  90                  95

Arg Ile Gln Thr Glu Glu Lys Leu Glu Ser Asn Ser Thr Val Trp Gln
            100                 105                 110

Lys Gln Ala Gly Ser Gly Ser Thr Val Glu Thr Leu Lys Leu Pro Ser
        115                 120                 125

Phe Glu Gly Pro Ala Leu Pro Lys Leu Thr Ala Pro Gly Gly Tyr Ile
    130                 135                 140

Ala Asp Ile Pro Lys Gly Asn Leu Lys Thr Glu Ile Glu Lys Leu Ala
145                 150                 155                 160
```

```
Lys Gln Pro Glu Tyr Ala Tyr Leu Lys Gln Leu Gln Thr Val Lys Asp
                165                 170                 175
Val Asn Trp Asn Gln Val Gln Leu Ala Tyr Asp Lys Trp Asp Tyr Lys
                180                 185                 190
Gln Glu Gly Leu Thr Gly Ala Gly Ala Ala Ile Ile Ala Leu Ala Val
                195                 200                 205
Thr Val Val Thr Ser Gly Ala Gly Thr Gly Ala Val Leu Gly Leu Asn
                210                 215                 220
Gly Ala Ala Ala Ala Thr Asp Ala Ala Phe Ala Ser Leu Ala Ser
225                 230                 235                 240
Gln Ala Ser Val Ser Phe Ile Asn Asn Lys Gly Asn Ile Gly Asn Thr
                245                 250                 255
Leu Lys Glu Leu Gly Arg Ser Ser Thr Val Lys Asn Leu Met Val Ala
                260                 265                 270
Val Ala Thr Ala Gly Val Ala Asp Lys Ile Gly Ala Ser Ala Leu Asn
                275                 280                 285
Asn Val Ser Asp Lys Gln Trp Ile Asn Asn Leu Thr Val Asn Leu Ala
                290                 295                 300
Asn Ala Gly Ser Ala Ala Leu Ile Asn Thr Ala Val Asn Gly Gly Ser
305                 310                 315                 320
Leu Lys Asp Asn Leu Glu Ala Asn Ile Leu Ala Ala Leu Val Asn Thr
                325                 330                 335
Ala His Gly Glu Ala Ala Ser Lys Ile Lys Gln Leu Asp Gln His Tyr
                340                 345                 350
Ile Ala His Lys Ile Ala His Ala Ile Ala Gly Cys Ala Ala Ala Ala
                355                 360                 365
Ala Asn Lys Gly Lys Cys Gln Asp Gly Ala Ile Gly Ala Ala Val Gly
                370                 375                 380
Glu Ile Leu Gly Glu Thr Leu Leu Asp Gly Arg Asp Pro Gly Ser Leu
385                 390                 395                 400
Asn Val Lys Asp Arg Ala Lys Ile Ile Ala Lys Ala Lys Leu Ala Ala
                405                 410                 415
Gly Ala Val Ala Ala Leu Ser Lys Gly Asp Val Ser Thr Ala Ala Asn
                420                 425                 430
Ala Ala Ala Val Ala Val Glu Asn Asn Ser Leu Asn Asp Ile Gln Asp
                435                 440                 445
Arg Leu Leu Ser Gly Asn Tyr Ala Leu Cys Met Ser Ala Gly Gly Ala
450                 455                 460
Glu Ser Phe Cys Glu Ser Tyr Arg Pro Leu Gly Leu Pro His Phe Val
465                 470                 475                 480
Ser Val Ser Gly Glu Met Lys Leu Pro Asn Lys Phe Gly Asn Arg Met
                485                 490                 495
Val Asn Gly Lys Leu Ile Ile Asn Thr Arg Asn Gly Asn Val Tyr Phe
                500                 505                 510
Ser Val Gly Lys Ile Trp Ser Thr Val Lys Ser Thr Lys Ser Asn Ile
                515                 520                 525
Ser Gly Val Ser Val Gly Trp Val Leu Asn Val Ser
530                 535                 540

<210> SEQ ID NO 169
<211> LENGTH: 210
<212> TYPE: PRT
<213> ORGANISM: Artificial Sequence
<220> FEATURE:
```

```
<223> OTHER INFORMATION: Description of Artificial Sequence: ORF39
<220> FEATURE:
<221> NAME/KEY: SITE
<222> LOCATION: (166)..(193)
<223> OTHER INFORMATION: place-holder

<400> SEQUENCE: 169
```

| Lys | Phe | Asp | Phe | Thr | Trp | Phe | Ile | Pro | Ala | Val | Ile | Lys | Tyr | Arg | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Leu Phe Phe Glu Val Leu Val Val Ser Val Val Leu Gln Leu Phe Ala
               20                  25                  30

Leu Ile Thr Pro Leu Phe Phe Gln Val Val Met Asp Lys Val Leu Val
           35                  40                  45

His Arg Gly Phe Ser Thr Leu Asp Val Val Ser Val Ala Leu Leu Val
       50                  55                  60

Val Ser Leu Phe Glu Ile Val Leu Gly Gly Leu Arg Thr Tyr Leu Phe
 65                  70                  75                  80

Ala His Thr Thr Ser Arg Ile Asp Val Glu Leu Gly Ala Arg Leu Phe
               85                  90                  95

Arg His Leu Leu Ser Leu Pro Leu Ser Tyr Phe Glu His Arg Arg Val
           100                 105                 110

Gly Asp Thr Val Ala Arg Val Arg Glu Leu Glu Gln Ile Arg Asn Phe
       115                 120                 125

Leu Thr Gly Gln Ala Leu Thr Ser Val Leu Asp Leu Ala Phe Ser Phe
130                 135                 140

Ile Phe Leu Ala Val Met Trp Tyr Tyr Ser Ser Thr Leu Thr Trp Val
145                 150                 155                 160

Val Leu Ala Ser Leu Xaa Xaa Xaa Xaa Xaa Xaa Xaa Xaa Xaa Xaa
               165                 170                 175

Xaa Xaa Xaa Xaa Xaa Xaa Xaa Xaa Xaa Xaa Xaa Xaa Xaa Xaa Xaa
           180                 185                 190

Xaa Ile Cys Ala Asn Arg Thr Val Leu Ile Ile Ala His Arg Leu Ser
       195                 200                 205

Thr Val
    210

```
<210> SEQ ID NO 170
<211> LENGTH: 240
<212> TYPE: PRT
<213> ORGANISM: Artificial Sequence
<220> FEATURE:
<223> OTHER INFORMATION: Description of Artificial Sequence: ORF39a

<400> SEQUENCE: 170
```

Ala Val Leu Ser Phe Ala Glu Phe Ser Asn Arg Tyr Ser Gly Lys Leu
 1               5                  10                  15

Ile Leu Val Ala Ser Arg Ala Ser Val Leu Gly Ser Leu Ala Lys Phe
               20                  25                  30

Asp Phe Thr Trp Phe Ile Pro Ala Val Ile Lys Tyr Arg Arg Leu Phe
           35                  40                  45

Phe Glu Val Leu Val Val Ser Val Val Leu Gln Leu Phe Ala Leu Ile
 50                  55                  60

Thr Pro Leu Phe Phe Gln Val Val Met Asp Lys Val Leu Val His Arg
 65                  70                  75                  80

Gly Phe Ser Thr Leu Asp Val Val Ser Val Ala Leu Leu Val Val Ser
               85                  90                  95

Leu Phe Glu Ile Val Leu Gly Gly Leu Arg Thr Tyr Leu Phe Ala His

-continued

```
                100                 105                 110
Thr Thr Ser Arg Ile Asp Val Glu Leu Gly Ala Arg Leu Phe Arg His
            115                 120                 125
Leu Leu Ser Leu Pro Leu Ser Tyr Phe Glu His Arg Arg Val Gly Asp
        130                 135                 140
Thr Val Ala Arg Val Arg Glu Leu Glu Gln Ile Arg Asn Phe Leu Thr
145                 150                 155                 160
Gly Gln Ala Leu Thr Ser Val Leu Asp Leu Ala Phe Ser Phe Ile Phe
                165                 170                 175
Leu Ala Val Met Trp Tyr Tyr Ser Ser Thr Leu Thr Trp Val Val Leu
            180                 185                 190
Ala Ser Leu Pro Ala Tyr Ala Phe Trp Ser Ala Phe Ile Ser Pro Ile
        195                 200                 205
Leu Arg Thr Arg Leu Asn Asp Lys Phe Ala Arg Asn Ala Asp Asn Gln
    210                 215                 220
Ser Phe Leu Val Glu Ser Ile Thr Ala Val Gly Thr Val Lys Ala Met
225                 230                 235                 240

<210> SEQ ID NO 171
<211> LENGTH: 690
<212> TYPE: PRT
<213> ORGANISM: Artificial Sequence
<220> FEATURE:
<223> OTHER INFORMATION: Description of Artificial Sequence: ORF39a
<220> FEATURE:
<221> NAME/KEY: SITE
<222> LOCATION: (29)..(40)
<223> OTHER INFORMATION: place-holder
<220> FEATURE:
<221> NAME/KEY: SITE
<222> LOCATION: (137)..(153)
<223> OTHER INFORMATION: place-holder
<220> FEATURE:
<221> NAME/KEY: SITE
<222> LOCATION: (173)..(187)
<223> OTHER INFORMATION: place-holder

<400> SEQUENCE: 171

Tyr His Gly Ile Ala Ala Asn Pro Ala Asp Ile Gln His Glu Phe Cys
1               5                   10                  15
Thr Ser Ala Gln Ser Asp Leu Asn Glu Thr Gln Trp Xaa Xaa Xaa Xaa
            20                  25                  30
Xaa Xaa Xaa Xaa Xaa Xaa Xaa Xaa Val Val Arg Gln Pro Ile Lys Arg
        35                  40                  45
Leu Ala Met Ala Thr Leu Pro Ala Leu Val Trp Cys Asp Asp Gly Asn
    50                  55                  60
His Phe Ile Leu Ala Lys Thr Asp Gly Gly Glu His Ala Gln Tyr
65                  70                  75              80
Leu Ile Gln Asp Leu Thr Thr Asn Lys Ser Ala Val Leu Ser Phe Ala
                85                  90                  95
Glu Phe Ser Asn Arg Tyr Ser Gly Lys Leu Ile Leu Val Ala Ser Arg
            100                 105                 110
Ala Ser Val Leu Gly Ser Leu Ala Lys Phe Asp Phe Thr Trp Phe Ile
        115                 120                 125
Pro Ala Val Ile Lys Tyr Arg Arg Xaa Xaa Xaa Xaa Xaa Xaa Xaa
    130                 135                 140
Xaa Xaa Xaa Xaa Xaa Xaa Xaa Xaa Ile Thr Pro Leu Phe Phe Gln
145                 150                 155                 160
Val Val Met Asp Lys Val Leu Val His Arg Gly Phe Xaa Xaa Xaa Xaa
```

-continued

```
                165                 170                 175
Xaa Xaa Xaa Xaa Xaa Xaa Xaa Xaa Xaa Phe Glu Ile Val Leu
            180                 185                 190
Gly Gly Leu Arg Thr Tyr Leu Phe Ala His Thr Thr Ser Arg Ile Asp
            195                 200                 205
Val Glu Leu Gly Ala Arg Leu Phe Arg His Leu Leu Ser Leu Pro Leu
            210                 215                 220
Ser Tyr Phe Glu His Arg Arg Val Gly Asp Thr Val Ala Arg Val Arg
225                 230                 235                 240
Glu Leu Glu Gln Ile Arg Asn Phe Leu Thr Gly Gln Ala Leu Thr Ser
                245                 250                 255
Val Leu Asp Leu Ala Phe Ser Phe Ile Phe Leu Ala Val Met Trp Tyr
                260                 265                 270
Tyr Ser Ser Thr Leu Thr Trp Val Val Leu Ala Ser Leu Pro Ala Tyr
                275                 280                 285
Ala Phe Trp Ser Ala Phe Ile Ser Pro Ile Leu Arg Thr Arg Leu Asn
            290                 295                 300
Asp Lys Phe Ala Arg Asn Ala Asp Asn Gln Ser Phe Leu Val Glu Ser
305                 310                 315                 320
Ile Thr Ala Val Gly Thr Val Lys Ala Met Ala Val Glu Pro Gln Met
                325                 330                 335
Thr Gln Arg Trp Asp Asn Gln Leu Ala Ala Tyr Val Ala Ser Gly Phe
                340                 345                 350
Arg Val Thr Lys Leu Ala Val Val Gly Gln Gln Gly Val Gln Leu Ile
            355                 360                 365
Gln Lys Leu Val Thr Val Ala Thr Leu Trp Ile Gly Ala Arg Leu Val
            370                 375                 380
Ile Glu Ser Lys Leu Thr Val Gly Gln Leu Ile Ala Phe Asn Met Leu
385                 390                 395                 400
Ser Gly Gln Val Ala Ala Pro Val Ile Arg Leu Ala Gln Leu Trp Gln
                405                 410                 415
Asp Phe Gln Gln Val Gly Ile Ser Val Ala Arg Leu Gly Asp Ile Leu
            420                 425                 430
Asn Ala Pro Thr Glu Asn Ala Ser Ser His Leu Ala Leu Pro Asp Ile
            435                 440                 445
Arg Gly Glu Ile Thr Phe Glu His Val Asp Phe Arg Tyr Lys Ala Asp
            450                 455                 460
Gly Arg Leu Ile Leu Gln Asp Leu Asn Leu Arg Ile Arg Ala Gly Glu
465                 470                 475                 480
Val Leu Gly Ile Val Gly Arg Ser Gly Ser Gly Lys Ser Thr Leu Thr
                485                 490                 495
Lys Leu Val Gln Arg Leu Tyr Val Pro Ala Gln Gly Arg Val Leu Val
                500                 505                 510
Asp Gly Asn Asp Leu Ala Leu Ala Ala Pro Ala Trp Leu Arg Arg Gln
            515                 520                 525
Val Gly Val Val Leu Gln Glu Asn Val Leu Leu Asn Arg Ser Ile Arg
            530                 535                 540
Asp Asn Ile Ala Leu Thr Asp Thr Gly Met Pro Leu Glu Arg Ile Ile
545                 550                 555                 560
Glu Ala Ala Lys Leu Ala Gly Ala His Glu Phe Ile Met Glu Leu Pro
                565                 570                 575
Glu Gly Tyr Gly Thr Val Val Gly Glu Gln Gly Ala Gly Leu Ser Gly
                580                 585                 590
```

Gly Gln Arg Gln Arg Ile Ala Ile Ala Arg Ala Leu Ile Thr Asn Pro
            595                 600                 605

Arg Ile Leu Ile Phe Asp Glu Ala Thr Ser Ala Leu Asp Tyr Glu Ser
        610                 615                 620

Glu Arg Ala Ile Met Gln Asn Met Gln Ala Ile Cys Ala Asn Arg Thr
625                 630                 635                 640

Val Leu Ile Ile Ala His Arg Leu Ser Thr Val Lys Thr Ala His Arg
                645                 650                 655

Ile Ile Ala Met Asp Lys Gly Arg Ile Val Glu Ala Gly Thr Gln Gln
            660                 665                 670

Glu Leu Leu Ala Lys Pro Asn Gly Tyr Tyr Arg Tyr Leu Tyr Asp Leu
        675                 680                 685

Gln Asn
    690

<210> SEQ ID NO 172
<211> LENGTH: 690
<212> TYPE: PRT
<213> ORGANISM: Artificial Sequence
<220> FEATURE:
<223> OTHER INFORMATION: Description of Artificial Sequence: homology
<220> FEATURE:
<221> NAME/KEY: SITE
<222> LOCATION: (3)
<223> OTHER INFORMATION: absent or positive
<220> FEATURE:
<221> NAME/KEY: SITE
<222> LOCATION: (6)
<223> OTHER INFORMATION: absent or positive
<220> FEATURE:
<221> NAME/KEY: SITE
<222> LOCATION: (9)..(12)
<223> OTHER INFORMATION: absent or positive
<220> FEATURE:
<221> NAME/KEY: SITE
<222> LOCATION: (14)
<223> OTHER INFORMATION: absent or positive
<220> FEATURE:
<221> NAME/KEY: SITE
<222> LOCATION: (16)..(22)
<223> OTHER INFORMATION: absent or positive
<220> FEATURE:
<221> NAME/KEY: SITE
<222> LOCATION: (24)..(25)
<223> OTHER INFORMATION: absent or positive
<220> FEATURE:
<221> NAME/KEY: SITE
<222> LOCATION: (27)
<223> OTHER INFORMATION: absent or positive
<220> FEATURE:
<221> NAME/KEY: SITE
<222> LOCATION: (29)..(41)
<223> OTHER INFORMATION: absent or positive
<220> FEATURE:
<221> NAME/KEY: SITE
<222> LOCATION: (43)..(45)
<223> OTHER INFORMATION: absent or positive
<220> FEATURE:
<221> NAME/KEY: SITE
<222> LOCATION: (47)
<223> OTHER INFORMATION: absent or positive
<220> FEATURE:
<221> NAME/KEY: SITE
<222> LOCATION: (51)..(53)
<223> OTHER INFORMATION: absent or positive
<220> FEATURE:
<221> NAME/KEY: SITE
<222> LOCATION: (60)..(61)
<223> OTHER INFORMATION: absent or positive
<220> FEATURE:
<221> NAME/KEY: SITE -continued

```
<222> LOCATION: (64)
<223> OTHER INFORMATION: absent or positive
<220> FEATURE:
<221> NAME/KEY: SITE
<222> LOCATION: (69)
<223> OTHER INFORMATION: absent or positive
<220> FEATURE:
<221> NAME/KEY: SITE
<222> LOCATION: (71)
<223> OTHER INFORMATION: absent or positive
<220> FEATURE:
<221> NAME/KEY: SITE
<222> LOCATION: (73)..(75)
<223> OTHER INFORMATION: absent or positive
<220> FEATURE:
<221> NAME/KEY: SITE
<222> LOCATION: (77)..(79)
<223> OTHER INFORMATION: absent or positive
<220> FEATURE:
<221> NAME/KEY: SITE
<222> LOCATION: (83)
<223> OTHER INFORMATION: absent or positive
<220> FEATURE:
<221> NAME/KEY: SITE
<222> LOCATION: (86)
<223> OTHER INFORMATION: absent or positive
<220> FEATURE:
<221> NAME/KEY: SITE
<222> LOCATION: (88)..(92)
<223> OTHER INFORMATION: absent or positive
<220> FEATURE:
<221> NAME/KEY: SITE
<222> LOCATION: (94)..(95)
<223> OTHER INFORMATION: absent or positive
<220> FEATURE:
<221> NAME/KEY: SITE
<222> LOCATION: (99)..(101)
<223> OTHER INFORMATION: absent or positive
<220> FEATURE:
<221> NAME/KEY: SITE
<222> LOCATION: (103)
<223> OTHER INFORMATION: absent or positive
<220> FEATURE:
<221> NAME/KEY: SITE
<222> LOCATION: (115)..(116)
<223> OTHER INFORMATION: absent or positive
<220> FEATURE:
<221> NAME/KEY: SITE
<222> LOCATION: (118)
<223> OTHER INFORMATION: absent or positive
<220> FEATURE:
<221> NAME/KEY: SITE
<222> LOCATION: (136)..(153)
<223> OTHER INFORMATION: absent or positive
<220> FEATURE:
<221> NAME/KEY: SITE
<222> LOCATION: (173)..(187)
<223> OTHER INFORMATION: absent or positive
<220> FEATURE:
<221> NAME/KEY: SITE
<222> LOCATION: (193)
<223> OTHER INFORMATION: absent or positive
<220> FEATURE:
<221> NAME/KEY: SITE
<222> LOCATION: (199)
<223> OTHER INFORMATION: absent or positive
<220> FEATURE:
<221> NAME/KEY: SITE
<222> LOCATION: (203)
<223> OTHER INFORMATION: absent or positive
<220> FEATURE:
<221> NAME/KEY: SITE
<222> LOCATION: (221)
<223> OTHER INFORMATION: absent or positive
<220> FEATURE:
<221> NAME/KEY: SITE
<222> LOCATION: (224)
<223> OTHER INFORMATION: absent or positive
<220> FEATURE:
```

```
<221> NAME/KEY: SITE
<222> LOCATION: (229)
<223> OTHER INFORMATION: absent or positive
<220> FEATURE:
<221> NAME/KEY: SITE
<222> LOCATION: (243)
<223> OTHER INFORMATION: absent or positive
<220> FEATURE:
<221> NAME/KEY: SITE
<222> LOCATION: (261)
<223> OTHER INFORMATION: absent or positive
<220> FEATURE:
<221> NAME/KEY: SITE
<222> LOCATION: (267)
<223> OTHER INFORMATION: absent or positive
<220> FEATURE:
<221> NAME/KEY: SITE
<222> LOCATION: (275)..(276)
<223> OTHER INFORMATION: absent or positive
<220> FEATURE:
<221> NAME/KEY: SITE
<222> LOCATION: (279)
<223> OTHER INFORMATION: absent or positive
<220> FEATURE:
<221> NAME/KEY: SITE
<222> LOCATION: (281)
<223> OTHER INFORMATION: absent or positive
<220> FEATURE:
<221> NAME/KEY: SITE
<222> LOCATION: (283)
<223> OTHER INFORMATION: absent or positive
<220> FEATURE:
<221> NAME/KEY: SITE
<222> LOCATION: (287)
<223> OTHER INFORMATION: absent or positive
<220> FEATURE:
<221> NAME/KEY: SITE
<222> LOCATION: (289)..(290)
<223> OTHER INFORMATION: absent or positive
<220> FEATURE:
<221> NAME/KEY: SITE
<222> LOCATION: (293)
<223> OTHER INFORMATION: absent or positive
<220> FEATURE:
<221> NAME/KEY: SITE
<222> LOCATION: (301)
<223> OTHER INFORMATION: absent or positive
<220> FEATURE:
<221> NAME/KEY: SITE
<222> LOCATION: (304)..(305)
<223> OTHER INFORMATION: absent or positive
<220> FEATURE:
<221> NAME/KEY: SITE
<222> LOCATION: (310)
<223> OTHER INFORMATION: absent or positive
<220> FEATURE:
<221> NAME/KEY: SITE
<222> LOCATION: (321)
<223> OTHER INFORMATION: absent or positive
<220> FEATURE:
<221> NAME/KEY: SITE
<222> LOCATION: (324)..(325)
<223> OTHER INFORMATION: absent or positive
<220> FEATURE:
<221> NAME/KEY: SITE
<222> LOCATION: (327)
<223> OTHER INFORMATION: absent or positive
<220> FEATURE:
<221> NAME/KEY: SITE
<222> LOCATION: (330)
<223> OTHER INFORMATION: absent or positive
<220> FEATURE:
<221> NAME/KEY: SITE
<222> LOCATION: (333)
<223> OTHER INFORMATION: absent or positive
<220> FEATURE:
<221> NAME/KEY: SITE
<222> LOCATION: (338)..(339)
<223> OTHER INFORMATION: absent or positive
```

-continued

```
<220> FEATURE:
<221> NAME/KEY: SITE
<222> LOCATION: (342)
<223> OTHER INFORMATION: absent or positive
<220> FEATURE:
<221> NAME/KEY: SITE
<222> LOCATION: (346)
<223> OTHER INFORMATION: absent or positive
<220> FEATURE:
<221> NAME/KEY: SITE
<222> LOCATION: (349)..(350)
<223> OTHER INFORMATION: absent or positive
<220> FEATURE:
<221> NAME/KEY: SITE
<222> LOCATION: (356)
<223> OTHER INFORMATION: absent or positive
<220> FEATURE:
<221> NAME/KEY: SITE
<222> LOCATION: (359)..(360)
<223> OTHER INFORMATION: absent or positive
<220> FEATURE:
<221> NAME/KEY: SITE
<222> LOCATION: (367)
<223> OTHER INFORMATION: absent or positive
<220> FEATURE:
<221> NAME/KEY: SITE
<222> LOCATION: (371)
<223> OTHER INFORMATION: absent or positive
<220> FEATURE:
<221> NAME/KEY: SITE
<222> LOCATION: (373)
<223> OTHER INFORMATION: absent or positive
<220> FEATURE:
<221> NAME/KEY: SITE
<222> LOCATION: (375)
<223> OTHER INFORMATION: absent or positive
<220> FEATURE:
<221> NAME/KEY: SITE
<222> LOCATION: (379)
<223> OTHER INFORMATION: absent or positive
<220> FEATURE:
<221> NAME/KEY: SITE
<222> LOCATION: (382)
<223> OTHER INFORMATION: absent or positive
<220> FEATURE:
<221> NAME/KEY: SITE
<222> LOCATION: (386)..(388)
<223> OTHER INFORMATION: absent or positive
<220> FEATURE:
<221> NAME/KEY: SITE
<222> LOCATION: (390)..(391)
<223> OTHER INFORMATION: absent or positive
<220> FEATURE:
<221> NAME/KEY: SITE
<222> LOCATION: (405)
<223> OTHER INFORMATION: absent or positive
<220> FEATURE:
<221> NAME/KEY: SITE
<222> LOCATION: (426)
<223> OTHER INFORMATION: absent or positive
<220> FEATURE:
<221> NAME/KEY: SITE
<222> LOCATION: (431)
<223> OTHER INFORMATION: absent or positive
<220> FEATURE:
<221> NAME/KEY: SITE
<222> LOCATION: (434)
<223> OTHER INFORMATION: absent or positive
<220> FEATURE:
<221> NAME/KEY: SITE
<222> LOCATION: (438)..(442)
<223> OTHER INFORMATION: absent or positive
<220> FEATURE:
<221> NAME/KEY: SITE
<222> LOCATION: (447)
<223> OTHER INFORMATION: absent or positive
<220> FEATURE:
<221> NAME/KEY: SITE
<222> LOCATION: (449)
```

```
<223> OTHER INFORMATION: absent or positive
<220> FEATURE:
<221> NAME/KEY: SITE
<222> LOCATION: (451)
<223> OTHER INFORMATION: absent or positive
<220> FEATURE:
<221> NAME/KEY: SITE
<222> LOCATION: (455)..(458)
<223> OTHER INFORMATION: absent or positive
<220> FEATURE:
<221> NAME/KEY: SITE
<222> LOCATION: (463)
<223> OTHER INFORMATION: absent or positive
<220> FEATURE:
<221> NAME/KEY: SITE
<222> LOCATION: (465)..(467)
<223> OTHER INFORMATION: absent or positive
<220> FEATURE:
<221> NAME/KEY: SITE
<222> LOCATION: (470)
<223> OTHER INFORMATION: absent or positive
<220> FEATURE:
<221> NAME/KEY: SITE
<222> LOCATION: (472)
<223> OTHER INFORMATION: absent or positive
<220> FEATURE:
<221> NAME/KEY: SITE
<222> LOCATION: (475)
<223> OTHER INFORMATION: absent or positive
<220> FEATURE:
<221> NAME/KEY: SITE
<222> LOCATION: (477)..(478)
<223> OTHER INFORMATION: absent or positive
<220> FEATURE:
<221> NAME/KEY: SITE
<222> LOCATION: (482)
<223> OTHER INFORMATION: absent or positive
<220> FEATURE:
<221> NAME/KEY: SITE
<222> LOCATION: (499)
<223> OTHER INFORMATION: absent or positive
<220> FEATURE:
<221> NAME/KEY: SITE
<222> LOCATION: (502)
<223> OTHER INFORMATION: absent or positive
<220> FEATURE:
<221> NAME/KEY: SITE
<222> LOCATION: (504)
<223> OTHER INFORMATION: absent or positive
<220> FEATURE:
<221> NAME/KEY: SITE
<222> LOCATION: (506)..(507)
<223> OTHER INFORMATION: absent or positive
<220> FEATURE:
<221> NAME/KEY: SITE
<222> LOCATION: (509)
<223> OTHER INFORMATION: absent or positive
<220> FEATURE:
<221> NAME/KEY: SITE
<222> LOCATION: (512)
<223> OTHER INFORMATION: absent or positive
<220> FEATURE:
<221> NAME/KEY: SITE
<222> LOCATION: (515)
<223> OTHER INFORMATION: absent or positive
<220> FEATURE:
<221> NAME/KEY: SITE
<222> LOCATION: (521)
<223> OTHER INFORMATION: absent or positive
<220> FEATURE:
<221> NAME/KEY: SITE
<222> LOCATION: (523)
<223> OTHER INFORMATION: absent or positive
<220> FEATURE:
<221> NAME/KEY: SITE
<222> LOCATION: (535)
<223> OTHER INFORMATION: absent or positive
<220> FEATURE:
<221> NAME/KEY: SITE
```

```
<222> LOCATION: (550)
<223> OTHER INFORMATION: absent or positive
<220> FEATURE:
<221> NAME/KEY: SITE
<222> LOCATION: (552)
<223> OTHER INFORMATION: absent or positive
<220> FEATURE:
<221> NAME/KEY: SITE
<222> LOCATION: (556)
<223> OTHER INFORMATION: absent or positive
<220> FEATURE:
<221> NAME/KEY: SITE
<222> LOCATION: (558)
<223> OTHER INFORMATION: absent or positive
<220> FEATURE:
<221> NAME/KEY: SITE
<222> LOCATION: (560)..(561)
<223> OTHER INFORMATION: absent or positive
<220> FEATURE:
<221> NAME/KEY: SITE
<222> LOCATION: (573)
<223> OTHER INFORMATION: absent or positive
<220> FEATURE:
<221> NAME/KEY: SITE
<222> LOCATION: (576)
<223> OTHER INFORMATION: absent or positive
<220> FEATURE:
<221> NAME/KEY: SITE
<222> LOCATION: (580)
<223> OTHER INFORMATION: absent or positive
<220> FEATURE:
<221> NAME/KEY: SITE
<222> LOCATION: (582)
<223> OTHER INFORMATION: absent or positive
<220> FEATURE:
<221> NAME/KEY: SITE
<222> LOCATION: (605)..(606)
<223> OTHER INFORMATION: absent or positive
<220> FEATURE:
<221> NAME/KEY: SITE
<222> LOCATION: (609)
<223> OTHER INFORMATION: absent or positive
<220> FEATURE:
<221> NAME/KEY: SITE
<222> LOCATION: (626)..(6272)
<223> OTHER INFORMATION: absent or positive
<220> FEATURE:
<221> NAME/KEY: SITE
<222> LOCATION: (630)
<223> OTHER INFORMATION: absent or positive
<220> FEATURE:
<221> NAME/KEY: SITE
<222> LOCATION: (633)..(634)
<223> OTHER INFORMATION: absent or positive
<220> FEATURE:
<221> NAME/KEY: SITE
<222> LOCATION: (637)..(638)
<223> OTHER INFORMATION: absent or positive
<220> FEATURE:
<221> NAME/KEY: SITE
<222> LOCATION: (642)
<223> OTHER INFORMATION: absent or positive
<220> FEATURE:
<221> NAME/KEY: SITE
<222> LOCATION: (653)
<223> OTHER INFORMATION: absent or positive
<220> FEATURE:
<221> NAME/KEY: SITE
<222> LOCATION: (655)
<223> OTHER INFORMATION: absent or positive
<220> FEATURE:
<221> NAME/KEY: SITE
<222> LOCATION: (659)
<223> OTHER INFORMATION: absent or positive
<220> FEATURE:
<221> NAME/KEY: SITE
<222> LOCATION: (661)
<223> OTHER INFORMATION: absent or positive
<220> FEATURE:
```

```
<221> NAME/KEY: SITE
<222> LOCATION: (664)
<223> OTHER INFORMATION: absent or positive
<220> FEATURE:
<221> NAME/KEY: SITE
<222> LOCATION: (668)
<223> OTHER INFORMATION: absent or positive
<220> FEATURE:
<221> NAME/KEY: SITE
<222> LOCATION: (670)..(672)
<223> OTHER INFORMATION: absent or positive
<220> FEATURE:
<221> NAME/KEY: SITE
<222> LOCATION: (677)
<223> OTHER INFORMATION: absent or positive
<220> FEATURE:
<221> NAME/KEY: SITE
<222> LOCATION: (681)
<223> OTHER INFORMATION: absent or positive
<220> FEATURE:
<221> NAME/KEY: SITE
<222> LOCATION: (683)
<223> OTHER INFORMATION: absent or positive
<220> FEATURE:
<221> NAME/KEY: SITE
<222> LOCATION: (686)..(687)
<223> OTHER INFORMATION: absent or positive
<220> FEATURE:
<221> NAME/KEY: SITE
<222> LOCATION: (690)
<223> OTHER INFORMATION: absent or positive

<400> SEQUENCE: 172

Tyr His Xaa Ile Ala Xaa Asn Pro Xaa Xaa Xaa Xaa His Xaa Phe Xaa
 1               5                  10                  15

Xaa Xaa Xaa Xaa Xaa Xaa Leu Xaa Xaa Thr Xaa Trp Xaa Xaa Xaa Xaa
            20                  25                  30

Xaa Xaa Xaa Xaa Xaa Xaa Xaa Xaa Val Xaa Xaa Xaa Ile Xaa Arg
        35                  40                  45

Leu Ala Xaa Xaa Xaa Leu Pro Ala Leu Val Trp Xaa Xaa Asp Gly Xaa
     50                  55                  60

His Phe Ile Leu Xaa Lys Xaa Asp Xaa Xaa Glu Xaa Xaa Xaa Tyr
 65                  70                  75                  80

Leu Ile Xaa Asp Leu Xaa Thr Xaa Xaa Xaa Xaa Xaa Leu Xaa Xaa Ala
             85                  90                  95

Glu Phe Xaa Xaa Xaa Tyr Xaa Gly Lys Leu Ile Leu Val Ala Ser Arg
            100                 105                 110

Ala Ser Xaa Xaa Gly Xaa Leu Ala Lys Phe Asp Phe Thr Trp Phe Ile
            115                 120                 125

Pro Ala Val Ile Lys Tyr Arg Xaa Xaa Xaa Xaa Xaa Xaa Xaa Xaa
130                 135                 140

Xaa Xaa Xaa Xaa Xaa Xaa Xaa Xaa Ile Thr Pro Leu Phe Phe Gln
145                 150                 155                 160

Val Val Met Asp Lys Val Leu Val His Arg Gly Phe Xaa Xaa Xaa Xaa
                165                 170                 175

Xaa Xaa Xaa Xaa Xaa Xaa Xaa Xaa Xaa Phe Glu Ile Val Leu
            180                 185                 190

Xaa Gly Leu Arg Thr Tyr Xaa Phe Ala His Xaa Thr Ser Arg Ile Asp
            195                 200                 205

Val Glu Leu Gly Ala Arg Leu Phe Arg His Leu Leu Xaa Leu Pro Xaa
            210                 215                 220

Ser Tyr Phe Glu Xaa Arg Arg Val Gly Asp Thr Val Ala Arg Val Arg
225                 230                 235                 240
```

-continued

```
Glu Leu Xaa Gln Ile Arg Asn Phe Leu Thr Gly Gln Ala Leu Thr Ser
            245                 250                 255

Val Leu Asp Leu Xaa Phe Ser Phe Ile Phe Xaa Ala Val Met Trp Tyr
            260                 265                 270

Tyr Ser Xaa Xaa Leu Thr Xaa Val Xaa Leu Xaa Ser Leu Pro Xaa Tyr
            275                 280                 285

Xaa Xaa Trp Ser Xaa Phe Ile Ser Pro Ile Leu Arg Xaa Arg Leu Xaa
            290                 295                 300

Xaa Lys Phe Ala Arg Xaa Ala Asp Asn Gln Ser Phe Leu Val Glu Ser
305                 310                 315                 320

Xaa Thr Ala Xaa Xaa Thr Xaa Lys Ala Xaa Ala Val Xaa Pro Gln Met
            325                 330                 335

Thr Xaa Xaa Trp Asp Xaa Gln Leu Ala Xaa Tyr Val Xaa Xaa Gly Phe
            340                 345                 350

Arg Val Thr Xaa Leu Ala Xaa Xaa Gly Gln Gln Gly Val Gln Xaa Ile
            355                 360                 365

Gln Lys Xaa Val Xaa Val Xaa Thr Leu Trp Xaa Gly Ala Xaa Leu Val
            370                 375                 380

Ile Xaa Xaa Xaa Leu Xaa Xaa Gly Gln Leu Ile Ala Phe Asn Met Leu
385                 390                 395                 400

Ser Gly Gln Val Xaa Ala Pro Val Ile Arg Leu Ala Gln Leu Trp Gln
            405                 410                 415

Asp Phe Gln Gln Val Gly Ile Ser Val Xaa Arg Leu Gly Asp Xaa Leu
            420                 425                 430

Asn Xaa Pro Thr Glu Xaa Xaa Xaa Xaa Xaa Leu Ala Leu Pro Xaa Ile
            435                 440                 445

Xaa Gly Xaa Ile Thr Phe Xaa Xaa Xaa Xaa Phe Arg Tyr Lys Xaa Asp
            450                 455                 460

Xaa Xaa Xaa Ile Leu Xaa Asp Xaa Asn Leu Xaa Ile Xaa Xaa Gly Glu
465                 470                 475                 480

Val Xaa Gly Ile Val Gly Arg Ser Gly Ser Gly Lys Ser Thr Leu Thr
            485                 490                 495

Lys Leu Xaa Gln Arg Xaa Tyr Xaa Pro Xaa Xaa Gly Xaa Val Leu Xaa
            500                 505                 510

Asp Gly Xaa Asp Leu Ala Leu Ala Xaa Pro Xaa Trp Leu Arg Arg Gln
            515                 520                 525

Val Gly Val Val Leu Gln Xaa Asn Val Leu Leu Asn Arg Ser Ile Arg
            530                 535                 540

Asp Asn Ile Ala Leu Xaa Asp Xaa Gly Met Pro Xaa Glu Xaa Ile Xaa
545                 550                 555                 560

Xaa Ala Ala Lys Leu Ala Gly Ala His Glu Phe Ile Xaa Glu Leu Xaa
            565                 570                 575

Glu Gly Tyr Xaa Thr Xaa Val Gly Glu Gln Gly Ala Gly Leu Ser Gly
            580                 585                 590

Gly Gln Arg Gln Arg Ile Ala Ile Ala Arg Ala Leu Xaa Xaa Asn Pro
            595                 600                 605

Xaa Ile Leu Ile Phe Asp Glu Ala Thr Ser Ala Leu Asp Tyr Glu Ser
            610                 615                 620

Glu Xaa Xaa Ile Met Xaa Asn Met Xaa Xaa Ile Cys Xaa Xaa Arg Thr
625                 630                 635                 640

Val Xaa Ile Ile Ala His Arg Leu Ser Thr Val Lys Xaa Ala Xaa Arg
            645                 650                 655

Ile Ile Xaa Met Xaa Lys Gly Xaa Ile Val Glu Xaa Gly Xaa Xaa Xaa
```

```
                    660               665               670
Glu Leu Leu Ala Xaa Pro Asn Gly Xaa Tyr Xaa Tyr Leu Xaa Xaa Leu
            675               680               685

Gln Xaa
    690

<210> SEQ ID NO 173
<211> LENGTH: 687
<212> TYPE: PRT
<213> ORGANISM: Artificial Sequence
<220> FEATURE:
<223> OTHER INFORMATION: Description of Artificial Sequence: cytolysin
      from A. pleuropneumoniae

<400> SEQUENCE: 173

Tyr His Asn Ile Ala Val Asn Pro Glu Glu Leu Lys His Lys Phe Asp
  1               5                  10                  15

Leu Glu Gly Lys Gly Leu Asp Leu Thr Ala Trp Leu Leu Ala Ala Lys
             20                  25                  30

Ser Leu Glu Leu Lys Ala Lys Gln Val Lys Lys Ala Ile Asp Arg Leu
         35                  40                  45

Ala Phe Ile Ala Leu Pro Ala Leu Val Trp Arg Glu Asp Gly Lys His
     50                  55                  60

Phe Ile Leu Thr Lys Ile Asp Asn Glu Ala Lys Lys Tyr Leu Ile Phe
 65                  70                  75                  80

Asp Leu Glu Thr His Asn Pro Arg Ile Leu Glu Gln Ala Glu Phe Glu
                 85                  90                  95

Ser Leu Tyr Gln Gly Lys Leu Ile Leu Val Ala Ser Arg Ala Ser Ile
            100                 105                 110

Val Gly Lys Leu Ala Lys Phe Asp Phe Thr Trp Phe Ile Pro Ala Val
        115                 120                 125

Ile Lys Tyr Arg Lys Ile Phe Ile Glu Thr Leu Ile Val Ser Ile Phe
    130                 135                 140

Leu Gln Ile Phe Ala Leu Ile Thr Pro Leu Phe Phe Gln Val Val Met
145                 150                 155                 160

Asp Lys Val Leu Val His Arg Gly Phe Ser Thr Leu Asn Val Ile Thr
                165                 170                 175

Val Ala Leu Ala Ile Val Val Leu Phe Glu Ile Val Leu Asn Gly Leu
            180                 185                 190

Arg Thr Tyr Ile Phe Ala His Ser Thr Ser Arg Ile Asp Val Glu Leu
        195                 200                 205

Gly Ala Arg Leu Phe Arg His Leu Leu Ala Leu Pro Ile Ser Tyr Phe
    210                 215                 220

Glu Asn Arg Arg Val Gly Asp Thr Val Ala Arg Val Arg Glu Leu Asp
225                 230                 235                 240

Gln Ile Arg Asn Phe Leu Thr Gly Gln Ala Leu Thr Ser Val Leu Asp
                245                 250                 255

Leu Met Phe Ser Phe Ile Phe Phe Ala Val Met Trp Tyr Tyr Ser Pro
            260                 265                 270

Lys Leu Thr Leu Val Ile Leu Gly Ser Leu Pro Phe Tyr Met Gly Trp
        275                 280                 285

Ser Ile Phe Ile Ser Pro Ile Leu Arg Arg Leu Asp Glu Lys Phe
    290                 295                 300

Ala Arg Gly Ala Asp Asn Gln Ser Phe Leu Val Glu Ser Val Thr Ala
305                 310                 315                 320
```

-continued

```
Ile Asn Thr Ile Lys Ala Leu Ala Val Thr Pro Gln Met Thr Asn Thr
            325                 330                 335

Trp Asp Lys Gln Leu Ala Ser Tyr Val Ser Ala Gly Phe Arg Val Thr
            340                 345                 350

Thr Leu Ala Thr Ile Gly Gln Gln Gly Val Gln Phe Ile Gln Lys Val
            355                 360                 365

Val Met Val Ile Thr Leu Trp Leu Gly Ala His Leu Val Ile Ser Gly
            370                 375                 380

Asp Leu Ser Ile Gly Gln Leu Ile Ala Phe Asn Met Leu Ser Gly Gln
385                 390                 395                 400

Val Ile Ala Pro Val Ile Arg Leu Ala Gln Leu Trp Gln Asp Phe Gln
                    405                 410                 415

Gln Val Gly Ile Ser Val Thr Arg Leu Gly Asp Val Leu Asn Ser Pro
            420                 425                 430

Thr Glu Ser Tyr Gln Gly Lys Leu Ala Leu Pro Glu Ile Lys Gly Asp
            435                 440                 445

Ile Thr Phe Arg Asn Ile Arg Phe Arg Tyr Lys Pro Asp Ala Pro Val
            450                 455                 460

Ile Leu Asn Asp Val Asn Leu Ser Ile Gln Gln Gly Glu Val Ile Gly
465                 470                 475                 480

Ile Val Gly Arg Ser Gly Ser Gly Lys Ser Thr Leu Thr Lys Leu Ile
            485                 490                 495

Gln Arg Phe Tyr Ile Pro Glu Asn Gly Gln Val Leu Ile Asp Gly His
            500                 505                 510

Asp Leu Ala Leu Ala Asp Pro Asn Trp Leu Arg Arg Gln Val Gly Val
            515                 520                 525

Val Leu Gln Asp Asn Val Leu Leu Asn Arg Ser Ile Arg Asp Asn Ile
            530                 535                 540

Ala Leu Ala Asp Pro Gly Met Pro Met Glu Lys Ile Val His Ala Ala
545                 550                 555                 560

Lys Leu Ala Gly Ala His Glu Phe Ile Ser Glu Leu Arg Glu Gly Tyr
            565                 570                 575

Asn Thr Ile Val Gly Glu Gln Gly Ala Gly Leu Ser Gly Gly Gln Arg
            580                 585                 590

Gln Arg Ile Ala Ile Ala Arg Ala Leu Val Asn Asn Pro Lys Ile Leu
            595                 600                 605

Ile Phe Asp Glu Ala Thr Ser Ala Leu Asp Tyr Glu Ser Glu His Ile
            610                 615                 620

Ile Met Arg Asn Met His Gln Ile Cys Lys Gly Arg Thr Val Ile Ile
625                 630                 635                 640

Ile Ala His Arg Leu Ser Thr Val Lys Asn Ala Asp Arg Ile Ile Val
            645                 650                 655

Met Glu Lys Gly Gln Ile Val Glu Gln Gly Lys His Lys Glu Leu Leu
            660                 665                 670

Ala Asp Pro Asn Gly Leu Tyr His Tyr Leu His Gln Leu Gln Ser
            675                 680                 685
```

<210> SEQ ID NO 174
<211> LENGTH: 222
<212> TYPE: PRT
<213> ORGANISM: Artificial Sequence
<220> FEATURE:
<223> OTHER INFORMATION: Description of Artificial Sequence: ORF39
<220> FEATURE:
<221> NAME/KEY: SITE
<222> LOCATION: (17)..(33)

```
<223> OTHER INFORMATION: place-holder
<220> FEATURE:
<221> NAME/KEY: SITE
<222> LOCATION: (53)..(67)
<223> OTHER INFORMATION: place-holder
<220> FEATURE:
<221> NAME/KEY: SITE
<222> LOCATION: (211)
<223> OTHER INFORMATION: place-holder

<400> SEQUENCE: 174

Lys Phe Asp Phe Thr Trp Phe Ile Pro Ala Val Ile Lys Tyr Arg Arg
 1               5                  10                  15

Xaa Xaa Xaa Xaa Xaa Xaa Xaa Xaa Xaa Xaa Xaa Xaa Xaa Xaa Xaa Xaa
                20                  25                  30

Xaa Ile Thr Pro Leu Phe Phe Gln Val Val Met Asp Lys Val Leu Val
         35                  40                  45

His Arg Gly Phe Xaa Xaa Xaa Xaa Xaa Xaa Xaa Xaa Xaa Xaa Xaa Xaa
     50                  55                  60

Xaa Xaa Xaa Phe Glu Ile Val Leu Gly Gly Leu Arg Thr Tyr Leu Phe
 65                  70                  75                  80

Ala His Thr Thr Ser Arg Ile Asp Val Glu Leu Gly Ala Arg Leu Phe
                 85                  90                  95

Arg His Leu Leu Ser Leu Pro Leu Ser Tyr Phe Glu His Arg Arg Val
            100                 105                 110

Gly Asp Thr Val Ala Arg Val Arg Glu Leu Glu Gln Ile Arg Asn Phe
        115                 120                 125

Leu Thr Gly Gln Ala Leu Thr Ser Val Leu Asp Leu Ala Phe Ser Phe
130                 135                 140

Ile Phe Leu Ala Val Met Trp Tyr Tyr Ser Ser Thr Leu Thr Trp Val
145                 150                 155                 160

Val Leu Ala Ser Leu Ile Cys Ile Cys Ala Asn Arg Thr Val Leu Ile
                165                 170                 175

Ile Ala His Arg Leu Ser Thr Val Lys Thr Ala His Arg Ile Ile Ala
            180                 185                 190

Met Asp Lys Gly Arg Ile Val Glu Ala Gly Thr Gln Gln Leu Leu
        195                 200                 205

Ala Asn Xaa Asn Gly Tyr Tyr Arg Tyr Leu Tyr Asp Leu Gln
210                 215                 220

<210> SEQ ID NO 175
<211> LENGTH: 222
<212> TYPE: PRT
<213> ORGANISM: Artificial Sequence
<220> FEATURE:
<223> OTHER INFORMATION: Description of Artificial Sequence: overlap
      identity
<220> FEATURE:
<221> NAME/KEY: SITE
<222> LOCATION: (16)..(33)
<223> OTHER INFORMATION: absent or positive
<220> FEATURE:
<221> NAME/KEY: SITE
<222> LOCATION: (53)..(67)
<223> OTHER INFORMATION: absent or positive
<220> FEATURE:
<221> NAME/KEY: SITE
<222> LOCATION: (71)
<223> OTHER INFORMATION: absent or positive
<220> FEATURE:
<221> NAME/KEY: SITE
<222> LOCATION: (79)
<223> OTHER INFORMATION: absent or positive
<220> FEATURE:
```

-continued

```
<221> NAME/KEY: SITE
<222> LOCATION: (83)
<223> OTHER INFORMATION: absent or positive
<220> FEATURE:
<221> NAME/KEY: SITE
<222> LOCATION: (101)
<223> OTHER INFORMATION: absent or positive
<220> FEATURE:
<221> NAME/KEY: SITE
<222> LOCATION: (104)
<223> OTHER INFORMATION: absent or positive
<220> FEATURE:
<221> NAME/KEY: SITE
<222> LOCATION: (109)
<223> OTHER INFORMATION: absent or positive
<220> FEATURE:
<221> NAME/KEY: SITE
<222> LOCATION: (123)
<223> OTHER INFORMATION: absent or positive
<220> FEATURE:
<221> NAME/KEY: SITE
<222> LOCATION: (137)
<223> OTHER INFORMATION: absent or positive
<220> FEATURE:
<221> NAME/KEY: SITE
<222> LOCATION: (141)
<223> OTHER INFORMATION: absent or positive
<220> FEATURE:
<221> NAME/KEY: SITE
<222> LOCATION: (147)
<223> OTHER INFORMATION: absent or positive
<220> FEATURE:
<221> NAME/KEY: SITE
<222> LOCATION: (155)..(156)
<223> OTHER INFORMATION: absent or positive
<220> FEATURE:
<221> NAME/KEY: SITE
<222> LOCATION: (159)
<223> OTHER INFORMATION: absent or positive
<220> FEATURE:
<221> NAME/KEY: SITE
<222> LOCATION: (163)
<223> OTHER INFORMATION: absent or positive
<220> FEATURE:
<221> NAME/KEY: SITE
<222> LOCATION: (166)
<223> OTHER INFORMATION: absent or positive
<220> FEATURE:
<221> NAME/KEY: SITE
<222> LOCATION: (170)
<223> OTHER INFORMATION: absent or positive
<220> FEATURE:
<221> NAME/KEY: SITE
<222> LOCATION: (186)
<223> OTHER INFORMATION: absent or positive
<220> FEATURE:
<221> NAME/KEY: SITE
<222> LOCATION: (188)
<223> OTHER INFORMATION: absent or positive
<220> FEATURE:
<221> NAME/KEY: SITE
<222> LOCATION: (192)
<223> OTHER INFORMATION: absent or positive
<220> FEATURE:
<221> NAME/KEY: SITE
<222> LOCATION: (197)
<223> OTHER INFORMATION: absent or positive
<220> FEATURE:
<221> NAME/KEY: SITE
<222> LOCATION: (199)
<223> OTHER INFORMATION: absent or positive
<220> FEATURE:
<221> NAME/KEY: SITE
<222> LOCATION: (201)
<223> OTHER INFORMATION: absent or positive
<220> FEATURE:
<221> NAME/KEY: SITE
<222> LOCATION: (203)..(204)
<223> OTHER INFORMATION: absent or positive
```

```
<220> FEATURE:
<221> NAME/KEY: SITE
<222> LOCATION: (209)..(212)
<223> OTHER INFORMATION: absent or positive
<220> FEATURE:
<221> NAME/KEY: SITE
<222> LOCATION: (214)
<223> OTHER INFORMATION: absent or positive
<220> FEATURE:
<221> NAME/KEY: SITE
<222> LOCATION: (216)
<223> OTHER INFORMATION: absent or positive
<220> FEATURE:
<221> NAME/KEY: SITE
<222> LOCATION: (219)..(220)
<223> OTHER INFORMATION: absent or positive

<400> SEQUENCE: 175

Lys Phe Asp Phe Thr Trp Phe Ile Pro Ala Val Ile Lys Tyr Arg Xaa
 1               5                  10                  15

Xaa Xaa Xaa Xaa Xaa Xaa Xaa Xaa Xaa Xaa Xaa Xaa Xaa Xaa Xaa Xaa
            20                  25                  30

Xaa Ile Thr Pro Leu Phe Phe Gln Val Val Met Asp Lys Val Leu Val
        35                  40                  45

His Arg Gly Phe Xaa Xaa Xaa Xaa Xaa Xaa Xaa Xaa Xaa Xaa Xaa Xaa
    50                  55                  60

Xaa Xaa Xaa Phe Glu Ile Xaa Leu Gly Gly Leu Arg Thr Tyr Xaa Phe
65                  70                  75                  80

Ala His Xaa Thr Ser Arg Ile Asp Val Glu Leu Gly Ala Arg Leu Phe
                85                  90                  95

Arg His Leu Leu Xaa Leu Pro Xaa Ser Tyr Phe Glu Xaa Arg Arg Val
            100                 105                 110

Gly Asp Thr Val Ala Arg Val Arg Glu Leu Xaa Gln Ile Arg Asn Phe
            115                 120                 125

Leu Thr Gly Gln Ala Leu Thr Ser Xaa Leu Asp Leu Xaa Phe Ser Phe
        130                 135                 140

Ile Phe Xaa Ala Val Met Trp Tyr Tyr Ser Xaa Xaa Leu Thr Xaa Val
145                 150                 155                 160

Val Leu Xaa Ser Leu Xaa Cys Ile Cys Xaa Asn Arg Thr Val Leu Ile
                165                 170                 175

Ile Ala His Arg Leu Ser Thr Val Lys Xaa Ala Xaa Arg Ile Ile Xaa
            180                 185                 190

Met Asp Lys Gly Xaa Ile Xaa Glu Xaa Gly Xaa Xaa Gln Glu Leu Leu
        195                 200                 205

Xaa Xaa Xaa Xaa Gly Xaa Tyr Xaa Tyr Leu Xaa Xaa Leu Gln
    210                 215                 220

<210> SEQ ID NO 176
<211> LENGTH: 222
<212> TYPE: PRT
<213> ORGANISM: Artificial Sequence
<220> FEATURE:
<223> OTHER INFORMATION: Description of Artificial Sequence: HlyB

<400> SEQUENCE: 176

Lys Phe Asp Phe Thr Trp Phe Ile Pro Ala Val Ile Lys Tyr Arg Lys
 1               5                  10                  15

Ile Phe Ile Glu Thr Leu Ile Val Ser Ile Phe Leu Gln Ile Phe Ala
            20                  25                  30

Leu Ile Thr Pro Leu Phe Phe Gln Val Val Met Asp Lys Val Leu Val
        35                  40                  45
```

```
His Arg Gly Phe Ser Thr Leu Asn Val Ile Thr Val Ala Leu Ala Ile
         50                  55                  60

Val Val Leu Phe Glu Ile Ile Leu Gly Gly Leu Arg Thr Tyr Val Phe
 65                  70                  75                  80

Ala His Ser Thr Ser Arg Ile Asp Val Glu Leu Gly Ala Arg Leu Phe
                 85                  90                  95

Arg His Leu Leu Ala Leu Pro Ile Ser Tyr Phe Glu Ala Arg Arg Val
            100                 105                 110

Gly Asp Thr Val Ala Arg Val Arg Glu Leu Asp Gln Ile Arg Asn Phe
            115                 120                 125

Leu Thr Gly Gln Ala Leu Thr Ser Ile Leu Asp Leu Leu Phe Ser Phe
130                 135                 140

Ile Phe Phe Ala Val Met Trp Tyr Tyr Ser Pro Lys Leu Thr Leu Val
145                 150                 155                 160

Val Leu Gly Ser Leu Pro Cys Ile Cys Gln Asn Arg Thr Val Leu Ile
                165                 170                 175

Ile Ala His Arg Leu Ser Thr Val Lys Asn Ala Asp Arg Ile Ile Val
            180                 185                 190

Met Asp Lys Gly Glu Ile Ile Glu Gln Gly Lys His Gln Glu Leu Leu
            195                 200                 205

Lys Asp Glu Lys Gly Leu Tyr Ser Tyr Leu His Gln Leu Gln
            210                 215                 220

<210> SEQ ID NO 177
<211> LENGTH: 240
<212> TYPE: PRT
<213> ORGANISM: Artificial Sequence
<220> FEATURE:
<223> OTHER INFORMATION: Description of Artificial Sequence: ORF112a
<220> FEATURE:
<221> NAME/KEY: SITE
<222> LOCATION: (50)
<223> OTHER INFORMATION: place-holder
<220> FEATURE:
<221> NAME/KEY: SITE
<222> LOCATION: (58)
<223> OTHER INFORMATION: place-holder
<220> FEATURE:
<221> NAME/KEY: SITE
<222> LOCATION: (77)
<223> OTHER INFORMATION: place-holder
<220> FEATURE:
<221> NAME/KEY: SITE
<222> LOCATION: (87)
<223> OTHER INFORMATION: place-holder
<220> FEATURE:
<221> NAME/KEY: SITE
<222> LOCATION: (223)
<223> OTHER INFORMATION: place-holder

<400> SEQUENCE: 177

Met Asn Leu Ile Ser Arg Tyr Ile Ile Arg Gln Met Ala Val Met Ala
  1               5                  10                  15

Val Tyr Ala Leu Leu Ala Phe Leu Ala Leu Tyr Ser Phe Phe Glu Ile
                 20                  25                  30

Leu Tyr Glu Thr Gly Asn Leu Gly Lys Gly Ser Tyr Gly Ile Trp Glu
             35                  40                  45

Met Xaa Gly Tyr Thr Ala Leu Lys Met Xaa Ala Arg Ala Tyr Glu Leu
         50                  55                  60

Met Pro Leu Ala Val Leu Ile Gly Gly Leu Val Ser Xaa Ser Gln Leu
 65                  70                  75                  80
```

```
Ala Ala Gly Ser Glu Leu Xaa Val Ile Lys Ala Ser Gly Met Ser Thr
                85                  90                  95

Lys Lys Leu Leu Leu Ile Leu Ser Gln Phe Gly Phe Ile Phe Ala Ile
            100                 105                 110

Ala Thr Val Ala Leu Gly Glu Trp Val Ala Pro Thr Leu Ser Gln Lys
            115                 120                 125

Ala Glu Asn Ile Lys Ala Ala Ile Asn Gly Lys Ile Ser Thr Gly
        130                 135                 140

Asn Thr Gly Leu Trp Leu Lys Glu Lys Asn Ser Ile Ile Asn Val Arg
145                 150                 155                 160

Glu Met Leu Pro Asp His Thr Leu Leu Gly Ile Lys Ile Trp Ala Arg
                165                 170                 175

Asn Asp Lys Asn Glu Leu Ala Glu Ala Val Glu Ala Asp Ser Ala Val
            180                 185                 190

Leu Asn Ser Asp Gly Ser Trp Gln Leu Lys Asn Ile Arg Arg Ser Thr
            195                 200                 205

Leu Gly Glu Asp Lys Val Glu Val Ser Ile Ala Ala Glu Glu Xaa Trp
    210                 215                 220

Pro Ile Ser Val Lys Arg Asn Leu Met Asp Val Leu Leu Val Lys Pro
225                 230                 235                 240
```

<210> SEQ ID NO 178
<211> LENGTH: 360
<212> TYPE: PRT
<213> ORGANISM: Artificial Sequence
<220> FEATURE:
<223> OTHER INFORMATION: Description of Artificial Sequence: ORF114a
<220> FEATURE:
<221> NAME/KEY: SITE
<222> LOCATION: (68)..(73)
<223> OTHER INFORMATION: place-holder
<220> FEATURE:
<221> NAME/KEY: SITE
<222> LOCATION: (85)
<223> OTHER INFORMATION: place-holder
<220> FEATURE:
<221> NAME/KEY: SITE
<222> LOCATION: (296)
<223> OTHER INFORMATION: place-holder
<220> FEATURE:
<221> NAME/KEY: SITE
<222> LOCATION: (343)
<223> OTHER INFORMATION: place-holder
<220> FEATURE:
<221> NAME/KEY: SITE
<222> LOCATION: (352)
<223> OTHER INFORMATION: place-holder

<400> SEQUENCE: 178

```
Met Asn Lys Gly Leu His Arg Ile Ile Phe Ser Lys Lys His Ser Thr
1               5                   10                  15

Met Val Ala Val Ala Glu Thr Ala Asn Ser Gln Gly Lys Gly Lys Gln
            20                  25                  30

Ala Gly Ser Ser Val Ser Val Ser Leu Lys Thr Ser Gly Asp Leu Cys
        35                  40                  45

Gly Lys Leu Lys Thr Thr Leu Lys Thr Leu Val Cys Ser Leu Val Ser
50                  55                  60

Leu Ser Met Xaa Xaa Xaa Xaa Xaa Gln Ile Thr Thr Asp Lys Ser
65                  70                  75                  80

Ala Pro Lys Asn Xaa Gln Val Val Ile Leu Lys Thr Asn Thr Gly Ala
                85                  90                  95

Pro Leu Val Asn Ile Gln Thr Pro Asn Gly Arg Gly Leu Ser His Asn
```

-continued

```
                100                 105                 110
Arg Tyr Thr Gln Phe Asp Val Asp Asn Lys Gly Ala Val Leu Asn Asn
        115                 120                 125

Asp Arg Asn Asn Asn Pro Phe Leu Val Lys Gly Ser Ala Gln Leu Ile
        130                 135                 140

Leu Asn Glu Val Arg Gly Thr Ala Ser Lys Leu Asn Gly Ile Val Thr
145                 150                 155                 160

Val Gly Gly Gln Lys Ala Asp Val Ile Ile Ala Asn Pro Asn Gly Ile
                165                 170                 175

Thr Val Asn Gly Gly Phe Lys Asn Val Gly Arg Gly Ile Leu Thr
            180                 185                 190

Ile Gly Ala Pro Gln Ile Gly Lys Asp Gly Ala Leu Thr Gly Phe Asp
        195                 200                 205

Val Arg Gln Gly Thr Leu Thr Val Gly Ala Ala Gly Trp Asn Asp Lys
    210                 215                 220

Gly Gly Ala Asp Tyr Thr Gly Val Leu Ala Arg Ala Val Ala Leu Gln
225                 230                 235                 240

Gly Lys Leu Gln Gly Lys Asn Leu Ala Val Ser Thr Gly Pro Gln Lys
                245                 250                 255

Val Asp Tyr Ala Ser Gly Glu Ile Ser Ala Gly Thr Ala Ala Gly Thr
            260                 265                 270

Lys Pro Thr Ile Ala Leu Asp Thr Ala Ala Leu Gly Gly Met Tyr Ala
        275                 280                 285

Asp Ser Ile Thr Leu Ile Ala Xaa Glu Lys Gly Val Gly Val Lys Asn
    290                 295                 300

Ala Gly Thr Leu Glu Ala Ala Lys Gln Leu Ile Val Thr Ser Ser Gly
305                 310                 315                 320

Arg Ile Glu Asn Ser Gly Arg Ile Ala Thr Thr Ala Asp Gly Thr Glu
                325                 330                 335

Ala Ser Pro Thr Tyr Leu Xaa Ile Glu Thr Thr Glu Lys Gly Ala Xaa
            340                 345                 350

Gly Thr Phe Ile Ser Asn Gly Gly
        355                 360

<210> SEQ ID NO 179
<211> LENGTH: 1574
<212> TYPE: PRT
<213> ORGANISM: Artificial Sequence
<220> FEATURE:
<223> OTHER INFORMATION: Description of Artificial Sequence: ORF114-1

<400> SEQUENCE: 179

Met Asn Lys Gly Leu His Arg Ile Ile Phe Ser Lys Lys His Ser Thr
1               5                   10                  15

Met Val Ala Val Ala Glu Thr Ala Asn Ser Gln Gly Lys Gly Lys Gln
            20                  25                  30

Ala Gly Ser Ser Val Ser Val Ser Leu Lys Thr Ser Gly Asp Leu Cys
        35                  40                  45

Gly Lys Leu Lys Thr Thr Leu Lys Thr Leu Val Cys Ser Leu Val Ser
    50                  55                  60

Leu Ser Met Val Leu Pro Ala His Ala Gln Ile Thr Thr Asp Lys Ser
65                  70                  75                  80

Ala Pro Lys Asn Gln Gln Val Val Ile Leu Lys Thr Asn Thr Gly Ala
                85                  90                  95

Pro Leu Val Asn Ile Gln Thr Pro Asn Gly Arg Gly Leu Ser His Asn
```

-continued

```
                100             105             110
Arg Tyr Thr Gln Phe Asp Val Asp Asn Lys Gly Ala Val Leu Asn Asn
            115             120             125

Asp Arg Asn Asn Asn Pro Phe Val Val Lys Gly Ser Ala Gln Leu Ile
            130             135             140

Leu Asn Glu Val Arg Gly Thr Ala Ser Lys Leu Asn Gly Ile Val Thr
145             150             155             160

Val Gly Gly Gln Lys Ala Asp Val Ile Ile Ala Asn Pro Asn Gly Ile
            165             170             175

Thr Val Asn Gly Gly Phe Lys Asn Val Gly Arg Gly Ile Leu Thr
            180             185             190

Thr Gly Ala Pro Gln Ile Gly Lys Asp Gly Ala Leu Thr Gly Phe Asp
            195             200             205

Val Arg Gln Gly Thr Leu Thr Val Gly Ala Ala Gly Trp Asn Asp Lys
            210             215             220

Gly Gly Ala Asp Tyr Thr Gly Val Leu Ala Arg Ala Val Ala Leu Gln
225             230             235             240

Gly Lys Leu Gln Gly Lys Asn Leu Ala Val Ser Thr Gly Pro Gln Lys
            245             250             255

Val Asp Tyr Ala Ser Gly Glu Ile Ser Ala Gly Thr Ala Ala Gly Thr
            260             265             270

Lys Pro Thr Ile Ala Leu Asp Thr Ala Ala Leu Gly Gly Met Tyr Ala
            275             280             285

Asp Ser Ile Thr Leu Ile Ala Asn Glu Lys Gly Val Gly Val Lys Asn
            290             295             300

Ala Gly Thr Leu Glu Ala Ala Lys Gln Leu Ile Val Thr Ser Ser Gly
305             310             315             320

Arg Ile Glu Asn Ser Gly Arg Ile Ala Thr Thr Ala Asp Gly Thr Glu
            325             330             335

Ala Ser Pro Thr Tyr Leu Ser Ile Glu Thr Thr Glu Lys Gly Ala Ala
            340             345             350

Gly Thr Phe Ile Ser Asn Gly Gly Arg Ile Glu Ser Lys Gly Leu Leu
            355             360             365

Val Ile Glu Thr Gly Glu Asp Ile Ser Leu Arg Asn Gly Ala Val Val
            370             375             380

Gln Asn Asn Gly Ser Arg Pro Ala Thr Thr Val Leu Asn Ala Gly His
385             390             395             400

Asn Leu Val Ile Glu Ser Lys Thr Asn Val Asn Asn Ala Lys Gly Pro
            405             410             415

Ala Thr Leu Ser Ala Asp Gly Arg Thr Val Ile Lys Glu Ala Ser Ile
            420             425             430

Gln Thr Gly Thr Thr Val Tyr Ser Ser Lys Gly Asn Ala Glu Leu
            435             440             445

Gly Asn Asn Thr Arg Ile Thr Gly Ala Asp Val Thr Val Leu Ser Asn
            450             455             460

Gly Thr Ile Ser Ser Ala Val Ile Asp Ala Lys Asp Thr Ala His
465             470             475             480

Ile Glu Ala Gly Lys Pro Leu Ser Leu Glu Ala Ser Thr Val Thr Ser
            485             490             495

Asp Ile Arg Leu Asn Gly Gly Ser Ile Lys Gly Gly Lys Gln Leu Ala
            500             505             510

Leu Leu Ala Asp Asp Asn Ile Thr Ala Lys Thr Thr Asn Leu Asn Thr
515             520             525
```

-continued

```
Pro Gly Asn Leu Tyr Val His Thr Gly Lys Asp Leu Asn Leu Asn Val
    530                 535                 540
Asp Lys Asp Leu Ser Ala Ala Ser Ile His Leu Lys Ser Asp Asn Ala
545                 550                 555                 560
Ala His Ile Thr Gly Thr Ser Lys Thr Leu Thr Ala Ser Lys Asp Met
                565                 570                 575
Gly Val Glu Ala Gly Ser Leu Asn Val Thr Asn Thr Asn Leu Arg Thr
            580                 585                 590
Asn Ser Gly Asn Leu His Ile Gln Ala Ala Lys Gly Asn Ile Gln Leu
        595                 600                 605
Arg Asn Thr Lys Leu Asn Ala Ala Lys Ala Leu Glu Thr Thr Ala Leu
    610                 615                 620
Gln Gly Asn Ile Val Ser Asp Gly Leu His Ala Val Ser Ala Asp Gly
625                 630                 635                 640
His Val Ser Leu Leu Ala Asn Gly Asn Ala Asp Phe Thr Gly His Asn
                645                 650                 655
Thr Leu Thr Ala Lys Ala Asp Val Asn Ala Gly Ser Val Gly Lys Gly
            660                 665                 670
Arg Leu Lys Ala Asp Asn Thr Asn Ile Thr Ser Ser Gly Asp Ile
        675                 680                 685
Thr Leu Val Ala Gly Asn Gly Ile Gln Leu Gly Asp Gly Lys Gln Arg
    690                 695                 700
Asn Ser Ile Asn Gly Lys His Ile Ser Ile Lys Asn Asn Gly Gly Asn
705                 710                 715                 720
Ala Asp Leu Lys Asn Leu Asn Val His Ala Lys Ser Gly Ala Leu Asn
                725                 730                 735
Ile His Ser Asp Arg Ala Leu Ser Ile Glu Asn Thr Lys Leu Glu Ser
            740                 745                 750
Thr His Asn Thr His Leu Asn Ala Gln His Glu Arg Val Thr Leu Asn
        755                 760                 765
Gln Val Asp Ala Tyr Ala His Arg His Leu Ser Ile Thr Gly Ser Gln
    770                 775                 780
Ile Trp Gln Asn Asp Lys Leu Pro Ser Ala Asn Lys Leu Val Ala Asn
785                 790                 795                 800
Gly Val Leu Ala Leu Asn Ala Arg Tyr Ser Gln Ile Ala Asp Asn Thr
                805                 810                 815
Thr Leu Arg Ala Gly Ala Ile Asn Leu Thr Ala Gly Thr Ala Leu Val
            820                 825                 830
Lys Arg Gly Asn Ile Asn Trp Ser Thr Val Ser Thr Lys Thr Leu Glu
        835                 840                 845
Asp Asn Ala Glu Leu Lys Pro Leu Ala Gly Arg Leu Asn Ile Glu Ala
    850                 855                 860
Gly Ser Gly Thr Leu Thr Ile Glu Pro Ala Asn Arg Ile Ser Ala His
865                 870                 875                 880
Thr Asp Leu Ser Ile Lys Thr Gly Gly Lys Leu Leu Leu Ser Ala Lys
                885                 890                 895
Gly Gly Asn Ala Gly Ala Pro Ser Ala Gln Val Ser Ser Leu Glu Ala
            900                 905                 910
Lys Gly Asn Ile Arg Leu Val Thr Gly Glu Thr Asp Leu Arg Gly Ser
        915                 920                 925
Lys Ile Thr Ala Gly Lys Asn Leu Val Val Ala Thr Thr Lys Gly Lys
    930                 935                 940
```

-continued

```
Leu Asn Ile Glu Ala Val Asn Ser Phe Ser Asn Tyr Phe Pro Thr
945                 950                 955                 960

Gln Lys Ala Ala Glu Leu Asn Gln Lys Ser Lys Glu Leu Glu Gln Gln
                965                 970                 975

Ile Ala Gln Leu Lys Lys Ser Ser Pro Lys Ser Lys Leu Ile Pro Thr
            980                 985                 990

Leu Gln Glu Glu Arg Asp Arg Leu Ala Phe Tyr Ile Gln Ala Ile Asn
        995                 1000                1005

Lys Glu Val Lys Gly Lys Lys Pro Lys Gly Lys Glu Tyr Leu Gln Ala
    1010                1015                1020

Lys Leu Ser Ala Gln Asn Ile Asp Leu Ile Ser Ala Gln Gly Ile Glu
1025                1030                1035                1040

Ile Ser Gly Ser Asp Ile Thr Ala Ser Lys Lys Leu Asn Leu His Ala
            1045                1050                1055

Ala Gly Val Leu Pro Lys Ala Ala Asp Ser Glu Ala Ala Ala Ile Leu
        1060                1065                1070

Ile Asp Gly Ile Thr Asp Gln Tyr Glu Ile Gly Lys Pro Thr Tyr Lys
    1075                1080                1085

Ser His Tyr Asp Lys Ala Ala Leu Asn Lys Pro Ser Arg Leu Thr Gly
    1090                1095                1100

Arg Thr Gly Val Ser Ile His Ala Ala Ala Leu Asp Asp Ala Arg
1105                1110                1115                1120

Ile Ile Ile Gly Ala Ser Glu Ile Lys Ala Pro Ser Gly Ser Ile Asp
            1125                1130                1135

Ile Lys Ala His Ser Asp Ile Val Leu Glu Ala Gly Gln Asn Asp Ala
        1140                1145                1150

Tyr Thr Phe Leu Lys Thr Lys Gly Lys Ser Gly Lys Ile Ile Arg Lys
    1155                1160                1165

Thr Lys Phe Thr Ser Thr Arg Asp His Leu Ile Met Pro Ala Pro Val
    1170                1175                1180

Glu Leu Thr Ala Asn Gly Ile Thr Leu Gln Ala Gly Gly Asn Ile Glu
1185                1190                1195                1200

Ala Asn Thr Thr Arg Phe Asn Ala Pro Ala Gly Lys Val Thr Leu Val
        1205                1210                1215

Ala Gly Glu Glu Leu Gln Leu Leu Ala Glu Glu Gly Ile His Lys His
        1220                1225                1230

Glu Leu Asp Val Gln Lys Ser Arg Arg Phe Ile Gly Ile Lys Val Gly
        1235                1240                1245

Lys Ser Asn Tyr Ser Lys Asn Glu Leu Asn Glu Thr Lys Leu Pro Val
    1250                1255                1260

Arg Val Val Ala Gln Thr Ala Thr Arg Ser Gly Trp Asp Thr Val
1265                1270                1275                1280

Leu Glu Gly Thr Glu Phe Lys Thr Thr Leu Ala Gly Ala Asp Ile Gln
        1285                1290                1295

Ala Gly Val Gly Glu Lys Ala Arg Ala Asp Ala Lys Ile Ile Leu Lys
        1300                1305                1310

Gly Ile Val Asn Arg Ile Gln Ser Glu Glu Lys Leu Glu Thr Asn Ser
    1315                1320                1325

Thr Val Trp Gln Lys Gln Ala Gly Arg Gly Ser Thr Ile Glu Thr Leu
    1330                1335                1340

Lys Leu Pro Ser Phe Glu Ser Pro Thr Pro Lys Leu Thr Ala Pro
1345                1350                1355                1360

Gly Gly Tyr Ile Val Asp Ile Pro Lys Gly Asn Leu Lys Thr Glu Ile
```

-continued

```
                  1365                1370                1375

Glu Lys Leu Ala Lys Gln Pro Glu Tyr Ala Tyr Leu Lys Gln Leu Gln
        1380                1385                1390

Val Ala Lys Asn Val Asn Trp Asn Gln Val Gln Leu Ala Tyr Asp Lys
    1395                1400                1405

Trp Asp Tyr Lys Gln Glu Gly Leu Thr Arg Ala Gly Ala Ala Ile Val
1410                1415                1420

Thr Ile Ile Val Thr Ala Leu Thr Tyr Gly Tyr Gly Ala Thr Ala Ala
1425                1430                1435                1440

Gly Gly Val Ala Ala Ser Gly Ser Ser Thr Ala Ala Ala Gly Thr
            1445                1450                1455

Ala Ala Thr Thr Thr Ala Ala Ala Thr Thr Val Ser Thr Ala Thr Ala
        1460                1465                1470

Met Gln Thr Ala Ala Leu Ala Ser Leu Tyr Ser Gln Ala Ala Val Ser
    1475                1480                1485

Ile Ile Asn Asn Lys Gly Asp Val Gly Lys Ala Leu Lys Asp Leu Gly
    1490                1495                1500

Thr Ser Asp Thr Val Lys Gln Ile Val Thr Ser Ala Leu Thr Ala Gly
1505                1510                1515                1520

Ala Leu Asn Gln Met Gly Ala Asp Ile Ala Gln Leu Asn Ser Lys Val
            1525                1530                1535

Arg Thr Glu Leu Phe Ser Ser Thr Gly Asn Gln Thr Ile Ala Asn Leu
        1540                1545                1550

Gly Gly Arg Leu Ala Thr Asn Leu Ser Asn Ala Gly Ile Ser Ala Gly
        1555                1560                1565

Ile Asn Thr Ala Val Asn
    1570

<210> SEQ ID NO 180
<211> LENGTH: 281
<212> TYPE: PRT
<213> ORGANISM: Artificial Sequence
<220> FEATURE:
<223> OTHER INFORMATION: Description of Artificial Sequence: ORF114
<220> FEATURE:
<221> NAME/KEY: SITE
<222> LOCATION: (29)..(51)
<223> OTHER INFORMATION: place-holder
<220> FEATURE:
<221> NAME/KEY: SITE
<222> LOCATION: (96)
<223> OTHER INFORMATION: place-holder
<220> FEATURE:
<221> NAME/KEY: SITE
<222> LOCATION: (199)
<223> OTHER INFORMATION: place-holder
<220> FEATURE:
<221> NAME/KEY: SITE
<222> LOCATION: (210)
<223> OTHER INFORMATION: place-holder
<220> FEATURE:
<221> NAME/KEY: SITE
<222> LOCATION: (225)..(226)
<223> OTHER INFORMATION: place-holder
<220> FEATURE:
<221> NAME/KEY: SITE
<222> LOCATION: (229)
<223> OTHER INFORMATION: place-holder

<400> SEQUENCE: 180

Ala Val Ala Glu Thr Ala Asn Ser Gln Gly Lys Gly Lys Gln Ala Gly
1               5                   10                  15

Ser Ser Val Ser Val Ser Leu Lys Thr Ser Gly Asp Xaa Xaa Xaa Xaa
```

```
                20                  25                  30
Xaa Xaa Xaa Xaa Xaa Xaa Xaa Xaa Xaa Xaa Xaa Xaa Xaa Xaa
        35                  40                  45
Xaa Xaa Xaa Pro Ala His Ala Gln Ile Thr Thr Asp Lys Ser Ala Pro
    50                  55                  60
Lys Asn Gln Gln Val Val Ile Leu Lys Thr Asn Thr Gly Ala Pro Leu
 65                  70                  75                  80
Val Asn Ile Gln Thr Pro Asn Gly Arg Gly Leu Ser His Asn Arg Xaa
                85                  90                  95
Tyr Ala Phe Asp Val Asp Asn Lys Gly Ala Val Leu Asn Asn Asp Arg
            100                 105                 110
Asn Asn Asn Pro Phe Val Val Lys Gly Ser Ala Gln Leu Ile Leu Asn
        115                 120                 125
Glu Val Arg Gly Thr Ala Ser Lys Leu Asn Gly Ile Val Thr Val Gly
    130                 135                 140
Gly Gln Lys Ala Asp Val Ile Ile Ala Asn Pro Asn Gly Ile Thr Val
145                 150                 155                 160
Asn Gly Gly Gly Phe Lys Asn Val Gly Arg Gly Ile Leu Thr Thr Gly
                165                 170                 175
Ala Pro Gln Ile Gly Lys Asp Gly Ala Leu Thr Gly Phe Asp Val Val
            180                 185                 190
Lys Ala His Trp Thr Val Xaa Ala Ala Gly Trp Asn Asp Lys Gly Gly
        195                 200                 205
Ala Xaa Tyr Thr Gly Val Leu Ala Arg Ala Val Ala Leu Gln Gly Lys
    210                 215                 220
Xaa Xaa Gly Lys Xaa Leu Ala Val Ser Thr Gly Pro Gln Lys Val Asp
225                 230                 235                 240
Tyr Ala Ser Gly Glu Ile Ser Ala Gly Thr Ala Ala Gly Thr Lys Pro
                245                 250                 255
Thr Ile Ala Leu Asp Thr Ala Ala Leu Gly Gly Met Tyr Ala Asp Ser
            260                 265                 270
Ile Thr Leu Ile Ala Asn Glu Lys Gly
        275                 280

<210> SEQ ID NO 181
<211> LENGTH: 302
<212> TYPE: PRT
<213> ORGANISM: Artificial Sequence
<220> FEATURE:
<223> OTHER INFORMATION: Description of Artificial Sequence: overlap
      identity
<220> FEATURE:
<221> NAME/KEY: SITE
<222> LOCATION: (5)..(9)
<223> OTHER INFORMATION: absent or positive
<220> FEATURE:
<221> NAME/KEY: SITE
<222> LOCATION: (12)..(13)
<223> OTHER INFORMATION: absent or positive
<220> FEATURE:
<221> NAME/KEY: SITE
<222> LOCATION: (15)..(19)
<223> OTHER INFORMATION: absent or positive
<220> FEATURE:
<221> NAME/KEY: SITE
<222> LOCATION: (22)..(29)
<223> OTHER INFORMATION: absent or positive
<220> FEATURE:
<221> NAME/KEY: SITE
<222> LOCATION: (31)..(55)
<223> OTHER INFORMATION: absent or positive
<220> FEATURE:
```

```
<221> NAME/KEY: SITE
<222> LOCATION: (58)
<223> OTHER INFORMATION: absent or positive
<220> FEATURE:
<221> NAME/KEY: SITE
<222> LOCATION: (60)..(61)
<223> OTHER INFORMATION: absent or positive
<220> FEATURE:
<221> NAME/KEY: SITE
<222> LOCATION: (63)..(64)
<223> OTHER INFORMATION: absent or positive
<220> FEATURE:
<221> NAME/KEY: SITE
<222> LOCATION: (74)
<223> OTHER INFORMATION: absent or positive
<220> FEATURE:
<221> NAME/KEY: SITE
<222> LOCATION: (78)
<223> OTHER INFORMATION: absent or positive
<220> FEATURE:
<221> NAME/KEY: SITE
<222> LOCATION: (80)..(81)
<223> OTHER INFORMATION: absent or positive
<220> FEATURE:
<221> NAME/KEY: SITE
<222> LOCATION: (83)
<223> OTHER INFORMATION: absent or positive
<220> FEATURE:
<221> NAME/KEY: SITE
<222> LOCATION: (85)
<223> OTHER INFORMATION: absent or positive
<220> FEATURE:
<221> NAME/KEY: SITE
<222> LOCATION: (92)..(94)
<223> OTHER INFORMATION: absent or positive
<220> FEATURE:
<221> NAME/KEY: SITE
<222> LOCATION: (96)
<223> OTHER INFORMATION: absent or positive
<220> FEATURE:
<221> NAME/KEY: SITE
<222> LOCATION: (98)
<223> OTHER INFORMATION: absent or positive
<220> FEATURE:
<221> NAME/KEY: SITE
<222> LOCATION: (101)..(103)
<223> OTHER INFORMATION: absent or positive
<220> FEATURE:
<221> NAME/KEY: SITE
<222> LOCATION: (108)
<223> OTHER INFORMATION: absent or positive
<220> FEATURE:
<221> NAME/KEY: SITE
<222> LOCATION: (111)..(112)
<223> OTHER INFORMATION: absent or positive
<220> FEATURE:
<221> NAME/KEY: SITE
<222> LOCATION: (116)
<223> OTHER INFORMATION: absent or positive
<220> FEATURE:
<221> NAME/KEY: SITE
<222> LOCATION: (118)
<223> OTHER INFORMATION: absent or positive
<220> FEATURE:
<221> NAME/KEY: SITE
<222> LOCATION: (120)..(130)
<223> OTHER INFORMATION: absent or positive
<220> FEATURE:
<221> NAME/KEY: SITE
<222> LOCATION: (133)..(136)
<223> OTHER INFORMATION: absent or positive
<220> FEATURE:
<221> NAME/KEY: SITE
<222> LOCATION: (138)
<223> OTHER INFORMATION: absent or positive
<220> FEATURE:
<221> NAME/KEY: SITE
<222> LOCATION: (140)..(141)
<223> OTHER INFORMATION: absent or positive
```

-continued

```
<220> FEATURE:
<221> NAME/KEY: SITE
<222> LOCATION: (143)
<223> OTHER INFORMATION: absent or positive
<220> FEATURE:
<221> NAME/KEY: SITE
<222> LOCATION: (145)..(151)
<223> OTHER INFORMATION: absent or positive
<220> FEATURE:
<221> NAME/KEY: SITE
<222> LOCATION: (153)
<223> OTHER INFORMATION: absent or positive
<220> FEATURE:
<221> NAME/KEY: SITE
<222> LOCATION: (157)..(159)
<223> OTHER INFORMATION: absent or positive
<220> FEATURE:
<221> NAME/KEY: SITE
<222> LOCATION: (163)..(164)
<223> OTHER INFORMATION: absent or positive
<220> FEATURE:
<221> NAME/KEY: SITE
<222> LOCATION: (166)
<223> OTHER INFORMATION: absent or positive
<220> FEATURE:
<221> NAME/KEY: SITE
<222> LOCATION: (168)..(169)
<223> OTHER INFORMATION: absent or positive
<220> FEATURE:
<221> NAME/KEY: SITE
<222> LOCATION: (173)
<223> OTHER INFORMATION: absent or positive
<220> FEATURE:
<221> NAME/KEY: SITE
<222> LOCATION: (176)
<223> OTHER INFORMATION: absent or positive
<220> FEATURE:
<221> NAME/KEY: SITE
<222> LOCATION: (182)..(183)
<223> OTHER INFORMATION: absent or positive
<220> FEATURE:
<221> NAME/KEY: SITE
<222> LOCATION: (185)..(189)
<223> OTHER INFORMATION: absent or positive
<220> FEATURE:
<221> NAME/KEY: SITE
<222> LOCATION: (192)
<223> OTHER INFORMATION: absent or positive
<220> FEATURE:
<221> NAME/KEY: SITE
<222> LOCATION: (194)
<223> OTHER INFORMATION: absent or positive
<220> FEATURE:
<221> NAME/KEY: SITE
<222> LOCATION: (196)..(200)
<223> OTHER INFORMATION: absent or positive
<220> FEATURE:
<221> NAME/KEY: SITE
<222> LOCATION: (202)
<223> OTHER INFORMATION: absent or positive
<220> FEATURE:
<221> NAME/KEY: SITE
<222> LOCATION: (209)..(218)
<223> OTHER INFORMATION: absent or positive
<220> FEATURE:
<221> NAME/KEY: SITE
<222> LOCATION: (220)..(221)
<223> OTHER INFORMATION: absent or positive
<220> FEATURE:
<221> NAME/KEY: SITE
<222> LOCATION: (223)..(225)
<223> OTHER INFORMATION: absent or positive
<220> FEATURE:
<221> NAME/KEY: SITE
<222> LOCATION: (227)
<223> OTHER INFORMATION: absent or positive
<220> FEATURE:
<221> NAME/KEY: SITE
<222> LOCATION: (230)..(231)
```

```
<223> OTHER INFORMATION: absent or positive
<220> FEATURE:
<221> NAME/KEY: SITE
<222> LOCATION: (233)
<223> OTHER INFORMATION: absent or positive
<220> FEATURE:
<221> NAME/KEY: SITE
<222> LOCATION: (236)..(243)
<223> OTHER INFORMATION: absent or positive
<220> FEATURE:
<221> NAME/KEY: SITE
<222> LOCATION: (246)..(248)
<223> OTHER INFORMATION: absent or positive
<220> FEATURE:
<221> NAME/KEY: SITE
<222> LOCATION: (250)..(251)
<223> OTHER INFORMATION: absent or positive
<220> FEATURE:
<221> NAME/KEY: SITE
<222> LOCATION: (253)..(254)
<223> OTHER INFORMATION: absent or positive
<220> FEATURE:
<221> NAME/KEY: SITE
<222> LOCATION: (256)
<223> OTHER INFORMATION: absent or positive
<220> FEATURE:
<221> NAME/KEY: SITE
<222> LOCATION: (258)..(267)
<223> OTHER INFORMATION: absent or positive
<220> FEATURE:
<221> NAME/KEY: SITE
<222> LOCATION: (269)..(276)
<223> OTHER INFORMATION: absent or positive
<220> FEATURE:
<221> NAME/KEY: SITE
<222> LOCATION: (279)
<223> OTHER INFORMATION: absent or positive
<220> FEATURE:
<221> NAME/KEY: SITE
<222> LOCATION: (281)
<223> OTHER INFORMATION: absent or positive
<220> FEATURE:
<221> NAME/KEY: SITE
<222> LOCATION: (285)
<223> OTHER INFORMATION: absent or positive
<220> FEATURE:
<221> NAME/KEY: SITE
<222> LOCATION: (293)
<223> OTHER INFORMATION: absent or positive
<220> FEATURE:
<221> NAME/KEY: SITE
<222> LOCATION: (298)..(301)
<223> OTHER INFORMATION: absent or positive

<400> SEQUENCE: 181

Ala Val Ala Glu Xaa Xaa Xaa Xaa Xaa Gly Lys Xaa Xaa Gln Xaa Xaa
  1               5                  10                  15

Xaa Xaa Xaa Ser Val Xaa Xaa Xaa Xaa Xaa Xaa Xaa Ser Xaa Xaa
             20                  25                  30

Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Pro Ala Xaa Ala Xaa Xaa Ile Xaa Xaa
         50                  55                  60

Asp Lys Ser Ala Pro Lys Asn Gln Gln Xaa Val Ile Leu Xaa Thr Xaa
 65                  70                  75                  80

Xaa Gly Xaa Pro Xaa Val Asn Ile Gln Thr Pro Xaa Xaa Xaa Gly Xaa
                 85                  90                  95

Ser Xaa Asn Arg Xaa Xaa Xaa Phe Asp Val Asp Xaa Lys Gly Xaa Xaa
            100                 105                 110

Leu Asn Asn Xaa Arg Xaa Asn Xaa Xaa Xaa Xaa Xaa Xaa Xaa Xaa
            115                 120                 125
```

```
Xaa Xaa Asn Pro Xaa Xaa Xaa Gly Xaa Ala Xaa Xaa Ile Xaa Asn
    130                 135                 140

Xaa Xaa Xaa Xaa Xaa Xaa Ser Xaa Leu Asn Gly Xaa Xaa Xaa Val
145                 150                 155                 160

Gly Gly Xaa Xaa Ala Xaa Val Xaa Xaa Ala Asn Pro Xaa Gly Ile Xaa
            165                 170                 175

Val Asn Gly Gly Gly Xaa Xaa Asn Xaa Xaa Xaa Xaa Leu Thr Xaa
            180                 185                 190

Gly Xaa Pro Xaa Xaa Xaa Xaa Xaa Gly Xaa Leu Thr Gly Phe Asp Val
        195                 200                 205

Xaa Xaa Xaa Xaa Xaa Xaa Xaa Xaa Xaa Gly Xaa Xaa Asp Xaa Xaa
    210                 215                 220

Xaa Ala Xaa Tyr Thr Xaa Xaa Leu Xaa Arg Ala Xaa Xaa Xaa Xaa Xaa
225                 230                 235                 240

Xaa Xaa Xaa Gly Lys Xaa Xaa Xaa Val Xaa Xaa Gly Xaa Xaa Lys Xaa
            245                 250                 255

Asp Xaa Xaa Xaa Xaa Xaa Xaa Xaa Xaa Ala Xaa Xaa Xaa Xaa
        260                 265                 270

Xaa Xaa Xaa Xaa Pro Thr Xaa Ala Xaa Asp Thr Ala Xaa Leu Gly Gly
    275                 280                 285

Met Tyr Ala Asp Xaa Ile Thr Leu Ile Xaa Xaa Xaa Xaa Gly
        290                 295                 300

<210> SEQ ID NO 182
<211> LENGTH: 300
<212> TYPE: PRT
<213> ORGANISM: Artificial Sequence
<220> FEATURE:
<223> OTHER INFORMATION: Description of Artificial Sequence: pspA

<400> SEQUENCE: 182

Ala Val Ala Glu Asn Val His Arg Asp Gly Lys Ser Met Gln Asp Ser
 1               5                  10                  15

Glu Ala Ala Ser Val Arg Val Thr Gly Ala Ala Ser Val Ser Ser Ala
            20                  25                  30

Arg Ala Ala Phe Gly Phe Arg Met Ala Ala Phe Ser Val Met Leu Ala
        35                  40                  45

Leu Gly Val Ala Ala Phe Ser Pro Ala Pro Ala Ser Gly Ile Ile Ala
    50                  55                  60

Asp Lys Ser Ala Pro Lys Asn Gln Gln Ala Val Ile Leu Gln Thr Ala
 65                  70                  75                  80

Asn Gly Leu Pro Gln Val Asn Ile Gln Thr Pro Ser Ser Gln Gly Val
                85                  90                  95

Ser Val Asn Arg Phe Lys Gln Phe Asp Val Asp Glu Lys Gly Val Ile
            100                 105                 110

Leu Asn Asn Ser Arg Ser Asn Thr Gln Thr Gln Leu Gly Gly Trp Ile
        115                 120                 125

Gln Gly Asn Pro His Leu Ala Arg Gly Glu Ala Arg Val Ile Val Asn
    130                 135                 140

Gln Ile Asp Ser Ser Asn Pro Ser Leu Leu Asn Gly Tyr Ile Glu Val
145                 150                 155                 160

Gly Gly Lys Arg Ala Glu Val Val Ala Asn Pro Ser Gly Ile Arg
                165                 170                 175

Val Asn Gly Gly Gly Leu Ile Asn Ala Ala Ser Val Thr Leu Thr Ser
            180                 185                 190
```

-continued

```
Gly Val Pro Val Leu Asn Asn Gly Asn Leu Thr Gly Phe Asp Val Ser
            195                 200                 205
Ser Gly Lys Val Val Ile Gly Gly Lys Gly Leu Asp Thr Ser Asp Ala
        210                 215                 220
Asp Tyr Thr Arg Ile Leu Ser Arg Ala Ala Glu Ile Asn Ala Gly Val
225                 230                 235                 240
Trp Gly Lys Asp Val Lys Val Val Ser Gly Lys Asn Lys Leu Asp Phe
                245                 250                 255
Asp Gly Ser Leu Ala Lys Thr Ala Ser Ala Pro Ser Ser Ser Asp Ser
            260                 265                 270
Val Thr Pro Thr Val Ala Ile Asp Thr Ala Thr Leu Gly Gly Met Tyr
        275                 280                 285
Ala Asp Lys Ile Thr Leu Ile Ser Thr Asp Asn Gly
        290                 295                 300

<210> SEQ ID NO 183
<211> LENGTH: 628
<212> TYPE: PRT
<213> ORGANISM: Artificial Sequence
<220> FEATURE:
<223> OTHER INFORMATION: Description of Artificial Sequence: ORF114a
<220> FEATURE:
<221> NAME/KEY: SITE
<222> LOCATION: (47)..(73)
<223> OTHER INFORMATION: place-holder
<220> FEATURE:
<221> NAME/KEY: SITE
<222> LOCATION: (85)
<223> OTHER INFORMATION: place-holder
<220> FEATURE:
<221> NAME/KEY: SITE
<222> LOCATION: (296)
<223> OTHER INFORMATION: place-holder
<220> FEATURE:
<221> NAME/KEY: SITE
<222> LOCATION: (343)
<223> OTHER INFORMATION: place-holder
<220> FEATURE:
<221> NAME/KEY: SITE
<222> LOCATION: (352)
<223> OTHER INFORMATION: place-holder
<220> FEATURE:
<221> NAME/KEY: SITE
<222> LOCATION: (377)
<223> OTHER INFORMATION: place-holder
<220> FEATURE:
<221> NAME/KEY: SITE
<222> LOCATION: (417)
<223> OTHER INFORMATION: place-holder
<220> FEATURE:
<221> NAME/KEY: SITE
<222> LOCATION: (447)
<223> OTHER INFORMATION: place-holder
<220> FEATURE:
<221> NAME/KEY: SITE
<222> LOCATION: (582)..(593)
<223> OTHER INFORMATION: place-holder

<400> SEQUENCE: 183

Met Asn Lys Gly Leu His Arg Ile Ile Phe Ser Lys Lys His Ser Thr
1               5                   10                  15
Met Val Ala Val Ala Glu Thr Ala Asn Ser Gln Gly Lys Gly Lys Gln
            20                  25                  30
Ala Gly Ser Ser Val Ser Val Ser Leu Lys Thr Ser Gly Asp Xaa Xaa
        35                  40                  45
Xaa Xaa Xaa Xaa Xaa Xaa Xaa Xaa Xaa Xaa Xaa Xaa Xaa Xaa Xaa Xaa
    50                  55                  60
```

-continued

```
Xaa Xaa Xaa Xaa Xaa Xaa Xaa Xaa Gln Ile Thr Thr Asp Lys Ser
 65                  70                  75                  80

Ala Pro Lys Asn Xaa Gln Val Val Ile Leu Lys Thr Asn Thr Gly Ala
                 85                  90                  95

Pro Leu Val Asn Ile Gln Thr Pro Asn Gly Arg Gly Leu Ser His Asn
            100                 105                 110

Arg Tyr Thr Gln Phe Asp Val Asp Asn Lys Gly Ala Val Leu Asn Asn
        115                 120                 125

Asp Arg Asn Asn Asn Pro Phe Leu Val Lys Gly Ser Ala Gln Leu Ile
130                 135                 140

Leu Asn Glu Val Arg Gly Thr Ala Ser Lys Leu Asn Gly Ile Val Thr
145                 150                 155                 160

Val Gly Gly Gln Lys Ala Asp Val Ile Ala Asn Pro Asn Gly Ile
                165                 170                 175

Thr Val Asn Gly Gly Gly Phe Lys Asn Val Gly Arg Gly Ile Leu Thr
            180                 185                 190

Ile Gly Ala Pro Gln Ile Gly Lys Asp Gly Ala Leu Thr Gly Phe Asp
        195                 200                 205

Val Arg Gln Gly Thr Leu Thr Val Gly Ala Ala Gly Trp Asn Asp Lys
    210                 215                 220

Gly Gly Ala Asp Tyr Thr Gly Val Leu Ala Arg Ala Val Ala Leu Gln
225                 230                 235                 240

Gly Lys Leu Gln Gly Lys Asn Leu Ala Val Ser Thr Gly Pro Gln Lys
                245                 250                 255

Val Asp Tyr Ala Ser Gly Glu Ile Ser Ala Gly Thr Ala Ala Gly Thr
            260                 265                 270

Lys Pro Thr Ile Ala Leu Asp Thr Ala Ala Leu Gly Gly Met Tyr Ala
        275                 280                 285

Asp Ser Ile Thr Leu Ile Ala Xaa Glu Lys Gly Val Gly Val Lys Asn
    290                 295                 300

Ala Gly Thr Leu Glu Ala Ala Lys Gln Leu Ile Val Thr Ser Ser Gly
305                 310                 315                 320

Arg Ile Glu Asn Ser Gly Arg Ile Ala Thr Thr Ala Asp Gly Thr Glu
                325                 330                 335

Ala Ser Pro Thr Tyr Leu Xaa Ile Glu Thr Thr Glu Lys Gly Ala Xaa
            340                 345                 350

Gly Thr Phe Ile Ser Asn Gly Gly Arg Ile Glu Ser Lys Gly Leu Leu
        355                 360                 365

Val Ile Glu Thr Gly Glu Asp Ile Xaa Leu Arg Asn Gly Ala Val Val
    370                 375                 380

Gln Asn Asn Gly Ser Arg Pro Ala Thr Thr Val Leu Asn Ala Gly His
385                 390                 395                 400

Asn Leu Val Ile Glu Ser Lys Thr Asn Val Asn Asn Ala Lys Gly Ser
                405                 410                 415

Xaa Asn Leu Ser Ala Gly Gly Arg Thr Thr Ile Asn Asp Ala Thr Ile
            420                 425                 430

Gln Ala Gly Ser Ser Val Tyr Ser Thr Lys Gly Asp Thr Xaa Leu
        435                 440                 445

Gly Glu Asn Thr Arg Ile Ile Ala Glu Asn Val Thr Val Leu Ser Asn
    450                 455                 460

Gly Ser Ile Gly Ser Ala Ala Val Ile Glu Ala Lys Asp Thr Ala His
465                 470                 475                 480
```

```
Ile Glu Ser Gly Lys Pro Leu Ser Leu Glu Thr Ser Thr Val Ala Ser
                485                 490                 495

Asn Ile Arg Leu Asn Asn Gly Asn Ile Lys Gly Gly Lys Gln Leu Ala
            500                 505                 510

Leu Leu Ala Asp Asp Asn Ile Thr Ala Lys Thr Asn Leu Asn Thr
        515                 520                 525

Pro Gly Asn Leu Tyr Val His Thr Gly Lys Asp Leu Asn Leu Asn Val
    530                 535                 540

Asp Lys Asp Leu Ser Ala Ser Ile His Leu Lys Ser Asp Asn Ala
545                 550                 555                 560

Ala His Ile Thr Gly Thr Ser Lys Thr Leu Thr Ala Ser Lys Asp Met
                565                 570                 575

Gly Val Glu Ala Gly Xaa Xaa Xaa Xaa Xaa Xaa Xaa Xaa Xaa Xaa
                580                 585                 590

Xaa Ser Gly Asn Leu His Ile Gln Ala Ala Lys Gly Asn Ile Gln Leu
            595                 600                 605

Arg Asn Thr Lys Leu Asn Ala Ala Lys Ala Leu Glu Thr Thr Ala Leu
        610                 615                 620

Gln Gly Asn Ile
625

<210> SEQ ID NO 184
<211> LENGTH: 663
<212> TYPE: PRT
<213> ORGANISM: Artificial Sequence
<220> FEATURE:
<223> OTHER INFORMATION: Description of Artificial Sequence: homology
<220> FEATURE:
<221> NAME/KEY: SITE
<222> LOCATION: (4)..(8)
<223> OTHER INFORMATION: absent or positive
<220> FEATURE:
<221> NAME/KEY: SITE
<222> LOCATION: (11)
<223> OTHER INFORMATION: absent or positive
<220> FEATURE:
<221> NAME/KEY: SITE
<222> LOCATION: (14)
<223> OTHER INFORMATION: absent or positive
<220> FEATURE:
<221> NAME/KEY: SITE
<222> LOCATION: (16)
<223> OTHER INFORMATION: absent or positive
<220> FEATURE:
<221> NAME/KEY: SITE
<222> LOCATION: (18)
<223> OTHER INFORMATION: absent or positive
<220> FEATURE:
<221> NAME/KEY: SITE
<222> LOCATION: (23)..(27)
<223> OTHER INFORMATION: absent or positive
<220> FEATURE:
<221> NAME/KEY: SITE
<222> LOCATION: (30)..(31)
<223> OTHER INFORMATION: absent or positive
<220> FEATURE:
<221> NAME/KEY: SITE
<222> LOCATION: (33)..(37)
<223> OTHER INFORMATION: absent or positive
<220> FEATURE:
<221> NAME/KEY: SITE
<222> LOCATION: (40)..(48)
<223> OTHER INFORMATION: absent or positive
<220> FEATURE:
<221> NAME/KEY: SITE
<222> LOCATION: (50)..(79)
<223> OTHER INFORMATION: absent or positive
<220> FEATURE:
<221> NAME/KEY: SITE
```

```
<222> LOCATION: (81)..(82)
<223> OTHER INFORMATION: absent or positive
<220> FEATURE:
<221> NAME/KEY: SITE
<222> LOCATION: (90)
<223> OTHER INFORMATION: absent or positive
<220> FEATURE:
<221> NAME/KEY: SITE
<222> LOCATION: (92)
<223> OTHER INFORMATION: absent or positive
<220> FEATURE:
<221> NAME/KEY: SITE
<222> LOCATION: (96)
<223> OTHER INFORMATION: absent or positive
<220> FEATURE:
<221> NAME/KEY: SITE
<222> LOCATION: (98)..(99)
<223> OTHER INFORMATION: absent or positive
<220> FEATURE:
<221> NAME/KEY: SITE
<222> LOCATION: (101)
<223> OTHER INFORMATION: absent or positive
<220> FEATURE:
<221> NAME/KEY: SITE
<222> LOCATION: (103)
<223> OTHER INFORMATION: absent or positive
<220> FEATURE:
<221> NAME/KEY: SITE
<222> LOCATION: (110)..(112)
<223> OTHER INFORMATION: absent or positive
<220> FEATURE:
<221> NAME/KEY: SITE
<222> LOCATION: (114)
<223> OTHER INFORMATION: absent or positive
<220> FEATURE:
<221> NAME/KEY: SITE
<222> LOCATION: (116)
<223> OTHER INFORMATION: absent or positive
<220> FEATURE:
<221> NAME/KEY: SITE
<222> LOCATION: (119)..(120)
<223> OTHER INFORMATION: absent or positive
<220> FEATURE:
<221> NAME/KEY: SITE
<222> LOCATION: (126)
<223> OTHER INFORMATION: absent or positive
<220> FEATURE:
<221> NAME/KEY: SITE
<222> LOCATION: (129)..(130)
<223> OTHER INFORMATION: absent or positive
<220> FEATURE:
<221> NAME/KEY: SITE
<222> LOCATION: (134)
<223> OTHER INFORMATION: absent or positive
<220> FEATURE:
<221> NAME/KEY: SITE
<222> LOCATION: (136)
<223> OTHER INFORMATION: absent or positive
<220> FEATURE:
<221> NAME/KEY: SITE
<222> LOCATION: (138)..(148)
<223> OTHER INFORMATION: absent or positive
<220> FEATURE:
<221> NAME/KEY: SITE
<222> LOCATION: (151)
<223> OTHER INFORMATION: absent or positive
<220> FEATURE:
<221> NAME/KEY: SITE
<222> LOCATION: (153)..(154)
<223> OTHER INFORMATION: absent or positive
<220> FEATURE:
<221> NAME/KEY: SITE
<222> LOCATION: (156)
<223> OTHER INFORMATION: absent or positive
<220> FEATURE:
<221> NAME/KEY: SITE
<222> LOCATION: (158)..(159)
<223> OTHER INFORMATION: absent or positive
<220> FEATURE:
```

-continued

```
<221> NAME/KEY: SITE
<222> LOCATION: (161)
<223> OTHER INFORMATION: absent or positive
<220> FEATURE:
<221> NAME/KEY: SITE
<222> LOCATION: (163)..(169)
<223> OTHER INFORMATION: absent or positive
<220> FEATURE:
<221> NAME/KEY: SITE
<222> LOCATION: (171)
<223> OTHER INFORMATION: absent or positive
<220> FEATURE:
<221> NAME/KEY: SITE
<222> LOCATION: (175)..(177)
<223> OTHER INFORMATION: absent or positive
<220> FEATURE:
<221> NAME/KEY: SITE
<222> LOCATION: (181)..(182)
<223> OTHER INFORMATION: absent or positive
<220> FEATURE:
<221> NAME/KEY: SITE
<222> LOCATION: (184)
<223> OTHER INFORMATION: absent or positive
<220> FEATURE:
<221> NAME/KEY: SITE
<222> LOCATION: (186)..(187)
<223> OTHER INFORMATION: absent or positive
<220> FEATURE:
<221> NAME/KEY: SITE
<222> LOCATION: (191)
<223> OTHER INFORMATION: absent or positive
<220> FEATURE:
<221> NAME/KEY: SITE
<222> LOCATION: (194)
<223> OTHER INFORMATION: absent or positive
<220> FEATURE:
<221> NAME/KEY: SITE
<222> LOCATION: (200)..(201)
<223> OTHER INFORMATION: absent or positive
<220> FEATURE:
<221> NAME/KEY: SITE
<222> LOCATION: (203)..(207)
<223> OTHER INFORMATION: absent or positive
<220> FEATURE:
<221> NAME/KEY: SITE
<222> LOCATION: (210)
<223> OTHER INFORMATION: absent or positive
<220> FEATURE:
<221> NAME/KEY: SITE
<222> LOCATION: (212)
<223> OTHER INFORMATION: absent or positive
<220> FEATURE:
<221> NAME/KEY: SITE
<222> LOCATION: (214)..(218)
<223> OTHER INFORMATION: absent or positive
<220> FEATURE:
<221> NAME/KEY: SITE
<222> LOCATION: (220)
<223> OTHER INFORMATION: absent or positive
<220> FEATURE:
<221> NAME/KEY: SITE
<222> LOCATION: (227)..(228)
<223> OTHER INFORMATION: absent or positive
<220> FEATURE:
<221> NAME/KEY: SITE
<222> LOCATION: (230)..(233)
<223> OTHER INFORMATION: absent or positive
<220> FEATURE:
<221> NAME/KEY: SITE
<222> LOCATION: (235)..(236)
<223> OTHER INFORMATION: absent or positive
<220> FEATURE:
<221> NAME/KEY: SITE
<222> LOCATION: (238)..(239)
<223> OTHER INFORMATION: absent or positive
<220> FEATURE:
<221> NAME/KEY: SITE
<222> LOCATION: (241)..(243)
<223> OTHER INFORMATION: absent or positive
```

```
<220> FEATURE:
<221> NAME/KEY: SITE
<222> LOCATION: (248)..(249)
<223> OTHER INFORMATION: absent or positive
<220> FEATURE:
<221> NAME/KEY: SITE
<222> LOCATION: (251)
<223> OTHER INFORMATION: absent or positive
<220> FEATURE:
<221> NAME/KEY: SITE
<222> LOCATION: (254)..(261)
<223> OTHER INFORMATION: absent or positive
<220> FEATURE:
<221> NAME/KEY: SITE
<222> LOCATION: (264)..(266)
<223> OTHER INFORMATION: absent or positive
<220> FEATURE:
<221> NAME/KEY: SITE
<222> LOCATION: (268)..(269)
<223> OTHER INFORMATION: absent or positive
<220> FEATURE:
<221> NAME/KEY: SITE
<222> LOCATION: (271)..(272)
<223> OTHER INFORMATION: absent or positive
<220> FEATURE:
<221> NAME/KEY: SITE
<222> LOCATION: (274)
<223> OTHER INFORMATION: absent or positive
<220> FEATURE:
<221> NAME/KEY: SITE
<222> LOCATION: (276)..(285)
<223> OTHER INFORMATION: absent or positive
<220> FEATURE:
<221> NAME/KEY: SITE
<222> LOCATION: (287)..(294)
<223> OTHER INFORMATION: absent or positive
<220> FEATURE:
<221> NAME/KEY: SITE
<222> LOCATION: (297)
<223> OTHER INFORMATION: absent or positive
<220> FEATURE:
<221> NAME/KEY: SITE
<222> LOCATION: (299)
<223> OTHER INFORMATION: absent or positive
<220> FEATURE:
<221> NAME/KEY: SITE
<222> LOCATION: (303)
<223> OTHER INFORMATION: absent or positive
<220> FEATURE:
<221> NAME/KEY: SITE
<222> LOCATION: (311)
<223> OTHER INFORMATION: absent or positive
<220> FEATURE:
<221> NAME/KEY: SITE
<222> LOCATION: (316)..(319)
<223> OTHER INFORMATION: absent or positive
<220> FEATURE:
<221> NAME/KEY: SITE
<222> LOCATION: (321)..(324)
<223> OTHER INFORMATION: absent or positive
<220> FEATURE:
<221> NAME/KEY: SITE
<222> LOCATION: (326)
<223> OTHER INFORMATION: absent or positive
<220> FEATURE:
<221> NAME/KEY: SITE
<222> LOCATION: (328)..(330)
<223> OTHER INFORMATION: absent or positive
<220> FEATURE:
<221> NAME/KEY: SITE
<222> LOCATION: (333)..(341)
<223> OTHER INFORMATION: absent or positive
<220> FEATURE:
<221> NAME/KEY: SITE
<222> LOCATION: (343)..(345)
<223> OTHER INFORMATION: absent or positive
<220> FEATURE:
<221> NAME/KEY: SITE
<222> LOCATION: (349)
```

-continued

```
<223> OTHER INFORMATION: absent or positive
<220> FEATURE:
<221> NAME/KEY: SITE
<222> LOCATION: (351)..(358)
<223> OTHER INFORMATION: absent or positive
<220> FEATURE:
<221> NAME/KEY: SITE
<222> LOCATION: (360)..(367)
<223> OTHER INFORMATION: absent or positive
<220> FEATURE:
<221> NAME/KEY: SITE
<222> LOCATION: (369)..(381)
<223> OTHER INFORMATION: absent or positive
<220> FEATURE:
<221> NAME/KEY: SITE
<222> LOCATION: (383)
<223> OTHER INFORMATION: absent or positive
<220> FEATURE:
<221> NAME/KEY: SITE
<222> LOCATION: (385)
<223> OTHER INFORMATION: absent or positive
<220> FEATURE:
<221> NAME/KEY: SITE
<222> LOCATION: (387)..(390)
<223> OTHER INFORMATION: absent or positive
<220> FEATURE:
<221> NAME/KEY: SITE
<222> LOCATION: (392)..(397)
<223> OTHER INFORMATION: absent or positive
<220> FEATURE:
<221> NAME/KEY: SITE
<222> LOCATION: (399)..(402)
<223> OTHER INFORMATION: absent or positive
<220> FEATURE:
<221> NAME/KEY: SITE
<222> LOCATION: (404)..(409)
<223> OTHER INFORMATION: absent or positive
<220> FEATURE:
<221> NAME/KEY: SITE
<222> LOCATION: (412)..(420)
<223> OTHER INFORMATION: absent or positive
<220> FEATURE:
<221> NAME/KEY: SITE
<222> LOCATION: (422)..(427)
<223> OTHER INFORMATION: absent or positive
<220> FEATURE:
<221> NAME/KEY: SITE
<222> LOCATION: (429)..(432)
<223> OTHER INFORMATION: absent or positive
<220> FEATURE:
<221> NAME/KEY: SITE
<222> LOCATION: (435)..(436)
<223> OTHER INFORMATION: absent or positive
<220> FEATURE:
<221> NAME/KEY: SITE
<222> LOCATION: (438)..(445)
<223> OTHER INFORMATION: absent or positive
<220> FEATURE:
<221> NAME/KEY: SITE
<222> LOCATION: (447)..(453)
<223> OTHER INFORMATION: absent or positive
<220> FEATURE:
<221> NAME/KEY: SITE
<222> LOCATION: (456)..(459)
<223> OTHER INFORMATION: absent or positive
<220> FEATURE:
<221> NAME/KEY: SITE
<222> LOCATION: (461)..(463)
<223> OTHER INFORMATION: absent or positive
<220> FEATURE:
<221> NAME/KEY: SITE
<222> LOCATION: (465)
<223> OTHER INFORMATION: absent or positive
<220> FEATURE:
<221> NAME/KEY: SITE
<222> LOCATION: (467)..(470)
<223> OTHER INFORMATION: absent or positive
<220> FEATURE:
<221> NAME/KEY: SITE
```

-continued

```
<222> LOCATION: (472)..(474)
<223> OTHER INFORMATION: absent or positive
<220> FEATURE:
<221> NAME/KEY: SITE
<222> LOCATION: (476)..(485)
<223> OTHER INFORMATION: absent or positive
<220> FEATURE:
<221> NAME/KEY: SITE
<222> LOCATION: (487)..(490)
<223> OTHER INFORMATION: absent or positive
<220> FEATURE:
<221> NAME/KEY: SITE
<222> LOCATION: (492)..(498)
<223> OTHER INFORMATION: absent or positive
<220> FEATURE:
<221> NAME/KEY: SITE
<222> LOCATION: (500)
<223> OTHER INFORMATION: absent or positive
<220> FEATURE:
<221> NAME/KEY: SITE
<222> LOCATION: (502)
<223> OTHER INFORMATION: absent or positive
<220> FEATURE:
<221> NAME/KEY: SITE
<222> LOCATION: (505)..(521)
<223> OTHER INFORMATION: absent or positive
<220> FEATURE:
<221> NAME/KEY: SITE
<222> LOCATION: (523)..(524)
<223> OTHER INFORMATION: absent or positive
<220> FEATURE:
<221> NAME/KEY: SITE
<222> LOCATION: (526)..(532)
<223> OTHER INFORMATION: absent or positive
<220> FEATURE:
<221> NAME/KEY: SITE
<222> LOCATION: (534)..(538)
<223> OTHER INFORMATION: absent or positive
<220> FEATURE:
<221> NAME/KEY: SITE
<222> LOCATION: (540)..(544)
<223> OTHER INFORMATION: absent or positive
<220> FEATURE:
<221> NAME/KEY: SITE
<222> LOCATION: (547)..(551)
<223> OTHER INFORMATION: absent or positive
<220> FEATURE:
<221> NAME/KEY: SITE
<222> LOCATION: (554)..(555)
<223> OTHER INFORMATION: absent or positive
<220> FEATURE:
<221> NAME/KEY: SITE
<222> LOCATION: (557)..(558)
<223> OTHER INFORMATION: absent or positive
<220> FEATURE:
<221> NAME/KEY: SITE
<222> LOCATION: (560)
<223> OTHER INFORMATION: absent or positive
<220> FEATURE:
<221> NAME/KEY: SITE
<222> LOCATION: (562)..(563)
<223> OTHER INFORMATION: absent or positive
<220> FEATURE:
<221> NAME/KEY: SITE
<222> LOCATION: (565)..(567)
<223> OTHER INFORMATION: absent or positive
<220> FEATURE:
<221> NAME/KEY: SITE
<222> LOCATION: (569)..(575)
<223> OTHER INFORMATION: absent or positive
<220> FEATURE:
<221> NAME/KEY: SITE
<222> LOCATION: (577)..(578)
<223> OTHER INFORMATION: absent or positive
<220> FEATURE:
<221> NAME/KEY: SITE
<222> LOCATION: (580)..(590)
<223> OTHER INFORMATION: absent or positive
<220> FEATURE:
```

```
<221> NAME/KEY: SITE
<222> LOCATION: (593)..(602)
<223> OTHER INFORMATION: absent or positive
<220> FEATURE:
<221> NAME/KEY: SITE
<222> LOCATION: (604)..(610)
<223> OTHER INFORMATION: absent or positive
<220> FEATURE:
<221> NAME/KEY: SITE
<222> LOCATION: (612)..(624)
<223> OTHER INFORMATION: absent or positive
<220> FEATURE:
<221> NAME/KEY: SITE
<222> LOCATION: (627)
<223> OTHER INFORMATION: absent or positive
<220> FEATURE:
<221> NAME/KEY: SITE
<222> LOCATION: (631)..(632)
<223> OTHER INFORMATION: absent or positive
<220> FEATURE:
<221> NAME/KEY: SITE
<222> LOCATION: (634)..(640)
<223> OTHER INFORMATION: absent or positive
<220> FEATURE:
<221> NAME/KEY: SITE
<222> LOCATION: (642)..(643)
<223> OTHER INFORMATION: absent or positive
<220> FEATURE:
<221> NAME/KEY: SITE
<222> LOCATION: (646)
<223> OTHER INFORMATION: absent or positive
<220> FEATURE:
<221> NAME/KEY: SITE
<222> LOCATION: (648)
<223> OTHER INFORMATION: absent or positive
<220> FEATURE:
<221> NAME/KEY: SITE
<222> LOCATION: (650)..(652)
<223> OTHER INFORMATION: absent or positive
<220> FEATURE:
<221> NAME/KEY: SITE
<222> LOCATION: (654)
<223> OTHER INFORMATION: absent or positive
<220> FEATURE:
<221> NAME/KEY: SITE
<222> LOCATION: (656)..(660)
<223> OTHER INFORMATION: absent or positive

<400> SEQUENCE: 184

Met Asn Lys Xaa Xaa Xaa Xaa Ile Phe Xaa Lys Lys Xaa Ser Xaa
  1               5                  10                  15

Met Xaa Ala Val Ala Glu Xaa Xaa Xaa Xaa Gly Lys Xaa Xaa Gln
             20                  25                  30

Xaa Xaa Xaa Xaa Xaa Ser Val Xaa Xaa Xaa Xaa Xaa Xaa Xaa Xaa
         35                  40                  45

Ser Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Ile
 65                  70                  75                  80

Xaa Xaa Asp Lys Ser Ala Pro Lys Asn Xaa Gln Xaa Val Ile Leu Xaa
             85                  90                  95

Thr Xaa Xaa Gly Xaa Pro Xaa Val Asn Ile Gln Thr Pro Xaa Xaa Xaa
            100                 105                 110

Gly Xaa Ser Xaa Asn Arg Xaa Xaa Gln Phe Asp Val Asp Xaa Lys Gly
            115                 120                 125

Xaa Xaa Leu Asn Asn Xaa Arg Xaa Asn Xaa Xaa Xaa Xaa Xaa Xaa
        130                 135                 140

Xaa Xaa Xaa Xaa Asn Pro Xaa Leu Xaa Xaa Gly Xaa Ala Xaa Xaa Ile
145                 150                 155                 160
```

```
Xaa Asn Xaa Xaa Xaa Xaa Xaa Xaa Ser Xaa Leu Asn Gly Xaa Xaa
                165                 170                 175

Xaa Val Gly Gly Xaa Xaa Ala Xaa Val Xaa Xaa Ala Asn Pro Xaa Gly
            180                 185                 190

Ile Xaa Val Asn Gly Gly Xaa Xaa Asn Xaa Xaa Xaa Xaa Xaa Leu
        195                 200                 205

Thr Xaa Gly Xaa Pro Xaa Xaa Xaa Xaa Gly Xaa Leu Thr Gly Phe
    210                 215                 220

Asp Val Xaa Xaa Gly Xaa Xaa Xaa Xaa Gly Xaa Xaa Gly Xaa Xaa Asp
225                 230                 235                 240

Xaa Xaa Xaa Ala Asp Tyr Thr Xaa Xaa Leu Xaa Arg Ala Xaa Xaa Xaa
            245                 250                 255

Xaa Xaa Xaa Xaa Xaa Gly Lys Xaa Xaa Xaa Val Xaa Xaa Gly Xaa Xaa
                260                 265                 270

Lys Xaa Asp Xaa Xaa Xaa Xaa Xaa Xaa Xaa Xaa Xaa Ala Xaa Xaa
        275                 280                 285

Xaa Xaa Xaa Xaa Xaa Xaa Pro Thr Xaa Ala Xaa Asp Thr Ala Xaa Leu
    290                 295                 300

Gly Gly Met Tyr Ala Asp Xaa Ile Thr Leu Ile Xaa Xaa Xaa Xaa Gly
305                 310                 315                 320

Xaa Xaa Xaa Xaa Asn Xaa Gly Xaa Xaa Xaa Ala Ala Xaa Xaa Xaa Xaa
                325                 330                 335

Xaa Xaa Xaa Xaa Xaa Gly Xaa Xaa Xaa Asn Ser Gly Xaa Ile Xaa Xaa
                340                 345                 350

Xaa Xaa Xaa Xaa Xaa Xaa Ala Xaa Xaa Xaa Xaa Xaa Xaa Xaa Thr
            355                 360                 365

Xaa Xaa Xaa Xaa Xaa Xaa Xaa Xaa Xaa Xaa Xaa Xaa Gly Xaa Ile
        370                 375                 380

Xaa Ser Xaa Xaa Xaa Xaa Val Xaa Xaa Xaa Xaa Xaa Ile Xaa Xaa
385                 390                 395                 400

Xaa Xaa Gly Xaa Xaa Xaa Xaa Xaa Xaa Gly Ser Xaa Xaa Xaa Xaa Xaa
            405                 410                 415

Xaa Xaa Xaa Xaa Gly Xaa Xaa Xaa Xaa Xaa Ser Xaa Xaa Xaa Xaa
            420                 425                 430

Asn Asn Xaa Xaa Gly Xaa Xaa Xaa Xaa Xaa Xaa Xaa Ser Xaa Xaa
            435                 440                 445

Xaa Xaa Xaa Xaa Xaa Asn Asp Xaa Xaa Xaa Xaa Ala Xaa Xaa Xaa Val
    450                 455                 460

Xaa Ser Xaa Xaa Xaa Xaa Asp Xaa Xaa Xaa Gly Xaa Xaa Xaa Xaa Xaa
465                 470                 475                 480

Xaa Xaa Xaa Xaa Xaa Thr Xaa Xaa Xaa Xaa Gly Xaa Xaa Xaa Xaa Xaa
            485                 490                 495

Xaa Xaa Ile Xaa Ala Xaa Asp Thr Xaa Xaa Xaa Xaa Xaa Xaa Xaa Xaa
            500                 505                 510

Xaa Xaa Xaa Xaa Xaa Xaa Xaa Xaa Ser Xaa Xaa Arg Xaa Xaa Xaa
            515                 520                 525

Xaa Xaa Xaa Xaa Gly Xaa Xaa Xaa Xaa Leu Xaa Xaa Xaa Xaa Xaa
            530                 535                 540

Ile Thr Xaa Xaa Xaa Xaa Xaa Ala Lys Xaa Xaa Asn Xaa Xaa Thr Xaa
545                 550                 555                 560

Gly Xaa Xaa Tyr Xaa Xaa Xaa Gly Xaa Xaa Xaa Xaa Xaa Xaa Asp
            565                 570                 575
```

-continued

```
Xaa Xaa Leu Xaa Xaa Xaa Xaa Xaa Xaa Xaa Xaa Xaa Xaa Ala Ala
        580                 585                 590
Xaa Xaa Xaa Xaa Xaa Xaa Xaa Xaa Ala Xaa Xaa Xaa Xaa Xaa
    595                 600                 605
Xaa Xaa Ala Xaa Xaa Xaa Xaa Xaa Xaa Xaa Xaa Xaa
    610                 615                 620
Ser Gly Xaa Leu His Ile Xaa Xaa Ala Xaa Xaa Xaa Xaa Xaa Xaa
625                 630                 635                 640
Gln Xaa Xaa Asn Thr Xaa Leu Xaa Asn Xaa Xaa Xaa Ala Xaa Glu Xaa
                645                 650                 655
Xaa Xaa Xaa Xaa Gly Asn Ile
            660

<210> SEQ ID NO 185
<211> LENGTH: 622
<212> TYPE: PRT
<213> ORGANISM: Artificial Sequence
<220> FEATURE:
<223> OTHER INFORMATION: Description of Artificial Sequence: pspA

<400> SEQUENCE: 185

Met Asn Lys Arg Cys Tyr Lys Val Ile Phe Asn Lys Arg Ser Cys
 1               5                  10                  15
Met Met Ala Val Ala Glu Asn Val His Arg Asp Gly Lys Ser Met Gln
            20                  25                  30
Asp Ser Glu Ala Ala Ser Val Arg Val Thr Gly Ala Ala Ser Val Ser
        35                  40                  45
Ser Ala Arg Ala Ala Phe Gly Phe Arg Met Ala Ala Phe Ser Val Met
    50                  55                  60
Leu Ala Leu Gly Val Ala Ala Phe Ser Pro Ala Pro Ala Ser Gly Ile
65                  70                  75                  80
Ile Ala Asp Lys Ser Ala Pro Lys Asn Gln Gln Ala Val Ile Leu Gln
                85                  90                  95
Thr Ala Asn Gly Leu Pro Gln Val Asn Ile Gln Thr Pro Ser Ser Gln
            100                 105                 110
Gly Val Ser Val Asn Arg Phe Lys Gln Phe Asp Val Asp Glu Lys Gly
        115                 120                 125
Val Ile Leu Asn Asn Ser Arg Ser Asn Thr Gln Thr Gln Leu Gly Gly
    130                 135                 140
Trp Ile Gln Gly Asn Pro His Leu Ala Arg Gly Glu Ala Arg Val Ile
145                 150                 155                 160
Val Asn Gln Ile Asp Ser Ser Asn Pro Ser Leu Leu Asn Gly Tyr Ile
                165                 170                 175
Glu Val Gly Gly Lys Arg Ala Glu Val Val Ala Asn Pro Ser Gly
            180                 185                 190
Ile Arg Val Asn Gly Gly Leu Ile Asn Ala Ala Ser Val Thr Leu
        195                 200                 205
Thr Ser Gly Val Pro Val Leu Asn Asn Gly Asn Leu Thr Gly Phe Asp
    210                 215                 220
Val Ser Ser Gly Lys Val Ile Gly Gly Lys Gly Leu Asp Thr Ser
225                 230                 235                 240
Asp Ala Asp Tyr Thr Arg Ile Leu Ser Arg Ala Ala Glu Ile Asn Ala
                245                 250                 255
Gly Val Trp Gly Lys Asp Val Lys Val Val Ser Gly Lys Asn Lys Leu
            260                 265                 270
```

-continued

```
Asp Phe Asp Gly Ser Leu Ala Lys Thr Ala Ser Ala Pro Ser Ser Ser
    275                 280                 285

Asp Ser Val Thr Pro Thr Val Ala Ile Asp Thr Ala Thr Leu Gly Gly
290                 295                 300

Met Tyr Ala Asp Lys Ile Thr Leu Ile Ser Thr Asp Asn Gly Ala Val
305                 310                 315                 320

Ile Arg Asn Lys Gly Arg Ile Phe Ala Ala Thr Gly Gly Val Thr Leu
                325                 330                 335

Ser Ala Asp Gly Lys Leu Ser Asn Ser Gly Ser Ile Asp Ala Ala Glu
            340                 345                 350

Ile Thr Ile Ser Ala Gln Thr Val Asp Asn Arg Gln Gly Phe Ile Arg
        355                 360                 365

Ser Gly Lys Gly Ser Val Leu Lys Val Ser Asp Gly Ile Asn Asn Gln
    370                 375                 380

Ala Gly Leu Ile Gly Ser Ala Gly Leu Leu Asp Ile Arg Asp Thr Gly
385                 390                 395                 400

Lys Ser Ser Leu His Ile Asn Asn Thr Asp Gly Thr Ile Ile Ala Gly
                405                 410                 415

Lys Asp Val Ser Leu Gln Ala Lys Ser Leu Asp Asn Asp Gly Ile Leu
            420                 425                 430

Thr Ala Ala Arg Asp Val Ser Val Ser Leu His Asp Asp Phe Ala Gly
        435                 440                 445

Lys Arg Asp Ile Glu Ala Gly Arg Thr Leu Thr Phe Ser Thr Gln Gly
    450                 455                 460

Arg Leu Lys Asn Thr Arg Ile Ile Gln Ala Gly Asp Thr Val Ser Leu
465                 470                 475                 480

Thr Ala Ala Gln Ile Asp Asn Thr Val Ser Gly Lys Ile Gln Ser Gly
                485                 490                 495

Asn Arg Thr Gly Leu Asn Gly Lys Asn Gly Ile Thr Asn Arg Gly Leu
            500                 505                 510

Ile Asn Ser Asn Gly Ile Thr Leu Leu Gln Thr Glu Ala Lys Ser Asp
        515                 520                 525

Asn Ala Gly Thr Gly Arg Ile Tyr Gly Ser Arg Val Ala Val Glu Ala
    530                 535                 540

Asp Thr Leu Leu Asn Arg Glu Glu Thr Val Asn Gly Glu Thr Lys Ala
545                 550                 555                 560

Ala Val Ile Ala Ala Arg Glu Arg Leu Asp Ile Gly Ala Arg Glu Ile
                565                 570                 575

Glu Asn Arg Glu Ala Ala Leu Leu Ser Ser Ser Gly Asp Leu His Ile
            580                 585                 590

Gly Ser Ala Leu Asn Gly Ser Arg Gln Val Gln Gly Ala Asn Thr Ser
    595                 600                 605

Leu His Asn Arg Ser Ala Ala Ile Glu Ser Ser Gly Asn Ile
    610                 615                 620

<210> SEQ ID NO 186
<211> LENGTH: 400
<212> TYPE: PRT
<213> ORGANISM: Artificial Sequence
<220> FEATURE:
<223> OTHER INFORMATION: Description of Artificial Sequence: ORF114a
<220> FEATURE:
<221> NAME/KEY: SITE
<222> LOCATION: (58)
<223> OTHER INFORMATION: place-holder
<220> FEATURE:
<221> NAME/KEY: SITE
```

```
<222> LOCATION: (105)
<223> OTHER INFORMATION: place-holder
<220> FEATURE:
<221> NAME/KEY: SITE
<222> LOCATION: (114)
<223> OTHER INFORMATION: place-holder
<220> FEATURE:
<221> NAME/KEY: SITE
<222> LOCATION: (139)
<223> OTHER INFORMATION: place-holder
<220> FEATURE:
<221> NAME/KEY: SITE
<222> LOCATION: (179)
<223> OTHER INFORMATION: place-holder
<220> FEATURE:
<221> NAME/KEY: SITE
<222> LOCATION: (209)
<223> OTHER INFORMATION: place-holder
<220> FEATURE:
<221> NAME/KEY: SITE
<222> LOCATION: (344)..(355)
<223> OTHER INFORMATION: place-holder

<400> SEQUENCE: 186
```

Leu Gln Gly Lys Leu Gln Gly Lys Asn Leu Ala Val Ser Thr Gly Pro
 1               5                  10                  15

Gln Lys Val Asp Tyr Ala Ser Gly Glu Ile Ser Ala Gly Thr Ala Ala
            20                  25                  30

Gly Thr Lys Pro Thr Ile Ala Leu Asp Thr Ala Ala Leu Gly Gly Met
        35                  40                  45

Tyr Ala Asp Ser Ile Thr Leu Ile Ala Xaa Glu Lys Gly Val Gly Val
    50                  55                  60

Lys Asn Ala Gly Thr Leu Glu Ala Ala Lys Gln Leu Ile Val Thr Ser
65                  70                  75                  80

Ser Gly Arg Ile Glu Asn Ser Gly Arg Ile Ala Thr Thr Ala Asp Gly
                85                  90                  95

Thr Glu Ala Ser Pro Thr Tyr Leu Xaa Ile Glu Thr Thr Glu Lys Gly
            100                 105                 110

Ala Xaa Gly Thr Phe Ile Ser Asn Gly Gly Arg Ile Glu Ser Lys Gly
        115                 120                 125

Leu Leu Val Ile Glu Thr Gly Glu Asp Ile Xaa Leu Arg Asn Gly Ala
    130                 135                 140

Val Val Gln Asn Asn Gly Ser Arg Pro Ala Thr Thr Val Leu Asn Ala
145                 150                 155                 160

Gly His Asn Leu Val Ile Glu Ser Lys Thr Asn Val Asn Asn Ala Lys
                165                 170                 175

Gly Ser Xaa Asn Leu Ser Ala Gly Gly Arg Thr Thr Ile Asn Asp Ala
            180                 185                 190

Thr Ile Gln Ala Gly Ser Ser Val Tyr Ser Thr Lys Gly Asp Thr
        195                 200                 205

Xaa Leu Gly Glu Asn Thr Arg Ile Ile Ala Glu Asn Val Thr Val Leu
    210                 215                 220

Ser Asn Gly Ser Ile Gly Ser Ala Ala Val Ile Glu Ala Lys Asp Thr
225                 230                 235                 240

Ala His Ile Glu Ser Gly Lys Pro Leu Ser Leu Glu Thr Ser Thr Val
                245                 250                 255

Ala Ser Asn Ile Arg Leu Asn Asn Gly Asn Ile Lys Gly Gly Lys Gln
            260                 265                 270

Leu Ala Leu Leu Ala Asp Asp Asn Ile Thr Ala Lys Thr Thr Asn Leu
        275                 280                 285

-continued

```
Asn Thr Pro Gly Asn Leu Tyr Val His Thr Gly Lys Asp Leu Asn Leu
    290                 295                 300

Asn Val Asp Lys Asp Leu Ser Ala Ala Ser Ile His Leu Lys Ser Asp
305                 310                 315                 320

Asn Ala Ala His Ile Thr Gly Thr Ser Lys Thr Leu Thr Ala Ser Lys
                325                 330                 335

Asp Met Gly Val Glu Ala Gly Xaa Xaa Xaa Xaa Xaa Xaa Xaa Xaa
            340                 345                 350

Xaa Xaa Xaa Ser Gly Asn Leu His Ile Gln Ala Ala Lys Gly Asn Ile
        355                 360                 365

Gln Leu Arg Asn Thr Lys Leu Asn Ala Ala Lys Ala Leu Glu Thr Thr
    370                 375                 380

Ala Leu Gln Gly Asn Ile Val Ser Asp Gly Leu His Ala Val Ser Ala
385                 390                 395                 400

<210> SEQ ID NO 187
<211> LENGTH: 432
<212> TYPE: PRT
<213> ORGANISM: Artificial Sequence
<220> FEATURE:
<223> OTHER INFORMATION: Description of Artificial Sequence: homology
<220> FEATURE:
<221> NAME/KEY: SITE
<222> LOCATION: (4)
<223> OTHER INFORMATION: absent or positive
<220> FEATURE:
<221> NAME/KEY: SITE
<222> LOCATION: (10)..(14)
<223> OTHER INFORMATION: absent or positive
<220> FEATURE:
<221> NAME/KEY: SITE
<222> LOCATION: (16)..(23)
<223> OTHER INFORMATION: absent or positive
<220> FEATURE:
<221> NAME/KEY: SITE
<222> LOCATION: (25)
<223> OTHER INFORMATION: absent or positive
<220> FEATURE:
<221> NAME/KEY: SITE
<222> LOCATION: (27)
<223> OTHER INFORMATION: absent or positive
<220> FEATURE:
<221> NAME/KEY: SITE
<222> LOCATION: (29)..(30)
<223> OTHER INFORMATION: absent or positive
<220> FEATURE:
<221> NAME/KEY: SITE
<222> LOCATION: (32)..(34)
<223> OTHER INFORMATION: absent or positive
<220> FEATURE:
<221> NAME/KEY: SITE
<222> LOCATION: (36)..(43)
<223> OTHER INFORMATION: absent or positive
<220> FEATURE:
<221> NAME/KEY: SITE
<222> LOCATION: (45)..(51)
<223> OTHER INFORMATION: absent or positive
<220> FEATURE:
<221> NAME/KEY: SITE
<222> LOCATION: (53)
<223> OTHER INFORMATION: absent or positive
<220> FEATURE:
<221> NAME/KEY: SITE
<222> LOCATION: (55)..(63)
<223> OTHER INFORMATION: absent or positive
<220> FEATURE:
<221> NAME/KEY: SITE
<222> LOCATION: (65)
<223> OTHER INFORMATION: absent or positive
<220> FEATURE:
<221> NAME/KEY: SITE
<222> LOCATION: (67)
```

```
<223> OTHER INFORMATION: absent or positive
<220> FEATURE:
<221> NAME/KEY: SITE
<222> LOCATION: (69)..(71)
<223> OTHER INFORMATION: absent or positive
<220> FEATURE:
<221> NAME/KEY: SITE
<222> LOCATION: (73)..(75)
<223> OTHER INFORMATION: absent or positive
<220> FEATURE:
<221> NAME/KEY: SITE
<222> LOCATION: (77)..(81)
<223> OTHER INFORMATION: absent or positive
<220> FEATURE:
<221> NAME/KEY: SITE
<222> LOCATION: (83)..(91)
<223> OTHER INFORMATION: absent or positive
<220> FEATURE:
<221> NAME/KEY: SITE
<222> LOCATION: (93)..(94)
<223> OTHER INFORMATION: absent or positive
<220> FEATURE:
<221> NAME/KEY: SITE
<222> LOCATION: (97)..(108)
<223> OTHER INFORMATION: absent or positive
<220> FEATURE:
<221> NAME/KEY: SITE
<222> LOCATION: (110)
<223> OTHER INFORMATION: absent or positive
<220> FEATURE:
<221> NAME/KEY: SITE
<222> LOCATION: (112)..(116)
<223> OTHER INFORMATION: absent or positive
<220> FEATURE:
<221> NAME/KEY: SITE
<222> LOCATION: (118)
<223> OTHER INFORMATION: absent or positive
<220> FEATURE:
<221> NAME/KEY: SITE
<222> LOCATION: (120)..(123)
<223> OTHER INFORMATION: absent or positive
<220> FEATURE:
<221> NAME/KEY: SITE
<222> LOCATION: (126)
<223> OTHER INFORMATION: absent or positive
<220> FEATURE:
<221> NAME/KEY: SITE
<222> LOCATION: (128)
<223> OTHER INFORMATION: absent or positive
<220> FEATURE:
<221> NAME/KEY: SITE
<222> LOCATION: (130)..(140)
<223> OTHER INFORMATION: absent or positive
<220> FEATURE:
<221> NAME/KEY: SITE
<222> LOCATION: (142)..(147)
<223> OTHER INFORMATION: absent or positive
<220> FEATURE:
<221> NAME/KEY: SITE
<222> LOCATION: (149)..(158)
<223> OTHER INFORMATION: absent or positive
<220> FEATURE:
<221> NAME/KEY: SITE
<222> LOCATION: (160)..(163)
<223> OTHER INFORMATION: absent or positive
<220> FEATURE:
<221> NAME/KEY: SITE
<222> LOCATION: (165)
<223> OTHER INFORMATION: absent or positive
<220> FEATURE:
<221> NAME/KEY: SITE
<222> LOCATION: (168)..(171)
<223> OTHER INFORMATION: absent or positive
<220> FEATURE:
<221> NAME/KEY: SITE
<222> LOCATION: (173)..(181)
<223> OTHER INFORMATION: absent or positive
<220> FEATURE:
<221> NAME/KEY: SITE
```

```
<222> LOCATION: (183)..(186)
<223> OTHER INFORMATION: absent or positive
<220> FEATURE:
<221> NAME/KEY: SITE
<222> LOCATION: (188)..(190)
<223> OTHER INFORMATION: absent or positive
<220> FEATURE:
<221> NAME/KEY: SITE
<222> LOCATION: (192)
<223> OTHER INFORMATION: absent or positive
<220> FEATURE:
<221> NAME/KEY: SITE
<222> LOCATION: (195)..(200)
<223> OTHER INFORMATION: absent or positive
<220> FEATURE:
<221> NAME/KEY: SITE
<222> LOCATION: (202)..(205)
<223> OTHER INFORMATION: absent or positive
<220> FEATURE:
<221> NAME/KEY: SITE
<222> LOCATION: (208)..(218)
<223> OTHER INFORMATION: absent or positive
<220> FEATURE:
<221> NAME/KEY: SITE
<222> LOCATION: (220)..(223)
<223> OTHER INFORMATION: absent or positive
<220> FEATURE:
<221> NAME/KEY: SITE
<222> LOCATION: (225)..(231)
<223> OTHER INFORMATION: absent or positive
<220> FEATURE:
<221> NAME/KEY: SITE
<222> LOCATION: (234)..(244)
<223> OTHER INFORMATION: absent or positive
<220> FEATURE:
<221> NAME/KEY: SITE
<222> LOCATION: (246)..(252)
<223> OTHER INFORMATION: absent or positive
<220> FEATURE:
<221> NAME/KEY: SITE
<222> LOCATION: (254)..(263)
<223> OTHER INFORMATION: absent or positive
<220> FEATURE:
<221> NAME/KEY: SITE
<222> LOCATION: (265)..(272)
<223> OTHER INFORMATION: absent or positive
<220> FEATURE:
<221> NAME/KEY: SITE
<222> LOCATION: (274)..(275)
<223> OTHER INFORMATION: absent or positive
<220> FEATURE:
<221> NAME/KEY: SITE
<222> LOCATION: (277)..(280)
<223> OTHER INFORMATION: absent or positive
<220> FEATURE:
<221> NAME/KEY: SITE
<222> LOCATION: (283)..(285)
<223> OTHER INFORMATION: absent or positive
<220> FEATURE:
<221> NAME/KEY: SITE
<222> LOCATION: (287)..(294)
<223> OTHER INFORMATION: absent or positive
<220> FEATURE:
<221> NAME/KEY: SITE
<222> LOCATION: (296)..(297)
<223> OTHER INFORMATION: absent or positive
<220> FEATURE:
<221> NAME/KEY: SITE
<222> LOCATION: (299)..(301)
<223> OTHER INFORMATION: absent or positive
<220> FEATURE:
<221> NAME/KEY: SITE
<222> LOCATION: (303)..(309)
<223> OTHER INFORMATION: absent or positive
<220> FEATURE:
<221> NAME/KEY: SITE
<222> LOCATION: (311)..(318)
<223> OTHER INFORMATION: absent or positive
<220> FEATURE:
```

```
<221> NAME/KEY: SITE
<222> LOCATION: (321)..(323)
<223> OTHER INFORMATION: absent or positive
<220> FEATURE:
<221> NAME/KEY: SITE
<222> LOCATION: (325)..(329)
<223> OTHER INFORMATION: absent or positive
<220> FEATURE:
<221> NAME/KEY: SITE
<222> LOCATION: (331)..(337)
<223> OTHER INFORMATION: absent or positive
<220> FEATURE:
<221> NAME/KEY: SITE
<222> LOCATION: (339)
<223> OTHER INFORMATION: absent or positive
<220> FEATURE:
<221> NAME/KEY: SITE
<222> LOCATION: (341)..(349)
<223> OTHER INFORMATION: absent or positive
<220> FEATURE:
<221> NAME/KEY: SITE
<222> LOCATION: (351)
<223> OTHER INFORMATION: absent or positive
<220> FEATURE:
<221> NAME/KEY: SITE
<222> LOCATION: (353)
<223> OTHER INFORMATION: absent or positive
<220> FEATURE:
<221> NAME/KEY: SITE
<222> LOCATION: (355)..(356)
<223> OTHER INFORMATION: absent or positive
<220> FEATURE:
<221> NAME/KEY: SITE
<222> LOCATION: (358)..(363)
<223> OTHER INFORMATION: absent or positive
<220> FEATURE:
<221> NAME/KEY: SITE
<222> LOCATION: (365)
<223> OTHER INFORMATION: absent or positive
<220> FEATURE:
<221> NAME/KEY: SITE
<222> LOCATION: (367)..(369)
<223> OTHER INFORMATION: absent or positive
<220> FEATURE:
<221> NAME/KEY: SITE
<222> LOCATION: (371)..(391)
<223> OTHER INFORMATION: absent or positive
<220> FEATURE:
<221> NAME/KEY: SITE
<222> LOCATION: (394)..(403)
<223> OTHER INFORMATION: absent or positive
<220> FEATURE:
<221> NAME/KEY: SITE
<222> LOCATION: (406)..(408)
<223> OTHER INFORMATION: absent or positive
<220> FEATURE:
<221> NAME/KEY: SITE
<222> LOCATION: (410)..(411)
<223> OTHER INFORMATION: absent or positive
<220> FEATURE:
<221> NAME/KEY: SITE
<222> LOCATION: (413)..(419)
<223> OTHER INFORMATION: absent or positive
<220> FEATURE:
<221> NAME/KEY: SITE
<222> LOCATION: (421)..(428)
<223> OTHER INFORMATION: absent or positive
<220> FEATURE:
<221> NAME/KEY: SITE
<222> LOCATION: (430)..(431)
<223> OTHER INFORMATION: absent or positive

<400> SEQUENCE: 187

Leu Gln Gly Xaa Leu Gln Gly Lys Asn Xaa Xaa Xaa Xaa Xaa Gly Xaa
 1               5                  10                  15

Xaa Xaa Xaa Xaa Xaa Xaa Xaa Gly Xaa Ile Xaa Ala Xaa Xaa Ala Xaa
             20                  25                  30
```

-continued

Xaa Xaa Lys Xaa Xaa Xaa Xaa Xaa Xaa Ala Xaa Xaa Xaa Xaa
         35                  40                  45

Xaa Xaa Xaa Ser Xaa Thr Xaa Xaa Xaa Xaa Xaa Xaa Xaa Val
     50                  55                  60

Xaa Asn Xaa Gly Xaa Xaa Ala Xaa Xaa Xaa Leu Xaa Xaa Xaa Xaa
 65              70              75                  80

Xaa Gly Xaa Xaa Xaa Xaa Xaa Xaa Xaa Xaa Ile Xaa Xaa Thr Ala
             85                  90                  95

Xaa Xaa Xaa Xaa Xaa Xaa Xaa Xaa Xaa Xaa Glu Xaa Thr Xaa
         100                 105                 110

Xaa Xaa Xaa Xaa Gly Xaa Thr Xaa Xaa Xaa Gly Gly Xaa Ile Xaa
         115                 120                 125

Ser Xaa Xaa Xaa Xaa Xaa Xaa Xaa Xaa Xaa Xaa Ile Xaa Xaa Xaa
     130                 135                 140

Xaa Xaa Xaa Val Xaa Xaa Xaa Xaa Xaa Xaa Xaa Xaa Thr Xaa
145             150                 155                 160

Xaa Xaa Xaa Gly Xaa Asn Leu Xaa Xaa Xaa Xaa Lys Xaa Xaa Xaa Xaa
             165                 170                 175

Xaa Xaa Xaa Xaa Xaa Val Xaa Xaa Xaa Xaa Gly Xaa Xaa Leu Xaa
         180                 185                 190

Ala Gly Xaa Xaa Xaa Xaa Xaa Xaa Asp Xaa Xaa Xaa Xaa Ala Gly Xaa
         195                 200                 205

Xaa Xaa Xaa Xaa Xaa Xaa Xaa Xaa Xaa Tyr Xaa Xaa Xaa Xaa Gly
     210                 215                 220

Xaa Xaa Xaa Xaa Xaa Xaa Xaa Thr Arg Xaa Xaa Xaa Xaa Xaa Xaa
225             230                 235                 240

Xaa Xaa Xaa Xaa Gly Xaa Xaa Xaa Xaa Xaa Xaa Ile Xaa Xaa Xaa
             245                 250                 255

Xaa Xaa Xaa Xaa Xaa Xaa Xaa Gly Xaa Xaa Xaa Xaa Xaa Xaa Xaa
         260                 265                 270

Thr Xaa Xaa Ser Xaa Xaa Xaa Xaa Asn Asn Xaa Xaa Xaa Lys Xaa Xaa
     275                 280                 285

Xaa Xaa Xaa Xaa Xaa Xaa Ala Xaa Xaa Asn Xaa Xaa Xaa Lys Xaa Xaa
         290                 295                 300

Xaa Xaa Xaa Xaa Xaa Gly Xaa Xaa Xaa Xaa Xaa Xaa Xaa Lys Asp
305             310                 315                 320

Xaa Xaa Xaa Asn Xaa Xaa Xaa Xaa Xaa Ser Xaa Xaa Xaa Xaa Xaa
         325                 330                 335

Xaa Ser Xaa Asn Xaa Xaa Xaa Xaa Xaa Xaa Xaa Xaa His Xaa Thr
         340                 345                 350

Xaa Thr Xaa Xaa Thr Xaa Xaa Xaa Xaa Xaa Asp Xaa Gly Xaa Xaa
     355                 360                 365

Xaa Gly Xaa Xaa Xaa Xaa Xaa Xaa Xaa Xaa Xaa Xaa Xaa Xaa
     370                 375                 380

Xaa Xaa Xaa Xaa Xaa Xaa Xaa Lys Gly Xaa Xaa Xaa Xaa Xaa Xaa
385                 390                 395                 400

Xaa Xaa Xaa Asn Thr Xaa Xaa Xaa Ala Xaa Xaa Ala Xaa Xaa Xaa
         405                 410                 415

Xaa Xaa Xaa Gly Xaa Xaa Xaa Xaa Xaa Xaa Xaa Ala Xaa Xaa Ala
         420                 425                 430

<210> SEQ ID NO 188
<211> LENGTH: 402

<212> TYPE: PRT
<213> ORGANISM: Artificial Sequence
<220> FEATURE:
<223> OTHER INFORMATION: Description of Artificial Sequence: pspA

<400> SEQUENCE: 188

```
Leu Gln Gly Asp Leu Gln Gly Lys Asn Ile Phe Ala Ala Ala Gly Ser
 1               5                  10                  15

Asp Ile Thr Asn Thr Gly Ser Ile Gly Ala Glu Asn Ala Leu Leu Leu
             20                  25                  30

Lys Ala Ser Asn Asn Ile Glu Ser Arg Ser Glu Thr Arg Ser Asn Gln
         35                  40                  45

Asn Glu Gln Gly Ser Val Arg Asn Ile Gly Arg Val Ala Gly Ile Tyr
     50                  55                  60

Leu Thr Gly Arg Gln Asn Gly Ser Val Leu Leu Asp Ala Gly Asn Asn
 65                  70                  75                  80

Ile Val Leu Thr Ala Ser Glu Leu Thr Asn Gln Ser Glu Asp Gly Gln
                 85                  90                  95

Thr Val Leu Asn Ala Gly Gly Asp Ile Arg Ser Asp Thr Thr Gly Ile
            100                 105                 110

Ser Arg Asn Gln Asn Thr Ile Phe Asp Ser Asp Asn Tyr Val Ile Arg
        115                 120                 125

Lys Glu Gln Asn Glu Val Gly Ser Thr Ile Arg Thr Arg Gly Asn Leu
130                 135                 140

Ser Leu Asn Ala Lys Gly Asp Ile Arg Ile Arg Ala Ala Glu Val Gly
145                 150                 155                 160

Ser Glu Gln Gly Arg Leu Lys Leu Ala Ala Gly Arg Asp Ile Lys Val
                165                 170                 175

Glu Ala Gly Lys Ala His Thr Glu Thr Glu Asp Ala Leu Lys Tyr Thr
            180                 185                 190

Gly Arg Ser Gly Gly Ile Lys Gln Lys Met Thr Arg His Leu Lys
        195                 200                 205

Asn Gln Asn Gly Gln Ala Val Ser Gly Thr Leu Asp Gly Lys Glu Ile
    210                 215                 220

Ile Leu Val Ser Gly Arg Asp Ile Thr Val Thr Gly Ser Asn Ile Ile
225                 230                 235                 240

Ala Asp Asn His Thr Ile Leu Ser Ala Lys Asn Ile Val Leu Lys
                245                 250                 255

Ala Ala Glu Thr Arg Ser Arg Ser Ala Glu Met Asn Lys Lys Glu Lys
            260                 265                 270

Ser Gly Leu Met Gly Ser Gly Gly Ile Gly Phe Thr Ala Gly Ser Lys
        275                 280                 285

Lys Asp Thr Gln Thr Asn Arg Ser Glu Thr Val Ser His Thr Glu Ser
    290                 295                 300

Val Val Gly Ser Leu Asn Gly Asn Thr Leu Ile Ser Ala Gly Lys His
305                 310                 315                 320

Tyr Thr Gln Thr Gly Ser Thr Ile Ser Ser Pro Gln Gly Asp Val Gly
                325                 330                 335

Ile Ser Ser Gly Lys Ile Ser Ile Asp Ala Ala Gln Asn Arg Tyr Ser
            340                 345                 350

Gln Glu Ser Lys Gln Val Tyr Glu Gln Lys Gly Val Thr Val Ala Ile
        355                 360                 365

Ser Val Pro Val Val Asn Thr Val Met Gly Ala Val Asp Ala Val Lys
    370                 375                 380
```

-continued

Ala Val Gln Thr Val Gly Lys Ser Lys Asn Ser Arg Val Asn Ala Met
385                 390                 395                 400

Ala Ala

<210> SEQ ID NO 189
<211> LENGTH: 497
<212> TYPE: PRT
<213> ORGANISM: Artificial Sequence
<220> FEATURE:
<223> OTHER INFORMATION: Description of Artificial Sequence: ORF116
<220> FEATURE:
<221> NAME/KEY: SITE
<222> LOCATION: (25)
<223> OTHER INFORMATION: place-holder
<220> FEATURE:
<221> NAME/KEY: SITE
<222> LOCATION: (59)..(74)
<223> OTHER INFORMATION: place-holder
<220> FEATURE:
<221> NAME/KEY: SITE
<222> LOCATION: (78)..(83)
<223> OTHER INFORMATION: place-holder
<220> FEATURE:
<221> NAME/KEY: SITE
<222> LOCATION: (129)
<223> OTHER INFORMATION: place-holder
<220> FEATURE:
<221> NAME/KEY: SITE
<222> LOCATION: (160)..(174)
<223> OTHER INFORMATION: place-holder
<220> FEATURE:
<221> NAME/KEY: SITE
<222> LOCATION: (183)..(191)
<223> OTHER INFORMATION: place-holder
<220> FEATURE:
<221> NAME/KEY: SITE
<222> LOCATION: (227)
<223> OTHER INFORMATION: place-holder
<220> FEATURE:
<221> NAME/KEY: SITE
<222> LOCATION: (282)
<223> OTHER INFORMATION: place-holder
<220> FEATURE:
<221> NAME/KEY: SITE
<222> LOCATION: (315)
<223> OTHER INFORMATION: place-holder
<220> FEATURE:
<221> NAME/KEY: SITE
<222> LOCATION: (328)..(339)
<223> OTHER INFORMATION: place-holder

<400> SEQUENCE: 189

Glu Ala Val Gly Ser Asn Ile Gly Gly Gly Lys Met Ile Val Ala Ala
 1               5                  10                  15

Gly Gln Asp Ile Asn Val Arg Gly Xaa Ser Leu Ile Ser Asp Lys Gly
            20                  25                  30

Ile Val Leu Lys Ala Gly His Asp Ile Asp Ile Ser Thr Ala His Asn
        35                  40                  45

Arg Tyr Thr Gly Asn Glu Tyr His Glu Ser Xaa Xaa Xaa Xaa Xaa Xaa
    50                  55                  60

Xaa Xaa Xaa Xaa Xaa Xaa Xaa Xaa Xaa Asn Arg Lys Xaa Xaa Xaa
65                  70                  75                  80

Xaa Xaa Xaa Arg Thr Asn Ile Val His Thr Gly Ser Ile Ile Gly Ser
                85                  90                  95

Leu Asn Gly Asp Thr Val Thr Val Ala Gly Asn Arg Tyr Arg Gln Thr
            100                 105                 110

Gly Ser Thr Val Ser Ser Pro Glu Gly Arg Asn Thr Val Thr Ala Lys
        115                 120                 125

```
Xaa Ile Asp Val Glu Phe Ala Asn Asn Arg Tyr Ala Thr Asp Tyr Ala
        130                 135                 140

His Thr Gln Glu Gln Lys Gly Leu Thr Val Ala Leu Asn Val Pro Xaa
145                 150                 155                 160

Xaa Xaa Xaa Xaa Xaa Xaa Xaa Xaa Xaa Xaa Xaa Xaa Xaa Xaa Gly Lys
                165                 170                 175

Ser Lys Asn Lys Arg Val Xaa Xaa Xaa Xaa Xaa Xaa Xaa Xaa Xaa Trp
            180                 185                 190

Gln Ser Tyr Gln Ala Thr Gln Gln Met Gln Gln Phe Ala Pro Ser Ser
            195                 200                 205

Ser Ala Gly Gln Gly Gln Asn Tyr Asn Gln Ser Pro Ser Ile Ser Val
        210                 215                 220

Ser Ile Xaa Tyr Gly Glu Gln Lys Ser Arg Asn Glu Gln Lys Arg His
225                 230                 235                 240

Tyr Thr Glu Ala Ala Ala Ser Gln Ile Ile Gly Lys Gly Gln Thr Thr
                245                 250                 255

Leu Ala Ala Thr Gly Ser Gly Glu Gln Ser Asn Ile Asn Ile Thr Gly
            260                 265                 270

Ser Asp Val Ile Gly His Ala Gly Thr Xaa Leu Ile Ala Asp Asn His
        275                 280                 285

Ile Arg Leu Gln Ser Ala Lys Gln Asp Gly Ser Glu Gln Ser Lys Asn
290                 295                 300

Lys Ser Ser Gly Trp Asn Ala Gly Val Arg Xaa Lys Ile Gly Asn Gly
305                 310                 315                 320

Ile Arg Phe Gly Ile Thr Ala Xaa Xaa Xaa Xaa Xaa Xaa Xaa Xaa Xaa
                325                 330                 335

Xaa Xaa Xaa Ser Thr Thr His Arg His Thr His Val Gly Ser Thr Thr
            340                 345                 350

Gly Lys Thr Thr Ile Arg Ser Gly Gly Asp Thr Thr Leu Lys Gly Val
            355                 360                 365

Gln Leu Ile Gly Lys Gly Ile Gln Ala Asp Thr Arg Asn Leu His Ile
370                 375                 380

Glu Ser Val Gln Asp Thr Glu Thr Tyr Gln Ser Lys Gln Asn Gly
385                 390                 395                 400

Asn Val Gln Val Thr Val Gly Tyr Gly Phe Ser Ala Ser Gly Ser Tyr
                405                 410                 415

Arg Gln Ser Lys Val Lys Ala Asp His Ala Ser Val Thr Gly Gln Ser
            420                 425                 430

Gly Ile Tyr Ala Gly Glu Asp Gly Tyr Gln Ile Lys Val Arg Asp Asn
        435                 440                 445

Thr Asp Leu Lys Gly Gly Ile Ile Thr Ser Gln Ser Ala Glu Asp
450                 455                 460

Lys Gly Lys Asn Leu Phe Gln Thr Ala Thr Leu Thr Ala Ser Asp Ile
465                 470                 475                 480

Gln Asn His Ser Arg Tyr Glu Gly Arg Ser Phe Gly Ile Gly Ser
                485                 490                 495

Phe

<210> SEQ ID NO 190
<211> LENGTH: 502
<212> TYPE: PRT
<213> ORGANISM: Artificial Sequence
<220> FEATURE:
<223> OTHER INFORMATION: Description of Artificial Sequence: overlap
      identity
```

-continued

```
<220> FEATURE:
<221> NAME/KEY: SITE
<222> LOCATION: (1)
<223> OTHER INFORMATION: absent or positive
<220> FEATURE:
<221> NAME/KEY: SITE
<222> LOCATION: (4)..(8)
<223> OTHER INFORMATION: absent or positive
<220> FEATURE:
<221> NAME/KEY: SITE
<222> LOCATION: (10)..(12)
<223> OTHER INFORMATION: absent or positive
<220> FEATURE:
<221> NAME/KEY: SITE
<222> LOCATION: (14)..(16)
<223> OTHER INFORMATION: absent or positive
<220> FEATURE:
<221> NAME/KEY: SITE
<222> LOCATION: (18)
<223> OTHER INFORMATION: absent or positive
<220> FEATURE:
<221> NAME/KEY: SITE
<222> LOCATION: (21)
<223> OTHER INFORMATION: absent or positive
<220> FEATURE:
<221> NAME/KEY: SITE
<222> LOCATION: (23)
<223> OTHER INFORMATION: absent or positive
<220> FEATURE:
<221> NAME/KEY: SITE
<222> LOCATION: (25)..(27)
<223> OTHER INFORMATION: absent or positive
<220> FEATURE:
<221> NAME/KEY: SITE
<222> LOCATION: (29)
<223> OTHER INFORMATION: absent or positive
<220> FEATURE:
<221> NAME/KEY: SITE
<222> LOCATION: (31)..(34)
<223> OTHER INFORMATION: absent or positive
<220> FEATURE:
<221> NAME/KEY: SITE
<222> LOCATION: (36)
<223> OTHER INFORMATION: absent or positive
<220> FEATURE:
<221> NAME/KEY: SITE
<222> LOCATION: (38)..(40)
<223> OTHER INFORMATION: absent or positive
<220> FEATURE:
<221> NAME/KEY: SITE
<222> LOCATION: (42)..(45)
<223> OTHER INFORMATION: absent or positive
<220> FEATURE:
<221> NAME/KEY: SITE
<222> LOCATION: (47)..(48)
<223> OTHER INFORMATION: absent or positive
<220> FEATURE:
<221> NAME/KEY: SITE
<222> LOCATION: (50)..(53)
<223> OTHER INFORMATION: absent or positive
<220> FEATURE:
<221> NAME/KEY: SITE
<222> LOCATION: (55)..(76)
<223> OTHER INFORMATION: absent or positive
<220> FEATURE:
<221> NAME/KEY: SITE
<222> LOCATION: (78)..(88)
<223> OTHER INFORMATION: absent or positive
<220> FEATURE:
<221> NAME/KEY: SITE
<222> LOCATION: (91)
<223> OTHER INFORMATION: absent or positive
<220> FEATURE:
<221> NAME/KEY: SITE
<222> LOCATION: (93)..(94)
<223> OTHER INFORMATION: absent or positive
<220> FEATURE:
<221> NAME/KEY: SITE
<222> LOCATION: (100)
```

```
<223> OTHER INFORMATION: absent or positive
<220> FEATURE:
<221> NAME/KEY: SITE
<222> LOCATION: (102)..(104)
<223> OTHER INFORMATION: absent or positive
<220> FEATURE:
<221> NAME/KEY: SITE
<222> LOCATION: (107)..(108)
<223> OTHER INFORMATION: absent or positive
<220> FEATURE:
<221> NAME/KEY: SITE
<222> LOCATION: (110)
<223> OTHER INFORMATION: absent or positive
<220> FEATURE:
<221> NAME/KEY: SITE
<222> LOCATION: (116)
<223> OTHER INFORMATION: absent or positive
<220> FEATURE:
<221> NAME/KEY: SITE
<222> LOCATION: (120)
<223> OTHER INFORMATION: absent or positive
<220> FEATURE:
<221> NAME/KEY: SITE
<222> LOCATION: (122)..(129)
<223> OTHER INFORMATION: absent or positive
<220> FEATURE:
<221> NAME/KEY: SITE
<222> LOCATION: (131)..(134)
<223> OTHER INFORMATION: absent or positive
<220> FEATURE:
<221> NAME/KEY: SITE
<222> LOCATION: (136)
<223> OTHER INFORMATION: absent or positive
<220> FEATURE:
<221> NAME/KEY: SITE
<222> LOCATION: (140)..(147)
<223> OTHER INFORMATION: absent or positive
<220> FEATURE:
<221> NAME/KEY: SITE
<222> LOCATION: (152)
<223> OTHER INFORMATION: absent or positive
<220> FEATURE:
<221> NAME/KEY: SITE
<222> LOCATION: (156)..(157)
<223> OTHER INFORMATION: absent or positive
<220> FEATURE:
<221> NAME/KEY: SITE
<222> LOCATION: (160)..(177)
<223> OTHER INFORMATION: absent or positive
<220> FEATURE:
<221> NAME/KEY: SITE
<222> LOCATION: (183)
<223> OTHER INFORMATION: absent or positive
<220> FEATURE:
<221> NAME/KEY: SITE
<222> LOCATION: (186)..(207)
<223> OTHER INFORMATION: absent or positive
<220> FEATURE:
<221> NAME/KEY: SITE
<222> LOCATION: (209)..(210)
<223> OTHER INFORMATION: absent or positive
<220> FEATURE:
<221> NAME/KEY: SITE
<222> LOCATION: (212)..(214)
<223> OTHER INFORMATION: absent or positive
<220> FEATURE:
<221> NAME/KEY: SITE
<222> LOCATION: (219)..(226)
<223> OTHER INFORMATION: absent or positive
<220> FEATURE:
<221> NAME/KEY: SITE
<222> LOCATION: (231)..(232)
<223> OTHER INFORMATION: absent or positive
<220> FEATURE:
<221> NAME/KEY: SITE
<222> LOCATION: (238)..(240)
<223> OTHER INFORMATION: absent or positive
<220> FEATURE:
<221> NAME/KEY: SITE
```

-continued

```
<222> LOCATION: (242)..(246)
<223> OTHER INFORMATION: absent or positive
<220> FEATURE:
<221> NAME/KEY: SITE
<222> LOCATION: (248)..(253)
<223> OTHER INFORMATION: absent or positive
<220> FEATURE:
<221> NAME/KEY: SITE
<222> LOCATION: (255)
<223> OTHER INFORMATION: absent or positive
<220> FEATURE:
<221> NAME/KEY: SITE
<222> LOCATION: (257)
<223> OTHER INFORMATION: absent or positive
<220> FEATURE:
<221> NAME/KEY: SITE
<222> LOCATION: (259)..(261)
<223> OTHER INFORMATION: absent or positive
<220> FEATURE:
<221> NAME/KEY: SITE
<222> LOCATION: (263)
<223> OTHER INFORMATION: absent or positive
<220> FEATURE:
<221> NAME/KEY: SITE
<222> LOCATION: (265)
<223> OTHER INFORMATION: absent or positive
<220> FEATURE:
<221> NAME/KEY: SITE
<222> LOCATION: (267)
<223> OTHER INFORMATION: absent or positive
<220> FEATURE:
<221> NAME/KEY: SITE
<222> LOCATION: (269)..(270)
<223> OTHER INFORMATION: absent or positive
<220> FEATURE:
<221> NAME/KEY: SITE
<222> LOCATION: (272)
<223> OTHER INFORMATION: absent or positive
<220> FEATURE:
<221> NAME/KEY: SITE
<222> LOCATION: (274)
<223> OTHER INFORMATION: absent or positive
<220> FEATURE:
<221> NAME/KEY: SITE
<222> LOCATION: (281)
<223> OTHER INFORMATION: absent or positive
<220> FEATURE:
<221> NAME/KEY: SITE
<222> LOCATION: (283)..(284)
<223> OTHER INFORMATION: absent or positive
<220> FEATURE:
<221> NAME/KEY: SITE
<222> LOCATION: (287)
<223> OTHER INFORMATION: absent or positive
<220> FEATURE:
<221> NAME/KEY: SITE
<222> LOCATION: (289)
<223> OTHER INFORMATION: absent or positive
<220> FEATURE:
<221> NAME/KEY: SITE
<222> LOCATION: (291)
<223> OTHER INFORMATION: absent or positive
<220> FEATURE:
<221> NAME/KEY: SITE
<222> LOCATION: (293)..(298)
<223> OTHER INFORMATION: absent or positive
<220> FEATURE:
<221> NAME/KEY: SITE
<222> LOCATION: (300)
<223> OTHER INFORMATION: absent or positive
<220> FEATURE:
<221> NAME/KEY: SITE
<222> LOCATION: (302)..(304)
<223> OTHER INFORMATION: absent or positive
<220> FEATURE:
<221> NAME/KEY: SITE
<222> LOCATION: (306)
<223> OTHER INFORMATION: absent or positive
<220> FEATURE:
```

-continued

```
<221> NAME/KEY: SITE
<222> LOCATION: (308)
<223> OTHER INFORMATION: absent or positive
<220> FEATURE:
<221> NAME/KEY: SITE
<222> LOCATION: (312)
<223> OTHER INFORMATION: absent or positive
<220> FEATURE:
<221> NAME/KEY: SITE
<222> LOCATION: (314)
<223> OTHER INFORMATION: absent or positive
<220> FEATURE:
<221> NAME/KEY: SITE
<222> LOCATION: (319)..(321)
<223> OTHER INFORMATION: absent or positive
<220> FEATURE:
<221> NAME/KEY: SITE
<222> LOCATION: (323)..(324)
<223> OTHER INFORMATION: absent or positive
<220> FEATURE:
<221> NAME/KEY: SITE
<222> LOCATION: (327)
<223> OTHER INFORMATION: absent or positive
<220> FEATURE:
<221> NAME/KEY: SITE
<222> LOCATION: (330)
<223> OTHER INFORMATION: absent or positive
<220> FEATURE:
<221> NAME/KEY: SITE
<222> LOCATION: (333)..(345)
<223> OTHER INFORMATION: absent or positive
<220> FEATURE:
<221> NAME/KEY: SITE
<222> LOCATION: (347)..(348)
<223> OTHER INFORMATION: absent or positive
<220> FEATURE:
<221> NAME/KEY: SITE
<222> LOCATION: (350)..(351)
<223> OTHER INFORMATION: absent or positive
<220> FEATURE:
<221> NAME/KEY: SITE
<222> LOCATION: (353)
<223> OTHER INFORMATION: absent or positive
<220> FEATURE:
<221> NAME/KEY: SITE
<222> LOCATION: (356)..(359)
<223> OTHER INFORMATION: absent or positive
<220> FEATURE:
<221> NAME/KEY: SITE
<222> LOCATION: (361)
<223> OTHER INFORMATION: absent or positive
<220> FEATURE:
<221> NAME/KEY: SITE
<222> LOCATION: (363)
<223> OTHER INFORMATION: absent or positive
<220> FEATURE:
<221> NAME/KEY: SITE
<222> LOCATION: (369)..(370)
<223> OTHER INFORMATION: absent or positive
<220> FEATURE:
<221> NAME/KEY: SITE
<222> LOCATION: (373)
<223> OTHER INFORMATION: absent or positive
<220> FEATURE:
<221> NAME/KEY: SITE
<222> LOCATION: (376)
<223> OTHER INFORMATION: absent or positive
<220> FEATURE:
<221> NAME/KEY: SITE
<222> LOCATION: (380)..(386)
<223> OTHER INFORMATION: absent or positive
<220> FEATURE:
<221> NAME/KEY: SITE
<222> LOCATION: (392)
<223> OTHER INFORMATION: absent or positive
<220> FEATURE:
<221> NAME/KEY: SITE
<222> LOCATION: (396)..(400)
<223> OTHER INFORMATION: absent or positive
```

```
-continued

<220> FEATURE:
<221> NAME/KEY: SITE
<222> LOCATION: (403)
<223> OTHER INFORMATION: absent or positive
<220> FEATURE:
<221> NAME/KEY: SITE
<222> LOCATION: (405)..(407)
<223> OTHER INFORMATION: absent or positive
<220> FEATURE:
<221> NAME/KEY: SITE
<222> LOCATION: (417)..(418)
<223> OTHER INFORMATION: absent or positive
<220> FEATURE:
<221> NAME/KEY: SITE
<222> LOCATION: (422)..(423)
<223> OTHER INFORMATION: absent or positive
<220> FEATURE:
<221> NAME/KEY: SITE
<222> LOCATION: (426)..(428)
<223> OTHER INFORMATION: absent or positive
<220> FEATURE:
<221> NAME/KEY: SITE
<222> LOCATION: (430)
<223> OTHER INFORMATION: absent or positive
<220> FEATURE:
<221> NAME/KEY: SITE
<222> LOCATION: (434)..(435)
<223> OTHER INFORMATION: absent or positive
<220> FEATURE:
<221> NAME/KEY: SITE
<222> LOCATION: (440)
<223> OTHER INFORMATION: absent or positive
<220> FEATURE:
<221> NAME/KEY: SITE
<222> LOCATION: (443)
<223> OTHER INFORMATION: absent or positive
<220> FEATURE:
<221> NAME/KEY: SITE
<222> LOCATION: (447)
<223> OTHER INFORMATION: absent or positive
<220> FEATURE:
<221> NAME/KEY: SITE
<222> LOCATION: (449)
<223> OTHER INFORMATION: absent or positive
<220> FEATURE:
<221> NAME/KEY: SITE
<222> LOCATION: (451)..(453)
<223> OTHER INFORMATION: absent or positive
<220> FEATURE:
<221> NAME/KEY: SITE
<222> LOCATION: (455)
<223> OTHER INFORMATION: absent or positive
<220> FEATURE:
<221> NAME/KEY: SITE
<222> LOCATION: (457)
<223> OTHER INFORMATION: absent or positive
<220> FEATURE:
<221> NAME/KEY: SITE
<222> LOCATION: (459)..(462)
<223> OTHER INFORMATION: absent or positive
<220> FEATURE:
<221> NAME/KEY: SITE
<222> LOCATION: (464)..(468)
<223> OTHER INFORMATION: absent or positive
<220> FEATURE:
<221> NAME/KEY: SITE
<222> LOCATION: (471)
<223> OTHER INFORMATION: absent or positive
<220> FEATURE:
<221> NAME/KEY: SITE
<222> LOCATION: (475)..(476)
<223> OTHER INFORMATION: absent or positive
<220> FEATURE:
<221> NAME/KEY: SITE
<222> LOCATION: (478)..(483)
<223> OTHER INFORMATION: absent or positive
<220> FEATURE:
<221> NAME/KEY: SITE
<222> LOCATION: (489)..(496)
```

-continued

```
<223> OTHER INFORMATION: absent or positive
<220> FEATURE:
<221> NAME/KEY: SITE
<222> LOCATION: (498)..(499)
<223> OTHER INFORMATION: absent or positive
<220> FEATURE:
<221> NAME/KEY: SITE
<222> LOCATION: (501)
<223> OTHER INFORMATION: absent or positive

<400> SEQUENCE: 190

Xaa Ala Val Xaa Xaa Xaa Xaa Gly Xaa Xaa Xaa Ile Xaa Xaa Xaa
  1               5                  10                  15

Gly Xaa Asp Ile Xaa Val Xaa Gly Xaa Xaa Ile Xaa Asp Xaa Xaa
             20                  25                  30

Xaa Xaa Leu Xaa Ala Xaa Xaa Xaa Ile Xaa Xaa Xaa Xaa Ala Xaa Xaa
         35                  40                  45

Arg Xaa Xaa Xaa Glu Xaa Xaa Xaa Xaa Xaa Xaa Xaa Xaa Xaa
         50                  55                  60

Xaa Xaa Xaa Xaa Xaa Xaa Xaa Xaa Xaa Lys Xaa Xaa Xaa
 65                  70                  75                  80

Xaa Xaa Xaa Xaa Xaa Xaa Xaa Xaa His Thr Xaa Ser Xaa Xaa Gly Ser
             85                  90                  95

Leu Asn Gly Xaa Thr Xaa Xaa Xaa Ala Gly Xaa Xaa Tyr Xaa Gln Thr
             100                 105                 110

Gly Ser Thr Xaa Ser Ser Pro Xaa Gly Xaa Xaa Xaa Xaa Xaa Xaa
         115                 120                 125

Xaa Ile Xaa Xaa Xaa Xaa Ala Xaa Asn Arg Tyr Xaa Xaa Xaa Xaa Xaa
         130                 135                 140

Xaa Xaa Xaa Glu Gln Lys Gly Xaa Thr Val Ala Xaa Xaa Val Pro Xaa
145                 150                 155                 160

Xaa Xaa Xaa Xaa Xaa Xaa Xaa Xaa Xaa Xaa Xaa Xaa Xaa Xaa Xaa
             165                 170                 175

Xaa Gly Lys Ser Lys Asn Xaa Arg Val Xaa Xaa Xaa Xaa Xaa Xaa
         180                 185                 190

Xaa Xaa Xaa Xaa Xaa Xaa Xaa Xaa Xaa Xaa Xaa Xaa Xaa Xaa Ala
             195                 200                 205

Xaa Xaa Pro Xaa Xaa Xaa Ala Gly Gln Gly Xaa Xaa Xaa Xaa Xaa
         210                 215                 220

Xaa Xaa Ile Ser Val Ser Xaa Xaa Tyr Gly Glu Gln Lys Xaa Xaa Xaa
225                 230                 235                 240

Glu Xaa Xaa Xaa Xaa Xaa Thr Xaa Xaa Xaa Xaa Xaa Xaa Ile Xaa Gly
             245                 250                 255

Xaa Gly Xaa Xaa Xaa Leu Xaa Ala Xaa Gly Xaa Gly Xaa Xaa Ser Xaa
         260                 265                 270

Ile Xaa Ile Thr Gly Ser Asp Val Xaa Gly Xaa Xaa Gly Thr Xaa Leu
         275                 280                 285

Xaa Ala Xaa Asn Xaa Xaa Xaa Xaa Xaa Ala Xaa Gln Xaa Xaa Xaa
         290                 295                 300

Glu Xaa Ser Xaa Asn Lys Ser Xaa Gly Xaa Asn Ala Gly Val Xaa Xaa
305                 310                 315                 320

Xaa Ile Xaa Xaa Gly Ile Xaa Phe Gly Xaa Thr Ala Xaa Xaa Xaa Xaa
             325                 330                 335

Xaa Xaa Xaa Xaa Xaa Xaa Xaa Xaa Xaa Thr Xaa Xaa Arg Xaa Xaa His
         340                 345                 350

Xaa Gly Ser Xaa Xaa Xaa Xaa Thr Xaa Ile Xaa Ser Gly Gly Asp Thr
```

```
                    355                 360                 365
Xaa Xaa Lys Gly Xaa Gln Leu Xaa Gly Lys Gly Xaa Xaa Xaa Xaa
            370                 375                 380

Xaa Xaa Leu His Ile Glu Ser Xaa Gln Asp Thr Xaa Xaa Xaa Xaa
385                 390                 395                 400

Lys Gln Xaa Asn Xaa Xaa Xaa Gln Val Thr Val Gly Tyr Gly Phe Ser
                405                 410                 415

Xaa Xaa Gly Ser Tyr Xaa Xaa Ser Lys Xaa Xaa Asp Xaa Ala Ser
                420                 425                 430

Val Xaa Xaa Gln Ser Gly Ile Xaa Ala Gly Xaa Asp Gly Tyr Xaa Ile
            435                 440                 445

Xaa Val Xaa Xaa Xaa Thr Xaa Leu Xaa Gly Xaa Xaa Xaa Ser Xaa
            450                 455                 460

Xaa Xaa Xaa Xaa Asp Lys Xaa Lys Asn Leu Xaa Xaa Thr Xaa Xaa Xaa
465                 470                 475                 480

Xaa Xaa Xaa Asp Ile Gln Asn His Xaa Xaa Xaa Xaa Xaa Xaa Xaa
                485                 490                 495

Gly Xaa Xaa Gly Xaa Phe
            500

<210> SEQ ID NO 191
<211> LENGTH: 491
<212> TYPE: PRT
<213> ORGANISM: Artificial Sequence
<220> FEATURE:
<223> OTHER INFORMATION: Description of Artificial Sequence: pspA

<400> SEQUENCE: 191

Gln Ala Val Ser Gly Thr Leu Asp Gly Lys Glu Ile Ile Leu Val Ser
1               5                   10                  15

Gly Arg Asp Ile Thr Val Thr Gly Ser Asn Ile Ile Ala Asp Asn His
            20                  25                  30

Thr Ile Leu Ser Ala Lys Asn Asn Ile Val Leu Lys Ala Ala Glu Thr
        35                  40                  45

Arg Ser Arg Ser Ala Glu Met Asn Lys Lys Glu Lys Ser Gly Leu Met
    50                  55                  60

Gly Ser Gly Gly Ile Gly Phe Thr Ala Gly Ser Lys Lys Asp Thr Gln
65                  70                  75                  80

Thr Asn Arg Ser Glu Thr Val Ser His Thr Glu Ser Val Val Gly Ser
                85                  90                  95

Leu Asn Gly Asn Thr Leu Ile Ser Ala Gly Lys His Tyr Thr Gln Thr
            100                 105                 110

Gly Ser Thr Ile Ser Ser Pro Gln Gly Asp Val Gly Ile Ser Ser Gly
        115                 120                 125

Lys Ile Ser Ile Asp Ala Ala Gln Asn Arg Tyr Ser Gln Glu Ser Lys
130                 135                 140

Gln Val Tyr Glu Gln Lys Gly Val Thr Val Ala Ile Ser Val Pro Val
145                 150                 155                 160

Val Asn Thr Val Met Gly Ala Val Asp Ala Val Lys Ala Val Gln Thr
                165                 170                 175

Val Gly Lys Ser Lys Asn Ser Arg Val Asn Ala Met Ala Ala Ala Asn
            180                 185                 190

Ala Leu Asn Lys Gly Val Asp Ser Gly Val Ala Leu Tyr Asn Ala Ala
        195                 200                 205

Arg Asn Pro Lys Lys Ala Ala Gly Gln Gly Ile Ser Val Ser Val Thr
```

-continued

```
            210                 215                 220
Tyr Gly Glu Gln Lys Asn Thr Ser Glu Ser Arg Ile Lys Gly Thr Gln
225                 230                 235                 240

Val Gln Glu Gly Lys Ile Thr Gly Gly Lys Val Ser Leu Thr Ala
                245                 250                 255

Ser Gly Ala Gly Lys Asp Ser Arg Ile Thr Ile Thr Gly Ser Asp Val
                260                 265                 270

Tyr Gly Gly Lys Gly Thr Arg Leu Lys Ala Glu Asn Ala Val Gln Ile
                275                 280                 285

Glu Ala Ala Arg Gln Thr His Gln Glu Arg Ser Glu Asn Lys Ser Ala
290                 295                 300

Gly Phe Asn Ala Gly Val Ala Ile Ala Ile Asn Lys Gly Ile Ser Phe
305                 310                 315                 320

Gly Phe Thr Ala Gly Ala Asn Tyr Gly Lys Gly Tyr Gly Asn Gly Asp
                325                 330                 335

Glu Thr Ala Tyr Arg Asn Ser His Ile Gly Ser Lys Asp Ser Gln Thr
                340                 345                 350

Ala Ile Glu Ser Gly Gly Asp Thr Val Ile Lys Gly Gly Gln Leu Lys
                355                 360                 365

Gly Lys Gly Val Gly Val Thr Ala Glu Ser Leu His Ile Glu Ser Leu
370                 375                 380

Gln Asp Thr Ala Val Phe Lys Gly Lys Gln Glu Asn Val Ser Ala Gln
385                 390                 395                 400

Val Thr Val Gly Tyr Gly Phe Ser Val Gly Ser Tyr Asn Arg Ser
                405                 410                 415

Lys Ser Ser Ser Asp Tyr Ala Ser Val Asn Glu Gln Ser Gly Ile Phe
                420                 425                 430

Ala Gly Gly Asp Gly Tyr Arg Ile Arg Val Asn Gly Lys Thr Gly Leu
                435                 440                 445

Val Gly Ala Ala Val Val Ser Asp Ala Asp Lys Ser Lys Asn Leu Leu
450                 455                 460

Lys Thr Ser Glu Ile Trp His Lys Asp Ile Gln Asn His Ala Ser Ala
465                 470                 475                 480

Ala Ala Ser Ala Leu Gly Leu Ser Gly Gly Phe
                485                 490
```

<210> SEQ ID NO 192
<211> LENGTH: 310
<212> TYPE: PRT
<213> ORGANISM: Artificial Sequence
<220> FEATURE:
<223> OTHER INFORMATION: Description of Artificial Sequence: ORF41
<220> FEATURE:
<221> NAME/KEY: SITE
<222> LOCATION: (19)
<223> OTHER INFORMATION: place-holder
<220> FEATURE:
<221> NAME/KEY: SITE
<222> LOCATION: (33)
<223> OTHER INFORMATION: place-holder
<220> FEATURE:
<221> NAME/KEY: SITE
<222> LOCATION: (47)
<223> OTHER INFORMATION: place-holder

<400> SEQUENCE: 192

```
Tyr Arg Arg His Leu Leu Cys Lys Tyr Ile Tyr Arg Phe Pro Ile Tyr
  1               5                  10                  15

Cys Pro Xaa Ala Cys Val Ala Glu Asp Thr Pro Tyr Ala Cys Tyr Leu
```

```
                    20                  25                  30

Xaa Gln Leu Gln Val Thr Lys Asp Val Asn Trp Asn Gln Val Xaa Leu
        35                  40                  45

Ala Tyr Asp Lys Trp Asp Tyr Lys Gln Glu Gly Leu Thr Gly Ala Gly
    50                  55                  60

Ala Ala Ile Ile Ala Leu Ala Val Thr Val Thr Ala Gly Ala Gly
65                  70                  75                  80

Ala Gly Ala Ala Leu Gly Leu Asn Gly Ala Ala Ala Ala Thr Asp
                85                  90                  95

Ala Ala Phe Ala Ser Leu Ala Ser Gln Ala Ser Val Ser Leu Ile Asn
            100                 105                 110

Asn Lys Gly Asn Ile Gly Asn Thr Leu Lys Glu Leu Gly Arg Ser Ser
        115                 120                 125

Thr Val Lys Asn Leu Met Val Ala Val Ala Thr Ala Gly Val Ala Asp
    130                 135                 140

Lys Ile Gly Ala Ser Ala Leu Asn Asn Val Ser Asp Lys Gln Trp Ile
145                 150                 155                 160

Asn Asn Leu Thr Val Asn Leu Ala Asn Ala Gly Ser Ala Ala Leu Ile
                165                 170                 175

Asn Thr Ala Val Asn Gly Gly Ser Leu Lys Asp Asn Leu Glu Ala Asn
            180                 185                 190

Ile Leu Ala Ala Leu Val Asn Thr Ala His Gly Glu Ala Ala Ser Lys
        195                 200                 205

Ile Lys Gln Leu Asp Gln His Tyr Ile Thr His Lys Ile Ala His Ala
    210                 215                 220

Ile Ala Gly Cys Ala Ala Ala Ala Asn Lys Gly Lys Cys Gln Asp
225                 230                 235                 240

Gly Ala Ile Gly Ala Ala Val Gly Glu Ile Val Gly Glu Ala Leu Thr
                245                 250                 255

Asn Gly Lys Asn Pro Asp Thr Leu Thr Ala Lys Glu Arg Glu Gln Ile
            260                 265                 270

Leu Ala Tyr Ser Lys Leu Val Ala Gly Thr Val Ser Gly Val Val Gly
        275                 280                 285

Gly Asp Val Asn Ala Ala Asn Ala Ala Glu Val Ala Val Lys Asn
    290                 295                 300

Asn Gln Leu Ser Asp Lys
305                 310

<210> SEQ ID NO 193
<211> LENGTH: 330
<212> TYPE: PRT
<213> ORGANISM: Artificial Sequence
<220> FEATURE:
<223> OTHER INFORMATION: Description of Artificial Sequence: ORF41a
<220> FEATURE:
<221> NAME/KEY: SITE
<222> LOCATION: (61)
<223> OTHER INFORMATION: place-holder
<220> FEATURE:
<221> NAME/KEY: SITE
<222> LOCATION: (122)
<223> OTHER INFORMATION: place-holder
<220> FEATURE:
<221> NAME/KEY: SITE
<222> LOCATION: (158)
<223> OTHER INFORMATION: place-holder
<220> FEATURE:
<221> NAME/KEY: SITE
<222> LOCATION: (280)
<223> OTHER INFORMATION: place-holder
```

```
<220> FEATURE:
<221> NAME/KEY: SITE
<222> LOCATION: (297)
<223> OTHER INFORMATION: place-holder

<400> SEQUENCE: 193

Tyr Leu Lys Gln Leu Gln Val Ala Lys Asn Ile Asn Trp Asn Gln Val
 1               5                   10                  15

Gln Leu Ala Tyr Asp Arg Trp Asp Tyr Lys Gln Glu Gly Leu Thr Glu
            20                  25                  30

Ala Gly Ala Ala Ile Ile Ala Leu Ala Val Thr Val Thr Ser Gly
        35                  40                  45

Ala Gly Thr Gly Ala Val Leu Gly Leu Asn Gly Ala Xaa Ala Ala Ala
    50                  55                  60

Thr Asp Ala Ala Phe Ala Ser Leu Ala Ser Gln Ala Ser Val Ser Phe
65                  70                  75                  80

Ile Asn Asn Lys Gly Asp Val Gly Lys Thr Leu Lys Glu Leu Gly Arg
                85                  90                  95

Ser Ser Thr Val Lys Asn Leu Val Val Ala Ala Thr Ala Gly Val
            100                 105                 110

Ala Asp Lys Ile Gly Ala Ser Ala Leu Xaa Asn Val Ser Asp Lys Gln
        115                 120                 125

Trp Ile Asn Asn Leu Thr Val Asn Leu Ala Asn Ala Gly Ser Ala Ala
    130                 135                 140

Leu Ile Asn Thr Ala Val Asn Gly Gly Ser Leu Lys Asp Xaa Leu Glu
145                 150                 155                 160

Ala Asn Ile Leu Ala Ala Leu Val Asn Thr Ala His Gly Glu Ala Ala
                165                 170                 175

Ser Lys Ile Lys Gln Leu Asp Gln His Tyr Ile Val His Lys Ile Ala
            180                 185                 190

His Ala Ile Ala Gly Cys Ala Ala Ala Ala Asn Lys Gly Lys Cys
        195                 200                 205

Gln Asp Gly Ala Ile Gly Ala Ala Val Gly Glu Ile Val Gly Glu Ala
    210                 215                 220

Leu Thr Asn Gly Lys Asn Pro Asp Thr Leu Thr Ala Lys Glu Arg Glu
225                 230                 235                 240

Gln Ile Leu Ala Tyr Ser Lys Leu Val Ala Gly Thr Val Ser Gly Val
                245                 250                 255

Val Gly Gly Asp Val Asn Ala Ala Asn Ala Ala Glu Val Ala Val
            260                 265                 270

Lys Asn Asn Gln Leu Ser Asp Xaa Glu Gly Arg Glu Phe Asp Asn Glu
        275                 280                 285

Met Thr Ala Cys Ala Lys Gln Asn Xaa Pro Gln Leu Cys Arg Lys Asn
    290                 295                 300

Thr Val Lys Lys Tyr Gln Asn Val Ala Asp Lys Arg Leu Ala Ala Ser
305                 310                 315                 320

Ile Ala Ile Cys Thr Asp Ile Ser Arg Ser
                325                 330

<210> SEQ ID NO 194
<211> LENGTH: 180
<212> TYPE: PRT
<213> ORGANISM: Artificial Sequence
<220> FEATURE:
<223> OTHER INFORMATION: Description of Artificial Sequence: ORF51a

<400> SEQUENCE: 194
```

```
Tyr Lys Leu Leu Ala Ile Gly Ser Val Val Gly Ser Ile Leu Gly Val
1               5                   10                  15

Lys Leu Leu Leu Ile Leu Pro Val Ser Trp Leu Leu Leu Leu Met Ala
            20                  25                  30

Ile Ile Thr Leu Tyr Tyr Ser Val Asn Gly Ile Leu Asn Val Cys Ala
            35                  40                  45

Lys Ala Lys Asn Ile Gln Val Val Ala Asn Lys Asn Met Val Leu
        50                  55                  60

Phe Gly Phe Leu Ala Gly Ile Ile Gly Gly Ser Thr Asn Ala Met Ser
65                  70                  75                  80

Pro Ile Leu Leu Ile Phe Leu Leu Ser Glu Thr Glu Asn Lys Asn Arg
                85                  90                  95

Ile Ala Lys Ser Ser Asn Leu Cys Tyr Leu Leu Ala Lys Ile Val Gln
            100                 105                 110

Ile Tyr Met Leu Arg Asp Gln Tyr Trp Leu Leu Asn Lys Ser Glu Tyr
            115                 120                 125

Gly Leu Ile Phe Leu Leu Ser Val Leu Ser Val Ile Gly Leu Tyr Val
130                 135                 140

Gly Ile Arg Leu Arg Thr Lys Ile Ser Pro Asn Phe Phe Lys Met Leu
145                 150                 155                 160

Ile Phe Ile Val Leu Leu Val Leu Ala Leu Lys Ile Gly Tyr Ser Gly
                165                 170                 175

Leu Ile Lys Leu
            180

<210> SEQ ID NO 195
<211> LENGTH: 180
<212> TYPE: PRT
<213> ORGANISM: Artificial Sequence
<220> FEATURE:
<223> OTHER INFORMATION: Description of Artificial Sequence: ORF82a

<400> SEQUENCE: 195

Met Arg His Met Lys Asn Lys Asn Tyr Leu Leu Val Phe Ile Val Leu
1               5                   10                  15

His Ile Thr Leu Ile Val Ile Asn Ile Val Phe Gly Tyr Phe Val Phe
            20                  25                  30

Leu Phe Asp Phe Phe Ala Phe Leu Phe Phe Ala Asn Val Phe Leu Ala
            35                  40                  45

Val Asn Leu Leu Phe Leu Glu Lys Asn Ile Lys Asn Lys Leu Leu Phe
        50                  55                  60

Leu Leu Pro Ile Ser Ile Ile Trp Met Val Ile His Ile Ser Met
65                  70                  75                  80

Ile Asn Ile Lys Phe Tyr Lys Phe Glu His Gln Ile Lys Glu Gln Asn
            85                  90                  95

Ile Ser Ser Ile Thr Gly Val Ile Lys Pro His Asp Ser Tyr Asn Tyr
            100                 105                 110

Val Tyr Asp Ser Asn Gly Tyr Ala Lys Leu Lys Asp Asn His Arg Tyr
            115                 120                 125

Gly Arg Val Ile Arg Glu Thr Pro Tyr Ile Asp Val Val Ala Ser Asp
130                 135                 140

Val Lys Asn Lys Ser Ile Arg Leu Ser Leu Val Cys Gly Ile His Ser
145                 150                 155                 160
```

```
Tyr Ala Pro Cys Ala Asn Phe Ile Lys Phe Ala Lys Lys Pro Val Lys
                165                 170                 175

Ile Tyr Phe Tyr
            180
```

"Meningococcal Antigens." Submitted in *Ruelle* v. *Scarlato*: Interference No. 105,551 as Exhibit No. 1003. 409 pages.

Chiron SpA. Patent Application No. 9822143.5. Submitted in *Ruelle* v. *Scarlato*: Interference No. 105,551 as Exhibit No. 1005. 127 pages.

Chiron SpA. Patent Application No. 9819015.0. Submitted in *Ruelle* v. *Scarlato*: Interference No. 105,551 as Exhibit No. 1006. 57 pages.

Chiron SpA. Patent Application No. 9800760.2. Submitted in *Ruelle* v. *Scarlato*: Interference No. 105,551 as Exhibit No. 1007. 43 pages.

Sequence Alignment. Submitted in *Ruelle* v. *Scarlato*: Interference No. 105,551 as Exhibit No. 1010. 2 pages.

Sequence Alignment. Submitted in *Ruelle* v. *Scarlato*: Interference No. 105,551 as Exhibit No. 1011. 2 pages.

Sequence Alignment. Submitted in *Ruelle* v. *Scarlato*: Interference No. 105,551 as Exhibit No. 1012. 2 pages.

Sequence Alignment. Submitted in *Ruelle* v. *Scarlato*: Interference No. 105,551 as Exhibit No. 1013. 2 pages.

Sequence Alignment. Submitted in *Ruelle* v. *Scarlato*: Interference No. 105,551 as Exhibit No. 1014. 2 pages.

Sequence Alignment. Submitted in *Ruelle* v. *Scarlato*: Interference No. 105,551 as Exhibit No. 1015. 2 pages.

Sequence Alignment. Submitted in *Ruelle* v. *Scarlato*: Interference No. 105,551 as Exhibit No. 1017. 2 pages.

Sequence Alignment. Submitted in *Ruelle* v. *Scarlato*: Interference No. 105,551 as Exhibit No. 1019. 2 pages.

Sequence Alignment. Submitted in *Ruelle* v. *Scarlato*: Interference No. 105,551 as Exhibit No. 1022. 2 pages.

Parker et al. (1986). "New Hydrophilicity Scale Derived from High-Performance Liquid Chromagraphy Peptide Retention Data: Correlation of Predicted Surface Residues with Antigenicity and X-ray-Derived Accessible Sites," Biochemistry, 25:5425-5432. (Submitted in *Ruelle* v. *Scarlato*: Interference No. 105,551 as Exhibit No. 1023.).

Karplus et al. (1985). "Prediction of Chain Flexibility in Proteins," Naturwissenschaften 72. 3 pages. (Submitted in *Ruelle* v. *Scarlato*: Interference No. 105,551 as Exhibit No. 1024.).

Emini et al. (Sep. 1985). "Induction of Hepatitis A Virus-Neutralizing Antibody by a Virus-Specific Synthetic Peptide," Journal of Virology, p. 836-839. (Submitted in *Ruelle* v. *Scarlato*: Interference No. 105,551 as Exhibit No. 1025.).

Janin et al. (1978). "Conformation of Amino Acid Side-chains in Proteins," Mol. Biol. 125:357-386. (Submitted in *Ruelle* v. *Scarlato*: Interference No. 105,551 as Exhibit No. 1026.).

Ponnuswamy et al. (1980). "Hydrophobic Packing And Spatial Arrangement Of Amino Acid Residues In Globular Proteins," Biochimica et Biophysica Acta, 623:301-316. (Submitted in *Ruelle* v. *Scarlato*: Interference No. 105,551 as Exhibit No. 1027.).

Sequence Alignment. Submitted in *Ruelle* v. *Scarlato*: Interference No. 105,551 as Exhibit No. 1028. 2 pages.

Sequence Data. Submitted in *Ruelle* v. *Scarlato*: Interference No. 105,551 as Exhibit No. 1029. 2 pages.

Sequence Alignment. Submitted in *Ruelle* v. *Scarlato*: Interference No. 105,551 as Exhibit No. 1031. 2 pages.

Sequence Alignment. Submitted in *Ruelle* v. *Scarlato*: Interference No. 105,551 as Exhibit No. 1032. 2 pages.

Sequence Alignment. Submitted in *Ruelle* v. *Scarlato*: Interference No. 105,551 as Exhibit No. 1033. 2 pages.

Scarselli et al. (2006). "*Neisseria meningitidis* NhhA is a multifunctional trimeric autotransporter adhesin," Molecular Microbiology 61(3):631-644. (Submitted in *Ruelle* v. *Scarlato*: Interference No. 105,551 as Exhibit No. 1034.).

Green et al. (1982). "Immunogenic Structure of the Influenza Virus Hemagglutinin," Cell 25:477-487. (Submitted in *Ruelle* v. *Scarlato*: Interference No. 105,551 as Exhibit No. 1035.).

Shinnick et al. (1983). "Synthetic Peptide Immunogens As Vaccines," Ann. Rev. Microbiol. 37:425-46. (Submitted in *Ruelle* v. *Scarlato*: Interference No. 105,551 as Exhibit No. 1036.).

Roitt, I.M. (1988). Essential Immunology. Sixth Edition. Blackwell Scientific Publications, pp. 15-30 and p. 68 (20 pages). (Submitted in *Ruelle* v. *Scarlato*: Interference No. 105,551 as Exhibit No. 1037.).

Declaration of Diana Lee. Submitted in *Ruelle* v. *Scarlato*: Interference No. 105,551 as Exhibit No. 1038. 10 pages.

Second Declaration of Garnett H. Helsoe, D.Sc. Submitted in *Ruelle* v. *Scarlato*: Interference No. 105,551 as Exhibit No. 1039. 21 pages.

Fredriksen et al. (Dec. 1991). "Production, Characterization And Control Of MenB-Vaccine <<Folkehelsa>>: An Outer Membrane Vescicle Vaccine Against Group B Meningococcal Disease," NIHP Annals 14(2): 67-80. (Submitted in *Ruelle* v. *Scarlato*: Interference No. 105,551 as Exhibit No. 1040.).

UniProtKB Entry: Q9JR18_NEIME. Submitted in *Ruelle* v. *Scarlato*: Interference No. 105,551 as Exhibit No. 1041. 3 pages.

Koeberling et al. (2007). "Improved immunogenicity of a H44/76 group B outer membrane vesicle vaccine with over-expressed genome-derived Neisserial antigen 1870," Vaccine 25:1912-1920. (Submitted in *Ruelle* v. *Scarlato*: Interference No. 105,551 as Exhibit No. 1042).

Achtman et al. (Aug. 1988). "Purification And Characterization Of Eight Class 5 Outer Membrane Protein Variants From A Clone Of *Neisseria meningitidis* Serogroup A," J. Exp. Med. 168: 507-525. (Submitted in *Ruelle* v. *Scarlato*: Interference No. 105,551 as Exhibit 1044.).

U.S. Appl. No. 10/896,778. Submitted in *Ruelle* v. *Scarlato*: Interference No. 105,551 as Exhibit 1045. 7 pages.

van Ulsen (2001). "In vivo expression of *Neisseria meningitidis* proteins homologous to the *Haemophilus influenzae* Hap and Hia autotransporters," FEMS Immunology and Medical Microbiology 32:53-64. (Submitted in Ruelle v. Scarlato: Interference No. 105,551 as Exhibit 1046.).

Second Declaration of Diana Lee. Submitted in *Ruelle* v. *Scarlato*: Interference No. 105,551 as Exhibit 1047. 5 pages.

Sequence Data. Submitted in *Ruelle* v. *Scarlato*: Interference No. 105,551 as Exhibit 1048. 6 pages.

Sequence Alignment. Submitted in *Ruelle* v. *Scarlato*: Interference No. 105,551 as Exhibit 1049. 1 pages.

Sequence Alignment. Submitted in *Ruelle* v. *Scarlato*: Interference No. 105,551 as Exhibit 1050. 1 pages.

Ruelle Priority Statement. Submitted in *Ruelle* v. *Scarlato*: Interference No. 105,551 as Exhibit 1052. 7 pages.

Deposition Upon Oral Examination Of Ralph C. Judd. Submitted in *Ruelle* v. *Scarlato*: Interference No. 105,551 as Exhibit 1053. 37 pages.

Deposition of Ralph C. Judd, PhD. Jan. 16, 2008. Submitted in *Ruelle* v. *Scarlato*: Interference No. 105,551 as Exhibit 1054. 10 pages.

United Kingdom Patent Application No. 9810276.7. Submitted in *Ruelle* v. *Scarlato*: Interference No. 105,551 as Exhibit 2001. 67 pages.

PCT Patent Application No. PCT/EP99/03255. Submitted in *Ruelle* v. *Scarlato*: Interference No. 105,551 as Exhibit 2002.. 79 pages.

Declaration of Ralph C. Judd, Ph.D. Submitted in *Ruelle* v. *Scarlato*: Interference No. 105,551 as Exhibit 2004. 19 pages.

Curriculum Vitae of Ralph C. Judd. Submitted in *Ruelle* v. *Scarlato*: Interference No. 105,551 as Exhibit 2005. 16 pages.

Comparison of SEQ ID No. 2 in United Kingdom Patent Application No. 9810276 and SEQ ID No. 2 in U.S. Patent No. 6,780,419. Submitted in *Ruelle* v. *Scarlato*: Interference No. 105,551 as Exhibit 2006. 3 pages.

Rosenqvist et al. (Dec. 1995). "Human Antibody Responses to Meningococcal Outer Membrane Antigens after Three Doses of the Norwegian Group B Meningococcal Vaccine," Infection and Immunity 63(12):4642-4652. (Submitted in *Ruelle* v. *Scarlato*: Interference No. 105,551 as Exhibit 2007.).

GenBank Submission with Accession No. AAF42523. Ruelle v. Scarlato: Interference No. 105,551. 2 pages. (Submitted in *Ruelle* v. *Scarlato*: Interference No. 105,551 as Exhibit 2008.).

U.S. Appl. No. 11/212,443. *Ruelle* v. *Scarlato*: Interference No. 105,551. 139 pages. (Submitted in *Ruelle* v. *Scarlato*: Interference No. 105,551 as Exhibit 2009 1(a).).

Declaration and Sequence Data for U.S. Appl. No. 11/212,443. Ruelle v. Scarlato: Interference No. 105,551. 136 pages. (Submitted in Ruelle v. Scarlato: Interference No. 105,551 as Exhibit 2009 1(b).).

Sequence Data for U.S. Appl. No. 11/212,443. *Ruelle* v. *Scarlato*: Interference No. 105,551. 146 pages. (Submitted in *Ruelle* v. *Scarlato*: Interference No. 105,551 as Exhibit 2009 1 (c).).

Sequence Data for U.S. Appl. No. 11/212,443. Submitted in *Ruelle* v. *Scarlato*: Interference No. 105,551 as Exhibit 2009 Part 2. 188 pages.

The American Heritage Dictionary. Second College Edition (1982). Library of Congress Cataloging in Publication Data. p. 680. (Submitted in *Ruelle* v. *Scarlato*: Interference No. 105,551 as Exhibit 2010.).

van der Ley et al. (Aug. 1992). "Construction of a Multivalent Meningococcal Vaccine Strain Based on the Class 1 Outer Membrane Protein," Infection and Immunity 60(8): 3156-3161. (Submitted in *Ruelle* v. *Scarlato*: Interference No. 105,551 as Exhibit 2011.).

Scarlato Clean Copy Of Claims 18-32 of U.S. Appl. No. 11/212,443. Submitted in *Ruelle* v. *Scarlato*: Interference No. 105,551 as Exhibit 2012.

U.S. Appl. No. 10/896,778. Submitted in *Ruelle* v. *Scarlato*: Interference No. 105,551 as Exhibit 2013. 70 pages.

Supplemental Amendment Filed Sep. 24, 2007 for U.S. Appl. No. 10/896,778. Submitted in *Ruelle* v. *Scarlato*: Interference No. 105,551 as Exhibit 2014. 5 pages.

Deposition of Garnett H. Kelsoe, D.Sc (Jan. 25, 2008). Submitted in *Ruelle* v. *Scarlato*: Interference No. 105,551 as Exhibit 2016. 72 pages.

Second Declaration of Ralph C. Judd, Ph.D. Submitted in *Ruelle* v. *Scarlato*: Interference No. 105,551 as Exhibit 2017. 20 pages.

Rogozin et al. (2002). "Congruent evolution of different classes of non-coding DNA in prokaryotic genomes," Nucleic Acids Research, 30(19):4264-4271. (Submitted in *Ruelle* v. *Scarlato*: Interference No. 105,551 as Exhibit 2020.).

Zhou et al. (2005). "A fractal method to distinguish coding and non-coding sequences in a complete genome based on a number sequence representation," Journal of Theoretical Biology 232:559-567. (Submitted in *Ruelle* v. *Scarlato*: Interference No. 105,551 as Exhibit 2021.).

Parkhill et al. (Mar. 2000). "Complete DNA sequence of a serogroup A strain of *Neisseria meningitidis* Z2491," Nature 404(30):2-6. (Submitted in *Ruelle* v. *Scarlato*: Interference No. 105,551 as Exhibit 2022.).

Jordens et al. (2005). "A novel porA-based real-time PCR for detection of meningococcal carriage," Journal of Medical Microbiology 54:463-466. (Submitted in *Ruelle* v. *Scarlato*: Interference No. 105,551 as Exhibit 2023.).

ORF Finder Results for SEQ ID No. 4 of Scarlato Exhibit 1007. Submitted in *Ruelle* v. *Scarlato*: Interference No. 105,551 as Exhibit 2024. 6 pages.

Handbook of Meningococcal Disease: Infection Biology, Vaccination, Clinical Management. Forsch, M. and Maiden M.C.J. (eds), Wiley-VCH Verlag GmbH & Co. KGaA. p. 84. (Submitted in *Ruelle* v. *Scarlato*: Interference No. 105,551 as Exhibit 2025.).

McCarvil et al. (1993). "Expression of meningococcal epitopes in LamB of *Escherichia coli* and the stimulation of serosubtype-specific antibody responses," Molecular Microbiology 10(1): 203-213.

van der Ley et al. (Oct. 1993). "Use of Transformation To Construct Antigenic Hybrids of the Class 1 Outer Membrane Protein in *Neisseria meningitidis*," Infection and Immunity 31(10): 4217-4224.

Ward et al. (1996). "Expression of *Neisseria meningitidis* class 1 porin as a fusion protein in *Escherichia coli*: the influence of liposomes and adjuvants on the production of a bactericidal immune response," Microbial Pathogenesis, 21:499-512.

Parkhill et al., "Complete DNA sequence of a serogroup A strain of *Neisseria meningitides* Z2491," *Nature* 404:502-506 (2000).

Tettelin et al., "Complete genome sequence of *Neisseria meningitides* Serogrroup B strain MC 58," Science 287:1809-1815 (2000).

\* cited by examiner

```
zn07_1    1  MNKIYRIIWNSALNAWVVVSELTRNHTKRASATVKTAVLATLLFATVQASANNEKQEEDL
zn20_1    1  MNKIYRIIWNSALNAWVVVSELTRNHTKRASATVKTAVLATLLFATVQASANNEKQEEDL
zn21_1    1  MNKIYRIIWNSALNAWVVVSELTRNHTKRASATVKTAVLATLLFATVQASANNEKQEEDL
zn06_1    1  MNKIYRIIWNSALNAWVVVSELTRNHTKRASATVETAVLATLLFATVQASANNEKQEEDL
zn19_1    1  MNKIYRIIWNSALNAWVVVSELTRNHTKRASATVKTAVLATLLFATVQASANNEKQEEDL
zn03_1    1  MNKIYRIIWNSALNAWVAVSELTRNHTKRASATVATAVLATLLFATVQASTT..D.DDDL
zn18_1    1  MNKIYRIIWNSALNAWVAVSELTRNHTKRASATVATAVLATLLFATVQASTT..D.DDDL
zn11_ass  1  MNKIYRIIWNSALNAWVVVSELTRNHTKRASATVATAVLATLLFATVQASTT..D.DDDL
zn02_1    1  MNKIYRIIWNSALNAWVVVSELTRNHTKRASATVATAVLATLLFATVQANAT..D.DDDL
zn04_1    1  MNKIYRIIWNSALNAWVVVSELTRNHTKRASATVATAVLATLLFATVQANAT..D.DDDL
zn16_1    1  MNKIYRIIWNSALNAWVVVSELTRNHTKRASATVATAVLATLLFATVQANAT..D.DDDL
zn14_1    1  MNKIYRIIWNSALNAWVAVSELTRNHTKRASATVKTAVLATLLFATVQANAT..DEDEEE
z2491     1  MNKIYRIIWNSALNAWVAVSELTRNHTKRASATVKTAVLATLLFATVQANATDEDEEEE.
zn10_1    1  MNKIYRIIWNSALNAWVAVSELTRNHTKRASATVKTAVLATLLFATVQANATDEDEEEE.
zn22_1    1  MNKIYRIIWNSALNAWVAVSELTRNHTKRASATVKTAVLATLLFATVQANATDEDEEEE.
zn23_1    1  MNKIYRIIWNSALNAWVAVSELTRNHTKRASATVKTAVLATLLFATVQANATDEDEEEE.
zn28_ass  1  MNKIYRIIWNSALNAWVAVSELTRNHTKRASATVKTAVLATLLFATVQANATDEDEEEE.
zn24_1    1  MNKIYRIIWNSALNAWVVVSELTRNHTKRASATVATAVLATLLSATVQANATDTDEDEE.
zn25_ass  1  MNKIYRIIWNSALNAWVVVSELTRNHTKRASATVATAVLATLLSATVQANATDTDEDEE.
zn08_1    1  MNKIYRIIWNSALNAWVVVSELTRNHTKRASATVETAVLATLLFATVQANATDTDEDDD.
zn29_ass  1  MNKIYRIIWNTALNAWVVVSELTRNHTKRASATVATAVLATLLSATVQANATDEKDNEE.

zn07_1    61  YLEPVQRVAVLIVNSDKEGGGEKEKVEENSDWAYYNEKGVLTRETLKAGDNLKIKQ
zn20_1    61  YLEPVQRVAVLIVNSDKEGGGEKEKVEENSDWAYYNEKGVLTRETLKAGDNLKIKQ
zn21_1    61  YLEPVQRVAVLIVNSDKEGGGEKEKVEENSDWAYYNEKGVLTRETLKAGDNLKIKQ
zn06_1    61  YLEPVQRVAVLIVNSDKEGGGEKEKVEENSDWAYYNEKGVLTRETLKAGDNLKIKQ
zn19_1    61  YLEPVQRVAVLIVNSDKEGGGEKEKVEENSDWAYYNEKGVLTRETLKAGDNLKIKQ
zn03_1    58  YLEPVQRAPVLSFHADSEGGGEKE.VTEDSNWGYYDKKGVLTGTTLKAGDNLKIKQ
zn18_1    58  YLEPVQRAPVLSFHADSEGGGEKE.VTEDSNWGYYDKKGVLTGTTLKAGDNLKIKQ
zn11_ass  58  YLEPVQRAPVLSFHADSEGGGEKE.VTEDSNWGYYDKKGVLTGTTLKAGDNLKIKQ
zn02_1    58  YLEPVQRAVVLSFRSDKEGGGEKE.GTEDSNWAYYDEKRVLKGATLKAGDNLKIKQ
zn04_1    58  YLEPVQRAVVLSFRSDKEGGGEKE.GTEDSNWAYYDEKRVLKGATLKAGDNLKIKQ
zn16_1    58  YLEPVQRAVVLSFRSDKEGGGEKE.GTEDSNWAYYDEKRVLKGATLKAGDNLKIKQ
zn14_1    59  ELEPVVRALVLQFMIDKEGNGENE.STGNIGWSYYDNHNTLHATTLKAGDNLKIKQ
z2491     60  .LESVQR..VVGSIQASMEGGGELETISLSMTND...SKEFVDPYIVTLKAGDNLKIKQ
zn10_1    60  .LESVQR..VVGSIQASMEGGGELETISLSMTND...SKEFVDPYIVTLKAGDNLKIKQ
zn22_1    60  .LESVQR..VVGSIQASMEGGGELETISLSMTND...SKEFVDPYIVTLKAGDNLKIKQ
zn23_1    60  .LESVQR..VVGSIQASMEGGGELETISLSMTND...SKEFVDPYIVTLKAGDNLKIKQ
zn28_ass  60  .LESVQR..VVGSIQASMEGGGELETISLSMTND...SKEFVDPYIVTLKAGDNLKIKQ
zn24_1    60  .LESVVRALVLQFMIDKEGNGEIESTG.DIGWSYYDDHNTLHATTLKAGDNLKIKQ
zn25_ass  60  .LESVVRALVLQFMIDKEGNGEIESTG.DIGWSYYDDHNTLHATTLKAGDNLKIKQ
zn08_1    60  .LEPVVRALVLQFMIDKEGNGEIESTG.DIGWSYYDDHNTLHATTLKAGDNLKIKQ
zn29_ass  60  .LEPVVRAPVLSFHSDKEGGGEKEEVGASSNLTYYDKNRVLKGTTLKAGDNLKIKQ zn07_1    121  ..........NNFTYSLKKDLTDLTSVGTEKLSFSANGNKVNITSDTKGLNFAKETAG
zn20_1    121  ..........NNFTYSLKKDLTDLTSVGTEKLSFSANGNKVNITSDTKGLNFAKETAG
zn21_1    121  ..........NNFTYSLKKDLTDLTSVGTEKLSFSANGNKVNITSDTKGLNFAKETAG
zn06_1    121  ..........NNFTYSLKKDLTDLTSVGTEKLSFSANGNKVNITSDTKGLNFAKETAG
zn19_1    121  ..........NNFTYSLKKDLTDLTSVGTEKLSFSANGNKVNITSDTKGLNFAKETAG
zn03_1    117  ....NTDENTNSFTYSLKKDLTDLTSVETEKLSFGANGKKVNITSDTKGLNFAKETAG
zn18_1    117  ....NTDENTNSFTYSLKKDLTDLTSVETEKLSFGANGKKVNITSDTKGLNFAKETAG
zn11_ass  117  ....NTDENTNSFTYSLKKDLTDLTSVETEKLSFGANGKKVNITSDTKGLNFAKETAG
zn02_1    117  ....NTNENTNDSFTYSLKKDLTDLTSVETEKLSFGANGNKVNITSDTKGLNFAKETAG
zn04_1    117  ....NTNENTNDSFTYSLKKDLTDLTSVETEKLSFGANGNKVNITSDTKGLNFAKETAG
zn16_1    117  NTNENTNENTNDSFTYSLKKDLTDLTSVETEKLSFGANGNKVNITSDTKGLNFAKETAG
zn14_1    118  NTNKNTNENTNDSFTYSLKKDLTDLTSVETEKLSFGANGNKVNITSDTKGLNFAKETAG
z2491     115  ....NTNENTNSFTYSLKKDLTGLINVETEKLSFGANGKKVNITSDTKGLNFAKETAG
zn10_1    115  ....NTNENTNSFTYSLKKDLTGLINVETEKLSFGANGKKVNITSDTKGLNFAKETAG
zn22_1    115  ....NTNENTNSFTYSLKKDLTGLINVETEKLSFGANGKKVNITSDTKGLNFAKETAG
zn23_1    115  ....NTNENTNSFTYSLKKDLTGLINVETEKLSFGANGKKVNITSDTKGLNFAKETAG
zn28_ass  115  ....NTNENTNSFTYSLKKDLTGLINVETEKLSFGANGKKVNITSDTKGLNFAKETAG
zn24_1    118  ..........SGKDFTYSLKKLLKDLTSVETEKLSFGANGNKVNITSDTKGLNFAKETAG
zn25_ass  118  ..........SGKDFTYSLKKLLKDLTSVETEKLSFGANGNKVNITSDTKGLNFAKETAG
zn08_1    118  ....NTDENTNSFTYSLKKDLTDLTSVGTEELSFGANGNKVNITSDTKGLNFAKRTAG
zn29_ass  119  NTNENTNENTNSFTYSLKKDLTGLINVETEKLSFGANGKKVNITSDTKGLNFAKETAG
```

*FIG. 8A*

```
zn07_1   171 TNGDTTVHLNGIGSTLTDTLLNGATNVTNDVTDDEKKRAASKDVLNAGWNIKGVKP
zn20_1   171 TNGDTTVHLNGIGSTLTDTLLNGATNVTNDVTDDEKKRAASKDVLNAGWNIKGVKP
zn21_1   171 TNGDTTVHLNGIGSTLTDTLLNGATNVTNDVTDDEKKRAASKDVLNAGWNIKGVKP
zn06_1   171 TNGDTTVHLNGIGSTLTDTLLNGATNVTNDVTDDEKKRAASKDVLNAGWNIKGVKP
zn19_1   171 TNGDTTVHLNGIGSTLTDTLLNGATNVTNDVTDDEKKRAASKDVLNAGWNIKGVKP
zn03_1   173 TNGDTTVHLNGIGSTLTDTLLNGATNVTNDVTDDEKKRAASKDVLNAGWNIKGVKP
zn18_1   173 TNGDTTVHLNGIGSTLTDTLLNGATNVTNDVTDDEKKRAASKDVLNAGWNIKGVKP
zn11_ass 173 TNGDTTVHLNGIGSTLTDTLLNGATNVTNDVTDDEKKRAASKDVLNAGWNIKGVKP
zn02_1   173 TNGDPTVHLNGIGSTLTDTLLNGATNVTNDVTDDEKKRAASKDVLNAGWNIKGVKP
zn04_1   173 TNGDPTVHLNGIGSTLTDTLLNGATNVTNDVTDDEKKRAASKDVLNAGWNIKGVKP
zn16_1   177 TNGDPTVHLNGIGSTLTDTLLNGATNVTNDVTDDEKKRAASKDVLNAGWNIKGVKP
zn14_1   178 TNGDTTVHLNGIGSTLTDTLLNGATNVTNDVTDDKKKRAASKDVLNAGWNIKGVKP
z2491    171 TNGDTTVHLNGIGSTLTDTLAGSSAHVDAGNST..HYTRAASKDVLNAGWNIKGVKT
zn10_1   171 TNGDTTVHLNGIGSTLTDTLAGSSAHVDAGNST..HYTRAASKDVLNAGWNIKGVKT
zn22_1   171 TNGDTTVHLNGIGSTLTDTLAGSSAHVDAGNST..HYTRAASKDVLNAGWNIKGVKT
zn23_1   171 TNGDTTVHLNGIGSTLTDTLAGSSAHVDAGNST..HYTRAASKDVLNAGWNIKGVKT
zn28_ass 171 TNGDTTVHLNGIGSTLTDMLLNGATNVTNDVTDDEKKRAASKDVLNAGWNIKGVKP
zn24_1   168 TNGDPTVHLNGIGSTLTDTLAGSSAHVDAGNST..HYTRAASKDVLNAGWNIKGVKT
zn25_ass 168 TNGDPTVHLNGIGSTLTDTLAGSSAHVDAGNST..HYTRAASKDVLNAGWNIKGVKT
zn08_1   174 TNGDTTVHLNGIGSTLTDTLAGSSAHVDAGNST..HYTRAASKDVLNAGWNIKGVKT
zn29_ass 179 TNGDPTVHLNGIGSTLTDTLAGSSAHVDAGNST..HYTRAASKDVLNAGWNIKGVKT zn07_1   231 GTTA..SNVDFVRTYDTVEFLSADTKTTTVNVESKDNGKTEVKIGAKTSVIKEKDGKL
zn20_1   231 GTTA..SNVDFVRTYDTVEFLSADTKTTTVNVESKDNGKTEVKIGAKTSVIKEKDGKL
zn21_1   231 GTTA..SNVDFVRTYDTVEFLSADTKTTTVNVESKDNGKTEVKIGAKTSVIKEKDGKL
zn06_1   231 GTTA..SNVDFVRTYDTVEFLSADTKTTTVNVESKDNGKTEVKIGAKTSVIKEKDGKL
zn19_1   231 GTTA..SNVDFVRTYDTVEFLSADTKTTTVNVESKDNGKTEVKIGAKTSVIKEKDGKL
zn03_1   233 GTTA..SNVDFVRTYDTVEFLSADTKTTTVNVESKDNGKTEVKIGAKTSVIKEKDGKL
zn18_1   233 GTTA..SNVDFVRTYDTVEFLSADTKTTTVNVESKDNGKTEVKIGAKTSVIKEKDGKL
zn11_ass 233 GTTA..SNVDFVRTYDTVEFLSADTKTTTVNVESKDNGKTEVKIGAKTSVIKEKDGKL
zn02_1   233 GTTA..SNVDFVRTYDTVEFLSADTKTTTVNVESKDNGKTEVKIGAKTSVIKEKDGKL
zn04_1   233 GTTA..SNVDFVRTYDTVEFLSADTKTTTVNVESKDNGKTEVKIGAKTSVIKEKDGKL
zn16_1   237 GTTA..SNVDFVRTYDTVEFLSADTKTTTVNVESKDNGKTEVKIGAKTSVIKEKDGKL
zn14_1   238 GTTA..SNVDFVHTYDTVEFLSADTKTTTVNVESKDNGKTEVKIGAKTSVIKEKDGKL
z2491    229 GTTGQSNVDFVRTYDTVEFLSADTKTTTVNVESKDNGKTEVKIGAKTSVIKEKDGKL
zn10_1   229 GTTGQSNVDFVRTYDTVEFLSADTKTTTVNVESKDNGKTEVKIGAKTSVIKEKDGKL
zn22_1   229 GTTGQSNVDFVRTYDTVEFLSADTKTTTVNVESKDNGKTEVKIGAKTSVIKEKDGKL
zn23_1   229 GTTGQSNVDFVRTYDTVEFLSADTKTTTVNVESKDNGKTEVKIGAKTSVIKEKDGKL
zn28_ass 231 GTTA..SNVDFVRTYDTVEFLSADTKTTTVNVESKDNGKTEVKIGAKTSVIKEKDGKL
zn24_1   226 GTTGQSNVDFVRTYDTVEFLSADTKTTTVNVESKDNGKTEVKIGAKTSVIKEKDGKL
zn25_ass 226 GTTGQSNVDFVRTYDTVEFLSADTKTTTVNVESKDNGKTEVKIGAKTSVIKEKDGKL
zn08_1   232 GTTGQSNVDFVRTYDTVEFLSADTKTTTVNVESKDNGKTEVKIGAKTSVIKEKDGKL
zn29_ass 237 GTTGQSNVDFVRTYDTVEFLSADTKTTTVNVESKDNGKTEVKIGAKTSVIKEKDGKL zn07_1   289 VTGKDKGENGSSTDEGEGLVTAKEVIDAVNKAGWRMKTTTANGQTGQADKFETVTSGTNV
zn20_1   289 VTGKDKGENGSSTDEGEGLVTAKEVIDAVNKAGWRMKTTTANGQTGQADKFETVTSGTNV
zn21_1   289 VTGKDKGENGSSTDEGEGLVTAKEVIDAVNKAGWRMKTTTANGQTGQADKFETVTSGTNV
zn06_1   289 VTGKDKGENGSSTDEGEGLVTAKEVIDAVNKAGWRMKTTTANGQTGQADKFETVTSGTNV
zn19_1   289 VTGKDKGENGSSTDEGEGLVTAKEVIDAVNKAGWRMKTTTANGQTGQADKFETVTSGTNV
zn03_1   291 VTGKDKGENGSSTDEGEGLVTAKEVIDAVNKAGWRMKTTTANGQTGQADKFETVTSGTKV
zn18_1   291 VTGKDKGENGSSTDEGEGLVTAKEVIDAVNKAGWRMKTTTANGQTGQADKFETVTSGTKV
zn11_ass 291 VTGKDKGENGSSTDEGEGLVTAKEVIDAVNKAGWRMKTTTANGQTGQADKFETVTSGTKV
zn02_1   291 VTGKGKDENGSSTDEGEGLVTAKEVIDAVNKAGWRMKTTTANGQTGQADKFETVTSGTNV
zn04_1   291 VTGKGKDENGSSTDEGEGLVTAKEVIDAVNKAGWRMKTTTANGQTGQADKFETVTSGTNV
zn16_1   295 VTGKGKDENGSSTDEGEGLVTAKEVIDAVNKAGWRMKTTTANGQTGQADKFETVTSGTKV
zn14_1   296 VTGKGKGENGSSTDEGEGLVTAKEVIDAVNKAGWRMKTTTANGQTGQADKFETVTSGTNV
z2491    289 VTGKGKGENGSSTDEGEGLVTAKEVIDAVNKAGWRMKTTTANGQTGQADKFETVTSGTNV
zn10_1   289 VTGKGKGENGSSTDEGEGLVTAKEVIDAVNKAGWRMKTTTANGQTGQADKFETVTSGTNV
zn22_1   289 VTGKGKGENGSSTDEGEGLVTAKEVIDAVNKAGWRMKTTTANGQTGQADKFETVTSGTNV
zn23_1   289 VTGKGKGENGSSTDEGEGLVTAKEVIDAVNKAGWRMKTTTANGQTGQADKFETVTSGTNV
zn28_ass 289 VTGKGKGENGSSTDEGEGLVTAKEVIDAVNKAGWRMKTTTANGQTGQADKFETVTSGTNV
zn24_1   286 VTGKGKGENGSSTDEGEGLVTAKEVIDAVNKAGWRMKTTTANGQTGQADKFETVTSGTKV
zn25_ass 286 VTGKGKGENGSSTDEGEGLVTAKEVIDAVNKAGWRMKTTTANGQTGQADKFETVTSGTKV
zn08_1   292 VTGKGKGENGSSTDEGEGLVTAKEVIDAVNKAGWRMKTTTANGQTGQADKFETVTSGTNV
zn29_ass 297 VTGKGKGENGSSTDEGEGLVTAKEVIDAVNKAGWRMKTTTANGQTGQADKFETVTSGTKV
```

*FIG. 8B*

```
zn07_1   349  TFASGKGTTATVSKDDQGNITVMYDVNVGDALNVNQLQNSGWNLDSKAVAGSSGKVISGN
zn20_1   349  TFASGKGTTATVSKDDQGNITVMYDVNVGDALNVNQLQNSGWNLDSKAVAGSSGKVISGN
zn21_1   349  TFASGKGTTATVSKDDQGNITVMYDVNVGDALNVNQLQNSGWNLDSKAVAGSSGKVISGN
zn06_1   349  TFASGKGTTATVSKDDQGNITVMYDVNVGDALNVNQLQNSGWNLDSKAVAGSSGKVISGN
zn19_1   349  TFASGKGTTATVSKDDQGNITVMYDVNVGDALNVNELQNSGWDLDSKAVAGSSGKVISGN
zn03_1   351  TFASGNGTTATVSKDDQGNITVKYDVNVGDALNVNQLQNSGWNLDSKAVAGSSGKVISGN
zn18_1   351  TFASGNGTTATVSKDDQGNITVKYDVNVGDALNVNQLQNSGWNLDSKAVAGSSGKVISGN
zn11_ass 351  TFASGNGTTATVSKDDQGNITVKYDVNVGDALNVNQLQNSGWNLDSKAVAGSSGKVISGN
zn02_1   351  TFASGKGTTATVSKDDQGNITVKYDVNVGDALNVNQLQNSGWNLDSKAVAGSSGKVISGN
zn04_1   351  TFASGKGTTATVSKDDQGNITVKYDVNVGDALNVNQLQNSGWNLDSKAVAGSSGKVISGN
zn16_1   355  TFASGNGTTATVSKDDQGNITVKYDVNVGDALNVNQLQNSGWNLDSKAVAGSSGKVISGN
zn14_1   356  TFASGKGTTATVSKDDQGNITVKYDVNVGDALNVNQLQNSGWNLDSKAVAGSSGKVISGN
z2491    349  TFASGKGTTATVSKDDQGNITVMYDVNVGDALNVNQLQNSGWNLDSKAVAGSSGKVISGN
zn10_1   349  TFASGKGTTATVSKDDQGNITVMYDVNVGDALNVNQLQNSGWNLDSKAVAGSSGKVISGN
zn22_1   349  TFASGKGTTATVSKDDQGNITVMYDVNVGDALNVNQLQNSGWNLDSKAVAGSSGKVISGN
zn23_1   349  TFASGKGTTATVSKDDQGNITVMYDVNVGDALNVNQLQNSGWNLDSKAVAGSSGKVISGN
zn28_ass 349  TFASGKGTTATVSKDDQGNITVMYDVNVGDALNVNQLQNSGWNLDSKAVAGSSGKVISGN
zn24_1   346  TFASGNGTTATVSKDDQGNITVKYDVNVGDALNVNQLQNSGWNLDSKAVAGSSGKVISGN
zn25_ass 346  TFASGNGTTATVSKDDQGNITVKYDVNVGDALNVNQLQNSGWNLDSKAVAGSSGKVISGN
zn08_1   352  TFASGKGTTATVSKDDQGNITVKYDVNVGDALNVNQLQNSGWNLDSKAVAGSSGKVISGN
zn29_ass 357  TFASGNGTTATVSKDDQGNITVKYDVNVGDALNVNQLQNSGWNLDSKAVAGSSGKVISGN zn07_1   409  VSPSKGKMDETVNINAGNNIEITRNGKNIDIATSMTPQFSSVSLGAGADAPTLSVDG..A
zn20_1   409  VSPSKGKMDETVNINAGNNIEITRNGKNIDIATSMTPQFSSVSLGAGADAPTLSVDG..A
zn21_1   409  VSPSKGKMDETVNINAGNNIEITRNGKNIDIATSMTPQFSSVSLGAGADAPTLSVDG..A
zn06_1   409  VSPSKGKMDETVNINAGNNIEITRNGKNIDIATSMTPQFSSVSLGAGADAPTLSVDG..A
zn19_1   409  VSPSKGKMDETVNINAGNNIEITRNGKNIDIATSMTPQFSSVSLGAGADAPTLSVDG.GA
zn03_1   411  VSPSKGKMDETVNINAGNNIEITRNGKNIDIATSMTPQFSSVSLGAGADAPTLSVDD.GA
zn18_1   411  VSPSKGKMDETVNINAGNNIEITRNGKNIDIATSMTPQFSSVSLGAGADAPTLSVDD.GA
zn11_ass 411  VSPSKGKMDETVNINAGNNIEITRNGKNIDIATSMTPQFSSVSLGAGADAPTLSVDD.GA
zn02_1   411  VSPSKGKMDETVNINAGNNIEITRNGKNIDIATSMAPQFSSVSLGAGADAPTLSVDD.GA
zn04_1   411  VSPSKGKMDETVNINAGNNIEITRNGKNIDIATSMAPQFSSVSLGAGADAPTLSVDD.GA
zn16_1   415  VSPSKGKMDETVNINAGNNIEITRNGKNIDIATSMTPQFSSVSLGAGADAPTLSVDD.GA
zn14_1   416  VSPSKGKMDETVNINAGNNIEITRNGKNIDIATSMTPQFSSVSLGAGADAPTLSVDD.GA
z2491    409  VSPSKGKMDETVNINAGNNIEIRNGKNIDIATSMAPQFSSVSLGAGADAPTLSVDD.GA
zn10_1   409  VSPSKGKMDETVNINAGNNIEIRNGKNIDIATSMAPQFSSVSLGAGADAPTLSVDD.GA
zn22_1   409  VSPSKGKMDETVNINAGNNIEIRNGKNIDIATSMAPQFSSVSLGAGADAPTLSVDD.GA
zn23_1   409  VSPSKGKMDETVNINAGNNIEIRNGKNIDIATSMAPQFSSVSLGAGADAPTLSVDD.GA
zn28_ass 409  VSPSKGKMDETVNINAGNNIEITRNGKNIDIATSMTPQFSSVSLGAGADAPTLSVDD.GA
zn24_1   406  VSPSKGKMDETVNINAGNNIEITRNGKNIDIATSMTPQFSSVSLGAGADAPTLSVDD.GA
zn25_ass 406  VSPSKGKMDETVNINAGNNIEITRNGKNIDIATSMTPQFSSVSLGAGADAPTLSVDD.GA
zn08_1   412  VSPSKGKMDETVNINAGNNIEITRNGKNIDIATSMTPQFSSVSLGAGADAPTLSVDD.GA
zn29_ass 417  VSPSKGKMDETVNINAGNNIEITRNGKNIDIATSMTPQFSSVSLGAGADAPTLSVDD.GA zn07_1   468  LNVGSKKDNKPVRITNVAPGVKEGDVTNVAQLKGVAQNLNNRIDNVDGNARAGIAQAIAT
zn20_1   468  LNVGSKKDNKPVRITNVAPGVKEGDVTNVAQLKGVAQNLNNRIDNVDGNARAGIAQAIAT
zn21_1   468  LNVGSKKDNKPVRITNVAPGVKEGDVTNVAQLKGVAQNLNNRIDNVDGNARAGIAQAIAT
zn06_1   468  LNVGSKKDNKPVRITNVAPGVKEGDVTNVAQLKGVAQNLNNRIDNVDGNARAGIAQAIAT
zn19_1   468  LNVGSKKDNKPVRITNVAPGVKEGDVTNVAQLKGVAQNLNNRIDNVDGNARAGIAQAIAT
zn03_1   471  LNVGSKDANKPVRITNVAPGVKEGDVTNVAQLKGVAQNLNNRIDNVDGNARAGIAQAIAT
zn18_1   471  LNVGSKDANKPVRITNVAPGVKEGDVTNVAQLKGVAQNLNNRIDNVDGNARAGIAQAIAT
zn11_ass 471  LNVGSKDANKPVRITNVAPGVKEGDVTNVAQLKGVAQNLNNRIDNVDGNARAGIAQAIAT
zn02_1   471  LNVGSKDTNKPVRITNVAPGVKEGDVTNVAQLKGVAQNLNNRIDNVDGNARAGIAQAIAT
zn04_1   471  LNVGSKDTNKPVRITNVAPGVKEGDVTNVAQLKGVAQNLNNRIDNVDGNARAGIAQAIAT
zn16_1   475  LNVGSKDANKPVRITNVAPGVKEGDVTNVAQLKGVAQNLNNRIDNVDGNARAGIAQAIAT
zn14_1   476  LNVGSKDANKPVRITNVAPGVKEGDVTNVAQLKGVAQNLNNRIDNVDGNARAGIAQAIAT
z2491    469  LNVGSKDANKPVRITNVAPGVKEGDVTNVAQLKGVAQNLNNRIDNVDGNARAGIAQAIAT
zn10_1   469  LNVGSKDANKPVRITNVAPGVKEGDVTNVAQLKGVAQNLNNRIDNVDGNARAGIAQAIAT
zn22_1   469  LNVGSKDANKPVRITNVAPGVKEGDVTNVAQLKGVAQNLNNRIDNVDGNARAGIAQAIAT
zn23_1   469  LNVGSKDANKPVRITNVAPGVKEGDVTNVAQLKGVAQNLNNRIDNVDGNARAGIAQAIAT
zn28_ass 469  LNVGSKDANKPVRITNVAPGVKEGDVTNVAQLKGVAQNLNNRIDNVDGNARAGIAQAIAT
zn24_1   466  LNVGSKDANKPVRITNVAPGVKEGDVTNVAQLKGVAQNLNNRIDNVDGNARAGIAQAIAT
zn25_ass 466  LNVGSKDANKPVRITNVAPGVKEGDVTNVAQLKGVAQNLNNRIDNVDGNARAGIAQAIAT
zn08_1   472  LNVGSKDANKPVRITNVAPGVKEGDVTNVAQLKGVAQNLNNRIDNVDGNARAGIAQAIAT
zn29_ass 477  LNVGSKDANKPVRITNVAPGVKEGDVTNVAQLKGVAQNLNNRIDNVDGNARAGIAQAIAT
```

*FIG. 8C*

```
zn07_1   528  AGLVQAYLPGKSMMAIGGGTYRGEAGYAIGYSSISDGGNWIIKGTASGNSRGHFGASASV
zn20_1   528  AGLVQAYLPGKSMMAIGGGTYRGEAGYAIGYSSISDGGNWIIKGTASGNSRGHFGASASV
zn21_1   528  AGLVQAYLPGKSMMAIGGGTYRGEAGYAIGYSSISDGGNWIIKGTASGNSRGHFGASASV
zn06_1   528  AGLVQAYLPGKSMMAIGGGTYRGEAGYAIGYSSISDGGNWIIKGTASGNSRGHFGASASV
zn19_1   528  AGLVQAYLPGKSMMAIGGGTYRGEAGYAIGYSSISDGGNWIIKGTASGNSRGHFGASASV
zn03_1   531  AGLVQAYLPGKSMMAIGGGTYRGEAGYAIGYSSISDGGNWIIKGTASGNSRGHFGASASV
zn18_1   531  AGLVQAYLPGKSMMAIGGGTYRGEAGYAIGYSSISDGGNWIIKGTASGNSRGHFGASASV
zn11_ass 531  ASLVQAYLPGKSMMAIGGGTYRGEAGYAIGYSSISDGGNWIIKGTASGNSRGHFGASASV
zn02_1   531  AGLVQAYLPGKSMMAIGGDTYRGEAGYAIGYSSISDGGNWIIKGTASGNSRGHFGASASV
zn04_1   531  AGLVQAYLPGKSMMAIGGDTYRGEAGYAIGYSSISDGGNWIIKGTASGNSRGHFGASASV
zn16_1   535  AGLAQAYLPGKSMMAIGGGTYRGEAGYAIGYSSISDTGNWIIKGTASGNSRGHFGASASV
zn14_1   536  AGLVQAYLPGKSMMAIGGGTYRGEAGYAIGYSSISDGGNWIIKGTASGNSRGHFGASASV
z2491    529  AGLVQAYLPGKSMMAIGGGTYRGEAGYAIGYSSISDGGNWIIKGTASGNSRGHFGASASV
zn10_1   529  AGLVQAYLPGKSMMAIGGGTYRGEAGYAIGYSSISDGGNWIIKGTASGNSRGHFGASASV
zn22_1   529  AGLVQAYLPGKSMMAIGGGTYRGEAGYAIGYSSISDGGNWIIKGTASGNSRGHFGASASV
zn23_1   529  AGLVQAYLPGKSMMAIGGGTYRGEAGYAIGYSSISDGGNWIIKGTASGNSRGHFGASASV
zn28_ass 529  AGLVQAYLPGKSMMAIGGGTYRGEAGYAIGYSSISDGGNWIIKGTASGNSRGHFGASASV
zn24_1   526  AGLAQAYLPGKSMMAIGGGTYRGEAGYAIGYSSISDTGNWIIKGTASGNSRGHFGTSASV
zn25_ass 526  AGLAQAYLPGKSMMAIGGGTYRGEAGYAIGYSSISDTGNWIIKGTASGNSRGHFGTSASV
zn08_1   532  AGLVQAYLPGKSMMAIGGGTYRGEAGYAIGYSSISDGGNWIIKGTASGNSRGHFGASASV
zn29_ass 537  AGLVQAYLPGKSMMAIGGGTYRGEAGYAIGYSSISDGGNWIIKGTASGNSRGHFGASASV zn07_1   588  GYQW*
zn20_1   588  GYQW*
zn21_1   588  GYQW*
zn06_1   588  GYQW*
zn19_1   588  GYQW*
zn03_1   591  GYQW*
zn18_1   591  GYQW*
zn11_ass 591  GYQW*
zn02_1   591  GYQW*
zn04_1   591  GYQW*
zn16_1   595  GYQW*
zn14_1   596  GYQW*
z2491    589  GYQW*
zn10_1   589  GYQW*
zn22_1   589  GYQW*
zn23_1   589  GYQW*
zn28_ass 589  GYQW*
zn24_1   586  GYQW*
zn25_ass 586  GYQW*
zn08_1   592  GYQW*
zn29_ass 597  GYQW*
```

*FIG. 8D*

MENINGOCOCCAL ANTIGENS

This application is a divisional application of U.S. patent application Ser. No. 09/302,626, filed Apr. 30, 1999, now U.S. Pat. No. 6,709,660, which is a continuation-in-part of international patent application PCT/IB99/00103, filed Jan. 14, 1999, from which priority is claimed under 35 U.S.C. §120, which claims priority under 35. U.S.C §119 to Great Britain application nos. GB9800022143.5, filed on Oct. 9, 1998, GB9819015.0, filed on Sep. 1, 1998, and GB9800760.2, filed on Jan. 14, 1998, which applications are incorporated herein by reference in their entireties.

This invention relates to antigens from the bacterium *Neisseria meningitidis*.

BACKGROUND

*Neisseria meningitidis* is a non-motile, gram negative diplococcus human pathogen. It colonises the pharynx, causing meningitis and, occasionally, septicaemia in the absence of meningitis. It is closely related to *N. gonorrhoeae*, although one feature that clearly differentiates meningococcus from gonococcus is the presence of a polysaccharide capsule that is present in all pathogenic meningococci.

*N. meningitidis* causes both endemic and epidemic disease. In the United States the attack rate is 0.6-1 per 100,000 persons per year, and it can be much greater during outbreaks (see Lieberman et al. (1996) Safety and Immunogenicity of a Serogroups A/C *Neisseria meningitidis* Oligosaccharide-Protein Conjugate Vaccine in Young Children. *JAMA* 275 (19):1499-1503; Schuchat et al (1997) Bacterial Meningitis in the United States in 1995. *N Engl J Med* 337(14):970-976). In developing countries, endemic disease rates are much higher and during epidemics incidence rates can reach 500 cases per 100,000 persons per year. Mortality is extremely high, at 10-20% in the United States, and much higher in developing countries. Following the introduction of the conjugate vaccine against *Haemophilus influenzae*, *N. meningitidis* is the major cause of bacterial meningitis at all ages in the United States (Schuchat et al (1997) supra).

Based on the organism's capsular polysaccharide, 12 serogroups of *N. meningitidis* have been identified. Group A is the pathogen most often implicated in epidemic disease in sub-Saharan Africa. Serogroups B and C are responsible for the vast majority of cases in the United States and in most developed countries. Serogroups W135 and Y are responsible for the rest of the cases in the United States and developed countries. The meningococcal vaccine currently in use is a tetravalent polysaccharide vaccine composed of serogroups A, C, Y and W135. Although efficacious in adolescents and adults, it induces a poor immune response and short duration of protection, and cannot be used in infants [eg. Morbidity and Mortality weekly report, Vol. 46, No. RR-5 (1997)]. This is because polysaccharides are T-cell independent antigens that induce a weak immune response that cannot be boosted by repeated immunization. Following the success of the vaccination against *H. influenzae*, conjugate vaccines against serogroups A and C have been developed and are at the final stage of clinical testing (Zollinger W D "New and Improved Vaccines Against Meningococcal Disease" in: *New Generation Vaccines*, supra, pp. 469-488; Lieberman et al (1996) supra; Costantino et al (1992) Development and phase I clinical testing of a conjugate vaccine against meningococcus A and C. *Vaccine* 10:691-698).

Meningococcus B remains a problem, however. This serotype currently is responsible for approximately 50% of total meningitis in the United States, Europe, and South America. The polysaccharide approach cannot be used because the menB capsular polysaccharide is a polymer of α(2-8)-linked N-acetyl neuraminic acid that is also present in mammalian tissue. This results in tolerance to the antigen; indeed, if an immune response were elicited, it would be anti-self, and therefore undesirable. In order to avoid induction of autoimmunity and to induce a protective immune response, the capsular polysaccharide has, for instance, been chemically modified substituting the N-acetyl groups with N-propionyl groups, leaving the specific antigenicity unaltered (Romero & Outschoorn (1994) Current status of Meningococcal group B vaccine candidates: capsular or non-capsular? *Clin Microbiol Rev* 7(4):559-575).

Alternative approaches to menB vaccines have used complex mixtures of outer membrane proteins (OMPs), containing either the OMPs alone, or OMPs enriched in porins, or deleted of the class 4 OMPs that are believed to induce antibodies that block bactericidal activity. This approach produces vaccines that are not well characterized. They are able to protect against the homologous strain, but are not effective at large where there are many antigenic variants of the outer membrane proteins. To overcome the antigenic variability, multivalent vaccines containing up to nine different porins have been constructed (eg. Poolman J T (1992) Development of a meningococcal vaccine. *Infect. Agents Dis.* 4:13-28). Additional proteins to be used in outer membrane vaccines have been the opa and opc proteins, but none of these approaches have been able to overcome the antigenic variability (eg. Ala'Aldeen & Borriello (1996) The meningococcal transferrin-binding proteins 1 and 2 are both surface exposed and generate bactericidal antibodies capable of killing homologous and heterologous strains. *Vaccine* 14(1):49-53).

A certain amount of sequence data is available for meningococcal and gonococcal genes and proteins (eg. EP-A-0467714, WO96/29412), but this is by no means complete. The provision of further sequences could provide an opportunity to identify secreted or surface-exposed proteins that are presumed targets for the immune system and which are not antigenically variable. For instance, some of the identified proteins could be components of efficacious vaccines against meningococcus B, some could be components of vaccines against all meningococcal serotypes, and others could be components of vaccines against all pathogenic Neisseriae.

THE INVENTION

The invention provides proteins comprising the *N. meningitidis* amino acid sequences disclosed in the examples.

It also provides proteins comprising sequences homologous (ie. having sequence identity) to the *N. meningitidis* amino acid sequences disclosed in the examples. Depending on the particular sequence, the degree of sequence identity is preferably greater than 50% (eg. 60%, 70%, 80%, 90%, 95%, 99% or more). These homologous proteins include mutants and allelic variants of the sequences disclosed in the examples. Typically, 50% identity or more between two proteins is considered to be an indication of functional equivalence. Identity between the proteins is preferably determined by the Smith-Waterman homology search algorithm as implemented in the MPSRCH program (Oxford Molecular), using an affine gap search with parameters gap open penalty=12 and gap extension penalty=1.

The invention further provides proteins comprising fragments of the *N. meningitidis* amino acid sequences disclosed in the examples. The fragments should comprise at least n consecutive amino acids from the sequences and, depending on the particular sequence, n is 7 or more (eg. 8, 10, 12, 14, 16, 18, 20 or more). Preferably the fragments comprise an epitope from the sequence.

The proteins of the invention can, of course, be prepared by various means (eg. recombinant expression, purification from cell culture, chemical synthesis etc.) and in various forms (eg. native, fusions etc.). They are preferably prepared in substantially pure form (ie. substantially free from other *N. meningitidis* or host cell proteins)

According to a further aspect, the invention provides antibodies which bind to these proteins. These may be polyclonal or monoclonal and may be produced by any suitable means.

According to a further aspect, the invention provides nucleic acid comprising the *N. meningitidis* nucleotide sequences disclosed in the examples. In addition, the invention provides nucleic acid comprising sequences homologous (ie. having sequence identity) to the *N. meningitidis* nucleotide sequences disclosed in the examples.

Furthermore, the invention provides nucleic acid which can hybridise to the *N. meningitidis* nucleic acid disclosed in the examples, preferably under "high stringency" conditions (eg. 65° C. in a 0.1×SSC, 0.5% SDS solution).

Nucleic acid comprising fragments of these sequences are also provided. These should comprise at least n consecutive nucleotides from the *N. meningitidis* sequences and, depending on the particular sequence, n is 10 or more (eg 12, 14, 15, 18, 20, 25, 30, 35, 40 or more). According to a further aspect, the invention provides nucleic acid encoding the proteins and protein fragments of the invention.

It should also be appreciated that the invention provides nucleic acid comprising sequences complementary to those described above (eg. for antisense or probing purposes).

Nucleic acid according to the invention can, of course, be prepared in many ways (eg. by chemical synthesis, from genomic or cDNA libraries, from the organism itself etc.) and can take various forms (eg. single stranded, double stranded, vectors, probes etc.).

In addition, the term "nucleic acid" includes DNA and RNA, and also their analogues, such as those containing modified backbones, and also peptide nucleic acids (PNA) etc.

According to a further aspect, the invention provides vectors comprising nucleotide sequences of the invention (eg. expression vectors) and host cells transformed with such vectors.

According to a further aspect, the invention provides compositions comprising protein, antibody, and/or nucleic acid according to the invention. These compositions may be suitable as vaccines, for instance, or as diagnostic reagents, or as immunogenic compositions.

The invention also provides nucleic acid, protein, or antibody according to the invention for use as medicaments (eg. as vaccines) or as diagnostic reagents. It also provides the use of nucleic acid, protein, or antibody according to the invention in the manufacture of: (i) a medicament for treating or preventing infection due to Neisserial bacteria; (ii) a diagnostic reagent for detecting the presence of Neisserial bacteria or of antibodies raised against Neisserial bacteria; and/or (iii) a reagent which can raise antibodies against Neisserial bacteria. Said Neisserial bacteria may be any species or strain (such as *N. gonorrhoeae*) but are preferably *N. meningitidis*, especially strain A, strain B or strain C.

The invention also provides a method of treating a patient, comprising administering to the patient a therapeutically effective amount of nucleic acid, protein, and/or antibody according to the invention.

According to further aspects, the invention provides various processes.

A process for producing proteins of the invention is provided, comprising the step of culturing a host cell according to the invention under conditions which induce protein expression.

A process for producing protein or nucleic acid of the invention is provided, wherein the protein or nucleic acid is synthesised in part or in whole using chemical means.

A process for detecting polynucleotides of the invention is provided, comprising the steps of: (a) contacting a nucleic probe according to the invention with a biological sample under hybridizing conditions to form duplexes; and (b) detecting said duplexes.

A process for detecting proteins of the invention is provided, comprising the steps of: (a) contacting an antibody according to the invention with a biological sample under conditions suitable for the formation of an antibody-antigen complexes; and (b) detecting said complexes.

Unlike the sequences disclosed in PCT/IB98/01665, the sequences disclosed in the present application are believed not to have any significant homologs in *N. gonorrhoeae*. Accordingly, the sequences of the present invention also find use in the preparation of reagents for distinguishing between *N. meningitidis* and *N. gonorrhoeae*

A summary of standard techniques and procedures which may be employed in order to perform the invention (eg. to utilise the disclosed sequences for vaccination or diagnostic purposes) follows. This summary is not a limitation on the invention but, rather, gives examples that may be used, but are not required.

General

The practice of the present invention will employ, unless otherwise indicated, conventional techniques of molecular biology, microbiology, recombinant DNA, and immunology, which are within the skill of the art. Such techniques are explained fully in the literature eg. Sambrook *Molecular Cloning; A Laboratory Manual, Second Edition* (1989); *DNA Cloning, Volumes I and ii* (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); the *Methods in Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), and *Handbook of Experimental Immunology, Volumes I-IV* (D. M. Weir and C. C. Blackwell eds 1986).

Standard abbreviations for nucleotides and amino acids are used in this specification.

All publications, patents, and patent applications cited herein are incorporated in full by reference. In particular, the contents of UK patent applications 9800760.2, 9819015.0 and 9822143.5 are incorporated herein.

DEFINITIONS

A composition containing X is "substantially free of" Y when at least 85% by weight of the total X+Y in the composition is X. Preferably, X comprises at least about 90% by weight of the total of X+Y in the composition, more preferably at least about 95% or even 99% by weight.

The term "comprising" means "including" as well as "consisting" eg. a composition "comprising" X may consist exclusively of X or may include something additional to X, such as X+Y.

A "conserved" *Neisseria* amino acid fragment or protein is one that is present in a particular Neisserial protein in at least x % of *Neisseria*. The value of x may be 50% or more, e.g., 66%, 75%, 80%, 90%, 95% or even 100% (i.e. the amino acid is found in the protein in question in all *Neisseria*). In order to determine whether an animo acid is "conserved" in a particular Neisserial protein, it is necessary to compare that amino acid residue in the sequences of the protein in question from a plurality of different *Neisseria* (a reference population). The reference population may include a number of different *Neisseria* species or may include a single species. The reference population may include a number of different serogroups of a particular species or a single serogroup. A preferred reference population consists of the 5 most common *Neisseria*.

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. Another example is where a Neisserial sequence is heterologous to a mouse host cell. A further examples would be two epitopes from the same or different proteins which have been assembled in a single protein in an arrangement not found in nature.

An "origin of replication" is a polynucleotide sequence that initiates and regulates replication of polynucleotides, such as an expression vector. The origin of replication behaves as an autonomous unit of polynucleotide replication within a cell, capable of replication under its own control. An origin of replication may be needed for a vector to replicate in a particular host cell. With certain origins of replication, an expression vector can be reproduced at a high copy number in the presence of the appropriate proteins within the cell. Examples of origins are the autonomously replicating sequences, which are effective in yeast; and the viral T-antigen, effective in COS-7 cells.

A "mutant" sequence is defined as DNA, RNA or amino acid sequence differing from but having sequence identity with the native or disclosed sequence. Depending on the particular sequence, the degree of sequence identity between the native or disclosed sequence and the mutant sequence is preferably greater than 50% (eg. 60%, 70%, 80%, 90%, 95%, 99% or more, calculated using the Smith-Waterman algorithm as described above). As used herein, an "allelic variant" of a nucleic acid molecule, or region, for which nucleic acid sequence is provided herein is a nucleic acid molecule, or region, that occurs essentially at the same locus in the genome of another or second isolate, and that, due to natural variation caused by, for example, mutation or recombination, has a similar but not identical nucleic acid sequence. A coding region allelic variant typically encodes a protein having similar activity to that of the protein encoded by the gene to which it is being compared. An allelic variant can also comprise an alteration in the 5' or 3' untranslated regions of the gene, such as in regulatory control regions (eg. see U.S. Pat. No. 5,753, 235).

Expression Systems

The Neisserial nucleotide sequences can be expressed in a variety of different expression systems; for example those used with mammalian cells, baculoviruses, plants, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (eg. structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual,* 2nd ed.].

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell,* 2nd ed.]. Enhancer elements derived from viruses may be particularly useful, because they usually have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gorman et al. (1982b) *Proc. Natl. Acad. Sci.* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) Cell 41:349; Proudfoot and Whitelaw (1988) "Termination and 3' end processing of eukaryotic RNA. In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminator/polyadenylation signals include those derived from SV40 [Sambrook et al (1989) "Expression of cloned genes in cultured mammalian cells." In *Molecular Cloning: A Laboratory Manual]*.

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (eg. plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replication systems, thus allowing it to be maintained, for example, in mammalian cells for expression and in a prokaryotic host for cloning and amplification. Examples of such mammalian-bacteria shuttle vectors include pMT2 [Kaufman et al. (1989) *Mol. Cell. Biol.* 9:946] and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (eg. Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art. Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, *Texas Agricultural Experiment Station Bulletin No. 1555* (1987) (hereinafter "Summers and Smith").

Prior to inserting the DNA sequence encoding the protein into the baculovirus genome, the above described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (eg. plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.*, 42:177) and a prokaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene,* 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA,* 82:8404; mouse IL-3, (Miyajima et al., (1987) *Gene* 58:273; and human glucocerebrosidase, Martin et al. (1988) *DNA,* 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2-5 kb section of the baculovirus genome. Methods for introducing heterologous DNA into the desired site in the baculovirus virus are known in the art. (See Summers and Smith supra; Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 µm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda,* and *Trichoplusia ni* (WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, eg. Summers and Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, eg. HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, eg. proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Plant Systems

There are many plant cell culture and whole plant genetic expression systems known in the art. Exemplary plant cellular genetic expression systems include those described in patents, such as: U.S. Pat. No. 5,693,506; U.S. Pat. No. 5,659, 122; and U.S. Pat. No. 5,608,143. Additional examples of genetic expression in plant cell culture has been described by Zenk, *Phytochemistry* 30:3861-3863 (1991). Descriptions of plant protein signal peptides may be found in addition to the references described above in Vaulcombe et al., *Mol. Gen. Genet.* 209:33-40 (1987); Chandler et al., *Plant Molecular Biology* 3:407-418 (1984); Rogers, *J. Biol. Chem.* 260:3731-3738 (1985); Rothstein et al., *Gene* 55:353-356 (1987); Whittier et al., Nucleic Acids Research 15:2515-2535 (1987); Wirsel et al., *Molecular Microbiology* 3:3-14 (1989); Yu et al., *Gene* 122:247-253 (1992). A description of the regulation of plant gene expression by the phytohormone, gibberellic acid and secreted enzymes induced by gibberellic acid can be found in R. L. Jones and J. MacMillin, Gibberellins: in: *Advanced Plant Physiology*, Malcolm B. Wilkins, ed., 1984 Pitman Publishing Limited, London, pp. 21-52. References that describe other metabolically-regulated genes: Sheen, *Plant Cell*, 2:1027-1038(1990); Maas et al., *EMBO J.* 9:3447-3452 (1990); Benkel and Hickey, *Proc. Natl. Acad. Sci.* 84:1337-1339 (1987)

Typically, using techniques known in the art, a desired polynucleotide sequence is inserted into an expression cassette comprising genetic regulatory elements designed for operation in plants. The expression cassette is inserted into a desired expression vector with companion sequences upstream and downstream from the expression cassette suitable for expression in a plant host. The companion sequences will be of plasmid or viral origin and provide necessary characteristics to the vector to permit the vectors to move DNA from an original cloning host, such as bacteria, to the desired plant host. The basic bacterial/plant vector construct will preferably provide a broad host range prokaryote replication origin; a prokaryote selectable marker; and, for Agrobacterium transformations, T DNA sequences for Agrobacterium-mediated transfer to plant chromosomes. Where the heterologous gene is not readily amenable to detection, the construct will preferably also have a selectable marker gene suitable for determining if a plant cell has been transformed. A general review of suitable markers, for example for the members of the grass family, is found in Wilmink and Dons, 1993, *Plant Mol. Biol. Reptr*, 11(2):165-185.

Sequences suitable for permitting integration of the heterologous sequence into the plant genome are also recommended. These might include transposon sequences and the like for homologous recombination as well as Ti sequences which permit random insertion of a heterologous expression cassette into a plant genome. Suitable prokaryote selectable markers include resistance toward antibiotics such as ampicillin or tetracycline. Other DNA sequences encoding additional functions may also be present in the vector, as is known in the art.

The nucleic acid molecules of the subject invention may be included into an expression cassette for expression of the protein(s) of interest. Usually, there will be only one expression cassette, although two or more are feasible. The recombinant expression cassette will contain in addition to the heterologous protein encoding sequence the following elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector.

A heterologous coding sequence may be for any protein relating to the present invention. The sequence encoding the protein of interest will encode a signal peptide which allows processing and translocation of the protein, as appropriate, and will usually lack any sequence which might result in the binding of the desired protein of the invention to a membrane. Since, for the most part, the transcriptional initiation region will be for a gene which is expressed and translocated during germination, by employing the signal peptide which provides for translocation, one may also provide for translocation of the protein of interest. In this way, the protein(s) of interest will be translocated from the cells in which they are expressed and may be efficiently harvested. Typically secretion in seeds are across the aleurone or scutellar epithelium layer into the endosperm of the seed. While it is not required that the protein be secreted from the cells in which the protein is produced, this facilitates the isolation and purification of the recombinant protein.

Since the ultimate expression of the desired gene product will be in a eucaryotic cell it is desirable to determine whether any portion of the cloned gene contains sequences which will be processed out as introns by the host's splicosome machinery. If so, site-directed mutagenesis of the "intron" region may be conducted to prevent losing a portion of the genetic message as a false intron code, Reed and Maniatis, *Cell* 41:95-105, 1985.

The vector can be microinjected directly into plant cells by use of micropipettes to mechanically transfer the recombinant DNA. Crossway, *Mol. Gen. Genet*, 202:179-185, 1985. The genetic material may also be transferred into the plant cell by using polyethylene glycol, Krens, et al., *Nature*, 296, 72-74, 1982. Another method of introduction of nucleic acid segments is high velocity ballistic penetration by small particles with the nucleic acid either within the matrix of small beads or particles, or on the surface, Klein, et al., *Nature*, 327, 70-73, 1987 and Knudsen and Muller, 1991, *Planta*, 185:330-336 teaching particle bombardment of barley endosperm to create transgenic barley. Yet another method of introduction would be fusion of protoplasts with other entities, either minicells, cells, lysosomes or other fusible lipid-surfaced bodies, Fraley, et al., *Proc. Natl. Acad. Sci. USA*, 79, 1859-1863, 1982.

The vector may also be introduced into the plant cells by electroporation. (Fromm et al., *Proc. Natl. Acad. Sci. USA* 82:5824, 1985). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Herocallis, Nemesia, Pelargonium, Panicum, Pennisetum, Ranunculus, Senecio, Salpiglossis, Cucumis, Browaalia, Glycine, Lolium, Zea, Triticum, Sorghum*, and *Datura*.

Means for regeneration vary from species to species of plants, but generally a suspension of transformed protoplasts containing copies of the heterologous gene is first provided. Callus tissue is formed and shoots may be induced from callus and subsequently rooted. Alternatively, embryo formation can be induced from the protoplast suspension. These embryos germinate as natural embryos to form plants. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In some plant cell culture systems, the desired protein of the invention may be excreted or alternatively, the protein may be extracted from the whole plant. Where the desired protein of the invention is secreted into the medium, it may be collected. Alternatively, the embryos and embryoless-half seeds or other plant tissue may be mechanically disrupted to release any secreted protein between cells and tissues. The mixture may be suspended in a buffer solution to retrieve soluble proteins. Conventional protein isolation and purification methods will be then used to purify the recombinant protein. Parameters of time, temperature pH, oxygen, and volumes will be adjusted through routine methods to optimize expression and recovery of heterologous protein.

iv. Bacterial Systems

Bacterial expression techniques are known in the art. A bacterial promoter is any DNA sequence capable of binding bacterial RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EP-A-0036776 and EP-A-0121775]. The g-laotamase (bla) promoter system [Weissmann (1981) "The cloning of interferon and other mistakes." In *Interferon* 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EPO-A-0 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual*].

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO-A-0 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) *J. Biotechnol.* 5:93; Makoff et al. (1989) *J. Gen. Microbiol.* 135:11], and Chey [EP-A-0 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (eg. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression*; Ghrayeb et al. (1984) *EMBO J.* 3:2437] and the *E. coli* alkaline phosphatase signal sequence (phoA) [Oka et al. (1985) *Proc. Natl. Acad. Sci.* 82:7212]. As an additional example, the signal sequence of the alpha-amylase gene from various Bacillus strains can be used to secrete heterologous proteins from *B. subtilis* [Palva et al. (1982) *Proc. Natl. Acad. Sci. USA* 79:5582; EP-A-0 244 042].

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription.

Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extra-chromosomal element (eg. plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome (EP-A-0 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci. USA* 79:5582; EP-A-0 036 259 and EP-A-O 063 953; WO 84/04541], *Escherichia coli* [Shimatake et al. (1981) *Nature* 292:128; Amann et al. (1985) *Gene* 40:183; Studier et al. (1986) *J. Mol. Biol.* 189:113; EP-A-0 036 776, EP-A-0 136 829 and EP-A-0 136 907*], Streptococcus cremoris* [Powell et al. (1988) *Appl. Environ. Microbiol.* 54:655*]; Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See eg. [Masson et al. (1989) *FEMS Microbiol. Lett.* 60:273; Palva et al. (1982) *Proc. Natl. Acad. Sci. USA* 79:5582; EP-A-0 036 259 and EP-A-0 063 953; WO 84/04541, *Bacillus*], [Miller et al. (1988) *Proc. Natl. Acad. Sci.* 85:856; Wang et al. (1990) *J. Bacteriol.* 172:949, *Campylobacter*], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus lactis* by electroporation, in: *Streptococcal Genetics* (ed. J. Ferretti and R. Curtiss III); Perry et al. (1981) *Infect. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus*].

v. Yeast Expression

Yeast expression systems are also known to one of ordinary skill in the art. A yeast promoter is any DNA sequence capable of binding yeast RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EP-A-0 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO-A-0 329 203). The yeast PHO5 gene, encoding acid phosphatase, also provides useful promoter sequences [Myanohara et al. (1983) *Proc. Natl. Acad. Sci. USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EP-A-0 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast *Saccharomyces cerevisiae*," in: *Plasmids of Medical, Environmental and Commercial Importance* (eds. K. N. Timmis and A. Puhler); Mercerau-Puigalon et al. (1980) *Gene* 11: 163; Panthier et al. (1980) *Curr. Genet.* 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See eg. EP-A-0 196 056. Another example is a ubiquitin fusion protein. Such a fusion protein is made with the ubiquitin region that preferably retains a site for a processing enzyme (eg. ubiquitin-specific processing protease) to cleave the ubiquitin from the foreign protein. Through this method, therefore, native foreign protein can be isolated (eg. WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EP-A-0 012 873; JPO. 62,096,086) and the A-factor gene (U.S. Pat. No. 4,588,684). Alternatively, leaders of non-yeast origin, such as an interferon leader, exist that also provide for secretion in yeast (EP-A-0 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EP-A-0 324 274). Additional leaders employing an alpha-factor leader fragment that provides for secretion include hybrid alpha-factor leaders made with a presequence of a first yeast, but a pro-region from a second yeast alphafactor. (eg. see WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extra-chromosomal element (eg. plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 [Botstein et al. (1979) *Gene* 8:17-24], pCI/1 [Brake et al. (1984) *Proc. Natl. Acad. Sci USA* 81:4642-4646], and YRp17 [Stinchcomb et al. (1982) *J. Mol. Biol.* 158:157]. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Enter a high or low copy number vector may be selected, depending upon the effect of the vector and the foreign protein on the host. See eg. Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) *Methods in Enzymol.* 101:228-245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) *Proc. Natl. Acad. Sci. USA*

80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) *Microbiol, Rev.* 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* [Kurtz, et al. (1986) *Mol. Cell. Biol.* 6:142], *Candida maltosa* [Kunze, et al. (1985) *J. Basic Microbiol.* 25:141]. *Hansenula polymorpha* [Gleeson, et al. (1986) *J. Gen. Microbiol.* 132:3459; Roggenkamp et al. (1986) *Mol. Gen. Genet.* 202:302*]*, *Kluyveromyces fragilis* [Das, et al. (1984) *J. Bacteriol.* 158:1165], *Kluyveromyces lactis* [De Louvencourt et al. (1983) *J. Bacteriol.* 154:737; Van den Berg et al. (1990) *Bio/Technology* 8:135*], Pichia guillerimondii* [Kunze et al. (1985) *J. Basic Microbiol.* 25:141], *Pichia pastoris* [Cregg, et al. (1985) *Mol. Cell. Biol.* 5:3376; U.S. Pat. Nos. 4,837,148 and 4,929,555], *Saccharomyces cerevisiae* [Hinnen et al. (1978) *Proc. Natl. Acad. Sci. USA* 75:1929; Ito et al. (1983) *J. Bacteriol.* 153:163], *Schizosaccharomyces pombe* [Beach and Nurse (1981) *Nature* 300:706], and *Yarrowia lipolytica* [Davidow, et al. (1985) *Curr. Genet.* 10:380471 Gaillardin, et al. (1985) *Curr. Genet.* 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See eg. [Kurtz et al. (1986) *Mol. Cell. Biol.* 6:142; Kunze et al. (1985) *J. Basic Microbiol.* 25:141*; Candida*]; [Gleeson et al. (1986) *J. Gen. Microbiol.* 132:3459; Roggenkamp et al. (1986) *Mol. Gen. Genet.* 202:302*; Hansenula*]; [Das et al. (1984) *J. Bacteriol.* 158:1165; De Louvencourt et al. (1983) *J. Bacterial.* 154: 1165; Van den Berg et al. (1990) *Bio/Technology* 8:135; *Kluyveromyces*]; [Cregg et al. (1985) *Mol. Cell. Biol.* 5:3376; Kunze et al. (1985) *J. Basic Microbiol.* 25:141; U.S. Pat. Nos. 4,837,148 and 4,929,555; *Pichia*]; [Hinnen et al. (1978) *Proc. Natl. Acad. Sci. USA* 75; 1929; Ito et al. (1983) *J. Bacteriol.* 153:163 *Saccharomyces*]; [Beach and Nurse (1981) *Nature* 300:706; *Schizosaccharomyces*]; [Davidow et al. (1985) *Curr. Genet.* 10:39; Gaillardin et al. (1985) *Curr. Genet.* 10:49*; Yarrowia*].

Antibodies

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies. Antibodies against the proteins of the invention are useful for affinity chromatography, immunoassays, and distinguishing/identifying Neisserial proteins.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 µg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera is obtained by bleeding the immunized animal into a glass or plastic container, incubating the blood at 25° C. for one hour, followed by incubating at 4° C. for 2-18 hours. The serum is recovered by centrifugation (eg. 1,000 g for 10 minutes). About 20-50 ml per bleed may be obtained from rabbits.

Monoclonal antibodies are prepared using the standard method of Kohler & Milstein [*Nature* (1975) 256:495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (eg. hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected MAb-secreting hybridomas are then cultured either in vitro (eg. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}$I may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}$I, or with an anti-biotin MAb labeled with HRP. Other permutations and possibilities will be readily apparent to those of ordinary skill in the art, and are considered as equivalents within the scope of the instant invention.

Pharmaceutical Compositions

Pharmaceutical compositions can comprise either polypeptides, antibodies, or nucleic acid of the invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the compositions of the invention can be administered directly to the subject. The subjects to be treated can be animals; in particular, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. see WO98/20734), needles, and gene guns or hyposprays. Dosage treatment may be a single dose schedule or a multiple dose schedule.

Vaccines

Vaccines according to the invention may either be prophylactic (ie. to prevent infection) or therapeutic (ie. to treat disease after infection).

Such vaccines comprise immunising antigen(s), immunogen(s), polypeptide(s), protein(s) or nucleic acid, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59™ (WO 90/14837; Chapter 10 in *Vaccine design: the subunit and adjuvant approach*, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor (TNF), etc; and (6) other substances that act as immunostimulating agents to enhance the effectiveness of the composition. Alum and MF59™ are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), etc.

The immunogenic compositions (eg. the immunising antigen/immunogen/polypeptide/protein/nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, eg. by injection, either subcutaneously, intramuscularly, or transdermally/transcutaneously (eg. WO98/20734). Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

As an alternative to protein-based vaccines, DNA vaccination may be employed [eg. Robinson & Torres (1997) *Seminars in Immunology* 9:271-283; Donnelly et al. (1997) *Annu Rev Immunol* 15:617-648; see later herein].

Gene Delivery Vehicles

Gene therapy vehicles for delivery of constructs including a coding sequence of a therapeutic of the invention, to be delivered to the mammal for expression in the mammal, can be administered either locally or systemically. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated.

The invention includes gene delivery vehicles capable of expressing the contemplated nucleic acid sequences. The gene delivery vehicle is preferably a viral vector and, more preferably, a retroviral, adenoviral, adeno-associated viral (AAV), herpes viral, or alphavirus vector. The viral vector can also be an astrovirus, coronavirus, orthomyxovirus, papovavirus, paramyxovirus, parvovirus, picornavirus, poxvirus, or togavirus viral vector. See generally, Jolly (1994) *Cancer Gene Therapy* 1:51-64; Kimura (1994) *Human Gene Therapy* 5:845-852; Connelly (1995) *Human Gene Therapy* 6:185-193; and Kaplitt (1994) *Nature Genetics* 6:148-153.

Retroviral vectors are well known in the art and we contemplate that any retroviral gene therapy vector is employable in the invention, including B, C and D type retroviruses, xenotropic retroviruses (for example, NZB-X1, NZB-X2 and NZB9-1 (see O'Neill (1985) *J. Virol.* 53:160) polytropic retroviruses eg. MCF and MCF-MLV (see Kelly (1983) *J. Virol.* 45:291), spumaviruses and lentiviruses. See RNA Tumor Viruses, Second Edition, Cold Spring Harbor Laboratory, 1985.

Portions of the retroviral gene therapy vector may be derived from different retroviruses. For example, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

These recombinant retroviral vectors may be used to generate transduction competent retroviral vector particles by introducing them into appropriate packaging cell lines (see U.S. Pat. No. 5,591,624). Retrovirus vectors can be constructed for site-specific integration into host cell DNA by incorporation of a chimeric integrase enzyme into the retroviral particle (see WO96/37626). It is preferable that the recombinant viral vector is a replication defective recombinant virus.

Packaging cell lines suitable for use with the above-described retrovirus vectors are well known in the art, are readily prepared (see WO95/30763 and WO92/05266), and can be used to create producer cell lines (also termed vector cell lines or "VCLs") for the production of recombinant vector particles. Preferably, the packaging cell lines are made from human parent cells (eg. HT1080 cells) or mink parent cell lines, which eliminates inactivation in human serum.

Preferred retroviruses for the construction of retroviral gene therapy vectors include Avian Leukosis Virus, Bovine Leukemia, Virus, Murine Leukemia Virus, Mink-Cell Focus-Inducing Virus, Murine Sarcoma Virus, Reticuloendotheliosis Virus and Rous Sarcoma Virus. Particularly preferred Murine Leukemia Viruses include 4070A and 1504A (Hartley and Rowe (1976) *J Virol* 19:19-25), Abelson (ATCC No. VR-999), Friend (ATCC No. VR-245), Graffi, Gross (ATCC Nol VR-590), Kirsten, Harvey Sarcoma Virus and Rauscher (ATCC No. VR-998) and Moloney Murine Leukemia Virus (ATCC No. VR-190). Such retroviruses may be obtained from depositories or collections such as the American Type Culture Collection ("ATCC") in Rockville, Md. or isolated from known sources using commonly available techniques.

Exemplary known retroviral gene therapy vectors employable in this invention include those described in patent applications GB2200651, EP0415731, EP0345242, EP0334301, WO89/02468; WO89/05349, WO89/09271, WO90/02806, WO90/07936, WO94/03622, WO93/25698, WO93/25234, WO93/11230, WO93/10218, WO91/02805, WO91/02825, WO95/07994, U.S. Pat. No. 5,219,740, U.S. Pat. No. 4,405,712, U.S. Pat. No. 4,861,719, U.S. Pat. No. 4,980,289, U.S.

Pat. No. 4,777,127, U.S. Pat. No. 5,591,624. See also Vile (1993) *Cancer Res* 53:3860-3864; Vile (1993) *Cancer Res* 53:962-967; Ram (1993) *Cancer Res* 53 (1993) 83-88; Takamiya (1992) *J Neurosci Res* 33:493-503; Baba (1993) *J Neurosurg* 79:729-735; Mann (1983) *Cell* 33:153; Cane (1984) *Proc Natl Acad Sci* 81:6349; and Miller (1990) *Human Gene Therapy* 1.

Human adenoviral gene therapy vectors are also known in the art and employable in this invention. See, for example, Berkner (1988) *Biotechniques* 6:616 and Rosenfeld (1991) *Science* 252:431, and WO93/07283, WO93/06223, and WO93/07282. Exemplary known adenoviral gene therapy vectors employable in this invention include those described in the above referenced documents and in WO94/12649, WO93/03769, WO93/19191, WO94/28938, WO95/11984, WO95/00655, WO95/27071, WO95/29993, WO95/34671, WO96/05320, WO94/08026, WO94/11506, WO93/06223, WO94/24299, WO95/14102, WO95/24297, WO95/02697, WO94/28152, WO94/24299, WO95/09241, WO95/25807, WO95/05835, WO94/18922 and WO95/09654. Alternatively, administration of DNA linked to killed adenovirus as described in Curiel (1992) *Hum. Gene Ther.* 3:147-154 may be employed. The gene delivery vehicles of the invention also include adenovirus associated virus (AAV) vectors. Leading and preferred examples of such vectors for use in this invention are the AAV-2 based vectors disclosed in Srivastava, WO93/09239. Most preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (ie. there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini (1993) *Gene* 124:257-262. Another example of such an AAV vector is psub201 (see Samulski (1987) *J. Virol.* 61:3096). Another exemplary AAV vector is the Double-D ITR vector. Construction of the Double-D ITR vector is disclosed in U.S. Pat. No. 5,478,745. Still other vectors are those disclosed in Carter U.S. Pat. No. 4,797,368 and Muzyczka U.S. Pat. No. 5,139,941, Chartejee U.S. Pat. No. 5,474,935, and Kotin WO94/288157. Yet a further example of an AAV vector employable in this invention is SSV9AFABTKneo, which contains the AFP enhancer and albumin promoter and directs expression predominantly in the liver. Its structure and construction are disclosed in Su (1996) *Human Gene Therapy* 7:463-470. Additional AAV gene therapy vectors are described in U.S. Pat. No. 5,354,678, U.S. Pat. No. 5,173,414, U.S. Pat. No. 5,139,941, and U.S. Pat. No. 5,252,479.

The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP0176170 (Roizman). Additional exemplary herpes simplex virus vectors include HFEM/ICP6-LacZ disclosed in WO95/04139 (Wistar Institute), pHSVlac described in Geller (1988) *Science* 241:1667-1669 and in WO90/09441 and WO92/07945, HSV Us3::pgC-lacZ described in Fink (1992) *Human Gene Therapy* 3:11-19 and HSV 7134, 2 RH 105 and GAL4 described in EP 0453242 (Breakefield), and those deposited with the ATCC as accession numbers ATCC VR-977 and ATCC VR-260.

Also contemplated are alpha virus gene therapy vectors that can be employed in this invention. Preferred alpha virus vectors are Sindbis viruses vectors. Togaviruses, Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309, 5,217,879, and WO92/10578. More particularly, those alpha virus vectors described in U.S. Ser. No. 08/405,627, filed Mar. 15, 1995, WO94/21792, WO92/10578, WO95/07994, U.S. Pat. No. 5,091,309 and U.S. Pat. No. 5,217,879 are employable. Such alpha viruses may be obtained from depositories or collections such as the ATCC in Rockville, Md. or isolated from known sources using commonly available techniques. Preferably, alphavirus vectors with reduced cytotoxicity are used (see U.S. Ser. No. 08/679,640).

DNA vector systems such as eukaryotic layered expression systems are also useful for expressing the nucleic acids of the invention. See WO95/07994 for a detailed description of eukaryotic layered expression systems. Preferably, the eukaryotic layered expression systems of the invention are derived from alphavirus vectors and most preferably from Sindbis viral vectors.

Other viral vectors suitable for use in the present invention include those derived from poliovirus, for example ATCC VR-58 and those described in Evans, Nature 339 (1989) 385 and Sabin (1973) *J. Biol. Standardization* 1:115; rhinovirus, for example ATCC VR-1110 and those described in Arnold (1990) *J Cell Biochem* L401; pox viruses such as canary pox virus or vaccinia virus, for example ATCC VR-111 and ATCC VR-2010 and those described in Fisher-Hoch (1989) *Proc Natl Acad Sci* 86:317; Flexner (1989) *Ann NY Acad Sci* 569: 86, Flexner (1990) *Vaccine* 8:17; in U.S. Pat. No. 4,603,112 and U.S. Pat. No. 4,769,330 and WO89/01973; SV40 virus, for example ATCC VR-305 and those described in Mulligan (1979) *Nature* 277:108 and Madzak (1992) *J Gen Virol* 73:1533; influenza virus, for example ATCC VR-797 and recombinant influenza viruses made employing reverse genetics techniques as described in U.S. Pat. No. 5,166,057 and in Enami (1990) *Proc Natl Acad Sci* 87:3802-3805; Enami & Palese (1991) *J Virol* 65:2711-2713 and Luytjes (1989) *Cell* 59:110, (see also McMichael (1983) *NEJ Med* 309:13, and Yap (1978) *Nature* 273:238 and *Nature* (1979) 277:108); human immunodeficiency virus as described in EP-0386882 and in Buchschacher (1992) *J. Virol.* 66:2731; measles virus, for example ATCC VR-67 and VR-1247 and those described in EP-0440219; Aura virus, for example ATCC VR-368; Bebaru virus, for example ATCC VR-600 and ATCC VR-1240; Cabassou virus, for example ATCC VR-922; Chikungunya virus, for example ATCC VR-64 and ATCC VR-1241; Fort Morgan Virus, for example ATCC VR-924; Getah virus, for example ATCC VR-369 and ATCC VR-1243; Kyzylagach virus, for example ATCC VR-927; Mayaro virus, for example ATCC VR-66; Mucambo virus, for example ATCC VR-580 and ATCC VR-1244; Ndumu virus, for example ATCC VR-371; Pixuna virus, for example ATCC VR-372 and ATCC VR-1245; Tonate virus, for example ATCC VR-925; Triniti virus, for example ATCC VR-469; Una virus, for example ATCC VR-374; Whataroa virus, for example ATCC VR-926; Y-62-33 virus, for example ATCC VR-375; O'Nyong virus, Eastern encephalitis virus, for example ATCC VR-65 and ATCC VR-1242; Western encephalitis virus, for example ATCC VR-70, ATCC VR-1251, ATCC VR-622 and ATCC VR-1252; and coronavirus, for example ATCC VR-740 and those described in Hamre (1966) *Proc Soc Exp Biol Med* 121:190.

Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994 and Curiel (1992) *Hum Gene Ther* 3:147-154 ligand linked DNA, for example see Wu (1989) *J Biol Chem* 264:16985-16987, eucaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655, ionizing radiation as described in U.S. Pat. No. 5,206,152 and in WO92/11033, nucleic charge neutralization or fusion with cell membranes. Additional approaches are described in Philip (1994) *Mol Cell Biol* 14:2411-2418 and in Woffendin (1994) *Proc Natl Acad Sci* 91:1581-1585.

Particle mediated gene transfer may be employed, for example see U.S. Ser. No. 60/023,867. Briefly, the sequence can be inserted into conventional vectors that contain conventional control sequences for high level expression, and then incubated with synthetic gene transfer molecules such as polymeric DNA-binding cations like polylysine, protamine, and albumin, linked to cell targeting ligands such as asialoorosomucoid, as described in Wu & Wu (1987) *J. Biol. Chem.* 262:4429-4432, insulin as described in Hucked (1990) *Biochem Pharmacol* 40:253-263, galactose as described in Plank (1992) *Bioconjugate Chem* 3:533-539, lactose or transferrin.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, WO95/13796, WO94/23697, WO91/14445 and EP-524,968. As described in U.S. Ser. No. 60/023,867, on non-viral delivery, the nucleic acid sequences encoding a polypeptide can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al (1994) *Proc. Natl. Acad. Sci. USA* 91(24): 11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and WO92/11033

Exemplary liposome and polycationic gene delivery vehicles are those described in U.S. Pat. Nos. 5,422,120 and 4,762,915; in WO 95/13796; WO94/23697; and WO91/14445; in EP-0524968; and in Stryer, Biochemistry, pages 236-240 (1975) W.H. Freeman, San Francisco; Szoka (1980) *Biochem Biophys Acta* 600: 1; Bayer (1979) *Biochem Biophys Acta* 550:464; Rivnay (1987) *Meth Enzymol* 149:119; Wang (1987) *Proc Natl Acad Sci* 84:7851; Plant (1989) *Anal Biochem* 176:420.

A polynucleotide composition can comprises therapeutically effective amount of a gene therapy vehicle, as the term is defined above. For purposes of the present invention, an effective dose will be from about 0.01 mg/kg to 50 mg/kg or 0.05 mg/kg to about 10 mg/kg of the DNA constructs in the individual to which it is administered.

Delivery Methods

Once formulated, the polynucleotide compositions of the invention can be administered (1) directly to the subject; (2) delivered ex vivo, to cells derived from the subject; or (3) in vitro for expression of recombinant proteins. The subjects to be treated can be mammals or birds. Also, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. see WO98/20734), needles, and gene guns or hyposprays. Dosage treatment may be a single dose schedule or a multiple dose schedule.

Methods for the ex vivo delivery and reimplantation of transformed cells into a subject are known in the art and described in eg. WO93/14778. Examples of cells useful in ex vivo applications include, for example, stem cells, particularly hematopoetic, lymph cells, macrophages, dendritic cells, or tumor cells.

Generally, delivery of nucleic acids for both ex vivo and in vitro applications can be accomplished by the following procedures, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Polynucleotide and Polypeptide Pharmaceutical Compositions

In addition to the pharmaceutically acceptable carriers and salts described above, the following additional agents can be used with polynucleotide and/or polypeptide compositions.

A. Polypeptides

One example are polypeptides which include, without limitation: asioloorosomucoid (ASOR); transferrin; asialoglycoproteins; antibodies; antibody fragments; ferritin; interleukins; interferons, granulocyte, macrophage colony stimulating factor (GM-CSF), granulocyte colony stimulating factor (G-CSF), macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of plasmodium falciparum known as RII.

B. Hormones, Vitamins, etc.

Other groups that can be included are, for example: hormones, steroids, androgens, estrogens, thyroid hormone, or vitamins, folic acid.

C. Polyalkylenes, Polysaccharides, etc.

Also, polyalkylene glycol can be included with the desired polynucleotides/polypeptides. In a preferred embodiment, the polyalkylene glycol is polyethlylene glycol. In addition, mono-, di-, or polysaccharides can be included. In a preferred embodiment of this aspect, the polysaccharide is dextran or DEAE-dextran. Also, chitosan and poly(lactide-co-glycolide)

D. Lipids, and Liposomes

The desired polynucleotide/polypeptide can also be encapsulated in lipids or packaged in liposomes prior to delivery to the subject or to cells derived therefrom.

Lipid encapsulation is generally accomplished using liposomes which are able to stably bind or entrap and retain nucleic acid. The ratio of condensed polynucleotide to lipid preparation can vary but will generally be around 1:1 (mg DNA:micromoles lipid), or more of lipid. For a review of the use of liposomes as carriers for delivery of nucleic acids, see, Hug and Sleight (1991) *Biochim. Biophys. Acta.* 1097:1-17; Straubinger (1983) *Meth. Enzymol.* 101:512-527.

Liposomal preparations for use in the present invention include cationic (positively charged), anionic (negatively charged) and neutral preparations. Cationic liposomes have been shown to mediate intracellular delivery of plasmid DNA (Felgner (1987) *Proc. Natl. Acad. Sci. USA* 84:7413-7416); mRNA (Malone (1989) *Proc. Natl. Acad. Sci USA* 86:6077-6081); and purified transcription factors (Debs (1990) *J. Biol. Chem.* 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner supra). Other commercially available liposomes include transfectace (DDAB/DOPE) and DOTAP/DOPE (Boerhinger). Other cationic liposomes can be prepared from readily available materials using techniques well known in the art. See, eg. Szoka (1978) *Proc. Natl. Acad. Sci. USA* 75:4194-4198; WO90/11092 for a description of the synthesis of DOTAP (1,2-bis(oleoyloxy)-3-(trimethylammonio) propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See eg Straubinger (1983) *Meth. Immunol.* 101:512-527; Szoka (1978) *Proc. Natl. Acad. Sci. USA* 75:4194-4198; Papahadjopoulos (1975) *Biochim. Biophys. Acta* 394:483; Wilson (1979) *Cell* 17:77); Deamer & Bangham (1976) *Biochim. Biophys. Acta* 443:629; Ostro (1977) *Biochem. Biophys. Res. Commun.* 76:836; Fraley (1979) *Proc. Natl. Acad. Sci. USA* 76:3348); Enoch & Strittmatter (1979) *Proc. Natl. Acad. Sci. USA* 76:145; Fraley (1980) *J. Biol. Chem.* (1980) 255:10431; Szoka & Papahadjopoulos (1978) *Proc. Natl. Acad. Sci. USA* 75:145; and Schaefer-Ridder (1982) *Science* 215:166.

E. Lipoproteins

In addition, lipoproteins can be included with the polynucleotide/polypeptide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are including with the polynucleotide to be delivered, no other targeting ligand is included in the composition.

Naturally occurring lipoproteins comprise a lipid and a protein portion. The protein portion are known as apoproteins. At the present, apoproteins A, B, C, D, and E have been isolated and identified. At least two of these contain several proteins, designated by Roman numerals, AI, AII, AIV; CI, CII, CIII.

A lipoprotein can comprise more than one apoprotein. For example, naturally occurring chylomicrons comprises of A, B, C, and E, over time these lipoproteins lose A and acquire C and E apoproteins. VLDL comprises A, B, C, and E apoproteins, LDL comprises apoprotein B; and HDL comprises apoproteins A, C, and E.

The ammo acid of these apoproteins are known and are described in, for example, Breslow (1985) Annu Rev. Biochem 54:699; Law (1986) Adv. Exp Med. Biol. 151:162; Chen (1986) J Biol Chem 261:12918; Kane (1980) Proc Natl Acad Sci USA 77:2465; and Utermann (1984) Hum Genet 65:232.

Lipoproteins contain a variety of lipids including, triglycerides, cholesterol (free and esters), and phospholipids. The composition of the lipids varies in naturally occurring lipoproteins. For example, chylomicrons comprise mainly triglycerides. A more detailed description of the lipid content of naturally occurring lipoproteins can be found, for example, in *Meth. Enzymol.* 128 (1986). The composition of the lipids are chosen to aid in conformation of the apoprotein for receptor binding activity. The composition of lipids can also be chosen to facilitate hydrophobic interaction and association with the polynucleotide binding molecule.

Naturally occurring lipoproteins can be isolated from serum by ultracentrifugation, for instance. Such methods are described in *Meth. Enzymol.* (supra); Pitas (1980) *J. Biochem.* 255:5454-5460 and Mahey (1979) *J. Clin. Invest* 64:743-750. Lipoproteins can also be produced by in vitro or recombinant methods by expression of the apoprotein genes in a desired host cell. See, for example, Atkinson (1986) *Annu Rev Biophys Chem* 15:403 and Radding (1958) *Biochim Biophys Acta* 30: 443. Lipoproteins can also be purchased from commercial suppliers, such as Biomedical Technologies, Inc., Stoughton, Mass., USA. Further description of lipoproteins can be found in Zuckermann et al. PCT/US97/14465.

F. Polycationic Agents

Polycationic agents can be included, with or without lipoprotein, in a composition with the desired polynucleotide/polypeptide to be delivered.

Polycationic agents, typically, exhibit a net positive charge at physiological relevant pH and are capable of neutralizing the electrical charge of nucleic acids to facilitate delivery to a desired location. These agents have both in vitro, ex vivo, and in vivo applications. Polycationic agents can be used to deliver nucleic acids to a living subject either intramuscularly, subcutaneously, etc.

The following are examples of useful polypeptides as polycationic agents: polylysine, polyarginine, polyornithine, and protamine. Other examples include histones, protamines, human serum albumin, DNA binding proteins, non-histone chromosomal proteins, coat proteins from DNA viruses, such as (X174, transcriptional factors also contain domains that bind DNA and therefore may be useful as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Organic Polycationic Agents Include: Spermine, Spermidine, and Purtrescine.

The dimensions and of the physical properties of a polycationic agent can be extrapolated from the list above, to construct other polypeptide polycationic agents or to produce synthetic polycationic agents.

Synthetic polycationic agents which are useful include, for example, DEAE-dextran, polybrene. Lipofectin™, and lipofectAMINE™ are monomers that form polycationic complexes when combined with polynucleotides/polypeptides.

Immunodiagnostic Assays

Neisserial antigens of the invention can be used in immunoassays to detect antibody levels (or, conversely, anti-Neisserial antibodies can be used to detect antigen levels). Immunoassays based on well defined, recombinant antigens can be developed to replace invasive diagnostics methods. Antibodies to Neisserial proteins within biological samples, including for example, blood or serum samples, can be detected. Design of the immunoassays is subject to a great deal of variation, and a variety of these are known in the art. Protocols for the immunoassay may bebased, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as a suitable set of assay instructions.

Nucleic Acid Hybridisation

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook et al. [supra] Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated Tm of the hybrid under study. The temperature and salt conditions can often be determined empirically in preliminary experiments in which samples of genomic DNA immobilized on filters are hybridized to the sequence of interest and then washed under conditions of different stringencies. See Sambrook et al. at page 9.50.

Variables to consider when performing, for example, a Southern blot are (1) the complexity of the DNA being blotted and (2) the homology between the probe and the sequences being detected. The total amount of the fragment(s) to be studied can vary a magnitude of 10, from 0.1 to 1 µg for a plasmid or phage digest to $10^{-9}$ to $10^{-8}$ g for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 µg of yeast DNA, blotting for two hours, and hybridizing for 4-8 hours with a probe of $10^8$ cpm/µg. For a single-copy mammalian gene a conservative approach would start with 10 µg of DNA, blot overnight, and hybridize overnight in the presence of 10% dextran sulfate using a probe of greater than 108 cpm/µg, resulting in an exposure time of ~24 hours.

Several factors can affect the melting temperature (Tm) of a DNA-DNA hybrid between the probe and the fragment of interest, and consequently the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm=81+16.6(\log_{10}Ci)+0.4[\%(G+C)]-0.6 \text{ (\% formamide)}-600/n-1.5 \text{ (\% mismatch)}.$$

where Ci is the salt concentration (monovalent ions) and n is the length of the hybrid in base pairs (slightly modified from Meinkoth & Wahl (1984) *Anal. Biochem.* 138: 267-284).

In designing a hybridization experiment, some factors affecting nucleic acid hybridization can be conveniently altered. The temperature of the hybridization and washes and the salt concentration during the washes are the simplest to adjust. As the temperature of the hybridization increases (ie. stringency), it becomes less likely for hybridization to occur between strands that are nonhomologous, and as a result, background decreases. If the radiolabeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology between the probe and the target fragment are not known, the simplest approach is to start with both hybridization and wash conditions which are nonstringent. If non-specific bands or high background are observed after autoradiography, the filter can be washed at high stringency and reexposed. If the time required for exposure makes this approach impractical, several hybridization and/or washing stringencies should be tested in parallel.

Nucleic Acid Probe Assays

Methods such as PCR, branched DNA probe assays, or blotting techniques utilizing nucleic acid probes according to the invention can determine the presence of cDNA or mRNA. A probe is said to "hybridize" with a sequence of the invention if it can form a duplex or double stranded complex, which is stable enough to be detected.

The nucleic acid probes will hybridize to the Neisserial nucleotide sequences of the invention (including both sense and antisense strands). Though many different nucleotide sequences will encode the amino acid sequence, the native Neisserial sequence is preferred because it is the actual sequence present in cells. mRNA represents a coding sequence and so a probe should be complementary to the coding sequence; single-stranded cDNA is complementary to mRNA, and so a cDNA probe should be complementary to the non-coding sequence.

The probe sequence need not be identical to the Neisserial sequence (or its complement)—some variation in the sequence and length can lead to increased assay sensitivity if the nucleic acid probe can form a duplex with target nucleotides, which can be detected. Also, the nucleic acid probe can include additional nucleotides to stabilize the formed duplex. Additional Neisserial sequence may also be helpful as a label to detect the formed duplex. For example, a non-complementary nucleotide sequence may be attached to the 5' end of the probe, with the remainder of the probe sequence being complementary to a Neisserial sequence. Alternatively, non-complementary bases or longer sequences can be interspersed into the probe, provided that the probe sequence has sufficient complementarity with the a Neisserial sequence in order to hybridize therewith and thereby form a duplex which can be detected.

The exact length and sequence of the probe will depend on the hybridization conditions, such as temperature, salt condition and the like. For example, for diagnostic applications, depending on the complexity of the analyte sequence, the nucleic acid probe typically contains at least 10-20 nucleotides, preferably 15-25, and more preferably at least 30 nucleotides, although it may be shorter than this. Short primers generally require cooler temperatures to form sufficiently stable hybrid complexes with the template.

Probes may be produced by synthetic procedures, such as the triester method of Matteucci et al. [*J. Am. Chem. Soc.* (1981) 103:3185], or according to Urdea et al. [*Proc. Natl. Acad. Sci. USA* (1983) 80: 7461], or using commercially available automated oligonucleotide synthesizers.

The chemical nature of the probe can be selected according to preference. For certain applications, DNA or RNA are appropriate. For other applications, modifications may be incorporated eg. backbone modifications, such as phosphorothioates or methylphosphonates, can be used to increase in vivo half-life, alter RNA affinity, increase nuclease resistance etc. [eg. see Agrawal & Iyer (1995) *Curr Opin Biotechnol* 6:12-19; Agrawal (1996) *TIBTECH* 14:376-387]; analogues such as peptide nucleic acids may also be used [eg. see Corey (1997) *TIBTECH* 15:224-229; Buchardt et al. (1993) *TIBTECH* 11:384-386].

Alternatively, the polymerase chain reaction (PCR) is another well-known means for detecting small amounts of target nucleic acids. The assay is described in: Mullis et al. [*Meth. Enzymol.* (1987) 155: 335-350]; U.S. Pat. Nos. 4,683,195 and 4,683,202. Two "primer" nucleotides hybridize with the target nucleic acids and are used to prime the reaction. The primers can comprise sequence that does not hybridize to the sequence of the amplification target (or its complement) to aid with duplex stability or, for example, to incorporate a convenient restriction site. Typically, such sequence will flank the desired Neisserial sequence.

A thermostable polymerase creases copies of target nucleic acids from the primers using the original target nucleic acids as a template. After a threshold amount of target nucleic acids are generated by the polymerase, they can be detected by more traditional methods, such as Southern blots. When using the Southern blot method, the labelled probe will hybridize to the Neisserial sequence (or its complement).

Also, mRNA or cDNA can be detected by traditional blotting techniques described in Sambrook et al [supra]. mRNA, or cDNA generated from mRNA using a polymerase enzyme, can be purified and separated using gel electrophoresis. The nucleic acids on the gel are then blotted onto a solid support, such as nitrocellulose. The solid support is exposed to a labelled probe and then washed to remove any unhybridized probe. Next, the duplexes containing the labeled probe are detected. Typically, the probe is labelled with a radioactive moiety.

BRIEF DESCRIPTION OF THE DRAWINGS

FIG. 1A shows the results of affinity purification and FIG. 1B shows the results of expression of the GST-fusion in *E. coli*, where M2 and M1 are molecular weight markers, and Arrows indicate the position of the main recombinant product. FIG. 1C shows the results of FACS analysis of the sera of mice that were immunized with the purified protein. FIG. 1D shows the results of bactericidal assay where a diamond (♦) shows preimmune data; a triangle (▲) shows GST control data; and a circle (●) shows data with recombinant *N. meningitidis* protein. FIG. 1E shows computer analysis showing a hydrophilicity plot (upper), an antigenic index plot (middle), and an AMPHI analysis (lower). The AMPHI program has been used to predict T-cell epitopes (Gao et al. (1989) *J. Immunol.* 143:3007; Roberts et al. (1996) *AIDS Res Hum Retrovir* 12:593; Quakyi et al. (1992) *Scad. Immunol* suppl. 11:9) and is available in the Protean Package of DNASTAR, Inc. (1228 South Park Street, Madison, Wis. 53715 USA).

FIG. 2A shows the results of affinity purification and FIG. 2B shows the results of expression of the GST-fusion in *E. coli*, where M2 and M1 are molecular weight markers, and Arrows indicate the position of the main recombinant product. FIG. 2C shows the results of FACS analysis of the sera of mice that were immunized with the purified protein. FIG. 2D shows the results of bactericidal assay where a diamond (♦) shows preimmune data; a triangle (▲) shows GST control data; and a circle (●) shows data with recombinant *N. meningitidis* protein. FIG. 2E shows plots of hydrophilicity plot (upper), an antigenic index plot (middle), and an AMPHI analysis (lower).

FIG. 3A shows the results of affinity purification and FIG. 3B shows the results of expression of the GST-fusion in *E. coli*, where M2 and M1 are molecular weight markers, and Arrows indicate the position of the main recombinant product. FIG. 3C shows the results of bactericidal assay where a diamond (♦) shows preimmune data; a triangle (▲) shows GST control data; and a circle (●) shows data with recombinant *N. meningitidis* protein. FIG. 3D shows plots of hydrophilicity plot (upper), an antigenic index plot (middle), and an AMPHI analysis (lower).

FIG. 8A-D shows an alignment comparison of amino acid sequences for ORF 40 far several strains of *Neisseria* (zn07_1, SEQ ID NO:96; zn20_1, SEQ ID NO:104; zn21_1, SEQ ID NO:105; zn06_1, SEQ ID NO:95; zn19_1, SEQ ID NO:103; zn03_1, SEQ ID NO:93; zn18_1, SEQ ID NO:102, zn11_ass, SEQ ID NO:99; zn02_1, SEQ ID NO:92; zn04_1, SEQ ID NO:94; zn16_1, SEQ ID NO:1011; zn14_1, SEQ ID NO:100; z2491, SEQ ID NO:91; zn10_1, SEQ ID NO:98; zn22_1, SEQ ID NO:106; zn23_1, SEQ ID NO:107; zn28_ass, SEQ ID NO:110; zn24_1, SEQ ID NO:108; zn25_ass, SEQ ID NO:109; zn08_1, SEQ ID NO:97; zn29_ass, SEQ ID NO:111). Dark shading indicates regions of homology, and gray shading indicates the conservation of amino acids with similar characteristics. The Figure demonstrates a high degree of conservation among the various strains, further confirming its utility as an antigen for both vaccines and diagnostics.

EXAMPLES

Figure 1A:
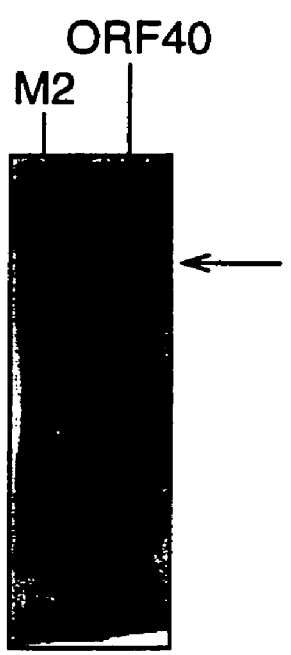
FIGS. 1A-E show biochemical data and sequence analysis pertaining to ORF 40.

The examples describe nucleic acid sequences which have been identified in *N. meningitidis*, along with their putative translation products. Not all of the nucleic acid sequences are complete ie. they encode less than the full-length wild-type protein. It is believed at present that none of the DNA sequences described herein have significant homologs in *N. gonorrhoeae*.

The examples are generally in the following format:

- a nucleotide sequence which has been identified in *N. meningitidis* (strain B)
- the putative translation product of this sequence
- a computer analysis of the translation product based on database comparisons
- a corresponding gene and protein sequence identified in *N. meningitidis* (strain A)
- a description of the characteristics of the proteins which indicates that they might be suitably antigenic
- results of biochemical analysis (expression, purification, ELISA, FACS etc.)

The examples typically include details of sequence homology between species and strains. Proteins that are similar in sequence are generally similar in both structure and function, and the homology often indicates a common evolutionary origin. Comparison with sequences of proteins of known function is widely used as a guide for the assignment of putative protein function to a new sequence and has proved particularly useful in whole-genome analyses.

Sequence comparisons were performed at NCBI (http://www.ncbi.nlm.nih.gov) using the algorithms BLAST, BLAST2, BLASTn, BLASTp, tBLASTn, BLASTx, & tBLASTx [eg. see also Altschul et al. (1997) Gapped BLAST and PSI-BLAST: a new generation of protein database search programs. *Nucleic Acids Research* 25:2289-3402]. Searches were performed against the following databases: non-redundant GenBank+EMBL+DDBJ+PDB sequences and non-redundant GenBank CDS translations+PDB+SwissProt+SP-update+PIR sequences.

Dots within nucleotide sequences (eg. position 288 in Example 12) represent nucleotides which have been arbitrarily introduced in order to maintain a reading frame. In the same way, double-underlined nucleotides were removed. Lower case letters (eg. position 589 in Example 12) represent ambiguities which arose during alignment of independent sequencing reactions (some of the nucleotide sequences in the examples are derived from combining the results of two or more experiments).

Nucleotide sequences were scanned in all six reading frames to predict the presence of hydrophobic domains using an algorithm based on the statistical studies of Esposti et al. [Critical evaluation of the hydropathy of membrane proteins (1990) *Eur J Biochem* 190:207-219]. These domains represent potential transmembrane regions or hydrophobic leader sequences.

Open reading frames were predicted from fragmented nucleotide sequences using the program ORFFINDER (NCBI).

Underlined amino acid sequences indicate possible transmembrane domains or leader sequences in the ORFs, as predicted by the PSORT algorithm (http://www.psort.nibb.ac.jp). Functional domains were also predicted using the MOTIFS program (GCG Wisconsin & PROSITE).

Various tests can be used to assess the in vivo immunogenicity of the proteins identified in the examples. For example, the proteins can be expressed recombinantly and used to screen patient sera by immunoblot. A positive reaction between the protein and patient serum indicates that the patient has previously mounted an immune response to the protein in question ie. the protein is an immunogen. This method can also be used to identify immunodominant proteins.

The recombinant protein can also be conveniently used to prepare antibodies eg. in a mouse. These can be used for direct confirmation that a protein is located on the cell-surface. Labelled antibody (eg. fluorescent labelling for FACS) can be incubated with intact bacteria and the presence of label on the bacterial surface confirms the location of the protein.

In particular, the following methods (A) to (S) were used to express, purify and biochemically characterise the proteins of the invention:

A) Chromosomal DNA Preparation

*N. meningitidis* strain 2996 was grown to exponential phase in 100 ml of GC medium, harvested by centrifugation, and resuspended in 5 ml buffer (20% Sucrose, 50 mM Tris-HCl, 50 mM EDTA, pH8). After 10 minutes incubation on ice, the bacteria were lysed by adding 10 ml lysis solution (50 mM NaCl, 1% Na-Sarkosyl, 501 g/ml Proteinase K), and the suspension was incubated at 37° C. for 2 hours. Two phenol extractions (equilibrated to pH 8) and one $ChCl_3$/isoamylalcohol (24:1) extraction were performed. DNA was precipitated by addition of 0.3M sodium acetate and 2 volumes ethanol, and was collected by centrifugation. The pellet was washed once with 70% ethanol and redissolved in 4 ml buffer (10 mM Tris-HCl, 1 mM EDTA, pH 8). The DNA concentration was measured by reading the OD at 260 nm.

B) Oligonucleotide Design

Synthetic oligonucleotide primers were designed on the basis of the coding sequence of each ORF, using (a) the meningococcus B sequence when available, or (b) the gonococcus/meningococcus A sequence, adapted to the codon preference usage of meningococcus as necessary. Any predicted signal peptides were omitted, by deducing the 5'-end amplification primer sequence immediately downstream from the predicted leader sequence.

The 5' primers included two restriction enzyme recognition sites (BamHI-NdeI, BamHI-NheI, or EcoRI-NheI, depending on the gene's own restriction pattern); the 3' primers included a XhoI restriction site. This procedure was established in order to direct the cloning of each amplification product (corresponding to each ORF) into two different expression systems: pGEX-KG (using either BamHI-XhoI or EcoRI-XhoI), and pET21b+(using either NdeI-XhoI or NheI-XhoI).

```
5'-end primer tail:  CGCGGATCCCATATG    (BamHI-NdeI)    (SEQ ID NO:134)
                     CGCGGATCCGCTAGC    (BamHI-NheI)    (SEQ ID NO:135)
                     CCGGAATTCTAGCTAGC  (EcoRI-NheI)    (SEQ ID NO:136)

3'-end primer tail:  CCCGCTCGAG         (XhoI)          (SEQ ID NO:137)
```

As well as containing the restriction enzyme recognition sequences, the primers included nucleotides which hybridised to the sequence to be amplified. The number of hybridizing nucleotides depended on the melting temperature of the whole primer, and was determined for each primer using the formulae:

$$T_m = 4(G+C) + 2(A+T) \text{ (tail excluded)}$$

$$T_m = 64.9 + 0.41 \ (\% \ GC) - 600/N \text{ (whole primer)}$$

The average melting temperature of the selected oligos were 65-70° C. for the whole oligo and 50-55° C. for the hybridising region alone.

Table I shows the forward and reverse primers used for each amplification. Oligos were synthesized by a Perkin Elmer 394 DNA/RNA Synthesizer, eluted from the columns in 2 ml NH$_4$OH, and deprotected by 5 hours incubation at 56° C. The oligos were precipitated by addition of 0.3M Na-Acetate and 2 volumes ethanol. The samples were then centrifuged and the pellets resuspended in either 100 µl or 1 ml of water. OD$_{260}$ was determined using a Perkin Elmer Lambda Bio spectrophotometer and the concentration was determined and adjusted to 2-10 pmol/µl.

C) Amplification

The standard PCR protocol was as follows: 50-200 ng of genomic DNA were used as a template in the presence of 20-40 µM of each oligo, 400-800 µM dNTPs solution, 1×PCR buffer (including 1.5 mM MgCl$_2$), 2.5 units TaqI DNA polymerase (using Perkin-Elmer AmpliTaQ, GIBCO Platinum, Pwo DNA polymerase, or Tahara Shuzo Taq polymerase).

In some cases, PCR was optimised by the addition of 10 µl DMSO or 50 µM betaine.

After a hot start (adding the polymerase during a preliminary 3 minute incubation of the whole mix at 95° C.), each sample underwent a double-step amplification: the first 5 cycles were performed using as the hybridization temperature the one of the oligos excluding the restriction enzymes tail, followed by 30 cycles performed according to the hybridization temperature of the whole length oligos. The cycles were followed by a final 10 minute extension step at 72° C.

TABLE I

PCR primers

| ORF | Primer | Sequence | Restriction sites |
|---|---|---|---|
| ORF 38 | Forward | CGCGGATCCCATATG-TCGCCGCAAAATTCCGA <SEQ ID 112> | BamHI-NdeI |
| | Reverse | CCCGCTCGAG-TTTTGCCGCGTTAAAAGC <SEQ ID 113> | XhoI |
| ORF 40 | Forward | CGCGGATCCCATATG-ACCGTGAAGACCGCC <SEQ ID 114> | BamHI-NdeI |
| | Reverse | CCCGCTCGAG-CCACTGATAACCGACAGA <SEQ ID 115> | XhoI |
| ORF 41 | Forward | CGCGGATCCCATATG-TATTTGAAACAGCTCCAAG <SEQ ID 116> | BamHI-NdeI |
| | Reverse | CCCGCTCGAG-TTCTGGGTGAATGTTA <SEQ ID 117> | XhoI |
| ORF 44 | Forward | GCGGATCCCATATG-GGCACGGACAACCCC <SEQ ID 118> | BamHI-NdeI |
| | Reverse | CCCGCTCGAGACGTGGGGAACAGTCT <SEQ ID 119> | |
| ORF 51 | Forward | GCGGATCCCATATG-AAAAATATTCAAGTAGTTGC <SEQ ID 120> | BamHI-NdeI |
| | Reverse | CCCGCTCGAG-AAGTTTGATTAAACCCG <SEQ ID 121> | XhoI |
| ORF 52 | Forward | CGCGGATCCCATATG-TGCCAACCGCAATCCG <SEQ ID 122> | BamHI-NdeI |
| | Reverse | CCCGCTCGAG-TTTTTCCAGCTCCGGCA <SEQ ID 123> | XhoI |
| ORF 56 | Forward | GCGGATCCCATATG-GTTATCGGAATATTACTCG <SEQ ID 124> | BamHI-NdeI |
| | Reverse | CCCGCTCGAG-GGCTGCAGAAGCTGG <SEQ ID 125> | XhoI |
| ORF 69 | Forward | CGCGGATCCCATATG-CGGACGTGGTTGGTTTT <SEQ ID 126> | BamHI-NdeI |
| | Reverse | CCCGCTCGAG-ATATCTTCCGTTTTTTCAC <SEQ ID 127> | XhoI |
| ORF 82 | Forward | CGCGGATCCGCTAGC0GTAAATTTATTATTTTTAGAA <SEQ ID 128> | BamHI-NheI |
| | Reverse | CCCGCTCGAG-TTCCAACTCATTGAAGTA <SEQ ID 129> | XhoI |
| ORF 114 | Forward | CGCGGATCCCATATG-AATAAAGGTTTACATGCAT <SEQ ID 130> | BamHI-NheI |
| | Reverse | CCCGCTCGAG-AATCGCTGCACCGGCT <SEQ ID 131> | XhoI |
| ORF 124 | Forward | CGCGGATCCCATATG-ACTGCCTTTTCGACA <SEQ ID 132> | BamHI-NheI |
| | Reverse | CCCGCTCGAG-GCGTGAAGCGTCAGGA <SEQ ID 133> | XhoI |

The standard cycles were as follows:

|  | Denaturation | Hybridisation | Elongation |
|---|---|---|---|
| First 5 cycles | 30 seconds 95° C. | 30 seconds 50-55° C. | 30-60 seconds 72° C. |
| Last 30 cycles | 30 seconds 95° C. | 30 seconds 65-70° C. | 30-60 seconds 72° C. |

The elongation time varied according to the length of the ORF to be amplified.

The amplifications were performed using either a 9600 or a 2400 Perkin Elmer GeneAmp PCR System. To check the results, 1/10 of the amplification volume was loaded onto a 1-1.5% agarose gel and the size of each amplified fragment compared with a DNA molecular weight marker.

The amplified DNA was either loaded directly on a 1% agarose gel or first precipitated with ethanol and resuspended in a suitable volume to be loaded on a 1% agarose gel. The DNA fragment corresponding to the right size band was then eluted and purified from gel, using the Qiagen Gel Extraction Kit, following the instructions of the manufacturer. The final volume of the DNA fragment was 30 μl or 50 μl of either water or 10 mM Tris, pH 8.5.

D) Digestion of PCR Fragments

The purified DNA corresponding to the amplified fragment was split into 2 aliquots and double-digested with:

NdeI/XhoI or NheI/XhoI for cloning into pET-21b+ and further expression of the protein as a C-terminus His-tag fusion BamHI/XhoI or EcoRI/XhoI for cloning into pGEX-KG and further expression of the protein as N-terminus GST fusion.

EcoRI/PstI, EcoRI/SalI, SalI/PstI for cloning into pGex-His and further expression of the protein as N-terminus His-tag fusion Each purified DNA fragment was incubated (37° C. for 3 hours to overnight) with 20 units of each restriction enzyme (New England Biolabs) in a either 30 or 40 μl final volume in the presence of the appropriate buffer. The digestion product was then purified using the QIAquick PCR purification kit, following the manufacturer's instructions, and eluted in a final volume of 30 or 50 μl of either water or 10 mM Tris-HCl, pH 8.5. The final DNA concentration was determined by 1% agarose gel electrophoresis in the presence of titrated molecular weight marker.

E) Digestion of the Cloning Vectors (pET22B, pGEX-KG, pTRC-His A, and pGex-His)

10 μg plasmid was double-digested with 50 units of each restriction enzyme in 200 μl reaction volume in the presence of appropriate buffer by overnight incubation at 37° C. After loading the whole digestion on a 1% agarose gel, the band corresponding to the digested vector was purified from the gel using the Qiagen QIAquick Gel Extraction Kit and the DNA was eluted in 50 μl of 10 mM Tris-HCl, pH 8.5. The DNA concentration was evaluated by measuring $OD_{260}$ of the sample, and adjusted to 50 μg/μl. 1 μl of plasmid was used for each cloning procedure.

The vector pGEX-His is a modified pGEX-2T vector carrying a region encoding six histidine residues upstream to the thrombin cleavage site and containing the multiple cloning site of the vector pTRC99 (Pharmacia).

F) Cloning

The fragments corresponding to each ORF, previously digested and purified, were ligated in both pET22b and pGEX-KG. In a final volume of 201, a molar ratio of 3:1 fragment/vector was ligated using 0.5 μl of NEB T4 DNA ligase (400 units/μl), in the presence of the buffer supplied by the manufacturer. The reaction was incubated at room temperature for 3 hours. In some experiments, ligation was performed using the Boehringer "Rapid Ligation Kit", following the manufacturer's instructions.

In order to introduce the recombinant plasmid in a suitable strain, 100 μl E. coli DH5 competent cells were incubated with the ligase reaction solution for 40 minutes on ice, then at 37° C. for 3 minutes, then, after adding 800 μl LB broth, again at 37° C. for 20 minutes. The cells were then centrifuged at maximum speed in an Eppendorf microfuge and resuspended in approximately 200 μl of the supernatant. The suspension was then plated on LB ampicillin (100 mg/ml).

The screening of the recombinant clones was performed by growing 5 randomly-chosen colonies overnight at 37° C. in either 2 ml (pGEX or pTC clones) or 5 ml (pET clones) LB broth+100 μg/ml ampicillin. The cells were then pelletted and the DNA extracted using the Qiagen QIAprep Spin Miniprep Kit, following the manufacturer's instructions, to a final volume of 30 μl. 5 μl of each individual miniprep (approximately 1 g) were digested with either NdeI/XhoI or BamHI/XhoI and the whole digestion loaded onto a 1-1.5% agarose gel (depending on the expected insert size), in parallel with the molecular weight marker (1 Kb DNA Ladder, GIBCO). The screening of the positive clones was made on the base of the correct insert size.

G) Expression

Each ORF cloned into the expression vector was transformed into the strain suitable for expression of the recombinant protein product. 1 μl of each construct was used to transform 30 μl of E. coli BL21 (pGEX vector), E. coli TOP 10 (pTRC vector) or E. coli BL21-DE3 (pET vector), as described above. In the case of the pGEX-His vector, the same E. coli strain (W3110) was used for initial cloning and expression. Single recombinant colonies were inoculated into 2 ml LB+Amp (100 μg/ml), incubated at 37° C. overnight, then diluted 1:30 in 20 ml of LB+Amp (100 μg/ml) in 100 ml flasks, making sure that the $OD_{600}$ ranged between 0.1 and 0.15. The flasks were incubated at 30° C. into gyratory water bath shakers until OD indicated exponential growth suitable for induction of expression (0.4-0.8 OD for pET and pTRC vectors; 0.8-1 OD for pGEX and pGEX-His vectors). For the pET, pTRC and pGEX-His vectors, the protein expression was induced by addition of 1 mM IPTG, whereas in the case of pGEX system the final concentration of IPTG was 0.2 mM. After 3 hours incubation at 30° C., the final concentration of the sample was checked by OD. In order to check expression, 1 ml of each sample was removed, centrifuged in a microfuge, the pellet resuspended in PBS, and analysed by 12% SDS-PAGE with Coomassie Blue staining. The whole sample was centrifuged at 6000 g and the pellet resuspended in PBS for further use.

H) GST-Fusion Proteins Large-Scale Purification.

A single colony was grown overnight at 37° C. on LB+Amp agar plate. The bacteria were inoculated into 20 ml of LB+Amp liquid culture in a water bath shaker and grown overnight. Bacteria were diluted 1:30 into 600 ml of fresh medium and allowed to grow at the optimal temperature (20-37° C.) to $OD_{550}$ 0.8-1. Protein expression was induced with 0.2 mM IPTG followed by three hours incubation. The culture was centrifuged at 8000 rpm at 4° C. The supernatant was discarded and the bacterial pellet was resuspended in 7.5 ml cold PBS. The cells were disrupted by sonication on ice for 30 sec at 40 W using a Branson sonifier B-15, frozen and thawed twice and centrifuged again. The supernatant was collected and mixed with 150 µl Glutatione-Sepharose 4B resin (Pharmacia) (previously washed with PBS) and incubated at room temperature for 30 minutes. The sample was centrifuged at 700 g for 5 minutes at 4° C. The resin was washed twice with 100 ml cold PBS for 10 minutes, resuspended in 1 ml cold PBS, and loaded on a disposable column. The resin was washed twice with 2 ml cold PBS until the flow-through reached $OD_{280}$ of 0.02-0.06. The GST-fusion protein was eluted by addition of 700 µl cold Glutathione elution buffer (10 mM reduced glutathione, 50 mM Tris-HCl) and fractions collected until the $OD_{280}$ was 0.1. 21 µl of each fraction were loaded on a 12% SDS gel using either Biorad SDS-PAGE Molecular weight standard broad range (M1) (200, 116.25, 97.4, 66.2, 45, 31, 21.5, 14.4, 6.5 kDa) or Amersham Rainbow Marker (M2) (220, 66, 46, 30, 21.5, 14.3 kDa) as standards. As the MW of GST is 26 kDa, this value must be added to the MW of each GST-fusion protein.

I) His-Fusion Solubility Analysis

To analyse the solubility of the His-fusion expression products, pellets of 3 ml cultures were resuspended in buffer M1 [500 µl PBS pH 7.2]. 25 µl lysozyme (10 mg/ml) was added and the bacteria were incubated for 15 min at 4° C. The pellets were sonicated for 30 sec at 40 W using a Branson sonifier B-15, frozen and thawed twice and then separated again into pellet and supernatant by a centrifugation step. The supernatant was collected and the pellet was resuspended in buffer M2 [8M urea, 0.5M NaCl, 20 mM imidazole and 0.1M $NaH_2PO_4$] and incubated for 3 to 4 hours at 4° C. After centrifugation, the supernatant was collected and the pellet was resuspended in buffer M3 [6M guanidinium-HCl, 0.5M NaCl, 20 mM imidazole and 0.1M $NaH_2PO_4$] overnight at 4° C. The supernatants from all steps were analysed by SDS-PAGE.

J) His-Fusion Large-Scale Purification.

A single colony was grown overnight at 37° C. on a LB+Amp agar plate. The bacteria were inoculated into 20 ml of LB+Amp liquid culture and incubated overnight in a water bath shaker. Bacteria were diluted 1:30 into 600 ml fresh medium and allowed to grow at the optimal temperature (20-37° C.) to $OD_{550}$ 0.6-0.8. Protein expression was induced by addition of 1 mM IPTG and the culture further incubated for three hours. The culture was centrifuged at 8000 rpm at 4° C., the supernatant was discarded and the bacterial pellet was resuspended in 7.5 ml of either (i) cold buffer A (300 mM NaCl, 50 mM phosphate buffer, 10 mM imidazole, pH 8) for soluble proteins or (ii) buffer B (urea 8M, 10 mM Tris-HCl, 100 mM phosphate buffer, pH 8.8) for insoluble proteins.

The cells were disrupted by sonication on ice for 30 sec at 40 W using a Branson sonifier B-15, frozen and thawed two times and centrifuged again.

For insoluble proteins, the supernatant was stored at −20° C., while the pellets were resuspended in 2 ml buffer C (6M guanidine hydrochloride, 100 mM phosphate buffer, 10 mM Tris-HCl, pH 7.5) and treated in a homogenizer for 10 cycles. The product was centrifuged at 13000 rpm for 40 minutes.

Supernatants were collected and mixed with 150 µl $Ni^{2+}$-resin (Pharmacia) (previously washed with either buffer A or buffer B, as appropriate) and incubated at room temperature with gentle agitation for 30 minutes. The sample was centrifuged at 700 g for 5 minutes at 4° C. The resin was washed twice with 10 ml buffer A or B for 10 minutes, resuspended in 1 ml buffer A or B and loaded on a disposable column. The resin was washed at either (i) 4° C. with 2 ml cold buffer A or (ii) room temperature with 2 ml buffer B, until the flow-through reached $OD_{280}$ of 0.02-0.06.

The resin was washed with either (i) 2 ml cold 20 mM imidazole buffer (300 mM NaCl, 50 mM phosphate buffer, 20 mM imidazole, pH 8) or (ii) buffer D (urea 8M, 10 mM Tris-HCl, 100 mM phosphate buffer, pH 6.3) until the flow-through reached the $O.D_{280}$ of 0.02-0.06. The His-fusion protein was eluted by addition of 700 µl of either (i) cold elution buffer A (300 mM NaCl, 50 mM phosphate buffer, 250 mM imidazole, pH 8) or (ii) elution buffer B (urea 8M, 10 mM Tris-HCl, 100 mM phosphate buffer, pH 4.5) and fractions collected until the $O.D_{280}$ was 0.1. 21 µl of each fraction were loaded on a 12% SDS gel.

K) His-Fusion Proteins Renaturation

10% glycerol was added to the denatured proteins. The proteins were then diluted to 20 µg/ml using dialysis buffer I (10% glycerol, 0.5M arginine, 50 mM phosphate buffer, 5 mM reduced glutathione, 0.5 mM oxidised glutathione, 2M urea, pH 8.8) and dialysed against the same buffer at 4° C. for 12-14 hours. The protein was further dialysed against dialysis buffer II (10% glycerol, 0.5M arginine, 50 mM phosphate buffer, 5 mM reduced glutathione, 0.5 mM oxidised glutathione, pH 8.8) for 12-14 hours at 4° C. Protein concentration was evaluated using the formula:

Protein (mg/ml)=$(1.55 \times OD_{280}) - (0.76 \times OD_{260})$

L) His-Fusion Large-Scale Purification 500 ml of bacterial cultures were induced and the fusion proteins were obtained soluble in buffer M1, M2 or M3 using the procedure described above. The crude extract of the bacteria was loaded onto a Ni-NTA superflow column (Qiagen) equilibrated with buffer M1, M2 or M3 depending on the solubilization buffer of the fusion proteins. Unbound material was eluted by washing the column with the same buffer. The specific protein was eluted with the corresponding buffer containing 500 mM imidazole and dialysed against the corresponding buffer without imidazole. After each run the columns were sanitized by washing with at least two column volumes of 0.5 M sodium hydroxide and reequilibrated before the next use.

M) Mice Immunisations

20 µg of each purified protein were used to immunise mice intraperitoneally. In the case of ORF 44, CD1 mice were immunised with $Al(OH)_3$ as adjuvant on days 1, 21 and 42, and immune response was monitored in samples taken on day 56. For ORF 40, CD1 mice were immunised using Freund's adjuvant, rather than $Al(OH)_3$, and the same immunisation protocol was used, except that the immune response was measured on day 42, rather than 56. Similarly, for ORF 38, CD1 mice were immunised with Freund's adjuvant, but the immune response was measured on day 49.

N) ELISA Assay (Sera Analysis)

The acapsulated MenB M7 strain was plated on chocolate agar plates and incubated overnight at 37° C. Bacterial colonies were collected from the agar plates using a sterile dracon swab and inoculated into 7 ml of Mueller-Hinton Broth (Difco) containing 0.25% Glucose. Bacterial growth was monitored every 30 minutes by following $OD_{620}$. The bacteria were let to grow until the OD reached the value of 0.3-0.4. The culture was centrifuged for 10 minutes at 10000 rpm. The supernatant was discarded and bacteria were washed once with PBS, resuspended in PBS containing 0.025% formaldehyde, and incubated for 2 hours at room temperature and then overnight at 4° C. with stirring. 100 µl bacterial cells were added to each well of a 96 well Greiner plate and incubated overnight at 4° C. The wells were then washed three times with PBT washing buffer (0.1% Tween-20 in PBS). 200 µl of saturation buffer (2.7% Polyvinylpyrrolidone 10 in water) was added to each well and the plates incubated for 2 hours at 37° C. Wells were washed three times with PBT. 200 µl of diluted sera (Dilution buffer: 1% BSA, 0.1% Tween-20, 0.1% NaN$_3$ in PBS) were added to each well and the plates incubated for 90 minutes at 37° C. Wells were washed three times with PBT. 100 µl of HRP-conjugated rabbit anti-mouse (Dako) serum diluted 1:2000 in dilution buffer were added to each well and the plates were incubated for 90 minutes at 37° C. Wells were washed three times with PBT buffer. 100 µl of substrate buffer for HRP (25 ml of citrate buffer pH5, 10 mg of O-phenildiamine and 10 µl of H$_2$O) were added to each well and the plates were left at room temperature for 20 minutes. 100 µl H$_2$SO$_4$ was added to each well and OD$_{490}$ was followed. The ELISA was considered positive when OD$_{490}$ was 2.5 times the respective pre-immune sera.

O) FACScan Bacteria Binding Assay Procedure.

The acapsulated MenB M7 strain was plated on chocolate agar plates and incubated overnight at 37° C. Bacterial colonies were collected from the agar plates using a sterile dracon swab and inoculated into 4 tubes containing 8 ml each Mueller-Hinton Broth (Difco) containing 0.25% glucose. Bacterial growth was monitored every 30 minutes by following OD$_{620}$. The bacteria were let to grow until the OD reached the value of 0.35-0.5. The culture was centrifuged for 10 minutes at 4000 rpm. The supernatant was discarded and the pellet was resuspended in blocking buffer (1% BSA, 0.4% NaN$_3$) and centrifuged for 5 minutes at 4000 rpm. Cells were resuspended in blocking buffer to reach OD$_{620}$ of 0.07. 100 µl bacterial cells were added to each well of a Costar 96 well plate. 100 µl of diluted (1:200) sera (in blocking buffer) were added to each well and plates incubated for 2 hours at 4° C. Cells were centrifuged for 5 minutes at 4000 rpm, the supernatant aspirated and cells washed by addition of 200 µl/well of blocking buffer in each well. 100 µl of R-Phicoerytrin conjugated F(ab)$_2$ goat anti-mouse, diluted 1:100, was added to each well and plates incubated for 1 hour at 4° C. Cells were spun down by centrifugation at 4000 rpm for 5 minutes and washed by addition of 200 µl/well of blocking buffer. The supernatant was aspirated and cells resuspended in 200 µl/well of PBS, 0.25% formaldehyde. Samples were transferred to FACScan tubes and read. The condition for FACScan setting were: FL1 on, FL2 and FL3 off; FSC-H threshold: 92; FSC PMT Voltage: E 02; SSC PMT: 474; Amp. Gains 7.1; FL-2 PMT: 539; compensation values: 0.

P) OMV Preparations

Bacteria were grown overnight on 5 GC plates, harvested with a loop and resuspended in 10 ml 20 mM Tris-HCl. Heat inactivation was performed at 56° C. for 30 minutes and the bacteria disrupted by sonication for 10 minutes on ice (50% duty cycle, 50% output). Unbroken cells were removed by centrifugation at 5000 g for 10 minutes and the total cell envelope fraction recovered by centrifugation at 50000 g at 4° C. for 75 minutes. To extract cytoplasmic membrane proteins from the crude outer membranes, the whole fraction was resuspended in 2% sarkosyl (Sigma) and incubated at room temperature for 20 minutes. The suspension was centrifuged at 10000 g for 10 minutes to remove aggregates, and the supernatant further ultracentrifuged at 50000 g for 75 minutes to pellet the outer membranes. The outer membranes were resuspended in 10 mM Tris-HCl, pH8 and the protein concentration measured by the Bio-Rad Protein assay, using BSA as a standard.

Q) Whole Extracts Preparation

Bacteria were grown overnight on a GC plate, harvested with a loop and resuspended in 1 ml of 20 mM Tris-HCl. Heat inactivation was performed at 56° C. for 30 minutes.

R) Western Blotting

Purified proteins (500 ng/lane), outer membrane vesicles (5 µg) and total cell extracts (25 µg) derived from MenB strain 2996 were loaded on 15% SDS-PAGE and transferred to a nitrocellulose membrane. The transfer was performed for 2 hours at 150 mA at 4° C., in transferring buffer (0.3% Tris base, 1.44% glycine, 20% methanol). The membrane was saturated by overnight incubation at 4° C. in saturation buffer (10% skimmed milk, 0.1% Triton X100 in PBS). The membrane was washed twice with washing buffer (3% skimmed milk, 0.1% Triton X100 in PBS) and incubated for 2 hours at 37° C. with mice sera diluted 1:200 in washing buffer. The membrane was washed twice and incubated for 90 minutes with a 1:2000 dilution of horseradish peroxidase labelled anti-mouse Ig. The membrane was washed twice with 0.1% Triton X100 in PBS and developed with the Opti-4 CN Substrate Kit (Bio-Rad). The reaction was stopped by adding water.

S) Bactericidal Assay

MC58 strain was grown overnight at 37° C. on chocolate agar plates. 5-7 colonies were collected and used to inoculate 7 ml Mueller-Hinton broth. The suspension was incubated at 37° C. on a nutator and let to grow until OD$_{620}$ was 0.5-0.8. The culture was aliquoted into sterile 1.5 ml Eppendorf tubes and centrifuged for 20 minutes at maximum speed in a microfuge. The pellet was washed once in Gey's buffer (Gibco) and resuspended in the same buffer to an OD$_{620}$ of 0.5, diluted 1:20000 in Gey's buffer and stored at 25° C.

50 µl of Gey's buffer/1% BSA was added to each well of a 96-well tissue culture plate. 25 µl of diluted mice sera (1:100 in Gey's buffer/0.2% BSA) were added to each well and the plate incubated at 4° C. 25 µl of the previously described bacterial suspension were added to each well. 25 µl of either heat-inactivated (56° C. waterbath for 30 minutes) or normal baby rabbit complement were added to each well. Immediately after the addition of the baby rabbit complement, 22 µl of each sample/well were plated on Mueller-Hinton agar plates (time 0). The 96-well plate was incubated for 1 hour at 37° C. with rotation and then 22 µl of each sample/well were plated on Mueller-Hinton agar plates (time 1). After overnight incubation the colonies corresponding to time 0 and time 1 hour were counted.

Table II gives a summary of the cloning, expression and purification results.

TABLE II

Cloning, expression and purification

| ORF | PCR/cloning | His-fusion expression | GST-fusion expression | Purification |
|---|---|---|---|---|
| orf 38 | + | + | + | His-fusion |
| orf 40 | + | + | + | His-fusion |
| orf 41 | + | n.d. | n.d. | |
| orf 44 | + | + | + | His-fusion |
| orf 51 | + | n.d. | n.d. | |
| orf 52 | + | n.d. | + | GST-fusion |
| orf 56 | + | n.d. | n.d. | |
| orf 69 | + | n.d. | n.d. | |
| orf 82 | + | n.d. | n.d. | |
| orf 114 | + | n.d. | + | GST-fusion |
| orf 124 | + | n.d. | n.d. | |

Example 1

The following partial DNA sequence was identified in *N. meningitidis* <SEQ ID 1>:

```
  1   ..ACACTGTTGT TTGCAACGGT TCAGGCAAGT GCTAACCAAT GAAGAGCAAG
 51     AAGAAGATTT ATATTTAGAC CCCGTACAAC GCACTGTTGC CGTGTTGATA
101     GTCAATTCCG ATAAAGAAGG CACGGGAGAA AAAGAAAAAG TAGAAGAAAA
151     TTCAGATTGG GCAGTATATT TCAACGAGAA AGGAGTACTA ACAGCCAGAG
201     AAATCACCyT CAAAGCCGGC GACAACCTGA AAATCAAACA AAACGGCACA
251     AACTTCACCT ACTCGCTGAA AAAAGACCTC AcAGATCTGA CCAGTGTTGG
301     AACTGAAAAA TTATCGTTTA CCGCAAACGG CAATAAAGTC AACATCACAA
351     GCGACACCAA AGGCTTGAAT TTTGCGAAAG AAACGGCTGG sACGAACGgC
401     GACACCACGG TTCATCTGAA CGGTATTGGT TCGACTTTGA CCGATACGCT
451     GCTGAATACC GGAGCGACCA CAAACGTAAC CAACGACAAC GTTACCGATG
501     ACGAGAAAAA ACGTGCGGCA AGCGTTAAAG ACGTATTAAA CGCTGGCTGG
551     AACATTAAAG GCGTTAAACC CGGTACAACA GCTTCCGATA ACGTTGATTT
601     CGTCCGCACT TACGACACAG TCGAGTTCTT GAGCGCAGAT ACGAAAACAA
651     CGACTGTTAA TGTGGAAAGC AAAGACAACG GCAAGAAAAC CGAAGTTAAA
701     ATCGGTGCGA AGACTTCTGT TATTAAAGAA AAAGAC...
```

This corresponds to the amino acid sequence <SEQ ID 2; ORF40>:

```
  1   ..TLLFATVQAS ANQEEQEEDL YLDPVQRTVA VLIVNSDKEG TGEKEKVEEN
 51     SDWAVYFNEK GVLTAREITX KAGDNLKIKQ NGTNFTYSLK KDLTDLTSVG
101     TEKLSFSANG NKVNITSDTK GLNFAKETAG TNGDTTVHLN GIGSTLTDTL
151     LNTGATTNVT NDNVTDDEKK RAASVKDVLN AGWWIKGVKP GTTASDNVDF
201     VRTYDTVEFL SADTKTTTVN VESKDNGKKT EVKIGAKTSV IKEKE...
```

Further work revealed the complete DNA sequence <SEQ ID 3>:

```
  1 ATGAACAAAA TATACCGCAT CATTTGGAAT AGTGCCCTCA ATGCCTGGGT
 51 CGTCGTATCC GAGCTCACAC GCAACCACAC CAAACGCGCC TCCGCAACCG
101 TGAAGACCGC CGTATTGGCG ACACTGTTGT TTGCAACGGT TCAGGCAAGT
151 GCTAACAATG AAGAGCAAGA AGAAGATTTA TATTTAGACC CCGTACAACG
201 CACTGTTGCC GTGTTGATAG TCAATTCCGA TAAAGAAGGC ACGGGAGAAA
251 AAGAAAAAGT AGAAGAAAAT TCAGATTGGG CAGTATATTT CAACGAGAAA
301 GGAGTACTAA CAGCCAGAGA ATCACCCTC AAAGCCGGCG ACAACCTGAA
351 AATCAAACAA AACGGCACAA ACTTCACCTA CTCGCTGAAA AAAGACCTCA
401 CAGATCTGAC CAGTGTTGGA ACTGAAAAAT TATCGTTTAG CGCAAACGGC
451 AATAAAGTCA ACATCACAAG CGACACCAAA GGCTTGAATT TTGCGAAAGA
501 AACGGCTGGG ACGAACGGCG ACACCACGGT TCATCTGAAC GGTATTGGTT
```

```
 551 CGACTTTGAC CGATACGCTG CTGAATACCG GAGCGACCAC AAACGTAACC
 601 AACGACAACG TTACCGATGA CGAGAAAAAA CGTGCGGCAA GCGTTAAAGA
 651 CGTATTAAAC GCTGGCTGGA ACATTAAAGG CGTTAAACCC GGTACAACAG
 701 CTTCCGATAA CGTTGATTTC GTCCGCACTT ACGACACAGT CGAGTTCTTG
 751 AGCGCAGATA CGAAAACAAC GACTGTTAAT GTGGAAAGCA AGACAACGG
 801 CAAGAAAACC GAAGTTAAAA TCGGTGCGAA GACTTCTGTT ATTAAAGAAA
 851 AAGACGGTAA GTTGGTTACT GGTAAAGACA AAGGCGAGAA TGGTTCTTCT
 901 ACAGACGAAG GCGAAGGCTT AGTGACTGCA AAAGAAGTGA TTGATGCAGT
 951 AAACAAGGCT GGTTGGAGAA TGAAAACAAC AACCGCTAAT GGTCAAACAG
1001 GTCAAGCTGA CAAGTTTGAA ACCGTTACAT CAGGCACAAA TGTAACCTTT
1051 GCTAGTGGTA AAGGTACAAC TGCGACTGTA AGTAAAGATG ATCAAGGCAA
1101 CATCACTGTT ATGTATGATG TAAATGTCGG CGATGCCCTA AACGTCAATC
1151 AGCTGCAAAA CAGCGGTTGG AATTTGGATT CCAAAGCGGT TGCAGGTTCT
1201 TCGGGCAAAG TCATCAGCGG CAATGTTTCG CCGAGCAAGG GAAAGATGGA
1251 TGAAACCGTC AACATTAATG CCGGCAACAA CATCGAGATT ACCCGCAACG
1301 GTAAAAATAT CGACATCGCC ACTTCGATGA CCCCGCAGTT TTCCAGCGTT
1351 TCGCTCGGCG CGGGGGCGGA TGCGCCCACT TTGAGCGTGG ATGGGACGC
1401 ATTGAATGTC GGCAGCAAGA AGGACAACAA ACCCGTCCGC ATTACCAATG
1451 TCGCCCCGGG CGTTAAAGAG GGGGATGTTA CAAACGTCGC ACAACTTAAA
1501 GGCGTGGCGC AAAACTTGAA CAACCGCATC GACAATGTGG ACGGCAACGC
1551 GCGTGCGGGC ATCGCCCAAG CGATTGCAAC CGCAGGTCTG GTTCAGGCGT
1601 ATTTGCCCGG CAAGAGTATG ATGGCGATCG GCGGCGGCAC TTATCGCGGC
1651 GAAGCCGGTT ACGCCATCGG CTACTCCAGT ATTTCCGACG GCGGAAATTG
1701 GATTATCAAA GGCACGGCTT CCGGCAATTC GCGCGGCCAT TTCGGTGCTT
1751 CCGCATCTGT CGGTTATCAG TGGTAA
```

This corresponds to the amino acid sequence <SEQ ID 4; ORF40-1>:

```
  1 MNKIYRIIWN SALNAWVVVS ELTRNHTKRA SATVKTAVLA TLLFATVQAS
 51 ANNEEQEEDL YLDPVQRTVA VLIVNSDKEG TGEKEKVEEN SDWAVYFNEK
101 GVLTAREITL KAGDNLKIKQ NGTNFTYSLK KDLTDLTSVG TEKLSFSANG
151 NKVNITSDTK GLNFAKETAG TNGDTTVHLN GIGSTLTDTL LNTGATTNVT
201 NDNVTDDEKK RAASVKDVLN AGWNIKGVKP GTTASDNVDF VRTYDTVEFL
251 SADTKTTTVN VESKDNGKKT EVKIGAXTSV IKEKDGKLVT GKDKGENGSS
301 TDEGEGLVTA KEVIDAVNKA GWRMKTTTAN GQTGQADKFE TVTSGTNVTF
351 ASGKGTTATV SKDDQGbUTV MYDVNVGDAL NVNQLQNSGW NLDSKAVAGS
401 SGKVISGNVS PSKGKMDETV NINAGNNIEI TRNGKNIDIA TSMTPQFSSV
451 SLGAGADAPT LSVDGDALNV GSKKDNKPVR ITNVAPGVKE GDVTNVAQLK
```

-continued

```
501  GVAQNLNNRI DNVDGNARAG IAQAIATAGL VQAYLPGKSM MAIGGGTYRG
551  EAGYAIGYSS ISDGGNWIIK GTASGNSRGH FGASASVGYQ W*
```

Further work identified the corresponding gene in strain A of *N. meningitidis* <SEQ ID 5>:

```
   1 ATGAACAAAA TATACCGCAT CATTTGGAAT AGTGCCCTCA ATGCCTGNGT
  51 CGCCGTATCC GAGCTCACAC GCAACCACAC CAAACGCGCC TCCGCAACCG
 101 TGAAGACCGC CGTATTGGCG ACACTGTTGT TTGCAACGGT TCAGGCGAAT
 151 GCTACCGATG AAGATGAAGA AGAAGAGTTA GAATCCGTAC AACGCTCTGT
 201 CGTAGGGAGC ATTCAAGCCA GTATGGAAGG CAGCGGCGAA TTGGAAACGA
 251 TATCATTATC AATGACTAAC GACAGCAAGG AATTTGTAGA CCCATACATA
 301 GTAGTTACCC TCAAAGCCGG CGACAACCTG AAAATCAAAC AAAACACCAA
 351 TGAAAACACC AATGCCAGTA GCTTCACCTA CTCGCTGAAA AAAGACCTCA
 401 CAGGCCTGAT CAATGTTGAN ACTGAAAAAT TATCGTTTGG CGCAAACGGC
 451 AAGAAAGTCA ACATCATAAG CGACACCAAA GGCTTGAATT TCGCGAAAGA
 501 AACGGCTGGG ACGAACGGCG ACACCACGGT TCATCTGAAC GGTATCGGTT
 551 CGACTTTGAC CGATACGCTT GCGGGTTCTT CTGCTTCTCA CGTTGATGCG
 601 GGTAACCNAA GTACACATTA CACTCGTGCA GCAAGTATTA AGGATGTGTT
 651 GAATGCGGGT TGGAATATTA AGGGTGTTAA ANNNGGCTCA ACAACTGGTC
 701 AATCAGAAAA TGTCGATTTC GTCCGCACTT ACGACACAGT CGAGTTCTTG
 751 AGCGCAGATA CGNAAACAAC GACNGTTAAT GTGGAAAGCA AAGACAACGG
 801 CAAGAGAACC GAAGTTAAAA TCGGTGCGAA GACTTCTGTT ATTAAAGAAA
 851 AAGACGGTAA GTTGGTTACT GGTAAAGGCA AAGGCGAGAA TGGTTCTTCT
 901 ACAGACGAAG GCGAAGGCTT AGTGACTGCA AAAGAAGTGA TTGATGCAGT
 951 AAACAAGGCT GGTTGGAGAA TGAAAACAAC AACCGCTAAT GGTCAAACAG
1001 GTCAAGCTGA CAAGTTTGAA ACCGTTACAT CAGGCACAAA TGTAACCTTT
1051 GCTAGTGGTA AAGGTACAAC TGCGACTGTA AGTAAAGATG ATCAAGGCAA
1101 CATCACTGTT ATGTATGATG TAAATGTCGG CGATGCCCTA AACGTCAATC
1151 AGCTGCAAAA CAGCGGTTGG AATTTGGATT CCAAAGCGGT TGCAGGTTCT
1201 TCGGGCAAAG TCATCAGCGG CAATGTTTCG CCGAGCAAGG GAAAGATGGA
1251 TGAAACCGTC AACATTAATG CCGGCAACAA CATCGAGATT AGCCGCAACG
1301 GTAAAAATAT CGACATCGCC ACTTCGATGG CGCCGCAGTT TTCCAGCGTT
1351 TCGCTCGGCG CGGGGGCAGA TGCSCCCACT TTAAGCGTGG ATGACGAGGG
1401 CGCGTTGAAT GTCGGCAGCA AGGATGCCAA CAAACCCGTC CGCATTACCA
1451 ATGTCGCCCC GGGCGTTAAA GANGGGGATG TTACAAACGT CNCACAACTT
1501 AAAGGCGTGG CGCAAAACTT GAACAACCGC ATCGACAATG TGGACGGCAA
1551 CGCGCGTGCN GGCATCGCCC AAGCGATTGC AACCGCAGGT CTGGTTCAGG
1601 CGTATCTGCC CGGCAAGAGT ATGATGGCGA TCGGCGGCGG CACTTATCGC
1651 GGCGAAGCCG GTTACGCCAT CGGCTACTCC AGTATTTCCG ACGGCGGAAA
```

```
1701 TTGGATTATC AAAGGCACGG CTTCCGGCAA TTCGCGCGGC CATTTCGGTG

1751 CTTCCGCATC TGTCGGTTAT CAGTGGTAA
```

This encodes a protein having amino acid sequence <SEQ ID 6; ORF40a>:

```
  1 MNKIYRIIWN SALNAXVAVS ELTRNHTKRA SATVKTAVLA TLLFATVQAN

51 ATDEDEEEEL ESVQRSVVGS IQASMEGSGE LETISLSMTN DSKEFVDPYI

101 VVTLKAGDNL KIKQNTNENT NASSFTYSLK KDLTGLINVX TEKLSFGANG

151 KKVNIISDTK GLNFAKETAG TNGDTTVHLN GIGSTLTDTL AGSSASHVDA

201 GNXSTHYTRA ASIKDVLNAG WNIKGVKXGS TTGQSEWVDF VRTYDTVEFL

251 SADTXTTTVN VESKDNGKRT EVKIGAKTSV IKEKDGKLVT GKGKGENGSS

301 TDEGEGLVTA KEVIDAVNKA GWRMKTTTAN GQTGQADKFE TVTSGTWVTF

351 ASGKGTTATV SKDDQGNITV MYDVNVGDAL NVNQLQNSGW NLDSKAVAGS

401 SGKVISGNVS PSKGKMDETV NINAGNNIEI SRNGKNIDIA TSMAPQFSSV

451 SLGAGADAPT LSVDDEGALN VGSKDANKPV RITNVAPGVK XGDVTNVXQL

501 KGVAQNLNNR IDNVDGNARA GIAQAIATAG LVQAYLPGKS MMAIGGGTYR

551 GEAGYAIGYS SISDGGNWII KGTASGNSRG HFGASASVGY QW*
```

The originally-identified partial strain B sequence (ORF40 (SEQ ID NO:2)) shows 65.7% identity over a 254aa overlap with ORF40a (SEQ ID NO:138):

```
                                   10         20         30
orf40.pep                          TLLFATVQASANQEEQEEDLYLDPVQRTVA
                                   ||||||||||:|::|::||:|  :  |||:|
orf40a      SALNAXVAVSELTRNHTKRASATVKTAVLATLLFATVQANATDEDEEEEL--ESVQRSV-
                      20        30        50        50        60

40        50        60        70        80
orf40.pep   VLIVNSDKEGTGEKEKVEEN-SDWAVYFNEKGVLTAREITXKAGDNLKIKQN------GT
            |  ::::  ||:|| |   :  : :::   |  :  ::   :| ||||||||||     ::
orf40a      VGSIQASMEGSGELETISLSMTNDSKEFVDPYIV----VTLKAGDNLKILQNTNENTNAS
                70        80        90       100       110       120

90       100       110       120       130       140
orf40.pep   NFTYSLKKDLTDLTSVGTEKLSFSANGNKVNITSDTKGLNFAKETAGTNGDTTVHLNGIG
            :||||||||| | :|  |||||:|||:|||| |||||||||||||||||||||||||||||
orf40a      SFTYSLKKDLTGLINVXTEKLSFGANGKKVNIISDTKGLNFAKETAGTNGDTTVHLNGIG
              130       140       150       160       170       180

150       160       170       180       190       200
orf40.pep   STLTDTLLNTGATTNVTNDNVTDDEKKRAASVKDVLNAGWNIKGVKPGTTA--SDNVDFV
            |||||||   :::|:  :|   |:   : ||||:||||||||||||||||:|: | :|||||
orf40a      STLTDTLAGSSAS-HVDAGNXST-HYTRAASIKDVLNAGWNIKGVKXGSTTGQSENVDFV
              190       200       210       220       230       240

210       220       230       240
orf40.pep   RTYDTVEFLSADTKTTTVNVESKDNGKKTEVKIGAKTSVIKEKD
            ||||||||||||||:|||||||||||||||||||||||||||||
orf40a      RTYDTVEFLSADTXTTTVNVESKDNGKKTEVKIGAKTSVIKEKDGKLVTGKGKGENGSST
              250       260       270       280       290       300
```

The complete strain B sequence (ORF40-1 (SEQ ID NO:4)) and ORF40a (SEQ ID NO:6) show 83.7% identity in 601 aa overlap:

```
             10        20        30        40        50        60
orf40-1.pep  MNKIYRIIWNSALNAWVVVSELTRNHTKRASATVKTAVLATLLFATVQASANNEEQEEDL
             ||||||||||||||:||||||||||||||||||||||||||||||||:|::|::||:|
orf40a       MNKIYRIIWNSALNAXVAVSELTRNHTKRASATVKTAVLATLLFATVQANATDEDEEEEL
             10        20        30        50        50        60

70        80        90       100       100       119
orf40-1.pep  YLDPVQRTVAVLIVNSDKEGTGEKEKVEEN-SDWAVYFNEKGVLTAREITLKAGDNLKIK
              :|||:|  | ::::||:||  ||:|: : |:  |   :     :||||||||||||
orf40a       --ESVQRSV-VGSIQASMEGSGELETISLSMTNDSKEFVDPYIV----VTLKAGDNLKIK
               70        80        90       100            110

120       130       140       150       160       170
orf40-1.pep  QN------GTNFTYSLKKDLTDLTSVGTEKLSFSANGNKVNITSDTKGLNFAKETAGTNG
             ||      :::||||||||||||  |:| ||||||:|||||:||||||||||||||||
orf40a       QNTNENTNASSFTYSLKKDLTGLINVXTEKLSFGANGKKVNIISDTKGLNFAKETAGTNG
             120       130       140       150       160       170

180       190       200       210       220       230
orf40-1.pep  DTTVHLNGIGSTLTDTLLNTGATTNVTNDNVTDDEKKRAASVKDVLNAGWNIKGVKPGTT
             |||||||||||||||||   |:  :|   :   :   ||||:||||||||||||| ||
orf40a       DTTVHLNGIGSTLTDTLAGSSAS-HVDAGNXST-HYTRAASIKDVLNAGWNIKGVKXGST
             180       190       200       210       220       230

240       250       260       270       280       290
orf40-1.pep  A--SDNVDFVRTYDTVEFLLSADTKTTTVNVESKDNGKKTEVKIGAKTSVIKEKDGLVTG
                :|||||||||||||||||||||||||||||||||||:|||||||||||||||||||
orf40a       TGQSENVDFVRTYDTVEFLLSADTKTTTVNVESKDNGKRTEVKIGAKTSVIKEKDGLVTG
             240       250       260       270       280       290

300       310       320       330       340       350
orf40-1.pep  KDKGENGSSTDEGEELVTAKEVIDAVNKAGWRMKTTTANGQTGQADKFETVTSGTNVTFA
             |:||||||||||||||||||||||||||||||||||||||||||||||||||||||||
orf40a       KGKGENGSSTDEGEELVTAKEVIDAVNKAGWRMKTTTANGQTGQADKFETVTSGTNVTFA
             300       310       320       330       340       350

360       370       380       390       400       410
orf40-1.pep  SGKGTTATVSKDDQGNITVMYDVNVGDALNVNQLQNSGWNLDSKAVAGSSGKVISGNVSP
             ||||||||||||||||||||||||||||||||||||||||||||||||||||||||||
orf40a       SGKGTTATVSKDDQGNITVMYDVNVGDALNVNQLQNSGWNLDSKAVAGSSGKVISGNVSP
             360       370       380       390       400       410

420       430       440       450       460       470
orf40-1.pep  SKGKMDETVNINAGNNIEITRNGKNIDIATSMTPQFSSVSLGAGADAPTLSVDGD-ALNV
             |||||||||||||||||||:|||||||||||:||||||||||||||||||||  :||||
orf40a       SKGKMDETVNINAGNNIEISRNGKNIDIATSMAPQFSSVSLGAGADAPTLSVDDEGALNV
             420       430       440       450       460       470

480       490       500       510       520       530
orf40-1.pep  GSKKDNKPVRITNVAPGVKEGDVTNVAQLKGVAQNLNNRIDNVDGNARAGIAQAIATAGL
             |||:|:|||||||||||||:||||||:|||||||||||||||||||||||||||||||
orf40a       GSKDANKPVRITNVAPGVKXGDVTNVXQLKGVAQNLNNRIDNVDGNARAGIAQAIATAGL
             480       490       500       510       520       530

540       550       560       570       580       590
orf40-1.pep  VQAYLPGKSMMAIGGGTYRGEAGYAIGYSSISDGGNWIIKGTASGNSRGHFGASASVGYQ
             ||||||||||||||||||||||||||||||||||||||||||||||||||||||||||
orf40a       VQAYLPGKSMMAIGGGTYRGEAGYAIGYSSISDGGNWIIKGTASGNSRGHFGASASVGYQ
             540       550       560       570       580       590 orf40-1.pep  WX
             ||
orf40a       WX
```

Computer analysis of these amino acid sequences gave the following results:

Homology with Hsf Protein Encoded by the Type b Surface Fibrils Locus of *H. influenzae* (Accession Number U41852) ORF40 (SEQ ID NO:2) and Hsf protein (SEQ ID NO:139) show 54% aa identity (SEQ ID NO:140) in 251 aa overlap:

```
Orf40    1   TLLFATVQASANQEEQEEDLYLDPVQRTVAVLIVNSDXXXXXXXXXXXXXNSDWAVYFNEK   60
             TLLFATVQA+A  E++E    LDPV RT  VL  +SD             NS+W +YF+ K
Hsf     41   TLLFATVQANATDEDEE----LDPVVRTAPVLSFHSDKEGTGEKEVTE-NSNWGIYFDNK   95

Orf40   61   GVLTAREITXKAGDNLKIKQN------GTNFTYSLKKDLTDLTSVGTEKLSFSANGNKVN   114
             GVL A  IT KAGDNLKIKQN      ++FTYSLKKDLTDLTSV TEKLSF ANG+KV+
Hsf     96   GVLKAGAITLKAGDNLKIKQNTDESTNASSFTYSLKKDLTDLTSVATEKLSFGANGDKVD   155

Orf40  115   ITSDTKGLNFAKETAGTNGDTTVHLNGIGSTLTDTLLNTGAXXXXXXXXXXXXXEKKRAAS   174
             ITSD  GL AK       G+  VHLNG+ STL D + NTG             EK RAA+
Hsf    156   ITSDANGLKLAK-----TGNGNVHLNGLDSTLPDAVTNTGVLSSSSFTPNDV-EKTRAAT   209

Orf40  175   VKDVLNAGWNIKGVKPGTTASDNVDFVRTYDTVEFLSADTKTTTVNVESKDNGKKTEVKI   234
             VKDVLNAGWNIKG K      ++VG V  Y+ VEF++ D   T   V  +K+NGK TEVK
Hsf    210   VKDVLNAGWNIKGAKTAGGNVESVDLVSAYNNVEFITGDKNTLDVVLTAKENGKTTEVKF   269

Orf40  235   GAKTSVIKEKD                                                  245
               KTSVIKEKD
Hsf    270   TPKTSVIKEKD                                                  280
```

ORF40a also shows homology to Hsf:

gi|1666683 (U41852) hsf gene product [*Haemophilus influenzae*] Length=2353
  Score=153 (67.7 bits), Expect=1.5e−116, Sum P(11) =1.5e−116

```
 Identities = 33/36 (91%), Positives = 34/36 (94%)

Query:   16  VAVSELTRNHTKRASATVKTAVLATLLFATVQANAT  51   (SEQ ID NO:141)
             V VSELTR HTKRASATV+TAVLATLLFATVQANAT      (SEQ ID NO:142)
Sbjct:   17  VVVSELTRTHTKRASATVETAVLATLLFATVQANAT  52   (SEQ ID NO:143)

Score = 161 (71.2 bits), Expect = 1.5e-116, Sum P(11) = 1.5e-116
 Identities = 32/38 (84%), Positives = 36/38 (94%)

Query:  101  VTLKAGDNLKIKQNTNENTNASSFTYSLKKDLTGLINV  138  (SEQ ID NO:144)
             +TLKAGDNLKIKQNT+E+TNASSFTYSLKKDLT L +V      (SEQ ID NO:145)
Sbjct:  103  ITLKAGDNLKIKQNTDESTNASSFTYSLKKDLTDLTSV  140  (SEQ ID NO:146)

Score = 110 (48.7 bits), Expect = 1.5e-116, Sum P(11) = 1.5e-116
 Identities = 21/29 (72%), Positives = 25/29 (86%)

Query:  138  VTEKLSFGANGKKVNIISDTKGLNFAKET  166  (SEQ ID NO:147)
             V++KLS G NG KVNI SDTKGLNFAK++      (SEQ ID NO:148)
Sbjct: 1439  VSDKLSLGTNGNKVNITSDTKGLNFAKDS  1467 (SEQ ID NO:149)

Score = 85 (37.6 bits), Expect = 1.5e-116, Sum P(11) 1.5e-116
 Identities = 18/32 (56%), Positives = 20/32 (62%)

Query:  169  TNGDTTVHLNGIGSTLTDTLAGSSASHVDAGN   200  (SEQ ID NO:150)
             T D +HLNGI STLTDTL  S A+     GN       (SEQ ID NO:151)
Sbjct: 1469  TGDDANIHLNGIASTLTDTLLNSGATTNLGGN  1500 (SEQ ID NO:152)

Score = 92 (40.7 bits), Expect = 1.5e-116, Sum P(11) = 1.5e-116
 Identities 16/19 (84%), Positives = 19/19 (100%)

Query:  206  RAASIKDVLNAGWNIKGVK  224  (SEQ ID NO:153)
             RAAS+KDVLNAGWN++GVK      (SEQ ID NO:154)
Sbjct: 1509  RAASVKDVLNAGWNVRGVK  1527 (SEQ ID NO:155)

Score = 90 (39.8 bits), Expect = 1.5e-116, Sum P(11) = 1.5e-116
 Identities = 17/28 (60%), Positives = 20/28 (71%)

Query:  226  STTGQSENVDFVRTYDTVEFLSADTTTT     253  (SEQ ID NO:156)
             S  Q EN+DFV TYDTV+F+S D  TT          (SEQ ID NO:157)
Sbjct: 1530  SANNQVENIDFVATYDTVDFVSGDKDTT   1557 (SEQ ID NO:158)
```

Based on homology with Hsf, it was predicted that this protein from *N. meningitidis*, and its epitopes, could be useful antigens for vaccines or diagnostics.

Figure 1B:
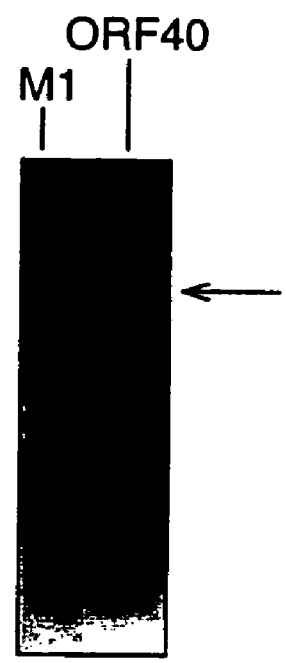
Figure 1C:
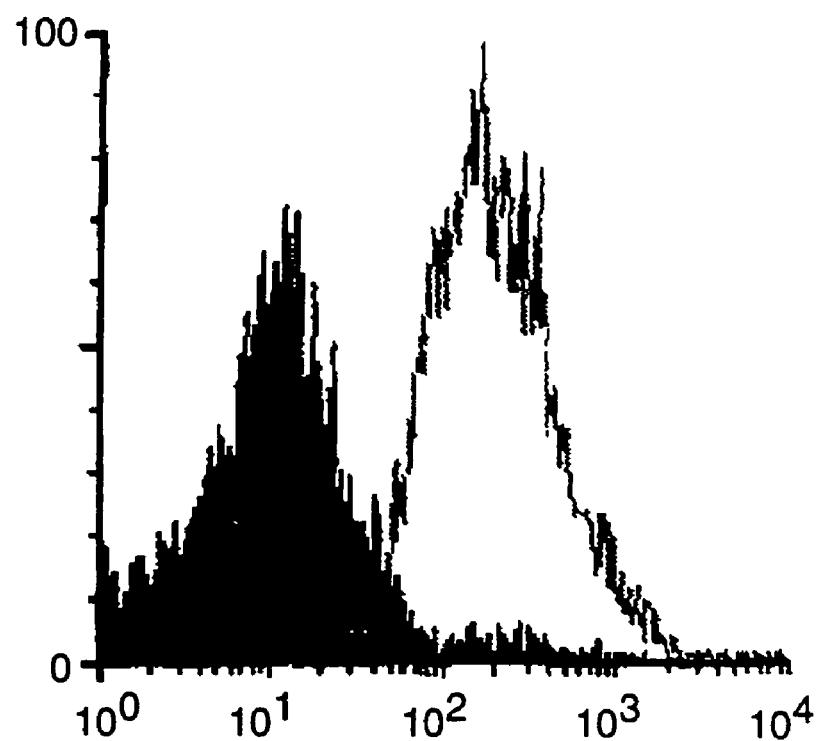
Figure 1D:
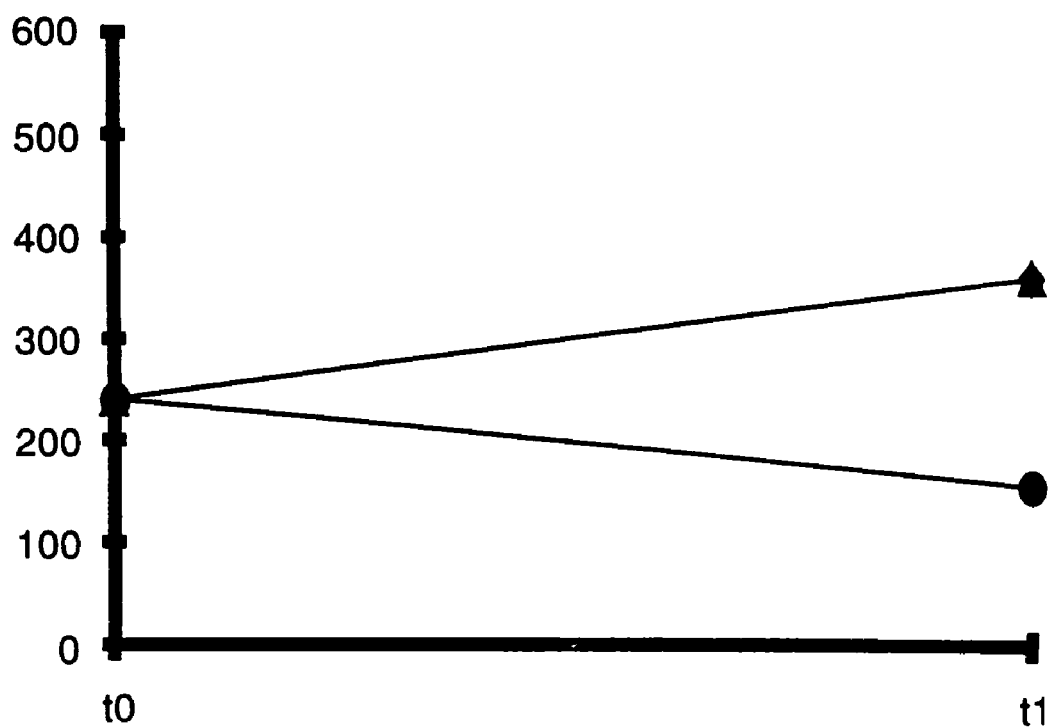

ORF40-1 (61 kDa) was cloned in pET and pGex vectors and expressed in *E. coli*, as described above. The products of protein expression and purification were analyzed by SDS-PAGE. FIG. 1A shows the results of affinity purification of the His-fusion protein, and FIG. 1B shows the results of expression of the GST-fusion in *E. coli*. Purified His-fusion protein was used to immunise mice, whose sera were used for FACS analysis (FIG. 1C), a bactericidal assay (FIG. 1D), and ELISA (positive result). These experiments confirm that ORF40-1 is a surface-exposed protein, and that it is a useful immunogen.

Figure 1E:
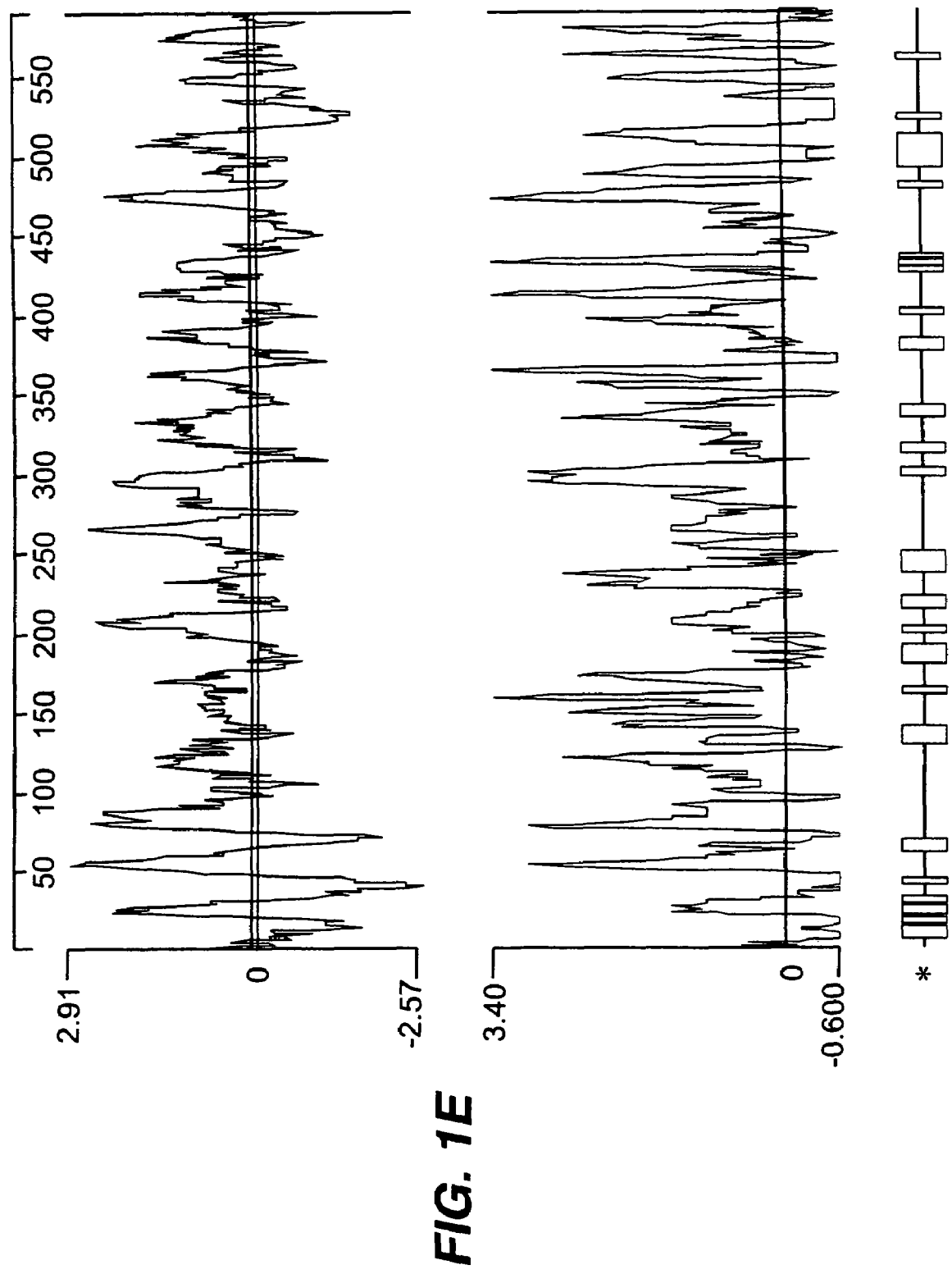

FIG. 1E shows plots of hydrophilicity, antigenic index, and AMPHI regions for ORF40-1.

Example 2

The following partial DNA sequence was identified in *N. meningitidis* <SEQ ID 7>

```
  1 ATGTTACGTt TGACTGCtTT AGCCGTATGC ACCGCCCTCG CTTTGGGCGC
 51 GTGTTCGCCG CAAAATTCCG ACTCTGCCCC ACAAGCCAAA GaACAGGCGG
101 TTTCCGCCGC ACAAACCGAA GgCGCGTCCG TTACCGTCAA AACCGCGCGC
151 GGCGACGTTC AAATACCGCA AAACCCCGAA CGCATCGCCG TTTACGATTT
201 GGGTATGCTC GACACCTTGA GCAAACTGGG CGTGAAAACC GGTTTGTCCG
251 TCGATAAAAA CCGCCTCCCG TATTTAGAGG AATATTTCAA AACGACAAAA
301 CCTGCCGGCA CTTTGTTCGA GCCGGATTAC GAAACGCTCA ACGCTTACAA
351 ACCGCAGCTC ATCATCATCG GCAGCCGCGC CgCCAAGGCG TTTGACAAAT
401 TGAAcGAAAT CGCGCCGACC ATCGrmwTGA CCGCCGATAC CGCCAACCTC
451 AAAGAAAGTG CCAArGAGGC ATCGACGCTG GCGCAAATCT TC..
```

This corresponds to the amino acid sequence <SEQ ID 8; ORF38>:

```
  1 MLRLTALAVC TALALGACSP QNSDSAPQAK EQAVSAAQTE GASVTVKTAR
 51 GDVQIPQNPE RIAVYDLGML DTLSKLGVKT GLSVDKNRLP YLEEYFKTTK
101 PAGTLFEPDY ETLNAYKPQL IIIGSPAAKA FDKLNEIAPT IXXTADTANL
151 KESAKEASTL AQIF..
```

Further work revealed the complete nucleotide sequence <SEQ ID 9>:

```
  1 ATGTTACGTT TGACTGCTTT AGCCGTATGC ACCGCCCTCG CTTTGGGCGC
 51 GTGTTCGCCG CAAAATTCCG ACTCTGCCCC ACAAGCCAAA GAACAGGCGG
101 TTTCCGCCGC ACAAACCGAA GGCGCGTCCG TTACCGTCAA AACCGCGCGC
151 GGCGACGTTC AAATACCGCA AAACCCCGAA CGCATCGCCG TTTACGATTT
201 GGGTATGCTC GACACCTTGA GCAAACTGGG CGTGAAAACC GGTTTGTCCG
251 TCGATAAAAA CCGCCTGCCG TATTTAGAGG AATATTTCAA AACGACAAAA
301 CCTGCCGGCA CTTTGTTCGA GCCGGATTAC GAAACGCTCA ACGCTTACAA
351 ACCGCAGCTC ATCATCATCG GCAGCCGCGC CGCCAAGGCG TTTGACAAAT
401 TGAACGAAAT CGCGCCGACC ATCGAAATGA CCGCCGATAC CGCCAACCTC
451 AAAGAAAGTG CCAAAGAGCG CATCGACGCG CTCGCGCAAA TCTTCGGCAA
501 ACAGGCGGAA GCCGACAAGC TGAAGGCGGA AATCGACGCG TCTTTTGAAG
551 CCGCGAAAAC TGCCGCACAA GGTAAGGGCA AAGGTTTGGT GATTTTGGTC
601 AACGGCGGCA AGATGTCGGC TTTCGGCCCG TCTTCACGCT TGGGCGGCTG
```

-continued

651 GCTGCACAAA GACATCGGCG TTCCCGCTGT CGATGAATCA ATTAAAGAAG

701 GCAGCCACGG TCAGCCTATC AGCTTTGAAT ACCTGAAAGA GAAAAATCCC

751 GACTGGCTGT TTGTCCTTGA CCGAAGCGCG GCCATCGGCG AAGAGGGTCA

801 GGCGGCGAAA GACGTGTTGG ATAATCCGCT GGTTGCCGAA ACAACCGCTT

851 GGAAAAAAGG ACAGGTCGTG TACCTCGTTC CTGAAACTTA TTTGGCAGCC

901 GGTGGCGCGC AAGAGCTGCT GAATGCAAGC AAACAGGTTG CCGACGCTTT

951 TAACGCGGCA AAATAA

This corresponds to the amino acid sequence <SEQ ID 10; ORF38-1>:

1 MLRLTALAVC TALALGACSP QNSDSAPQAK EQAVSAAQTE GASVTVKTAR

51 GDVQIPQNPE RIAVYDLGML DTLSKLGVKT GLSVDKNRLP YLEEYFKTTK

101 PAGTLFEPDY ETLNAYKPQL IIIGSRAAKA FDKLNEIAPT IEMTADTANL

151 KESAKERIDA LAQIFGKQAE ADKLKAEIDA SFEAAKTAAQ GKGKGLVILV

201 NGGKMSAFGP SSRLGGWLHK DIGVPAVDES IKEGSHGQPI SFEYLKEKNP

251 DWLFVLDRSA AIGEEGQAAK DVLDNPLVAE TTAWKKGQVV YLVPETYLAA

301 GGAQELLNAS KQVADAFNAA K*

Computer analysis of this amino acid sequence reveals a putative prokaryotic membrane lipoprotein lipid attachment site (underlined).

Further work identified the corresponding gene in strain A of *N. meningitidis* <SEQ ID 11>:

1 ATGTTACGTT TGACTGCTTT AGCCGTATGC ACCGCCCTCG CTTTGGGCGC

51 GTGTTCGCCG CAAAATTCCG ACTCTGCCCC ACAAGCCAAA GAACAGGCGG

101 TTTCCGCCGC ACAATCCGAA GGCGTGTCCG TTACCGTCAA AACGGCGCGC

151 GGCGATGTTC AAATACCGCA AAACCCCGAA CGTATCGCCG TTTACGATTT

201 GGGTATGCTC GACACCTTGA GCAAACTGGG CGTGAAAACC CGTTTGTCCG

251 TCGATAAAAA CCGCCTGCCG TATTTAGAGG AATATTTCAA AACGACAAAA

301 CCTGCCGGAA CTTTGTTCGA GCCGGATTAC GAAACGCTCA ACGCTTACAA

351 ACCGCAGCTC ATCATCATCG GCAGCCGCGC AGCCAAAGCG TTTGACAAAT

401 TGAACGAAAT CGCGCCGACC ATCGAAATGA CCGCCGATAC CGCCAACCTC

451 AAAGAAAGTG CCAAAGAGCG TATCGACGCG CTGGCGCAAA TCTTCGGCAA

501 AAAGGCGGAA GCCGACAAGC TGAAGGCGGA AATCGACGCG TCTTTTGAAG

551 CCGCGAAAAC TGCCGCGCAA GGCAAAGGCA AGGGTTTGGT GATTTTGGTC

601 AACGGCGGCA AGATGTCCGC CTTCGGCCCG TCTTCACGAC TGGGCGGCTG

651 GCTGCACAAA GACATCGGCG TTCCCGCTGT TGACGAAGCC ATCAAAGAAG

701 GCAGCCACGG TCAGCCTATC AGCTTTGAAT ACCTGAAAGA GAAAAATCCC

751 GACTGGCTGT TTGTCCTTGA CCGCAGCGCG GCCATCGGCG AAGAGGGTCA

801 GGCGGCGAAA GACGTGTTGA ACAATCCGCT GGTTGCCGAA ACAACCGCTT

```
851 GGAAAAAAGG ACAAGTCGTT TACCTTGTTC CTGAAACTTA TTTGGCAGCC

901 GGTGGCGCGC AAGAGCTACT GAATGCAAGC AAACAGGTTG CCGACGCTTT

951 TAACGCGGCA AAATAA
```

This encodes a protein having amino acid sequence <SEQ ID 12; ORF38a>:

```
  1 MLRLTALAVC TALALGACSP QNSDSAPQAK EQAVSAAQSE GVSVTVKTAR

51 GDVQIPQNPE RIAVYDLGML DTLSKLGVKT GLSVDKNRLP YLEEYFKTTh

101 PAGTLFEPDY ETLNAYKPQL IIIGSRAAKA FDKLNEIAPT IEMTADTANL

151 KESAKERIDA LAQIFGKKAE ADKLKAEIDA SFEAAXTAAQ GKGKGLVILV

201 NGGKMSAEGP SSRLGGWLHK DIGVPAVDEA IKEGSHGQPI SFEYLKEKNP

251 DWLFVLDRSA AIGEEGQAAK DVLNNPLVAE TTAWKKGQVV YLVPETYLAA

301 GGAQELLNAS KQVADAFWAA K*
```

The originally-identified partial strain B sequence (ORF38 (SEQ ID NO:8)) shows 95.2% identity over a 165aa overlap with ORF38a (SEQ ID NO:159):

```
                   10         20         30         40         50         60
orf38.pep  MLRLTALAVCTALALGACSPQNSDSAPQAKEQAVSAAQTEGASVTVKTARGDVQIPQNPE
           ||||||||||||||||||||||||||||||||||||||:||:||||||||||||||||||
orf38a     MLRLTALAVCTALALGACSPQNSDSAPQAKEQAVSAAQSEGVSVTVKTARGDVQIPQNPE
                   10         20         30         40         50         60

70         80         90        100        110        120
orf38.pep  RIAVYDLGMLDTLSKLGVKTGLSVDKNRLPYLEEYFKTTKPAGTLFEPDYETLNAYKPQL
           ||||||||||||||||||||||||||||||||||||||||||||||||||||||||||||
orf38a     RIAVYDLGMLDTLSKLGVKTGLSVDKNRLPYLEEYFKTTKPAGTLFEPDYETLNAYKPQL
                   70         80         90        100        110        120

130        140        150        160
orf38.pep  IIIGSRAAKAFDKLNEIAPTIXXTADTANLKESAKE-ASTLAQIF
           |||||||||||||||||||||  |||||||||||||| ::||||
orf38a     IIIGSRAAKAFDKLNEIAPTIEMTADTANLKESAKERIDALAQIFGKKAEADKLKAEIDA
                  130        140        150        160        170        180 orf38a     SFEAAKTAAQGKGKGLVILVNGGKMSAFGPSSRLGGWLHKDIGVPAVDEAIKEGSHGQPI
                  190        200        210        220        230        240
```

The complete strain B sequence (ORF38-1 (SEQ ID NO:10)) and ORF38a (SEQ ID NO:12) show 98.4% identity in 321 aa overlap:

```
orf38a.pep  MLRLTALAVCTALALGACSPQNSDSAPQAKEQAVSAAQSEGVSVTVKTARGDVQIPQNPE
            ||||||||||||||||||||||||||||||||||||||:||:||||||||||||||||||
orf38-1     MLRLTALAVCTALALGACSPQNSDSAPQAKEQAVSAAQTEGASVTVKTARGDVQIPQNPE orf38a.pep  RIAVYDLGMLDTLSKLGVKTGLSVDKNRLPYLEEYFKTTKPAGTLFEPDYETLNAYKPQL
            ||||||||||||||||||||||||||||||||||||||||||||||||||||||||||||
orf38-1     RIAVYDLGMLDTLSKLGVKTGLSVDKNRLPYLEEYFKTTKPAGTLFEPDYETLNAYKPQL
```

```
orf38a.pep   IIIGSRAAKAFDKLNEIAPTIEMTADTANLKESAKERIDALAQIFGKKAEADKLKAEIDA
             ||||||||||||||||||||||||||||||||||||||||||||:|||||||||||||
orf38-1      IIIGSRAAKAFDKLNEIAPTIEMTADTANLKESAKERIDALAQIFGKQAEADKLKAEIDA orf38a.pep   SFEAAKTAAQGKGKGLVILVNGGKMSAFGPSSRLGGWLHKDIGVPAVDEAIKEGSHGQPI
             ||||||||||||||||||||||||||||||||||||||||||||||:|||||||||||
orf38-1      SFEAAKTAAQGKGKGLVILVNGGKMSAFGPSSRLGGWLHKDIGVPAVDESIKEGSHGQPI orf38a.pep   SFEYLKEKNPDWLFVLDRSAAIGEEGQAAKDVLNNPLVAETTAWKKGQVVYLVPETYLAA
             |||||||||||||||||||||||||||||||||:||||||||||||||||||||||||
orf38-1      SFEYLKEKNPDWLFVLDRSAAIGEEGQAAKDVLDNPLVAETTAWKKGQVVYLVPETYLAA orf38a.pep   GGAQELLNASKQVDADAFNAAK
             ||||||||||||||||||||||
orf38-1      GGAQELLNASKQVDADAFNAAK
```

Computer analysis of these sequences revealed the following:

Homology with a Lipoprotein (Lipo) of *C. jejuni* (Accession Number X82427)

ORF38 (SEQ ID NO:160) and lipo (SEQ ID NO:162) show 38% aa identity (SEQ ID NO:161) in 96 aa overlap:

```
Orf38:   1   EGASVTVKTARGDVQIPQNPERIAVYDLGMLDTLSKLGVKTGLS-VDKNRLPYLEEYFKT   98
             EG  S   VK + G+ + P+NP ++ + DLG+LDT   L +  ++ V    LP   + FK
Lipo:    51  EGDSFLVKDSLGENKTPKNPSKVVILDLGILDTFDALKLNDKVAGVPAKNLPKYLQQFKN   110

Orf38:   99  TKPAGTLFEPDYETLNAYKPQLIIIGSRAAKAFDKL                          134
                G + + D+E +NA KP LIII  R +K +DKL
Lipo:    111 KPSVGGVQQVDFEAINALKODLIIISGRQSKFYDKL                          146
```

Based on this analysis, it was predicted that this protein from *N. meningitidis*, and its epitopes, could be useful antigens for vaccines or diagnostics.

Figure 2A:
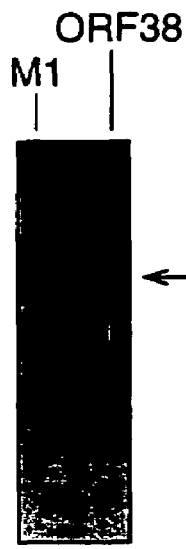
FIGS. 2A-E show biochemical data and sequence analysis pertaining to ORF 38-1.
Figure 2B:
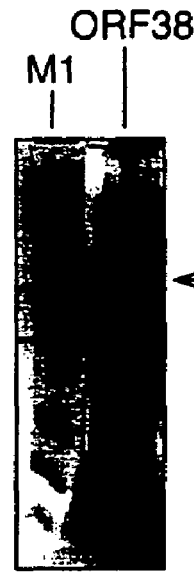
Figure 2C:
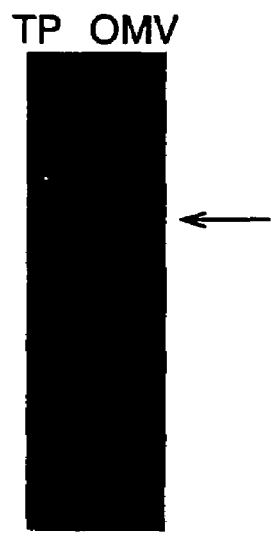
Figure 2D:
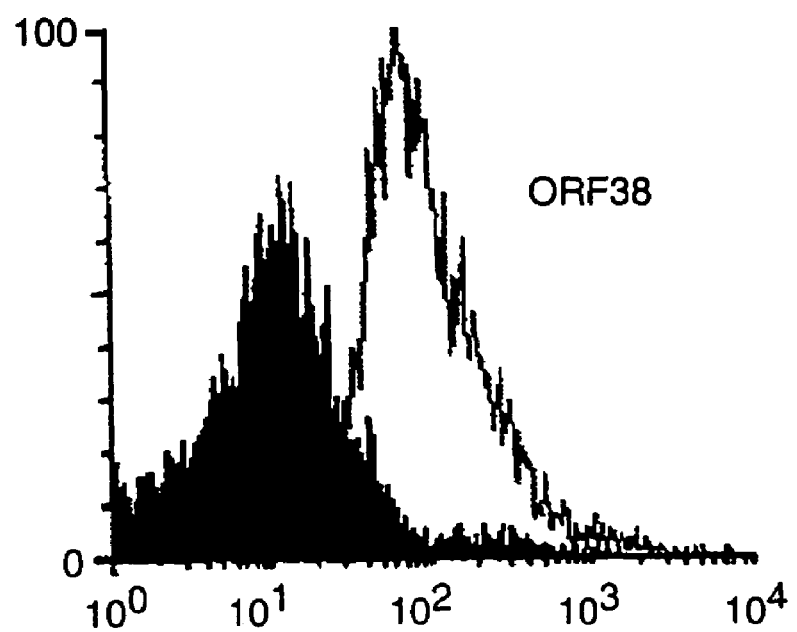

ORF38-1 (32 kDa) was cloned in pET and pGex vectors and expressed in *E. coli*, as described above. The products of protein expression and purification were analyzed by SDS-PAGE. FIG. 2A shows the results of affinity purification of the His-fusion protein, and FIG. 2B shows the results of expression of the GST-fusion in *E. coli*. Purified His-fusion protein was used to immunise mice, whose sera were used for Western blot analysis (FIG. 2C) and FACS analysis (FIG. 2D). These experiments confirm that ORF38-1 is a surface-exposed protein, and that it is a useful immunogen.

Figure 2E:
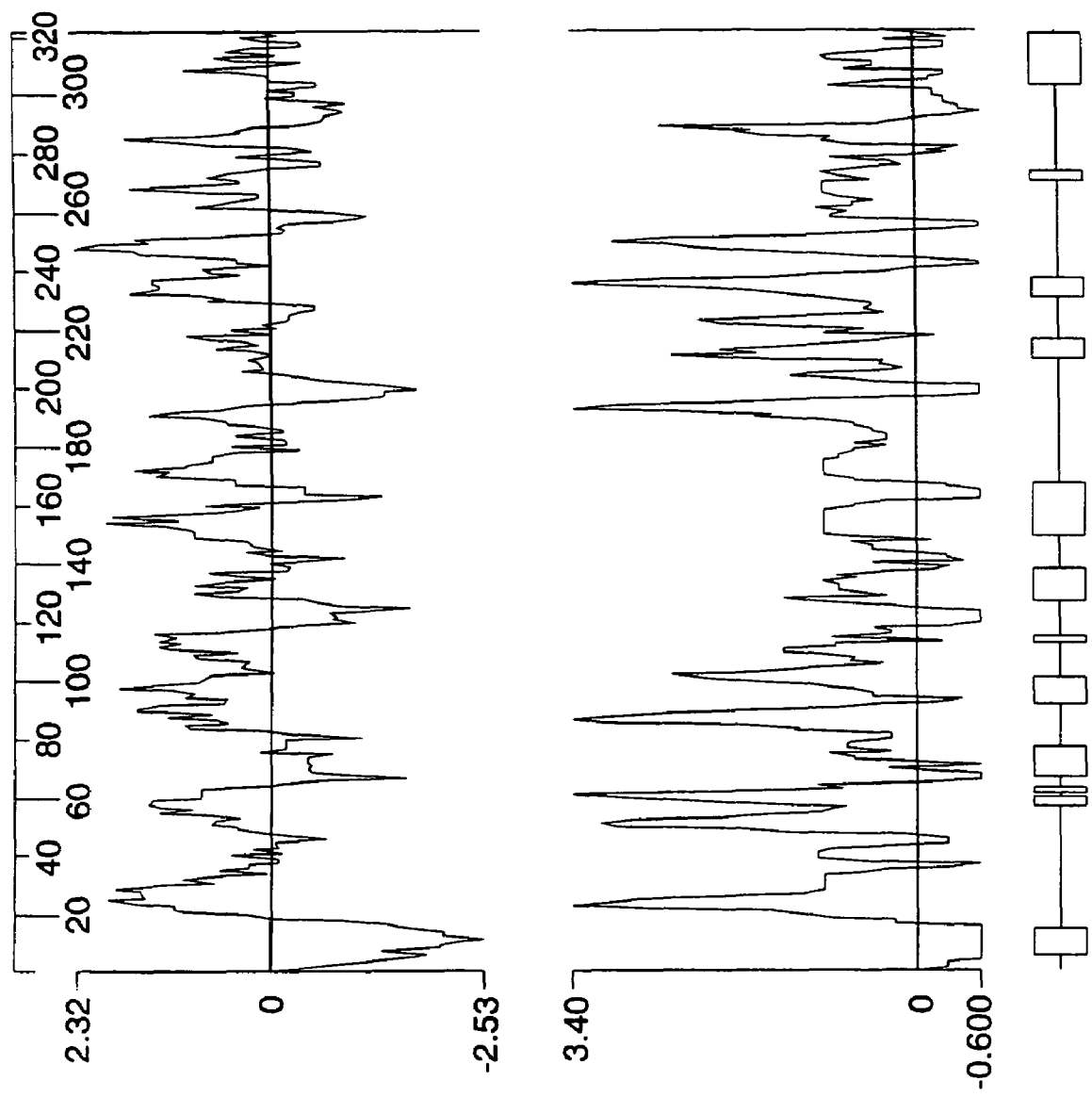

FIG. 2E shows plots of hydrophilicity, antigenic index, and AMPHI regions for ORF38-1.

Example 3

The following *N. meningitidis* DNA sequence was identified <SEQ ID 13>:

```
  1  ATGAAACTTC TGACCACCGC AATCCTGTCT TCCGCAATCG CGCTCAGCAG
 51  TATGGCTGCC GCCGCTGGCA CGGACAACCC CACTGTTGCA AAAAAAACCG
101  TCAGCTACGT CTGCCAGCAA GGTAAAAAAG TCAAAGTAAC CTACGGCTTC
151  AACAAACAGG GTCTGACCAC ATACGCTTCC GCCGTCATCA ACGGCAAACG
201  CGTGCAAATG CCTGTCAATT TGGACAAATC CGACAATGTG GAAACATTCT
251  ACGGCAAAGA AGGCGGTTAT GTTTTGGGTA CCGGCGTGAT GGATGGCAAA
301  TCCTACCGCA AACAGCCCAT TATGATTACC GCACCTGACA ACCAAATCGT
351  CTTCAAAGAC TGTTCCCCAC GTTAA
```

This corresponds to the amino acid sequence <SEQ ID 14; ORF44>:

```
  1  MKLLTTAILS SAIALSSMAA AAGTDNPTVA KKTVSYVCQQ GKKVKVTYGF

51  NKQGLTTYAS AVINGKRVQM PVNLDKSDNV ETFYGKEGGY VLGTGVMDGK

101  SYRKQPIMIT APDNQIVFKD CSPR*
```

Computer analysis of this amino acid sequence predicted the leader peptide shown underlined.

Further work identified the corresponding gene in strain A of *N. meningitidis* <SEQ ID 15>:

```
  1    ATGAAACTTC TGACCACCGC AATCCTGTCT TCCGCAATCG CGCTCAGCAG

51    TATGGCTGCT GCTGCCGGCA CGAACAACCC CACCGTTCCC AAAAAAACCG

101    TCAGCTACGT CTGCCAGCAA GGTAAAAAAG TCAAAGTAAC CTACGGCTTT

151    AACAAACAGG GCCTGACCAC ATACGCTTCC GCCGTCATCA ACGGCAAACG

201    TGTGCAAATG CCTGTCAATT TGGACAAATC CGACAATGTG GAAACATTCT

251    ACGGCAAAGA AGGCGCTTAT GTTTTGGGTA CCGGCGTGAT GGATGGCAAA

301    TCCTATCGCA AACAGCCTAT TATGATTACC GCACCTGACA ACCAAATCGT

351    CTTCAAAGAC TGTTCCCCAC GTTAA
```

This encodes a protein having amino acid sequence <SEQ ID 16; ORF44a>:

```
  1    MKLLTTAILS SAIALSSMAA AAGTNNPTVA KKTVSYVCQQ GKKVKVTYGF

53    NKQGLTTYAS AVINGKRVQM PVNLDKSDNV ETFYGKEGGY VLGTGVNDGK

101    SYRKQPIMIT APDNQIVFKD CSPR*
```

The strain B sequence (ORF44 (SEQ ID NO:14)) shows 99.2% identity over a 124aa overlap with ORF44a (SEQ ID NO:16):

```
                    10        20        30        40        50        60
orf44.pep   MKLLTTAILSSAIALSSMAAAAGTDNPTVAKKTVSYVCQQGKKVKVTYGFNKQGLTTYAS
            ||||||||||||||||||||||:|||||||||||||||||||||||||||||||||||||
orf44a      MKLLTTAILSSAIALSSMAAAAGTNNPTVAKKTVSYVCQQGKKVKVTYGFNKQGLTTYAS
                    10        20        30        40        50        60

70        80        90       100       110       120
orf44.pep   AVINGKRVQMPVNLDKSDNVETFYGKEGGYVLGTGVMDGKSYTKQPIMITAPDNQIVFKD
            ||||||||||||||||||||||||||||||||||||||||||||||||||||||||||||
orf44a      AVINGKRVQMPVNLDKSDNVETFYGKEGGYVLGTGVMDGKSYTKQPIMITAPDNQIVFKD
                    70        80        90       100       110       120 orf44.pep   CSPRX
            |||||
orf44a      CSPRX
```

Computer analysis gave the following results:

Homology with the LecA Adhesin of *Eikenella corrodens* (Accession Number D78153)

ORF44 (SEQ ID NO:163) and LecA (SEQ ID NO:165) protein show 45% aa identity (SEQ ID NO:164) in 91 aa overlap:

```
Orf44   33    TVSYVCQQGKKVKVTYGFNKQGLTTYASAVINGKRVQMPVNLDKSDNVETFYGKEKKYVL   92
              +V+YVCQQG+++ V Y FN  G+ T A   +N + +++P NL  SDNV+T +    GY L
LecA   135    SVAYCCQQGRRLNVNYRFNSAGVPTSAELRVNNRNLRLPYNLSASDNVDTVF-SANGYRL  193

Orf44   93    GTGVMDGKSYRKQPIMITAPDNQIVFKDCSP                               123
               T  MD  +YR Q I+++AP+ Q+++KDCSP
LecA   194    TTNAMDSANYRSQDIIVSAPNGQMLYKDCSP                               224
```

Based on homology with the adhesin, it was predicted that this protein from *N. meningitidis*, and its epitopes, could be useful antigens for vaccines or diagnostics.

Figure 3A:
FIGS. 3A-D show biochemical data and sequence analysis pertaining to ORF 44-1.
Figure 3B:
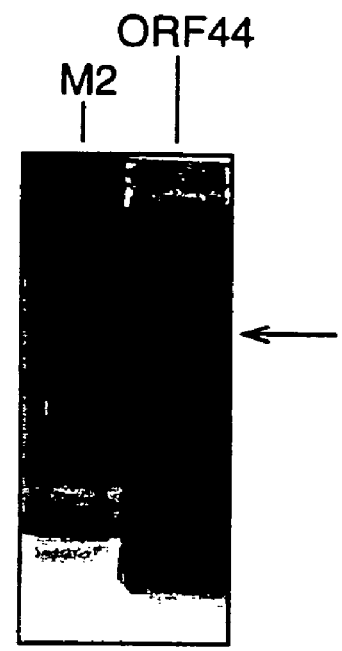
Figure 3C:
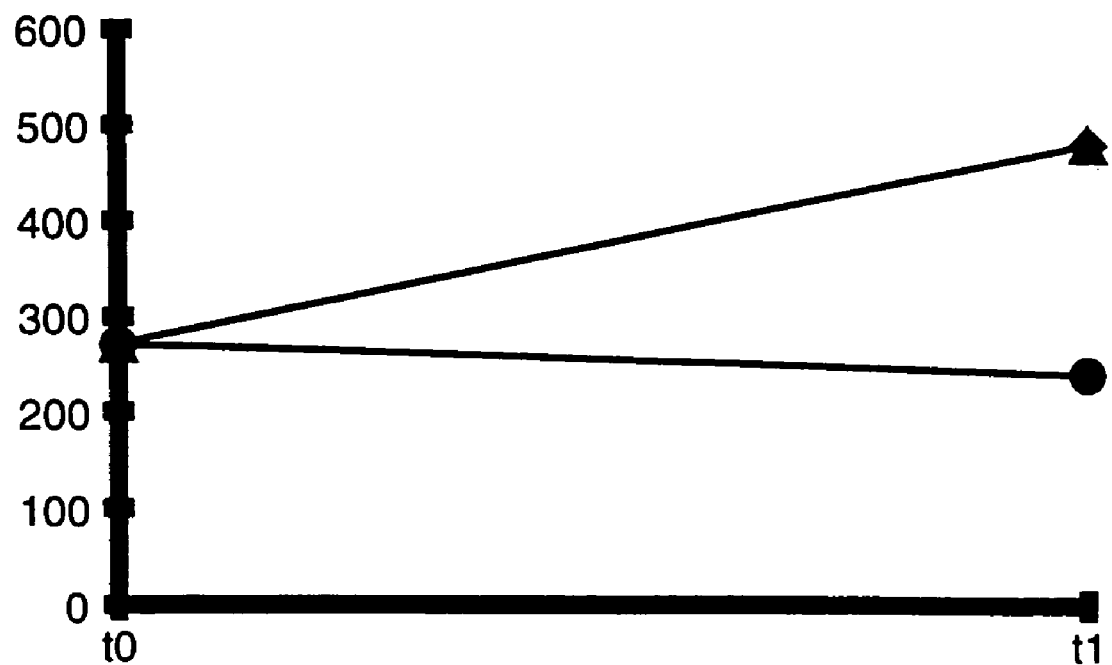

ORF44-1 (11.2 kDA) was cloned in pET and pGex vectors and expressed in *E. coli*, as described above. The products of protein expression and purification were analyzed by SDS-PAGE. FIG. 3A shows the results of affinity purification of the His-fusion protein, and FIG. 3B shows the results of expression of the GST-fusion in *E. coli*. Purified His-fusion protein was used to immunise mice, whose sera were used for ELISA, which gave positive results, and for a bactericidal assay (FIG. 3C). These experiments confirm that ORF44-1 is a surface-exposed protein, and that it is a useful immunogen.

Figure 3D:
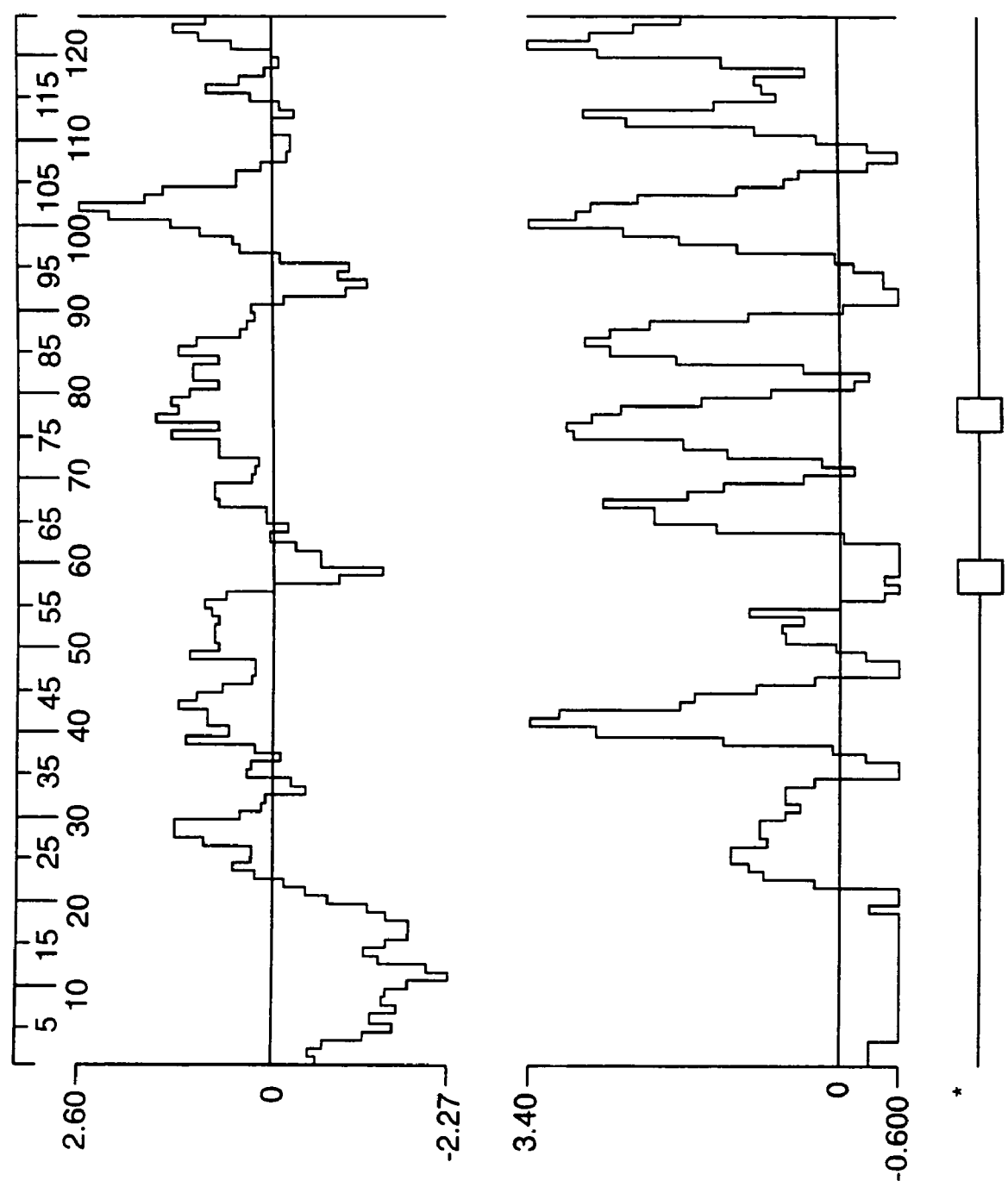

FIG. 3D shows plots of hydrophilicity, antigenic index, and AMPHI regions for ORF44-1.

Example 4

The following partial DNA sequence was identified in *N. meningitidis* <SEQ ID 17>

```
  1 ..GGCACCGAAT TCAAAACCAC CCTTTCCGGA GCCGACATAC AGGCAGGGGT
 51   GGGTGAAAAA GCCCGAGCCG ATGCGAAAAT TATCCTAAAA GGCATCGTTA
101   ACCGCATCCA AACCGAAGAA AAGCTGGAAT CCAACTCGAC CGTATGGCAA
151   AAGCAGGCCG GAAGCGGCAG CACGGTTGAA ACGCTGAAGC TACCGAGCTT
201   TGAAGGGCCG GCACTGCCTA AGCTGACCGC TCCCGGCGGC TATATCGCCG
251   ACATCCCCAA AGGCAACCTC AAAACCGAAA TCGAAAAGCT GGCCAAACAG
301   CCCGAATATG CCTATCTGAA ACAGCTTCAG ACGGTCAAGG ACGTGAACTG
351   GAACCAAGTA CAGCTCGCTT ACGACAAATG GGACTATAAA CAGGAAGGCC
401   TAACCGGAGC CGGAGCCGCA ATTANCGCAC TGGCCGTTAC CGTGGTCACC
451   TCAGGCGCAG GAACCGGAGC CGTATTGGGA TTAANACGNG TGGCCGCCGC
501   CGCAACCGAT GCAGCATTT...
```

This corresponds to the amino acid sequence <SEQ ID 18; ORF49>:

```
1     ..GTEFKTTLSG ADIQAGVGEK ARADAKIILK GIVNRIQTEE KLESNSTVWQ

51    KQAGSGSTVE TLKLPSFEGP ALPKLTAPGG YIADIPKGNL KTEIEKLAKQ

101   PEYAYLKQLQ TVKDVNWNQV QLAYDKWDYK QEGLTGAGAA IXALAVTVVT

151   SGAGTGAVLG LXRVAAAATD AAF..
```

Further work revealed the complete nucleotide sequence <SEQ ID 19>:

```
1     ATGCAACTGC TGGCAGCCGA AGGCATTCAC CAACACCAAT TGAATGTTCA

51    GAAAAGTACC CGTTTCATCG GCATCAAAGT GGGTAAAAGC GATTACAGCA

101   AAAACGAGCT GAACGAAACC AAACTGCCCG TACGCGTTAT CGCCCAAACA

151   GCCAAAACCC GTTCCGGCTG GGATACCGTA CTCGAAGGCA CCGAATTCAA

201   AACCACCCTT TCCGGAGCCG ACATACAGGC AGGGGTGGGT GAAAAAGCCC

251   GAGCCGATGC GAAAATTATC CTAAAAGGCA TCGTTAACCG CATCCAAACC

301   GAAGAAAAGC TGGAATCCAA CTCGACCGTA TGGCAAAAGC AGGCCGGAAG

351   CGGCAGCACG GTTGAAACGC TGAAGCTACC GAGCTTTGAA GGGCCGGCAC

401   TGCCTAAGCT GACCGCTCCC GGCGGCTATA TCGCCGACAT CCCCAAAGGC

451   AACCTCAAAA CCGAAATCGA AAAGCTGGCC AAACAGCCCG AATATGCCTA

501   TCTGAAACAG CTTCAGACGG TCAAGGACGT GAACTGGAAC CAAGTACAGC

551   TCGCTTACGA CAAATGGGAC TATAAACAGG AAGGCCTAAC CGGAGCCGGA

601   GCCGCAATTA TCGCACTGGC CGTTACCGTG GTCACCTCAG GCGCAGGAAC

651   CGGAGCCGTA TTGGGATTAA ACGGTGCGGC CGCCGCCGCA ACCGATGCAG

701   CATTTGCCTC TTTGGCCAGC CAGGCTTCCG TATCGTTCAT CAACAACAAA

751   GGCAATATCG GTAACACCCT GAAAGAGCTG GCAGAAGCA GCACGGTGAA

801   AAATCTGATG GTTGCCGTCG CTACCGCAGG CGTAGCCGAC AAAATCGGTG

851   CTTCGGCACT GAACAATGTC AGCGATAAGC AGTGGATCAA CAACCTGACC

901   GTCAACCTGG CCAATGCGGG CAGTGCCGCA CTGATTAATA CCGCTGTCAA

951   CGGCGGCAGC CTGAAAGACA ATCTGGAAGC GAATATCCTT GCGGCTTTGG

1001  TGAATACTGC GCATGGAGAG GCAGCAAGTA AAATCAAACA GTTGGATCAG

1051  CACTACATTG CCCATAAGAT TGCCCATGCC ATAGCGGGCT GTGCGGCAGC

1101  GGCGGCGAAT AAGGGCAAGT GTCAAGATGG TGCGATCGGT GCGGCGGTCG

1151  GTGAAATCCT TGGCGAAACC CTACTGGACG GCAGAGACCC TGGCAGCCTG

1201  AATGTGAAGG ACAGGGCAAA ATCATTGCT AAGGCGAAGC TGGCAGCAGG

1251  GGCGGTTGCG GCGTTGAGTA AGGGGGATGT GAGTACGGCG GCGAATGCGG

1301  CTGCTGTGGC GGTAGAGAAT AATTCTTTAA ATGATATACA GGATCGTTTG

1351  TTGAGTGGAA ATTATGCTTT ATGTATGAGT GCAGGAGGAG CAGAAAGCTT

1401  TTGTGAGTCT TATCGACCAC TGGGCTTGCC ACACTTTGTA AGTGTTTCAG

1451  GAGAAATGAA ATTACCTAAT AAATTCGGGA ATCGTATGGT TAATGGAAAA

1531  TTAATTATTA ACACTAGAAA TGGCAATGTA TATTTCTCTG TAGGTAAAAT
```

```
-continued
1551  ATGGAGTACT GTAAAATCAA CAAAATCAAA TATAAGTGGG GTATCTGTCG

1601  GTTGGGTTTT AAATGTTTCC CCTAATGATT ATTTAAAAGA AGCATCTATG

1651  AATGATTTCA GAAATAGTAA TCAAAATAAA GCCTATGCAG AAATGATTTC

1701  CCAGACTTTG GTAGGTGAGA GTGTTGGTGG TAGTCTTTGT CTGACAAGAG

1751  CCTGCTTTTC GGTAAGTTCA ACAATATCTA AATCTAAATC TCCTTTTAAA

1801  GATTCAAAAA TTATTGGGGA AATCGGTTTG GGAAGTGGTG TTGCTGCAGG

1851  AGTAGAAAAA ACAATATACA TAGGTAACAT AAAAGATATT GATAAATTTA

1901  TTAGTGCAAA CATAAAAAAA TAG
```

This corresponds to the amino acid sequence <SEQ ID 20; ORF49-1>:

```
  1  MQLLAAEGIH QHQLNVQKST RFIGIKVGKS NYSKWELNET KLPVRVIAQT

51  AKTRSGWOTV LEGTEFKTTL SGADIQAGVG EKARADAKII LKGIVNRIQT

101  EEKLESNSTV WQKQAGSGST VETLKLPSFE GPALPKLTAP GGYIADIPKG

151  NLKTEIEKLA KQPEYAYLKQ LQTVKDVNWN QVQLAYDKWD YKQEGLTGAG

201  AAIIALAVTV VTSGAGTGAV LGLNGAAAAA TDAAFASLAS QASVSFINNK

251  GNIGNTLKEL GRSSTVKNLM VAVATAGVAD KIGASALNNV SDKQWINNLT

301  VNLANAGSAA LINTAVNGGS LKDNLEANIL AALVNTAHGE AASKIKQLDQ

351  HYIAHKIAHA IAGCAAAAAN KGKCQDGAIG AAVGEILGET LLDGRDPGSL

401  NVKDRAKIIA KAKLAAGAVA ALSKGDVSTA ANAAAVAVEN NSLNDIQDRL

451  LSGNYALCMS AGGAESFCES YRPLGLPHEV SVSGEMKLPN KFGNRMVNGK

501  LIINTRNGNV YFSVGKIWST VKSTKSNISG VSVGWVLNVS PNDYLKEASM

551  NDFRNSNQNK AYAEMISQTL VGESVGGSLC LTRACFSVSS TISKSKSPFK

601  DSKIIGEIGL GSGVAAGVEK TIYIGNIKDI DEFISANIKK *
```

Computer analysis predicts a transmembrane domain and also indicates that ORF49 has no significant amino acid homology with known proteins. A corresponding ORF from *N. meningitidis* strain A was, however, identified:

ORF49 (SEQ ID NO:18) shows 86.1% identity over a 173aa overlap with an ORF (ORF49a (SEQ ID NO:166)) from strain A of *N. meningitidis*:

```
                             10         20         30
orf49.pep                    GTEFKTTLSGADIQAGVGEKARADAKIILK
                             ||||||||:||||||| |||:|||||||||
orf49a     SKNELNETKLPVRVVAQXAATRSGWDTVLEGTEFKTTLAGADIQAGVXEKARVDAKIILK
               40         50         60         70         80         90

40         50         60         70         80         90
orf49.pep  GIVNRIQTEEKLESNSTVWQKQAGSGSTVETLKLPSFEGPALPKLTAPGGYIADIPKGNL
           ||||||:||||||:|||||||||||:|||:||||||||:|| |||||:||||:||||||
orf49a     GIVNRIQSEEKLETNSTVWQKQAGRGSTIETLKLPSFESPTPPKLSAPGGYIVDIPKGNL
              100        110        120        130        140        150

100        110        120        130        140        150
orf49.pep  KTEIEKLAKQPEYAYLKQLQTVKDVNWNQVQLAYDKWDYKQEGLTGAGAAIXALAVTVVT
           |||||||:|||||||||||:|:::|||||||||||:|||||||||||:|||| |||||||
orf49a     KTEIEKLSKQPEYAYLKQLQVAKNINWNQVQLAYDRWDYKQEGLTEAGAAIIALAVTVVT
              160        170        180        190        200        210
```

```
                                      -continued
                      160        170
orf49.pep   SGAGTGAVLGLXRVAAAATDAAF
            ||||||||||| : ||||||||
orf49a      SGAGTGAVLGLNGAXAAATDAAFASLASQASVSFINNKGDVGKTLKELGRSSTVKNLVVA
                      220        230       240       250       260       270
```

ORF49-1 (SEQ ID NO:168) and ORF49a (SEQ ID NO:167) show 83.2% identity in 457 aa overlap:

```
orf49a.pep  XQLLAEEGIHKHELDVQKSRRFIGIKVGGXSNYSKNELNETKLPVRVVAQXAATRSGWDT
            |||| |||| :|:|:|||| ||||||||| |||||||||||||||||| :|:| ||||||
orf49-1     MQLLAAEGIHQHQLNVQKSTRFIGIKVGGKSNYSKNELNETKLPVRVIAQTAKTRSGWDT orf49a.pep  LEGTEFKTTLAGADIQAGVXEKARVDAKIILKGIVNRIQSEEKLETNSTVWQKQAGRGST
            |||||||||| |||||||| |||| ||||||||||||||| |||||:|||||||||| ||
orf49-1     LEGTEFKTTLSGADIQAGVGEKARADAKIILKGIVNRIQTEEKLESNSTVWQKQAGSGST orf49a.pep  IETLKLPSFESPTPPKLSAPGGYIVDIPKGNLKTEIEKLSKQPEYAYLKQLQVAKNINWN
            :|||||||||:|: ||| |||||:|||||||||||||||| ||||||||||||::|::|||
orf49-1     VETLKLPSFEGPALPKLTAPGGYIADIPKGNLKTEIEKLAKQPEYAYLKQLQTVKDVNWN orf49a.pep  QVQLAYDRWDYKQEGLTEAGAAIIALAVTVVTSGAGTGAVLGLNGAXAAATDAAFASLAS
            ||||||| :|||||||| ||||||||||||||| ||||||||||||| ||||||||||||
orf49-1     QVQLAYDKWDYKQEGLTGAGAAIIALAVTVVTSKAGTGAVLGLNGAAAAATDAAFASLAS orf49a.pep  QASVSFINNKGDVGKTLKELGRSSTVKNLVVAAATAGVADKIGASALXNVSDKQWINNLT
            ||||||||||:|::||||||||||||||||:||:||||||||||||| |||||||||||||
orf49-1     QASVSFINNKGNIGNTLKELGRSSTVKNLMVAVATAGVADKIGASALNNVSDKQWINNLT orf49a.pep  VNLANAGSAALINTAVNGGSLKDXLEANILAALVNTAHGEAASKIKQLDQHYIVHKIAHA
            ||||||||||||||||||||||||:|||||||||||||||||||||||||||||| |||| |
orf49-1     VNLANAGSAALINTAVNGGSLKDNLEANILAALVNTAHGEAASKIKQLDQHYIAHAGTVS orf49a.pep  IAGCAAAAANKGKCQDGAIGAAVGEIVGEALTNGKNPDTLTAKEREQILAYSKLVAGTVS
            ||||||||||||||||||||||||||:|||  :|::  :|::|:  :|:|  :||:||:
orf49-1     IAGCAAAAANKGKCQDGAIGAAVGEILGETLLDGRDPGSLNVKDRAKIIAKAKLAAGAVA orf49a.pep  GVVGGDVNAAANAAEVAVKNNQLSDXEGREFDNEMTACAKQNXPQLCRKNTVKKYQNVAD
            :: |||::||||| |||:|:| |  |  ::::::  |
orf49-1     ALSKGDVSTAANAAAVAVENNSLNDIQDRLLSGNYALCMSAGGAESFCESYRPLGLPHFV orf49a.pep  KRLAASIAICTDISRSTECRTIRKQHLIDSRSLHSSWEAGLIGKDDEWYKLFSKSYTQAD orf49-1     SVSGEMKLPNKFGNRMVNGKLIINTRNGNVYFSVGKIWSTVKSTKSNISGVSVGWVLNVS
```

The complete length ORF49a nucleotide sequence <SEQ ID 21> is:

```
  1 NTGCAACTGC TGGCAGAAGA AGGCATCCAC AAGCACGAGT TGGATGTCCA
 51 AAAAAGCCGC CGCTTTATCG GCATCAAGGT AGGTNAGAGC AATTACAGTA
101 AAAACGAACT GAACGAAACC AAATTGCCTG TCCGCGTCGT CGCCCAAANT
151 GCAGCCACCC GTTCAGGCTG GGATACCGTG CTCGAAGGTA CCGAATTCAA
201 AACCACGCTG GCCGGTGCCG ACATTCAGGC AGGTGTANGC GAAAAAGCCC
251 GTGTCGATGC GAAAATTATC CTCAAAGGCA TTGTGAACCG TATCCAGTCG
301 GAAGAAAAAT TAGAAACCAA CTCAACCGTA TGGCAGAAAC AGGCCGGACG
351 CGGCAGCACT ATCGAAACGC TAAAACTGCC CAGCTTCGAA AGCCCTACTC
401 CGCCCAAATT GTCCGCACCC GGCGGNTATA TCGTCGACAT TCCGAAAGGC
451 AATCTGAAAA CCGAAATCGA AAAGCTGTCC AAACAGCCCG AGTATGCCTA
501 TCTGAAACAG CTCCAAGTAG CGAAAAACAT CAACTGGAAT CAGGTGCAGC
551 TTGCTTACGA CAGATGGGAC TACAAACAGG AGGGCTTAAC CGAAGCAGGT
```

-continued

```
 601 GCGGCGATTA TCGCACTGGC CGTTACCGTG GTCACCTCAG GCGCAGGAAC

651 CGGAGCCGTA TTGGGATTAA ACGGTGCGNC CGCCGCCGCA ACCGATGCAG

701 CATTCGCCTC TTTGGCCAGC CAGGCTTCCG TATCGTTCAT CAACAACAAA

751 GGCGATGTCG GCAAAACCCT GAAAGAGCTG GCAGAAGCA GCACGGTGAA

801 AAATCTGGTG GTTGCCGCCG CTACCGCAGG CGTAGCCGAC AAAATCGGCG

851 CTTCGGCACT GANCAATGTC AGCGATAAGC AGTGGATCAA CAACCTGACC

901 GTCAACCTAG CCAATGCGGG CAGTGCCGCA CTGATTAATA CCGCTGTCAA

951 CGGCGGCAGC CTGAAAGACA NTCTGGAAGC GAATATCCTT GCGGCTTTGG

1001 TCAATACCGC GCATGGAGAA GCAGCCAGTA AAATCAAACA GTTGGATCAG

1051 CACTACATAG TCCACAAGAT TGCCCATGCC ATAGCGGGCT GTGCGGCAGC

1101 GGCGGCGAAT AAGGGCAAGT GTCAGGATGG TGCGATAGGT GCGGCTGTGG

1151 GCGAGATAGT CGGGGAGGCT TTGACAAACG GCAAAATCC TGACACTTTG

1201 ACAGCTAAAG AACGCGAACA GATTTTGGCA TACAGCAAAC TGGTTGCCGG

1251 TACGGTAAGC GGTGTGGTCG GCGGCGATGT AAATGCGGCG GCGAATGCGG

1301 CTGAGGTAGC GGTGAAAAAT AATCAGCTTA GCGACNAAGA GGGTAGAGAA

1351 TTTGATAACG AAATGACTGC ATGCGCCAAA CAGAATANTC CTCAACTGTG

1401 CAGAAAAAAT ACTGTAAAAA AGTATCAAAA TGTTGCTGAT AAAAGACTTG

1451 CTGCTTCGAT TGCAATATGT ACGGATATAT CCCGTAGTAC TGAATGTAGA

1501 ACAATCAGAA AACAACATTT GATCGATAGT AGAAGCCTTC ATTCATCTTG

1551 GGAAGCAGGT CTAATTGGTA AAGATGATGA ATGGTATAAA TTATTCAGCA

1601 AATCTTACAC CCAAGCAGAT TTGGCTTTAC AGTCTTATCA TTTGAATACT

1651 GCTGCTAAAT CTTGGCTTCA ATCGGGCAAT ACAAAGCCTT TATCCGAATG

1701 GATGTCCGAC CAAGGTTATA CACTTATTTC AGGAGTTAAT CCTAGATTCA

1751 TTCCAATACC AAGAGGGTTT GTAAAACAAA ATACACCTAT TACTAATGTC

1801 AAATACCCGG AAGGCATCAG TTTCGATACA AACCTANAAA GACATCTGGC

1851 AAATGCTGAT GGTTTTAGTC AAGAACAGGG CATTAAAGGA GCCCATAACC

1901 GCACCAATNT TATGGCAGAA CTAAATTCAC GAGGAGGANG NGTAAAATCT

1951 GAAACCCANA CTGATATTGA AGGCATTACC CGAATTAAAT ATGAGATTCC

2001 TACACTAGAC AGGACAGGTA AACCTGATGG TGGATTTAAG GAAATTTCAA

2051 GTATAAAAAC TGTTTATAAT CCTAAAAANT TTTNNGATGA TAAAATACTT

2101 CAAATGGCTC AANATGCTGN TTCACAAGGA TATTCAAAG CCTCTAAAAT

2151 TGCTCAAAAT GAAAGAACTA AATCAATATC GGAAAGAAAA AATGTCATTC

2201 AATTCTCAGA AACCTTTGAC GGAATCAAAT TTAGANNNTA TNTNGATGTA

2251 AATACAGGAA GAATTACAAA CATTCACCCA GAATAATTTA A
```

This encodes a protein having amino acid sequence <SEQ ID 22>:

```
  1  XQLLAEEGIH KHELDVQKSR RFIGIKVGXS NYSKNELNET KLPVRVVAQX
 51  AATRSGWDTV LEGTEFKTTL AGADIQAGVX EKARVOAKII LKGIVNRIQS
101  EEKLETNSTV WQKQAGRGST IETLKLPSFE SPTPPKLSAP GGYIVDIPKG
151  WLKTEIEKLS KQPEYAYLKQ LQVAKNIWWN QVQLAYDRWD YKQEGLTEAG
201  AAIIALAVTV VTSGAGTGAV LGLNGAXAAA TDAAFASLAS QASVSFINNK
251  GDVGKTLKEL GRSSTVKNLV VAAATAGVAD KIGASALXNV SDKQWINNLT
301  VNLANAGSAA LINTAVNGGS LKDXLEANIL AALVNTAHGE AASKIKQLDQ
351  HYIVHKIAHA IAGCAAAAAN KGKCQDGAIG AAVGEIVGEA LTNGKNPDTL
401  TAKEREQILA YSKLVAGTVS GVVGGDVNAA ANAAEVAVKN NQLSDXEGRE
451  FDNEMTACAK QNXPQLCRKN TVKKYQNVAD KRLAASIAIC TDISRSTECR
501  TIRKQHLIDS RSLHSSWEAG LIGKDDEWYK LESKSYTQAD LALQSYHLNT
551  AAKSWLQSGN TKPLSEWMSD QGYTLISGVN PREIPIPRGF VKQNTPITNV
601  KYPEGISFDT NLXRHLANAD GFSQEQGIKG AHNRTNXMAE LNSRGGXVKS
651  ETXTDIEGIT RIKYEIPTLD RTGKPDGGFK EISSIKTVYN PKXFXDDKIL
701  QMAQXAXSQG YSKASKIAQN ERTKSISERK NVIQFSETFD GIKFRXYXDV
751  NTGRITNIHP E*
```

Based on the presence of a putative transmembrane domain, it is predicted that these proteins from *N. meningitidis*, and their epitopes, could be useful antigens for vaccines or diagnostics.

Example 5

The following partial DNA sequence was identified in *N. meningitidis* <SEQ ID 23>

```
  1  ..CGGATCGTTG TAGGTTTGCG GATTTCTTGC GCCGTAGTCA CCGTAGTCCC
 51    AAGTATAACC CAAGGCTTTG TCTTCGCCTT TCATTCCGAT AAGGGATATG
101    ACGCTTTGGT CGGTATAGCC GTCTTGGGAA CCTTTGTCCA CCCAACGCAT
151    ATCTGCCTGC GGATTCTCAT TGCCGCTTCT TGGCTGCTGA TTTTTCTGCC
201    TTCGCGTTTT TCAACTTCGC GCTTGAGGGC TTCGGCATAT TTGTCGGCCA
251    ACGCCATTTC TTTCGGATGC AGCTGCCTAT TGTTCCAATC TACATTCGCA
301    CCCACCACAG CACCACCACT ACCACCAGTT GCATAG
```

This corresponds to the amino acid sequence <SEQ ID 24; ORF50>:

```
  1  ..RIVVGLRISC AVVTVVPSIT QGFVFAFHSD KGYDALVGIA VLGTFVHPTH
 51    ICLRILIAAS WLLIFLPSRF STSRLRASAY LSANAISFGC SCLLFQSTFA
101    PTTAPPLPPV A*
```

Computer analysis predicts two transmembrane domains and also indicates that ORF50 has no significant amino acid homology with known proteins.

Based on the presence of a putative transmembrane domain, it is predicted that this protein from *N. meningitidis*, and its epitopes, could be useful antigens for vaccines or diagnostics.

Example 6

The following partial DNA sequence was identified in *N. meningitidis* <SEQ ID 25>

```
   1  ..AAGTTTGACT TTACCTGGTT TATTCCGGCG GTAATCAAAT ACCGCCGGTT
  51    GTTTTTTGAA GTATTGGTGG TGTCGGTGGT GTTGCAGCTG TTTGCGCTGA
 101    TTACGCCTCT GTTTTTCCAA GTGGTGATGG ACAAGGTGCT GGTACATCGG
 151    GGATTCTCTA CTTTGGATGT GGTGTCGGTG GCTTTGTTGG TGGTGTCGCT
 201    GTTTGAGATT GTGTTGGGCG GTTTGCGGAC GTATCTGTTT GCACATACGA
 251    CTTCACGTAT TGATGTGGAA TTGGGCGCGC GTTTGTTCCG GCATCTGCTT
 301    TCCCTGCCTT TATCCTATTT CGAGCACAGA CGAGTGGGTG ATACGGTGGC
 351    TCGGGTGCGG GAATTGGAGC AGATTCGCAA TTTCTTGACC GGTCAGGCGC
 401    TGACTTCGGT GTTGGATTTG GCGTTTTCGT TTATCTTTCT GGCGGTGATG
 451    TGGTATTACA GCTCCACTCT GACTTGGGTG GTATTGGCTT CGTTG.....
                                  //
1451    .......... .......... .......... .......... ..........
1501    .......... .......... .......... .......... ..ATTTGCGC
1551    CAACCGGACG GTGCTGATTA TCGCCCACCG TCTGTCCACT GTTAAAACGG
1601    CACACCGGAT CATTGCCATG GATAAAGGCA GGATTGTGGA AGCGGGAACA
1651    CAGCAGGAAT TGCTGGCGAA CG..AACGGA TATTACCGCT ATCTGTATGA
1701    TTTACAGAAC GGGTAG
```

This corresponds to the amino acid sequence <SEQ ID 26; ORF39>:

```
   1  ..KFDFTWFIPA VIKYRRLFFE VLVVSVVLQL FALITPLFFQ VVMDKVLVHR
  51    GFSTLDVVSV ALLVVSLFEI VLGGLRTYLF AHTTSRIDVE LGARLFRHLL
 101    SLPLSYFEHR RVGDTVARVR ELEQIRNFLT GQALTSVLDL AFSFIFLAVM
 151    WYYSSTLTWV VLASL..... .......... .......... ..........
                                  //
 501    .......... ....ICANRT VLIIAHRLST VKTAHRIIAN DKGRIVEAGT
 551    QQELLANXNG YYRYLYDLQN G*
```

Further work revealed the complete nucleotide sequence <SEQ ID 27>:

```
   1  ATGTCTATCG TATCCGCACC GCTCCCCGCC CTTTCCGCCC TCATCATCCT
  51  CGCCCATTAC CACGGCATTG CCGCCAATCC TGCCGATATA CAGCATGAAT
 101  TTTGTACTTC CGCACAGAGC GATTTAAATG AAACGCAATG GCTGTTAGCC
```

-continued

```
 151 GCCAAATCTT TGGGATTGAA GGCAAAGGTA GTCCGCCAGC CTATTAAACG
 201 TTTGGCTATG GCGACTTTAC CCGCATTGGT ATGGTGTGAT GACGGCAACC
 251 ATTTCATTTT GGCCAAAACA GACGGTGAGG GTGAGCATGC CCAATTTTTG
 301 ATACAGGATT TGGTTACGAA TAAGTCTGCG GTATTGTCTT TTGCCGAATT
 351 TTCTAACAGA TATTCGGGCA AACTGATATT GGTTGCTTCC CGCGCTTCGG
 401 TATTGGGCAG TTTGGCAAAG TTTGACTTTA CCTGGTTTAT TCCGGCGGTA
 451 ATCAAATACC GCCGGTTGTT TTTTGAAGTA TTGGTGGTGT CGGTGGTGTT
 501 GCAGCTGTTT GCGCTGATTA CGCCTCTGTT TTTCCAAGTG GTGATGGACA
 551 AGGTGCTGGT ACATCGGGGA TTCTCTACTT TGGATGTGGT GTCGGTGGCT
 601 TTGTTGGTGG TGTCGCTGTT TGAGATTGTG TTGGGCGGTT GCGGACGTA
 651 TCTGTTTGCA CATACGACTT CACGTATTGA TGTGGAATTG GGCGCGCGTT
 701 TGTTCCGGCA TCTGCTTTCC CTGCCTTTAT CCTATTTCGA GCACAGACGA
 751 GTGGGTGATA CGGTGGCTCG GGTGCGGGAA TTGGAGCAGA TTCGCAATTT
 801 CTTGACCGGT CAGGCGCTGA CTTCGGTGTT GGATTTGGCG TTTTCGTTTA
 851 TCTTTCTGGC GGTGATGTGG TATTACAGCT CCACTCTGAC TTGGGTGGTA
 901 TTGGCTTCGT TGCCTGCCTA TGCGTTTTGG TCGGCATTTA TCAGTCCGAT
 951 ACTGCGGACG CGTCTGAACG ATAAGTTCGC GCGCAATGCA GACAACCAGT
1001 CGTTTTTAGT AGAAAGCATC ACTGCGGTGG GTACGGTAAA GGCGATGGCG
1051 GTGGAGCCGC AGATGACGCA GCGTTGGGAC AATCAGTTGG CGGCTTATGT
1101 GGCTTCGGGA TTTCGGGTAA CGAAGTTGGC GGTGGTCGGC CAGCAGGGGG
1151 TGCAGCTGAT TCAGAAGCTG GTGACGGTGG CGACGTTGTG GATTGGCGCA
1201 CGGCTGGTAA TTGAGAGCAA GCTGACGGTG GGGCAGCTGA TTGCGTTTAA
1251 TATGCTCTCG GGACAGGTGG CGGCGCCTGT TATCCGTTTG GCGCAGTTGT
1301 GGCAGGATTT CCAGCAGGTG GGGATTTCGG TGGCGCGTTT GGGGGATATT
1351 CTGAATGCGC CGACCGAGAA TGCGTCTTCG CATTTGGCTT TGCCCGATAT
1401 CCGGGGGGAG ATTACGTTCG AACATGTCGA TTTCCGCTAT AAGGCGGACG
1451 GCAGGCTGAT TTTGCAGGAT TTGAACCTGC GGATTCGGGC GGGGGAAGTG
1501 CTGGGGATTG TGGGACGTTC GGGGTCGGGC AAATCCACAC TCACCAAATT
1551 GGTGCAGCGT CTGTATGTAC CGGAGCAGGG ACGGGTGTTG GTGGACGGCA
1601 ACGATTGGC TTTGGCCGCT CCTGCCTGGC TGCGGCGGCA GGTCGGCGTG
1651 GTCTTGCAGG AGAATGTGCT GCTCAACCGC AGCATACGCG ACAATATCGC
1701 GCTGACGGAT ACGGGTATGC CGCTGGAACG CATTATCGAA GCAGCCAAAC
1751 TGGCGGGCGC ACACGAGTTT ATTATGGAGC TGCCGGAAGG CTACGGCACC
1801 GTGGTGGGCG AACAAGGGGC CGGCTTGTCG GGCGGACAGC GGCAGCGTAT
1851 TGCGATTGCC CGCGCGTTAA TCACCAATCC GCGCATTCTG ATTTTTGATG
1901 AAGCCACCAG CGCGCTGGAT TATGAAAGTG AACGAGCGAT TATGCAGAAC
1951 ATGCAGGCCA TTTGCGCCAA CCGGACGGTG CTGATTATCG CCCACCGTCT
2001 GTCCACTGTT AAAACGGCAC ACCGGATCAT TGCCATGGAT AAAGGCAGGA
2051 TTGTGGAAGC GGGAACACAG CAGGAATTGC TGGCGAAGCC GAACGGATAT
2101 TACCGCTATC TGTATGATTT ACAGAACGGG TAG
```

This corresponds to the amino acid sequence <SEQ ID 28; ORF39-1>:

```
  1 MSIVSAPLPA LSALIILAHY HGIAANPADI QHEFCTSAQS DLNETQWLLA

51 AKSLGLKAKV VRQPIKRLAM ATLPALVWCD DGNHFILAKT DGEGEHAQFL

101 IQDLVTNKSA VLSFAEFSNR YSGKLILVAS RASVLGSLAK FDFTWFIPAV

151 IKYRRLFFEV LVVSVVLQLF ALITPLFFQV VMDKVLVHRG FSTLDVVSVA

201 LLVVSLFEIV LGGLRTYLFA HTTSRIDVEL GARLFRHLLS LPLSYFEHRR

251 VGDTVARVRE LEQIRNFLTG QALTSVLDLA FSFIFLAVMW YYSSTLTWVV

301 LASLPAYAFW SAFISPILRT RLNDKFARNA DNQSFLVESI TAVGTVKAMA

351 VEPQMTQRWD NQLAAYVASG FRVTKLAVVG QQGVQLIQKL VTVATLWIGA

401 RLVIESKLTV GQLIAFNMLS GQVAAPVIRL AQLWQDFQQV GISVARLGDI

451 LNAPTENASS HLALPDIRGE ITFEHVDFRY KADGRLILQD LNLRIRAGEV

501 LGIVGRSGSG KSTLTKLVQR LYVPEQGRVL VDGNDLALAA PAWLRRQVGV

551 VLQEWVLLNR SIRDNIALTD TGMPLERIIE AAKLAGAHEF IMELPEGYGT

601 VVGEQGAGLS GGQRQRIAIA RALITNPRIL IFDEATSALD YESERAIMQN

651 MQAICANRTV LIIAHRLSTV KTAHRIIAMD KGRIVEAGTQ QELLAKPNGY

701 YRYLYDLQNG *
```

Computer analysis of this amino acid sequence gave the following results:

Homology with a Predicted ORF from *N. Meningitidis* (Strain A)

ORF39 (SEQ ID NO:169) shows 100% identity over a 165aa overlap with an ORF (ORF39a (SEQ ID NO:170)) from strain A of *N. meningitidis*:

```
                                   10        20        30
orf39.pep                 KFDFTWFIPAVIKYRRLFEEVLVVSVVLQL
                          ||||||||||||||||||||||||||||||
orf39a    AVLSFAEFSNRYSGKLILVASRASVLGSLAKFDFTWFIPAVIKYRRLFEEVLVVSVVLQL
                110       120       130       140       150       160

40        50        60        70        80        90
orf39.pep   FALITPLFFQVVMDKVLVHRGFSTLDVVSVALLVVSLFEIVLGGLRTYLFAHTTSRIDVE
            ||||||||||||||||||||||||||||||||||||||||||||||||||||||||||||
orf39a      FALITPLFFQVVMDKVLVHRGFSTLDVVSVALLVVSLFEIVLGGLRTYLFAHTTSRIDVE
                170       180       190       200       210       220

100       110       120       130       140       150
orf39.pep   LGARLFRHLLSLPLSYFEHRRVGDTCARVRELEQIRNFTLGQALTSVLDLAFSFIFLAVM
            ||||||||||||||||||||||||||||||||||||||||||||||||||||||||||||
orf39a      LGARLFRHLLSLPLSYFEHRRVGDTCARVRELEQIRNFTLGQALTSVLDLAFSFIFLAVM
                230       240       250       260       270       280

160       170       180       190       200       210
orf39.pep   WYYSSTLTWVVLASLXXXXXXXXXXXXXXXXXXXXXXXXXXXXXXICANRTVLIIAHRLSTV
            |||||||||||||||
orf39a      WYYSSTLTWVVLASLPAYAFWSAFISPILRTRLNDKFARNADNQSFLVESITAVGTVKAM
                290       300       310       320       330       340
```

ORF39-1 (SEQ ID NO:28) and ORF39a (SEQ ID NO:30) show 99.4% identity in 710 aa overlap:

```
orf39-1.pep    MSIVSAPLPALSALIILAHYHGIAANPADIQHEFCTSAQSDLNETQWLLAAKSLGLKAKV
               ||||||||||||||||||||||||||||||||||||||||||||||||||||||||||||
orf39a         MSIVSAPLPALSALIILAHYHGIAANPADIQHEFCTSAQSDLNETQWLLAAKSLGLKAKV orf39-1.pep    VRQPIKRLAMATLPALVWCDDGNHFILAKTDGEGEHAQFLIQDLVTNKSAVLSFAEFSNR
               |||||||||||||||||||||||||||||||||||:||||:||||||||||||||||||
orf39a         VRQPIKRLAMATLPALVWCDDGNHFILAKTDGGGEHAQYLIQDLTTNKSAVLSFAEFSNR orf39-1.pep    YSGKLILVASRASVLGSLAKFDFTWVIPAVIKYRRLFFEVLVVSVVLQLFALITPLFFQV
               ||||||||||||||||||||||||||||||||||||||||||||||||||||||||||||
orf39a         YSGKLILVASRASVLGSLAKFDFTWVIPAVIKYRRLFFEVLVVSVVLQLFALITPLFFQV orf39-1.pep    VMDKVLVHRGFSTLDVVSVALLVVSLFEIVLGGLRTYLFAHTTSRIDVELGARLFRHLLS
               ||||||||||||||||||||||||||||||||||||||||||||||||||||||||||||
orf39a         VMDKVLVHRGFSTLDVVSVALLVVSLFEIVLGGLRTYLFAHTTSRIDVELGARLFRHLLS orf39-1.pep    LPLSYFEHRRVGDTVARVRELEQIRNFLTGQALTSVLDLAFSFIFLAVMWYYSSTLTWVV
               ||||||||||||||||||||||||||||||||||||||||||||||||||||||||||||
orf39a         LPLSYFEHRRVGDTVARVRELEQIRNFLTGQALTSVLDLAFSFIFLAVMWYYSSTLTWVV orf39-1.pep    LASLPAYAFWSAFISPILRTRLNDKFARNADNQSFLVESITAVGTVKAMAVEPQMTQRWD
               ||||||||||||||||||||||||||||||||||||||||||||||||||||||||||||
orf39a         LASLPAYAFWSAFISPILRTRLNDKFARNADNQSFLVESITAVGTVKAMAVEPQMTQRWD orf39-1.pep    NQLAAYVASGFRVTKLAVVGQQGVQLIQKLVTVATLWIGARLVIESKLTVGQLIAFNMLS
               ||||||||||||||||||||||||||||||||||||||||||||||||||||||||||||
orf39a         NQLAAYVASGFRVTKLAVVGQQGVQLIQKLVTVATLWIGARLVIESKLTVGQLIAFNMLS orf39-1.pep    GQVAAPVIRLAQLWQDFQQVGISVARLGDILNAPTENASSHLALPDIRGEITFEHVDFRY
               ||||||||||||||||||||||||||||||||||||||||||||||||||||||||||||
orf39a         GQVAAPVIRLAQLWQDFQQVGISVARLGDILNAPTENASSHLALPDIRGEITFEHVDFRY orf39-1.pep    KADGRLILQDLNLRIRAGEVLGIVGRSGSGKSTLTKLVQRLYVPEQGRVLVDGNDLALAA
               |||||||||||||||||||||||||||||||||||||||||||| |||||||||||||||
orf39a         KADGRLILQDLNLRIRAGEVLGIVGRSGSGKSTLTKLVQRLYVPAQGRVLVDGNDLALAA orf39-1.pep    PAWLRRQVGVVLQENVLLNRSIRDNIALTDTGMPLERIIEAAKLAGAHEFIMELPEGYGT
               ||||||||||||||||||||||||||||||||||||||||||||||||||||||||||||
orf39a         PAWLRRQVGVVLQENVLLNRSIRDNIALTDTGMPLERIIEAAKLAGAHEFIMELPEGYGT orf39-1.pep    VVGEQGAGLSGGQRQRIAIARALITNPRILIFDEATSALDYESERAIMQNMQAICANRTV
               ||||||||||||||||||||||||||||||||||||||||||||||||||||||||||||
orf39a         VVGEQGAGLSGGQRQRIAIARALITNPRILIFDEATSALDYESERAIMQNMQAICANRTV orf39-1.pep    LIIAHRLSTVKTAHRIIAMDKGRIVEAGTQQELLAKPNGYYRYLYDLQNGX
               ||||||||||||||||||||||||||||||||||||||||||||||||||
orf39a         LIIAHRLSTVKTAHRIIAMDKGRIVEAGTQQELLAKPNGYYRYLYDLQNGX
```

The complete length ORF39a nucleotide sequence <SEQ ID 29> is:

```
  1  ATGTCTATCG TATCCGCACC GCTCCCCGCC CTTTCCGCCC TCATCATCCT
 51  CGCCCATTAC CACGGCATTG CCGCCAATCC TGCCGATATA CAGCATGAAT
101  TTTGTACTTC CGCACAGAGC GATTTAAATG AAACGCAATG GCTGTTAGCC
151  GCCAAATCTT TGGGATTGAA GGCAAAGGTA GTCCGCCAGC CTATTAAACG
201  TTTGGCTATG GCGACTTTAC CCGCATTGGT ATGGTGTGAT GACGGCAACC
251  ATTTTATTTT GGCTAAAACA GACGGTGGGG GTGAGCATGC CCAATATCTA
301  ATACAGGATT AACTACGAA TAAGTCTGCG GTATTGTCTT TTGCCGAATT
351  TTCTAACAGA TATTCGGGCA AACTGATATT GGTTGCTTCC CGCGCTTCGG
401  TATTGGGCAG TTTGGCAAAG TTTGACTTTA CCTGGTTTAT TCCGGCGGTA
```

```
 451 ATCAAATACC GCCGGTTGTT TTTTGAAGTA TTGGTGGTGT CGGTGGTGTT

501 GCAGCTGTTT GCGCTGATTA CGCCTCTGTT TTTCCAAGTG GTGATGGACA

551 AGGTGCTGGT ACATCGGGGA TTCTCTACTT GGATGTGGT GTCGGTGGCT

601 TTGTTGGTGG TGTCGCTGTT TGAGATTGTG TTGGGCGGTT TGCGGACGTA

651 TCTGTTTGCA CATACGACTT CACGTATTGA TGTGGAATTG GGCGCGCGTT

701 TGTTCCGGCA TCTGCTTTCC CTGCCTTTAT CCTATTTCGA GCACAGACGA

751 GTGGGTGATA CGGTGGCTCG GGTGCGGGAA TTGGAGCAGA TTCGCAATTT

801 CTTGACCGGT CAGGCGCTGA CTTCGGTGTT GGATTTGGCG TTTTCGTTTA

851 TCTTTCTGGC GGTGATGTGG TATTACAGCT CCACTCTGAC TTGGGTGGTA

901 TTGGCTTCGT TGCCTGCCTA TGCGTTTTGG TCGGCATTTA TCAGTCCGAT

951 ACTGCGGACG CGTCTGAACG ATAAGTTCGC GCGCAATGCA GACAACCAGT

1001 CGTTTTTAGT AGAAAGCATC ACTGCGGTGG GTACGGTAAA GGCGATGGCG

1051 GTGGAGCCGC AGATGACGCA GCGTTGGGAC AATCAGTTGG CGGCTTATGT

1101 GGCTTCGGGA TTTCGGGTAA CGAAGTTGGC GGTGGTCGGC CAGCAGGGGG

1151 TGCAGCTGAT TCAGAAGCTG GTGACGGTGG CGACGTTGTG GATTGGCGCA

1201 CGGCTGGTAA TTGAGAGCAA GCTGACGGTG GGGCAGCTGA TTGCGTTTAA

1251 TATGCTCTCG GGACAGGTGG CGGCGCCTGT TATCCGTTTG GCGCAGTTGT

1301 GGCAGGATTT CCAGCAGGTG GGGATTTCGG TGGCGCGTTT GGGGGATATT

1351 CTGAATGCGC CGACCGAGAA TGCGTCTTCG CATTTGGCTT TGCCCGATAT

1401 CCGGGGGGAG ATTACGTTCG AACATGTCGA TTTCCGCTAT AAGGCGGACG

1451 GCAGGCTGAT TTTGCAGGAT TTGAACCTGC GGATTCGGGC GGGGGAAGTG

1501 CTGGGGATTG TGGGACGTTC GGGGTCGGGC AAATCCACAC TCACCAAATT

1551 GGTGCAGCGT CTGTATGTAC CGGCGCAGGG ACGGGTGTTG GTGGACGGCA

1601 ACGATTTGGC TTTGGCCGCT CCTGCTTGGC TGCGGCGGCA GGTCGGCGTG

1651 GTCTTGCAGG AGAATGTGCT GCTCAACCGC AGCATACGCG ACAATATCGC

1701 GCTGACGGAT ACGGGTATGC CGCTGGAACG CATTATCGAA GCAGCCAAAC

1751 TGGCGGGCGC ACACGAGTTT ATTATGGAGC TGCCGGAAGG CTACGGCACC

1801 GTGGTGGGCG AACAAGGGGC CGGCTTGTCG GGCGGACAGC GGCAGCGTAT

1851 TGCGATTGCC CGCGCGTTAA TCACCAATCC GCGCATTCTG ATTTTTGATG

1901 AAGCCACCAG CGCGCTGGAT TATGAAAGTG AACGAGCGAT TATGCAGAAC

1951 ATGCAGGCCA TTTGCGCCAA CCGGACGGTG CTGATTATCG CCCACCGTCT

2001 GTCCACTGTT AAAACGGCAC ACCGGATCAT TGCCATGGAT AAAGGCAGGA

2051 TTGTGGAAGC GGGAACACAG CAGGAATTGC TGGCGAAGCC GAACGGATAT

2101 TACCGCTATC TGTATGATTT ACAGAACGGG TAG
```

This encodes a protein having amino acid sequence <SEQ ID 30>:

```
  1 MSIVSAPLPA LSALIILAHY HGIAANPADI QHEFCTSAQS DLNETQWLLA

51 AKSLGLKAKV VRQPIKRLAM ATLPALVWCD DGNHFILAKT DGGGEHAQYL
```

-continued

```
101 IQDLTTNKSA VLSFAEFSNR YSGKLILVAS RASVLGSLAK FDFTWFIPAV

151 IKYRRLFFEV LVVSVVLQLF ALITPLFFQV VMDKVLVHRG FSTLDVVSVA

201 LLVVSLFEIV LGGLRTYLFA HTTSRIDVEL GARLFRHLLS LPLSYFEHRR

251 VGDTVARVRE LEQIRNFLTG QALTSVLDLA FSFIFLAVMW YYSSTLTWVV

301 LASLPAYAFW SAFISPILRT RLNDKFARNA DNQSFLVESI TAVGTVKAMA

351 VEPQMTQRWD NQLAAYVASG FRVTKLAVVG QQGVQLIQKL VTVATLWIGA

401 RLVIESKLTV GQLIAFNMLS GQVAAPVIRL AQLWQDFQQV GISVARLGDI

451 LNAPTENASS HLALPDIRGE ITFEEVDFRY KADGRLILQD LNLRIRAGEV

501 LGIVGRSGSG KSTLTKLVQR LYVPAQGRVL VDGNDLALAA PAWLRRQVGV

551 VLQENVLLNR SIRDNIALTD TGMPLERIIE AAKLAGAHEF IMELPEGYGT

601 VVGEQGAGLS GGQRQRIAIA RALITNPRIL IFDEATSALD YESERAIMQN

651 MQAICANRTV LIIAHRLSTV KTAHRIIAMD KGRIVEAGTQ QELLAKPNGY

701 YRYLYDLQNG *
```

ORF39a is homologous to a cytolysin from *A. pleuropneumoniae*:

```
sp|P26760|RT1B_ACTPL RTX-I TOXIN DETERMINANT B (TOXIN RTX-I SECRETION ATP-
BINDING PROTEIN) (APX-IB) (HLY-IB) (CYTOLYSIN IB) (CLY-IB)
>gi|97137|pir||D43599 cytolysin IB - Actinobacillus pleuropneumoniae (serotype 9)
>GI|38944 (x61112) ClyI-B protein [Actinobacillus pleuropneumoniae] Length = 707
Score = 931 bits (2379), Expect = 0.0
Identities = 472/690 (68%), Positives = 540/690 (77%), Gaps = 3/690 (0%)

Query:   20 YHGIAANPADIQHEFCTSAQSDLNETQWXXXXXXXXXXXXVVRQPIKRLAMATLPALVWC   79
            YH  IA NP +++H+F    +   L+ T W            V++ I RLA   LPALVW
Sbjct:   20 YHNIAVNPEELKHKFDLEGKG-LDLTAWLLAAKSLELKAKQVKKAIDRLAFIALPALVWR   78

Query:   80 DDGNHFILAKTDGGGEHAQYLIQDLTTNKSAVLSFAEFSNRYSGKLILVASRASVLGSLA  139
            +DG HFIL K D   E +YLI DL T+   +L  AEF + Y GKLILVASRAS++G LA
Sbjct:   79 EDGKHFILTKIDN--EAAKYLIFDLETHNPRILEQAEFESLYQGKLILVASRASIVGKLA  136

Query:  140 KFDFTWFIPAVIKYRRXXXXXXXXXXXXXXXXXXITPLFFQVVMDKVLVHRGFXXXXXXX  199
            KFDFTWFIPAVIKYR+                  ITPLFFQVVMDKVLVHRGF
Sbjct:  137 KFDFTWFIPAVIKYRKIFIETLIVSIFLQIFALITPLFFQVVMDKVLVHRGFSTLNVITV  196

Query:  260 ELEQIRNFLTGQALTSVLDLAFSFIFLAVMWYYSSTLTWVVLASLPAYAFWSAFISPILR  319
            EL+QIRNFLTGQALTSVLDL FSFIF AVMWYYS  LT V+L SLP Y  WS FISPILR
Sbjct:  257 ELDQIRNFLTGQALTSVLDLMFSFIFLAVMWYYSPKLTLVILGSLPFYMGWSIFISPILR  316

Query:  260 TRLNDKFARNADNQSFLVESITAVGTVKAMAVEPQMTQRWDNQLAAYVASGFRVTKLAVV  319
            RL++KFAR ADNQSFLVES+TA+  T+KA+AV PQMT  WD QLA+YV++GFRVT LA +
Sbjct:  257 RRLDEKFARGADNQSFLVESVTAIGTVKAMAVTPQMTNTWDKQLASYVSAGFRVTTLATI  316

Query:  380 GQQGVQLIQKLVTVATLWIGARLVIESKLTVGQLIAFNMLSGQVAAPVIRLAQLWQDFQQ  439
            GQQGVQ IQK+V V TLW+GA LVI    L++GQLIAFNMLSGQV APVIRLAQLWQDFQQ
Sbjct:  377 GQQGVQFIQKVVMVITLWLGAHLVISGDLSIGQLIAFNMLSGQVIAPVIRLAQLWQDFQQ  436

Query:  440 VGISVARLGDILNAPTENASSHLALPDIRGEITFEHVDFRYKADGRLILQDLNLRIRAGE  499
            VGISV RLGD+LN PTE+    LALP+I+G+ITF ++ FRYK D    +IL D+NL I+ GE
Sbjct:  437 VGISVTRLGDVLNSPTESYQGKLALPEIKGDITFRNIRFRYKPDAPVILNDVNLSIQQGE  496

Query:  500 VLGIVGRSGSGKSTLTKLVQRLYVPAQGRVLVDGNDLALAAPAWLRRQVGVVLQENVLLN  559
            V+GIVGRSGSGKSTLTKL+QR Y+P  G+VL+DG+DLALA P WLRRQVGVVLQ+NVLLN
Sbjct:  497 VIGIVGRSGSGKSTLTKLIQRFYIPENGQVLIDGHDLALADPNWLRRQVGVVLQDNVLLN  556

Query:  560 RSIRDNIALTDTGMPLERIIEAAKLAGAHEFIMELPEGYGTVVGEQGAGLSGGQRQRIAI  619
            RSIRDNIAL D GMP+E+I  AAKLAGAHEFI EL EGY T+VGEQGAGLSGGQRQRIAI
Sbjct:  557 RSIRDNIALADPGMPMEKIVHAAKLAGAHEFISELREGYNTIVGEQGAGLSGGQRQRIAI  616

Query:  620 ARALITNPRILIFDEATSALDYESERAIMQNMQAICANRTVLIIAHRLSTVKTAHRIIAM  679
            ARAL+ NP+ILIFDEATSALDYESE  IM+NM  IC  RTV+IIAHRLSTVK A RII M
Sbjct:  617 ARALVNNPKILIFDEATSALDYESEHIIMQNMHQICKGRTVIIIAHRLSTVKNADRIIVM  676
```

-continued

```
Query:  680  DKGRIVEAGTQQELLAKPNGYYRYLYDLQN                        709 (SEQ ID NO:171)
             +KG+IVE G  +ELLA PNG Y YL+ LQ+                            (SEQ ID NO:172)
Sbjct:  677  EKGQIVEQGKHKELLADPNGLYHYLHQLQS                        706 (SEQ ID NO:173)
```

Homology with the HlyB Leucotoxin Secretion ATP-Binding Protein of *Haemophilus actinomycetemcomitans* (Accession Number X53955)

ORF39 (SEQ ID NO:174) and HlyB (SEQ ID NO:176) protein show 71% and 69% amino acid identity (SEQ ID NO:175) in 167 and 55 overlap at the N- and C-terminal regions, respectively:

```
Orf39    1 KFDFTWFIPAVIKYRRXXXXXXXXXXXXXXXXXITPLFFQVVMDKVLVHRGFXXXXXXXX   60
           KFDFTWFIPAVIKYR+                 ITPLPTQVVMDKVLVHRGF
HlyB   137 KFDFTWFIPAVIKYRKIFIETLIVSIFLQIFALITPLFFQVVMDKVLVHRGFSTLNVITV  196

Orf39   61 XXXXXXXFEIVLGGLRTYLFAHTTSRIDVELGARLFRHLLSLPLSYFEHRRVGDTVARVR  120
                  FEI+LGGLRTY+FAH+TSRIDVELGARLFRHLL+LP+SYFE RRVGDTVARVR
HlyB   197 ALAIVVLFEIILGGLRTYVFAHSTSRIDVELGARLFRHLLALPISYFEARRVGDTVARAR

Orf39  121 ELEQIRNFLTGQALTSVLDLAFSFIFLAVMWYYSSTLTWVVLASLIC              167
           EL+QIRNFLTGQALTS+LDL FSFIF AVMWYYS  LT VVL SL C
HlyB   257 ELDQIRNFLTGQALTSILDLLFSFIFFAVMWYYSPKLTLVVLGSLPC              303
                                          //
Orf39  166 ICANRTVLIIAHRLSTVKTAHRIIAMDKGRIVEAGTQQELLANXNGYYRYLYDLQ      220
           IC NRTVLIIAHRLSTVK A RII MDKG I+E G  QELL +  G Y YL+ LQ
HlyB   651 ICQNRTVLIIAHRLSTVKNADRIIVMDKGEIIEQGKHQELLKDEKGLYSYLHQLQ      705
```

Based on this analysis, it is predicted that this protein from *N. meningitidis*, and its epitopes, could be useful antigens for vaccines or diagnostics.

Example 7

The following partial DNA sequence was identified in *N. meningitidis* <SEQ ID 31>

```
  1 ATGAAATACT TGATCCGCAC CGCCTTACTC GCAGTCGCAG CCGCCGGCAT
 51 CTACGCCTGC CAACCGCAAT CCGAAGCCGC AGTGCAAGTC AAGGCTGAAA
101 ACAGCCTGAC CGCTATGCGC TTAGCCGTCG CCGACAAACA GGCAGAGATT
151 GACGGGTTGA ACGCCCAAAk sGACGCCGAA ATCAGA...
```

This corresponds to the amino acid sequence <SEQ ID 32; ORF52>:

```
  1 MKYLIRTALL AVAAAGIYAC QPQSEAAVQV KAENSLTAMR LAVADKQAEI
 51 DGLNAQXDAE IR..
```

Further work revealed the complete nucleotide sequence <SEQ ID 33>:

```
  1 ATGAAATACT TGATCCGCAC CGCCTTACTC GCAGTCGCAG CCGCCGGCAT
 51 CTACGCCTGC CAACCGCAAT CCGAAGCCGC AGTGCAAGTC AAGGCTGAAA
101 ACAGCCTGAC CGCTATGCGC TTAGCCGTCG CCGACAAACA GGCAGAGATT
151 GACGGGTTGA ACGCCCAAAT CGACGCCGAA ATCAGACAAC GCGAAGCCGA
201 AGAATTGAAA GACTACCGAT GGATACACGG CGACGCGGAA GTGCCGGAGC
251 TGGAAAAATG A
```

This corresponds to the amino acid sequence <SEQ ID 34; ORF52-1>:

```
 1 MKYLIRTALL AVAAAGIYAC QPQSEAAVQV KAENSLTAMR LAVADKQAEI
51 DGLNAQIDAE IRQREAEELK DYRWIHGDAE VPELEK*
```

Computer analysis of this amino acid sequence predicts a prokaryotic membrane lipoprotein lipid attachment site (underlined).

Figure 4A:
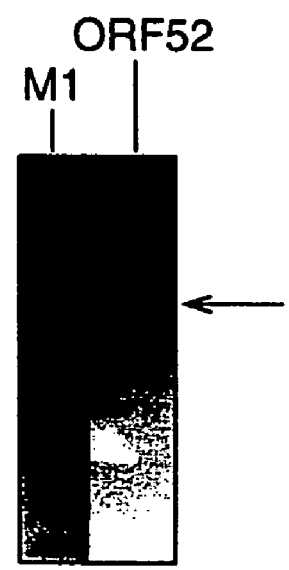
FIG. 4A shows the results of affinity purification of ORF 52, where M1 is a molecular weight marker, and the arrow indicates the position of the main recombinant product.
Figure 4B:
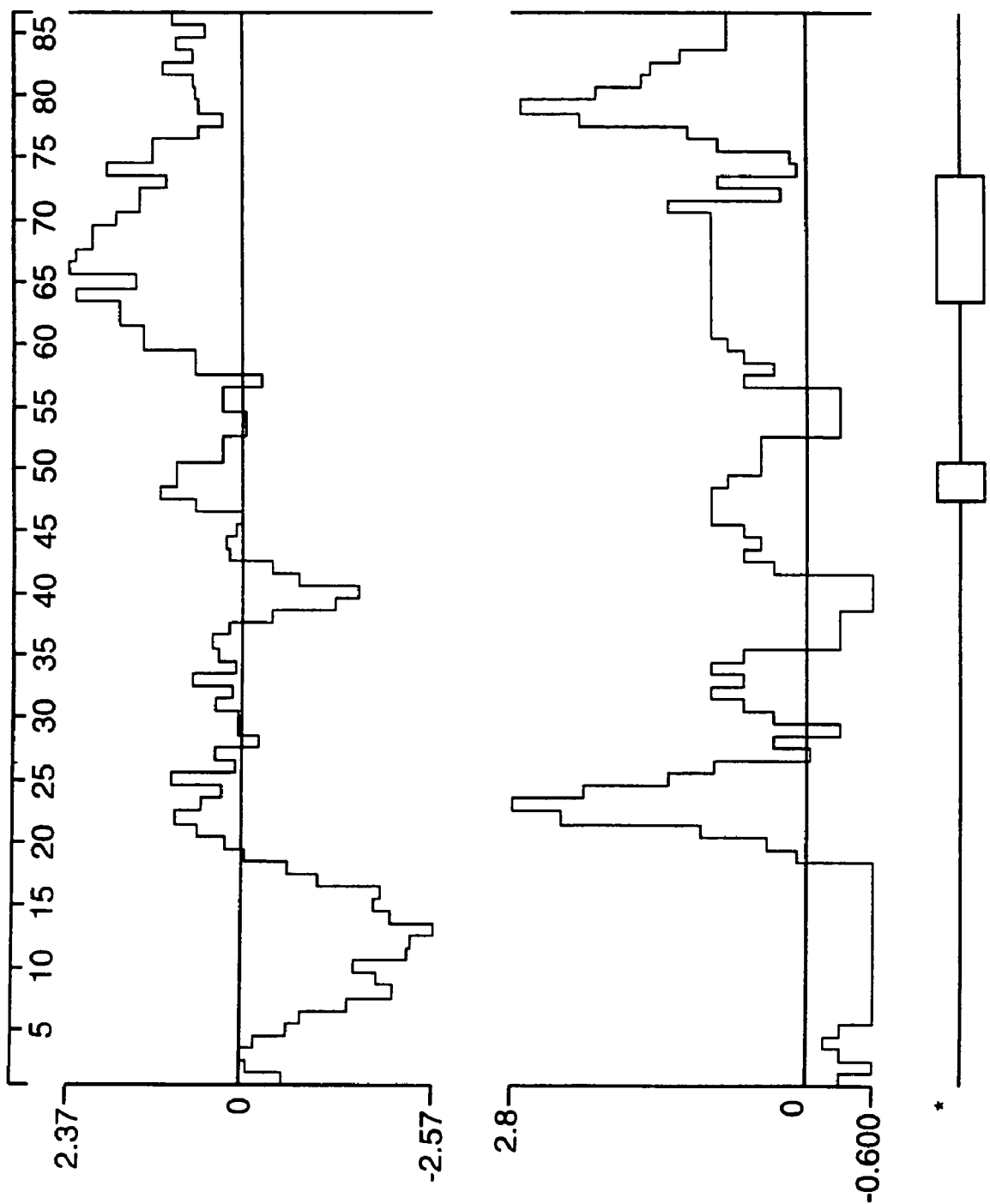
FIG. 4B shows a hydrophilicity plot (upper), an antigenic index plot (middle), and an AMPHI analysis (lower).

ORF52-1 (7 kDa) was cloned in the pGex vectors and expressed in *E. coli*, as described above. The products of protein expression and purification were analyzed by SDS-PAGE. FIG. 4A shows the results of affinity purification of the GST-fusion. FIG. 4B shows plots of hydrophilicity, antigenic index, and AMPHI regions for ORF52-1.

Based on this analysis, it is predicted that this protein from *N. meningitidis*, and its epitopes, could be useful antigens for vaccines or diagnostics.

Example 8

The following DNA sequence was identified in *N. meningitidis* <SEQ ID 35>

```
  1 ATGGTTATCG GAATATTACT CGCATCAAGC AAGCATGCTC TTGTCATTAC
 51 TCTATTGTTA AATCCCGTCT TCCATGCATC CAGTTGCGTA TCGCGTTsGG
101 CAATACGGAA TAAAAtCTGC TGTTCTGCTT TGGCTAAATT TGCCAAATTG
151 TTTATTGTTT CTTTAGGaGC AGCTTGCTTA GCCGCCTTCG CTTTCGACAA
201 CGCCCCCACA GGCGCTTCCC AAGCgTTGCC TACCGTTACC GCACCCGTGG
251 CGATTCCCGC GCCCGCTTCG GCAGCCTGA
```

This corresponds to the amino acid sequence <SEQ ID 36; ORF56>:

```
 1 MVIGILLASS KHALVITLLL NPVFHASSCV SRXAIRNKIC CSALAKFAKL
51 FIVSLGAACL AAFAFDNAPT GASQALPTVT APVAIPAPAS AA*
```

Further work revealed the complete nucleotide sequence <SEQ ID 37>:

```
  1 ATGGCTTGTA CAGGTTTGAT GGTTTTTCCG TTAATGGTTA TCGGAATATT

51 ACTTGCATCA AGCAAGCCTG CTCCTTTCCT TACTCTATTG TTAAATCCCG

101 TCTTCCATGC ATCCAGTTCC GTATCGCGTT GGGCAATACG GAATAAAATC

151 TGCTGTTCTG CTTTGGCTAA ATTTGCCAAA TTGTTTATTG TTTCTTTAGG

201 AGCAGCTTGC TTAGCCGCCT TCGCTTTCGA CAACGCCCCC ACAGGCGCTT

251 CCCAAGCGTT GCCTACCGTT ACCGCACCCG TGGCGATTCC CGCGCCCGCT

301 TCGGCAGCCT GA
```

This corresponds to the amino acid sequence <SEQ ID 38; ORF56-1>:

```
  1 MACTGLMVFP LMVICILLAS SKPAPFLTLL LNPVFHASSC VSRWAIRNKI

51 CCSALAKFAK LFIVSLGAAC LAAFAEDNAP TGASQALPTV TAPVAIPAPA

101 SAA*
```

Computer analysis of this amino acid sequence predicts a leader peptide (underlined) and suggests that ORF56 might be a membrane or periplasmic protein.

Based on this analysis, it is predicted that this protein from *N. meningitidis*, and its epitopes, could be useful antigens for vaccines or diagnostics.

Example 9

The following partial DNA sequence was identified in *N. meningitidis* <SEQ ID 39>

```
  1 ATGTTCAGTA TTTTAAATGT GTTTTTCCAT TGTATTCTGG CTTGTGTAGT
 51 CTCTGGTGAG ACGCCTACTA TATTTGGTAT CCTTGCTCTT TTTTACTTAT
101 TGTATCTTTC TTATCTTGCT GTTTTTAAGA TTTTCTTTTC TTTTTTCTTA
151 GACAGAGTTT CACTCCGGTC TCCCAGGCTG GAGTGCAAAT GGCATGACCC
201 TTTGGCTCAC TGGCTCACGG CCACTTCTGC TATTCTGCCG CCTCAGCCTC
251 CAGGG...
```

This corresponds to the amino acid sequence <SEQ ID 40; ORF63>:

```
 1 MFSILNVFLH CILACVVSGE TPTIFGILAL FYLLYLSYLA VFKIFFSFFL
51 DRVSLRSPRL ECKWHDPLAH WLTATSAILP PQPPG...
```

Computer analysis of this amino acid sequence predicts a transmembrane region.

Based on this analysis, it is predicted that this protein from *N. meningitidis*, and its epitopes, could be useful antigens for vaccines or diagnostics.

Example 10

The following partial DNA sequence was identified in *N. meningitidis* <SEQ ID 41>

```
  1 . . . GTGCGGACGT GGTTGGTTTT TTGGTTGCAG CGTTTGAAAT ACCCGTTGTT

51       GCTTTGGATT GCGGATATGT TGCTGTACCG GTTGTTGGGC GGCGCGGAAA

101       TCGAATGCGG CCGTTGCCCT GTGCCGCCGA TGACGGATTG GCAGCATTTT

151       TTGCCGGCGA TGGGAACGGT GTCGGCTTGG GTGGCGGTGA TTTGGGCATA

201       CCTGATGATT GAAAGTGAAA AAAACGGAAG ATATTGA
```

This corresponds to the amino acid sequence <SEQ ID 42; ORF69>:

```
 1 . . . VRTWLVFWLQ RLKYPLLLWI ADMLLYRLLG GAEIECGRCP VPPMTDWQHF

51       LPAMGTVSAW VAVIWAYLMI ESEKNGRY*
```

Computer analysis of this amino acid sequence predicts a transmembrane region.

A corresponding ORF from strain A of *N. meningitidis* was also identified:

Homology with a Predicted ORF from *N. meningitidis* (Strain A)

ORF69 (SEQ ID NO:42) shows 96.2% identity over a 78aa overlap with an ORF (ORF69a (SEQ ID NO:44)) from strain A of *N. meningitidis*:

```
                    10        20        30        40        50        60
orf69.pep   VRTWLVFWLQRLKYPLLLWIADMLLYRLLGGAEIECGRCPVPPMTDWQHFLPAMGTVSAW
            |||||||||||||||||| |||||||||||||||||||||||||||||||||:||||:||
orf69a      VRTWLVFWLQRLKYPLLLCIADMLLYRLLGGAEIECGRCPVPPMTDWQHFLPTMGTVAAW
                    10        20        30        40        50        60

70        79
orf69.pep   VAVIWAYLMIESEKNGRYX
            |||||||||||||||||||
orf69a      VAVIWAYLMIESEKNGRYX
                    70
```

The ORF69a nucleotide sequence <SEQ ID 43> is:

```
  1 GTGCGGACGT GGTTGGTTTT TTGGTTGCAG CGTTTGAAAT ACCCGTTGTT

51 GCTTTGTATT GCGGATATGC TGCTGTACCG GTTGTTGGGC GGCGCGGAAA

101 TCGAATGCGG CCGTTGCCCT GTACCGCCGA TGACGGATTG GCAGCATTTT

151 TTGCCGACGA TGGGAACGGT GGCGGCTTGG GTGGCGGTGA TTTGGGCATA

201 CCTGATGATT GAAAGTGAAA AAAACGGAAG ATATTGA
```

This encodes a protein having amino acid sequence <SEQ ID 44>:

```
  1 VRTWLVFWLQ RLKYPLLLCI ADMLLYRLLG GAEIECGRCP VPPMTDWQHF
 53 LPTMGTVAAW VAVIWAYLMI ESEKNGRY*
```

Based on this analysis, it is predicted that this protein from *N. meningitidis*, and its epitopes, could be useful antigens for vaccines or diagnostics.

Example 11

The following DNA sequence was identified in *N. meningitidis* <SEQ ID 45>

```
  1 ATGTTTCAAA ATTTTGATTT GGGCGTGTTC CTGCTTGCCG TCCTCCCCGT
 51 GCTGCCCTCC ATTACCGTCT CGCACGTGGC GCGCGGCTAT ACGGCGCGCT
101 ACTGGGGAGA CAACACTGCC GAACAATACG GCAGGCTGAC ACTGAACCCC
151 CTGCCCCATA TCGATTTGGT CGGCACAATC ATCgTACCGC TGCTTACTTT
201 GATGTTCACG CCCTTCCTGT TCGGCTGGGC GCGTCCGATT CCTATCGATT
251 CGCGCAACTT CCGCAACCCG cGCCTTGCCT GGCGTTGCGT TGCCGCGTCC
301 GGCCCGCTGT CGAATCTAGC GATGGCTGTw CTGTGGGGCG TGGTTTTGGT
351 GCTGACTCCG TATGTCGGCG GGGCGTATCA GATGCCGTTG GCTCAAATGG
401 CAAACTACGG TATTCTGATC AATGCGATTC TGTTCGCGCT CAACATCATC
451 CCCATCCTGC CTTGGGACGG CGGCATTTTC ATCGACACCT TCCTGTCGGC
501 GAAATATTCG CAAGCGTTCC GCAAAATCGA ACCTTATGGG ACGTGGATTA
551 TCCTACTGCT GATGCTGACC sGGGTTTTGG GTGCGTTTAT wGCACCGATT
601 sTGCGGmTGc GTGATTGCrT TTGTGCAGAT GTwCGTCTGA CTGGCTTTCA
651 GACGGCATAA
```

This corresponds to the amino acid sequence <SEQ ID 46; ORF77>:

```
  1 MFQNFDLGVF LLAVLPVLPS ITVSHVARGY TARYWGDNTA EQYGRLTLNP
 51 LPHIDLVGTI IVPLLTLMFT PFLFGWARPI PIDSRNFRNP RLAWRCVAAS
101 GPLSNLAMAV LWGVVLVLTP YVGGAYQMPL AQMANYGILI NAILFALNII
151 PILPWDGGIF IDTFLSAKYS QAFRKIEPYG TWIILLLMLT XVLGAFIAPI
201 XRXRDCXCAD VRLTGFQTA*
```

Further work revealed the complete nucleotide sequence <SEQ ID 47>:

```
  1 ATGTTTCAAA ATTTTGATTT GGGCGTGTTT CTGCTTGCCG TCCTGCCCGT
 51 GCTGCTCTCC ATTACCGTCA GGGAGGTGGC GCGCGGCTAT ACGGCGCGCT
101 ACTGGGGAGA CAACACTGCC GAACAATACG GCAGGCTGAC ACTGAACCCC
151 CTGCCCCATA TCGATTTGGT CGGCACAATC ATCGTACCGC TGCTTACTTT
```

```
201 GATGTTCACG CCCTTCCTGT TCGGCTGGGC GCGTCCGATT CCTATCGATT

251 CGCGCAACTT CCGCAACCCG CGCCTTGCCT GGCGTTGCGT TGCCGCGTCC

301 GGCCCGCTGT CGAATCTAGC GATGGCTGTT CTGTGGGGCG TGGTTTTGGT

351 GCTGACTCCG TATGTCGGCG GGGCGTATCA GATGCCGTTG GCTCAAATGG

401 CAAACTACGG TATTCTGATC AATGCGATTC TGTTCGCGCT CAACATCATC

451 CCCATCCTGC CTTGGGACGG CGGCATTTTC ATCGACACCT TCCTGTCGGC

501 GAAATATTCG CAAGCGTTCC GCAAAATCGA ACCTTATGGG ACGTGGATTA

551 TCCTACTGCT GATGCTGACC GGGGTTTTGG GTGCGTTTAT TGCACCGATT

601 GTGCGGCTGG TGATTGCGTT TGTGCAGATG TTCGTCTGA
```

This corresponds to the amino acid sequence <SEQ ID 48; ORF77-1>:

```
  1 MFQNFDLGVF LLAVLPVLLS ITVREVARGY TARYWGDNTA EQYGRLTLNP

51 LPHIDLVGTI IVPLLTLMFT PFLFGWARPI PIDSRNFRNP RLAWRCVAAS

101 GPLSNLAMAV LWGVVLVLTP YVGGAYQMPL AQMANYGILI NAILFALNII

151 PILPWDGGIF IDTFLSAKYS QAFRKIEPYG TWIILLLMLT GVLGAFIAPI

201 VRLVIAFVQM FV*
```

Computer analysis of this amino acid sequence reveals a putative leader sequence and several transmembrane domains.

A corresponding ORF from strain A of *N. meningitidis* was also identified:

Homology with a Predicted ORF from *N. meningitidis* (Strain A)

ORF77 (SEQ ID NO:46) shows 96.5% identity over a 173aa overlap with an ORF (ORF77a (SEQ ID NO:50)) from strain A of *N. meningitidis*:

```
                10        20        30        40        50        60
orf77.pep   MFQNFDLGVFLLAVLPVLPSITVSHVARGYTARYWGDNTAEQYGRLTLNPLPHIDLVGTI
                                     |||||||||||||||||||||||||||||||
orf77a                               RGYTARYWGDNTAEQYGRLTLNPLPHIDLVGTI
                                              10        20        30

70        80        90       100       110       120
orf77.pep   IVPLLTLMFTPFLFGWARPIPIDSRNFRNPRLAWRCVAASGPLSNLAMAVLWGVVLVLTP
            ||||||||||||||||||||||||||||||||||||||||||||||||||||||||||||
orf77a      IVPLLTLMFTPFLFGWARPIPIDSRNFRNPRLAWRCVAASGPLSNLAMAVLWGVVLVLTP
                40        50        60        70        80        90

130       140       150       160       170       180
orf77.pep   YVGGAYQMPLAQMANYGILINAILFALNIIPILPWDGGIFIDTFLSAKYSQAFRKIEPYG
            |||||||||||||||||||| |||||| ||||||||||||||||||||| ||||||||||
orf77a      YVGGAYQMPLAQMANYXILINAILXALNIIPILPWDGGIFIDTFLSAKXSQAFRKIEPYG
                100       110       120       130       140       150

190       200       210       220
orf77.pep   TWIILLLMLTXVLGAFIAPIXRXRDCXCADVRLTGFQTAX
            |||| |||||||||| |||| ||| ||||
orf77a      TWIIXLLMLTGVLGAXIAPIVQLVIAFVQMFVX
                160       170       180
```

ORF77-1 (SEQ ID NO:48) and ORF77a (SEQ ID NO:50) show 96.8% identity in 185 aa overlap:

```
                  10        20        30        40        50        60
orf77-1.pep  MFQNFDLGVFLLAVLPVLLSITVREVARGYTARYWGDNTAEQYGRLTLNPLPHIDLVGTI
                                       ||||||||||||||||||||||||||||||||
orf77a                              RGYTARYWGDNTAEQYGRLTLNPLPHIDLVGTI
                                            10        20        30

70        80        90       100       110       120
orf77-1.pep  IVPLLTLMFTPFLFGWARPIPIDSRNFRNPRLAWRCVAASGPLSNLAMAVLWGVVLVLTP
             ||||||||||||||||||||||||||||||||||||||||||||||||||||||||||||
orf77a       IVPLLTLMFTPFLFGWARPIPIDSRNFRNPRLAWRCVAASGPLSNLAMAVLWGVVLVLTP
                 40        50        60        70        80        90

130       140       150       160       170       180
orf77-1.pep  YVGGAYQMPLAQMANYGILINAILFALNIIPILPWDGGIFIDTFLSAKYSQAFRKIEPYG
             |||||||||||||||||||| ||||| ||||||||||||||||||||| |||||||||||
orf77a       YVGGAYQMPLAQMANYXILINAILXALNIIPILPWDGGIFIDTFLSAKXSQAFRKIEPYG
                100       110       120       130       140       150

190       200       210
orf77-1.pep  TWIILLLMLTGVLGAFIAPIVRLVIAFVQMFVX
             ||||  ||||||||||| ||||:||||||||||
orf77a       TWIIXLLMLTGVLFAXIAPIVQLVIAFVQMFVX
                160       170       180
```

A partial ORF77a nucleotide sequence <SEQ ID 49> was identified:

```
  1..CGCCGCTATA CAGCGCGCTA CTGGGGTGAC AACACTGCCG AACAATACGG

51   CAGGCTGACA CTGAACCCCC TGCCCCATAT CGATTTGGTC GGCACAATCA

101   TCGTACCGCT GCTTACTTTG ATGTTTACGC CCTTCCTGTT CGGCTGGGCG

151   CGTCCGATTC CTATCGATTC GCGCAACTTC CGCAACCCGC GCCTTGCCTG

201   GCGTTGCGTT GCCGCGTCCG GCCCGCTGTC GAATCTGGCG ATGGCTGTTC

251   TGTGGGGCGT GGTTTTCGTG CTGACTCCGT ATGTCGGTGG GGCGTATCAG

301   ATGCCGTTGG CNCAAATGGC AAACTACNNN ATTCTGATCA ATGCGATTCT

351   GTNCGCGCTC AACATCATCC CCATCCTGCC TTGGGACGGC GGCATTTTCA

401   TCGACACCTT CCTGTCGGCN AAATANTCGC AAGCGTTCCG CAAAATCGAA

451   CCTTATGGGA CGTGGATTAT CCNGCTGCTT ATGCTGACCG GGGTTTTGGG

501   TGCGTNTATT GCACCGATTG TGCAGCTGGT GATTGCGTTT GTGCAGATGT

551   TCGTCTGA
```

This encodes a protein having amino acid sequence <SEQ ID 50>:

```
  1..RGYTARYWGD NTAEQYGRLT LNPLPHIDLV GTIIVPLLTL MFTPFLFGWA

51   RPIPIDSRNF RNPRLAWRCV AASGPLSNLA MAVLWGVVLV LTPYVGGAYQ

101   MPLAQMANYX ILINAILXAL NIIPILPWDG GIFIDTFLSA KXSQAFRKIE

151   PYGTWIIXLL MLTGVLGAXI APIVQLVIAF VQMFV*
```

Based on this analysis, it is predicted that this protein from *N. meningitidis*, and its epitopes, could be useful antigens for vaccines or diagnostics.

Example 12

The following partial DNA sequence was identified in *N. meningitidis* <SEQ ID 51>

```
  1 ATGAACCTGA TTTCACGTTA CATCATCCGT CAAATGGCGG TTATGGCGGT
 51 TTACGCGCTC CTTGCCTTCC TCGCTTTGTA CAGCTTTTTT GAAATCCTGT
101 ACGAAACCGG CAACCTCGGC AAAGGCAGTT ACGGCATATG GGAAATGCTG
151 GGCTACACCG CCCTCAAAAT GCCCGCCCGC GCCTACGAAC TGATTCCCCT
201 CGCCGTCCTT ATCGGCGGAC TGGTCTCCCT CAGCCAGCTT GCCGCCGGCA
251 GCGAACTGAC CGTCATCAAA GCCAGCGGCA TGAGCACCAA AAAGCTGCTG
301 TTGATTCTGT CGCAGTTCGG TTTTATTTTT GCTATTGCCA CCGTCGCGCT
351 CGGCGAATGG GTTGCGCCCA CACTGAGCCA AAAAGCCGAA AACATCAAAG
401 CCGCCGCCAT CAACGGCAAA ATCAGCACCG GCAATACCGG CCTTTGGCTG
451 AAAGAAAAAA ACAGCGTGAT CAATGTGCGC GAAATGTTGC CCGACCAT..
```

This corresponds to the amino acid sequence <SEQ ID 52; ORF112>:

```
  1 MNLISRYIIR QMAVMAVYAL LAFLALYSFF EILYETGNLG KGSYGIWEML
 51 GYTALKMPAR AYELIPLAVL IGGLVSLSQL AAGSELTVIK ASGMSTKKLL
101 LILSQFGFIF AIATVALGEW VAPTLSQKAE NIKAAAINGK ISTGNTGLWL
151 KEKNSVINVR EMLPDH...
```

Further work revealed further partial nucleotide sequence <SEQ ID 53>:

```
  1 ATGAACCTGA TTTCACGTTA CATCATCCGT CAAATGGCGG TTATGGCGGT
 51 TTACGCGCTC CTTGCCTTCC TCGCTTTGTA CAGCTTTTTT GAAATCCTGT
101 ACGAAACCGG CAACCTCGGC AAAGGCAGTT ACGGCATATG GGAAATGCTG
151 gGCTACACCG CCCTCAAAAT GCCCGCCCGC GCCTACGAAC TGATTCCCCT
201 CGCCGTCCTT ATCGGCGGAC TGGTCTCCCT CAGCCAGCTT GCCGCCGGCA
251 GCGAACTGAC CGTCATCAAA GCCAGCGGCA TGAGCACCAA AAAGCTGCTG
301 TTGATTCTGT CGCAGTTCGG TTTTATTTTT GCTATTGCCA CCGTCCCGCT
351 CGGCGAATGG GTTGCGCCCA CACTGAGCCA AAAAGCCGAA AACATCAAAG
401 CCGCCGCCAT CAACGGCAAA ATCAGCACCG GCAATACCGG CCTTTGGCTG
451 AAAGAAAAAA ACAGCrTkAT CAATGTGCGC GAAATGTTGC CCGACCATAC
501 GCTTTTGGGC ATCAAAATTT GGGCGCGCAA CGATAAAAAC GAATTGGCAG
551 AGGCAGTCGA AGCCGATTCC GCCGTTTTGA ACAGCGACGG CAGTTGGCAG
601 TTGAAAAACA TCCGCCGCAG CACGCTTGGC GAAGACAAAG TCGAGGTCTC
651 TATTGCGGCT GAAGAAAACT GGCCGATTTC CGTCAAACGC AACCTGATGG
701 ACGTATTGCT CGTCAAACCC GACCAAATGT CCGTCGGCGA ACTGACCACC
```

```
751 TACATCCGCC ACCTCCAAAA CAACAGCCAA AACACCCGAA TCTACGCCAT

801 CGCATGGTGG CGCAAATTGG TTTACCCCGC CGCAGCCTGG GTGATGGCGC

851 TCGTCGCCTT TGCCTTTACC CCGCAAACCA CCCGCCACGG CAATATGGGC

901 TTAAAACTCT TCGGCGGCAT CTGTSTCGGA TTGCTGTTCC ACCTTGCCGG

951 ACGGCTCTTT GGGTTTACCA GCCAACTCGG...
```

This corresponds to the amino acid sequence <SEQ ID 54; ORF 112-1>:

```
  1 MNLISRYIIR QMAVMAVYAL LAFLALYSFF EILYETGNLG KGSYGIWEML

51 GYTALKMPAR AYELIPLAVL IGGLVSLSQL AAGSELTVIK ASGMSTKKLL

101 LILSQFGFIF AIATVALGEW VAPTLSQKAE NIKAAAINGK ISTGNTGLWL

151 KEKNSXINVR EMLPDHTLLG IKIWARNDKN ELAEAVEADS AVLNSDGSWQ

201 LKNIRRSTLG EDKVEVSIAA EENWPISVKR NLMDVLLVKP DQMSVGELTT

251 YIRHLQNNSQ NTRIYAIAWW RKLVYPAAAW VMALVAFAFT PQTTRHGWMG

301 LKLFGGICXG LLFHLAGRLF GFTSQL...
```

Computer analysis of this amino acid sequence predicts two transmembrane domains.

A corresponding ORF from strain A of *N. meningitidis* was also identified:

Homology with a Predicted ORF from *N. Meningitidis* (Strain A)

ORF112 (SEQ ID NO:52) shows 96.4% identity over a 16-6aa overlap with an ORF (ORF112a (SEQ ID NO:177)) from strain A of *N. meningitidis*:

```
                    10         20         30         40         50         60
orf112.pep  MNLISRYIIRQMAVMAVYALLAFLALYSFFEILYETGNLGKGSYGIWEMLGYTALKMPAP
            ||||||||||||||||||||||||||||||||||||||||||||||||| ||||||| ||
orf112a     MNLISRYIIRQMAVMAVYALLAFLALYSFFEILYETGNLGKGSYGIWEMXGYTALKMXAR
                    10         20         30         40         50         60

70         80         90        100        110        120
orf112.pep  AYELIPLAVLIGGLVSLSQLAAGSELTVIKASGMSTKKLLLILSQFGFIFAIATVALGEW
            ||||:|||||||||||||:|||||||||:|||||||||||||||||||||||||||||||
orf112a     AYELMPLAVLIGGLVSXSQLAAGSELXVIKASGMSTKKLLLILSQFGFIFAIATVALGEW
                    70         80         90        100        110        120

130        140        150        160
orf112.pep  VAPTLSQKAENIKAAAINGKISTGNTGLWLKEKNSVINVREMLPDH
            |||||||||||||||||||||||||||||||||||:|||||||||
orf112a     VAPTLSQKAENIKAAAINGKISTGNTGLWLKEKNSIINVREMLPDHTLLGIKIWARNDKN
                   130        140        150        160        170        180 orf112a     ELAEAVEADSAVLNSDGSWQLKNIRRSTLGEDKVEVSIAAEEXWPISVKRNLMDVLLVKP
                   190        200        210        220        230        240
```

A partial ORF112a nucleotide sequence <SEQ ID 55> was identified:

```
  1 ATGAACCTGA TTTCACGTTA CATCATCCGT CAAATGGCGG TTATGGCGGT

51 TTACGCGCTC CTTGCCTTCC TCGCTTTGTA CAGCTTTTTT GAAATCCTGT
```

-continued

```
 101 ACGAAACCGG CAACCTCGGC AAAGGCAGTT ACGGCATATG GGAAATGNTG
 151 GGNTACACCG CCCTCAAAAT GNCCGCCCGC GCCTACGAAC TGATGCCCCT
 201 CGCCGTCCTT ATCGGCGGAC TGGTCTCTNT CAGCCAGCTT GCCGCCGGCA
 251 GCGAACTGAN CGTCATCAAA GCCAGCGGCA TGAGCACCAA AAAGCTGCTG
 301 TTGATTCTGT CGCAGTTCGG TTTTATTTTT GCTATTGCCA CCGTCGCGCT
 351 CGGCGAATGG GTTGCGCCCA CACTGAGCCA AAAAGCCGAA AACATCAAAG
 401 CCGCGGCCAT CAACGGCAAA ATCAGTACCC GCAATACCGG CCTTTGGCTG
 451 AAAGAAAAAA ACAGCATTAT CAATGTGCGC GAAATGTTGC CCGACCATAC
 501 CCTGCTGGGC ATTAAAATCT GGGCCCGCAA CGATAAAAAC GAACTGGCAG
 551 AGGCAGTGGA AGCCGATTCC GCCGTTTTGA ACAGCGACGG CAGTTGGCAG
 601 TTGAAAAACA TCCGCCGCAG CACGCTTGGC GAAGACAAAG TCGAGGTCTC
 651 TATTGCGGCT GAAGAAAANT GGCCGATTTC CGTCAAACGC AACCTGATGG
 701 ACGTATTGCT CGTCAAACCC GACCAAATGT CCGTCGGCGA ACTGACCACC
 751 TACATCCGCC ACCTCCAAAN NNACAGCCAA AACACCCGAA TCTACGCCAT
 801 CGCATGGTGG CGCAAATTGG TTTACCCCGC CGCAGCCTGG GTGATGGCGC
 851 TCGTCGCCTT TGCCTTTACC CCGCAAACCA CCCGCCACGG CAATATGGGC
 901 TTAAAANTCT TCGGCGGCAT CTGTCTCGGA TTGCTGTTCC ACCTTGCCGG
 951 NCGGCTCTTC NGGTTTACCA GCCAACTCTA CGGCATCCCG CCCTTCCTCG
1001 NCGGCGCACT ACCTACCATA GCCTTCGCCT TGCTCGCCGT TTGGCTGATA
1051 CGCAAACAGG AAAAACGCTA A
```
                                                               35

This encodes a protein having amino acid sequence <SEQ ID 56>:

```
  1 MNLISRYIIR QMAVMAVYAL LAFLALYSFF EILYETGNLG KGSYGIWEMX
 51 GYTALKMXAR AYELMPLAVL IGGLVSXSQL AAGSELXVIK ASGMSTKKLL
101 LILSQFGFIF AIATVALGEW VAPTLSQKAE NIKAAAINGK ISTGNTGLWL
151 KEKNSIINVR EMLPDHTLLG IKIWARNDKN ELAEAVEADS AVLNSDGSWQ
201 LKNIRRSTLG EDKVEVSIAA EEXWPISVKR NLMDVLLVKP DQMSVGELTT
251 YIRHLQXXSQ NTRIYAIAWW RKLVYPAAAW VMALVAFAFT PQTTRHGNMG
301 LKXFGGICLG LLFHLAGRLF XFTSQLYGIP PFLXGALPTI AFALLAVWLI
351 RKQEKR*
```

ORF112a (SEQ ID NO:56) and ORF112-1 (SEQ ID NO:54) show 96.3% identity in 326 aa overlap:

```
orf112a.pep  MNLISRYIIRQMAVMAVYALLAFLALYSFFEILYETGNLGKGSYGIWEMXGYTALKMXAR
             |||||||||||||||||||||||||||||||||||||||||||||||| ||||||| ||
orf112-1     MNLISRYIIRQMAVMAVYALLAFLALYSFFEILYETGNLGKGSYGIWEMLGYTALKMPAR orf112a.pep  AYELMPLAVLIGGLVSXSQLAAGSELXVIKASGMSTKKLLLILSQFGFIFAIATVALGEW
             ||||:|||||||||||||:|||||||:|||||||||||||||||||||||||||||||||
orf112-1     AYELIPLAVLIGGLVSLSQLAAGSELTVIKASGMSTKKLLLILSQFGFIFAIATVALGEW
```

-continued

```
orf112a.pep   VAPTLSQKAENIKAAAINGKISTGNTGLWLKEKNSIINVREMLPDHTLLGIKIWARNDKN
              ||||||||||||||||||||||||||||||||||| ||||||||||||||||||||||||
orf112-1      VAPTLSQKAENIKAAAINGKISTGNTGLWLKEKNSXINVREMLPDHTLLGIKIWARNDKN orf112a.pep   ELAEAVEADSAVLNSDGSWQLKNIRRSTLGEDKVEVSIAAEEXWPISVKRNLMDVLLVKP
              |||||||||||||||||||||||||||||||||||||||||| |||||||||||||||||
orf112-1      ELAEAVEADSAVLNSDGSWQLKNIRRSTLGEDKVEVSIAAEENWPISVKRNLMDVLLVKP orf112a.pep   DQMSVGELTTYIRHLQXXSQNTRIYAIAWWRKLVYPAAAWVMALVAFAFTPQTTRHGNMG
              ||||||||||||||||  ||||||||||||||||||||||||||||||||||||||||||
orf112-1      DQMSVGELTTYIRHLQNNSQNTRIYAIAWWRKLVYPAAAWVMALVAFAFTPQTTRHGNMG orf112a.pep   LKXFGGICLGLLFHLAGRLFXFTSQLYGIPPFLXGALPTIAFALLAVWLIRKQEKRX
              || ||||| ||||||||||| |||||
orf112-1      LKLFGGICXGLLFHLAGRLFGFTSQL
```

Based on this analysis, it is predicted that this protein from *N. meningitidis*, and its epitopes, could be useful antigens for vaccines or diagnostics.

Example 13

The following partial DNA sequence was identified in *N. meningitidis* <SEQ ID 57>

```
  1 GCAGTAGCCG AAACTGCCAA CAGCCAGGGC AAAGGTAAAC AGGCAGGCAG
 51 TTCGGTTTCT GTTTCACTGA AAACTTCAGG CGACCTTTGC GGCAAACTCA
101 AAACCACCCT TAAAACTTTG GTCTGCTCTT TGGTTTCCCT GAGTATGGTA
151 TTGCCTGCCC ATGCCCAAAT TACCACCGAC AAATCAGCAC CTAAAAACCA
201 GCAGGTCGTT ATCCTTAAAA CCAACACTGG TGCCCCCTTG GTGAATATCC
251 AAACTCCGAA TGGACGCGGA TTGAGCCACA ACCGCTA.TA CGCATTTGAT
301 GTTGACAACA AAGGGGCAGT GTTAAACAAC GACCGTAACA ATAATCCGTT
351 TGTGGTCAAA GGCAGTGCGC AATTGATTTT GAACGAGGTA CGCGGTACGG
401 CTAGCAAACT CAACGGCATC GTTACCGTAG GCGGTCAAAA GGCCGACGTG
451 ATTATTGCCA ACCCCAACCG CATTACCGTT AATGGCGGCG GCTTTAAAAA
501 TGTCGGTCGG GGCATCTTAA CTACCGGTGC GCCCCAAATC GGCAAAGACG
551 GTGCACTGAC AGGATTTGAT GTGCGTCAAG GCACATTGgA CCGTAGrAGC
601 AGCAGGTTGG AATGATAAAG GCGGAGCmrm yTACACCGGG GTACTTGCTC
651 GTGCAGTTGC TTTGCAGGGG AAATTWmmGG GTAAA.AACT GGCGGTTTCT
701 ACCGGTCCTC AGAAAGTAGA TTACGCCAGC GGCGAAATCA GTGCAGGTAC
751 GGCAGCGGGT ACGAAACCGA CTATTGCCCT TGATACTGCC GCACTGGGCG
801 GTATGTACGC CGACAGCATC ACACTGATTG CCAATGAAAA AGGCGTAGGC
851 GTCTAA
```

This corresponds to the amino acid sequence <SEQ ID 58; ORF114>:

```
  1 AVAETANSQG KGKQAGSSVS VSLKTSGDLC GKLKTTLKTL VCSLVSLSMV
 51 LPAHAQITTD KSAPKNQQVV ILKTNTGAPL VNIQTPNGRG LSHNRXYAFD
101 VDNKGAVLNN DRNNNPFVVK GSAQLILNEV RGTASKLNGI VTVGGQKADV
```

```
151 IIANPNGITV NGGGFKNVGR GILTTGAPQI GKDGALTGFD VVKAHWTVXA

201 AGWNDKGGAX YTGVLARAVA LQGKXXGKXL AVSTGPQKVD YASGEISAGT

251 AAGTKPTIAL DTAALGGMYA DSITLIANEK GVGV*
```

Further work revealed the complete nucleotide sequence
<SEQ ID 59>:

```
   1 ATGAATAAAG GTTTACATCG CATTATCTTT AGTAAAAAGC ACAGCACCAT
  51 GGTTGCAGTA GCCGAAACTG CCAACAGCCA GGGCAAAGGT AAACAGGCAG
 101 GCAGTTCGGT TTCTGTTTCA CTGAAAACTT CAGGCGACCT TTGCGGCAAA
 151 CTCAAAACCA CCCTTAAAAC TTTGGTCTGC TCTTTGGTTT CCCTGAGTAT
 201 GGTATTGCCT GCCCATGCCC AAATTACCAC CGACAAATCA GCACCTAAAA
 251 ACCAGCAGGT CGTTATCCTT AAAACCAACA CTGGTGCCCC CTTGGTGAAT
 301 ATCCAAACTC CGAATGGACG CGGATTGAGC CACAACCGCT ATACGCAGTT
 351 TGATGTTGAC AACAAAGGGG CAGTGTTAAA CAACGACCGT AACAATAATC
 401 CGTTTGTGGT CAAAGGCAGT GCGCAATTGA TTTTGAACGA GGTACGCGGT
 451 ACGGCTAGCA AACTCAACGG CATCGTTACC GTAGGCGGTC AAAAGGCCGA
 501 CGTGATTATT GCCAACCCCA ACGGCATTAC CGTTAATGGC GGCGGCTTTA
 551 AAAATGTCGG TCGGGCATC TTAACTACCG GTGCGCCCCA AATCGGCAAA
 601 GACGGTGCAC TGACAGGATT TGATGTGCGT CAAGGCACAT TGACCGTAGG
 651 AGCAGCAGGT TGGAATGATA AAGGCGGAGC CGACTACACC GGGGTACTTG
 701 CTCGTGCAGT TGCTTTGCAG GGGAAATTAC AGGGTAAAAA CCTGGCGGTT
 751 TCTACCGGTC CTCAGAAAGT AGATTACGCC AGCGGCGAAA TCAGTGCAGG
 801 TACGGCAGCG GGTACGAAAC CGACTATTGC CCTTGATACT GCCGCACTGG
 851 GCGGTATGTA CGCCGACAGC ATCACACTGA TTGCCAATGA AAAAGGCGTA
 901 GGCGTCAAAA ATGCCGGCAC ACTCGAAGCG GCCAAGCAAT TGATTGTGAC
 951 TTCGTCAGGC CGCATTGAAA ACAGCGGCCG CATCGCCACC ACTGCCGACG
1001 GCACCGAAGC TTCACCGACT TATCTCTCCA TCGAAACCAC CGAAAAAGGA
1051 GCGGCAGGCA CATTTATCTC CAATGGTGGT CGGATCGAGA GCAAAGGCTT
1101 ATTGGTTATT GAGACGGGAG AAGATATCAG CTTGCGTAAC GGAGCCGTGG
1151 TGCAGAATAA CGGCAGTCGC CCAGCTACCA CGGTATTAAA TGCTGGTCAT
1201 AATTTGGTGA TTGAGAGCAA AACTAATGTG AACAATGCCA AGGCCCGGC
1251 TACTCTGTCG GCCGACGGCC GTACCGTCAT CAAGGAGGCC AGTATTCAGA
1301 CTGGCACTAC CGTATACAGT TCCAGCAAAG GCAACGCCGA ATTAGGCAAT
1351 AACACACGCA TTACCGGGGC AGATGTTACC GTATTATCCA ACGGCACCAT
1401 CAGCAGTTCC GCCGTAATAG ATGCCAAAGA CACCGCACAC ATCGAAGCAG
1451 GCAAACCGCT TTCTTTGGAA GCTTCAACAG TTACCTCCGA TATCCGCTTA
1501 AACGGAGGCA GTATCAAGGG CGGCAAGCAG CTTGCTTTAC TGGCAGACGA
1551 TAACATTACT GCCAAAACTA CCAATCTGAA TACTCCCGGC AATCTGTATG
1601 TTCATACAGG TAAAGATCTG AATTTGAATG TTGATAAAGA TTTGTCTGCC
1651 GCCAGCATCC ATTTGAAATC GGATAACGCT GCCCATATTA CCGGCACCAG
```

-continued

```
1701  TAAAACCCTC ACTGCCTCAA AAGACATGGG TGTGGAGGCA GGCTCGCTGA
1751  ATGTTACCAA TACCAATCTG CGTACCAACT CGGGTAATCT GCACATTCAG
1801  GCAGCCAAAG GCAATATTCA GCTTCGCAAT ACCAAGCTGA ACGCAGCCAA
1851  GGCTCTCGAA ACCACCGCAT TGCAGGGCAA TATCGTTTCA GACGGCCTTC
1901  ATGCTGTTTC TGCAGACGGT CATGTATCCT TATTGGCCAA CGGTAATGCC
1951  GACTTTACCG GTCACAATAC CCTGACAGCC AAGGCCGATG TCAATGCAGG
2001  ATCGGTTGGT AAAGGCCGTC TGAAAGCAGA CAATACCAAT ATCACTTCAT
2051  CTTCAGGAGA TATTACGTTG GTTGCCGGCA ACGGTATTCA GCTTGGTGAC
2101  GGAAAACAAC GCAATTCAAT CAACGGAAAA CACATCAGCA TCAAAAACAA
2151  CGGTGGTAAT GCCGACTTAA AAAACCTTAA CGTCCATGCC AAAAGCGGGG
2201  CATTGAACAT TCATTCCGAC CGGGCATTGA GCATAGAAAA TACCAAGCTG
2251  GAGTCTACCC ATAATACGCA TCTTAATGCA CAACACGAGC GGGTAACGCT
2301  CAACCAAGTA GATGCCTACG CACACCGTCA TCTAAGCATT ACCGGCAGCC
2351  AGATTTGGCA AAACGACAAA CTGCCTTCTG CCAACAAGCT GGTGGCTAAC
2401  GGTGTATTGG CACTCAATGC GCGCTATTCC CAAATTGCCG ACAACACCAC
2451  GCTGAGAGCG GGTGCAATCA ACCTTACTGC CGGTACCGCC CTAGTCAAGC
2501  GCGGCAACAT CAATTGGAGT ACCGTTTCGA CCAAAACTTT GGAAGATAAT
2551  GCCGAATTAA AACCATTGGC CGGACGGCTG AATATTGAAG CAGGTAGCGC
2601  CACATTAACC ATCGAACCTG CCAACCGCAT CAGTGCGCAT ACCGACCTGA
2651  GCATCAAAAC AGGCGGAAAA TTGCTGTTGT CTGCAAAAGG AGGAAATGCA
2701  GGTGCGCCTA GTGCTCAAGT TTCCTCATTG AAGCAAAAG GCAATATCCG
2751  TCTGGTTACA GGAGAAACAG ATTTAAGAGG TTCTAAAATT AZAGCCGGTA
2801  AAAACTTGGT TGTCGCCACC ACCAAAGGCA AGTTGAATAT CGAAGCCGTA
2851  AACAACTCAT TCAGCAATTA TTTTCCTACA CAAAAAGCGG CTGAACTCAA
2901  CCAAAAATCC AAAGAATTGG AACAGCAGAT TGCGCAGTTG AAAAAAACCT
2951  CGCCTAAAAG CAAGCTGATT CCAACCCTGC AAGAAGAACG CGACCGTCTC
3001  GCTTTCTATA TTCAAGCCAT CAACAAGGAA GTTAAAGGTA AAAACCCAA
3051  AGGCAAAGAA TACCTGCAAG CCAAGCTTTC TGCACAAAAT ATTGACTTGA
3101  TTTCCGCACA AGGCATCGAA ATCAGCGGTT CCGATATTAC CGCTTCCAAA
3151  AAACTGAACC TTCACGCCGC AGGCGTATTG CCAAAGGCAG CAGATTCAGA
3201  GGCGCCTGCT ATTCTGATTG ACGGCATAAC CGACCAATAT GAAATTGGCA
3251  AGCCCACCTA CAAGAGTCAC TACGACAAAG CTGCTCTCAA CAAGCCTTCA
3301  CGTTTGACCG GACGTACAGG GGTAAGTATT CATGCAGCTG CGGCACTCGA
3351  TGATGCACGT ATTATTATCG GTGCATCCGA AATCAAAGCT CCCTCAGGCA
3401  GCATAGACAT CAAAGCCCAT AGTGATATTG TACTGGAGGC TGGACAAAAC
3451  GATGCCTATA CCTTCTTAAA AACCAAAGGT AAAAGCGGCA AAATCATCAG
3501  AAAAACCAAG TTTACCAGCA CCCGCGACCA CCTGATTATG CCAGCCCCCG
3551  TCGAGCTGAC CGCCAACGGC ATAACGCTTC AGGCAGGCGG CAACATCGAA
3601  GCTAATACCA CCCGCTTCAA TGCCCCTGCA GGTAAAGTTA CCCTGGTTGC
3651  GGGTGAAGAG CTGCAACTGC TGGCAGAAGA AGGCATCCAC AAGCACGAGT
```

```
                       -continued
3701   TGGATGTCCA AAAAAGCCGC CGCTTTATCG GCATCAAGGT AGGCAAGAGC

3751   AATTACAGTA AAAACGAACT GAACGAAACC AAATTGCCTG TCCGCGTCGT

3801   CGCCCAAACT GCAGCCACCC GTTCAGGCTG GGATACCGTG CTCGAAGGTA

3851   CCGAATTCAA AACCACGCTG GCCGGTGCGG ACATTCAGGC AGGTGTAGGC

3901   GAAAAGCCC GTGCCGATGC GAAAATTATC CTCAAAGGCA TTGTGAACCG

3951   TATCCAGTCG GAAGAAAAAT TAGAAACCAA CTCAACCGTA TGGCAGAAAC

4001   AGGCCGGACG CGGCAGCACT ATCGAAACGC TGAAACTGCC CAGCTTCGAA

4051   AGCCCTACTC CGCCCAAACT GACCGCCCCC GGTGGCTATA TCGTCGACAT

4101   TCCGAAAGGC AATTTGAAAA CCGAAATCGA AAAGCTGGCC AAACAGCCCG

4151   AGTATGCCTA TCTGAAACAG CTCCAAGTAG CGAAAAACGT CAACTGGAAC

4201   CAGGTGCAAC TGGCTTACGA TAAATGGGAC TATAAGCAGG AAGGCTTAAC

4251   CAGAGCCGGT GCAGCGATTG TTACCATAAT CGTAACCGCA CTGACTTATG

4301   GATACGGCGC AACCGCAGCG GGCGGTGTAG CCGCTTCAGG AAGTAGTACA

4351   GCCGCAGCTG CCGGAACAGC CGCCACAACG ACAGCAGCAG CTACTACCGT

4401   TTCTACAGCG ACTGCCATGC AAACCGCTGC TTTAGCCTCC TTGTATAGCC

4451   AAGCAGCTGT ATCCATCATC AATAATAAAG GTGATGTCGG CAAAGCGTTG

4501   AAAGATCTCG GCACCAGTGA TACGGTCAAG CAGATTGTCA CTTCTGCCCT

4551   GACGGCGGGT GCATTAAATC AGATGGGCGC AGATATTGCC CAATTGAACA

4601   GCAAGGTAAG AACCGAACTG TTCAGCAGTA CGGGCAATCA AACTATTGCC

4651   AACCTTGGAG GCAGACTGGC TACCAATCTC AGTAATGCAG GTATCTCAGC

4701   TGGTATCAAT ACCGCCGTCA ACGGCGGCAG CCTGAAAGAC AACTTAGGCA

4751   ATGCCGCATT AGGAGCATTG GTTAATAGCT TCCAAGGAGA AGCCGCCAGC

4801   AAAATCAAAA CAACCTTCAG CGACGATTAT GTTGCCAAAC AGTTCGCCCA

4851   CGCTTTGGCT GGGTGTGTTA GCGGATTGGT ACAAGGAAAA TGTAAAGACG

4901   GGGCAATTGG CGCAGCAGTT GGGGAAATCG TAGCCGACTC CATGCTTGGC

4951   GGCAGAAACC CTGCTACACT CAGCGATGCG GAAAACCATA AGCTTATCAG

5001   TTACTCGAAG ATTATTGCCG GCAGCGTGGC GGCACTCAAC GGCGGCGATG

5051   TGAATACTGC GGCGAATGCG GCTGAGGTGG CGGTAGTGAA TAATGCTTTG

5101   AATTTTGACA GTACCCCTAC CAATGCGAAA AAGCATCAAC CGCAGAAGCC

5151   CGACAAAACC GCACTGGAAA AAATTATCCA AGGTATTATG CCTGCACATG

5201   CAGCAGGTGC GATGACTAAT CCGCAGGATA AGGATGCTGC CATTTGGATA

5251   AGCAATATCC GTAATGGCAT CACAGGCCCG ATTGTGATTA CCAGCTATGG

5301   GGTTTATGCT GCAGGTTGGA CAGCTCCGCT GATCGGTACA GCGGGTAAAT

5351   TAGCTATCAG CACCTGCATG GCTAATCCTT CTGGTTGTAC TGTCATGGTC

5401   ACTCAGGCTG CCGAAGCGGG CGCGGGAATC GCCACGGGTG CGGTAACGGT

5451   AGGCAACGCT TGGGAAGCGC CTGTGGGGGC GTTGTCGAAA GCGAAGGCGG

5501   CCAAGCAGGC TATACCAACC CAGACAGTTA AGAACTTGA TGGCTTACTA

5551   CAAGAATCAA AAAATATAGG TGCTGTAAAT ACACGAATTA ATATAGCGAA

5601   TAGTACTACT CGATATACAC CAATGAGACA AACGGGACAA CCGGTATCTG

5651   CTGGCTTTGA CCATGTTCTT GAGGC3CACT TCCATAGGCC TATTGCGAAT
```

```
5701  AACCGTTCAG TTTTTACCAT CTCCCCAAAT GAATTGAAGG TTATACTTCA
5751  AAGTAATAAA GTAGTTTCTT CTCCCGTATC GATCACTCCT GATGGCCAAT
5801  ATATGCGGAC TGTCGATGTA GGAAAAGTTA TTGGTACTAC TTCTATTAAA
5851  GAAGGTGGAC AACCCACAAC TACAATTAAA GTATTTACAG ATAAGTCAGG
5901  AAATTTGATT ACTACATACC CAGTAAAAGG AAACTAA
```

This corresponds to the amino acid sequence <SEQ ID 60; ORF114-1>:

```
   1  MNKGLHRIIF SKKHSTMVAV AETANSQGKG KQAGSSVSVS LKTSGDLCGK
  51  LKTTLKTLVC SLVSLSMVLP AHAQITTOKS APKNQQVVIL KTNTGAPLVN
 101  IQTPNGRGLS HNRYTQFDVD NKGAVLNNDR NNNPFVVKGS AQLILNEVRG
 151  TASKLNGIVT VGGQKADVII ANPNGITVNG GGFKNVGRGI LTTGAPQIGK
 201  DGALTGFDVR QGTLTVGAAG WNDKGGADYT GVLARAVALQ GKLQGKNLAV
 251  STGPQKVDYA SGEISAGTAA GTKPTIALDT AALGGMYADS ITLIANEKGV
 301  GVKNAGTLEA AKQLIVTSSG RIENSGRIAT TADGTEASPT YLSIETTEKG
 351  AAGTFISNGG RIESKGLLVI ETGEDISLRN GAVVQNNGSR PATTVLNAGH
 401  NLVIESKTNV NWAKGPATLS ADGRTVIKEA SIQTGTTVYS SSKGNAELGN
 451  NTRITGADVT VLSNGTISSS AVIDAKDTAH IEAGKPLSLE ASTVTSDIRL
 501  NGGSIKGGKQ LALLADONIT AKTTNLNTPG NLYVHTGKDL NLNVDKDLSA
 551  ASIHLKSDNA AHITGTSKTL TASKDMGVEA GSLNVTNTNL RTWSGNLHIQ
 601  AAKGNIQLRN TKLNAAKALE TTALQGNIVS DGLHAVSADG HVSLLANGNA
 651  DFTGHNTLTA KADVNAGSVG KGRLKADNTN ITSSSGDITL VAGNGIQLGD
 701  GKQRNSINGK HISIKNNGGN ADLKNLNVHA KSGALNIHSD RALSIENTKL
 751  ESTHNTHLNA QHERVTLNQV DAYAHRHLSI TGSQIWQNDK LPSANKLVAN
 801  GVLALNARYS QIADNTTLRA GAINLTAGTA LVKRGNINWS TVSTKTLEDN
 851  AELKPLAGRL NIEAGSGTLT IEPANRISAM TDLSIKTGGK LLLSAKGGNA
 901  GAPSAQVSSL EAKGNIRLVT GETDLRGSKI TAGKNLVVAT TKGKLNIEAV
 951  NNSFSNYFPT QKAAELNQKS KELEQQIAQL KKSSPKSKLI PTLQEERDRL
1001  AFYIQAINKE VKGKKPKGKE YLQAKLSAQN IDLISAQGIE ISGSDITASK
1051  KLNLHAAGVL PKAADSEAAA ILIDGITOQY EIGKPTYKSH YDKAALNKPS
1101  RLTGRTGVSI HAAAALDDAR IIIGASEIKA PSGSIDIKAH SDIVLEAGQN
1151  DAYTFLKTKG KSGKIIRKTK FTSTRDHLIN PAPVELTANG ITLQAGGNIE
1201  ANTTRFNAPA GKVTLVAGEE LQLLAEEGIH KHELDVQKSR RFIGIKVGKS
1251  NYSKNELNET KLPVRVVAQT AATRSGWDTV LEGTEFKTTL AGADIQAGVG
1301  EKARADAKII LKGIVNRIQS EEKLETNSTV WQKQAGRGST IETLKLPSFE
1351  SPTPPKLTAP GGYIVDIPKG NLKTEIEKLA KQPEYAYLKQ LQVAKNVNWN
1401  QVQLAYDKWD YKQEGLTRAG AAIVTIIVTA LTYGYGATAA GGVAASGSST
1451  AAAAGTAATT TAAATTVSTA TANOTAALAS LYSQAAVSII NNKGDVGKAL
1501  KDLGTSDTVK QIVTSALTAG ALNQMGADIA QLNSKVRTEL FSSTGNQTIA
```

```
-continued
1551  NLGGRLATNL SNAGISAGIN TAVNGGSLKD NLGNAALGAL VNSFQGEAAS

1601  KIKTTFSDDY VAKQFAHALA GCVSGLVQGK CKDGAIGAAV GEIVADSMLG

1651  GRNPATLSDA EKHKVISYSK IIAGSVAALN GGDVNTAANA AEVAVVNNAL

1701  NFDSTPTNAK KHQPQKPDKT ALEKIIQGIM PAHAAGAKTN PQDKDAAIWI

1751  SNIRNGITGP IVITSYGVYA AGWTAPLIGT AGKLAISTCM ANPSGCTVMV

1801  TQAAEAGAGI ATGAVTVGNA WEAPVGALSK AKAAKQAIPT QTVKELDGLL

1851  QESKNIGAVN TRINIANSTT RYTPMRQTGQ PVSAGFEHVL EGHFHRPIAN

1901  NRSVFTISPN ELKVILQSNK VVSSPVSMTP DGQYMRTVDV GKVIGTTSIK

1951  EGGQPTTTIK VETDKSGNLI TTYPVKGN*
```

Computer analysis of this amino acid sequence predicts a transmembrane region and also gives the following results:

Homology with a Predicted ORF from *N. meningitidis* (Strain A)

ORF114 (SEQ ID NO:58) shows 91.9% identity over a 284aa overlap with an ORF (ORF114a (SEQ ID NO:178)) from strain A of *N. meningitidis*:

```
                        10         20         30         40
orf114.pep              AVAETANSQGKGKQAGSSVSVSLKTSGDLCGKLKTTLKTLVC
                        |||||||||||||||||||||||||||||||||||||||||
orf114a    MNKGLHRIIFSKKHSTMVAVAETANSQGKGKQAGSSVSVSLKTSGDLCGKLKTTLKTLVC
                   10         20         30         40         50         60

50         60         70         80         90        100
orf114.pep  SLVSLSMVLPAHAQITTDKSAPKNQQVVILKTNTGAPLVNIQTPNGRGLSHNRXYAFDVD
            |||||||       ||||||||||||| ||||||||||||||||||||||||||  ||||
orf114a     SLVSLSMXXXXXXXQITTDKSAPKNXQVVILKTNTGAPLVNIQTPNGRGLSHNRYTQFDVD
                    70         80         90        100        110        120

110        120        130        140        150        160
orf114.pep  NKGAVLNNDRNNNPFVVKGSAQLILNEVRGTASKLNGIVTVGGQKADVIIANPNGITVNG
            ||||||||||||||| :|||||||||||||||||||||||||||||||||||||||||||
orf114a     NKGAVLNNDRNNNPFLVKGSAQLILNEVRGTASKLNGIVTVGGQKADVIIANPNGITVNG
                   130        140        150        160        170        180

170        180        190        200        210        220
orf114.pep  GGFKNVGRGILTTGAPQIGKDGALTGFDVVKAHWTVXAAGWNDKGGAXYTGVLARAVALQ
            |||||||||||| |||||||||||||||||  ::  || ||||||||||| |||||||||
orf114a     GGFKNVGRGILTIGAPQIGKDGALTGFDVRQGTLTVGAAGWNDKGGADYTGVLARAVALQ
                   190        200        210        220        230        240

230        240        250        260        270        280
orf114.pep  GKXXGKXLAVSTGPQKVDYASGEISAGTAAGTKPTIALDTAALGGMYADSITLIANEKGV
            ||  ||| |||||||||||||||||||||||||||||||||||||||||||||| |||||
orf114a     GKLQGKNLAVSTGPQKVDYASGEISAGTAAGTKPTIALDTAALGGMYADSITLIAXEKGV
                   250        260        270        280        290        300 orf114.pep  GVX
            |||
orf114a     GVKNAGTLEAAKQLIVTSSGRIENSGRIATTADGTEASPTYLXIETTEKGAXGTFISNGG
                   310        320        330        340        350        360
```

The complete length ORF114a nucleotide sequence <SEQ ID 61> is:

```
  1  ATGAATAAAG GTTTACATCG CATTATCTTT AGTAAAAAGC ACAGCACCAT

51  GGTTGCAGTA GCCGAAACTG CCAACAGCCA GGGCAAAGGT AAACAGGCAG

101  GCAGTTCGGT TTCTGTTTCA CTGAAAACTT CAGGCGACCT TTGCGGCAAA
```

-continued

```
 151  CTCAAAACCA CCCTTAAAAC CTTGGTCTGC TCTTTGGTTT CCCTGAGTAT
 201  GGNATTNCNN NNCNNTNCCC AAATTACCAC CGACAAATCA GCACCTAAAA
 251  ACCANCAGGT CGTTATCCTT AAAACCAACA CTGGTGCCCC CTTGGTGAAT
 301  ATCCAAACTC CGAATGGACG CGGATTGAGC CACAACCGCT ATACGCAGTT
 351  TGATGTTGAC AACAAAGGGG CAGTGTTAAA CAACCACCGT AACAATAATC
 401  CGTTTCTGGT CAAAGGCAGT GCGCAATTGA TTTTGAACGA GGTACGCGGT
 451  ACGGCTAGCA AACTCAACGG CATCGTTACC GTAGGCGGTC AAAAGGCCGA
 501  CGTGATTATT GCCAACCCCA ACGGCATTAC CGTTAATGGC GGCGGCTTTA
 551  AAAATGTCGG TCGGGGCATC TTAACTATCG GTGCGCCCCA AATCGGCAAA
 601  GACGGTGCAC TGACAGGATT TGATGTGCGT CAAGGCACAT TGACCGTAGG
 651  AGCAGCAGGT TGGAATGATA AAGGCGGAGC CGACTACACC GGGGTACTTG
 701  CTCGTGCAGT TGCTTTGCAG GGGAAATTAC AGGGTAAAAA CCTGGCGGTT
 751  TCTACCGGTC CTCAGAAAGT AGATTACGCC AGCGGCGAAA TCACTGCAGG
 801  TACGGCAGCG GGTACGAAAC CGACTATTGC CCTTGATACT GCCGCACTGG
 851  GCGGTATGTA CGCCGACAGC ATCACACTGA TTGCCANTGA AAAAGGCGTA
 901  GGCGTCAAAA ATGCCGGCAC ACTCGAAGCG CCAAGCAAT TGATTGTGAC
 951  TTCGTCAGGC CGCATTGAAA ACAGCGGCCG CATCGCCACC ACTGCCGACG
1001  GCACCGAAGC TTCACCGACT TATCTNNCNA TCCAAACCAC CGAAAAAGGA
1051  GCNNCAGGCA CATTTATCTC CAATGGTGGT CGGATCGAGA GCAAAGGCTT
1101  ATTGGTTATT GAGACGGGAG AAGATATCAN CTTGCGTAAC GGAGCCGTGG
1151  TGCAGAATAA CGGCAGTCGC CCAGCTACCA CGGTATTAAA TGCTGGTCAT
1201  AATTTGGTGA TTGAGAGTAA AACTAATGTG AACAATGCCA AAGGCTCGNC
1251  TAATCTGTCG GCCGGCGGTC GTACTACGAT CAATGATGCT ACTATTCAAG
1301  CGGGCAGTTC CGTGTACAGC TCCACCAAAG GCGATACTGA NTTGGGTGAA
1351  AATACCCGTA TTATTGCTGA AAACGTAACC GTATTATCTA ACGGTAGTAT
1401  TGGCAGTGCT GCTGTAATTG AGGCTAAAGA CACTGCACAC ATTGAATCGG
1451  GCAAACCGCT TTCTTTAGAA ACCTCGACCG TTGCCTCCAA CATCCGTTTG
1501  AACAACGGTA ACATTAAAGG CGGAAAGCAG CTTGCTTTAC TGGCAGACGA
1551  TAACATTACT GCCAAAACTA CCAATCTGAA TACTCCCGGC AATCTGTATG
1601  TTCATACAGG TAAAGATCTG AATTTGAATG TTGATAAAGA TTTGTCTGCC
1651  GCCAGCATCC ATTTGAAATC GGATAACGCT GCCCATATTA CCGGCACCAG
1701  TAAAACCCTC ACTGCCTCAA AAGACATGGG TGTGGAGGCA GGCTTGCTGA
1751  ATGTTACCAA TACCAATCTG CGTACCAACT CGGGTAATCT GCACATTCAG
1801  GCAGCCAAAG GCAATATTCA GCTTCGCAAT ACCAAGCTGA ACGCAGCCAA
1851  GGCTCTCGAA ACCACCGCAT TGCAGGGCAA TATCGTTTCA GACGGCCTTC
1901  ATGCTGTTTC TGCAGACGGT CATGTATCCT TATTGGCCAA CGGTAATGCC
1951  GACTTTACCG GTCACAATAC CCTGACAGCC AAGGCCGATG TCNATGCAGG
2001  ATCGGTTGGT AAAGGCCGTC TGAAAGCAGA CAATACCAAT ATCACTTCAT
2051  CTTCAGGAGA TATTACGTTG GTTGCCGNNN NCGGTATTCA GCTTGGTGAC
2101  GGAAAACAAC GCAATTCAAT CAACGGAAAA CACATCAGCA TCAAAAACAA
```

-continued

```
2151  CGGTGGTAAT GCCGACTTAA AAAACCTTAA CGTCCATGCC AAAAGCGGGG
2201  CATTGAACAT TCATTCCGAC CGGGCATTGA GCATAGAAAA TACNAAGCTG
2251  GAGTCTACCC ATAATACGCA TCTTAATGCA CAACACGAGC GGGTAACGCT
2301  CAACCAAGTA GATGCCTACG CACACCGTCA TCTAAGCATT ANCGGCAGCC
2351  AGATTTGGCA AAACGACAAA CTGCCTTCTG CCAACAAGCT GGTGGCTAAC
2401  GGTGTATTGG CANTCAATGC GCGCTATTCC CAAATTGCCG ACAACACCAC
2451  GCTGAGAGCG GGTGCAATCA ACCTTACTGC CGGTACCGCC CTAGTCAAGC
2501  GCGGCAACAT CAATTGGAGT ACCGTTTCGA CCAAGACTTT GGAAGATAAT
2551  GCCGAATTAA AACCATTGGC CGGACGGCTG AATATTGAAG CAGGTAGCGG
2601  CACATTAACC ATCGAACCTC CCAACCGCAT CAGTGCGCAT ACCGACCTGA
2651  GCATCAAAAC AGGCGGAAAA TTGCTGTTGT CTGCAAAAGG AGGAAATGCA
2701  GGTGCGCNTA GTGCTCAAGT TTCCTCATTG GAAGCAAAAG GCAATATCCG
2751  TCTGGTTACA GGAGNAACAG ATTTAAGAGG TTCTAAAATT ACAGCCGGTA
2801  AAAACTTGGT TGTCGCCACC ACCAAAGGCA AGTTGAATAT CGAAGCCGTA
2651  AACAACTCAT TCAGCAATTA TTTTCNTACA CAAAAAGNGN NNGNNCTCAA
2901  CCAAAAATCC AAAGAATTGG AACAGCAGAT TGCGCAGTTG AAAAAAAGCT
2951  CGCNTAAAAG CAAGCTGATT CCAACCCTGC AAGAAGAACG CGACCGTCTC
3001  GCTTTCTATA TTCAAGCCAT CAACAAGGAA GTTAAAGGTA AAAAACCCAA
3051  AGGCAAAGAA TACCTGCAAG CCAAGCTTTC TGCACAAAAT ATTGACTTGA
3101  TTTCCGCACA AGGCATCGAA ATCAGCGGTT CCGATATTAC CGCTTCCAAA
3151  AAACTGAACC TTCACGCCGC AGGCGTATTG CCAAAGGCAG CAGATTCAGA
3201  GGCGGCTGCT ATTCTGATTG ACGGCATAAC CGACCAATAT GAAATTGGCA
3251  AGCCCACCTA CAAGAGTCAC TACGACAAAG CTGCTCTGAA CAAGCCTTCA
3301  CGTTTGACCG GACGTACGGG GGTAAGTATT CATGCAGCTG CGGCACTCGA
3351  TGATGCACGT ATTATTATCG GTGCATCCGA AATCAAAGCT CCCTCAGGCA
3401  GCATAGACAT CAAAGCCCAT AGTGATATTG TACTGGAGGC TGGACAAAAC
3451  GATGCCTATA CCTTCTTANA AACCAAAGGT AAAAGCGGCA NAATNATCAG
3501  AAAAACNAAG TTTACCAGCA CCNGCGANCA CCTGATTATG CCAGCCCCNG
3551  TCGAGCTGAC CGCCAACGGT ATCACGCTTC AGGCAGGCGG CAACATCGAA
3601  GCTAATACCA CCCGCTTCAA TGCCCCTGCA GGTAAAGTTA CCCTGGTTGC
3651  GGGTGAANAG NTGCAACTGC TGGCAGAAGA AGGCATCCAC AAGCACGAGT
3701  TGGATGTCCA AAAAAGCCGC CGCTTTATCG GCATCAAGGT AGGTNAGAGC
3751  AATTACAGTA AAAACGAACT GAACGAAACC AAATTGCCTG TCCGCGTCGT
3801  CGCCCAAANT GCAGCCACCC GTTCAGGCTG GGATACCGTG CTCGAAGGTA
3851  CCGAATTCAA AACCACGCTG GCCGGTGCCG ACATTCAGGC AGGTGTANGC
3901  GAAAAGCCCC GTGTCGATGC GAAAATTATC CTCAAAGGCA TTGTGAACCG
3951  TATCCAGTCG GAAGAAAAAT TAGAAACCAA CTCAACCGTA TGGCAGAAAC
4001  AGGCCGGACG CGGCAGCACT ATCGAAACGC TAAAACTGCC CAGCTTCGAA
4051  AGCCCTACTC CGCCCAAATT GTCCGCACCC GGCGGNTATA TCGTCGACAT
4101  TCCGAAAGGC AATCTGAAAA CCGAAATCGA AAAGCTGTCC AAACAGCCCG
```

```
                         -continued
4151    AGTATGCCTA TCTGAAACAG CTCCAAGTAG CGAAAAACAT CAACTGGAAT

4201    CAGGTGCAGC TTGCTTACGA CAGATGGGAC TACAAACAGG AGGGCTTAAC

4251    CGAAGCAGGT GCGGCGATTA TCGCACTGGC CGTTACCGTG GTCACCTCAG

4301    GCGCAGGAAC CGGAGCCGTA TTGGGATTAA ACGGTGCGNC CGCCGCCGCA

4351    ACCGATGCAC CATTCGCCTC TTTGGCCAGC CAGGCTTCCG TATCGTTCAT

4401    CAACAACAAA GGCGATGTCG GCAAAACCCT GAAAGAGCTG GCAGAAGCA

4451    GCACGGTGAA AAATCTGGTG GTTGCCGCCG CTACCGCAGG CGTAGCCGAC

4501    AAAATCGGCG CTTCGGCACT GANCAATGTC AGCGATAAGC AGTGGATCAA

4551    CAACCTGACC GTCAACCTAG CCAATGNCGG GCAGTGCCGC ACTGAttaa
```

This encodes a protein having amino acid sequence <SEQ ID 62>:

```
   1    MNKGLHRIIF SKKHSTMVAV AETANSQGKG KQAGSSVSVS LKTSGDLCGK

51    LKTTLKTLVC SLVSLSMXXX XXXQITTDKS APKNXQVVIL KTNTGAPLVN

101    IQTPNGRGLS HNRYTQFDVD NKGAVLNNDR NWNPFLVKGS AQLILNEVRG

151    TASKLNGIVT VGGQKADVII ANPNGITVNG GGFKNVGRGI LTIGAPQIGK

201    DGALTGFDVR QGTLTVGAAG WNDKGGADYT GVLARAVALQ GKLQGKNLAV

251    STGPQKVDYA SGEISAGTAA GTKPTIALDT AALGGMYADS ITLIAXEKGV

301    GVKNAGTLEA AKQLIVTSSG RIENSGRIAT TADGTEASPT YLXIETTEKG

351    AXGTFISNGG RIESKCLLVI ETGEDIXLRN GAVVQNNGSR PATTVLNAGH

401    NLVIESKTNV NNAKGSXNLS AGGRTTINDA TIQAGSSVYS STKGDTXLGE

451    NTRIIAENVT VLSNGSIGSA AVIEAKDTAH IESGKPLSLE TSTVASNIRL

501    NNGNIKGGKQ LALLADDNIT AKTTNLNTPG NLYVHTGKDL NLNVDKDLSA

551    ASIHLKSDNA AHITGTSKTL TASKDMGVEA GLLNVTWTNL RTNSGNLHIQ

601    AAKGNIQLRN TKLNAAKALE TTALQGNIVS DGLHAVSADG HVSLLAMGNA

651    DFTGHNTLTA KADVXAGSVG KGRLKADNTN ITSSSGDITL VAXXGIQLGD

701    GKQRNSINGK HISIKNNGGN ADLKNLNVHA KSGALNIHSD RALSIENTKL

751    ESTHNTHLNA QHERVTU4QV DAYAHRHLSI XGSQIWQNDK LPSANKLVAN

801    GVLAXNARYS QIADNTTLRA GAINLTAGTA LVKRGNINWS TVSTKTLEDN

851    AELKPLAGRL NIEAGSGTLT IEPANRISAH TDLSIKTGGK LLLSAKGGNA

901    GAXSAQVSSL EAKGNIRLVT GXTDLRGSKI TAGKNLVVAT TKGKLNIEAV

951    NNSFSNYFXT QKXXXLNQKS KELEQQIAQL KKSSXKSKLI PTLQEERDRL

1001    AFYIQAINKE VKGKKPKGKE YLQAKLSAQN IDLISAQGIE ISGSDITASK

1051    KLNLHAAGVL PKAADSEAAA ILIDGITOQY EIGKPTYKSH YDKAALNKPS

1101    RLTGRTGVSI HAAAALDDAR IIIGASEIKA PSGSIDIKAH SDIVLEAGQN

1151    DAYTFLXTKG KSGXXIRKTK FTSTXXHLIM PAPVELTANG ITLQAGGNIE

1201    ANTTRENAPA GKVTLVAGEX XQLLAEEEGIH KHELDVQKSR RFIGIKVGXS

1251    NYSKNELNET KLPVRVVAQX AATRSGWDTV LEGTEFKTTL AGADIQAGVX

1301    EKARVDAKII LKGIVNRIQS EEKLETNSTV WQKQAGRGST IETLKLPSFE

1351    SPTPPKLSAP GGYIVDIPKG NLKTEIEKLS KQPEYAYLKQ LQVAKNINWN
```

```
1401   QVQLAYDRWD YKQEGLTEAG AAIIALAVTV VTSGAGTGAV LGLWGAXAAA

1451   TDAAFASLAS QASVSFINNK GDVGKTLKEL GRSSTVKNLV VAAATAGVAD

1501   KIGASALXNV SDKQWINNLT VNLANXGQCR TD*
```

ORF114-1 (SEQ ID NO:179) and ORF114a (SEQ ID NO:62) show 89.8% identity in 1564 aa overlap

```
orf114a.pep    MNKGLHRIIFSKKHSTMVAVAETANSQGKGKQAGSSVSVSLKTSGDLCGKLKTTLKTLVC
               ||||||||||||||||||||||||||||||||||||||||||||||||||||||||||||
orf114-1       MNKGLHRIIFSKKHSTMVAVAETANSQGKGKQAGSSVSVSLKTSGDLCGKLKTTLKTLVC orf114a.pep    SLVSLSMXXXXXXQITTDKSAPKNXQVVILKTNTGAPLVNIQTPNGRGLSHNRYTQFDVD
               |||||||       |||||||||| |||||||||||||||||||||||||||||||||||
orf114-1       SLVSLSMVLPAHAQITTDKSAPKNQQVVILKTNTGAPLVNIQTPNGRGLSHNRYTQFDVD orf114a.pep    NKGAVLNNDRNNNPFLVKGSAQLILNEVRGTASKLNGIVTVGGQKADVIIANPNGITVNG
               |||||||||||||||:||||||||||||||||||||||||||||:||||||||||||||
orf114-1       NKGAVLNNDRNNNPFVVKGSAQLILNEVRGTASKLNGIVTVGGQKADVIIANPNGITVNG orf114a.pep    GGFKNVGRGILTIGAPQIGKDGALTGFDVRQGTLTVGAAGWNDKGGADYTGVLARAVALQ
               |||||||||||| |||||||||||||||||||||||||||||||||||||||||||||||
orf114-1       GGFKNVGRGILTTGAPQIGKDGALTGFDVRQGTLTVGAAGWNDKGGADYTGVLARAVALQ orf114a.pep    GKLQGKNLAVSTGPQKVDYASGEISAGTAAGTKPTIALDTAALGGMYADSITLIAXEKGV
               |||||||||||||||||||||||||||||||||||||||||||||||||||||| ||||
orf114-1       GKLQGKNLAVSTGPQKVDYASGEISAGTAAGTKPTIALDTAALGGMYADSITLIANEKGV orf114a.pep    GVKNAGTLEAAKQLIVTSSGRIENSGRIATTADGTEASPTYLXIETTEKGAXGTFISNGG
               |||||||||||||||||||||||||||||||||||||||| |||||||| |||||||||
orf114-1       GVKNAGTLEAAKQLIVTSSGRIENSGRIATTADGTEASPTYLSIETTEKGAAGTFISNGG orf114a.pep    RIESKGLLVIETGEDIXLRNGAVVQNNGSRPATTVLNAGHNLVIESKTNVNNAKGSXNLS
               |||||||||||||||| ||||||||||||||||||||||||||||||||||||| :||
orf114-1       RIESKGLLVIETGEDISLRNGAVVQNNGSRPATTVLNAGHNLVIESKTNVNNAKGPATLS orf114a.pep    AGGRTTINDATIQAGSSVYSSTKGDTXLGENTRIIAENVTVLSNGSIGSAAVIEAKDTAH
               | |||:|::|:||:|::|||| |:: ||:|||  :|||||||:|:|:|||||||||||
orf114-1       ADGRTVIKEASIQTGTTVYSSSKGNAELGNNTRITGADVTVLSNGTISSSAVIDAKDTAH orf114a.pep    IESGKPLSLETSTVASNIRLNNGNIKGGKQLALLADDNITAKTTNLNTPGNLYVHTGKDL
               ||:||||||:|||:||:||||||:|||||||||||||||||||||||||||||||||||
orf114-1       IEAGKPLSLEASTVTSDIRLNGGSIKGGKQLALLADDNITAKTTNLNTPGNLYVHTGKDL orf114a.pep    NLNVDKDLSAASIHLKSDNAAHITGTSKTLTASKDMGVEAGLLNVTNTNLRTNSGNLHIQ
               ||||||||||||||||||||||||||||||||||||||||| |||||||||||||||||
orf114-1       NLNVDKDLSAASIHLKSDNAAHITGTSKTLTASKDMGVEAGSLNVTNTNLRTNSGNLHIQ orf114a.pep    AAKGNIQLRNTKLNAAKALETTALQGNIVSDGLHAVSADGHVSLLANGNADFTGHNTLTA
               ||||||||||||||||||||||||||||||||||||||||||||||||||||||||||||
orf114-1       AAKGNIQLRNTKLNAAKALETTALQGNIVSDGLHAVSADGHVSLLANGNADFTGHNTLTA orf114a.pep    KADVXAGSVGKGRLKADNTNITSSSGDITLVAXXGIQLGDGKQRNSINGKHISIKNNGGN
               ||||  ||||||||||||||||||||||||||  ||||||||||||||||||||||||||
orf114-1       KADVNAGSVGKGRLKADNTNITSSSGDITLVAGNGIQLGDGKQRNSINGKHISIKNNGGN orf114a.pep    ADLKNLNVHAKSGALNIHSDRALSIENTKLESTHNTHLNAQHERVTLNQVDAYAHRHLSI
               ||||||||||||||||||||||||||||||||||||||||||||||||||||||||||||
orf114-1       ADLKNLNVHAKSGALNIHSDRALSIENTKLESTHNTHLNAQHERVTLNQVDAYAHRHLSI orf114a.pep    XGSQIWQNDKLPSANKLVANGVLAXNARYSQIADNTTLRAGAINLTAGTALVKRGNINWS
               :||||||||||||||||||||||| |||||||||||||||||||||||||||||||||||
orf114-1       TGSQIWQNDKLPSANKLVANGVLALNARYSQIADNTTLRAGAINLTAGTALVKRGNINWS
```

-continued

```
orf114a.pep    TVSTKTLEDNAELKPLAGRLNIEAGSGTLTIEPANRISAHTDLSIKTGGKLLLSAKGGNA
               ||||||||||||||||||||||||||||||||||||||||||||||||||||||||||||
orf114-1       TVSTKTLEDNAELKPLAGRLNIEAGSGTLTIEPANRISAHTDLSIKTGGKLLLSAKGGNA orf114a.pep    GAXSAQVSSLEAKGNIRLVTGXTDLRGSKITAGKNLVVATTKGKLNIEAVNNSFSNYFXT
               || ||||||||||||||||||| |||||||||||||||||||||||||||||||||||| 
orf114-1       GAPSAQVSSLEAKGNIRLVTGETDLRGSKITAGKNLVVATTKGKLNIEAVNNSFSNYFPT orf114a.pep    QKXXXLNQKSKELEQQIAQLKKSSXKSKLIPTLQEERDRLAFYIQAINKEVKGKKPKGKE
               ||   |||||||||||||||||| ||||||||||||||||||||||||||||||||||||
orf114-1       QKAAELNQKSKELEQQIAQLKKSSPKSKLIPTLQEERDRLAFYIQAINKEVKGKKPKGKE orf114a.pep    YLQAKLSAQNIDLISAQGIEISGSDITASKKLNLHAAGVLPKAADSEAAAILIDGITDQY
               ||||||||||||||||||||||||||||||||||||||||||||||||||||||||||||
orf114-1       YLQAKLSAQNIDLISAQGIEISGSDITASKKLNLHAAGVLPKAADSEAAAILIDGITDQY orf114a.pep    EIGKPTYKSHYDKAALNKPSRLTGRTGVSIHAAAALDDARIIIGASEIKAPSGSIDIKAH
               ||||||||||||||||||||||||||||||||||||||||||||||||||||||||||||
orf114-1       YLQAKLSAQNIDLISAQGIEISGSDITASKKLNLHAAGVLPKAADSEAAAILIDGITDQY orf114a.pep    SDIVLEAGQNDAYTFLXTKGKSGXXIRKTKFTSTXXHLIMPAPVELTANGITLQAGGNIE
               |||||||||||||||| ||||||  |||||||||  ||||||||||||||||||||||||
orf114-1       SDIVLEAGQNDAYTFLKTKGKSGKIIRKTKFTSTRDHLIMPAPVELTANGITLQAGGNIE orf114a.pep    ANTTRFNAPAGKVTLVAGEXXQLLAEEGIHKHELDVQKSRRFIGIKVGXSNYSKNELNET
               ||||||||||||||||||||  |||||||||||||||||||||||||||||||||||||
orf114-1       ANTTRFNAPAGKVTLVAGEELQLLAEEGIHKHELDVQKSRRFIGIKVGKSNYSKNELNET orf114a.pep    KLPVRVVAQXAATRSGWDTVLEGTEFKTTLAGADIQAGVXEKARVDAKIILKGIVNRIQS
               |||||||||:|||||||||||||||||||||||||||||| |||| |||||||||||||
orf114-1       KLPVRVVAQTAATRSGWDTVLEGTEFKTTLAGADIQAGVGEKARADAKIILKGIVNRIQS orf114a.pep    EEKLETNSTVWQKQAGRGSTIETLKLPSFESPTPPKLSAPGGYIVDIPKGNLKTEIEKLS
               |||||||||||||||||||||||||||||||||||||:||||||||||||||||||||:
orf114-1       EEKLETNSTVWQKQAGRGSTIETLKLPSFESPTPPKLTAPGGYIVDIPKGNLKTEIEKLA orf114a.pep    KQPEYAYLKQLQVAKNINWNQVQLAYDRWDYKQEGLTEAGAAIIALAVTVVTSGAGTGAV
               ||||||||||||||||:||||||||||:|||||||| ||||| | : | |:   |   |
orf114-1       KQPEYAYLKQLQVAKNVNWNQVQLAYDKWDYKQEGLTRAGAAIVTIIVTALTYGYGTGAV orf114a.pep    LGLNGA---------------XAAATD---------AAFASLASQASVSFINNKGDVGKTL    1477
                |: ::                :||||         ||:||| |||:||||||||||||:|
orf114-1       GGVAASGSSTAAAAGTAATTTAAATTCSTATAMQTAALASLYSQAAVSIINNKGDVGKAL    1500 orf114a.pep    KELGRSSTVKNLVVAAATAGVADKIGA----------SALXNVSDKQWINNL----TVNL    1523
               :||  :|:::||:||: :::||  :||          : |  :::| || |    ::||
orf114-1       KDLGTSDTVKQIVTSALTAGALNQMGADIAQLNSKVRTELFSSTGNQTIANLGGRLATNL    1560 orf114a.pep    ANXGQCRTDX
               :| |
orf114-1       SNAGISAGINTAVN...
```

Homology with pspA Putative Secreted Protein of *N. meningitidis* (Accession Number AF030941)

ORF114 (SEQ ID NO:180) and pspA (SEQ ID NO:182) protein show 36% aa identity (SEQ ID NO:181) in 302aa overlap:

```
Orf114:    1 AVAETANSQGKGKQAGSSVSVSL----KTSGDXXXXXXXXXXXXXXXXXXXXXXXXPAHAQ    56
             AVAE  + GK Q  +SV +       S                            PA A
pspA:     19 AVAENVHRDGKSMQDSEAASVRVTGAASVSSARAAFGFRMAAFSVMLALGVAAFSPAPAS    78
```

```
                             -continued
Orf114:  57  -ITTDKSAPKNQQVVILKTNTGAPLVNIQTPNGRGLSHNRXYAFDVDNKGAVLNNDRNN- 114
               I DKSAPKNQQ VIL+T  G P VNIQTP+ +G+S NR   FDVD KG +LNN R+N
pspA:    79  GIIADKSAPKNQQAVILQTANGLPQVNIQTPSSQGVSVNRFKQFDVDEKGVILNNSRNNT 138

Orf114: 115  ----------NPFVVKGSAQLILNEV-RGTASKLNGIVTVGGQKADVIIANPNGITVNGG 163
                       NP + +G A++I+N++    S LNG + VGG++A+V++ANP+GI VNGG
pspA:   139  QTQLGGWIQGNPHLARGEARVIVNQIDSSNPSLLNGYIEVGGKRAEVVVANPSGIRVNGG 198

Orf114: 115  ----------NPFVVKGSAQLILNEV-RGTASKLNGIVTVGGQKADVIIANPNGITVNGG 163
                       NP + +G A++I+N++    S LNG + VGG++A+V++ANP+GI VNGG
pspA:   139  QTQLGGWIQGNPHLARGEARVIVNQIDSSNPSLLNGYIEVGGKRAEVVVANPSGIRVNGG 198

Orf114: 164  GFKNVGRGILTTGAPQIGKDGALTGFDVVKAHWTVXAAGWNDKGGAXYTGVLARAVALQG 223
             G  N     LT+G P + +G LTGFDV     +   G  D  A YT +L+RA  +
pspA:   199  GLINAASVTLTSGVPVL-NNGNLTGFDVSSGKVVIGGKGL-DTSDADYTRILSRAAEINA 256

Orf114: 224  KXXGKXLAVSTGPQKVDYASGEISAGTAAGTK----PTIALDTAALGGMYADSITLIANE 279
                GK + V +G K+D+       +A +       PT+A+DTA LGGMYAD  ITLI+ +
pspA:   257  GVWGKDVKVYSGKNKLDFDGSLAKTASAPSSSDSVTPTVAIDTATLGGMYADKITLISTD 316

Orf114: 380  KG 281
             G
pspA:   317  NG 318
```

ORF114a is also homologous to pspA:

```
gi|2623258 (AF030941) putative secreted protein (Neisseria meningitidis) Length = 2273
Score = 261 bits (6559), Expect = 3e-68
Identities = 203/663 (30%), Positives = 314/663 (46%), Gaps = 76/663 (11%)

Query:    1  MNKGLHRIIFSKKHSTMVAVAETANSQGKGKQAGSSVSVSLK-----TSGDXXXXXXXXX  55
             MNK  +++IF+KK S M+AVAE +   GK Q    + SV +      +S
Sbjct:    1  MNKRCYKVIFNKKRSCMMAVAENVHRDGKSMQDSEAASVRVTGAASVSSARAAFGFRMAA  60

Query:   56  XXXXXXXXXXXXXXXXXXQITTDKSAPKNXQVVILKTNTGAPLVNIQTPNGRGLSHNRYT 115
                               I DKSAPKN Q VIL+T  G P VNIQTP+ +g+s NR+
Sbjct:   61  FSVMLALGVAAFSPAPASGIIADKSAPKNQQAVILQTANGLPQVNIQTPSSQGVSVNRFK 120

Query:  116  QFDVDNKGAVLNNDRNN-----------NPFLVKGSAQLILNEV-RGTASKLNGIVTVGG 163
             QFDVD KG +LNN R+N           NP L +G A++I+N++    S LNG + VGG
Sbjct:  121  QFDVDEKGVILNNSRSNTQTQLGGWIQGNPHLARGEARVIVNQIDSSNPSLLNGYIEVGG 180

Query:  164  QKADVIIANPNGITVNGGGFKNVGRGILTIGAPQIGKDGALTGFDVRQGTLTVGAAGWND 223
             ++A+V++ANP+GI VNGGG  N     LT G P + +G LTGFDV     G + G  D
Sbjct:  181  KRAEVVVANPSGIRVNGGGLINAASVTLTSGVPVL-NNGNLTGFDVSSGKVVIGGKGL-D 238

Query:  224  KGGADYTGVLARAVALQGKLQGKNLAVSTGPQKVDYASGEISAGTAAGTK----PTIALD 279
                 ADYT +L+RA  +   + GK++ V +G K+D+       +A +       PT+A+D
Sbjct:  239  TSDADYTRILSRAAEINAGVWGKDVKVVSGKNKLDFDGSLAKTASAPSSSDSVTPTVAID 298

Query:  280  TAALGGMYADSITLIAXEKGVGVKNAGTLEAAK-QLIVTSSGRIENSGRIATTADGTEAS 338
             TA LGGMYAD ITLI+ + G  ++N G + AA   +++ G++  NSG I
Sbjct:  299  TATLGGMYADKITLISTDNGAVIRNKGRIFAATGGVTLSADGKLSNSGSI-------DAA 351

Query:  339  PTYLXIETTEKGAXGTFISNGGRIESKGLLVIETGEDIXLRNGAVVQNNGSRPATTVLNA 398
                 +T +         G I S    V++   i + G +      GS      + +
Sbjct:  352  EITISAQTVD--------NRQGFIRSGKGSVLKVSDGINNQAGLI----GSAGLLDIRDT 399

Query:  399  GHNLVIESKTNVNNAKGS----XNLSAGGRTTINDATIQAGSSVYSSTKGDTXLGENTRI 454
             G    +S  ++NN G+       ++S  ++  ND  A   VS +  D   G+
Sbjct:  400  G-----KSSLHINNTDGTIIAGKDVSLQAKSLDNDGILTAARDV-SVSLHDDFAGKRDIE 453

Query:  455  IAENVTVLSNGSIGSAAVIEAKDTAHIESGKPLSLETSTVASNIRLNNGNIKGGKQLALL 514
              +T + G + +    +I+A DT  + +        + + S R  N G       L+
Sbjct:  454  AGRTLTFSTQGRLKNTRIIQAGDTVSLTAAQIDNTVSGKIQSGNRTGLNGKNGITNRGLI 513

Query:  515  ADDNIT-----AKTTNLNTPGNLYVHTGKDLNLNVDKDLSAASIHLKSDNAAHITGTSKT 569
             + IT      AK+ N T G +Y   G + +  D L+          AA
Sbjct:  514  NSNGITLLQTEAKSDNAGT-GRIY---GSRVAVEADTLLNREETVNGETKAA-------V 562

Query:  570  LTASKDMGVEAGXXXXXXXXXXXXXSGNLHIQAA---KGNIQLRNTKL-NAAKALETTALQ 625
             + A + + A                SG+LHI +A   +Q  NT L N + A+E++
Sbjct:  563  IAARERLDIGAREIENREAALLSSSGDLHIGSALNGSRQVQGANTSLHNRSAAIESS--- 619
```

-continued

```
Query:   626  GNI                                                             628   (SEQ ID NO: 183)
              GNI                                                                    (SEQ ID NO: 184)
Sbjct:   620  GNI                                                             622   (SEQ ID NO: 185)

Score = 37.5 bits (85), Expect = 0.53
Identities = 87/432 (20%), Positives = 159/432 (36%), Gaps = 62/432 (14%)

Query:   239  LQGKLQGKNLAVSTGPQKVDYASGEISAGTAAGTKPTIALDTAALGGMYADSITLIAXEK  298
              LQG LQGKN+  + G    +  +G I  A   A    K     A  + + S T        +
Sbjct:  1023  LQGDLQGKNIFAAAGSDITN--TGSIGAENALLLK--------ASNNIESRSETRSNQNE  1072

Query:   299  GVGVKNAGTLEAAKQLIVTSSGRI--ENSGRIATTADGTEASPTYLXIETTEKGAXG-TF  355
                V+N G + A    L      +G +  +    I  TA            E T +    G T
Sbjct:  1073  QGSVRNIGRV-AGIYLTGRQNGSVLLDAGNNIVLTAS-----------ELTNQSEDGQTV  1120

Query:   356  ISNGGRIESKGLLVIETGEDIXLRNGAVVQNNGSRPATTVLNAGHNLVIESK-------T  408
              ++ GG I S    +        i   +  V++   +    +T+     G NL  + +K
Sbjct:  1121  LNAGGDIRSDTTGISRNQNTIFDSDNYVIRKEQNEVGSTIRTRG-NLSLNAKGDIRIRAA  1179

Query:   409  NVNNAKGSXNLSAGGRTTINDATIQAGSS--------VYSSTKGDTXLGENTRIIAENVT  460
                V  + +G    L+AG         D   ++AG +            Y+    G       + TR  +
Sbjct:  1180  EVGSEQGRLKLAAG-----RDIKVEAGKAHTETEDALKYTGRSGGGIKQKMTRHLKNQNG  1234

Query:   461  VLSNGSIGSAAVIEAKDTAHIESGKPLSLETSTVASNIRLNNGNIKGGKQLALLADDNIT  520
                  +G++      +I          +G  +   +  T+ S       NN   +K   +     + A+ N
Sbjct:  1235  QAVSGTLDGKEIILVSGRDITVTGSNIIADNHTILS--AKNNIVLKAAETRSRSAEMNKK  1292

Query:   521  AKTTNLNTPG-NLYVHTGKDLNLNVDKDLSAASIHLKSDN-------AAHITGTSKTLTA  572
                K+  + + G     + KD     N  + +S       + S N           H T T  T+++
Sbjct:  1293  EKSGLMGSGGIGFTAGSKKDTQTNRSETVSHTESVVGSLNGNTLISAGKHYTQTGSTISS  1352

Query:   573  SK-DMGVEAGXXXXXXXXXXXXXSGNLHIQAAKG-----NIQLRNTKLNAAKALETTALQG  626
               + D+G+  +G                                  KG      ++ +  NT +  A   A++         G
Sbjct:  1353  PQGDVGISSGKISIDAAQNRYSQESKQVYEQKGVTVAISVPVVNTVMGAVDAVKAVQTVG  1412

Query:   627  NIVSDGLHAVSA                                                  638   (SEQ ID NO: 186)
              +     ++A++A                                                        (SEQ ID NO: 187)
Sbjct:  1413  KSKNSRVNAMAA                                                 1424   (SEQ ID NO: 188)
```

Figure 5:
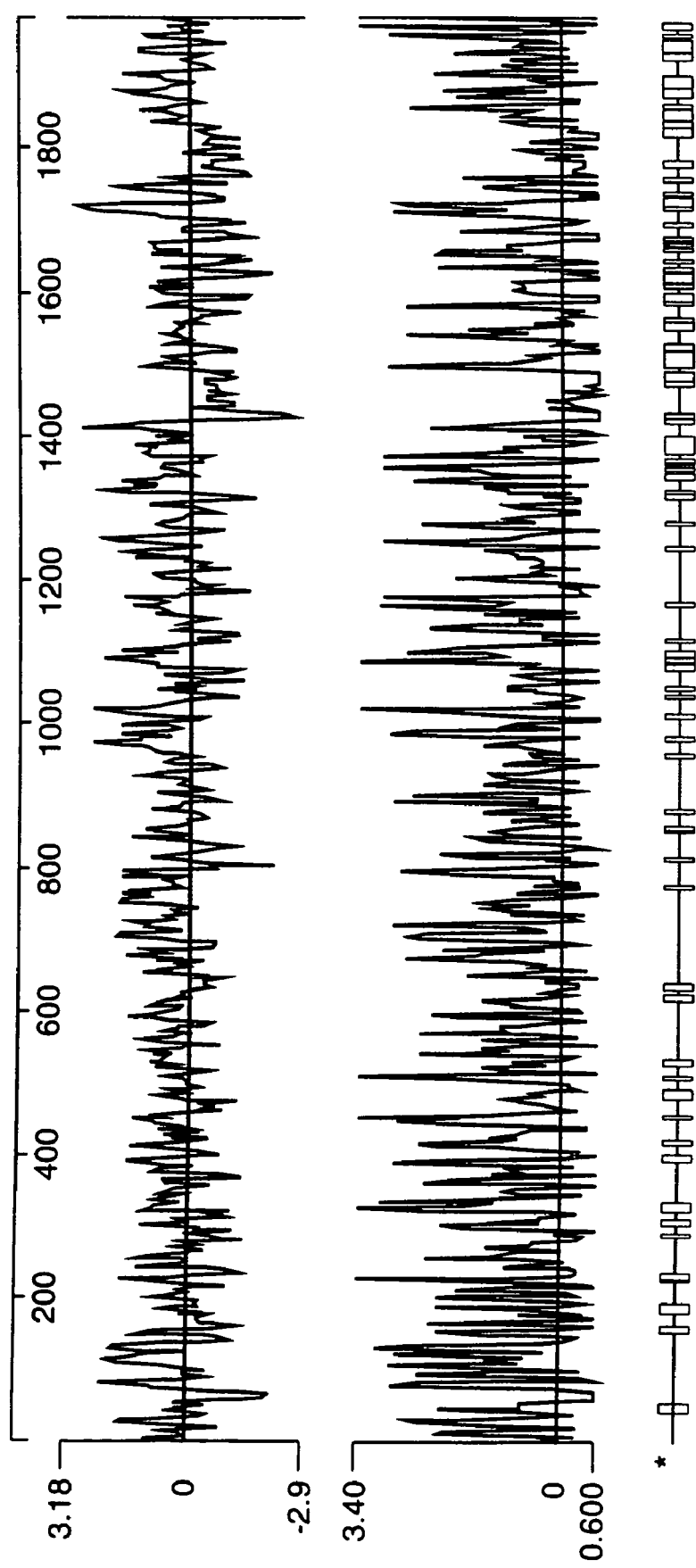
FIG. 5 shows a hydrophilicity plot (upper), an antigenic index plot (middle), and an AMPHI analysis (lower) for ORF 114.

Amino acids 1-1423 of ORF114-1 were cloned in the pGex vector and expressed in *E. coli*, as described above. GST-fusion expression was visible using SDS-PAGE, and FIG. 5 shows plots of hydrophilicity, antigenic index, and AMPHI regions for ORF 114-1.

Based on these results, including the homology with the putative secreted protein of *N. meningitidis* and on the presence of a transmembrane domain, it is predicted that this protein from *N. meningitidis*, and its epitopes, could be useful antigens for vaccines or diagnostics.

Example 14

The following partial DNA sequence was identified in *N. meningitidis* <SEQ ID 63>

```
  1    ..CGCTTCATTC ATGATGAAGC AGTCGGCAGC AACATCGGCG GCGGCAAAAT

51     GATTGTTGCA GCCGGGCAGG ATATCAATGT ACGCGGCAnA AGCCTTATTT

101     CTGATAAGGG CATTGTTTTA AAAGCAGGAC ACGACATCGA TATTTCTACT

151     GCCCATAATC GCTATACCGG CAATGAATAC CACGAGAGCA wAAAwTCAGG

201     CGTCATGGGT ACTGGCGGAT TGGGCTTTAC TATCGGTAAC CGGAAAACTA

251     CCGATGACAC TGATCGTACC AATATTGTsC ATACAGGCAG CATTATAGGC

301     AGCCTGAaTG GAGACACCGT TACAGTTGCA GGAAACCGCT ACCGACAAAC

351     CGGCAGTACC GTCTCCAGCC CCGAGGGGCG CAATACCGTC ACAGCCAAAw

401     GCATAGATGT AGAGTTCGCA AACAACCGGT ATGCCACTGA CTACGcCCAT
```

```
                 -continued
 451    ACCCAgGGAA CAAAAAGGCC TTACCGTCGC CCTCAATGTC CCGGTTGTCC

501    AAGCTGCACA AAACTTCATA CAAGCAGCCC AAAATGTGGG CAAAAGTAAA

551    AATAAACGCG TTAATGCCAT GGCTGCACCC AATGCTGCAT GGCAGAGTTA

601    TCAAGCAACC CAACAAATGC AACAATTTGC TCCAAGCAGC AGTGCGGGAC

651    AAGGTCAAAA CTACAATCAA AGCCCCAGTA TCAGTGTGTC CATTAC.TAC

701    GGCGAACAGA AAAGTCGTAA CGAGCAAAAA AGACATTACA CCGAAgCGGC

751    AgCAAGTCAA ATTATCGGCA AAGGGCAAAC CACACTTGCG GCAACAGGAA

801    GTGGGGAGCA GTCCAATATC AATATTACAG GTTCCGATGT CATCGGCCAT

851    GCAGGTACTC C.CTCATTGC CGACAACCAT ATCAGACTCC AATCTGCCAA

901    ACAGGACGGC AGCGAGCAAA GCAAAAACAA AGCAGTGGT TGGAATGCAG

951    GCGTACGTnn CAAAATAGGC AACGGCATCA GGTTTGGAAT TACCGCCGGA

1001    GGAAATATCG GTAAAGGTAA AGAGCAAGGG GGAAGTACTA CCCACCGCCA

1051    CACCCATGTC GGCAGCACAA CCGGCAAAAC TACCATCCGA AGCGGCGGGg

1101    GATACCACCC TCAAGGTGT GCAGCTCATC GGCAAAGGCA TACAGGCAGA

1151    TACGCGCAAC CTGCATATAG AAAGTGTTCA AGATACTGAA ACCTATCAGA

1201    GCAAACAGCA AAACGGCAAT GTCCAAGTTt ACTGTCGGTT ACGGATTCAG

1251    TGCAAGCGGC AGTTACCGCC AAAGCAAAGT CAAAGCAGAC CATGCCTCCG

1301    TAACCGGGCA AAgCGGTATT TATGCCGGAG AAGACGGCTA TCAAATyAAA

1351    GTyAGAGACA ACACAGACCT yAAGGGCGGT ATCATCACGT CTAGCCAAAG

1401    CGCAGAAGAT AAGGGCAAAA ACCTTTTTCA GACGGCCACC CTTACTGCCA

1451    GCGACATTCA AAACCACAGC CGCTACGAAG GCAGAAGCTT CGGCATAGGC

1501    GGCAGTTTCG ACCTGAACGG CGGCTGGGAC GGCACGGTTA CCGACAAACA

1551    AGGCAGGCCT ACCGACAGGA TAAGCCCGGC AGCCGGCTAC GGCAGCGACG

1601    GAGACAGCAA AAACAGCACC ACCCGCAGCG GCGTCAACAC CCACAACATA

1651    CACATCACCG ACGAAGCGGG ACAACTTGCC CGAACAGGCA GGACTGCAAA

1701    AGAAACCGAA GCGCGTATCT ACACCGGCAT CGACACCGAA ACTGCGGATC

1751    AACACTCAGG CCATCTGAAA AACAGCTTCG AC..
```

This corresponds to the amino acid sequence <SEQ ID 64; ORF116>:

```
  1    ..RFIHDEAVGS NIGGGKMIVA AGQDINVRGX SLISDKGIVL KAGHDIDIST

51    AHNRYTGNEY HESXXSGVNG TGGLGFTIGN RKTTDDTDRT NIVHTGSIIG

101    SLNGDTVTVA GNRYRQTGST VSSPEGRNTV TAKXIDVEFA NNRYATDYAH

151    TQEQKGLTVA LNVPVVQAAQ NFIQAAQNVG KSKWKRVNAM AAANAAWQSY

201    QATQQMQQFA PSSSAGQGQN YNQSPSISVS IXYGEQKSRN EQKRHYTEAA

251    ASQIIGKGQT TLAATGSGEQ SNINITGSDV IGHAGTXLIA DWHIRLQSAK

301    QOGSEQSKNK SSGWNAGVRX KIGNGIRFGI TAGGNIGKGK EQGGSTTHRH

351    THVGSTTGKT TIRSGGDTTL KGVQLIGKGI QADTRNLHIE SVQDTETYQS

401    KQQNGNVQVT VGYGFSASGS YRQSKVKADH ASVTGQSGIY AGEDGYQIKV

451    RDNTDLKGGI ITSSQSAEDK GKNLFQTATL TASDIQNHSR YEGRSFGIGG
```

-continued

```
501   SFDLNGGWDG TVTDKQGRPT DRISPAAGYG SDGDSKNSTT RSGVNTHNIH

551   ITDEAGQLAR TGRTAKETEA RIYTGIOTET ADQHSGHLKN SFD..
```

Computer analysis of this amino acid sequence gave the following results:

Homology with pspA Putative Secreted Protein of *N. meningitidis* (Accession Number AF030941)

ORF116 (SEQ ID NO:189) and pspA (SEQ ID NO:191) protein show 38% aa identity (SEQ ID NO:190) in 502aa overlap:

```
Orf116:     6  EAVGSNIGGGKMIVAAGQDINVRGXSLISDKGIVLKAGHDIDISTAHNRYTGNEYHESXX    65
               +AV   + G ++I+ +G+DI V G ++I+D   +L A ++I +  A  R    E ++
PspA:    1235  QAVSGTLDGKEIILVSGRDITVTGSNIIADNHTILSAKNNIVLKAAETRSRSAEMNKKEK  1294

Orf116:    66  XXXXXXXXXXXXXNRKXXXXXXXRTNIVHTGSIIGSLNGDTVTVAGNRYRQTGSTVSSPE   125
                            ++K          + HT S++GSLNG+T+  AG  Y QTGST+SSP+
PspA:    1295  SGLMGSGGIGFTAGSKKDTQTNRSETVSHTESVVGSLNGNTLISAGKHYTQTGSTISSPQ  1354

Orf116:   126  GRNTVTAKXIDVEFANNRYATDYAHTQEQKGLTVALNVPXXXX---XXXXXXXXXXXGKS   182
               G   +++  o ++ A MRU+ +     EQLG+TVA++VP                  GKS
PspA:    1355  GDVGISSGKISIDAAQNRYSQESKQVYEQKGVTVAISVPVVNTVMGAVDAVKAVQTVGKS  1414

Orf116:   183  KNKRVXXXXXXXXXXWQSYQATQQMQQFA--PSSSAGQGQNYNQSPSISVSIXYGEQKSRN   240
               KN RV          +   +   +   A  P  +AGQG        ISVS+ YGEQK+ +
PspA:    1415  KNSRVNAMAAANALNKGVDSGVALYNAARNPKKAAGQG--------ISVSVTYGEQKNTS  1466

Orf116:   241  EQKRHYTEAAASQIIGKGQTTLAATGSGEQSNINITGSDVIGHAGTXLIADNHIRLQSAK   300
               E +   T+    +I G G+ +L A+G+G+ S I ITGSDV G  GT L A+n +++++A+
PspA:    1467  ESRIKGTQVQEGKITGGGKVSLTASGAGKDSRITITGSDVYGGKGTRLKAENAVQIEAAR  1526

Orf116:   301  QDGSEQSKNKSSGWNAGVRXKIGNGIRFGITAXXXXXXXXXXXXXSTTHRHTHVGSTTGKT   360
               Q   E+S+NKS+G+NAGV   I  GI FG TA             T +R++H+GS   +T
PspA:    1527  QTHQERSENKSAGFNAGVAIAINKGISFGFTAGANYGKGYGNGDETAYRNSHIGSKDSQT  1586

Orf116:   361  TIRSGGDTTLKGVQLIGKGIQADTRNLHIESVQDTETYQSKQQNGNVQVTVGYGFSASGS   420
                I SGGDT +KG QL GKG+     +LHIES+QDT  ++ KQ+N + QVTVGYGFS  GS
PspA:    1587  AIESGGDTVIKGGQLKGKGVGVTAESLHIESLQDTAVFKGKQENVSAQVTVGYGFSVGGS  1646

Orf116:   421  YRQSKVKADHASVTGQSGIYAGEDGYQIKVRDNTDLKGGIITSSQSAEDKGKNLFQTATL   480
               Y +SK  +D+ASV  QSGI+AG DGY+I+V   T L G  + S     DK KNL +T+ +
PspA:    1647  YNRSKSSSDYASVNEQSGIFAGGDGYRIRVNGKTGLVGAAVVSD---ADKSKNLLKTSEI  1703

Orf116:   481  TASDIQNHSRYEGRSFGIGGSF                                         502
                  DIQNH+     + G+ G F
PspA:    1704  WHKDIQNHASAAASALGLSGGF                                        1725
```

Based on homology with pspA, it is predicted that this protein from *N. meningitidis*, and its epitopes, could be useful antigens for vaccines or diagnostics.

Example 15

The following partial DNA sequence was identified in *N. meningitidis* <SEQ ID 65>

```
  1 ..ACGACCGGCA GCCTCGGCGG CATACTGGCC GGCGGCGGCA CTTCCCTTGC

51   CGCACCGTAT TTGGACAAAG CGGCGGAAAA CCTCGGTCCG GCGGGCAAAG

101   CGGCGGTCAA CGCACTGGGC GGTGCGGCCA TCGGCTATGC AACTGGTGGT

151   AGTGGTGGTG CTGTGGTGGG TGCGAATGTA GATTGGAACA ATAGGCAGCT

201   GCATCCGAAA GAAATGGCGT TGGCCGACAA ATATGCCGAA GCCCTCAAGC
```

-continued

```
251   GCGAAGTTGA AAAACGCGAA GGCAGAAAPA TCAGCAGCCA AGAAGCGGCA

301   ATGAGAATCC GCAGGCAGAT ATGCGTTGGG TGGACAAAGG TTCCCAAGAC

351   GGCTATACCG ACCAAAGCGT CATATCCCTT ATCGGAATGA
```

This corresponds to the amino acid sequence <SEQ ID 66; ORF118>:

```
  1 ..TTGSLGGILA GGGTSLAAPY LDKAAENLGP AGKAAVNALG GAAIGYATGG

51   SGGAVVGANV DWNNRQLHPK EMALADKYAE ALKREVEKRE GRKISSQEAA

101   MRIRRQICVG WTKVPKTAIP TKASYPLSE*
```

Computer analysis of this amino acid sequence reveals two putative transmembrane domains.

Based on this analysis, it is predicted that this protein from *N. meningitidis*, and its epitopes, could be useful antigens for vaccines or diagnostics.

Example 16

The following partial DNA sequence was identified in *N. meningitidis* <SEQ ID 67>

```
  1 ..CAATGCCGTC TGAAAAGCTC ACAATTTTAC AGACGGCATT TGTTATGCAA

51   GTACATATAC AGATTCCCTA TATACTCCCC AGrkGCGTGC GTgGCTGAAG

101   ACACCCCCTA CGCTTGCTAT TTGrAACAGC TCCAAGTCAC CAAAGACGTC

151   AACTGGAACC AGGTACwACT GGCGTACGAC AAATGGGACT ATAAACAGGA

201   AGGCTTAACC GGAGCCGGAG CAGCGATTAT TGCGCTGGCT GTTACCGTGG

251   TTACTGCGGG CGCGGGAgCC GGAGCCGCAC TGGGcTTAAA CGGCGCGGCc

301   GCAGCGGCAA CCGATGCCGC ATTCGCCTCG CTGGCCAGCC AGGcTTCCGT

351   ATCGCTCATC AaCAACAAAG GCAATATCGG TAaCACCCTG AAAGAGCTGG

401   GCAGAAGCAG CACGGTGAAA AATCTGATGG TTGCCGTCGc tACCGCAgGC

451   GTagCcgaCA AAATCGGTGC TTCGGCACTG AACAATGTCA GCGATAAGCA

501   GTGGATCAAC AACCTGACCG TCAACCTGGC CAATGCGGGC AGTGCCGCAC

551   TGATTAATAC CGCTGTCAAC GGCGGCAGCc tgAAAGACAA TCTGGAAGCG

601   AATATCCTTG CGGCTTTGGT GAATACTGCG CATGGAGAAG CAGCCAGTAA

651   AATCAAACAG TTGGATCAGC ACTACATTAC CCACAAGATT GCCCaTGCCA

701   TAGCGGGCTG TGCGGcTGCG GCGGCGAATA AGGGCAAGTG TCAGGATGGT

751   GCGATAgGTG CGGCTGTGGG CGAGATAGTC GGGGAgGCTT TGACAAACGG

801   CAAAAATCCT GACACTTTGA CAGCTAAAgA ACGCGaACAG ATTTTGGCAT

851   ACAGCAAACT GGTTGCCGGT ACGGTAAGCG GTGTGGTCGG CGGCGATGTA

901   AATGCGGCGG CGAATGCGGC TGAGGTAGCG GTGAAAAATA ATCAGCTTAG

951   CGACAAAtGA
```

This corresponds to the amino acid sequence <SEQ ID 68; ORF41>:

```
  1 ..QCRLKSSQFY RRHLLCKYIY RFPIYCPXAC VAEDTPYACY LXQLQVTKDV
 51 NWNQVXLAYD KWDYKQEGLT GAGAAIIALA VTVVTAGAGA GAALGLNGAA
101 AAATDAAFAS LASQASVSLI NNKGNIGNTL KELGRSSTVK NLMVAVATAG
151 VADKIGASAL NNVSDKQWIN NLTVNLANAG SAALINTAVN GGSLKDNLEA
201 NILAALVNTA HGEAASKIKQ LDQHYITRKI AHAIAGCAAA AANKGKCQDG
251 AIGAAVGEIV GEALTNGKNP DTLTAKEREQ ILAYSKLVAG TVSGVVGGDV
301 NAAANAAEVA VKNNQLSDK*
```

Further work revealed the complete nucleotide sequence <SEQ ID 69>:

```
   1 ATGCAAGTAA ATATTCAGAT TCCCTATATA CTGCCCAGAT GCGTGCGTGC
  51 TGAAGACACC CCCTACGCTT GCTATTTGAA ACAGCTCCAA GTCACCAAAG
 101 ACGTCAACTG GAACCAGGTA CAACTGGCGT ACGACAAATG GGACTATAAA
 151 CAGGAAGGCT TAACCGGAGC CGGAGCAGCG ATTATTGCGC TGGCTGTTAC
 201 CGTGGTTACT GCGGGCGCGG GAGCCGGAGC CGCACTGGGC TTAAACGGCG
 251 CGGCCGCAGC GGCAACCGAT GCCGCATTCG CCTCGCTGGC CAGCCAGGCT
 301 TCCGTATCGC TCATCAACAA CAAAGGCAAT ATCGGTAACA CCCTGAAAGA
 351 GCTGGGCAGA AGCAGCACGG TGAAAAATCT GATGGTTGCC GTCGCTACCG
 401 CAGGCGTAGC CGACAAAATC GGTGCTTCGG CACTGAACAA TGTCAGCGAT
 451 AAGCAGTGGA TCAACAACCT GACCGTCAAC CTGGCCAATG CGGGCAGTGC
 501 CGCACTGATT AATACCGCTG TCAACGGCGG CAGCCTGAAA GACAATCTGG
 551 AAGCGAATAT CCTTGCGGCT TTGGTGAATA CTGCGCATGG AGAAGCAGCC
 601 AGTAAAATCA PACAGTTGGA TCAGCACTAC ATTACCCACA AGATTGCCCA
 651 TGCCATAGCG GGCTGTGCGG CTGCGGCGGC GAATAAGGGC AAGTGTCAGG
 701 ATGGTGCGAT AGGTGCGGCT GTGGGCGAGA TAGTCGGGGA GGCTTTGACA
 751 AACGGCAAAA ATCCTGACAC TTTGACAGCT AAAGAACGCG AACAGATTTT
 801 GGCATACAGC AAACTGGTTG CCGGTACGGT AAGCGGTGTG GTCGGCGGCG
 851 ATGTAAATGC GGCGGCGAAT GCGGCTGAGG TAGCGGTGAA AAATAATCAG
 901 CTTAGCGACA AGAGGGTAG AGAATTTGAT AACGAAATGA CTGCATGCGC
 951 CAAACAGAAT AATCCTCAAC TGTGCAGAAA AATATACTGTA AAAAGTATC
1001 AAAATGTTGC TGATAAAAGA CTTGCTGCTT CGATTGCAAT ATGTACGGAT
1051 ATATCCCGTA GTACTGAATG TAGAACAATC AGAAAACAAC ATTTGATCGA
1101 TAGTAGAAGC CTTCATTCAT CTTGGGAAGC AGGTCTAATT GGTAAAGATG
1151 ATGAATGGTA TAAATTATTC AGCAAATCTT ACACCCAAGC AGATTTGGCT
1201 TTACAGTCTT ATCATTTGAA TACTGCTGCT AAATCTTGGC TTCAATCGGG
1251 CAATACAAAG CCTTTATCCG AATGGATGTC CGACCAAGGT TATACACTTA
1301 TTTCAGGAGT TAATCCTAGA TTCATTCCAA TACCAAGAGG GTTTGTAAAA
1351 CAAAATACAC CTATTACTAA TGTCAAATAC CCGGAAGGCA TCAGTTTCGA
```

```
                       -continued
1401 TACAAACCTA AAAAGACATC TGGCAAATGC TGATGGTTTT AGTCAAAAAC

1451 AGGGCATTAA AGGAGCCCAT AACCGCACCA ATTTTATGGC AGAACTAAAT

1501 TCACGAGGAG GACGCGTAAA ATCTGAAACC CAAACTGATA TTGAAGGCAT

1551 TACCCGAATT AAATATGAGA TTCCTACACT AGACAGGACA GGTAAACCTG

1601 ATGGTGGATT TAAGGAAATT TCAAGTATAA AAACTGTTTA TAATCCTAAA

1651 AAATTTTCTG ATGATAAAAT ACTTCAAATG GCTCAAAATG CTGCTTCACA

1701 AGGATATTCA AAAGCCTCTA AAATTGCTCA AAATGAAAGA ACTAAATCAA

1751 TATCGGAAAG AAAAAATGTC ATTCAATTCT CAGAAACCTT TGACGGAATC

1801 AAATTTAGAT CATATTTTGA TGTAAATACA GGAAGAATTA CAAACATTCA

1851 CCCAGAATAA
```

This corresponds to the amino acid sequence <SEQ ID 70; ORF41-1>:

```
  1 MQVNIQIPYI LPRCVRAEDT PYACYLKQLQ VTKDVNWNQV QLAYDKWDYK

51 QEGLTGAGAA IIALAVTVVT AGAGAGAALG LNGAAAAATD AAFASLASQA

101 SVSLINNKGN IGNTLKELGR SSTVKNLNVA VATAGVADKI GASALWNVSD

151 KQWINNLTVN LANACSAALI NTAVNGGSLK DNLEANILAA LVNTAHGEAA

201 SKIKQLDQHY ITHKIAHAIA GCAAAAANKG KCQDGAIGAA VGEIVGEALT

251 NGKNPDTLTA KEREQILAYS KLVAGTVSGV VGGDVNAAAN AAEVAVKNNQ

301 LSDKEGREFD NEMTACAKQN NPQLCRKNTV KKYQNVADKR LAASIAICTD

351 ISRSTECRTI RKQHLIDSRS LHSSWEAGLI GKDDEWYKLF SKSYTQADLA

401 LQSYHLNTAA KSWLQSGNTK PLSEWMSDOG YTLISGVNPR FIPIPRGFVK

451 QNTPITNVKY PEGISFDTNL KRHLANADGF SQKQGIKGAH NRTNFMAELN

501 SRGGRVKSET QTDIEGITRI KYEIPTLDRT GKPDGGFKEI SSIKTVYNPK

551 KFSDDKILQM AQNAASQGYS KASKIAQNER TKSISERKNV IQFSETFDGI

601 KERSYFDVNT GRITNIHPE*
```

Computer analysis of this amino acid sequence predicts a transmembrane domain, and homology with an ORF from *N. meningitidis* (strain A) was also found.

ORF41 (SEQ ID NO:192) shows 92.8% identity over a 279aa overlap with an ORF (ORF41a (SEQ ID NO:193)) from strain A of *N. meningitidis*:

```
                10         20         30         40         50         60        69
orf41.pep    YRRHLLCKYIYRFPIYCPXACVAEDTPYACYLXQLQVTKDVNWNQVXLAYDKWDYKQEGL
                          ||   ||||:|::|||||  ||||:||||||||
orf41a                         YLKQLQVAKNINWNQVQLAYDRWDYKQEGL
                                        10         20         30

70         80         90        100        110        120       129
orf41.pep    TGAGAAIIALAVTVVTAGAGAGAALGLNGAAAAATDAAFASLASQASVSLINNKGNIGNT
             ||||||||||||||||:|||:||||||| ||||||||||||||||||:||||::|:|
orf41a       TEAGAAIIALAVTVVTSGAGAGAALGLNGAXAAATDAAFASLASQASVSFINNKGDVGKT
                        40         50         60         70         80         90
```

```
                130       140       150       160       170       180      189
orf41.pep   LKELGRSSTVKNLMVAVATAGVADKIKASALNNVSDKQWINNLTVNLANAGSAALINTAV
            |||||||||||||:||:||||||||||||||| ||||||||||||||||||||||||||
orf41a      LKELGRSSTVKNLVVAVAATAGVADKIKASAXNVSDKQWINNLTVNLANAGSAALINTAV
                100       110       120       130       140       150

190       200       210       220       230       240      249
orf41.pep   NGGSLKDNLEANILAALVNTAHGEAASKIKQLDQHYITHKIAHAIGCAAAAANKGKCQD
            ||||||| |||||||||||||||||||||||||||||||:||||||||||||||||||
orf41a      NGGSLKDXLEANILAALVNTAHGEAASKIKQLDQHYIVHKIAHAIGCAAAAANKGKCQD
                160       170       180       190       200       210

250       260       270       280       290       300      309
orf41.pep   GAIGAAVGEIVGEALTNGKNPDTLTAKEREQILAYSKLVAGTVSGVVGGDYNAAANAAEV
            ||||||||||||||||||||||||||||||||||||||||||||||||||||||||||||
orf41a      GAIGAAVGEIVGEALTNGKNPDTLTAKEREQILAYSKLVAGTVSGVVGGDYNAAANAAEV
                220       230       240       250       260       270

310       320
orf41.pep   AVKNNQLSDKX
            |||||||||
orf41a      AVKNNQLSDXEGREFDNEMTACAKQNXPQLCRKNTVKKYQNVADKRLAASIAICTDISRS
                280       290       300       310       220       330
```

A partial ORF41a nucleotide sequence <SEQ ID 71> is:

```
   1 ..TATCTGAAAC AGCTCCAAGT AGCGAAAAAC ATCAACTGGA ATCAGGTGCA

51   GCTTGCTTAC GACAGATGGG ACTACAAACA GGAGGGCTTA ACCGAAGCAG

101   GTGCGGCGAT TATCGCACTG GCCGTTACCG TGGTCACCTC AGGCGCAGGA

151   ACCGGAGCCG TATTGGGATT AAACGGTGCG NCCGCCGCCG CAACCGATGC

201   AGCATTCGCC TCTTTGGCCA GCCAGGCTTC CGTATCGTTC ATCAACAACA

251   AAGGCGATGT CGGCAAAACC CTGAAAGAGC TGGGCAGAAG CAGCACGGTG

301   AAAAATCTGG TGGTTGCCGC CGCTACCGCA GGCGTAGCCG ACAAAATCGG

351   CGCTTCGGCA CTGANCAATG TCAGCGATAA GCAGTGGATC AACAACCTGA

401   CCGTCAACCT AGCCAATGCG GGCAGTGCCG CACTGATTAA TACCGCTGTC

451   AACGGCGGCA GCCTGAAAGA CANTCTGGAA GCGAATATCC TTGCGGCTTT

501   GGTCAATACC GCGCATGGAG AAGCAGCCAG TAAAATCAAA CAGTTGGATC

551   AGCACTACAT AGTCCACAAG ATTGCCCATG CCATAGCGGG CTGTGCGGCA

601   GCGGCGGCGA ATAAGGGCAA GTGTCAGGAT GGTGCGATAG GTGCGGCTGT

651   GGGCGAGATA GTCGGGGAGG CTTTGACAAA CGGCAAAAAT CCTGACACTT

701   TGACAGCTAA AGAACGCGAA CAGATTTTGG CATACAGCAA ACTGGTTGCC

751   GGTACGGTAA GCGGTGTGGT CGGCGGCGAT GTAAATGCGG CGGCGAATGC

801   GGCTGAGGTA GCGGTGAAAA ATAATCAGCT TAGCGACNAA GAGGGTAGAG

851   AATTTGATAA CGAAATGACT GCATGCGCCA AACAGAATAN TCCTCAACTG

901   TGCAGAAAAA ATACTGTAAA AAAGTATCAA AATGTTGCTG ATAAAAGACT

951   TGCTGCTTCG ATTGCAATAT GTACGGATAT ATCCCGTAGT ACTGAATGTA

1001   GAACAATCAG AAAACAACAT TTGATCGATA GTAGAAGCCT TCATTCATCT

1051   TGGGAAGCAG GTCTAATTGG TAAAGATGAT GAATGGTATA AATTATTCAG

1101   CAAATCTTAC ACCCAAGCAG ATTTGGCTTT ACAGTCTTAT CATTTGAATA

1151   CTGCTGCTAA ATCTTGGCTT CAATCGGGCA ATACAAAGCC TTTATCCGAA

1201   TGGATGTCCG ACCAAGGTTA TACACTTATT TCAGGAGTTA ATCCTAGATT
```

```
1251  CATTCCAATA CCAAGAGGGT TTGTAAAACA AAATACACCT ATTACTAATG
1301  TCAAATACCC GGAAGGCATC AGTTTCGATA CAAACCTANA AAGACATCTG
1351  GCAAATGCTG ATGGTTTTAG TCAAGAACAG GGCATTAAAG GAGCCCATAA
1401  CCGCACCAAT NTTATGGCAG AACTAAATTC ACGAGGAGGA NGNGTAAAAT
1451  CTGAAACCCA NACTGATATT GAAGGCATTA CCCGAATTAA ATATGAGATT
1501  CCTACACTAG ACAGGACAGG TAAACCTGAT GGTGGATTTA AGGAAATTTC
1551  AAGTATAAAA ACTGTTTATA ATCCTAAAAA NTTTTNNGAT GATAAAATAC
1601  TTCAAATGGC TCAANATGCT GNTTCACAAG GATATTCAAA AGCCTCTAAA
1651  ATTGCTCAAA ATGAAAGAAC TAAATCAATA TCGGAAAGAA AAAATGTCAT
1701  TCAATTCTCA GAAACCTTTG ACGGAATCAA ATTTAGANNN TATNTNGATG
1751  TAAATACAGG AAGAATTACA AACATTCACC CAGAATAA
```

This encodes a protein having the partial amino acid sequence <SEQ ID 72>:

```
  1  YLKQLQVAKN INWNQVQLAY DRWDYKQEGL TEAGAAIIAL AVTVVTSGAG
 51  TGAVLGLNGA XAAATDAAFA SLASQASVSF INNKGDVGKT LKELGRSSTV
101  KNLVVAAATA GVADKIGASA LXNVSDKQWI NNLTVNLANA GSAALINTAV
151  NGGSLKDXLE ANILAALVNT AHGEAASKIK QLDQHYIVHK IAHAIAGCAA
201  AAANKGKCQD GAIGAAVGEI VGEALTNGKN PDTLTAKERE QILAYSKLVA
251  GTVSGVVGGD VNAAANAAEV AVKNNQLSDX EGREFDNEMT ACAKQNXPQL
301  CRKNTVKKYQ NVADKRLAAS IAICTDISRS TECRTIRKQH LIDSRSLHSS
351  WEAGLIGKDD EWYKLFSKSY TQADLALQSY HLNTAAKSWL QSGNTKPLSE
401  WMSDQGYTLI SGVNPRFIPI PRGFVKQNTP ITNVKYPEGI SFDTNLXRHL
451  ANADGFSQEQ GIKGAHNRTN XMAELNSRGG XVKSETXTDI EGITRIKYEI
501  PTLDRTGKPD GGFKEISSIK TVYNPKXFXD DKILQMAQXA XSQGYSKASK
551  IAQNERTKSI SERKNVIQFS ETFDGIKFRX YXDVNTGRIT NIHPE*
                                                     45
```

ORF41a (SEQ ID NO:72) and ORF41-1 (SEQ ID NO:70) show 94.8% identity in 595 aa overlap:

```
                        10         20         30
orf41a.pep              YLKQLQVAKNINWNQVQLAYDRWDYKQEGLTEAGAA
                        ||||||:|::||||||||||:|||||||||  ||||
orf41-1     MQVNIQIPYILPRCVRAEDTPYACYLKQLQVTKDVNWNQVQLAYDKWDYKQEGLTGAGAA
                10         20         30         30         50         60

40         50         60         70         80         90
orf41a.pep          IIALAVTVVTSGAGTGAVLGLNGAXAAATDAAFASLASQASVSFINNKGDVGKTLKELGR
                    |||||||||||:|||:||||||||  |||||||||||||||||:||||::|:||||||
orf41-1             IIALAVTVVTAGAGAGAALGLNGAAAAATDAAFASLASQASVSLINNKGNIGMTLKELGR
                        70         80         90        100        110        120

100        110        120        130        140        150
orf41a.pep              SSTVKNLVVAAATAGVADKIGASALXNVSDKQWINNLTVNLANAGSAALINTAVNGGSLK
                        ||||||:||:|||||||||||||||  ||||||||||||||||||||||||||||||||
orf41-1                 SSTVKNLMVAVATAGVADKIGASALNNVSDKQWINNLTVNLANAGSAALINTAVNGGSLK
                            130        140        150        160        170        180
```

```
                    160       170        180        190       200       210
orf41a.pep  DXLEANILAALVNTAHGEAASKIKQLDQHYIVHKIAHAIAGCAAAAANKGKCQDGAIGAA
            ||||||||||||||||||||||||||||||:|||||||||||||||||||||||||||||
orf41-1     DNLEANILAALVNTAHGEAASKIKQLDQHYITHKIAHAIAGCAAAAANKGKCQDGAIGAA
                    190       200        210        220       230       240

220       230        240        250       260       270
orf41a.pep  VGEIVGEALTNGKNPDTLTAKEREQILAYSKLVAGTVSGVVGGDVNAAANAAEVAVKNNQ
            ||||||||||||||||||||||||||||||||||||||||||||||||||||||||||||
orf41-1     VGEIVGEALTNGKNPDTLTAKEREQILAYSKLVAGTVSGVVGGDVNAAANAAEVAVKNNQ
                    250       260        270        280       290       300

280       290        300        310       320       330
orf41a.pep  LSDXEGREFDNEMTACAKQNXPQLCRKNTVKKYQNVADKRLAASIAICTDISRSTECRTI
            |||:||||||||||||||||:|||||||||||||||||||||||||||||||||||||||
orf41-1     LSDKEGREFDNEMTACAKQNNPQLCRKNTVKKYQNVADKRLAASIAICTDISRSTECRTI
                    310       320        330        340       350       360

340       350        360        370       380       390
orf41a.pep  RKQHLIDSRSLHSSWEAGLIGKDDEWYKLFSKSYTQADLALQSYHLNTAAKSWLQSGNTK
            ||||||||||||||||||||||||||||||||||||||||||||||||||||||||||||
orf41-1     RKQHLIDSRSLHSSWEAGLIGKDDEWYKLFSKSYTQADLALQSYHLNTAAKSWLQSGNTK
                    370       380        390        400       410       420

400       410        420        430       440       450
orf41a.pep  PLSEWMSDQGYTLISGVNPRFIPIPRGFVKQNTPITNVKYPEGISFDTNLXRHLANADGF
            ||||||||||||||||||||||||||||||||||||||||||||||||||||:|||||||
orf41-1     PLSEWMSDQGYTLISGVNPRFIPIPRGFVKQNTPITNVKYPEGISFDTNLKRHLANADGF
                    430       440        450        460       470       480

460       470        480        490       500       510
orf41a.pep  SQEQGIKGAHNRTNXMAELNSRGGXVKSETXTDIEGITRIKYEIPTLDRTGKPDGGFKEI
            ||:|||||||||||||:|||||||:|||||:|||||||||||||||||||||||||||||
orf41-1     SQKQGIKGAHNRTNFMAELNSRGGRVKSETQTDIEGITRIKYEIPTLDRTGKPDGGFKEI
                    490       500        510        520       530       540

520       530        540        550       560       570
orf41a.pep  SSIKTVYNPKXFXDDKILQMAQXAXSQGYSKASKIAQNERTKSISERKNVIQFSETFDGI
            ||||||||||:|:|||||||||:|:|||||||||||||||||||||||||||||||||||
orf41-1     SSIKTVYNPKKFSDDKILQMAQNAASQGYSKASKIAQNERTKSISERKNVIQFSETFDGI
                    550       560        570        580       590       600

580       590
orf41a.pep  KFRXYXDVNTGRITNIHPEX
            |||:|:||||||||||||||
orf41-1     KFRSYFDVNTGRITNIHPEX
                    610       620
```

Figure 6:
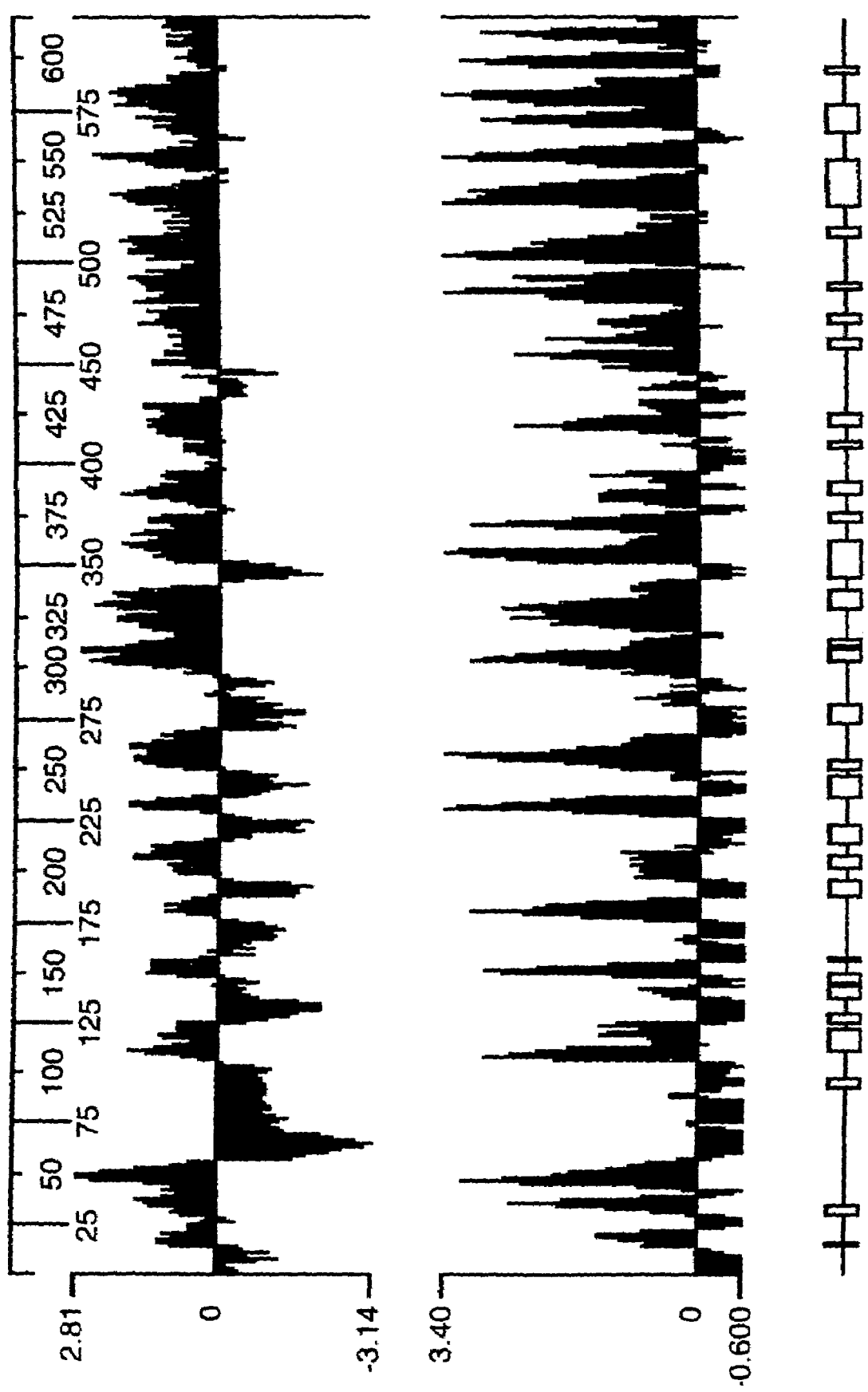
FIG. 6 shows a hydrophilicity plot (upper), an antigenic index plot (middle), and an AMPHI analysis (lower) for ORF 41.

Amino acids 25-619 of ORF41-1 were amplified as described above. FIG. 6 shows plots of hydrophilicity, antigenic index, and AMPHI regions for ORF41-1.

Based on this analysis, it is predicted that this protein from *N. meningitidis*, and its epitopes, could be useful antigens for vaccines or diagnostics.

Example 17

The following DNA sequence was identified in *N. meningitidis* <SEQ ID 73>

```
  1  ATGGCAATCA TTACATTGTA TTATTCTGTC AATGGTATTT TAAATGTATG

51  TGCAAAAGCA AAAAATATTC AAGTAGTTGC CAATAATAAG AATATGGTTC

101  TTTTTGGGTT TTTGGsmrGC ATCATCGGCG GTTCAACCAA TGCCATGTCT

151  CCCATATTGT TAATATTTTT GCTTAGCGAA ACAGAAAATA AAAATcgTAT

201  CGTAAAATCA AGCAATCTAT GCTATCTTTT GGCGAAAATT GTTCAAATAT

251  ATATGCTAAG AGACCACTAT TGGTTATTAA ATAAGAGTGA ATACGdTTTA
```

```
-continued
301  ATATTTTTAC TGTCCGTATT GTCTGTTATT GGATTGTATG TTGGAATTCG
351  GTTAAGGACT AAGATTAGCC CAaATTTTTT TAAAATGTTA ATTTTTATTG
401  tTTTATTGGT ATTGGCtCTG AAAATCGGGC AttCGGGTTT AAtCAAACTT
451  TAA
```

This corresponds to the amino acid sequence <SEQ ID 74; ORF51>:

```
  1  MAIITLYYSV NGILNVCAKA KNIQVVANNK NNVLFGFLXX IIGGSTNAMS
 51  PILLIFLLSE TENKNRIVKS SNLCYLLAKI VQIYMLRDQY WLLNKSEYXL
101  IFLLSVLSVI GLYVGIRLRT KISPNFFKML IFIVLLVLAL KIGHSGLIKL
151  *
```

Further work revealed the complete nucleotide sequence <SEQ ID 75>:

```
  1  ATGCAAGAAA TAATGCAATC TATCGTTTTT GTTGCTGCCG CAATACTGCA
 51  CGGAATTACA GGCATGGGAT TCCGATGCT CGGTACAACC GCATTGGCTT
101  TTATCATGCC ATTGTCTAAG GTTGTTGCCT TGGTGGCATT ACCAAGCCTG
151  TTAATGAGCT TGTTGGTTCT ATGCAGCAAT AACAAAAAGG GTTTTTGGCA
201  AGAGATTGTT TATTATTTAA AAACCTATAA ATTGCTTGCT ATCGGCAGCG
251  TCGTTGGCAG CATTTTGGGG GTGAAGTTGC TTTTGATACT TCCAGTGTCT
301  TGGCTGCTTT TACTGATGGC AATCATTACA TTGTATTATT CTGTCAATGG
351  TATTTTAAAT GTATGTGCAA AAGCAAAAAA TATTCAAGTA GTTGCCAATA
401  ATAAGAATAT GGTTCTTTTT GGGTTTTTGG CAGGCATCAT CGGCGGTTCA
451  ACCAATGCCA TGTCTCCCAT ATTGTTAATA TTTTTGCTTA GCGAAACAGA
501  AAATAAAAAT CGTATCGTAA AATCAAGCAA TCTATGCTAT CTTTTGGCGA
551  AAATTGTTCA AATATATATG CTAAGAGACC AGTATTGGTT ATTAAATAAG
601  AGTGAATACG GTTAATATT TTTACTGTCC GTATTGTCTG TTATTGGATT
651  GTATGTTGGA ATTCGGTTAA GGACTAAGAT TAGCCCAAAT TTTTTTAAAA
701  TGTTAATTTT TATTGTTTTA TTGGTATTGG CTCTGAAAAT CGGGCATTCG
751  GGTTAATCA AACTTTAA
```

This corresponds to the amino acid sequence <SEQ ID 76; ORF51-1>:

```
  1  MQEIMQSIVF VAAAILHGIT GMGFPMLGTT ALAFIMPLSK VVALVALPSL
 51  LMSLLVLCSN NKKGFWQEIV YYLKTYKLLA IGSVVGSILG VKLLLILPVS
101  WLLLLMAIIT LYYSVNGILN VCAKAIQUQV VANNKNMVLF GFLAGIIGGS
151  TNAMSPILLI FLLSETENKN RIVKSSNLCY LLAKIVQIYM LRDQYWLLNK
201  SEYGLIFLLS VLSVIGLYVG IRLRTKISPN FFKMLIFIVL LVLALKIGHS
251  GLIKL*
```

Computer analysis of this amino acid sequence reveals three putative transmembrane domains. A corresponding ORF from strain A of *N. meningitidis* was also identified:

Homology with a Predicted ORF from *N. Meningitidis* (Strain A)

ORF51 (SEQ ID NO:74) shows 96.7% identity over a 150aa overlap with an ORF (ORF51a (SEQ ID NO:194)) from strain A of *N. meningitidis*:

```
                                  10        20        30
orf51.pep                   MAIITLYYSVNGILNVCAKAKNIQVVANNK
                            ||||||||||||||||||||||||||||||
orf51a    YKLLAIGSVVGSILGVKLLLILPVSWLLLLMAIITLYYSVNGILNVCAKAKNIQVVANNK
              80        90       100       110       120       130

40        50        60        70        80        90
orf51.pep  NMVLFGFLXXIIGGSTNAMSPILLIFLLSETENKNRIVKSSNLCYLLAKIVQIYMLRDQY
           ||||||||   |||||||||||||||||||||||||||:|||||||||||||||||||||
orf51a     NMVLFGFLAGIIGGSTNAMSPILLIFLLSETENKNRIAKSSNLCYLLAKIVQIYMLRDQY
              140       150       160       170       180       190

100       110       120       130       140       150
orf51.pep  WLLNKSEYXLIFLLSVLSVIGLYVGIRLRTKISPNFFKMLIFIVLLVLALKIGHSGLIKL
           |||||||| |||||||||||||||||||||||||||||||||||||||||||:||||||
orf51a     WLLNKSEYGLIFLLSVLSVIGLYVGIRLRTKISPNFFKMLIFIVLLVLALKIGYSGLIKL
              200       210       220       230       240       250
```

ORF51-1 (SEQ ID NO:76) and ORF51a (SEQ ID NO:78) show 99.2% identity in 255 aa overlap:

```
orf51a.pep  MQEIMQSIVFVAAAILHGITGMGFPMLGTTALAFIMPLSKVVALVALPSLLMSLLVLCSN
            ||||||||||||||||||||||||||||||||||||||||||||||||||||||||||||
orf51-1     MQEIMQSIVFVAAAILHGITGMGFPMLGTTALAFIMPLSKVVALVALPSLLMSLLVLCSN orf51a.pep  NKKGFWQEIVYYLKTYKLLAIGSVVGSILGVKLLLILPVSWLLLLMAIITLYYSVNGILN
            ||||||||||||||||||||||||||||||||||||||||||||||||||||||||||||
orf51-1     NKKGFWQEIVYYLKTYKLLAIGSVVGSILGVKLLLILPVSWLLLLMAIITLYYSVNGILN orf51a.pep  VCAKAKNIQVVANNKNMVLFGFLAGIIGGSTNAMSPILLIFLLSETENKNRIAKSSNLCY
            |||||||||||||||||||||||||||||||||||||||||||||||||||||:||||||
orf51-1     VCAKAKNIQVVANNKNMVLFGFLAGIIGGSTNAMSPILLIFLLSETENKNRIVKSSNLCY orf51a.pep  LLAKIVQIYMLRDQYWLLNKSEYGLIFLLSVLSVIGLYVGIRLRTKISPNFFKMLIFIVL
            ||||||||||||||||||||||||||||||||||||||||||||||||||||||||||||
orf51-1     LLAKIVQIYMLRDQYWLLNKSEYGLIFLLSVLSVIGLYVGIRLRTKISPNFFKMLIFIVL orf51a.pep  LVLALKIGYSGLIKLX
            ||||||||:|||||||
orf51-1     LVLALKIGHSGLIKLX
```

The complete length ORF51a nucleotide sequence <SEQ ID 77> is:

```
  1  ATGCAAGAAA TAATGCAATC TATCGTTTTT GTTGCTGCCG CAATACTGCA

51  CGGAATTACA GGCATGGGAT TTCCGATGCT CGGTACAACC GCATTGGCTT

101  TTATCATGCC ATTGTCTAAG GTTGTTGCCT TGGTGGCATT ACCAAGCCTG

151  TTAATGAGCT TGTTGGTTCT ATGCAGCAAT AACAAAAAGG GTTTTTGGCA

201  AGAGATTGTT TATTATTTAA AAACCTATAA ATTGCTTGCT ATCGGCAGCG

251  TCGTTGGCAG CATTTTGGGG GTGAAGTTGC TTTTGATACT TCCAGTGTCT

301  TGGCTGCTTT TACTGATGGC AATCATTACA TTGTATTATT CTGTCAATGG
```

-continued

```
351  TATTTTAAAT GTATGTGCAA AAGCAAAAAA TATTCAAGTA GTTGCCAATA
401  ATAAGAATAT GGTTCTTTTT GGGTTTTTGG CAGGCATCAT CGGCGGTTCA
451  ACCAATGCCA TGTCTCCCAT ATTGTTAATA TTTTTGCTTA GCGAAACAGA
501  GAATAAAAAT CGTATCGCAA AATCAAGCAA TCTATGCTAT CTTTTGGCAA
551  AAATTGTTCA AATATATATG CTAAGAGACC AGTATTGGTT ATTAAATAAG
601  AGTGAATACG GTTTAATATT TTTACTGTCC GTATTGTCTG TTATTGGATT
651  GTATGTTGGA ATTCGGTTAA GGACTAAGAT TAGCCCAAAT TTTTTTAAAA
701  TGTTAATTTT TATTGTTTTA TTGGTATTGG CTCTGAAAAT CGGGTATTCA
751  GGTTTAATCA AACTTTAA
```

This encodes a protein having amino acid sequence <SEQ ID 78>:

```
  1  MQEIMQSIVF VAAAILHGIT GMGFPMLGTT ALAFIMPLSK VVALVALPSL
 51  LMSLLVLCSN NKKGFWQEIV YYLKTYKLLA IGSVVGSILG VKLLLILPVS
101  WLLLLMAIIT LYYSVNGILN VCAKAKNIQV VANNKNMVLF GFLAGIIGGS
151  TNAMSPILLI FLLSETENKN RIAKSSNLCY LLAKIVQIYM LRDQYWLLWK
201  SEYGLIFLLS VLSVIGLYVG IRLRTKISPN FFKMLIFIVL LVLALKIGYS
251  GLIKL*
```

Based on this analysis, it is predicted that this protein from *N. meningitidis*, and its epitopes, could be useful antigens for vaccines or diagnostics.

Example 18

The following partial DNA sequence was identified in *N. meningitidis* <SEQ ID 79>

```
  1  ATGAGACATA TGAAAATACA AAATTATTTA CTAGTATTTA TAGTTTTACA
 51  TATAGCCTTG ATAGTAATTA ATATAGTGTT TGGTTATTTT GTTTTTCTAT
101  TTGATTTTTT TGCGTTTTTG TTTTTTGCAA ACGTCTTTCT TGCTGTAAAT
151  TTATTATTTT TAGAAAAAAA CATAAAAAAC AAATTATTGT TTTTATTGCC
201  GATTTCTATT ATTATATGGA TGGTAATTCA TATTAGTATG ATAAATATAA
251  AATTTTATAA ATTTCAGCAT CAAATAAAGG AACAAAATAT ATCCTCGATT
301  ACTGGGGTGA TAAAACCACA TGATAGTTAT AATTATGTTT ATGACTCAAA
351  TGGATATGCT AAATTAAAAG ATAATCATAG ATATGGTAGG GTAATTAGAG
401  AAACACCTTA TATTGATGTA GTTGCATCTG ATGTTAAAAA TAAATCCATA
451  AGATTAAGCT TGGTTTGTGG TATTCATTCA TATGCTCCAT GTGCCAATTT
501  TATAAAATTT GTCAGG . . .
```

This corresponds to the amino acid sequence <SEQ ID 80; ORF82>:

```
  1 MRHMKIQNYL LVFIVLHIAL IVINIVFGYF VFLFDFFAFL FFANVFLAVN
 51 LLFLEKNIKN KLLFLLPISI IIWNVIHISM INIKFYKFEH QIKEQNISSI
101 TGVIKPHDSY NYVYDSNGYA KLKDNHRYGR VIRETPYIDV VASDVKNKSI
151 RLSLVCGIHS YAPCANFIKF VR..
```

Further work revealed the complete nucleotide sequence <SEQ ID 81>:

```
  1 ATGAGACATA TGAAAAATAA AAATTATTTA CTAGTATTTA TAGTTTTACA
 51 TATAGCCTTG ATAGTAATTA ATATAGTGTT TGGTTATTTT GTTTTTCTAT
101 TTGATTTTTT TGCGTTTTTG TTTTTTGCAA ACGTCTTTCT TGCTGTAAAT
151 TTATTATTTT TAGAAAAAAA CATAAAAAAC AAATTATTGT TTTTATTGCC
201 GATTTCTATT ATTATATGGA TGGTAATTCA TATTAGTATG ATAAATATAA
251 AATTTTATAA ATTTGAGCAT CAAATAAAGG AACAAAATAT ATCCTCGATT
301 ACTGGGGTGA TAAAACCACA TGATAGTTAT AATTATGTTT ATGACTCAAA
351 TGGATATGCT AAATTAAAAG ATAATCATAG ATATGGTAGG GTAATTAGAG
401 AAACACCTTA TATTGATGTA GTTGCATCTG ATGTTAAAAA TAAATCCATA
451 AGATTAAGCT TGGTTTGTGG TATTCATTCA TATGCTCCAT GTGCCAATTT
501 TATAAAATTT GCAAAAAAAC CTGTTAAAAT TTATTTTTAT AATCAACCTC
551 AAGGAGATTT TATAGATAAT GTAATATTTG AAATTAATGA TGGAAACAAA
601 AGTTTGTACT TGTTAGATAA GTATAAAACA TTTTTTCTTA TTGAAAACAG
651 TGTTTGTATC GTATTAATTA TTTTATATTT AAAATTTAAT TTGCTTTTAT
701 ATAGGACTTA CTTCAATGAG TTGGAATAG
```

This corresponds to the amino acid sequence <SEQ ID 82; ORF82-1>:

```
  1 MRHMKNKNYL LVFIVLHIAL IVINIVFGYF VFLFDFFAFL FFANVELAVN
 51 LLFLEKNIKN KLLFLLPISI IIWNVIHISM INIKFYKFEH QIKEQNISSI
101 TGVIKPHDSY NYVYDSNGYA KLKDNHRYGR VIRETPYIDV VASDVKNKSI
151 RLSLVCGIHS YAPCANFIKF AKKPVKIYEY NQPQGDFIDN VIFEINDGNK
201 SLYLLDKYKT FFLIENSVCI VLIILYLKFN LLLYRTYFNE LE*
```

Computer analysis of this amino acid sequence reveals a predicted leader peptide.

A corresponding ORF from strain A of *N. meningitidis* was also identified:

Homology with a Predicted ORF from *N. meningitidis* (Strain A)

ORF82 (SEQ ID NO:80) shows 97.1% identity over a 172aa overlap with an ORF (ORF82a (SEQ ID NO:195)) from strain A of *N. meningitidis*:

```
                  10        20        30        40        50        60
orf82.pep  MRHMKIQNYLLVFIVLHIALIVINIVFGYFVFLFDFFAFLFFANVFLAVNLLFLEKNIKN
           |||||:|||||||||||:||||||||||||||||||||||||||||||||||||||||||
orf82a     MRHMKNKNYLLVFIVLHITLIVINIVFGYFVFLFDFFAFLFFANVFLAVNLLFLEKNIKN
                  10        20        30        40        50        60

70        80        90       100       110       120
orf82.pep  KLLFLLPISIIIWMVIHISMINIKFYKFEHQIKEQNISSITGVIKPHDSYNYVYDSNGYA
           ||||||||||||||||||||||||||||||||||||||||||||||||||||||||||||
orf82a     KLLFLLPISIIIWMVIHISMINIKFYKFEHQIKEQNISSITGVIKPHDSYNYVYDSNGYA
                  70        80        90       100       110       120

130       140       150       160       170
orf82.pep  KLKDNHRYGRVIRETPYIDVVASDVKNKSIRLSVLCGIHSYAPCANFIKFVR
           ||||||||||||||||||||||||||||||||||||||||||||||||::
orf82a     KLKDNHRYGRVIRETPYIDVVASDVKNKSIRLSVLCGIHSYAPCANFIKFAKKPVKIYFY
                 130       140       150       160       170       180
```

ORF82a (SEQ ID NO:84) and ORF82-1 (SEQ ID NO:82) show 99.2% identity in 242 aa overlap:

```
orf82a.pep  MRHMKNKNYLLVFIVLHITLIVINIVFGYFVFLFDFFAFLFFANVFLAVNLLFLEKNIKN
            |||||||||||||||||:||||||||||||||||||||||||||||||||||||||||||
orf82-1     MRHMKNKNYLLVFIVLHIALIVINIVFGYFVFLFDFFAFLFFANVFLAVNLLFLEKNIKN orf82a.pep  KLLFLLPISIIIWMVIHISMINIKFYKFEHQIKEQNISSITGVIKPHDSYNYVYDSNGYA
            ||||||||||||||||||||||||||||||||||||||||||||||||||||||||||||
orf82-1     KLLFLLPISIIIWMVIHISMINIKFYKFEHQIKEQNISSITGVIKPHDSYNYVYDSNGYA orf82a.pep  KLKDNHRYGRVIRETPYIDVVASDVKNKSIRLSVLCGIHSYAPCANFIKFAKKPVKIYFY
            ||||||||||||||||||||||||||||||||||||||||||||||||||||||||||||
orf82-1     KLKDNHRYGRVIRETPYIDVVASDVKNKSIRLSVLCGIHSYAPCANFIKFAKKPVKIYFY orf82a.pep  NQPQGDFIDNVIFEINDGKKSLYLLDKYKTFFLIENSVCIVLIILYLKFNLLLYRTYFNE
            ||||||||||||||||||||||||||||||||||||||||||||||||||||||||||||
orf82-1     NQPQGDFIDNVIFEINDGKKSLYLLDKYKTFFLIENSVCIVLIILYLKFNLLLYRTYFNE orf82a.pep  LEX
            |||
orf82-1     LEX
                                                40
```

The complete length ORF82a nucleotide sequence <SEQ ID 83> is:

```
  1 ATGAGACATA TGAAAAATAA AAATTATTTA CTAGTATTTA TAGTTTTACA

51 TATAACCTTG ATAGTAATTA ATATAGTGTT TGGTTATTTT GTTTTTCTAT

101 TTGATTTTTT TGCGTTTTTG TTTTTTGCAA ACGTCTTTCT TGCTGTAAAT

151 TTATTATTTT TAGAAAAAAA CATAAAAAAC AAATTATTGT TTTTATTGCC

201 GATTTCTATT ATTATATGGA TGGTAATTCA TATTAGTATG ATAAATATAA

251 AATTTTATAA ATTTGAGCAT CAAATAAAGG AACAAATATA TCCTCGATT

301 ACTGGGGTGA TAAAACCACA TGATAGTTAT AATTATGTTT ATGACTCAAA

351 TGGATATGCT AAATTAAAAG ATAATCATAG ATATGGTAGG GTAATTAGAG

401 AAACACCTTA TATTGATGTA GTTGCATCTG ATGTTAAAAA TAAATCCATA

451 AGATTAAGCT TGGTTTGTGG TATTCATTCA TATGCTCCAT GTGCCAATTT

501 TATAAAATTT GCAAAAAAAC CTGTTAAAAT TTATTTTTAT AATCAACCTC

551 AAGGAGATTT TATAGATAAT GTAATATTTG AAATTAATGA TGGAAAAAAA

601 AGTTTGTACT TGTTAGATAA GTATAAAACA TTTTTTCTTA TTGAAAACAG
```

-continued
```
651 TGTTTGTATC GTATTAATTA TTTTATATTT AAAATTTAAT TTGCTTTTAT

701 ATAGGACTTA CTTCAATGAG TTGGAATAG
```

This encodes a protein having amino acid sequence <SEQ ID 84>:

```
  1 MRHMKNKNYL LVFIVLHITL IVINIVFGYF VFLFDFFAFL FFANVFLAVN
 51 LLFLEKNIKN KLLFLLPISI IIWMVIHISM INIKFYKFEH QIKEQNISSI
101 TGVIKPHDSY NYVYDSNGYA KLKDNHRYGR VIRETPYIDV VASDVKNKSI

151 RLSLVCGIHS YAPCANFIKF AKKPVKIYFY NQPQGDFIDN VIFEINDGKK

201 SLYLLDKYKT FFLIENSVCI VLIILYLKWN LLLYRTYFNE LE*
```

Based on this analysis, it is predicted that this protein from *N. meningitidis*, and its epitopes, could be useful antigens for vaccines or diagnostics.

Example 19

The following partial DNA sequence was identified in *N. meningitidis* <SEQ ID 85>

```
  1   ..ACCCCCAACA GCGTGACCGT CTTGCCGTCT TTCGGCGGAT TCGGGCGTAC
 51     CGGCGCGACC ATCAATGCAG CAGGCGGGGT CGGCATGACT GCCTTTTCGA
101     CAACCTTAAT TTCCGTAGCC GAGGGCGCGG TTGTAGAGCT GCAGGCCGTG
151     AGAGCCAAAG CCGTCAATGC AACCGCCGCT TGCATTTTTA CGGTCTTGAG
201     TAAGGACATT TTCGATTTCC TTTTTATTTT CCGTTTTCAG ACGGCTGACT
251     TCCGCCTGTA TTTTCGCCAA AGCCATGCCG ACAGCGTGCG CCTTGACTTC
301     ATATTTAAAA GCTTCCGCGC GTGCCAGTTC CAGTTCGCGC GCATAGTTTT
351     GAGCCGACAA CAGCAGGGCT TGCGCCTTGT CGCGCTCCAT CTTGTCGATG
401     ACCGCCTGCA GCTTCGCAAA TGCCGACTTG TAGCCTTGAT GGTGCGACAC
451     AGCCAAGCCC GTGCCGACAA GCGCGATAAT GGCAATCGGT TGCCAGTAAT
501     TCGCCAGCAG TTTCACGAGA TTCATTCTCG ACCTCCTGAC GCTTCACGCT
551     GA
```

This corresponds to the amino acid sequence <SEQ ID 86; ORF124>:

```
  1   ..TPNSVTVLPS FGGFGRTCAT INAAGGVGMT AFSTTLISVA EGAVVELQAV
 51     RAKAVVATAA CIFTVLSKDI FDFLFIFRFQ TADFRLYFRQ SHADSVRLDF
101     IEKSFRACQF QFARIVLSRQ QQGLRLVALH LVDDRLQLRK CRLVALMVRH
151     SQARADKRDN GNRLPVIRQQ FHEIHSRPPD ASR*
```

Computer analysis of this amino acid sequence predicts a transmembrane domain.

Further work revealed the complete nucleotide sequence <SEQ ID 87>:

```
  1 ATGACTGCCT TTTCGACAAC CTTAATTTCC GTAGCCGAGG GCGCGGTTGT

51 AGAGCTGCAG GCCGTGAGAG CCAAAGCCGT CAATGCAACC GCCGCTTGCA

101 TTTTTACGGT CTTGAGTAAG GACATTTTCG ATTTCCTTTT TATTTTCCGT

151 TTTCAGACGG CTGACTTCCG CCTGTTTTTT CGCCAAAGCC ATGCCGACAG

201 CGTGCGCCTT GACTTCATAT TTTTTAGCTT CCGCCCGTGC CAGTTCCAGT

251 TCGCGCGCAT AGTTTTGAGC CGACAACAGC AGGGCTTGCG CCTTGTCGCG

301 CTCCATCTTG TCGATGACCG CCTGCTGCTT CGCAAATGCC GACTTGTAGC

351 CTTGATGGTG CGACACAGCC AAGCCCGTGC CGACAAGCGC GATAATGGCA

401 ATCGGTTGCC AGTTATTCGC CAGCAGTTTC ACGAGATTCA TTCTCGACCT

451 CCTGACGCTT CACGCTGA
```

This corresponds to the amino acid sequence <SEQ ID 88; ORF124-1>:

```
  1 MTAFSTTLIS VAEGAVVELQ AVRAKAVNAT AACIFTVLSK DIFDFLFIFR

51 FQTADFRLFF RQSHADSVRL DFIFFSFRAC QFQFARIVLS RQQQGLRLVA

101 LHLVDDRLLL RKCRLVALMV RHSQARADKR DNGNRLPVIR QQFHEIHSRP

151 PDASR*
```

A corresponding ORF from strain A of *N. meningitidis* was also identified:

Homology with a Predicted ORF from *N. meningitidis* (Strain A)

ORF124 (SEQ ID NO:86) shows 87.5% identity over a 152aa overlap with an ORF (ORF124a (SEQ II) NO:90)) from strain A of *N. meningitidis*:

```
                       10         20         30         40         50         60
orf124.pep  TPNSVTVLPSFGGFGRTGATINAAGGVGMTAFSTTLISVAEGAVVELQAVRAKAVNATAA
                                       ||||||||||||:||||| |||||:|||
orf124a                                MTAFSTTLISVAEGALVELQAVMAKAVNTTAA
                                               40         50         60

70         80         90        100        110        120
orf124.pep  CIFTVLSKDIFDFLFIFRFQTADFRLYFRQSHADSVRLDFIFKSFRACQFQFARIVLSRQ
            ||||||||||||||||||||||||||:||||||:|||||||| :  |||| :|||||
orf124a     CIFTVLSKDIFDFLFIFRFQTADFRLFFRQSHADGVRLDFIFFSFRTRLFQFAGVVLSRQ
                   40         50         60         70         80         90

130        140        150        160        170        180
orf124.pep  QQGLRLCALHLVDDRLQLRKCRLVALMVRHSQARADKRDNGNRLPVIRQQFHEIHSRPPD
            ||||||||||:::|||  ||| |||||||||||:||||||:|||||||||||||||||||
orf124a     QQGLRLCALHFLNDRLLLRKSRLVALMVRHRQTRADKRDDGNRLPVIRQQFHEIHSRPPD
                  100        110        120        130        140        150 orf124.pep  ASRX
            :
orf124a     VX
```

ORF124a (SEQ ID NO:90) and ORF124-1 (SEQ ID NO:88) show 89.5% identity in 152 aa overlap:

```
orf124-1.pep  MTAFSTTLISVAEGAVVELQAVRAKAVNATAACIFTVLSKDIFDFLFIFRFQTADFRLFF
              |||||||||||||||:||||||  |||||:||||||||||||||||||||||||||||||
orf124a       MTAFSTTLISVAEGALVELQAVMAKAVNTTAACIFTVLSKDIFDFLFIFRFQTADFRLFF orf124-1.pep  RQSHADSVRLDFIFFSFRACQFQFARIVLSRQQQGLRLVALHLVDDRLLLRKCRLVALMV
              ||||||:|||||||||||  :||||  :||||||||||||||||| |||||||:||||||
orf124a       RQSHADGVRLDFIFFSFRTRLFQFAGVVLSRQQQGLRLVALHFLNDRLLLRKSRLVALMV orf124-1.pep  RHSQARADKRDNGNRLPVIRQQFHEIHSRPPDASRX
              ||  |:||||||:||||||:||||||||||||||
orf124a       RHRQTRADKRDDGNRLPVIRQQFHEIHSRPPDVX
```

The complete length ORF124a nucleotide sequence <SEQ ID 89> is:

```
  1 ATGACCGCCT TTTCGACAAC CTTAATTTCC GTAGCCGAGG GCGCGCTTGT

51 AGAGCTGCAA GCCGTGATGG CCAAAGCCGT CAATACAACC GCCGCCTGCA

101 TTTTTACGGT CTTGAGTAAG GACATTTTCG ATTTCCTTTT TATTTTCCGT

151 TTTCAGACGG CTGACTTCCG CCTGTTTTTT CGCCAAAGCC ATGCCGACGG

201 CGTGCGCCTT GACTTCATAT TTTTTAGCTT CCGCACGCGC CTGTTCCAGT

251 TCGCGGGCGT AGTTTTGAGC CGACAACAGC AGGGCTTGCG CCTTGTCGCG

301 CTTCATTTTC TCAATGACCG CCTGCTGCTT CGCAAAGCC GACTTGTAGC

351 CTTGATGGTG CGACACCGCC AAACCCGTGC CGACAAGCGC GATGATGGCA

401 ATCGGTTGCC AGTTATTCGC CAGCAGTTTC ACGAGATTCA TTCTCGACCT

451 CCTGACGTTT GA
```

This encodes a protein having amino acid sequence <SEQ ID 90>:

```
  1 MTAFSTTLIS VAEGALVELQ AVMAKAVNTT AACIEIWLSK DIFDFLFIFR

51 FQTADFRLFF RQSHADGVRL DFIFFSFRTR LFQFAGVVLS RQQQGLRLVA

101 LHFLNDRLLL RKSRLVALMV RHRQTRADKR DDGNRLPVIR QQFHEIHSRP

151 PDV*
```

Figure 7:
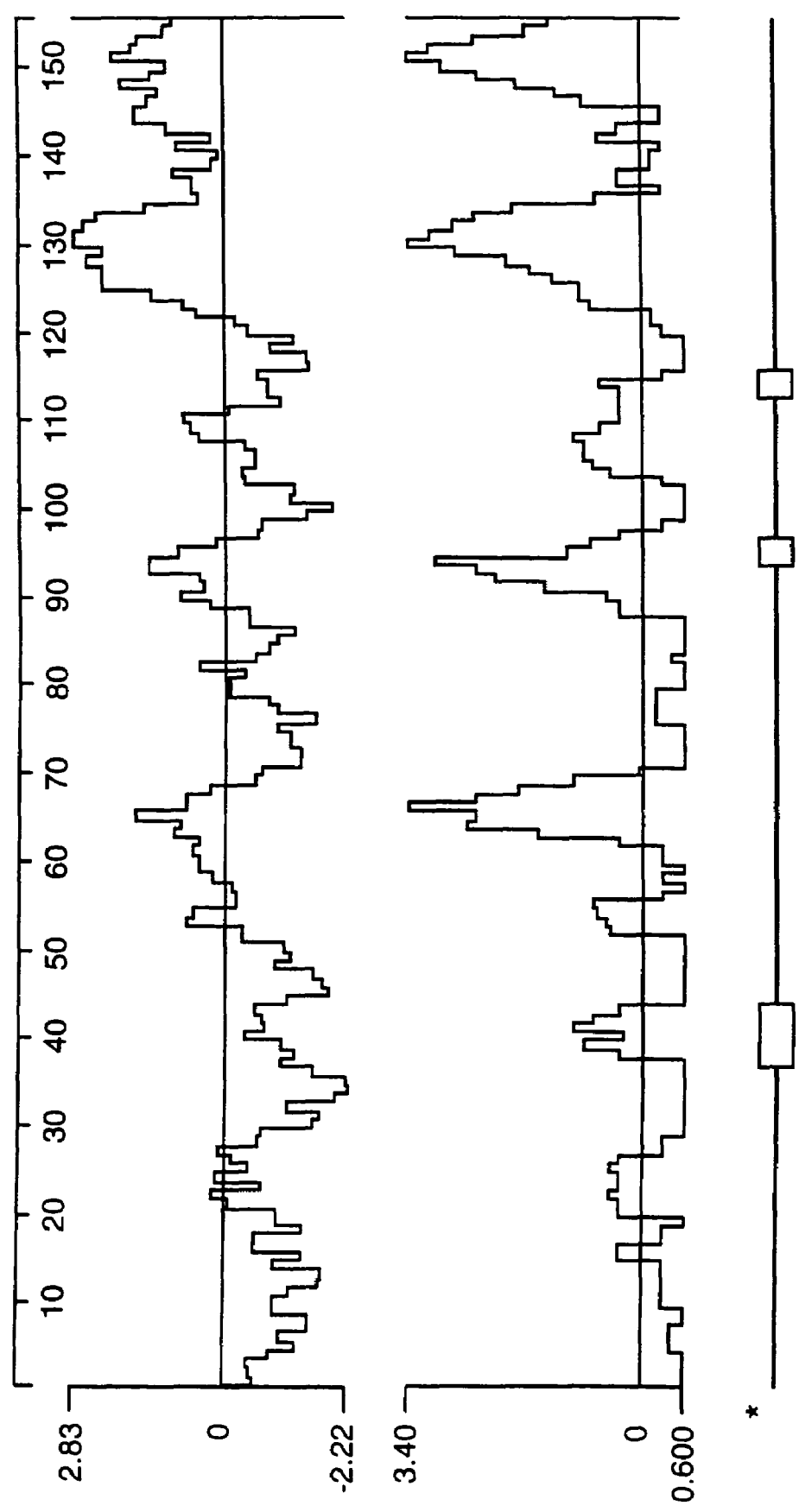
FIG. 7 shows a hydrophilicity plot (upper), an antigenic index plot (middle), and an AMPHI analysis (lower) for ORF 124.

ORF124-1 was amplified as described above. FIG. 7 shows plots of hydrophilicity, antigenic index, and AMPHI regions for ORF 124-1.

Based on this analysis, it is predicted that this protein from *N. meningitidis*, and its epitopes, could be useful antigens for vaccines or diagnostics.

Example 20

Table III lists several *Neisseria* strains which were used to assess the conservation of the sequence of ORF 40 among different strains.

TABLE III

List of Neisseria Strains Used for Gene Variability Study of ORF 40

| Identification number | Strains | Source/reference |
|---|---|---|
| | Group B | |
| zn02_1 | BZ198 | R. Moxon/Seiler et al., 1996 |
| zn03_1 | NG3/88 | R. Moxon/Seiler et al., 1996 |
| zn04_1 | 297-0 | R. Moxon/Seiler et al., 1996 |
| zn06_1 | BZ147 | R. Moxon/Seiler et al., 1996 |
| zn07_1 | BZ169 | R. Moxon/Seiler et al., 1996 |
| zn08_1 | 528 | R. Moxon/Seiler et al., 1996 |
| zn10_1 | BZ133 | R. Moxon/Seiler et al., 1996 |

TABLE III-continued

List of Neisseria Strains Used for Gene Variability Study of ORF 40

| Identification number | Strains | Source/reference |
|---|---|---|
| zn11_1ass | NGE31 | R. Moxon/Seiler et al., 1996 |
| zn14_1 | NGH38 | R. Moxon/Seiler et al., 1996 |
| zn16_1 | NGH15 | R. Moxon/Seiler et al., 1996 |
| zn18_1 | BZ232 | R. Moxon/Seiler et al., 1996 |
| zn19_1 | BZ83 | R. Moxon/Seiler et al., 1996 |
| zn20_1 | 44/76 | R. Moxon/Seiler et al., 1996 |
| zn21_1 | MC58 | R. Moxon |
| | Group A | |
| zn22_1 | 205900 | R. Moxon |
| zn23_1 | F6124 | R. Moxon |
| z2491_1 | Z2491 | R. Moxon/Maiden et al., 1998 |
| | Group C | |
| zn24_1 | 90/18311 | R. Moxon |
| zn25_1ass | 93/4286 | R. Moxon |
| | Others | |
| zn28_1ass | 860800 (group Y) | R. Moxon/Maiden et al., 1998 |
| zn29_1ass | E32 (group Z) | R. Moxon/Maiden et al., 1998 |

References:
Seiler A. et al., Mol. Microbiol., 1996, 19(4): 841-856.
Maiden et al., Proc. Natl. Acad. Sci. USA, 1998, 95: 3140-3145.

The amino acid sequences for each listed strain are as follows:

```
>Z2491                                              <SEQ ID 91>
MNKIYRIIWNSALNAWJAVSELTRNHTKRASATVKTAVLATLLFATVQAN

ATDEDEEEELESVQRSVVGSIQASMEGSGELETISLSMTNDSKEFVDPYI

VVTLKAGDNLKIKQNTNENTNASSFTYSLKKDLTGLINVETEKLSFGANG

KKVNIISDTKGLNFAKETAGTNGDTTVHLNGIGSTLTDTLAGSSASHVDA

GNQSTHYTRAASIKDVLNAGWNIKGVKTGSTTGQSENVDFVRTYDTVEFL

SADTKTTTVNVESKDNGKRTEVKIGAKTSVIKEKDGKLVTGKGKGENGSS

TDEGEGLVTAKEVIDAVNKAGWRMKTTTANGQTGQADKFETVTSGTNVTF

ASGKGTTATVSKDDQGNITVMYDVNVGDALNVNQLQNSGWNLDSKAVAGS

SGKVISGNVSPSKGKMDETVNINAGNNIEISRNGKNIDIATSMAPOFSSV

SLGAGADAPTLSVDDEGALNVGSKDANKPVRITNVAPGVKEGDVTNVAQL

KGVAQNLNNRIDNVDGNARAGIAQAIATAGLVQAYLPGKSMMAIGGGTYR

GEAGYAIGYSSISDGGNWIIKGTASGNSRGHFGASASVGYQW*

>ZN02_1                                             <SEQ ID 92>
MNKIYRIIWNSALWAWVVVSELTRNHTKRASATVATAVLATLLFATVQA

NATDDDDLYLEPVQRTAVVLSFRSDEEGTGEKEGTEDSNWAVYFDEKRV

LKAGAITLKAGDNLKIKQNTNENTNDSSFTYSLKKDLTDLTSVETEKLS

FGANGNKVNITSDTKGLNFAKETAGTNGDPTVHLNGIGSTLTDTLLNTG

ATTNVTNDNVTDDEKKRAASVKDVLNAGWNIKGVKPGTTASDNVDFVRT

YDTVEFLSADTKTTTVNVESKDNGKKTEVKIGAKTSVIKEKDGKLVTGK

GKDENGSSTDEGEGLVTAKEVIDAVNKAGWRNKTTTANGQTGQADKFET

VTSGTNVTFASGKGTTATVSKDDQGNITVKYDVNVGDALNVNQLQNSGW

NLDSKAVAGSSGKVISGNVSPSKGKMDETVNINAGNNIEITRNGKNIDI

ATSMAPQFSSVSLGAGADAPTLSVDDEGALNVGSKDTNKPVRITNVAPG

VKEGDVTNVAQLKGVAQNLNNRIDNVDGNARAGIAQAIATAGLVQAYLP

GKSNMAIGGDTYRGEAGYAIGYSSISDGGNWIIKGTASGNSRGHFGASA

SVGYQW*

>ZN03_1                                             <SEQ ID 93>
MNKIYRIIWNSALNAWVVAVSELTRNHTKRASATVATAVLATLLFATVQA

STTDDDDLYLEPVQRTAPVLSFHADSEGTGEKEVTEDSNWGVYFDKKGV

LTAGTITLKAGDNLKIKQNTDENTNASSFTYSLKKDLTDLTSVETEKLS

FGANGKKVNITSDTKGLNFAKETAGTNGDTTVHLNGIGSTLTDTLLNTG

ATTNVTNDNVTDDEKKRAASVKDVLNAGWNIKGVKPGTTASDNVDFVRT

YDTVEFLSADTKTTTVNVESKDNGKKTEVKIGAKTSVIKEKDGKLVTGK

DKGENGSSTDEGEGLVTAKEVIDAVNKAGWRMKTTTANGQTGQADKFET

VTSGTKVTFASGNGTTATVSKDDQGNITVKYDVNVGDALNVNQLQNSGW

NLDSKAVAGSSGKVISGNVSPSKGKMDETNVINAGNNIEITRNGKNIDI

ATSMTPQFSSVSLGAGADAPTLSVDDEGALNVGSKDANKPVRITNVAPG

VKEGDVTNVAQLKGVAQNLNNHIDNVDGNARAGIAQAIATAGLVQAYLP

GKSMMAIGGGTYRGEAGYAIGYSSISDGGNWIIKGTASGNSRGHFGASA

SVGYQW*

>ZN04_1                                             <SEQ ID 94>
MNKIYRIIWNSALNAWVVVSELTRNHTKRASATVATAVLATLLFATVQA

NATDDDDLYLEPVQRTAVVLSFRSDKEGTGEKEGTEDSNWAVYFDEKRV

LKAGAITLKAGDNLKIKQNTNENTNDSSFTYSLKKDLTDLTSVETEKLS

FGANGNKVNITSDTKGLNFAKETAGTNGDPTVHLNGIGSTLTDTLLNTG

ATTNVTNDNVTDDEKKRAASVKDVLNAGWNIKGVKPGTTASDNVDFVRT

YDTVEFLSADTKTTTVNVESKDNGKKTEVKIGAKTSVIKEKDGKLVTGK

GKDENGSSTDEGEGLVTAKEVIDAVNKAGWRMKTTTANGQTGQADKFET

VTSGTNVTFASGKGTTATVSKDDQGNITVKYDVNVGDALNVNQLQNSGW

NLDSKAVAGSSGKVISGNVSPSKGKMDETVNINAGNNIEITRNGKNIDI

ATSMAPQFSSVSLGAGADAPTLSVDDEGALNVGSKDTNKPVRITNVAPG

VKEGDVTNVAQLKGVAQNLNNRIDNVDGNARAGIAQAIATAGLVQAYLP

GKSMMAIGGDTYRGEAGYAIGYSSISDGGNWIIKGTASGNSRGHFGASA

SVGYQW*

>ZN06_1                                             <SEQ ID 95>
MNKIYRIIWNSALNAWVVVSELTRNHTKRASATVKTAVLATLLFATVQA

SANNEEQEEDLYLDPVQRTVAVLIVNSDKEGTGEKEKVEENSDWAVYEN

EKGVLTAREITLKAGDNLKIKQNGTNFTYSLKKDLTDLTSVGTEKLSFS

ANGNKVNITSDTKGLNFAKETAGTNGDTTVHLNGIGSTLTDTLLNTGAT

TNVTNDNVTDDEKKRAASVKDVLNAGWNIKGVKPGTTASDNVDFVRTYD

TVEFLSADTKTTTVNVESKDNGKKTEVKIGARTSVIKEKDGKLVTGKDK

GENGSSTDEGEGLVTAKEVIDAVNKAGWRMKTTTANGQTGQADKFETVT

SGTNVTFASGKGTTATVSKDDQGNITVMYDVNVGGALNVNQLQNSGWNL
```

-continued
```
DSKAVAGSSGKVISGNVSPSKGKNDETVNINAGNNIEITRNGKNIDIAT

SMTPQFSSVSLGAGADAPTLSVDGDALNVGSKKDNKPVRITNVAPGVKE

GDVTNVAQLKGVAQNLNNRIDNVDGNARAGIAQAIATAGLVQAYLPGKS

MMAIGGGTYRGEAGYAIGYSSISDGGNWIIKGTASGNSRGHFGASASVG

YQW*

>ZN07_1                                      <SEQ ID 96>
MNKIYRIIWNSALNAWVVVSELTRNHTKRASATVKTAVLATLLLFATVQA

SANNEEQEEDLYLDPVQRTVAVLIVNSDKEGTGEKEKVEENSDWAVYFN

EKGVLTAREITLKAGDNLKIKQNGTNFTYSLKKDLTDLTSVGTEKLSFS

ANGNKVNITSDTKGLNFAKETAGTNGDTTVHLNGIGSTLTDTLLNTGAT

TNVTNDNVTDDEKKRAASVKDVLNAGWNIKGVKPGTTASDNVDFVRTYD

TVEFLSADTKTTTVNVESKDNGKKTEVKIGAKTSVIKEKDGKLVTGKDK

GENGSSTDEGEGLVTAKEVIDAVNKAGWRMKTTTANGQTGQADKFETVT

SGTNVTFASGKGTTATVSKDDQGNITVMYDVNVGDALNVNQLQNSGWNL

DSKAVAGSSGKVISGNVSPSKGKMDETVNINAGNNIEITRNGKNIDIAT

SMTPQFSSVSLGAGADAPTLSVDGDALNVGSKKDNKPVRITNVAPGVKE

GDVTNVAQLKGVAQNLNNRIDNVDGNARAGIAQAIATAGLVQAYLPGKS

MMAIGGGTYRGEAGYAIGYSSISDGGNWIIKGTASGNSRGHFGASASVG

YQW*

>ZN08_1                                      <SEQ ID 97>
MNKIYRIIWNSALNAWVVVSELTRNHTKRASATVETAVLATLLLFATVQA

NATDTDEDDELEPVVRSALVLQFNIDKEGNGEIESTGDIGWSIYYDDHN

TLHGATVTLKAGDNLKIKQNTDENTUASSFTYSLKKDLTDLTSVGTEEL

SEGANGNKVNITSDTKGLNFAKKTAGTNGDTTVHLNGIGSTLTDTLAGS

SASHVDAGNQSTHYTRAASIKDVLNAGWNIKGVKTGSTTGQSENVDFVR

TYDTVEFLSADTKTTTVNVESKDNGKRTEVKIGAKTSVIKEKDGKLVTG

KGKGENGSSTDEGEGLVTAKEVIDAVNKAGWRMKTTTANGQTGQADKFE

TVTSGTNVTFASGKGTTATVSKDDQGNITVKYDVNVGDALNVNQLQNSG

WNLDSKAVAGSSGKVISSNVSPSKGKNDETVNINAGNNIEITRNGKNID

IATSMTPQFSSVSLGAGADAPTLSVDDEGALNVGSKDANKPVRITNVAP

GVKEGDVTNVAQLKGVAQNLNNHIDNVDGNARAGIAQAIATAGLVQAYL

PGKSMMAIGGGTYRGEAGYAIGYSSISDGGNWIIKGTASGNSRGHFGAS

ASVGYQW*

>ZN10_1                                      <SEQ ID 98>
MNKIYRIIWNSALNAWVAVSELTRNHTKRASATVKTAVLATLLLFATVQA

NATDEDEEEELESVQRSVVGSIQASMEGSGELETISLSMTNDSKEFVDP

YIVVTLKAGDNLKIKQNTNENTNASSFTYSLKKDLTGLINVETEKLSFG

ANGKKVNIISDTKGLNFAKETAGTNGDTTVHLNGIGSTLTDTLAGSSAS

HVDAGNQSTHYTRAASIKDVLNAGWNIKGVKTGSTTGQSENVDFVRTYD

TVEFLSADTKTTTVNVESKDNGKRTEVKIGAKTSVIKEKDGKLVTGKGK

GENGSSTDEGEGLVTAKEVIDAVNKAGWRMKTTTANGQTGQADKFETVT

SGTNVTFASGKGTTATVSKDDQGNITVMYDVNVGDALNVNQLQNSGWNL

DSKAVAGSSGKVISGNVSPSKGKMDETVNINAGNNIEISRNGKNIDIAT

SMAPQFSSVSLGAGADAPTLSVDDEGALNVGSKDANKPVRITNVAPGVK

EGDVTNVAQLKGVAQNLNNRIDNVDGNARAGIAQAIATAGLVQAYLPGK

SMNAIGGGTYRGEAGYAIGYSSISDGGNWIIKGTASGNSRGHFGASASV

GYQW*

>ZN11_ASS                                    <SEQ ID 99>
MNKIYRIIWNSALNAWVVVSELTRNHTKRASATVATAVLATLLFATVQA

STTDDDDLYLEPVQRTAPVLSFHADSEGTGEKEVTEDSNWGVYFDKKGV

LTAGTITLKAGDNLKIKQNTDENTNASSFTYSLKKDLTDLTSVETEKLS

FGANGKKVNITSDTKGLNFAKETAGTNGDTTVHLNGIGSTLTDTLLNTG

ATTNVTNDNVTDDEKKRAASVKDVLNAGWNIKGVKPGTTASDNVDFVRT

YDTVEFLSADTKTTTVNVESKDNGKKTEVKIGAKTSVIKEKDGKLVTGK

DKGENGSSTDEGEGLVTAKEVIDAVNKAGWRMKTTTANGQTGQADKFET

VTSGTKVTFASGNGTTATVSKDDQGNITVKYDVNVGDALNVNQLQNSGW

NLDSKAVAGSSGKVISGNVSPSKGKMDETVNINAGNNIEITRNGKNIDI

ATSMTPQFSSFSLGAGADAPTLSVDDEGALNVGSKDANKPVRITNVAPG

VKEGDVTNVAQLKGVAQNLNNHIDNVDGNARAGIAQAIATASLVQAYLP

GKSMMAIGGGTYRGEAGYAIGYSSISDGGNWIIKGTASGNSRGHFGASA

SVGYQW*

>ZN14_1                                     <SEQ ID 100>
MNKIYRIIWNSALNAWVAVSELTRNHTKRASATVKTAVLATLLFATVQN

AATDEDEEEELEPVVRSALVLQFMIDKEGNGENESTGNIGWSIYYTNHN

TLHGATVTLKAGDNLKIKQNTNKNTNENTNDSSFTYSLKKDLTDLTSVE

TEKLSFGANGNKVNITSDTKGLNFAKETAGTNGDTTVHLNGIGSTLTDT

LLNTGATTNVTNDNVTDDKKKRAASVKDVLNAGWNIKGVKPGTTASDNV

DFVHTYDTVEFLSADTKTTTVNVESKDNGKRTEVKIGAKTSVIKEKDGK

LVTGKGKGENGSSTDEGEGLVTAKEVIDAVNKAGWRAMKTTTANGQTGQ

ADKFETVTSGTNVFASGKGTTATVSKDDQGNITVKYDVNVGDALNVNQL

QNSGWNLDSKAVAGSSGKVISGNVSPSKGKMDETVNINAGNNIEITRNG

KNIDIATSMTPQFSSVSLGAGADAPTLSV0DKGALNVGSKDANKPVRIT

NVAPGVKEGDVTNVAQLKGVAQNLNNRIDNVDGNARAGIAQAIATAGLV

QAYLPGKSMMAIGGGTYRGEAGYAIGYSSISDGGNWIIKGTASGNSRGH

FGASASVGYQW*

>ZN16_1                                     <SEQ ID 101>
MNKIYRIIWNSALNAWVVVSELTRNHTKRASATVATAVLATLLFATVQA

NATDDDDLYLEPVQRTAVVLSFRSDKEGTGEKEGTEDSNWAVYFDEKRV

LRAGAITLKAGDNLKIKQNTNENTNENTNDSSFTYSLKKDLTDLTSVET

EKLSFGANGNKVNITSDTKGLNFAKETAGTNGDPTVHLNGIGSTLTDTL

LNTGATTNVTNDNVTDDEKKRAASVEDVLNAGWNIKGVKPGTTASDNVD

FVRTYDTVEFLSADTKTTTVNVESKDNGKKTEVKIGAKTSVIKEKDGKL

VTGKGKDENGSSTDEGEGLVTAKEVIDAVNKAGWRMKTTTANGQTGQAD
```

```
KFETVTSGTKVTFASGNGTTATVSKDDQGNITVKYDVNVGDALNVQLQ
NSGWNLDSKAVAGSSGKVISGNVSPSKGKMDETVNINAGNNIEITRNGK
NIDIATSMTPQFSSVSLGAGADAPTLSVDDEGALNVGSKDANKPVRITN
VAPGVKEGDVTNVAQLKGVAQNLNNRIDNVDGNARAGIAQAIATAGLAQ
AYLPGRSMMAIGGGTYRGEAGYAIGYSSISDTGNWVIKGTASGNSRGHF
GASASVGYQW*

>ZN18_1                                    <SEQ ID 102>
MNKIYRIIWNSALNAWVAVSELTRNHTKRASATVATAVLATLLFATVQA
STTDDDDLYLEPVQRTAPVLSFHADSEGTGEKEVTEDSNWGVYFDKKGV
LTAGTITLKAGDNLKIKQNTDENTNASSFTYSLKKDLTDLTSVETEKLS
FGANGKKVNITSDTKGLNFAKETAGTNGDTTVHLNGIGSTLTDTLLNTG
ATTNVTNDNVTDDEKKRAASVKDVLNAGWNIKGVKPGTTASDNVDFVRT
YDTVEFLSADTKTTTVNVESKDNGKKTEVKIGAKTSVIKEKDGKLVTGK
DKGENGSSTDEGEGLVTAKEVIDAVNKAGWRMKTTTANGQTGQADKFET
VTSGTKVTFASGNGTTATVSKDDQGNITVKYDVNVGDALNVQLQNSGW
NLDSKAVAGSSGKVISGNVSPSKGKMDETVNINAGNNIEITRNGKNIDI
ATSMTPQFSSVSLGAGADAPTLSVDDEGALNVGSKDANKPVRITNVAPG
VKEGDVTNVAQLKGVAQNLNNHIDNVDGNARAGIAQAIATAGLVQAYLP
GKSMMAIGGGTYRGEAGYAIGYSSISDGGNWIIKGTASGNSRGHFGASA
SVGYQW*

>ZN19_1                                    <SEQ ID 103>
MNKIYRIIWNSALNAWVVVSELTRNHTKRASATVKTAVLATLLFATVQA
SANNEEQEEDLYLDPVQRTVAVLIVNSDKEGTGEKEKVEENSDWAVYFN
EKGVLTAREITLKAGDNLKIKQNGTNFTYSLKKDLTDLTSVGTEKLSFS
ANGNKVNITSDTKGLNFAKETAGTNGDTTVMLNGIGSTLTDTLLNTGAT
TNVTNDNVTDDEKKRAASVKDVLNAGWNIKGVKPGTTASDNVDFVRTYD
TVEFLSADTKTTTVNVESKDNGKKTEVKIGAKTSVIKEKDGKLVTGKDK
GENGSSTDEGEGLVTAKEVIDAVNKAGWRMKTTTANGQTGQADKFETVT
SGTNVTFASGKGTTATVSKDDQGNITVMYDVNVGDALNVNHLQNSGWDL
DSKAVAGSSCKVISGNVSPSKGKMDETVNINAGNNIEITRNGKNIDIAT
SMTPQFSSVSLGAGADAPTLSVDGDALNVGSKKDNKPVRITNVAPGVKE
GDVTNVAQLKGVAQNLNNRIDNVDGNARAGIAQAIATAGLVQAYLPGKS
MMAIGGGTYRGEAGYAIGYSSISDGGNWIIKGTASGNSRGHFGASASVG
YQW*

>ZN20_1                                    <SEQ ID 104>
MNKIYRIIWNSALNAWVVVSELTRNHTKRASATVXTAVLATLLFATVQA
SANNEEQEEDLYLDPVQRTVAVLIVNSDKEGTGEKEKVEENSDWAVYFN
EKGVLTAREITLKAGDNLKIKQNGTNFTYSLKKDLTDLTSVGTEKLSFS
ANGNKVNITSDTKGLNFAKETAGTNGDTTVHLNGIGSTLTDTLLNTGAT
TNVTNDNVTDDEKKRAASVKDVLNAGWNIKGVKPGTTASDNVDFVRTYD
TVEFLSADTKTTTVNVESKDNGKKTEVKIGAKTSVIKEKDGKLVTGKDK
GENGSSTDEGEGLVTAKEVIDAVNKAGWRMKTTTANGQTGQADKFETVT
SGTNVTFASGKGTTATVSKDDQGNITVMYDVNVGDALNVQLQNSGWNL
DSKAVAGSSGKVISGNVSPSKGKMDETVNINAGNNIEITRNGKNIDIAT
SMTPQFSSVSLGAGADAPTLSVDGDALNVGSKKDNKPVRITNVAPGVKE
GDVTNVAQLKGVAQNLNNRIDNVDGNARAGIAQAIATAGLVQAYLPGKS
MMAIGGGTYRGEAGYAIGYSSISDGGNWIIKGTASGNSRGHFGASASVG
YQW*

>ZN21_1                                    <SEQ ID 105>
MNKIYRIIWNSALNAWVVVSELTRNHTKRASATVKTAVLATLLFATVQA
SANNEEQEEDLYLDPVQRTVAVLIVNSDKEGTGEKEKVEENSDWAVYFN
EKGVLTAREITLKAGDNLKIKQNGTNFTYSLKKDLTDLTSVGTEKLSFS
ANGNKVNITSDTKGLNFAKETAGTNGDTTVHLNGIGSTLTDTLLNTGAT
TNVTNDNVTDDEKKRAASVKDVLNAGWNIKGVKPGTTASDNVDFVRTYD
TVEFLSADTKTTTVNVESKDNGKKTEVKIGAKTSVIKEKDGKLVTGKDK
GENGSSTDEGEGLVTAKEVIDAVNKAGWRMKTTTANGQTGQADKFETVT
SGTNVTFASGKGTTATVSKDDQGNITVMYDVNVGDALNVQLQNSGWNL
DSKAVAGSSGRVISGNVSPSKGKMDETVNINAGNNIEITRNGKNIDIAT
SMTPQFSSVSLGAGADAPTLSVDGDALNVGSKKDNKPVRITNVAPGVKE
GDVTNVAQLKGVAQNLNNRIDNVDGNARAGIAQAIATAGLVQAYLPGKS
MMAIGGGTYRGEAGYAIGYSSISDGGNWIIKGTASGNSRGHFGASASVG
YQW*

>ZN22_1                                    <SEQ ID 106>
MNKIYRIIWNSALNAWVAVSELTRNHTKRASATVKTAVLATLLFATVQA
NATDEDEEEELESVQRSVVGSIQASMEGSGELETISLSMTNDSKEFVDP
YIVVTLKAGDNLKIKQNTNENTNASSFTYSLKKDLTGLINVETEKLSFG
ANGKKVNIISDTKGLNFAKETAGTNGDTTVHLNGIGSTLTDTLAGSSAS
HVDAGNQSTHYTRAASIKDVLNAGWNIKGVKTGSTTGQSENVDFVRTYD
TVEFLSADTKTTTVNVESKDNGKRTEVKIGAKTSVIKEKDGKLVTGKGK
GENGSSTDEGEGLVTAKEVIDAVNKAGWRMKTTTANGQTGQADKFETVT
SGTNVTFASGKGTTATVSKDDQGNITVMYDVNVGDALNVQLQNSGWNL
DSKAVAGSSGKVISGNVSPSKGKMDETVNINAGNNIEISRNGKNIDIAT
SMAPQFSSVSLGAGADAPTLSVDDEGALNVGSKDANKPVRITNVAPGVK
EGDVTNVAQLKGVAQNLNNRIDNVDGNARAGIAQAIATAGLVQAYLPGK
SMMAIGGGTYRGEAGYAIGYSSISDGGNWIIKGTASGNSRGHFGASASV
GYQW*

>ZN23_1                                    <SEQ ID 107>
MNKIYRIIWNSALNAWVAVSELTRNHTKRASATVKTAVLATLLFATVQA
NATDEDEEEELESVQRSVVGSIQASMEGSGELETISLSMTNDSKEFVDP
YIVVTLKAGDNLKIKQNTNENTNASSFTYSLKKDLTGLINVETEKLSFG
ANGKKVNIISDTKGLNFAKETAGTNGDTTVHLNGIGSTLTDTLAGSSAS
HVDAGNQSTHYTRAASIKDVLNAGWNIKGVKTGSTTGQSENVDFVRTYD
TVEFLSADTKTTTVNVESKDNGKRTEVKIGAKTSVIKEKDGKLVTGKGK
```

```
GENGSSTDEGEGLVTAKEVIDAVNKAGWRMKTTTANGQTGQADKFETVT

SGTNVTFASGKGTTATVSKDDQGNITVMYDVNVGDALNVNQLQNSGWNL

DSKAVAGSSGKVISGNVSPSKGKNDETVNINAGNNIEISRNGKNIDIAT

SMAPQFSSVSLGAGADAPTLSVDDEGALNVGSKDANKPVRITNVAPGVK

EGDVTNVAQLKGVAQNLNNRIDNVDGNARAGIAQAIATAGLVQAYLPGK

SHMAIGGGTYRGEAGYAIGYSSISDGGNWIIKGTASGNSRGHFGASASV

GYQW*
>ZN24_1                                         <SEQ ID 108>
MNKIYRIIWNSALNAWVVVSELTRNHTKRASATVATAVLATLLSATVQA

NATDTDEDEELESVVRSALVLQFMIDKEGNGEIESTGDIGWSIYYDDHN

TLHGATVTLKAGDNLKIKQSGKDFTYSLKKELKDLTSVETEKLSFGANG

NKVNITSDTKGLNFAKETAGTNCDPTVHLNGIGSTLTDTLAGSSASHVD

AGNQSTHYTHAASIKDVLNAGWNIKGVKTGSTTGQSENVDFVRTYDTVE

FLSADTKTTTVNVESKDNGKRTEVKIGAKTSVIKEKDGKLVTGKGKGEN

GSSTDEGEGLVTAKEVIDAVNKAGWRMKTTTANGQTGQADKFETVTSGT

KVTFASGNGTTATVSKDDQGNITVKYDVNVGDALNVNQLQNSGWNLDSK

AVAGSSGKVISGNVSPSKGKMDETVNINAGNNIEITRNGKNIDIATSMT

PQFSSVSLGAGADAPTLSVDDEGALNVGSKDANKPVRITNVAPGVKEGD

VTNVAQLKGVAQNLNNRIDNVDGNARAGIAQAIATAGLAQAYLPGKSMM

AIGGGTYRGEAGYAIGYSSISDTGNWVIKGTASGNSRGHFGTSASVGYQ

W*
>ZN25_ASS                                       <SEQ ID 109>
MNKIYRIIWNSALNAWVVVSELTRNHTKRASATVATAVLATLLSATVQA

NATDTDEDEELESVVRSALVLQFMIDKEGNGEIESTGDIGWSIYYDDHN

TLHGATVTLKAGDNLKIKQSGKDFTYSLKKELKDLTSVETEKLSFGANG

NKVNITSDTKGLNFAKETAGTNGDPTVHLNGIGSTLTDTLAGSSASHVD

AGNQSTHYTRAASIKDVLNAGWNIKGVKTGSTTGQSENVDFVRTYDTVE

FLSADTKTTTVNVESKDNGKRTEVKIGAKTSVIKEKDGKLVTGKGKGEN

GSSTDEGEGLVTAKEVIDAVNKAGWRMKTTTANGQTGQADKFETVTSGT

KVTFASGNGTTATVSKDDQGNITVKYDVNVGDALNVNQLQNSGWNLDSK

AVAGSSGKVISGNVSPSKGKMDETVNINAGNNIEITRNGKNIDIATSMT

PQFSSVSLGAGADAPTLSVDDEGALNVGSKDANKPVRITNVAPGVKEGD

VTNVAQLKGVAQNLNNRIDNVDGNARAGIAQAIATAGLAQAYLPGKSHM

AIGGGTYRGEAGYAIGYSSISDTGNWVIKGTASGNSRGHFGTSASVGYQ

W*
>ZN28_ASS                                       <SEQ ID 110>
MNKIYRIIWNSALNAWVAVSELTRNHTKRASATVKTAVLATLLFATVQA

NATDEDEEEELESVQRSVVGSIQASMEGSGELETISLSMTNDSKEFVDP

YIVVTLKAGDNLKIKQNTNENTNASSFTYSLKKDLTGLINVETEKLSFG

ANGKKVNIISDTKGLNFAKETAGTNGDTTVHLNGIGSTLTDMLLNTGAT

TNVTNDNVTDDEKKRAASVKDVLNAGWNIKGVKPGTTASDNVDFVRTYD

TVEFLSADTKTTTVNVESKDNGKKTEVKIGAKTSVIKEKDGKLVTGKGK

GENGSSTDEGEGLVTAKEVIDAVNKAGWRMKTTTANGQTGQADKFETVT

SGTNVTFASGKGTTATVSKDDQGNITVMYDVNVGDALNVNQLQNSGWNL

DSKAVAGSSGKVISGNVSPSKGEMDETVNINAGNNIEITRNGKNIDIAT

SMTPQFSSVSLGAGADAPTLSVDDKGALNVGSKDANKPVRITNVAPGVK

EGDVTNVAQLKGVAQNLNNRIDNVDGNARAGIAQAIATAGLVQAYLPGK

SNMAIGGGTYRGEAGYAIGYSSISDGGNWIIKGTASGNSRGHFGASASV

GYQW*
>ZN29_ASS                                       <SEQ ID 111>
MNKIYRIIWNIALNAWVVVSELTRNHTKRASATVATAVLATLLSATVQA

NATDEEDNEDLEPVVRTAPVLSFHSDKEGTGEKEEVGASSNLTVYFDKN

RVLKAGTITLKAGDNLKIKQNTNENTNENTNASSFTYSLKEDLTGLINV

ETEKLSFGANGKKVNIISDTKGLNFAKETAGTNGDPTVHLNGIGSTLTD

TLAGSSASHVDAGNQSTHYTRAASIKDVLNAGWNIKGVKTGSTTGQSEN

VDFVRTYDTVEFLSADTKTTTVNVESKDNGKRTEVKIGAKTSVIKEKDG

KLVTGKGEGENGSSTDEGEGLVTAKEVIDAVNKAGWRMKTTTANGQTGQ

ADKFETVTSGTKVTFASGNGTTATVSKDDQGNITVKYDVNVGDALNVNQ

LQNSGWNLDSKAVAGSSGKVISGNVSPSKGKMDETVNINAGNNIEITRN

GKNIDIATSMTPQFSSVSLGAGADAPTLSVDDEGALNVGSRDANKPVRI

TNVAPGVKEGDVTNVAQLKGVAQNLNNRIDNVDGNARAGIAQAIATAGL

VQAYLPGKSNMAIGGGTYRGEAGYAIGYSSISDGGNWIIKGTASGNSRG

MFGASASVGYQW*
```

FIG. 8 shows the results of aligning the sequences of each of these strains. Dark shading indicates regions of homology, and gray shading indicates the conservation of amino acids with similar characteristics. As is readily discernible, there is significant conservation among the various strains of ORF 40, further confirming its utility as an antigen for both vaccines and diagnostics.

It will be appreciated that the invention has been described by means of example only, and that modifications may be made whilst remaining within the spirit and scope of the invention.

The invention claimed is:

1. An isolated nucleic acid molecule which encodes a protein comprising an amino acid sequence of SEQ ID NO:4.

2. A nucleic acid molecule according to claim 1, comprising a nucleotide sequence of SEQ ID NO:3.

3. An isolated nucleic acid molecule encoding an immunogenic polypeptide having 90% or greater sequence identity to an amino acid sequence of SEQ ID NO:4, wherein the immunogenic polypeptide can raise antibodies which specifically bind to SEQ ID NO:4.

4. An isolated nucleic acid molecule comprising a fragment of 25 or more nucleotides of a nucleotide sequence of SEQ ID NO:3, wherein the fragment is capable of detecting *N. meningitidis* nucleic acids through hybridization under high stringency conditions comprising a wash in 0.1×SSC, 0.5% SDS solution at 65° C.

5. An isolated nucleic acid molecule encoding an immunogenic polypeptide, wherein the isolated nucleic acid molecule can hybridize to a nucleic acid molecule which encodes a protein comprising an amino acid sequence of SEQ ID NO:4 under high stringency conditions comprising a wash in 0.1×SSC, 0.5% SDS solution at 65° C., wherein the isolated nucleic acid molecule is capable of detecting *N. meningitidis* nucleic acids through hybridization.

6. An isolated nucleic acid molecule that encodes a protein comprising an immunogenic fragment of at least 20 consecutive amino acids of an amino acid sequence of SEQ ID NO:4, wherein the immunogenic fragment can raise antibodies which specifically bind to SEQ ID NO:4.

7. The isolated nucleic acid molecule of claim 3 wherein the immunogenic polypeptide has 99% or greater sequence identity to an amino acid sequence of SEQ ID NO:4.

8. The isolated nucleic acid molecule of claim 3 wherein the immunogenic polypeptide has 95% or greater sequence identity to an amino acid sequence of SEQ ID NO:4.

* * * * *

UNITED STATES PATENT AND TRADEMARK OFFICE
CERTIFICATE OF CORRECTION

PATENT NO. : 7,714,121 B2
APPLICATION NO. : 10/695499
DATED : May 11, 2010
INVENTOR(S) : Vincenzo Scarlato et al.

Page 1 of 2

It is certified that error appears in the above-identified patent and that said Letters Patent is hereby corrected as shown below:

At Column 47, Line 29, delete " 1 MNKIYRIIWN SALNAWVVVS ELTRNHTKRA SATVKTAVLA TLLFATVQAS " and replace with -- 1 MNKIYRIIWN SALNAWVVVS ELTRNIITKRA SATVKTAVLA TLLFATVQAS --

At Column 47, Line 59, delete "251 SADTKTTTVN VESKDNGKKT EVKIGAXTSV IKEKDGKLVT GKDKGENGSS " and replace with -- 251 SADTKTTTVN VESKDNGKKT EVKIGAKTSV IKEKDGKLVT GKDKGENGSS --

At Column 47, Line 63, delete " 351 ASGKGTTATV SKDDQGbUTV MYDVNVGDAL NVNQLQNSGW NLDSKAVAGS " and replace with -- 351 ASGKGTTATV SKDDQGNITV MYDVNVGDAL NVNQLQNSGW NLDSKAVAGS --

At Column 53, Lines 32-34, delete

```
orf40-1.pep  A -SDNVDFVRTYDTVEF LSADTKTTTVNVESKDNGKKTEVKIGAKTSVIKEKDGLVTG
             : |: || || || ||  | ||||||  ||  |:  |  |.|   :  ||
orf40a       TGQSENVDFVRTYDTVEF LSADDKTTTVNVESKDNGKRTEVKIGAKTSVIKEKDGLVTG
``` and replace with

```
orf40-1.pep  A--SDNVDFVRTYDTVEFLSADTKTTTVNVESKDNGKKTEVKIGAKTSVIKEKDGKLVTG
             : |:| ||| ||  | ||| ||||:|  ||:|||| |.| || |:
orf40a       TGQSENVDFVRTYDTVEFLSADTXTTTVNVESKDNGKRTEVKIGAKTSVIKEKDGKLVTG
```

At Column 53, Line 37, delete " orf40-1.pep KDKGENGSSTDEGEELVTAKEVIDAVNKAGWRMKTTTANGQTGQADKFETVTSGTNVTFA " and replace with -- orf40-1.pep KDKGENGSSTDEGEGLVTAKEVIDAVNKAGWRMKTTTANGQTGQADKFETVTSGTNVTFA --

Signed and Sealed this
Twentieth Day of December, 2011

David J. Kappos
*Director of the United States Patent and Trademark Office*

CERTIFICATE OF CORRECTION (continued)
U.S. Pat. No. 7,714,121 B2

At Column 53, Line 39, delete " orf40a
KGKGENGSSTDEGEELVTAKEVIDAVNKAGWRMKTTTANGQTGQADKFETVTSGTNVTFA " and replace with -- orf40a
KGKGENGSSTDEGEGLVTAKEVIDAVNKAGWRMKTTTANGQTGQADKFETVTSGTNVTFA --